(12) United States Patent
Naito et al.

(10) Patent No.: US 11,274,100 B2
(45) Date of Patent: Mar. 15, 2022

(54) EP300/CREBBP INHIBITOR

(71) Applicant: Daiichi Sankyo Company, Limited, Tokyo (JP)

(72) Inventors: Hiroyuki Naito, Eogawa-ku (JP); Yoshiko Kagoshima, Edogawa-ku (JP); Hideaki Funami, Setagaya-ku (JP); Akifumi Nakamura, Ota-ku (JP); Masayoshi Asano, Matsudo (JP); Makoto Haruta, Yachiyo (JP); Takashi Suzuki, Edogawa-ku (JP); Jun Watanabe, Shinagawa-ku (JP); Ryutaro Kanada, Nagareyama (JP); Saito Higuchi, Koto-ku (JP); Kentaro Ito, Bunkyo-ku (JP); Akiko Egami, Musashino (JP); Katsuhiro Kobayashi, Kita-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/625,578

(22) PCT Filed: Jun. 21, 2018

(86) PCT No.: PCT/JP2018/024476
§ 371 (c)(1),
(2) Date: Dec. 20, 2019

(87) PCT Pub. No.: WO2018/235966
PCT Pub. Date: Dec. 27, 2018

(65) Prior Publication Data
US 2021/0171520 A1   Jun. 10, 2021

(30) Foreign Application Priority Data
Jun. 21, 2017   (JP) .............................. JP2017-121454

(51) Int. Cl.
*C07D 471/04* (2006.01)

(52) U.S. Cl.
CPC .................................. *C07D 471/04* (2013.01)

(58) Field of Classification Search
CPC ..................................................... C07D 471/04
USPC ....................................................... 514/303
See application file for complete search history.

(56) References Cited

U.S. PATENT DOCUMENTS

| | | |
|---|---|---|
| 2004/0152747 A1 | 8/2004 | Chen et al. |
| 2013/0142887 A1 | 6/2013 | Alani et al. |
| 2016/0158207 A1 | 6/2016 | Adler et al. |
| 2017/0182054 A1 | 6/2017 | Arancio et al. |

FOREIGN PATENT DOCUMENTS

| | | |
|---|---|---|
| JP | 2006-504796 A | 2/2006 |
| WO | 98/22432 A1 | 5/1998 |
| WO | 2004/033439 A1 | 4/2004 |
| WO | 2007082666 A1 | 7/2007 |
| WO | 2011/085039 A2 | 7/2011 |
| WO | 2015/153410 A1 | 10/2015 |
| WO | 2016/044777 A1 | 3/2016 |
| WO | 2016/086200 A9 | 6/2016 |

OTHER PUBLICATIONS

Bannister, A.J., and T. Kouzarides, "The CBP Co-Activator Is a Histone Acetyltransferase," Nature 384(6610):641-643, Dec. 1996.
Bowers, E.M., et al., "Virtual Ligand Screening of the p300/CBP Histone Acetyltransferase: Identification of a Selective Small Molecule Inhibitor," Chem. Biol. 17(5):471-482, May 2010.
Chan, H.M., and N.B. La Thangue, "p300/CBP Proteins: HATs for Transcriptional Bridges and Scaffolds," J. Cell Sci. 114(Pt 13):2363-2373, 2001.
Chen, J., and Q. Li, "Life and Death of Transcriptional Co-Activator p300," Epigenetics 6(8):957-961, 2011.
Chrivia, J.C., et al., "Phosphorylated CREB Binds Specifically to the Nuclear Protein CBP," Nature 365(6449):855-859, 1993.
Cianfrocca, R., et al., "Nuclear β-Arrestin1 Is a Critical Cofactor of Hypoxia-Inducible Factor-1α Signaling in Endothelin-1-Induced Ovarian Tumor Progression," Oncotarget 7(14):17790-17804, Feb. 2016.
Cole, P.A., "Chemical Probes for Histone-Modifying Enzymes," Nat. Chem. Biol. 4(10):590-597, Oct. 2008.
Dutta, R., et al., "CBP/p300 Acetyltransferase Activity in Hematologic Malignancies," Mol. Genet. Metab. 119(1-2):37-43, 2016.
Fu, M., et al., "p300 and p300/cAMP-Response Element-Binding Protein-Associated Factor Acetylate the Androgen Receptor at Sites Governing Hormone-Dependent Transactivation," J. Biol. Chem. 275(27):20853-20860, Jul. 2000.
Gao, Y., et al., "Expression of p300 and CBP is Associated With Poor Prognosis in Small Cell Lung Cancer," Int. J. Clin. Exp. Pathol. 7(2):760-767, 2014.

(Continued)

*Primary Examiner* — Niloofar Rahmani
(74) *Attorney, Agent, or Firm* — Christensen O'Connor Johnson Kindness PLLC

(57) ABSTRACT

The present invention provides a compound having excellent histone acetyl transferase inhibitory activity against EP300 and/or CREBBP, or a pharmacologically acceptable salt thereof. The compound is represented by the following formula (1) or a pharmacologically acceptable salt thereof:

[Formula 1]

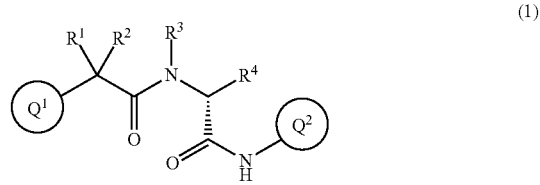

(1)

wherein ring $Q^1$, ring $Q^2$, $R^1$, $R^2$, $R^3$ and $R^4$ respectively have the same meanings as defined in the specification.

25 Claims, 10 Drawing Sheets

(56) References Cited

OTHER PUBLICATIONS

Gayther, S.A., et al., "Mutations Truncating the EP300 Acetylase in Human Cancers," Nat. Genet. 24(3):300-303, Mar. 2000.
Goll, M.G., and T.H. Bestor, "Histone Modification and Replacement in Chromatin Activation," Genes Dev. 16(14):1739-1742, Jan. 2002.
Gu, M.-L., et al., "An Inhibitor of the Acetyltransferases CBP/p300 Exerts Antineoplastic Effects on Gastrointestinal Stromal Tumor Cells," Oncol. Rep. 36(5):2763-2770, 2016.
Gu, W. and R.G. Roeder, "Activation of p53 Sequence-Specific DNA Binding by Acetylation of the p53 C-Terminal Domain," Cell 90(4):595-606, Aug. 1997.
Gui, Y., et al., "Frequent Mutations of Chromatin Remodeling Genes in Transitional Cell Carcinoma of the Bladder," Nat. Genet. 43(9):875-878, Sep. 2011.
Harlow, E., et al., "Association of Adenovirus Early-Region 1A Proteins With Cellular Polypeptides," Mol. Cell. Biol. 6(5): 1579-1589, May 1986.
Heemers, H.V., et al., "The Role of the Transcriptional Coactivator p300 in Prostate Cancer Progression," Adv. Exp. Med. Biol. 617:535-540, 2008.
Isharwal, S., et al., "p300 (Histone Acetyltransferase) Biomarker Predicts Prostate Cancer Biochemical Recurrence and Correlates With Changes in Epithelia Nuclear Size and Shape," The Prostate 68(10): 1097-1104, 2008.
Kishimoto, M., et al., "Mutations and Deletions of the CBP Gene in Human Lung Cancer," Clin. Cancer Res. 11(2 Pt1):512-519, Jan. 2005.
Li, M., et al., "High Expression of Transcriptional Coactivator p300 Correlates With Aggressive Features and Poor Prognosis of Hepatocellular Carcinoma," J Transl. Med. 2011, 9:5.
Muraoka, M., et al., "p300 Gene Alterations in Colorectal and Gastric Carcinomas," Oncogene 12(7): 1565-1569, 1996.
Ogryzko, V.V., et al., "The Transcriptional Coactivators p300 and CBP Are Histone Acetyltransferases," Cell 87(5):953-959, Nov. 1996.
Peifer, M., et al., Integrative Genome Analyses Identify Key Somatic Driver Mutations of Small-Cell Lung Cancer, Nat. Genet. 44(10):1104-1110, Oct. 2012.
Polesskaya, A., et al., "CREB-Binding Protein/p300 Activates MyoD by Acetylation," J. Biol. Chem. 275 (44):34359-34364, Nov. 2000.
Saeed, S., et al., "Chromatin Accessibility, p300, and Histone Acetylation Define PML-RARα and AML1-ETO Binding Sites in Acute Myeloid Leukemia," Blood 120(15):3058-3068, Oct. 2012.
Sobulo, O.M., et al., "MLL is Fused to CBP, a Histone Acetyltransferase, in Therapy-Related Acute Myeloid Leukemia With a t(11;16)(q23;p13.3)," Proc. Natl. Acad. Sci. USA 94(16):8732-8737, Aug. 1997.
Wang, R., and J. You, "Mechanistic Analysis of the Role of Bromodomain-Containing Protein 4 (BRD4) in BRD4-NUT Oncoprotein-Induced Transcriptional Activation," J. Biol. Chem. 290(5):2744-2758, Jan. 2015.
Yee, S.-P., and P.E. Branton, "Detection of Cellular Proteins Associated with Human Adenovirus Type 5 Early Region IA Polypeptides," Virology 147(1):142-153, 1985.
Yuan, Z., et al., "Stat3 Dimerization Regulated by Reversible Acetylation of a Single Lysine Residue," Science 307(5707):269-273, Jan. 2005.
Yokomizo, C. et al., "High Expression of p300 in HCC Predicts Shortened Overall Survival in Association With Enhanced Epithelial Mesenchymal Transition of HCC Cells," Cancer Letters 310:140-147, Jun. 2011.
Zhao, L., et al., "The Adenoviral E1A N-terminal Domain Represses MYC Transcription in Human Cancer Cells by Targeting Both p300 and TRRAP and Inhibiting MYC Promoter Acetylation of H3K18 and H4K16," Genes & Cancer 7(3-4):98-109, Mar. 2016.
International Search Report and Written Opinion dated Aug. 7, 2018, issued in corresponding International Application No. PCT/JP2018/024476, filed Jun. 21, 2018, 12 pages.

EP300/CREBBP INHIBITOR

TECHNICAL FIELD

The present invention relates to a low molecular weight compound having an excellent histone acetyltransferase inhibitory activity against EP300 and/or CREBBP, or a pharmacologically acceptable salt thereof.

BACKGROUND ART

A chromosome dynamically controls gene replication and transcription by changing its higher order structure through methylation modification of DNA, that is, its structural element, and various modifications (such as acetylation, methylation, phosphorylation and ubiquitination) of histone (including histone H2A, H2B, H3 and H4) (Non Patent Reference 1).

Reversible acetylation of histone or another protein is post-translational modification that can frequently occur in a eukaryote. Histone acetyltransferase is an enzyme that metastasizes an acetyl group to a lysine side-chain of histone, and histone deacetylase is an enzyme that removes an acetyl group from a lysine residue. Histone acetyltransferase is roughly divided, based on amino acid sequence homology, higher order structure and function, into four groups of EP300/CREBBP (E1A binding protein p300/CREB Binding Protein), GCN5/PCAF (general control non-repressed-protein 5/P300/CBP-associated factor), MYST (MOZ, Ybf2/Sas3, Sas2 and Tip60), and Rtt109 (Regulator of Ty1 Transposition gene production 109). EP300 and its paralogue, CREBBP, have an amino acid sequence homology of 90% or more, and include, in addition to the HAT domain, CH1/CH2/CH3 domains (cysteine-histidine rich domains), KIX domain, bromo domain and the like (Non Patent Reference 2).

EP300 and CREBBP were discovered as respective binding partners of E1A adenoviral protein and cAMP-regulated enhancer binding protein (Non Patent References 3 to 5). Thereafter, it was found that EP300/CREBBP have histone acetyltransferase activity (Non Patent References 6 and 7), and their substrate specificity was also scrutinized, and as a result, it was reported that they acetylate not only a lysine residue of histone (H2A, H2B, H3 and H4) but also p53 (Non Patent Reference 8), MyoD (Non Patent Reference 9), STAT3 (Non Patent Reference 10), Androgen receptor (Non Patent Reference 11) and the like. EP300 works not only as histone acetyltransferase but also as a configuration factor of a transcription factor, or is involved in activation of transcription by binding a transcription factor to another protein involved in the transcription (Non Patent References 12 and 13). Besides, EP300/CREBBP are also involved in a large number of biological reactions such as division, proliferation and differentiation (Non Patent Reference 12).

It has been reported that high level expression, mutation or hyperfunction of EP300/CREBBP is related to various cancers. Examples include prostate cancer (Non Patent References 14 and 15), liver cancer (Non Patent References 16 and 17), lung cancer (Non Patent References 18, 19 and 20), breast cancer (Non Patent Reference 21), colon cancer and stomach cancer (Non Patent Reference 22), blood cancer (Non Patent References 23 and 24), pancreatic cancer (Non Patent Reference 25), bladder cancer (Non Patent Reference 26), gastrointestinal stromal tumor (Non Patent Reference 27), NUT midline carcinoma (Non Patent Reference 28) and ovarian cancer (Non Patent Reference 29).

Therefore, a drug that inhibits the histone acetyltransferase activity of EP300/CREBBP is expected to be useful as an antitumor agent. It is, however, difficult to search for a compound having strong inhibitory activity and having more specific histone acetyltransferase inhibitory activity (Non Patent Reference 30). Recently, C646 has been found as a specific EP300 inhibitor (Non Patent Reference 31), but there is still a demand for the development of a compound having a novel structure and having stronger inhibitory activity and selectivity.

CITATION LIST

Non Patent References

Non Patent Reference 1: Genes Dev. 2002, 16 (14): 1739-1742
Non Patent Reference 2: Mol Genet Metab. 2016, 119 (1-2): 37-43
Non Patent Reference 3: Virology. 1985, 147 (1): 142-153
Non Patent Reference 4: Mol Cell Biol. 1986, 6 (5): 1579-1589
Non Patent Reference 5: Nature. 1993, 365 (6449): 855-859
Non Patent Reference 6: Cell. 1996, 87 (5): 953-959
Non Patent Reference 7: Nature. 1996, 384 (6610): 641-643
Non Patent Reference 8: Cell. 1997, 90 (4): 595-606
Non Patent Reference 9: J. Biol. Chem. 2000, 275 (44): 34359-34364
Non Patent Reference 10: Science. 2005, 307 (5707): 269-273
Non Patent Reference 11: J. Biol. Chem. 2000, 275 (27), 20853-20860
Non Patent Reference 12: J. Cell Sci. 2001, 114 (Pt 13): 2363-2373
Non Patent Reference 13: Epigenetics. 2011, 6 (8): 957-961
Non Patent Reference 14: Adv. Exp. Med. Biol. 2008; 617: 535-540
Non Patent Reference 15: Prostate. 2008, 68 (10): 1097-1104
Non Patent Reference 16: Cancer Lett. 2011, 310 (2): 140-147
Non Patent Reference 17: J. Transl. Med. 2011, 9:5
Non Patent Reference 18: Int. J. Clin. Exp. Pathol. 2014, 7 (2): 760-767
Non Patent Reference 19: Nat. Genet. 2012, 44 (10): 1104-1110
Non Patent Reference 20: Clin. Cancer Res. 2005, 11 (2 Pt1): 512-519
Non Patent Reference 21: Genes Cancer. 2016, 7 (3-4): 98-109
Non Patent Reference 22: Oncogene. 1996, 12 (7): 1565-1569
Non Patent Reference 23: Proc. Natl. Acad. Sci. USA. 1997, 94 (16): 8732-8737
Non Patent Reference 24: Blood. 2012, 120 (15) 3058-3068
Non Patent Reference 25: Nat. Genet. 2000, 24 (3): 300-303
Non Patent Reference 26: Nat. Genet. 2011, 43 (9): 875-878
Non Patent Reference 27: Oncol. Rep. 2016, 36 (5): 2763-2770
Non Patent Reference 28: J. Biol. Chem. 2015, 290 (5): 2744-2758
Non Patent Reference 29: Oncotarget. 2016, 7 (14): 17790-17804
Non Patent Reference 30: Nat. Chem. Biol. 2008, 4 (10): 590-597
Non Patent Reference 31: Chem. Biol. 2010, 17 (5): 471-482

SUMMARY OF INVENTION

Technical Problem

The present invention provides a novel low molecular weight compound that has an inhibitory action on the histone acetyltransferase activities of both EP300 and CREBBP, and exhibits anticancer action against a cancer dependent on EP300 and/or CREBBP.

Solution to Problem

The present invention relates to the following [1] to [21]:

[1] A compound represented by the following general formula (1) or a pharmacologically acceptable salt thereof:

[Formula 1]

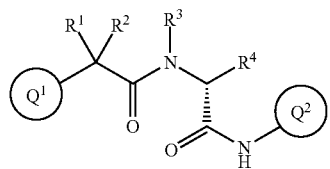

(1)

wherein ring $Q^1$ represents a phenyl group optionally having 1 to 3 substituents independently selected from the following group A, or a 5-membered or 6-membered aromatic heterocyclic group having 1 to 2 nitrogen atoms in a ring (wherein the 5-membered or 6-membered aromatic heterocyclic group optionally has 1 to 3 substituents independently selected from the following group A);

ring $Q^2$ represents a phenyl group optionally having 1 to 3 substituents independently selected from the following group B, a naphthyl group optionally having 1 to 3 substituents independently selected from the following group B, a 5-membered or 6-membered aromatic heterocyclic group having 1 to 3 nitrogen atoms in a ring (wherein the 5-membered or 6-membered aromatic heterocyclic group optionally has 1 to 3 substituents independently selected from the following group B), or an 8-membered to 10-membered bicyclic aromatic heterocyclic group optionally having, in a ring, 1 to 4 hetero atoms independently selected from the group consisting of a nitrogen atom, an oxygen atom and a sulfur atom (wherein the 8-membered to 10-membered bicyclic aromatic heterocyclic group optionally has 1 to 3 substituents independently selected from the following group B);

$R^1$ and $R^2$ each independently represent a $C_{1-6}$ alkyl group or a $C_{1-6}$ alkoxy group, or $R^1$ and $R^2$ form, together with a carbon atom to which $R^1$ and $R^2$ are bonded, a 3-membered to 7-membered cycloalkyl ring optionally having 1 to 3 substituents independently selected from the following group C, a tetrahydropyran ring optionally having 1 to 3 substituents independently selected from the following group C, or a dioxane ring optionally having 1 to 3 substituents independently selected from the following group C;

$R^3$ represents a hydrogen atom, a $C_{1-6}$ alkyl group or a hydroxy $C_{2-6}$ alkyl group, and $R^4$ represents a hydrogen atom, a $C_{1-6}$ alkyl group, a hydroxy $C_{1-6}$ alkyl group or a $C_{1-6}$ alkylsulfonyl $C_{1-6}$ alkyl group, or $R^3$ and $R^4$ form, together with a nitrogen atom to which $R^3$ is bonded and a carbon atom to which $R^4$ is bonded, an azetidine ring optionally having 1 to 3 substituents independently selected from the following group D, a pyrrolidine ring optionally having 1 to 3 substituents independently selected from the following group D, a hexamethyleneimine ring optionally having 1 to 3 substituents independently selected from the following group D, a thiazolidine ring optionally having 1 to 3 substituents independently selected from the following group D, a 1-oxothiazolidine ring optionally having 1 to 3 substituents independently selected from the following group D, a 1,1-dioxothiazolidine ring optionally having 1 to 3 substituents independently selected from the following group D, or a 4-oxopyrrolidine ring optionally having 1 to 3 substituents independently selected from the following group D:

Group A: a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group, a phenylsulfonylamino group, a carbamoyl group, a $C_{1-6}$ alkylcarbamoyl group, a di-$C_{1-6}$ alkylcarbamoyl group, a benzyloxycarbonyl group, a $C_{3-7}$ cycloalkylsulfonylcarbamoyl group, a halo $C_{1-6}$ alkylsulfonyloxy group and a phenyl sulfonyl group, Group B: a halogen atom, a cyano group, an amino group, a $C_{1-6}$ alkyl group, a $C_{1-6}$ alkoxy group, a hydroxy $C_{1-6}$ alkyl group, a $C_{1-6}$ alkylamino group, a $C_{1-6}$ alkylamino $C_{1-6}$ alkyl group, a morpholinyl $C_{1-6}$ alkyloxy group, a phenyl group, a benzyloxy group, a $C_{1-6}$ alkoxy $C_{1-6}$ alkyl group, a hydroxy group, a halo $C_{1-6}$ alkyl group, a $C_{1-6}$ alkoxycarbonyl group, a $C_{2-7}$ alkanoylamino group, a halo $C_{1-6}$ alkoxy group, a $C_{1-6}$ alkoxy $C_{1-6}$ alkoxy group, a $C_{1-6}$ alkylsulfonylamino group, a morpholinyl $C_{1-6}$ alkyl group and a $C_{1-6}$ alkylsulfonyl group, Group C: a halogen atom, a $C_{1-6}$ alkyl group and a $C_{1-6}$ alkoxy group, and Group D: a halogen atom, a hydroxy group, a $C_{1-6}$ alkyl group, a $C_{1-6}$ alkoxy group, a $C_{1-6}$ alkoxy $C_{1-6}$ alkoxy group, a $C_{2-6}$ alkynyl group, a $C_{2-7}$ alkanoylamino group, an amino group and a di-$C_{1-6}$ alkylamino group.

[2] A compound according to [1], or a pharmacologically acceptable salt thereof, wherein the ring $Q^1$ represents any one of the following formulae (2A) to (2D);

[Formula 2]

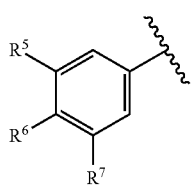

(2A)

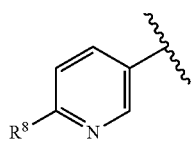

(2B)

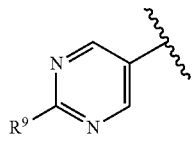

(2C)

-continued (2D)
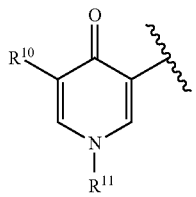

wherein $R^5$, $R^6$ and $R^7$ each independently represent a hydrogen atom, a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group or a phenylsulfonylamino group, $R^8$, $R^9$ and $R^{11}$ each independently represent a hydrogen atom or a $C_{1-6}$ alkoxy group, and $R^{10}$ represents a hydrogen atom or a carboxy group;

[3] A compound according to [1], or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group;

[4] A compound according to any one of [1] to [3], or a pharmacologically acceptable salt thereof, wherein the ring $Q^2$ is a phenyl group optionally having 1 or 2 substituents independently selected from the following group E, a pyridinyl group optionally having 1 or 2 substituents independently selected from the following group F, a pyrimidinyl group or a 1-methylpyrazolyl group;

Group E: a halogen atom, a cyano group, a hydroxy group, a $C_{1-6}$ alkyl group, a $C_{1-6}$ alkoxy group, a morpholinyl $C_{1-6}$ alkyloxy group and a benzyloxy group, and Group F: an amino group and a $C_{1-6}$ alkylamino group

[5] A compound according to any one of [1] to [3], or a pharmacologically acceptable salt thereof, wherein the ring $Q^2$ is a phenyl group optionally having 1 or 2 substituents independently selected from the group consisting of a hydroxy group, a fluorine atom, a chlorine atom, a cyano group, a methyl group, a methoxy group and a benzyloxy group;

[6] A compound according to any one of [1] to [3], or a pharmacologically acceptable salt thereof, wherein the ring $Q^2$ represents any one of the following formulae (3A) to (3F);

[Formula 3]

(3A)
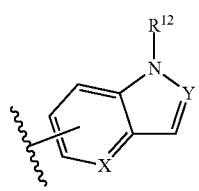

(3B)
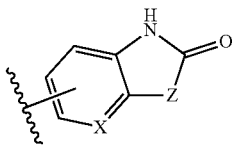

(3C)
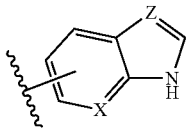

(3D)
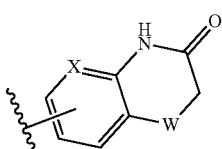

(3E)
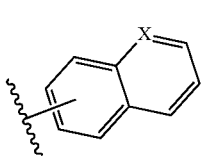

(3F)
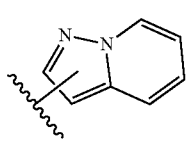

wherein X represents a nitrogen atom or —$CR^{13}$;
Y represents a nitrogen atom or —$CR^{14}$;
Z represents —NH or —$CH_2$ in the formula (3B), and a nitrogen atom or —CH in the formula (3C);
W represents an oxygen atom or —$CH_2$;
$R^{12}$ represents a hydrogen atom or a $C_{1-6}$ alkyl group;
$R^{13}$ represents a hydrogen atom, a fluorine atom or a cyano group; and
$R^{14}$ represents a hydrogen atom, a $C_{1-6}$ alkyl group, a hydroxy $C_{1-6}$ alkyl group, a $C_{1-6}$ alkylamino $C_{1-6}$ alkyl group or a phenyl group.

[7] A compound according to any one of [1] to [3], or a pharmacologically acceptable salt thereof, wherein the ring $Q^2$ represents any one of the following formulae (4A) to (4D);

[Formula 4]

(4A)
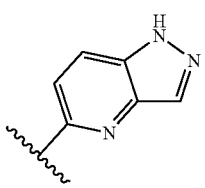

(4B)
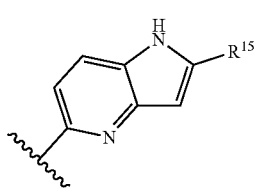

-continued (4C)
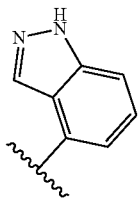

(4D)
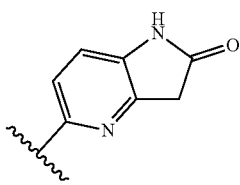

wherein $R^{15}$ represents a hydrogen atom, a methyl group, a hydroxymethyl group or a methylaminomethyl group.

[8] A compound according to any one of [1] to [7], or a pharmacologically acceptable salt thereof, wherein $R^1$ and $R^2$ each independently represent a methyl group;

[9] A compound according to any one of [1] to [7], or a pharmacologically acceptable salt thereof, wherein $R^1$ and $R^2$ form, together with a carbon atom to which $R^1$ and $R^2$ are bonded, a cyclobutane ring, a 3,3-dihalocyclobutane ring, a 3,3-di-$C_{1-6}$ alkyl cyclobutane ring, a cyclopentane ring, a cyclohexane ring, a 4,4-dihalocyclohexane ring, a tetrahydropyran ring, a cycloheptane ring or a spiro[3.3]heptane ring;

[10] A compound according to any one of [1] to [7], or a pharmacologically acceptable salt thereof, wherein $R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring;

[11] A compound according to any one of [1] to [10], or a pharmacologically acceptable salt thereof, wherein $R^3$ is a methyl group, and $R^4$ is a hydroxymethyl group or a 1-hydroxyethyl group;

[12] A compound according to any one of [1] to [10], or a pharmacologically acceptable salt thereof, wherein $R^3$ and $R^4$ represent, together with a nitrogen atom to which $R^3$ is bonded and a carbon atom to which $R^4$ is bonded, any one of the following formulae (5A) to (5D);

[Formula 5]

(5A)
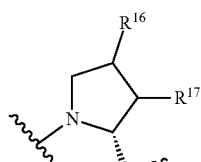

(5B)
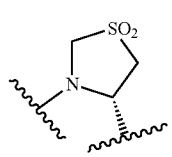

(5C)
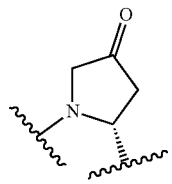

(5D)
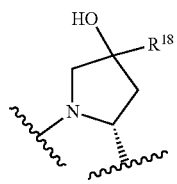

wherein $R^{16}$ represents a hydrogen atom, a halogen atom, a hydroxy group, a $C_{1-6}$ alkoxy group or a di-$C_{1-6}$ alkylamino group;

$R^{17}$ represents a hydrogen atom or a hydroxy group; and $R^{18}$ represents a $C_{1-6}$ alkyl group or a $C_{2-6}$ alkynyl group.

[13] A compound according to any one of [1] to [10], or a pharmacologically acceptable salt thereof, wherein $R^3$ and $R^4$ represent, together with a nitrogen atom to which $R^3$ is bonded and a carbon atom to which $R^4$ is bonded, any one of the following formulae (6A) to (6C):

[Formula 6]

(6A)
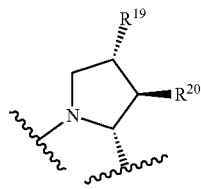

(6B)
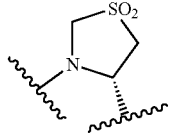

(6C)
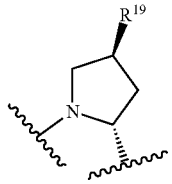

wherein $R^{19}$ represents a hydrogen atom, a fluorine atom or a hydroxy group; and $R^{20}$ represents a hydrogen atom or a hydroxy group.

[14] A compound according to [1], or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group;

the ring Q² represents any one of the following formulae (4A) to (4D):

[Formula 7]

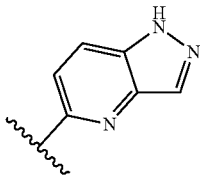
(4A)

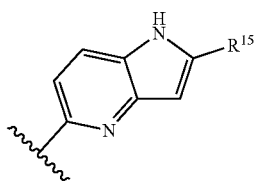
(4B)

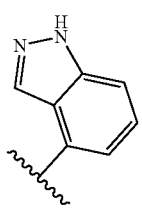
(4C)

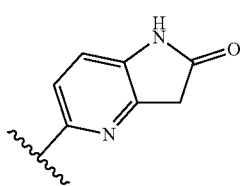
(4D)

wherein $R^{15}$ represents a hydrogen atom, a methyl group, a hydroxymethyl group or a methylaminomethyl group;

$R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring; and $R^3$ and $R^4$ represent, together with a nitrogen atom to which $R^3$ is bonded and a carbon atom to which $R^4$ is bonded, any one of the following formulae (6A) to (6C):

[Formula 8]

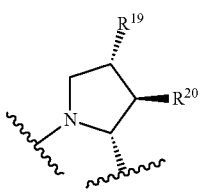
(6A)

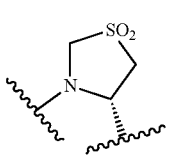
(6B)

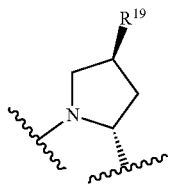
(6C)

wherein $R^{19}$ represents a hydrogen atom, a fluorine atom or a hydroxy group; and $R^{20}$ represents a hydrogen atom or a hydroxy group.

[15] a compound selected from the following group, or a pharmacologically acceptable salt thereof:

(4R)-4-fluoro-1-{[1-(4-methoxyphenyl)cyclohexyl]carbonyl}-N-1H-pyrazolo[4,3-b]pyridin-5-yl-D-prolineamide, (4R)-4-fluoro-1-{[1-(3-fluoro-4-methoxyphenyl)cyclohexyl]carbonyl}-N-1H-pyrazolo[4,3-b]pyridin-5-yl-D-prolineamide, (4R)-4-fluoro-1-{[4-(4-methoxyphenyl)tetrahydro-2H-pyran-4-yl]carbonyl}-N-1H-pyrazolo[4,3-b]pyridin-5-yl-D-prolineamide, (4R)-4-fluoro-1-[2-(4-methoxyphenyl)-2-methylpropanoyl]-N-1H-pyrazolo[4,3-b]pyridin-5-yl-D-prolineamide, (4R)-4-fluoro-1-({1-[4-(fluoromethoxy)phenyl]cyclopentyl}carbonyl)-N-1H-pyrazolo[4,3-b]pyridin-5-yl-D-prolineamide, (4R)-4-fluoro-1-{[1-(6-methoxypyridin-3-yl)cyclohexyl]carbonyl}-N-1H-pyrazolo[4,3-b]pyridin-5-yl-D-prolineamide, (4R)-1-{[4,4-difluoro-1-(4-methoxyphenyl)cyclohexyl]carbonyl}-4-fluoro-N-1H-pyrazolo[4,3-b]pyridin-5-yl-D-prolineamide, (4R)-4-fluoro-N-1H-pyrazolo[4,3-b]pyridin-5-yl-1-({1-[4-(trifluoroacetyl)phenyl]cyclohexyl}carbonyl)-D-prolineamide, (4R)-4-fluoro-1-{[1-(4-methoxyphenyl)cyclohexyl]carbonyl}-N-1H-pyrrolo[3,2-b]pyridin-5-yl-D-prolineamide, (4R)-4-fluoro-1-{[1-(4-methoxyphenyl)cyclohexyl]carbonyl}-N-(2-oxo-2,3-dihydro-1H-pyrrolo[3,2-b]pyridin-5-yl)-D-prolineamide, 4,4-difluoro-N-[(2R)-3-hydroxy-1-oxo-1-(1H-pyrazolo[4,3-b]pyridin-5-ylamino)propan-2-yl]-1-(4-methoxyphenyl)-N-methylcyclohexanecarboxamide, (4R)-1-{[4,4-difluoro-1-(4-methoxyphenyl)cyclohexyl]carbonyl}-4-fluoro-N-(2-oxo-2,3-dihydro-1H-pyrrolo[3,2-b]pyridin-5-yl)-D-prolineamide, 4,4-difluoro-N-[(2R)-3-hydroxy-1-oxo-1-(1H-pyrrolo[3,2-b]pyridin-5-ylamino)propan-2-yl]-1-(4-methoxyphenyl)-N—(²H₃)methylcyclohexanecarboxamide, (4R)-4-fluoro-1-{2-methyl-2-[4-(trifluoromethoxy)phenyl]propanoyl}-N-1H-pyrazolo[4,3-b]pyridin-5-yl-D-prolineamide, 4,4-difluoro-N-[(2R,3S)-3-hydroxy-1-oxo-1-(1H-pyrazolo[4,3-b]pyridin-5-ylamino)butan-2-yl]-1-(4-methoxyphenyl)-N-methylcyclohexanecarboxamide, (4R)-4-fluoro-1-({1-[4-(2-hydroxypropan-2-yl)phenyl]cyclohexyl}carbonyl)-N-1H-pyrazolo[4,3-b]pyridin-5-yl-D-prolineamide, (4R)-1-{[1-(4-acetylphenyl)cyclohexyl]carbonyl}-4-fluoro-N-1H-pyrazolo[4,3-b]pyridin-5-yl-D-prolineamide, (4R)-1-({1-[4-(difluoromethoxy)phenyl]-4,4-difluorocyclohexyl}carbonyl)-4-fluoro-N-1H-pyrazolo[4,3-b]pyridin-5-yl-D-prolineamide, (4R)-1-({4,4-difluoro-1-[3-fluoro-4-(fluoromethoxy)phenyl]cyclohexyl}carbonyl)-4-fluoro-N-1H-pyrazolo[4,3-b]pyridin-5-yl-D-prolineamide, (4R)-1-({3,3-difluoro-1-[3-fluoro-4-(2,2,2-trifluoroethoxy)phenyl]cyclobutyl}carbonyl)-4-fluoro-N-1H-pyrazolo[4,3-b]pyridin-5-yl-D-prolineamide, (4R)-1-[(4,4-difluoro-1-{3-fluoro-4-[($^2$H$_3$)methyloxy]phenyl}cyclohexyl)carbonyl]-4-fluoro-N-1H-pyrazolo[4,3-b]pyridin-5-yl-D-prolineamide, (4R)-1-[(4,4-difluoro-1-{4-[($^2$H$_3$)methyloxy]phenyl}cyclohexyl)carbonyl]-4-fluoro-N-1H-pyrazolo[4,3-b]pyridin-5-yl-D-prolineamide, (4R)-1-({4,4-difluoro-1-[4-(fluoromethoxy)phenyl]cyclohexyl}carbonyl)-4-fluoro-N-1H-pyrazolo[4,3-b]pyridin-5-yl-D-prolineamide, (4R)-1-{[4,4-difluoro-1-(4-methoxyphenyl)cyclohexyl]carbonyl}-4-fluoro-N-(2-methyl-1H-pyrrolo[3,2-b]pyridin-5-yl)-D-prolineamide, (4R)-1-({1-[4-(difluoromethoxy)phenyl]-3,3-difluorocyclobutyl}carbonyl)-4-fluoro-N-1H-pyrazolo[4,3-b]pyridin-5-yl-D-prolineamide, (3S,4S)-1-({1-[4-(difluoromethoxy)phenyl]-4,4-difluorocyclohexyl}carbonyl)-4-fluoro-3-hydroxy-N-1H-pyrazolo[4,3-b]pyridin-5-yl-D-prolineamide, (4R)-1-({1-[4-(difluoromethoxy)phenyl]-4,4-difluorocyclohexyl}carbonyl)-4-fluoro-N-[2-(hydroxymethyl)-1H-pyrrolo[3,2-b]pyridin-5-yl]-D-prolineamide, (4R)-4-fluoro-1-{[1-(4-methoxyphenyl)cyclohexyl]carbonyl}-N-1H-pyrrolo[2,3-b]pyridin-6-yl-D-prolineamide, and (4S)-3-{[4,4-difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide;

[16] A pharmaceutical composition comprising, as an active ingredient, a compound according to any one of [1] to [15], or a pharmacologically acceptable salt thereof;

[17] An EP300 and/or CREBBP inhibitor comprising, as an active ingredient, a compound according to any one of [1] to [15], or a pharmacologically acceptable salt thereof;

[18] An antitumor agent comprising, as an active ingredient, a compound according to any one of [1] to [15], or a pharmacologically acceptable salt thereof.

[19] An antitumor agent according to [18], wherein the tumor is prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma or ovarian cancer.

[20] A method for treating a tumor, comprising administering a compound according to any one of [1] to [15], or a pharmacologically acceptable salt thereof;

[21] A treatment method according to [20], wherein the tumor is prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma or ovarian cancer.

Besides, the present invention relates to the following [A1] to [A50]:

[A1] A compound represented by the following general formula (1), or a pharmacologically acceptable salt thereof:

[Formula 9]

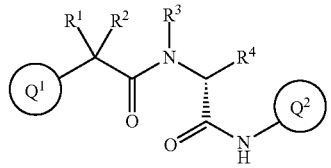

(1)

wherein ring $Q^1$ represents a phenyl group optionally having 1 to 3 substituents independently selected from the following group A, or a 5-membered or 6-membered aromatic heterocyclic group having 1 to 3 nitrogen atoms in a ring (wherein the 5-membered or 6-membered aromatic heterocyclic group optionally has 1 to 3 substituents independently selected from the following group A);

ring $Q^2$ represents a phenyl group optionally having 1 to 3 substituents independently selected from the following group B, a naphthyl group optionally having 1 to 3 substituents independently selected from the following group B, a 5-membered or 6-membered aromatic heterocyclic group having 1 to 3 nitrogen atoms in a ring (wherein the 5-membered or 6-membered aromatic heterocyclic group optionally has 1 to 3 substituents independently selected from the following group B), or an 8-membered to 10-membered bicyclic aromatic heterocyclic group optionally having, in a ring, 1 to 4 hetero atoms independently selected from the group consisting of a nitrogen atom, an oxygen atom and a sulfur atom (wherein the 8-membered to 10-membered bicyclic aromatic heterocyclic group optionally has 1 to 3 substituents independently selected from the following group B);

$R^1$ and $R^2$ each independently represent a $C_{1-6}$ alkyl group or a $C_{1-6}$ alkoxy group, or $R^1$ and $R^2$ form, together with a carbon atom to which $R^1$ and $R^2$ are bonded, a 3-membered to 7-membered cycloalkyl ring optionally having 1 to 3 substituents independently selected from the following group C, a tetrahydropyran ring optionally having 1 to 3 substituents independently selected from the following group C, or a dioxane ring optionally having 1 to 3 substituents independently selected from the following group C;

$R^3$ represents a hydrogen atom, a $C_{1-6}$ alkyl group or a hydroxy $C_{2-6}$ alkyl group, and $R^4$ represents a hydrogen atom, a $C_{1-6}$ alkyl group, a hydroxy $C_{1-6}$ alkyl group or a $C_{1-6}$ alkylsulfonyl $C_{1-6}$ alkyl group, or $R^3$ and $R^4$ form, together with a nitrogen atom to which $R^3$ is bonded and a carbon atom to which $R^4$ is bonded, an azetidine ring optionally having 1 to 3 substituents independently selected from the following group D, a pyrrolidine ring optionally having 1 to 3 substituents independently selected from the following group D, a hexamethyleneimine ring optionally having 1 to 3 substituents independently selected from the following group D, a thiazolidine ring optionally having 1 to 3 substituents independently selected from the following group D, a 1-oxothiazolidine ring optionally having 1 to 3 substituents independently selected from the following group D, a 1,1-dioxothiazolidine ring optionally having 1 to 3 substituents independently selected from the following group D, or a 4-oxopyrrolidine ring optionally having 1 to 3 substituents independently selected from the following group D:

Group A: a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group, a phenylsulfonylamino group, a carbamoyl group, a $C_{1-6}$ alkylcarbamoyl group, a di-$C_{1-6}$ alkylcarbamoyl group, a benzyloxycarbonyl group, a $C_{3-7}$ cycloalkylsulfonylcarbamoyl group, a halo $C_{1-6}$ alkylsulfonyloxy group and a phenyl sulfonyl group, Group B: a halogen atom, a cyano group, an amino group, a $C_{1-6}$ alkyl group, a $C_{1-6}$ alkoxy group, a hydroxy $C_{1-6}$ alkyl group, a $C_{1-6}$ alkylamino group, a $C_{1-6}$ alkylamino $C_{1-6}$ alkyl group, a morpholinyl $C_{1-6}$ alkyloxy group, a phenyl group, a benzyloxy group, a $C_{1-6}$ alkoxy $C_{1-6}$ alkyl group, a hydroxy group, a halo $C_{1-6}$ alkyl group, a $C_{1-6}$ alkoxycarbonyl group, a $C_{2-7}$ alkanoylamino group, a halo $C_{1-6}$ alkoxy group, a $C_{1-6}$ alkoxy $C_{1-6}$ alkoxy group, a $C_{1-6}$ alkylsulfonylamino group, a morpholinyl $C_{1-6}$ alkyl group and a $C_{1-6}$ alkylsulfonyl group, Group C: a halogen atom, a $C_{1-6}$ alkyl group and a $C_{1-6}$ alkoxy group, and Group D: a halogen atom, a hydroxy group, a $C_{1-6}$ alkyl group, a $C_{1-6}$ alkoxy group, a $C_{1-6}$ alkoxy $C_{1-6}$ alkoxy group, a $C_{2-6}$ alkynyl group, a $C_{2-7}$ alkanoylamino group, an amino group and a di-$C_{1-6}$ alkylamino group.

[A2] A compound according to [A1], or a pharmacologically acceptable salt thereof, wherein the ring $Q^1$ represents any one of the following formulae (2A) to (2D):

[Formula 10]

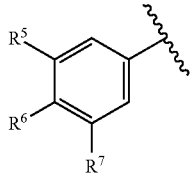

(2A)

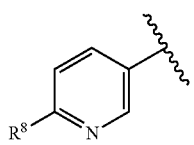

(2B)

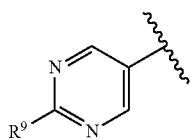

(2C)

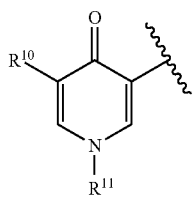

(2D)

wherein $R^5$, $R^6$ and $R^7$ each independently represent a hydrogen atom, a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group or a phenylsulfonylamino group, $R^8$, $R^9$ and $R^{11}$ each independently represent a hydrogen atom or a $C_{1-6}$ alkoxy group, and $R^{10}$ represents a hydrogen atom or a carboxy group.

[A3] A compound according to [A1], or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group.

[A4] A compound according to any one of [A1] to [A3], or a pharmacologically acceptable salt thereof, wherein the ring $Q^2$ is a phenyl group optionally having 1 or 2 substituents independently selected from the following group E, a pyridinyl group optionally having 1 or 2 substituents independently selected from the following group F, a pyrimidinyl group or a 1-methylpyrazolyl group:

Group E: a halogen atom, a cyano group, a hydroxy group, a $C_{1-6}$ alkyl group, a $C_{1-6}$ alkoxy group, a morpholinyl $C_{1-6}$ alkyloxy group and a benzyloxy group, and Group F: an amino group and a $C_{1-6}$ alkylamino group.

[A5] A compound according to any one of [A1] to [A3], or a pharmacologically acceptable salt thereof, wherein the ring $Q^2$ is a phenyl group optionally having 1 or 2 substituents independently selected from the group consisting of a hydroxy group, a fluorine atom, a chlorine atom, a cyano group, a methyl group, a methoxy group and a benzyloxy group.

[A6] A compound according to any one of [A1] to [A3], or a pharmacologically acceptable salt thereof, wherein the ring $Q^2$ represents any one of the following formulae (3A) to (3F):

[Formula 11]

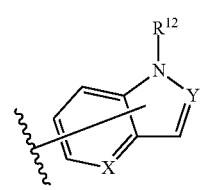

(3A)

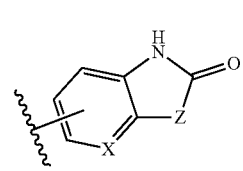

(3B)

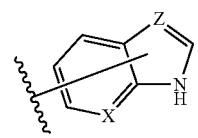

(3C)

-continued (3D)
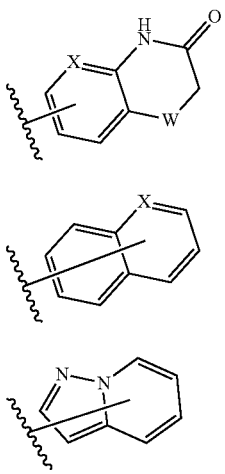

(3E)

(3F)

wherein X represents a nitrogen atom or —CR¹³;

Y represents a nitrogen atom or —CR¹⁴;

Z represents —NH or —CH₂ in the formula (3B), and a nitrogen atom or —CH in the formula (3C);

W represents an oxygen atom or —CH₂;

$R^{12}$ represents a hydrogen atom or a $C_{1-6}$ alkyl group;

$R^{13}$ represents a hydrogen atom, a fluorine atom or a cyano group; and $R^{14}$ represents a hydrogen atom, a $C_{1-6}$ alkyl group, a hydroxy $C_{1-6}$ alkyl group, a $C_{1-6}$ alkylamino $C_{1-6}$ alkyl group or a phenyl group.

[A7] A compound according to any one of [A1] to [A3], or a pharmacologically acceptable salt thereof, wherein the ring $Q^2$ represents any one of the following formulae (4A) to (4D):

[Formula 12]

(4A)
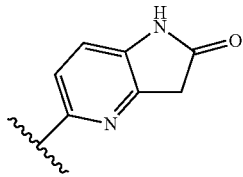

(4B)
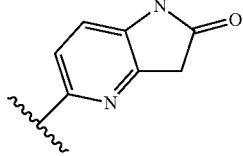

(4C)
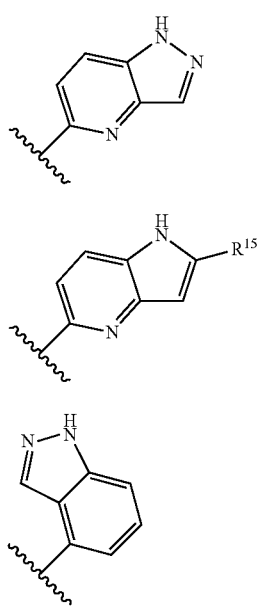

-continued (4D)

wherein $R^{15}$ represents a hydrogen atom, a methyl group, a hydroxymethyl group or a methylaminomethyl group.

[A8] A compound according to any one of [A1] to [A7], or a pharmacologically acceptable salt thereof, wherein $R^1$ and $R^2$ each independently represent a methyl group.

[A9] A compound according to any one of [A1] to [A7], or a pharmacologically acceptable salt thereof, wherein $R^1$ and $R^2$ form, together with a carbon atom to which $R^1$ and $R^2$ are bonded, a cyclobutane ring, a 3,3-dihalocyclobutane ring, a 3,3-di-$C_{1-6}$ alkyl cyclobutane ring, a cyclopentane ring, a cyclohexane ring, a 4,4-dihalocyclohexane ring, a tetrahydropyran ring, a cycloheptane ring or a spiro[3.3]heptane ring.

[A10] A compound according to any one of [A1] to [A7], or a pharmacologically acceptable salt thereof, wherein $R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring.

[A11] A compound according to any one of [A1] to [A10], or a pharmacologically acceptable salt thereof, wherein $R^3$ is a methyl group, and $R^4$ is a hydroxymethyl group or a 1-hydroxyethyl group.

[A12] A compound according to any one of [A1] to [A10], or a pharmacologically acceptable salt thereof, wherein $R^3$ and $R^4$ represent, together with a nitrogen atom to which $R^3$ is bonded and a carbon atom to which $R^4$ is bonded, any one of the following formulae (5A) to (5D):

[Formula 13]

(5A)
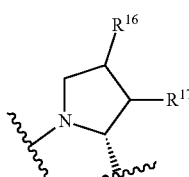

(5B)
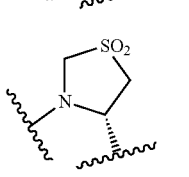

(5C)
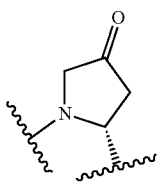

-continued (5D)

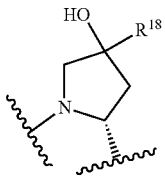

wherein $R^{16}$ represents a hydrogen atom, a halogen atom, a hydroxy group, a $C_{1-6}$ alkoxy group or a di-$C_{1-6}$ alkylamino group;

$R^{17}$ represents a hydrogen atom or a hydroxy group; and $R^{18}$ represents a $C_{1-6}$ alkyl group or a $C_{2-6}$ alkynyl group.

[A13] A compound according to any one of [A1] to [A10], or a pharmacologically acceptable salt thereof, wherein $R^3$ and $R^4$ represent, together with a nitrogen atom to which $R^3$ is bonded and a carbon atom to which $R^4$ is bonded, any one of the following formulae (6A) to (6C):

[Formula 14]

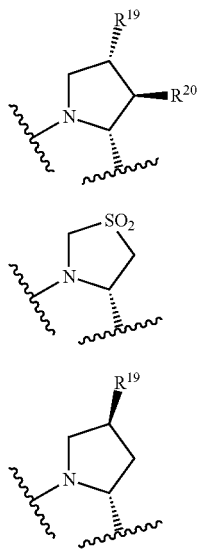

(6A)

(6B)

(6C)

wherein $R^{19}$ represents a hydrogen atom, a fluorine atom or a hydroxy group; and $R^{20}$ represents a hydrogen atom or a hydroxy group.

[A14] A compound according to any one of [A1] to [A10], or a pharmacologically acceptable salt thereof, wherein $R^3$ and $R^4$ represent, together with a nitrogen atom to which $R^3$ is bonded and a carbon atom to which $R^4$ is bonded, the following formula (6A-2):

[Formula 15]

(6A-2)

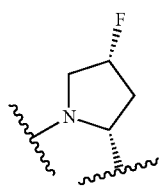

[A15] A compound according to [A1], or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group;

the ring $Q^2$ represents any one of the following formulae (4A) to (4D):

[Formula 16]

(4A)

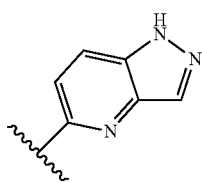

(4B)

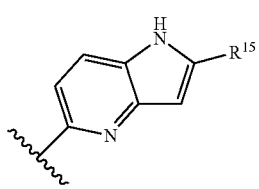

(4C)

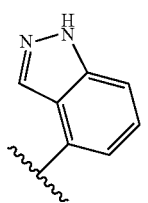

(4D)

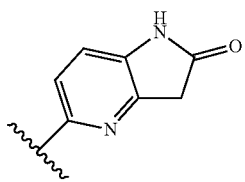

wherein $R^{15}$ represents a hydrogen atom, a methyl group, a hydroxymethyl group or a methylaminomethyl group;

$R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring; and $R^3$ and $R^4$ represent, together with a nitrogen atom to which $R^3$ is bonded and a carbon atom to which $R^4$ is bonded, any one of the following formulae (6A) to (6C):

[Formula 17]

(6A)

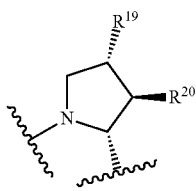

-continued

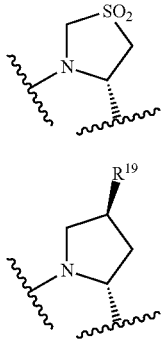

(6B)

(6C)

wherein R[19] represents a hydrogen atom, a fluorine atom or a hydroxy group; and
R[20] represents a hydrogen atom or a hydroxy group.

[A16] Any one compound selected from the following group, or a pharmacologically acceptable salt thereof:

(4R)-4-fluoro-1-{[1-(4-methoxyphenyl)cyclohexyl]carbonyl}-N-1H-pyrazolo[4,3-b]pyridin-5-yl-D-prolineamide, (4R)-4-fluoro-1-{[1-(3-fluoro-4-methoxyphenyl)cyclohexyl]carbonyl}-N-1H-pyrazolo[4,3-b]pyridin-5-yl-D-prolineamide, (4R)-4-fluoro-1-{[4-(4-methoxyphenyl)tetrahydro-2H-pyran-4-yl]carbonyl}-N-1H-pyrazolo[4,3-b]pyridin-5-yl-D-prolineamide, (4R)-4-fluoro-1-[2-(4-methoxyphenyl)-2-methylpropanoyl]-N-1H-pyrazolo[4,3-b]pyridin-5-yl-D-prolineamide, (4R)-4-fluoro-1-({1-[4-(fluoromethoxy)phenyl]cyclopentyl}carbonyl)-N-1H-pyrazolo[4,3-b]pyridin-5-yl-D-prolineamide, (4R)-4-fluoro-1-{[1-(6-methoxypyridin-3-yl)cyclohexyl]carbonyl}-N-1H-pyrazolo[4,3-b]pyridin-5-yl-D-prolineamide, (4R)-1-{[4,4-difluoro-1-(4-methoxyphenyl)cyclohexyl]carbonyl}-4-fluoro-N-1H-pyrazolo[4,3-b]pyridin-5-yl-D-prolineamide, (4R)-4-fluoro-N-1H-pyrazolo[4,3-b]pyridin-5-yl-1-({1-[4-(trifluoroacetyl)phenyl]cyclohexyl}carbonyl)-D-prolineamide, (4R)-4-fluoro-1-{[1-(4-methoxyphenyl)cyclohexyl]carbonyl}-N-1H-pyrrolo[3,2-b]pyridin-5-yl-D-prolineamide, (4R)-4-fluoro-1-{[1-(4-methoxyphenyl)cyclohexyl]carbonyl}-N-(2-oxo-2,3-dihydro-1H-pyrrolo[3,2-b]pyridin-5-yl)-D-prolineamide, 4,4-difluoro-N-[(2R)-3-hydroxy-1-oxo-1-(1H-pyrazolo[4,3-b]pyridin-5-ylamino)propan-2-yl]-1-(4-methoxyphenyl)-N-methylcyclohexanecarboxamide, (4R)-1-{[4,4-difluoro-1-(4-methoxyphenyl)cyclohexyl]carbonyl}-4-fluoro-N-(2-oxo-2,3-dihydro-1H-pyrrolo[3,2-b]pyridin-5-yl)-D-prolineamide, 4,4-difluoro-N-[(2R)-3-hydroxy-1-oxo-1-(1H-pyrrolo[3,2-b]pyridin-5-ylamino)propan-2-yl]-1-(4-methoxyphenyl)-N—($^2$H$_3$)methylcyclohexanecarboxamide, (4R)-4-fluoro-1-{2-methyl-2-[4-(trifluoromethoxy)phenyl]propanoyl}-N-1H-pyrazolo[4,3-b]pyridin-5-yl-D-prolineamide, 4,4-difluoro-N-[(2R,3S)-3-hydroxy-1-oxo-1-(1H-pyrazolo[4,3-b]pyridin-5-ylamino)butan-2-yl]-1-(4-methoxyphenyl)-N-methylcyclohexanecarboxamide, (4R)-4-fluoro-1-({1-[4-(2-hydroxypropan-2-yl)phenyl]cyclohexyl}carbonyl)-N-1H-pyrazolo[4,3-b]pyridin-5-yl-D-prolineamide, (4R)-1-{[1-(4-acetylphenyl)cyclohexyl]carbonyl}-4-fluoro-N-1H-pyrazolo[4,3-b]pyridin-5-yl-D-prolineamide, (4R)-1-({1-[4-(difluoromethoxy)phenyl]-4,4-difluorocyclohexyl}carbonyl)-4-fluoro-N-1H-pyrazolo[4,3-b]pyridin-5-yl-D-prolineamide, (4R)-1-({4,4-difluoro-1-[3-fluoro-4-(fluoromethoxy)phenyl]cyclohexyl}carbonyl)-4-fluoro-N-1H-pyrazolo[4,3-b]pyridin-5-yl-D-prolineamide, (4R)-1-({3,3-difluoro-1-[3-fluoro-4-(2,2,2-trifluoroethoxy)phenyl]cyclobutyl}carbonyl)-4-fluoro-N-1H-pyrazolo[4,3-b]pyridin-5-yl-D-prolineamide, (4R)-1-[(4,4-difluoro-1-{3-fluoro-4-[($^2$H$_3$)methyloxy]phenyl}cyclohexyl)carbonyl]-4-fluoro-N-1H-pyrazolo[4,3-b]pyridin-5-yl-D-prolineamide, (4R)-1-[(4,4-difluoro-1-{4-[($^2$H$_3$)methyloxy]phenyl}cyclohexyl)carbonyl]-4-fluoro-N-1H-pyrazolo[4,3-b]pyridin-5-yl-D-prolineamide, (4R)-1-({4,4-difluoro-1-[4-(fluoromethoxy)phenyl]cyclohexyl}carbonyl)-4-fluoro-N-1H-pyrazolo[4,3-b]pyridin-5-yl-D-prolineamide, (4R)-1-{[4,4-difluoro-1-(4-methoxyphenyl)cyclohexyl]carbonyl}-4-fluoro-N-(2-methyl-1H-pyrrolo[3,2-b]pyridin-5-yl)-D-prolineamide, (4R)-1-({1-[4-(difluoromethoxy)phenyl]-3,3-difluorocyclobutyl}carbonyl)-4-fluoro-N-1H-pyrazolo[4,3-b]pyridin-5-yl-D-prolineamide, (3S,4S)-1-({1-[4-(difluoromethoxy)phenyl]-4,4-difluorocyclohexyl}carbonyl)-4-fluoro-3-hydroxy-N-1H-pyrazolo[4,3-b]pyridin-5-yl-D-prolineamide, (4R)-1-({1-[4-(difluoromethoxy)phenyl]-4,4-difluorocyclohexyl}carbonyl)-4-fluoro-N-[2-(hydroxymethyl)-1H-pyrrolo[3,2-b]pyridin-5-yl]-D-prolineamide, (4R)-4-fluoro-1-{[1-(4-methoxyphenyl)cyclohexyl]carbonyl}-N-1H-pyrrolo[2,3-b]pyridin-6-yl-D-prolineamide, and (4S)-3-{[4,4-difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide.

[A17] (4R)-4-Fluoro-1-{[1-(4-methoxyphenyl)cyclohexyl]carbonyl}-N-1H-pyrazolo[4,3-b]pyridin-5-yl-D-prolineamide, or a pharmacologically acceptable salt thereof.

[A18] (4R)-4-Fluoro-1-{[1-(3-fluoro-4-methoxyphenyl)cyclohexyl]carbonyl}-N-1H-pyrazolo[4,3-b]pyridin-5-yl-D-prolineamide, or a pharmacologically acceptable salt thereof.

[A19] (4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolineamide, or a pharmacologically acceptable salt thereof.

[A20] A hydrochloride of a compound according to any one of [A17] to [A19].

[A21] (4R)-1-{[4,4-Difluoro-1-(4-methoxyphenyl)cyclohexyl]carbonyl}-4-fluoro-N-1H-pyrazolo[4,3-b]pyridin-5-yl-D-prolineamide, or a pharmacologically acceptable salt thereof.

[A22] A hydrochloride, a hydrobromide, a nitrate, a sulfate, a methanesulfonate, an ethanesulfonate, a benzenesulfonate, a p-toluenesulfonate, a 1,2-ethanedisulfonate or a 1,5-naphthalenedisulfonate of the compound according to [A21].

[A23] A hydrochloride of the compound according to [A21].

[A24] A compound according to [A17], having a crystal form exhibiting characteristic peaks at diffraction angles 2θ of 7.08, 10.86, 12.46, 12.74, 16.56, 19.18, 19.50, 20.22, 21.20 and 21.88 in a powder X-ray diffraction diagram obtained through irradiation with copper Kα line (λ=1.54 angstroms).

[A25] A hydrochloride of the compound according to [A17], having a crystal form exhibiting characteristic peaks at diffraction angles 2θ of 9.54, 12.66, 14.32, 16.60, 17.50, 19.34, 20.88, 22.56, 24.44 and 25.54 in a powder X-ray diffraction diagram obtained through irradiation with copper Kα line (λ=1.54 angstroms).

[A26] A hydrochloride of the compound according to [A18], having a crystal form exhibiting characteristic peaks at diffraction angles 2θ of 9.48, 12.66, 14.26, 16.14, 16.58, 17.52, 19.10, 20.86, 22.56 and 24.42 in a powder X-ray diffraction diagram obtained through irradiation with copper Kα line (λ=1.54 angstroms).

[A27] A compound according to [A19], having a crystal form exhibiting characteristic peaks at diffraction angles 2θ of 10.34, 15.60, 16.48, 16.74, 17.16, 18.04, 19.12, 20.30, 21.30 and 22.38 in a powder X-ray diffraction diagram obtained through irradiation with copper Kα line (λ=1.54 angstroms).

[A28] A hydrochloride of the compound according to [A19], having a crystal form exhibiting characteristic peaks at diffraction angles 2θ of 9.40, 16.32, 17.40, 17.88, 19.10, 20.60, 22.34, 24.18, 25.16 and 25.92 in a powder X-ray diffraction diagram obtained through irradiation with copper Kα line (λ=1.54 angstroms).

[A29] A compound according to [A21], having a crystal form exhibiting characteristic peaks at diffraction angles 2θ of 10.48, 11.72, 16.50, 17.06, 18.34, 19.38, 20.52, 21.12, 22.70 and 23.64 in a powder X-ray diffraction diagram obtained through irradiation with copper Kα line (λ=1.54 angstroms).

[A30] A compound according to [A21], having a crystal form exhibiting characteristic peaks at diffraction angles 2θ of 10.48, 11.74, 17.20, 17.66, 18.62, 19.10, 21.28, 22.50, 23.30 and 23.74 in a powder X-ray diffraction diagram obtained through irradiation with copper Kα line (λ=1.54 angstroms).

[A31] A hydrochloride of the compound according to [A23], having a crystal form exhibiting characteristic peaks at diffraction angles 2θ of 9.36, 9.54, 12.56, 16.58, 17.48, 19.28, 20.74, 22.42, 24.40 and 25.96 in a powder X-ray diffraction diagram obtained through irradiation with copper Kα line (λ=1.54 angstroms).

[A32] A hydrobromide of the compound according to [A22], having a crystal form exhibiting characteristic peaks at diffraction angles 2θ of 14.22, 16.22, 16.54, 17.42, 18.06, 19.20, 20.60, 22.28, 24.30 and 25.78 in a powder X-ray diffraction diagram obtained through irradiation with copper Kα line (λ=1.54 angstroms).

[A33] A nitrate of the compound according to [A22], having a crystal form exhibiting characteristic peaks at diffraction angles 2θ of 8.96, 9.50, 12.30, 16.36, 17.34, 17.76, 19.12, 20.42, 22.14 and 24.24 in a powder X-ray diffraction diagram obtained through irradiation with copper Kα line (λ=1.54 angstroms).

[A34] A nitrate of the compound according to [A22], having a crystal form exhibiting characteristic peaks at diffraction angles 2θ of 8.62, 13.88, 16.20, 16.70, 17.50, 18.52, 19.08, 19.48, 22.78 and 24.58 in a powder X-ray diffraction diagram obtained through irradiation with copper Kα line (λ=1.54 angstroms).

[A35] A sulfate of the compound according to [A22], having a crystal form exhibiting characteristic peaks at diffraction angles 2θ of 8.56, 10.56, 13.74, 16.60, 17.28, 18.28, 18.82, 20.66, 23.60 and 24.14 in a powder X-ray diffraction diagram obtained through irradiation with copper Kα line (λ=1.54 angstroms).

[A36] A methanesulfonate of the compound according to [A22], having a crystal form exhibiting characteristic peaks at diffraction angles 2θ of 9.52, 13.70, 16.42, 17.10, 18.30, 19.16, 20.14, 21.54, 21.92 and 22.20 in a powder X-ray diffraction diagram obtained through irradiation with copper Kα line (λ=1.54 angstroms).

[A37] An ethanesulfonate of the compound according to [A22], having a crystal form exhibiting characteristic peaks at diffraction angles 2θ of 13.42, 16.36, 16.98, 17.22, 18.96, 19.82, 20.94, 21.62, 22.56 and 24.68 in a powder X-ray diffraction diagram obtained through irradiation with copper Kα line (λ=1.54 angstroms).

[A38] A benzenesulfonate of the compound according to [A22], having a crystal form exhibiting characteristic peaks at diffraction angles 2θ of 5.48, 9.44, 12.92, 17.02, 17.30, 20.04, 22.20, 22.76, 23.38 and 25.00 in a powder X-ray diffraction diagram obtained through irradiation with copper Kα line (λ=1.54 angstroms).

[A39] A p-toluenesulfonate of the compound according to [A22], having a crystal form exhibiting characteristic peaks at diffraction angles 2θ of 5.24, 8.34, 8.76, 13.46, 17.82, 19.14, 21.22, 23.80, 25.38 and 26.62 in a powder X-ray diffraction diagram obtained through irradiation with copper Kα line (λ=1.54 angstroms).

[A40] A 1,2-ethanedisulfonate of the compound according to [A22], having a crystal form exhibiting characteristic peaks at diffraction angles 2θ of 8.46, 8.76, 13.06, 16.58, 17.30, 18.28, 19.34, 21.26, 21.76 and 24.54 in a powder X-ray diffraction diagram obtained through irradiation with copper Kα line (λ=1.54 angstroms).

[A41] A 1,5-naphthalenedisulfonate of the compound according to [A22], having a crystal form exhibiting characteristic peaks at diffraction angles 2θ of 5.64, 9.00, 10.78, 16.56, 17.10, 19.58, 21.59, 22.22, 22.42 and 22.60 in a powder X-ray diffraction diagram obtained through irradiation with copper Kα line (λ=1.54 angstroms).

[A42] A 1,5-naphthalenedisulfonate of the compound according to [A22], having a crystal form exhibiting characteristic peaks at diffraction angles 2θ of 4.02, 9.20, 12.14, 12.96, 16.28, 18.34, 18.52, 20.38, 23.74 and 25.88 in a powder X-ray diffraction diagram obtained through irradiation with copper Kα line (λ=1.54 angstroms).

[A43] A pharmaceutical composition comprising, as an active ingredient, a compound according to any one of [A1] to [A42], or a pharmacologically acceptable salt thereof.

[A44] An EP300 and/or CREBBP inhibitor comprising, as an active ingredient, a compound according to any one of [A1] to [A42], or a pharmacologically acceptable salt thereof.

[A45] An antitumor agent comprising, as an active ingredient, a compound according to any one of [A1] to [A42], or a pharmacologically acceptable salt thereof.

[A46] An antitumor agent according to [A45], wherein a tumor is prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma or ovarian cancer.

[A47] A treatment method for a tumor comprising administering a compound according to any one of [A1] to [A42], or a pharmacologically acceptable salt thereof.

[A48] A treatment method according to [A47], wherein the tumor is prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma or ovarian cancer.

[A49] A compound according to any one of [A1] to [A42], or a pharmacologically acceptable salt thereof for treatment of a tumor.

[A50] A compound according to [A49], or a pharmacologically acceptable salt thereof, wherein the tumor is prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma or ovarian cancer.

Advantageous Effects of Invention

A compound according to the present invention or a pharmacologically acceptable salt thereof exhibits excellent EP300 and/or CREBBP inhibitory activity. Specifically, administration of a pharmaceutical composition containing a compound of the present invention or a pharmacologically acceptable salt thereof to a mammal (such as a human, a bovine, a horse or a pig) or a bird (such as a chicken) can be employed for treatment of a cancer dependent on EP300 and/or CREBBP. Accordingly, a compound of the present invention or a pharmacologically acceptable salt thereof can be used as an active ingredient of an antitumor agent. Examples of a tumor include prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma and ovarian cancer.

DESCRIPTION OF EMBODIMENT

Figure 1:
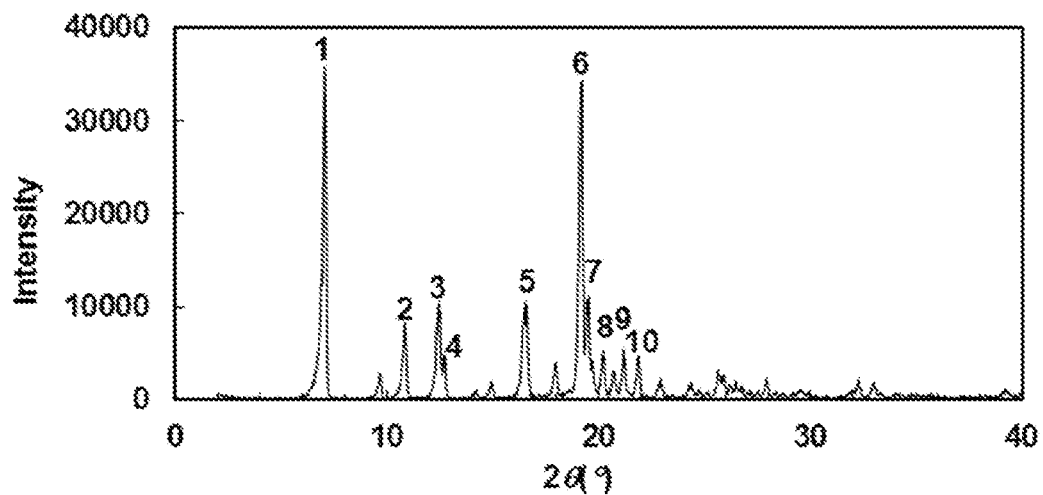
FIG. 1 is a powder X-ray diffraction diagram of a crystal obtained in Step 2 of Example 35. The ordinate indicates diffraction intensity (Intensity) in counts/sec (cps), and the abscissa indicates a value of the diffraction angle 2θ.

In the present invention, the term "halogen atom" refers to a fluorine atom, a chlorine atom, a bromine atom or an iodine atom, and is preferably a fluorine atom.

In the present invention, the term "$C_{1-6}$ alkyl group" refers to a linear or branched alkyl group having 1 to 6 carbon atoms. Examples include a methyl group, an ethyl group, a n-propyl group, an isopropyl group, a n-butyl group, a sec-butyl group, a tert-butyl group, a n-pentyl group, an isopentyl group, a 2-methylbutyl group, a neopentyl group, a 1-ethylpropyl group, a n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and a 2-ethylbutyl group.

In the present invention, the term "$C_{1-6}$ alkoxy group" refers to a group in which a "$C_{1-6}$ alkyl group" is bonded to an oxygen atom. Examples include a methoxy group, an ethoxy group, a n-propoxy group, an isopropoxy group, a n-butoxy group, a sec-butoxy group, a tert-butoxy group, a n-pentoxy group, an isopentoxy group, a 2-methylbutoxy group and a n-hexyloxy group.

In the present invention, the terms "$C_{3-7}$ cycloalkyl group" and "3-membered to 7-membered cycloalkyl ring" refer to a 3-membered to 7-membered monocyclic or spirocyclic saturated hydrocarbon group (ring). Examples include a cyclopropyl group, a cyclobutyl group, a cyclopentyl group, a cyclohexyl group, a cycloheptyl group and a spiro [3.3] heptyl group.

In the present invention, the term "hydroxy $C_{1-6}$ alkyl group" refers to a group in which one or two hydrogen atoms of a "$C_{1-6}$ alkyl group" are substituted by a hydroxy group. Examples include a hydroxymethyl group, a 1-hydroxyethyl group, a 2-hydroxyethyl group, a 1-hydroxypropyl group, a 2-hydroxypropyl group, a 1-hydroxyisopropyl group, a 1-hydroxybutyl group, a 2-hydroxybutyl group, a 1-hydroxypentyl group, a 2-hydroxypentyl group, 1-hydroxyhexyl and a 1,2-dihydroxyethyl group.

In the present invention, the term "hydroxy $C_{2-6}$ alkyl group" refers to a group in which one or two hydrogen atoms of a linear or branched alkyl group having 2 to 6 carbon atoms are substituted by a hydroxy group. Examples include a 1-hydroxyethyl group, a 2-hydroxyethyl group, a 1-hydroxypropyl group, a 2-hydroxypropyl group, a 1-hydroxyisopropyl group, a 1-hydroxybutyl group, a 2-hydroxybutyl group, a 1-hydroxypentyl group, a 2-hydroxypentyl group, a 1-hydroxyhexyl group and a 2,3-dihydroxypropyl group.

In the present invention, the term "halo $C_{1-6}$ alkyl group" refers to a group in which one to three hydrogen atoms of a "$C_{1-6}$ alkyl group" are substituted by a "halogen atom". Examples include a fluoromethyl group, a difluoromethyl group, a trifluoromethyl group, a chloromethyl group, a dichloromethyl group, a trichloromethyl group, a 1-fluoroethyl group, a 1-chloroethyl group, a 2-fluoroethyl group, a 1,2-difluoropropyl group and a 2,2,2-trifluoroethyl group.

In the present invention, the term "halo $C_{1-6}$ alkoxy group" refers to a group in which one to three hydrogen atoms of a "$C_{1-6}$ alkoxy group" are substituted by a "halogen atom". Examples include a fluoromethoxy group, a difluoromethoxy group, a trifluoromethoxy group, a chloromethoxy group, a dichloromethoxy group, a trichloromethoxy group, a 1-fluoroethoxy group, a 1-chloroethoxy group, a 2-fluoroethoxy group, a 1,2-difluoropropoxy group and a 2,2,2-trifluoroethoxy group.

In the present invention, the term "$C_{1-6}$ alkoxycarbonyl group" refers to a group in which a "$C_{1-6}$ alkoxy group" is bonded to the carbon atom of a carbonyl group. Examples include a methoxycarbonyl group, an ethoxycarbonyl group, a n-propoxycarbonyl group, an isopropoxycarbonyl group, a n-butoxycarbonyl group, a sec-butoxycarbonyl group and a tert-butoxycarbonyl group.

In the present invention, the term "$C_{2-7}$ alkanoyl group" refers to a group in which a "$C_{1-6}$ alkyl group" is bonded to the carbon atom of a carbonyl group. Examples include an acetyl group, a propionyl group, a butyryl group, an isobutyryl group, a pivaloyl group, a valeryl group, an isovaleryl group, a hexanoyl group and a heptanoyl group.

In the present invention, the term "halo $C_{2-7}$ alkanoyl group" refers to a group in which one to three hydrogen atoms of a "$C_{2-7}$ alkanoyl group" are substituted by a "halogen atom". Examples include a fluoroacetyl group, a trifluoroacetyl group, a chloroacetyl group, a trichloroacetyl group, a fluoropropionyl group and a fluorobutyryl group.

In the present invention, the term "$C_{2-7}$ alkanoylamino group" refers to a group in which a "$C_{2-7}$ alkanoyl group" is bonded to an amino group. Examples include an acetylamino group, a propionylamino group, a butyrylamino group, an isobutyrylamino group and a pentanoylamino group.

In the present invention, the term "$C_{1-6}$ alkylsulfonyl group" refers to a group in which a "$C_{1-6}$ alkyl group" is bonded to the sulfur atom of a sulfonyl group. Examples include a methylsulfonyl group, an ethylsulfonyl group, a n-propylsulfonyl group, an isopropylsulfonyl group, a n-butylsulfonyl group, a sec-butylsulfonyl group, a tert-butylsulfonyl group and a n-pentylsulfonyl group.

In the present invention, the term "$C_{1-6}$ alkylsulfonylamino group" refers to a group in which a "$C_{1-6}$ alkylsulfonyl group" is bonded to an amino group. Examples include a methylsulfonylamino group, an ethylsulfonylamino group, a n-propylsulfonylamino group, an isopropylsulfonylamino group, a n-butylsulfonylamino group, a sec-butylsulfonylamino group, a tert-butylsulfonylamino group and a n-pentylsulfonylamino group.

In the present invention, the term "$C_{3-7}$ cycloalkylsulfonylamino group" refers to a group in which a "$C_{3-7}$ cycloalkyl group" is bonded to a sulfonylamino group. Examples include a cyclopropylsulfonylamino group, a cyclobutylsulfonylamino group, a cyclopentylsulfonylamino group, a cyclohexylsulfonylamino group and a cycloheptylsulfonylamino group.

In the present invention, the term "$C_{1-6}$ alkylcarbamoyl group" refers to a group in which one hydrogen atom of a carbamoyl group is substituted by a "$C_{1-6}$ alkyl group". Examples include a methylcarbamoyl group, an ethylcarbamoyl group, a n-propylcarbamoyl group, an isopropylcarbamoyl group, a n-butylcarbamoyl group, a sec-butylcarbamoyl group, a tert-butylcarbamoyl group and a n-pentylcarbamoyl group.

In the present invention, the term "di-$C_{1-6}$ alkylcarbamoyl group" refers to a group in which two hydrogen atoms of a carbamoyl group are respectively substituted by a "$C_{1-6}$ alkyl group". Examples include a dimethylcarbamoyl group, a methylethylcarbamoyl group, a methylpropylcarbamoyl group, a diethylcarbamoyl group, a dipropylcarbamoyl group and diisopropylcarbamoyl group.

In the present invention, the term "$C_{3-7}$ cycloalkylsulfonylcarbamoyl group" refers to a group in which a "$C_{3-7}$ cycloalkylsulfonyl group" is bonded to a carbamoyl group. Examples include a cyclopropylsulfonylcarbamoyl group, a cyclobutylsulfonylcarbamoyl group, a cyclopentylsulfonylcarbamoyl group, a cyclohexylsulfonylcarbamoyl group and a cycloheptylsulfonylcarbamoyl group.

In the present invention, the term "halo $C_{1-6}$ alkylsulfonyloxy group" refers to a group in which a "halo $C_{1-6}$ alkyl group" is bonded to the sulfur atom of a sulfonyloxy group. Examples include a fluoromethylsulfonyloxy group, a difluoromethylsulfonyloxy group, a trifluoromethylsulfonyloxy group, a chloromethylsulfonyloxy group, a 1-fluoroethylsulfonyloxy group and a 2-fluoroethylsulfonyloxy group.

In the present invention, the term "$C_{1-6}$ alkylamino group" refers to a group in which one hydrogen atom of an amino group is substituted by a "$C_{1-6}$ alkyl group". Examples include a methylamino group, an ethylamino group, a n-propylamino group, an isopropylamino group, a n-butylamino group, a sec-butylamino group, a tert-butylamino group and n-pentylamino group.

In the present invention, the term "$C_{1-6}$ alkylamino $C_{1-6}$ alkyl group" refers to a group in which one hydrogen atom of a "$C_{1-6}$ alkyl group" is substituted by a "$C_{1-6}$ alkylamino group". Examples include a methylaminomethyl group, a methylaminoethyl group, an ethylaminomethyl group, a n-propylaminomethyl group, an isopropylaminomethyl group, a n-butylaminomethyl group, a sec-butylaminomethyl group, a tert-butylaminomethyl group, a tert-butylaminoethyl group and a n-pentylaminomethyl group.

In the present invention, the term "morpholinyl $C_{1-6}$ alkyl group" refers to a group in which one hydrogen atom of a "$C_{1-6}$ alkyl group" is substituted by a morpholinyl group. Examples include a morpholinylmethyl group, a 2-morpholinylethyl group, a 3-morpholinylpropyl group, a 4-morpholinylbutyl group, a 5-morpholinylpentyl group and a 6-morpholinylhexyl group.

In the present invention, the term "morpholinyl $C_{1-6}$ alkyloxy group" refers to a group in which a "morpholinyl $C_{1-6}$ alkyl group" is bonded to an oxygen atom. Examples include a morpholinylmethoxy group, a 2-morpholinylethoxy group, a 3-morpholinylpropoxy group, a 4-morpholinylbutoxy group, a 5-morpholinylpentoxy group and a 6-morpholinylhexoxy group.

In the present invention, the term "$C_{1-6}$ alkoxy $C_{1-6}$ alkyl group" refers to a group in which one hydrogen atom of a "$C_{1-6}$ alkyl group" is substituted by a "$C_{1-6}$ alkoxy group". Examples include a methoxymethyl group, an ethoxymethyl group, a n-propoxymethyl group, an isopropoxymethyl group, a methoxyethyl group, an ethoxyethyl group, a propoxyethyl group and an isopropoxyethyl group.

In the present invention, the term "$C_{1-6}$ alkoxy $C_{1-6}$ alkoxy group" refers to a group in which one hydrogen atom of a "$C_{1-6}$ alkoxy group" is substituted by a "$C_{1-6}$ alkoxy group". Examples include a methoxymethoxy group, an ethoxymethoxy group, a n-propoxymethoxy group, an isopropoxymethoxy group, a methoxyethoxy group, an ethoxyethoxy group, a n-propoxyethoxy group and an isopropoxyethoxy group.

In the present invention, the term "$C_{2-6}$ alkynyl group" refers to a linear or branched alkynyl group having 2 to 6 carbon atoms. Examples include an ethynyl group, a 1-propynyl group, a 2-propynyl group, a 1-butynyl group, a 2-butynyl group, a 3-butynyl group, a 1-ethynyl-2-propynyl group, a 1-methyl-2-propynyl group, a 1-pentynyl group, a 1-hexynyl group, a 1,3-hexadiynyl group and a 1,5-hexadiynyl group.

In the present invention, the term "di-$C_{1-6}$ alkylamino group" refers to a group in which each of two hydrogen atoms of an amino group is substituted by a "$C_{1-6}$ alkyl group". Examples include a dimethylamino group, a diethylamino group, a dipropylamino group, a diisopropylamino group, a dibutylamino group, a diisobutylamino group, a dipentylamino group, a dineopentylamino group, a dihexylamino group, a N-ethyl-N-methylamino group, a N-methyl-N-propylamino group, a N-isopropyl-N-methylamino group, a N-butyl-N-methylamino group, a N-isobutyl-N-methylamino group, a N-ethyl-N-propylamino group, a N-ethyl-N-isopropylamino group, a N-butyl-N-ethylamino group and a N-ethyl-N-isopentylamino group.

In the present invention, the term "$C_{1-6}$ alkylsulfonyl $C_{1-6}$ alkyl group" refers to a group in which one hydrogen atom of a "$C_{1-6}$ alkyl group" is substituted by a "$C_{1-6}$ alkylsulfonyl group". Examples include a methylsulfonylmethyl group, a methylsulfonylethyl group, an ethylsulfonylmethyl group, a n-propylsulfonylmethyl group, an isopropylsulfonylmethyl group, a n-butylsulfonylmethyl group, a sec-butylsulfonylmethyl group, a tert-butylsulfonylmethyl group, a tert-butylsulfonylethyl group and a n-pentylsulfonylmethyl group.

In the present invention, the term "5-membered or 6-membered aromatic heterocyclic group having 1 to 3 nitrogen atoms in a ring" refers to a group derived from a 5-membered or 6-membered monocyclic aromatic compound having, in addition to a carbon atom, 1 to 3 nitrogen atoms as constituent atoms of a ring. Examples include a pyridinyl group, a pyrimidinyl group, a pyridazinyl group, a pyrazinyl group, a triazinyl group, a pyrrolyl group, a pyrazolyl group, an imidazolyl group and an oxopyridinyl group. The "5-membered or 6-membered aromatic heterocyclic group having 1 to 3 nitrogen atoms in a ring" of ring $Q^1$ is preferably a pyridinyl group, a pyrimidinyl group or an oxopyridinyl group. The "5-membered or 6-membered aromatic heterocyclic group having 1 to 3 nitrogen atoms in a ring" of ring $Q^2$ is preferably a pyridinyl group, a pyrimidinyl group or pyrazolyl group.

In the present invention, the term "8-membered to 10-membered bicyclic aromatic heterocyclic group optionally having, in a ring, 1 to 4 hetero atoms independently selected from the group consisting of a nitrogen atom, an oxygen atom and a sulfur atom" refers to a group derived from a 8-membered to 10-membered condensed aromatic compound having, in addition to a carbon atom, 1 to 4 hetero atoms (a nitrogen atom, an oxygen atom or a sulfur atom) as constituent atoms of a ring, and optionally has a saturated bond in a part of the bicyclic ring. Examples include a pyrrolopyrazolyl group, an indazolyl group, a quinolyl group, a benzimidazolyl group, a pyrrolopyridinyl group, a 2-oxo-2,3-dihydro-1H-pyrrolopyridinyl group, a 2-oxo-2,3-dihydro-1H-benzimidazolyl group, a pyrazolopyridinyl group, a 3-oxo-3,4-dihydro-2H-pyrido[1,4]oxadinyl group, a 2-oxo-1,2,3,4-tetrahydroquinolinyl group, an isoindolinyl group, an indolinyl group, an indolizinyl group, a purinyl group, a quinolizinyl group, an isoquinolizinyl group, a naphthyridinyl group, a phthaladinyl group, a quinoxalinyl group, a quinazolinyl group and a pteridinyl group. The "8-membered to 10-membered bicyclic aromatic heterocyclic group optionally having, in a ring, 1 to 4 hetero atoms independently selected from the group consisting of a nitrogen atom, an oxygen atom and a sulfur atom" of the ring $Q^2$ is preferably a pyrazolopyridinyl group, a pyrrolopyridinyl group, an indazolyl group or a 2-oxo-2,3-dihydro-1H-pyrrolopyridinyl group.

In the present invention, tumor, malignant tumor, cancer, malignant neoplasm, carcinoma, sarcoma and the like are generically designated as "tumor" or "cancer".

In the present invention, the term "inhibition of EP300" means inhibition of histone acetyltransferase activity of EP300.

In the present invention, the term "inhibition of CREBBP" means inhibition of histone acetyltransferase activity of CREBBP.

In the present invention, the term "histone acetyltransferase activity of EP300 and/or CREBBP" means enzyme activity of EP300 and/or CREBBP to acetylate the 27th lysine of histone H3.

Suitable substituents in a compound of the present invention will now be described.

The ring $Q^1$ is preferably any one of the following (2A) to (2D):

[Formula 18]

(2A)

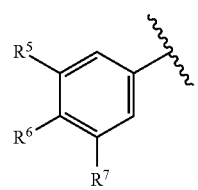

-continued (2B)
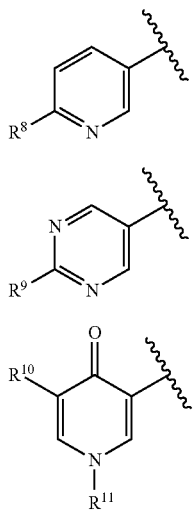

(2C)

(2D)

wherein R⁵, R⁶ and R⁷ each independently represent a hydrogen atom, a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group or a phenylsulfonylamino group;

R⁸, R⁹ and R¹¹ each independently represent a hydrogen atom or a $C_{1-6}$ alkoxy group; and R¹⁰ represents a hydrogen atom or a carboxy group.

The ring Q¹ is more preferably a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group, a m-fluoro-p-difluoromethoxyphenyl group, a m-methoxyphenyl group, a p-carboxyphenyl group, a p-methoxycarbonylphenyl group, a p-methylsulfonylphenyl group, a p-acetylaminophenyl group, a 3,3-difluoro-4-methoxyphenyl group, a 2-methoxy-5-pyrimidyl group, a 3-fluoro-4-phenylphenyl group, a 3-fluoro-4-(2,2,2-trifluoroethoxy)phenyl group or a 4-methylsulfonylaminophenyl group.

The ring Q¹ is further preferably a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group.

The ring Q² is preferably a phenyl group optionally having one or two substituents independently selected from the group consisting of a hydroxy group, a fluorine atom, a chlorine atom, a cyano group, a methyl group, a methoxy group and a benzyloxy group, or a pyridinyl group optionally having one or two substituents independently selected from the group consisting of an amino group and a methylamino group, and is more preferably a phenyl group optionally having one or two substituents independently selected from the group consisting of a hydroxy group, a fluorine atom, a chlorine atom, a cyano group, a methyl group, a methoxy group and a benzyloxy group. It is further preferred that the ring Q² is an o-cyanophenyl group, an o-chlorophenyl group, a m-chloro-p-hydroxyphenyl group, a m-methylphenyl group, an o-methoxyphenyl group, a p-benzyloxyphenyl group, a 2-cyano-4-[2-(morpholin-4-yl)ethoxy]phenyl group, a 6-amino-2-pyridinyl group or a 6-methylamino-2-pyridinyl group.

The ring Q² is preferably any one of the following (3A) to (3F):

[Formula 19]

(3A)
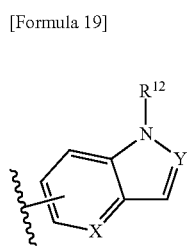

(3B)
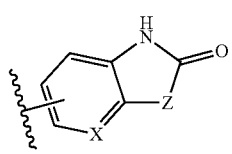

(3C)
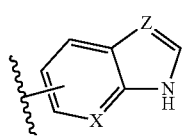

(3D)
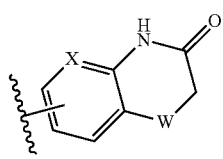

(3E)
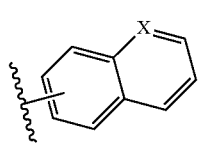

(3F)
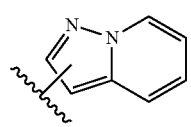

wherein X represents a nitrogen atom or —CR¹³;

Y represents a nitrogen atom or —CR¹⁴;

Z represents —NH or —CH₂ in the formula (3B), and represents a nitrogen atom or —CH in the formula (3C);

W represents an oxygen atom or —CH₂;

R¹² represents a hydrogen atom or a $C_{1-6}$ alkyl group;

R¹³ represents a hydrogen atom, a fluorine atom or a cyano group; and

R¹⁴ represents a hydrogen atom, a $C_{1-6}$ alkyl group, a hydroxy $C_{1-6}$ alkyl group, a $C_{1-6}$ alkylamino $C_{1-6}$ alkyl or a phenyl group.

The ring $Q^2$ is more preferably any one of the following (4A) to (4D):

[Formula 20]

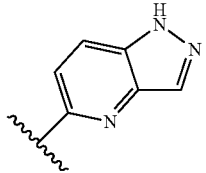
(4A)

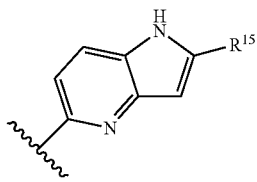
(4B)

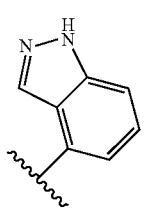
(4C)

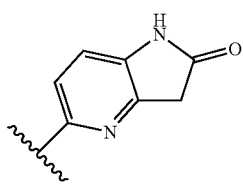
(4D)

wherein $R^{15}$ represents a hydrogen atom, a methyl group, a hydroxymethyl group or a methylaminomethyl group.

Each of $R^1$ and $R^2$ is preferably a methyl group.

$R^1$ and $R^2$ preferably form, together with the carbon atom to which $R^1$ and $R^2$ are bonded, a cyclobutane ring, a 3,3-dihalocyclobutane ring, a 3,3-di-$C_{1-6}$ alkyl cyclobutane ring, a cyclopentane ring, a cyclohexane ring, a 4,4-dihalocyclohexane ring, a tetrahydropyran ring, a cycloheptane ring or a spiro[3.3]heptane ring.

$R^1$ and $R^2$ more preferably form, together with the carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a tetrahydropyran ring.

$R^3$ is preferably a methyl group, an ethyl group or a hydroxyethyl group, and more preferably a methyl group.

$R^4$ is preferably a hydrogen atom, a methyl group, a hydroxymethyl group or a 1-hydroxyethyl group, more preferably a methyl group, a hydroxymethyl group or a 1-hydroxyethyl group. It is further preferred that $R^4$ is a hydroxymethyl group or a 1-hydroxyethyl group.

$R^3$ and $R^4$ preferably represent, together with the nitrogen atom to which $R^3$ is bonded and the carbon atom to which $R^4$ is bonded, any one of the following (5A) to (5D):

[Formula 21]

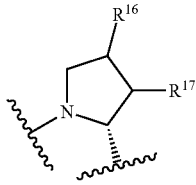
(5A)

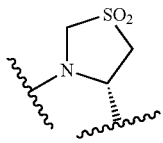
(5B)

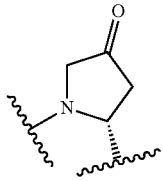
(5C)

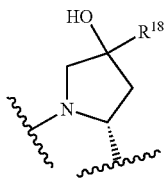
(5D)

wherein $R^{16}$ represents a hydrogen atom, a halogen atom, a hydroxy group, a $C_{1-6}$ alkoxy group or a $C_{1-6}$ alkylamino group, $R^{17}$ represents a hydrogen atom or a hydroxy group, and $R^{18}$ represents a $C_{1-6}$ alkyl group or a $C_{2-6}$ alkynyl group.

$R^3$ and $R^4$ more preferably represent, together with the nitrogen atom to which $R^3$ is bonded and the carbon atom to which $R^4$ is bonded, any one of the following (6A) to (6C):

[Formula 22]

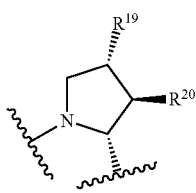
(6A)

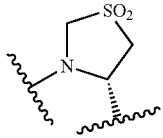
(6B)

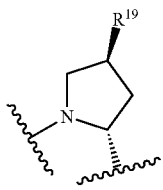
(6C)

wherein $R^{19}$ represents a hydrogen atom, a fluorine atom or a hydroxy group, and $R^{20}$ represents a hydrogen atom or a hydroxy group.

It is further preferred that $R^3$ and $R^4$ represent, together with the nitrogen atom to which $R^3$ is bonded and the carbon atom to which $R^4$ is bonded, any one of the following (6A-1) to (6C-2):

[Formula 23]

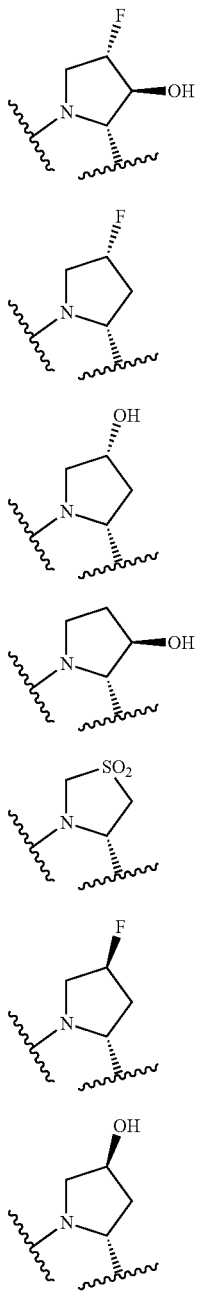

The compound of the present invention is preferably any one selected from the following compounds and pharmacologically acceptable salts thereof:

(4R)-4-fluoro-1-{[1-(4-methoxyphenyl)cyclohexyl]carbonyl}-N-1H-pyrazolo[4,3-b]pyridin-5-yl-D-prolineamide;

(4R)-4-fluoro-1-{[1-(3-fluoro-4-methoxyphenyl)cyclohexyl]carbonyl}-N-1H-pyrazolo[4,3-b]pyridin-5-yl-D-prolineamide;

(4R)-4-fluoro-1-{[4-(4-methoxyphenyl)tetrahydro-2H-pyran-4-yl]carbonyl}-N-1H-pyrazolo[4,3-b]pyridin-5-yl-D-prolineamide;

(4R)-4-fluoro-1-[2-(4-methoxyphenyl)-2-methylpropanoyl]-N-1H-pyrazolo[4,3-b]pyridin-5-yl-D-prolineamide;

(4R)-4-fluoro-1-({1-[4-(fluoromethoxy)phenyl]cyclopentyl}carbonyl)-N-1H-pyrazolo[4,3-b]pyridin-5-yl-D-prolineamide;

(4R)-4-fluoro-1-{[1-(6-methoxypyridin-3-yl)cyclohexyl]carbonyl}-N-1H-pyrazolo[4,3-b]pyridin-5-yl-D-prolineamide;

(4R)-1-{[4,4-difluoro-1-(4-methoxyphenyl)cyclohexyl]carbonyl}-4-fluoro-N-1H-pyrazolo[4,3-b]pyridin-5-yl-D-prolineamide;

(4R)-4-fluoro-N-1H-pyrazolo[4,3-b]pyridin-5-yl-1-({1-[4-(trifluoroacetyl)phenyl]cyclohexyl}carbonyl)-D-prolineamide;

(4R)-4-fluoro-1-{[1-(4-methoxyphenyl)cyclohexyl]carbonyl}-N-1H-pyrrolo[3,2-b]pyridin-5-yl-D-prolineamide;

(4R)-4-fluoro-1-{[1-(4-methoxyphenyl)cyclohexyl]carbonyl}-N-(2-oxo-2,3-dihydro-1H-pyrrolo[3,2-b]pyridin-5-yl)-D-prolineamide;

4,4-difluoro-N-[(2R)-3-hydroxy-1-oxo-1-(1H-pyrazolo[4,3-b]pyridin-5-ylamino)propan-2-yl]-1-(4-methoxyphenyl)-N-methylcyclohexanecarboxamide;

(4R)-1-{[4,4-difluoro-1-(4-methoxyphenyl)cyclohexyl]carbonyl}-4-fluoro-N-(2-oxo-2,3-dihydro-1H-pyrrolo[3,2-b]pyridin-5-yl)-D-prolineamide;

4,4-difluoro-N-[(2R)-3-hydroxy-1-oxo-1-(1H-pyrrolo[3,2-b]pyridin-5-ylamino)propan-2-yl]-1-(4-methoxyphenyl)-N—($^2H_3$)methylcyclohexanecarboxamide;

(4R)-4-fluoro-1-{2-methyl-2-[4-(trifluoromethoxy)phenyl]propanoyl}-N-1H-pyrazolo[4,3-b]pyridin-5-yl-D-prolineamide;

4,4-difluoro-N-[(2R,3S)-3-hydroxy-1-oxo-1-(1H-pyrazolo[4,3-b]pyridin-5-ylamino)butan-2-yl]-1-(4-methoxyphenyl)-N-methylcyclohexanecarboxamide;

(4R)-4-fluoro-1-({1-[4-(2-hydroxypropan-2-yl)phenyl]cyclohexyl}carbonyl)-N-1H-pyrazolo[4,3-b]pyridin-5-yl-D-prolineamide;

(4R)-1-{[1-(4-acetylphenyl)cyclohexyl]carbonyl}-4-fluoro-N-1H-pyrazolo[4,3-b]pyridin-5-yl-D-prolineamide;

(4R)-1-({1-[4-(difluoromethoxy)phenyl]-4,4-difluorocyclohexyl}carbonyl)-4-fluoro-N-1H-pyrazolo[4,3-b]pyridin-5-yl-D-prolineamide;

(4R)-1-({4,4-difluoro-1-[3-fluoro-4-(fluoromethoxy)phenyl]cyclohexyl}carbonyl)-4-fluoro-N-1H-pyrazolo[4,3-b]pyridin-5-yl-D-prolineamide;

(4R)-1-({3,3-difluoro-1-[3-fluoro-4-(2,2,2-trifluoroethoxy)phenyl]cyclobutyl}carbonyl)-4-fluoro-N-1H-pyrazolo[4,3-b]pyridin-5-yl-D-prolineamide;

(4R)-1-[(4,4-difluoro-1-{3-fluoro-4-[($^2H_3$)methyloxy]phenyl}cyclohexyl)carbonyl]-4-fluoro-N-1H-pyrazolo[4,3-b]pyridin-5-yl-D-prolineamide;

(4R)-1-[(4,4-difluoro-1-{4-[($H_3$)methyloxy]phenyl}cyclohexyl)carbonyl]-4-fluoro-N-1H-pyrazolo[4,3-b]pyridin-5-yl-D-prolineamide;

(4R)-1-({4,4-difluoro-1-[4-(fluoromethoxy)phenyl]cyclohexyl}carbonyl)-4-fluoro-N-1H-pyrazolo[4,3-b]pyridin-5-yl-D-prolineamide;

(4R)-1-{[4,4-difluoro-1-(4-methoxyphenyl)cyclohexyl]carbonyl}-4-fluoro-N-(2-methyl-1H-pyrrolo[3,2-b]pyridin-5-yl)-D-prolineamide;

(4R)-1-({1-[4-(difluoromethoxy)phenyl]-3,3-difluorocyclobutyl}carbonyl)-4-fluoro-N-1H-pyrazolo[4,3-b]pyridin-5-yl-D-prolineamide;

(3S,4S)-1-({1-[4-(difluoromethoxy)phenyl]-4,4-difluorocyclohexyl}carbonyl)-4-fluoro-3-hydroxy-N-1H-pyrazolo[4,3-b]pyridin-5-yl-D-prolineamide;

(4R)-1-({1-[4-(difluoromethoxy)phenyl]-4,4-difluorocyclohexyl}carbonyl)-4-fluoro-N-[2-(hydroxymethyl)-1H-pyrrolo[3,2-b]pyridin-5-yl]-D-prolineamide;

(4R)-4-fluoro-1-{[1-(4-methoxyphenyl)cyclohexyl]carbonyl}-N-1H-pyrrolo[2,3-b]pyridin-6-yl-D-prolineamide; and (4S)-3-{[4,4-difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide.

A compound of the present invention can have a geometric isomer or a tautomer depending on the type of substituents. Besides, when a compound of the present invention has an asymmetric carbon atom, the compound can have an optical isomer. The present invention embraces such an isomer separated (such as an enantiomer or a diastereomer), or a mixture thereof (such as a racemic mixture or a diastereomer mixture). Furthermore, the present invention embraces a labeled compound, namely, a compound obtained by substituting one or more atoms of the present compound with a corresponding radioactive isotope or non-radioactive isotope in an arbitrary ratio.

When the compound of the present invention has a basic group such as an amino group, a pharmacologically acceptable acid addition salt can be formed if desired. Examples of such an acid addition salt include a hydrohalic acid salt such as hydrofluoride, hydrochloride, hydrobromide or hydroiodide; an inorganic acid salt such as nitrate, perchlorate, sulfate or phosphate; lower alkanesulfonate such as methanesulfonate, trifluoromethanesulfonate or ethanesulfonate; arylsulfonate such as benzenesulfonate or p-toluenesulfonate; an organic acid salt such as acetate, malate, fumarate, succinate, citrate, tartrate, oxalate or maleate; and an amino acid salt such as ornithate, glutamate or aspartate, among which a hydrohalic acid salt and an organic acid salt are preferred. The acid addition salt preferably used in the compound of the present invention is hydrochloride, hydrobromide, nitrate, sulfate, methanesulfonate, ethanesulfonate, benzenesulfonate, p-toluenesulfonate, 1,2-ethanedisulfonate or 1,5-naphthalenedisulfonate, among which hydrochloride is most preferred.

When the compound of the present invention has an acidic group such as a carboxy group, a pharmacologically acceptable base addition salt can generally be formed. Examples of such a base addition salt include an alkali metal salt such as a sodium salt, a potassium salt or a lithium salt; an alkali earth metal salt such as a calcium salt or a magnesium salt; an inorganic salt such as an ammonium salt; and an organic amine salt such as a dibenzylamine salt, a morpholine salt, a phenylglycine alkyl ester salt, an ethylenediamine salt, a N-methylglucamine salt, a diethylamine salt, a triethylamine salt, a cyclohexylamine salt, a dicyclohexylamine salt, a N,N'-dibenzylethylenediamine salt, a diethanolamine salt, a N-benzyl-N-(2-phenylethoxy)amine salt, a piperazine salt, a tetramethylammonium salt or a tris(hydroxymethyl)aminomethane salt.

A compound of the present invention may be present as a non-solvate or a solvate. The solvate is not especially limited as long as it is pharmacologically acceptable, and specifically, is preferably a hydrate, an ethanol-solvate or the like. Besides, when a nitrogen atom is present in the compound represented by the general formula (1), the compound may be a N-oxide substance, and such solvate and oxide substances are embraced within the scope of the present invention.

A compound of the present invention can have, depending on the types and combinations of substituents, various isomers including a geometric isomer such as a cis-isomer or a trans-isomer, a tautomer, and an optical isomer such as a d-isomer or a l-isomer, and a compound of the present invention embraces all of these isomers and a mixture of any of these isomers in any ratio unless specifically limited.

Besides, a compound of the present invention can contain, in one or more atoms constituting the compound, an isotope at a non-natural abundance. Examples of the isotope include deuterium ($^2$H; D), tritium ($^3$H; T), iodine-125 ($^{125}$I) and carbon-14 ($^{14}$C). Furthermore, a compound of the present invention can be radiolabeled with a radioisotope such as tritium ($^3$H), iodine-125 ($^{125}$I) or carbon-14 ($^{14}$C). The radiolabeled compound is useful as a therapeutic or preventive agent, a research reagent (such as an assay reagent), or a diagnostic agent (such as an in vivo image diagnostic agent). A compound of the present invention containing any radioactive or non-radioactive isotope in any ratio is embraced within the scope of the present invention.

In the present invention, a crystal refers to a solid having an internal structure formed by regularly three-dimensionally repeating constituent atoms or molecules, and is distinguished from an amorphous solid or amorphous substance not having such a regular internal structure. It can be confirmed by employing powder X-ray crystal analysis or the like that a compound of the present invention or a salt thereof is in a crystalline state. In powder X-ray diffraction in general, a peak value may inherently vary due to a difference in the measurement apparatus, sample or sample preparation, and hence the diffraction angle (2θ) can be varied in a range of about ±0.2 (degrees). Therefore, it is understood that the value of the diffraction angle of the present invention embraces numerical values falling in a range of about ±0.2. Accordingly, not only a crystal having completely the same diffraction angle (2θ) of the powder X-ray diffraction but also a crystal having a diffraction angle in the range of about ±0.2 is embraced within the scope of the present invention.

[Production Methods]

Next, representative production methods for a compound represented by the general formula (1) will be described. A compound of the present invention can be produced by any of various production methods, and the following production methods are described merely as examples but are not intended to limit the present invention.

A production intermediate of a compound represented by the general formula (1) or a pharmacologically acceptable salt thereof can be produced by employing any of various known production methods utilizing characteristics based on a basic skeleton thereof or the type of substituent. Examples of the known methods include methods described in "ORGANIC FUNCTIONAL GROUP PREPARATIONS", second edition, ACADEMIC PRESS, INC., 1989, "Comprehensive Organic Transformations", VCH Publishers Inc., 1989, and the like.

In the production, depending on the type of functional group contained in the compound, it may sometimes be effective in the production technology to protect the functional group with an appropriate protecting group at the stage of a raw material or an intermediate, or to substitute by a group which is easily converted to the functional group.

Examples of such a functional group include an amino group, a hydroxy group and a carboxy group, and examples of such a protecting group include protecting groups described in "Protective Groups in Organic Synthesis (fifth edition, 2014)" written by P. G. Wuts.

The protecting group or the group easily converted into the functional group may be appropriately selected in accordance with the reaction conditions of the production method employed for producing the compound.

When such a method is employed, after the reaction is performed with the group introduced, the protecting group is removed or converted into the desired group if necessary, and thus the desired compound can be obtained.

A compound represented by the general formula (1) can be produced by, for example, the following method A or B. Compounds 2a, 2b, 3a and 6a corresponding to production intermediates can be produced by, for example, the following methods C to Q.

When a compound working as a reaction substrate in a reaction of each step of the methods A to Q described below has a functional group or a partial structure inhibiting the reaction of interest, such as an amino group, a hydroxy group, a carboxy group or a hetero atom on a cyclic compound, a protecting group may be introduced into it or an introduced protecting group may be removed therefrom appropriately if necessary. Such a protecting group is not especially limited as long as it is conventionally used, and can be, for example, any of the protecting groups described in the aforementioned literature, "Protective Groups in Organic Synthesis (fifth edition, 2014)". A reaction for introducing or removing such a protecting group can be performed by a conventional method described in the aforementioned literature.

In each compound of the methods A to Q, depending on the type of functional group contained in the compound, it can be substituted by a group which is easily converted to a desired functional group at the stage of a raw material or an intermediate. The conversion to the desired functional group can be performed at an appropriate stage by a known method. Examples of known methods include those described in the aforementioned literature, "ORGANIC FUNCTIONAL GROUP PREPARATIONS", "Comprehensive Organic Transformations" and the like.

Each compound of the methods A to Q is isolated and purified in the form of a non-solvate or any of various solvates such as a salt or a hydrate. A salt can be produced by a conventional method. Examples of the salt include hydrochloride and sulfate, and sodium salt and potassium salt.

The solvent used in the reaction of each step of the methods A to Q is not especially limited as long as it does not inhibit the reaction but partially dissolves a starting material, and is selected, for example, from the following group of solvents. The group of solvents includes aliphatic hydrocarbons such as hexane, pentane, petroleum ether and cyclohexane; aromatic hydrocarbons such as benzene, toluene and xylene; halogenated hydrocarbons such as dichloromethane (methylene chloride), chloroform, carbon tetrachloride, dichloroethane, chlorobenzene and dichlorobenzene; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone and cyclohexanone; esters such as ethyl acetate, propyl acetate and butyl acetate; nitriles such as acetonitrile, propionitrile, butyronitrile and isobutyronitrile; carboxylic acids such as acetic acid and propionic acid; alcohols such as methanol, ethanol, 1-propanol, 2-propanol, 1-butanol, 2-butanol, 2-methyl-1-propanol and 2-methyl-2-propanol; amides such as formamide, N,N-dimethylformamide, N,N-dimethylacetamide; N-methyl-2-pyrrolidone and hexamethylphosphorotriamide; sulfoxides such as dimethylsulfoxide and tetrahydrothiophene 1,1-dioxide; water; and a mixture of any of these.

The acid used in the reaction of each step of the methods A to Q is not especially limited as long as it does not inhibit the reaction, and is selected from the following group of acids. The group of acids includes inorganic acids such as hydrochloric acid, hydrobromic acid, hydroiodic acid, phosphoric acid, sulfuric acid and nitric acid; organic acids such as acetic acid, propionic acid, trifluoroacetic acid and pentafluoropropionic acid; organic sulfonic acids such as methanesulfonic acid, trifluoromethanesulfonic acid, p-toluenesulfonic acid and camphorsulfonic acid; and Lewis acids such as boron tribromide, indium (III) bromide, boron trifluoride, aluminum (III) chloride and trimethylsilyl trifluoromethanesulfonate.

The base used in the reaction of each step of the methods A to Q is not especially limited as long as it does not inhibit the reaction, and is selected from the following group of bases. The group of bases includes alkali metal carbonates such as lithium carbonate, sodium carbonate, potassium carbonate and cesium carbonate; alkali metal bicarbonates such as lithium hydrogen carbonate, sodium hydrogen carbonate and potassium hydrogen carbonate; alkali metal hydroxides such as lithium hydroxide, sodium hydroxide and potassium hydroxide; alkali earth metal hydroxides such as calcium hydroxide and barium hydroxide; alkali metal hydrides such as lithium hydride, sodium hydride and potassium hydride; alkali metal amides such as lithium amide, sodium amide and potassium amide; alkali metal alkoxides such as lithium methoxide, sodium methoxide, sodium ethoxide, sodium tert-butoxide and potassium tert-butoxide; lithium alkylamide such as lithium diisopropylamide; silylamide such as lithium bistrimethylsilylamide and sodium bistrimethylsilylamide; alkyllithium such as n-butyllithium, sec-butyllithium and tert-butyllithium; halogenated alkyl magnesium such as methyl magnesium chloride, methyl magnesium bromide, methyl magnesium iodide, ethyl magnesium chloride, ethyl magnesium bromide, isopropyl magnesium chloride, isopropyl magnesium bromide and isobutyl magnesium chloride; and organic amines such as triethylamine, tributylamine, N,N-diisopropylethylamine, 1-methylpiperidine, 4-methylmorpholine, 4-ethylmorpholine, pyridine, picoline, 4-dimethylaminopyridine, 4-pyrrolidinopyridine, 2,6-di-tert-butyl-4-methylpyridine, quinoline, N,N-dimethylaniline, N,N-diethylaniline, 1,5-diazabicyclo[4,3,0]-5-nonene (DBN), 1,4-diazabicyclo[2,2,2] octane (DABCO), 1,8-diazabicyclo[5,4,0]-7-undecene (DBU) and imidazole.

In the reaction of each step of the methods A to Q, the reaction temperature depends on the solvent, starting material, reagents and the like, and the reaction time depends on the solvent, starting material, reagents, reaction temperature and the like.

In the reaction of each step of the methods A to Q, a target compound of the step is isolated from the reaction mixture by a conventional method after completing the reaction. The target compound is obtained, for example, by (i) filtering off insoluble matter such as a catalyst if necessary, (ii) extracting the target compound by adding water and a solvent immiscible with water (such as dichloromethane, diethyl ether or ethyl acetate) to the reaction mixture, (iii) washing the organic layer and drying the resultant with a desiccant such as anhydrous calcium sulfate, and (iv) distilling off the solvent. The target compound obtained can be further purified, if necessary, by a conventional method such as recrystallization, reprecipitation, distillation or column chromatography (including normal phase chromatography and reverse phase chromatography) using silica gel, alumina or the like. The target compound obtained is identified by standard analysis techniques such as elemental analysis, NMR, mass spectroscopy or IR analysis, and its composition or purity can be thus analyzed. Alternatively, the target compound obtained in each step can be used directly in a subsequent reaction without purification.

In each step of the methods A to Q, an optical isomer can be separated and purified by functional crystallization using an optically active amine such as (R)-(+)- or (S)-(–)-1-phenethylamine, or an optically active carboxylic acid such as (+)- or (–)-10-camphorsulfonic acid, or by separation using an optically active column.

Raw materials and reagents used in the production of a compound of the present invention can be purchased from commercial suppliers, or can be synthesized by any method described in the literature or a similar method.

Method A

[Formula 24]

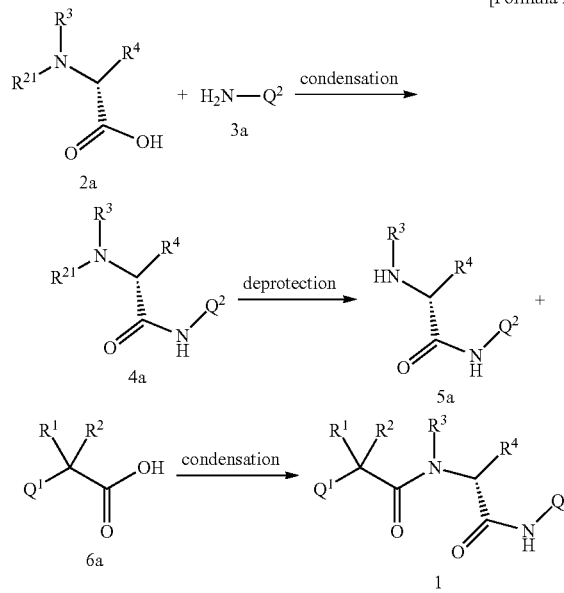

Method B

[Formula 25]

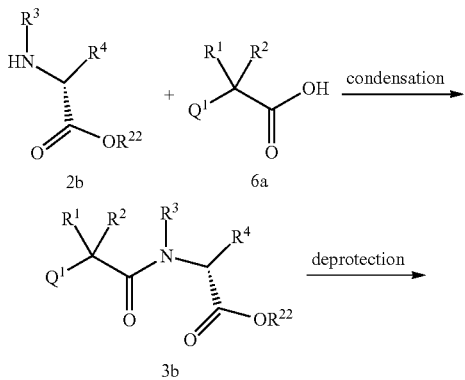

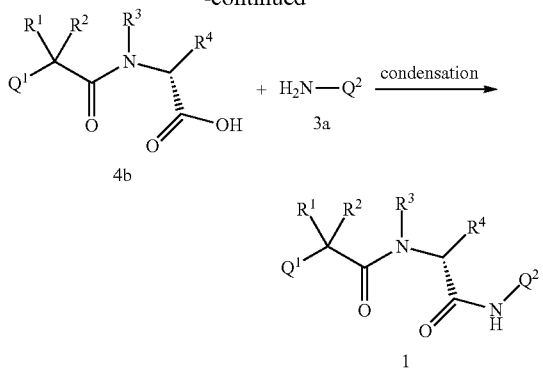

wherein $R^1$, $R^2$, $R^3$, $R^4$, $Q^1$ and $Q^2$ have the same meanings as defined above. $R^{21}$ represents a protecting group on a nitrogen atom, and examples include a tert-butoxycarbonyl group (Boc group), a 9-fluorenylmethyloxycarbonyl group (Fmoc group) and a benzyloxycarbonyl group (Cbz group). $R^{22}$ represents a hydrogen atom or a protecting group of a carboxy group, and examples include a methyl group, an ethyl group, a benzyl group and a tert-butyl group.

Now, the reactions of the respective steps of methods A and B will be described.

Method A (A-1) Conversion from Compound 3a to Compound 4a

This step can be performed by reacting a compound 3a with a carboxylic acid halide or carboxylic acid active ester derived from a compound 2a in a solvent which is inert to the reaction (such as dichloromethane, tetrahydrofuran, N,N-dimethylformamide or pyridine) in the presence of a base (such as triethylamine, N,N-diisopropylethylamine, pyridine, 4-dimethylaminopyridine or sodium hydrogen carbonate). Preferably, the reaction temperature is –15° C. to 100° C., and the reaction time is 5 minutes to 6 days.

(A-2) Conversion from Compound 4a to Compound 5a

Conversion from a compound 4a to a compound 5a is performed by different methods depending on $R^{21}$.

(A-2-1)

When $R^{21}$ is a Boc group, this step can be performed by treating the compound 4a containing the functional group with an acid (such as hydrogen chloride or trifluoroacetic acid) in a solvent which is inert to the reaction (such as methanol, ethanol, tetrahydrofuran, 1,4-dioxane or dichloromethane). Alternatively, the compound may be treated with an acid (such as trimethylsilyl trifluoromethanesulfonate) in the presence of a base (such as 2,6-lutidine). In either reaction, preferably, the reaction temperature is –15° C. to room temperature, and the reaction time is 30 minutes to 12 hours.

(A-2-2)

When $R^{21}$ is a Fmoc group, this step can be performed by treating the compound 4a containing the functional group with a base (such as piperidine or DBU) in a solvent which is inert to the reaction (such as dichloromethane, tetrahydrofuran or N,N-dimethylformamide). Preferably, the reaction temperature is –30° C. to 100° C., and the reaction time is 5 minutes to 24 hours.

(A-2-3)

When $R^{21}$ is a Cbz group, this step can be performed by stirring the compound 4a containing the functional group in a solvent which is inert to the reaction (such as methanol, ethanol or ethyl acetate) in the presence of a reduction catalyst (such as palladium-carbon, palladium hydroxide, Raney nickel, platinum-carbon or platinum oxide) under a hydrogen atmosphere. Preferably, the reaction temperature is room temperature to the boiling point of the solvent, and the reaction time is 30 minutes to 24 hours.

(A-3) Conversion from Compound 5a to Compound 1

Conversion from a compound 5a to a compound 1 can be performed by the same method as in Step A-1.

Method B (B-1) Conversion from Compound 2b to Compound 3b

Conversion from a compound 2b to a compound 3b can be performed by the same method as in Step A-1.

(B-2) Conversion from Compound 3b to Compound 4b

Conversion from a compound 3b to a compound 4b is performed by different methods depending on $R^{22}$. It is noted that this step is not necessary when $R^{22}$ is a hydrogen atom.

(B-2-1)

When $R^{22}$ is a methyl group, an ethyl group, a benzyl group or the like, this step can be performed by treating the compound 3b containing the functional group with a base (such as sodium hydroxide, potassium hydroxide, lithium hydroxide or tetrabutylammonium hydroxide) in a solvent which is inert to the reaction (such as methanol, ethanol, water, tetrahydrofuran, dioxane, or a mixed solvent of any of these; an organic solvent mixable with water in an arbitrary ratio being preferred). Preferably, the reaction temperature is −30° C. to the boiling point of the solvent, and the reaction time is 30 minutes to 3 days.

(B-2-2)

When $R^{22}$ is a benzyl group or the like, this step can be performed by the same method as in Step A-2-3.

(B-2-3)

When $R^{22}$ is a tert-butyl group or the like, this step can be performed by the same method as in Step A-2-1.

(B-3) Conversion from Compound 4b to Compound 1

Conversion from a compound 4b to a compound 1 can be performed by the same method as in Step A-1.

Next, a production method for a compound 2a will be described.

Compound 2a is a known compound, or produced from a known compound used as a starting material by a known method or a similar method. The known compound can be purchased from a commercial supplier, or can be easily synthesized by a method described in the literature or a similar method. As known references, a large number of references have been reported including WO2012/162635 A1, WO2015/118342 A1, J. Med. Chem., 35, 2582-2591 (1992), J. Org. Chem., 61, 566-572 (1996), J. Med. Chem., 46, 2057-2073 (2003), Adv. Synth. Catal., 354, 2635-2640 (2012), Synlett, 11, 1279-1281 (1998), Tetrahedron, 49, 4201-4210 (1993), U.S. Pat. No. 6,124,354 A, and J. Org. Chem., 63, 2442-2450 (1998).

Now, the methods C and E will be described as examples of the production method for a compound 2a, and it is noted that the synthesis method for the compound 2a is not limited to these.

In a structure represented by the general formula (2a), when $R^3$ is a $C_{1-6}$ alkyl group or a hydroxy $C_{2-6}$ alkyl group, and $R^4$ is a hydrogen atom, a $C_{1-6}$ alkyl group, a hydroxy $C_{1-6}$ alkyl group or a $C_{1-6}$ alkylsulfonyl $C_{1-6}$ alkyl group, a compound 2a can be produced by the following method C or D:

Method C

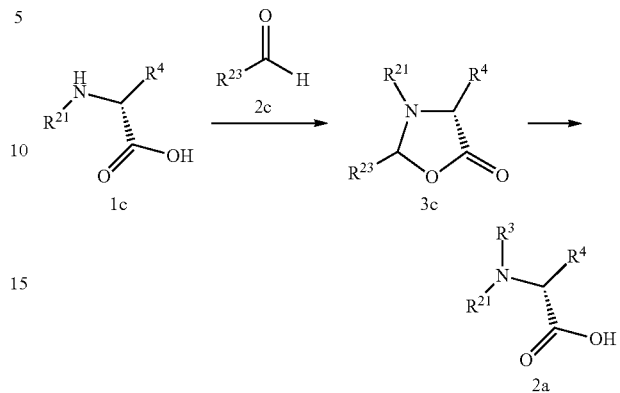

[Formula 26]

Method D

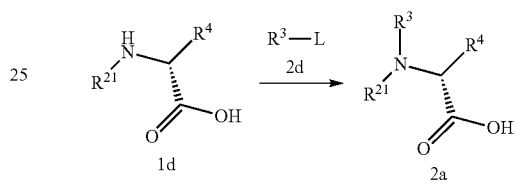

[Formula 27]

wherein $R^3$ represents a $C_{1-6}$ alkyl group or a hydroxy $C_{2-6}$ alkyl group in this case, $R^4$ represents a hydrogen atom, a $C_{1-6}$ alkyl group, a hydroxy $C_{1-6}$ alkyl group or a $C_{1-6}$ alkylsulfonyl $C_{1-6}$ alkyl group in this case. $R^{21}$ has the same meaning as defined above. $R^{23}$ represents a hydrogen atom or a $C_{1-5}$ alkyl group. L represents a leaving group, and examples include a chlorine atom, a bromine atom, an iodine atom, a methanesulfonyloxy group (MsO group) and a p-toluenesulfonyloxy group (TsO group).

The reactions of the respective steps of methods C and D will now be described.

Method C (C-1) Conversion from Compound 1c to Compound 3c

This step can be performed by reacting a compound 1c with a compound 2c in a solvent which is inert to the reaction (such as toluene or benzene) in the presence of an acid catalyst (such as p-toluenesulfonic acid or 10-camphorsulfonic acid). Preferably, the reaction temperature is room temperature to the boiling point of the solvent, and the reaction time is 30 minutes to 48 hours. This step is performed preferably under dehydration using a Dean-Stark apparatus.

(C-2) Conversion from Compound 3c to Compound 2a

This step can be performed by reacting a compound 3c with a reducing agent (such as triethylsilane or triisopropylsilane) in a solvent which is inert to the reaction (such as dichloromethane or chloroform) in the presence of an acid catalyst (such as trifluoroacetic acid or aluminum (III) chloride). Preferably, the reaction temperature is −30° C. to the boiling temperature of the solvent, and the reaction time is 30 minutes to 3 days.

As known references regarding the method C, for example, J. Org. Chem., 48, 77-81 (1983), Aust. J. Chem., 53, 425-433 (2000), and Tetrahedron Lett., 42, 3807-3809 (2001) can be cited.

Method D

This step can be performed by reacting a compound 1d with a compound 2d in a solvent which is inert to the reaction (such as N,N-dimethylformamide or tetrahydrofuran) in the presence of a base (such as lithium hydride or sodium hydride). Preferably, the reaction temperature is −30° C. to 70° C., and the reaction time is 30 minutes to 2 days.

As a known reference regarding the method D, for example, J. Med. Chem., 37, 888-896 (1994) can be cited.

When the compound represented by general formula (2a) is a compound 2a-1 represented as follows, it can be produced by the method E.

Method E

[Formula 28]

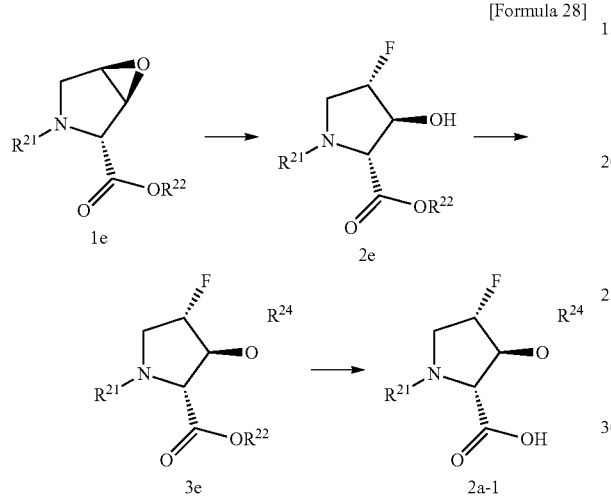

wherein $R^{21}$ and $R^{22}$ have the same meanings as defined above. $R^{24}$ represents a protecting group of a hydroxy group, and examples include a triethylsilyl group (TES group), a tert-butyldimethylsilyl group (TBDMS group) and a tert-butyldiphenylsilyl group (TBDPS group).

Method E (E-1) Conversion from Compound 1e to Compound 2e

This step can be performed by reacting a compound 1e with a fluorinating reagent (such as a tetrafluoroboric acid-diethyl ether complex) in a solvent which is inert to the reaction (such as dichloromethane or chloroform). Preferably, the reaction temperature is −100° C. to 0° C., and the reaction time is 30 minutes to 1 hour.

(E-2) Conversion from Compound 2e to Compound 3e

This step can be performed by reacting a compound 2e with a silylating reagent (such as chlorotriethylsilane or tert-butyldimethylchlorosilane) in a solvent which is inert to the reaction (such as N,N-dimethylformamide or tetrahydrofuran) in the presence of a base (such as imidazole). Preferably, the reaction temperature is −30° C. to 70° C., and the reaction time is 30 minutes to 3 days.

(E-3) Conversion from Compound 3e to Compound 2a-1

When $R^{22}$ is a benzyl group in the structure of a compound 3e, this step can be performed by the same method as in Step A-2-3.

As known references regarding the method E, for example, Tetrahedron, 54, 981-996 (1998), Tetrahedron Lett., 35, 4649-4652 (1994) and J. Org. Chem., 77, 7262-7281 (2012) can be cited.

Next, a production method for the compound 2b will be described.

Compound 2b is a known compound, or produced from a known compound used as a starting material by a known method or a similar method. The known compound can be purchased from a commercial supplier, or can be easily synthesized by a method described in the literature or a similar method. Examples of known references include those mentioned above with respect to the production method for the compound 2a.

Now, the methods F and G will be described as examples of the production method for a compound 2b, and it is noted that the synthesis method for the compound 2b is not limited to these.

Method F

[Formula 29]

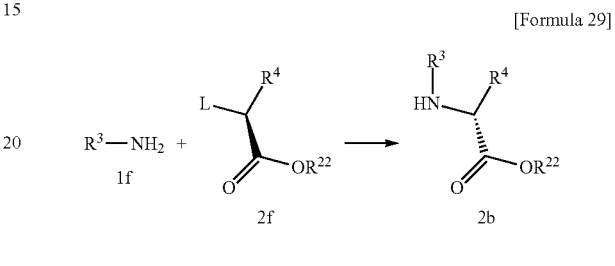

wherein $R^3$ represents a hydrogen atom, a $C_{1-6}$ alkyl group or a hydroxy $C_{2-6}$ alkyl group, and $R^4$ represents a hydrogen atom, a $C_{1-6}$ alkyl group, a hydroxy $C_{1-6}$ alkyl group or a $C_{1-6}$ alkylsulfonyl $C_{1-6}$ alkyl group. $R^{22}$ and L have the same meanings as defined above.

Method F

This step can be performed by reacting a compound 1f with a compound 2f in a solvent which is inert to the reaction (such as N,N-dimethylformamide or tetrahydrofuran) in the presence of a base (such as triethylamine or N,N-diisopropylethylamine). Preferably, the reaction temperature is −30° C. to the boiling point of the solvent, and the reaction time is 30 minutes to 5 days.

As known references regarding the method F, for example, Bioorg. Med. Chem. Lett., 16, 3981-3984 (2006), J. Med. Chem., 47, 530-549 (2004) and J. Org. Chem., 50, 1356-1359 (1985) can be cited.

When the compound represented by general formula (2b) is a compound 2b-1 represented as follows, it can be produced by the method G.

Method G

[Formula 30]

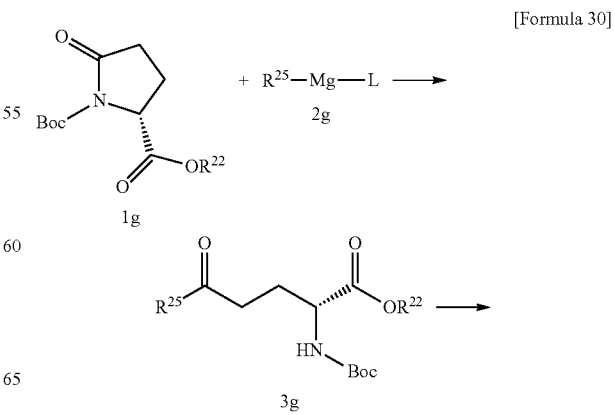

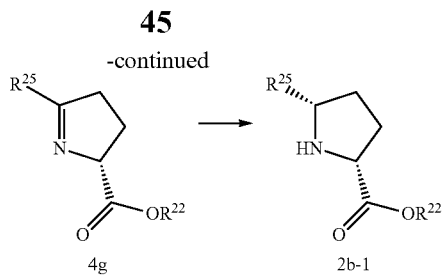

wherein $R^{22}$ and L have the same meanings as defined above. $R^{25}$ represents a $C_{1-6}$ alkyl group, and examples include a methyl group, an ethyl group and an isopropyl group.

Method G (G-1) Conversion from Compound 1g to Compound 3g

This step can be performed by reacting a compound 1g with a compound 2g in a solvent which is inert to the reaction (such as tetrahydrofuran). Preferably, the reaction temperature is −100° C. to room temperature, and the reaction time is 30 minutes to 24 hours.

(G-2) Conversion from Compound 3g to Compound 4g

This step can be performed by treating a compound 3g with an acid (such as trifluoroacetic acid) in a solvent which is inert to the reaction (such as dichloromethane). Preferably, the reaction temperature is −100° C. to the boiling point of the solvent, and the reaction time is 5 minutes to 24 hours.

(G-3) Conversion from Compound 4g to Compound 2b-1

Conversion from a compound 4g to a compound 2b-1 can be performed by the same method as in Step A-2-3. For the purpose of purifying the compound 2b-1, an amino group may be temporarily protected by a Boc group or the like.

As a known reference regarding method G, for example, J. Med. Chem., 49, 3520-3535 (2006) can be cited.

Next, a production method for compound 3a will be described.

Compound 3a is a known compound, or produced from a known compound used as a starting material by a known method or a similar method. Now, the methods H to L will be described as examples of the production method for the compound 3a, and it is noted that the synthesis methods for the compound 3a are not limited to these.

Method H

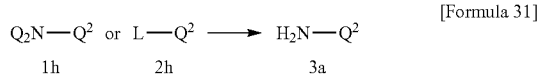

[Formula 31]

wherein $Q^2$ and L have the same meanings as defined above.

Method H

When a compound 1h or a compound 2h is known, compound 3a can be easily produced by a known method or a similar method. Examples of known methods include those described not only in the aforementioned references, "ORGANIC FUNCTIONAL GROUP PREPARATIONS" and "Comprehensive Organic Transformations" but also in Org. Lett., 3, 3417-3419 (2001) and Org. Lett., 3, 2729-2732 (2001).

When the compound represented by general formula (3a) is a compound 3a-1 represented as follows, it can be produced by the method I.

Method I

[Formula 32]

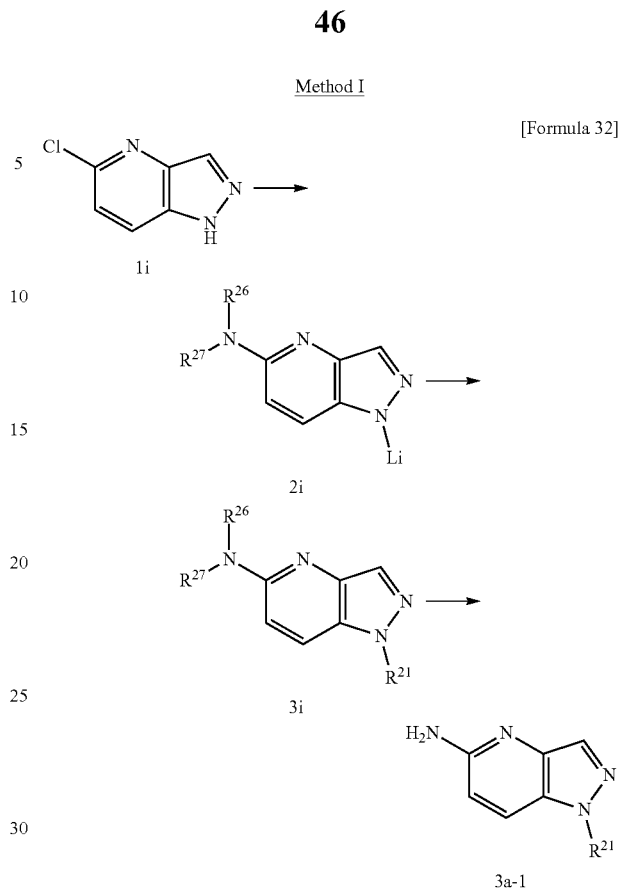

wherein $R^{21}$ has the same meaning as defined above. $R^{26}$ and $R^{27}$ represent a hydrogen atom or a protecting group on a nitrogen atom, and examples include a trimethylsilyl group (TMS group) or a triphenylsilyl group.

Method I (I-1) Conversion from Compound 1i to Compound 2i

This step can be performed by reacting a compound 1i with a silylamine compound (such as lithium bis(trimethylsilyl)amide or triphenylsilylamine) in a solvent which is inert to the reaction (such as tetrahydrofuran) in the presence of a metal catalyst (such as tris(dibenzylideneacetone)dipalladium (0)) and a ligand (such as 2-dicyclohexylphosphino-2',4',6'-triisopropylbiphenyl or 2-(di-tert-butylphosphino)biphenyl). Preferably, the reaction temperature is room temperature to the boiling temperature of the solvent, and the reaction time is 30 minutes to 24 hours. A compound 2i thus obtained is preferably used in the next reaction without isolation.

(I-2) Conversion from Compound 2i to Compound 3i

This step can be performed by reacting the compound 2i with a protecting group introducing reagent (such as di-tert-butyl dicarbonate or benzyl chloroformate) in a solvent which is inert to the reaction (such as tetrahydrofuran). Preferably, the reaction temperature is −30° C. to the boiling point of the solvent, and the reaction time is 5 minutes to 24 hours. A compound 3i thus obtained is preferably used in the next reaction without isolation.

(I-3) Conversion from Compound 3i to Compound 3a-1

This step can be performed by treating the compound 3i with a desilylating reagent (such as tetrabutylammonium fluoride or hydrogen fluoride) in a solvent which is inert to the reaction (such as tetrahydrofuran). Preferably, the reaction temperature is −30° C. to the boiling point of the solvent, and the reaction time is 5 minutes to 24 hours.

When the compound represented by general formula (3a) is a compound 3a-2 represented as follows, it can be produced by the method J.

Method J

[Formula 33]

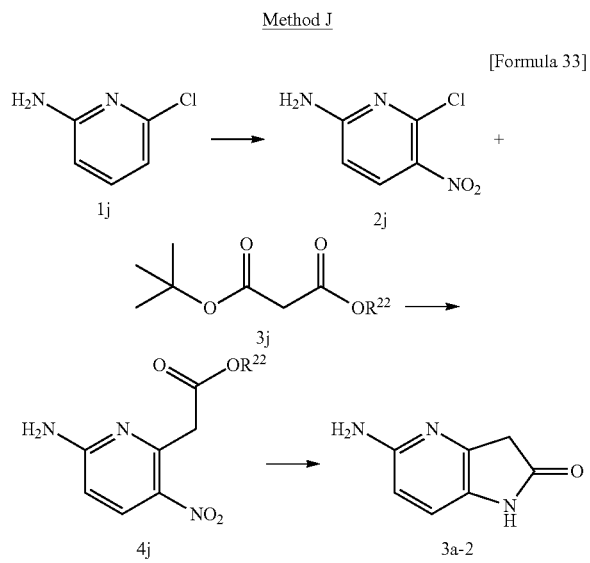

wherein R²² has the same meaning as defined above.

Method J (J-1) Conversion from Compound 1j to Compound 2j

This step can be performed by reacting compound 1j with concentrated nitric acid in concentrated sulfuric acid. Preferably, the reaction temperature is −100° C. to 90° C., and the reaction time is 5 minutes to 4 hours.

(J-2) Conversion from Compound 2j to Compound 4j

Compound 2j is reacted with a compound 3j (such as tert-butyl ethyl malonate) in a solvent which is inert to the reaction (such as N,N-dimethylformamide) in the presence of a base (such as sodium hydride or potassium hydride). Preferably, the reaction temperature is −30° C. to 100° C., and the reaction time is 30 minutes to 24 hours. When the product thus obtained is treated with an acid (such as trifluoroacetic acid) in a solvent which is inert to the reaction (such as dichloromethane), a compound 4j can be produced. Preferably, the reaction temperature is −30° C. to the boiling point of the solvent, and the reaction time is 5 minutes to 48 hours.

(J-3) Conversion from Compound 4j to Compound 3a-2

The compound 4j is reacted with a reducing agent (such as zinc) in a solvent which is inert to the reaction (such as methanol or ethanol) in the presence of an acid (such as acetic acid). Preferably, the reaction temperature is −30° C. to the boiling point of the solvent, and the reaction time is 5 minutes to 5 hours. Subsequently, the resultant reaction solution is treated with a base (such as ammonia water), and thus, compound 3a-2 can be produced. Preferably, the reaction temperature is −30° C. to 50° C., and the reaction time is 5 minutes to 10 hours.

When the compound represented by general formula (3a) is a compound 3a-3 represented as follows, it can be produced by the method K.

Method K

[Formula 34]

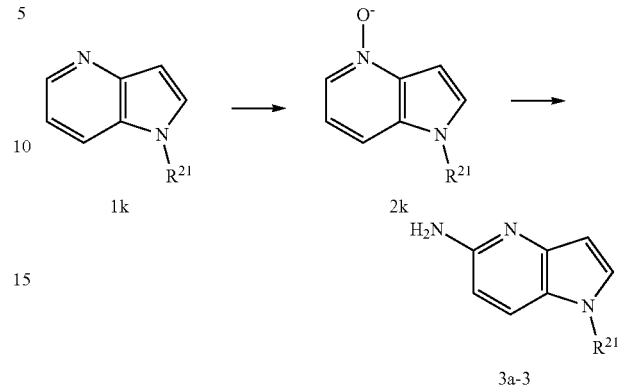

wherein R²¹ has the same meaning as defined above.

Method K (K-1) Conversion from Compound 1k to Compound 2k

This step can be performed by reacting a compound 1k with an oxidizing agent (such as 3-chloroperbenzoic acid) in a solvent which is inert to the reaction (such as dichloromethane). Preferably, the reaction temperature is −30° C. to the boiling point of the solvent, and the reaction time is 5 minutes to 5 hours.

(K-2) Conversion from Compound 2k to Compound 3a-3

This step can be performed by reacting a compound 2k with a condensing agent (such as bromotripyrrolidinophosphonium hexafluorophosphate (PyBroP) or 1H-benzotriazol-1-yloxytripyrrolidinophosphonium hexafluorophosphate (PyBop)) and ammonia in a solvent which is inert to the reaction (such as dichloromethane) in the presence of a base (such as triethylamine or N,N-diisopropylethylamine). Preferably, the reaction temperature is −30° C. to the boiling point of the solvent, and the reaction time is 5 minutes to 48 hours.

As a known reference regarding method K, for example, Org. Lett., 12, 5254-5257 (2010) can be cited.

When the compound represented by general formula (3a) is a compound 3a-4 represented as follows, it can be produced by the method L.

Method L

[Formula 35]

$R^{28}$—NH—[pyridine with L, NHR²⁹] + ≡—$R^{14}$
11     21

→

$R^{28}$—NH—[pyridine with C≡C-R¹⁴, NHR²⁹]
31

→

-continued

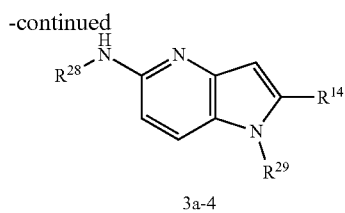

3a-4 wherein L and $R^{14}$ have the same meanings as defined above. $R^{28}$ and $R^{29}$ represent a hydrogen atom or a protecting group on a nitrogen atom, and examples include a Boc group, a Fmoc group, a Cbz group and a Ts group.

Method L (L-1) Conversion from Compound 1l to Compound 3l

This step can be performed by reacting a compound 1l with a compound 2l in a solvent which is inert to the reaction (such as N,N-dimethylformamide) in the presence of a base (such as triethylamine or N,N-diisopropylethylamine), a palladium catalyst (such as bis(triphenylphosphine)palladium (II) dichloride) and a copper catalyst (such as copper (I) iodide). Preferably, the reaction temperature is −30° C. to the boiling point of the solvent, and the reaction time is 5 minutes to 48 hours.

(L-2) Conversion from Compound 3l to Compound 3a-4

This step can be performed by treating a compound 3l with a metal catalyst (such as copper (I) iodide or gold (III) chloride) in a solvent which is inert to the reaction (such as N,N-dimethylformamide or ethanol) in the presence of a base (such as triethylamine or N,N-diisopropylethylamine). Preferably, the reaction temperature is −30° C. to the boiling point of the solvent, and the reaction time is 5 minutes to 24 hours. This conversion can proceed in the same system in Step L-1 depending on the type of substituent.

As a known reference regarding method L, for example, Tetrahedron Lett., 49, 7213-7216 (2008) can be cited.

Next, a production method for the compound 6a will be described.

Compound 6a is a known compound, or produced from a known compound used as a starting material by a known method or a similar method. Now, the methods M to Q will be described as examples of production methods for a compound 6a, and it is noted that the synthesis methods for the compound 6a are not limited to these.

Method M

[Formula 36]

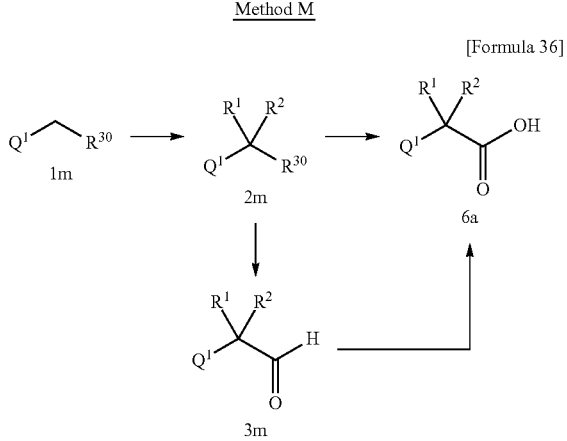

wherein $Q^1$, $R^1$ and $R^2$ have the same meanings as defined above. $R^{30}$ represents a cyano group, a benzyloxycarbonyl group or a $C_{1-6}$ alkoxycarbonyl group, and examples include a methoxycarbonyl group, an ethoxycarbonyl group and a tert-butoxycarbonyl group.

Method M (M-1) Conversion from Compound 1m to Compound 2m

This step can be performed by reacting a compound 1m with a halide (such as iodomethane, 1,3-dibromopropane, 1,4-dibromobutane, 1,5-dibromopentane or epichlorohydrin) or the like in a solvent which is inert to the reaction (such as N,N-dimethylformamide, dimethylsulfoxide or tetrahydrofuran) in the presence of a base (such as sodium hydride or potassium hydride). Preferably, the reaction temperature is −30° C. to 70° C., and the reaction time is 30 minutes to 3 days. A crown ether (such as 18-crown 6-ether) may be added as a reaction accelerator depending on combinations of substituents.

(M-2) Conversion from Compound 2m to Compound 6a

Conversion from a compound 2m to a compound 6a is performed by different methods depending on $R^{30}$.

(M-2-1)

When $R^{30}$ is a cyano group, a methoxycarbonyl group, an ethoxycarbonyl group or the like, this step can be performed by treating a compound 2m containing the functional group with a base (such as sodium hydroxide, potassium hydroxide or lithium hydroxide) or an acid (such as sulfuric acid or hydrochloric acid) in a solvent which is inert to the reaction (such as methanol, ethanol, ethylene glycol, water, tetrahydrofuran, dioxane or a mixed solvent of any of these; an organic solvent mixable with water in an arbitrary ratio being preferred). Preferably, the reaction temperature is room temperature to the boiling point of the solvent, and the reaction time is 5 minutes to 3 days.

(M-2-2)

When $R^{30}$ is a benzyloxycarbonyl group, this step can be performed by the same method as in Step A-2-3.

(M-2-3)

When $R^{30}$ is a tert-butoxycarbonyl group, this step can be performed by the same method as in Step A-2-1.

(M-2-4)

When $R^{30}$ is a cyano group, the compound 6a can be produced via a compound 3m.

Conversion from the compound 2m to the compound 3m can be performed by reacting the compound 2m with a reducing agent (such as diisobutylaluminum hydride) in a solvent which is inert to the reaction (such as toluene, hexane or tetrahydrofuran). Preferably, the reaction temperature is −100° C. to room temperature, and the reaction time is 5 minutes to 40 hours.

Conversion from the compound 3m to the compound 6a can be performed by reacting the compound 3m with an oxidizing agent (such as sodium chlorite) in a solvent inactive to the reaction (such as tert-butyl alcohol, water, acetonitrile or a mixed solvent of any of these) in the presence of 2-methyl-2-butene and sodium dihydrogen phosphate. Preferably, the reaction temperature is 0° C. to 50° C., and the reaction time is 5 minutes to 2 days.

As known references regarding method M, for example, J. Med. Chem., 58, 7341-7348 (2015), J. Org. Chem., 59, 6464-6469 (1994), Bioorg. Med. Chem. Lett., 21, 1438-1441 (2011), Bioorg. Med. Chem. Lett., 12, 2141-2144 (2002), Chem. Pharm. Bull., 53, 965-973 (2005) and Chem. Pharm. Bull., 59, 1376-1385 (2011) can be cited.

Method N

[Formula 37]

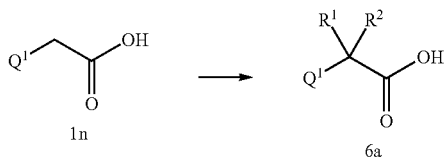

Method P

[Formula 39]

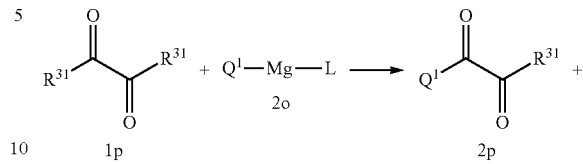

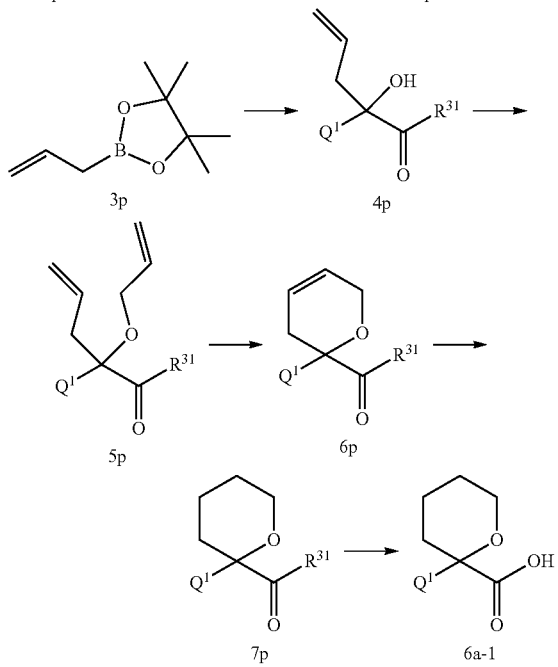

wherein $Q^1$, $R^1$ and $R^2$ have the same meanings as defined above.

Method N

This step can be performed by reacting a compound 1n with a halide or the like (such as iodomethane, dimethyl sulfate or epichlorohydrin) in a solvent which is inert to the reaction (such as tetrahydrofuran) in the presence of a base (such as isopropylmagnesium chloride or n-butyllithium). Preferably, the reaction temperature is −30° C. to 70° C., and the reaction time is 30 minutes to 5 days.

As a known reference regarding method N, for example, Org. Proc. Res. Dev., 16, 1069-1081 (2012) can be cited.

Method O

[Formula 38]

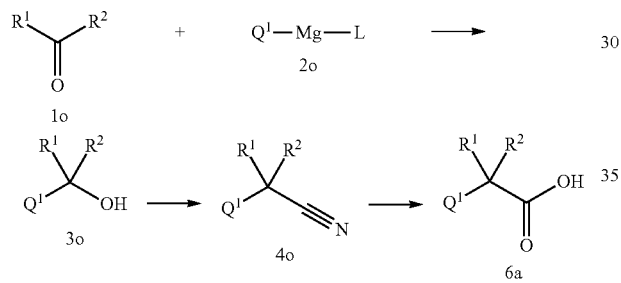

wherein $Q^1$, $R^1$, $R^2$ and L have the same meanings as defined above.

Method O (O-1) Conversion from Compound 1o to Compound 3o

This step can be performed by reacting a compound 1o with a compound 2o in a solvent which is inert to the reaction (such as tetrahydrofuran). Preferably, the reaction temperature is −100° C. to 70° C., and the reaction time is 30 minutes to 24 hours.

(O-2) Conversion from Compound 3o to Compound 4o

This step can be performed by reacting a compound 3o with a cyanating reagent (such as trimethylsilyl cyanide) in a solvent which is inert to the reaction (such as dichloromethane) in the presence of an acid (such as indium (III) bromide or a boron trifluoro-diethyl ether complex). Preferably, the reaction temperature is −100° C. to 50° C., and the reaction time is 5 minutes to 24 hours.

(O-3) Conversion from Compound 4o to Compound 6a

Conversion from a compound 4o to the compound 6a can be performed by the same method as in Step M-2-1 or M-2-4.

As known references regarding method 0, for example, Org. Lett., 10, 4573-4576 (2008), U.S. Pat. No. 6,531,511 B1 and US 2003/100772 A1 can be cited.

When the compound represented by general formula (6a) is a compound 6a-1 represented as follows, it can be produced by method P.

wherein $Q^1$ and L have the same meanings as defined above. $R^{31}$ represents a $C_{1-6}$ alkoxy group, and examples include a methoxy group and an ethoxy group.

Method P (P-1) Conversion from Compound 1p to Compound 2p

This step can be performed by reacting a compound 1p with a compound 2o in a solvent which is inert to the reaction (such as tetrahydrofuran, diethyl ether or a mixture of these). Preferably, the reaction temperature is −100° C. to 70° C., and the reaction time is 30 minutes to 24 hours.

(P-2) Conversion from Compound 2p to Compound 4p

This step can be performed by reacting a mixture of an organic zinc reagent (such as diethyl zinc), an alcohol (such as ethanol) and compound 3p with a compound 2p in a solvent which is inert to the reaction (such as tetrahydrofuran). Preferably, the reaction temperature is −30° C. to the boiling point of the solvent, and the reaction time is 30 minutes to 24 hours.

(P-3) Conversion from Compound 4p to Compound 5p

This step can be performed by reacting a compound 4p with an allyl halide (such as allyl bromide) in a solvent which is inert to the reaction (such as tetrahydrofuran or 1,2-dimethoxyethane) in the presence of a base (such as sodium hydride or potassium hydride). Preferably, the reaction temperature is −30° C. to the boiling point of the solvent, and the reaction time is 30 minutes to 24 hours.

(P-4) Conversion from Compound 5p to Compound 6p

This step can be performed by reacting the compound 5p with an olefin metathesis reaction catalyst (such as a grubbs catalyst 2nd generation) in a solvent which is inert to the reaction (such as dichloromethane). Preferably, the reaction temperature is −70° C. to the boiling point of the solvent, and the reaction time is 5 minutes to 24 hours.

(P-5) Conversion from Compound 6p to Compound 7p

Conversion from the compound 6p to a compound 7p can be performed by the same method as in Step A-2-3.

(P-6) Conversion from Compound 7p to Compound 6a-1

Conversion from the compound 7p to the compound 6a-1 can be performed by the same method as in Step M-2-1.

As known references regarding method P, for example, Chem. Eur. J., 18, 4375-4379 (2012), Org. Lett., 12, 3748-3751 (2010) and WO2015/5901 A1 can be cited.

Method Q

[Formula 40]

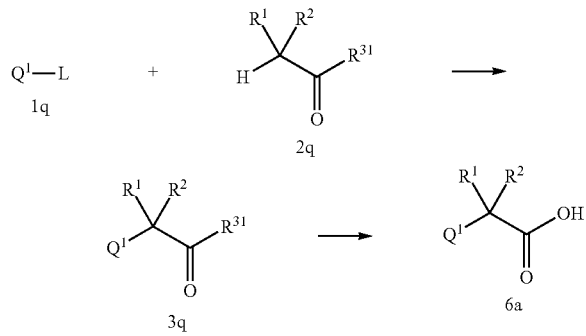

wherein $Q^1$, $R^1$, $R^2$, $R^{31}$ and L have the same meanings as defined above.

Method Q (Q-1) Conversion from Compound 1q to Compound 3q

This step can be performed by reacting a compound 1q with a compound 2q in a solvent which is inert to the reaction (such as toluene) in the presence of a base (such as lithium dicyclohexylamide), a metal catalyst (such as tris (dibenzylideneacetone)dipalladium (0)) and a ligand (such as tri-tert-butylphosphonium tetrafluoroborate). Preferably, the reaction temperature is −50° C. to the boiling point of the solvent, and the reaction time is 30 minutes to 48 hours.

(Q-2) Conversion from Compound 3q to Compound 6a

Conversion from a compound 3q to the compound 6a can be performed by the same method as in Step M-2-1.

As known references regarding method Q, for example, J. Am. Chem. Soc., 124, 12557-12565 (2002), Org. Lett., 10, 1549-1552 (2008) and J. Org. Chem., 78, 8250-8266 (2013) can be cited.

The histone acetyltransferase activity of EP300 or CREBBP can be measured by employing the histone acetyltransferase assay described in Test Example 1 or 2 below. Alternatively, for detection of the histone acetyltransferase activity, for example, a detection method with a radioisotope (Lau O D, et al., J. Biol. Chem. 2000; 275: 21953-21959), a method for detecting, using fluorescence, CoA-SH produced as a by-product in a histone acetyltransferase reaction (Gao T, et al., Methods Mol Biol. 2013; 981: 229-38), a detection method with NADH (Berndsen C E, Denu J M. Methods. 2005; 36: 321-33) or the like can be employed.

The cell growth inhibitory activity of a compound of the present invention or a pharmacologically acceptable salt thereof can be checked by employing a growth inhibitory test method conventionally employed by those skilled in the art. The cell growth inhibitory activity can be checked, for example, as described in Test Example 3 below, by comparing the degree of cell growth obtained in the presence of a test compound with that obtained in the absence of the test compound. The degree of growth can be checked by, for example, using a test system for measuring living cells. Examples of a method for measuring living cells include a [$^3$H]-thymidine uptake assay, a BrdU method and an MTT assay.

Besides, antitumor activity in vivo can be checked by an antitumor test method conventionally employed by those skilled in the art. For example, as described in Test Examples 4 to 8 below, various tumor cells are transplanted into a mouse, a rat or the like, and after confirming engraftment of the transplanted cells, a compound of the present invention is orally or intravenously administered. After several days or several weeks, tumor growth in a non-administration group and tumor growth in a compound administration group are compared, so that the antitumor activity in vivo according to the present invention can be checked.

Since the compound of the present invention or a pharmacologically acceptable salt thereof has an inhibitory action on the histone acetyltransferase activities of both EP300 and CREBBP, it is preferably used against a cancer dependent on EP300 and/or CREBBP. As tumors in which expression of EP300 and/or CREBBP is increased, prostate cancer, liver cancer, lung cancer, breast cancer, colon cancer, stomach cancer, blood cancer, pancreatic cancer, esophageal cancer, bladder cancer, gastrointestinal stromal tumor, NUT midline carcinoma and ovarian cancer are known.

It can be checked whether or not the expression of EP300 and/or CREBBP is increased by analyzing EP300 and/or CREBBP contained in a sample tissue of a patient (collected by, for example, blood collection, biopsy or the like) by any of known methods including analysis and pathological methods employing Southern blotting, Northern blotting, Western blotting, ELISA, DNA chip, FISH assay, tissue immunostaining and other known gene analysis methods {such as PCR, LCR (ligase chain reaction), SDA (standard displacement amplification), NASBA (nucleic acid sequence-based amplification), and ICAN (isothermal and chimeric primer-initiated amplification) and LAMP (loop-mediated isothermal amplification)}.

It can be checked whether or not EP300 and/or CREBBP has a mutation by examining a base sequence of genomic DNA.

A compound of the present invention or a pharmacologically acceptable salt thereof can be used together with a different antitumor agent. Examples include an alkylating agent, an antimetabolite, an antitumor antibiotic, an antitumor plant component, a BRM (biological response modifier), a hormone, a vitamin, an antitumor antibody, a molecular target drug, and other antitumor agents.

More specifically, examples of an alkylating agent include an alkylating agent such as nitrogen mustard, nitrogen mustard N-oxide or chlorambucil, an aziridine-based alkylating agent such as carboquone or thiotepa, an epoxide-based alkylating agent such as dibromomannitol or dibromo dulcitol, a nitrosourea-based alkylating agent such as carmustine, lomustine, semustine, nimustine hydrochloride, streptozocin, chlorozotocin or ranimustine, and busulfan, improsulfan tosylate and dacarbazine.

Examples of an antimetabolite include a purine antimetabolite such as 6-mercaptopurine, 6-thioguanine or thioinosine, a pyrimidine antimetabolite such as fluorouracil, tegafur, tegafur-uracil, carmofur, doxifluridine, broxuridine, cytarabine or enocitabine, and a folic acid antimetabolite such as methotrexate or trimetrexate.

Examples of an antitumor antibiotic include an anthracycline-based antibiotic antitumor agent such as mitomycin C, bleomycin, peplomycin, daunorubicin, aclarbicin, doxorubicin, pirarubicin, THP-adriamycin, 4'-epidoxorubicin or epirubicin, and chromomycin A3 and actinomycin D.

Examples of an antitumor plant component include a vinca alkaloid such as videsine, vincristine or vinblastine, a taxane such as paclitaxel or docetaxel, and an epipodophyllotoxin such as etoposide or teniposide.

Examples of a BRM include a tumor necrosis factor and indomethacin.

Examples of a hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone and medroxyprogesterone.

Examples of a vitamin include vitamin C and vitamin A.

Examples of an antitumor antibody and a molecular target drug include trastuzumab, rituximab, cetuximab, nimotuzumab, denosumab, bevacizumab, infliximab, imatinib mesylate, gefitinib, erlotinib, sunitinib, lapatinib and sorafenib.

Examples of other antitumor agents include cisplatin, carboplatin, oxaliplatin, tamoxifen, camptothecin, ifosfamide, cyclophosphamide, melphalan, L-asparaginase, aceglatone, schizophyllan, picibanil, procarbazine, pipobroman, neocarzinostatin, hydroxyurea, ubenimex and krestin.

A formulation containing a compound of the present invention or a pharmacologically acceptable salt thereof as an active ingredient is prepared by using a carrier used in a conventional formulation and an additive such as an excipient. Administration of a compound of the present invention can be by oral administration in the form of a tablet, a pill, a capsule, a granule, a powder, a liquid or the like, or parenteral administration in the form of an injection (such as intravenous injection or intramuscular injection), a suppository, a transdermal agent, a nasal agent, an inhalant or the like. The dose and the number of doses of a compound of the present invention are appropriately determined according to individual cases in consideration of the symptoms, and the age, the sex or the like of an administration target. The dose is usually 0.001 mg/kg to 100 mg/kg per dose for oral administration to an adult, and usually 0.0001 mg/kg to 10 mg/kg per dose for intravenous administration to an adult. The number of doses is usually once to six times per day, or once per day to once per 7 days.

A solid formulation for oral administration of the present invention can be a tablet, a powder, a granule or the like. Such a formulation can be produced by a conventional method by mixing one or more active substances with an inert excipient, a lubricant, a disintegrating agent, a dissolution assisting agent or the like. The excipient can be, for example, lactose, mannitol or glucose. The lubricant can be, for example, magnesium stearate. The disintegrating agent can be, for example, sodium carboxymethyl starch. A tablet or a pill can be coated with a sugar coat or a gastric-soluble or enteric coating agent if necessary.

A liquid formulation for oral administration can be a pharmaceutically acceptable emulsion, liquid, suspension, syrup or elixir. Such a formulation contains a generally used inert solvent (such as purified water or ethanol), and may further contain a solubilizing agent, a wetting agent, a suspending agent, a sweetener, a flavoring agent, an aromatic or a preservative.

An injection for parenteral administration can be an aseptic aqueous or nonaqueous liquid, suspension or emulsion. An aqueous solvent for injection can be, for example, distilled water or a normal saline solution. A nonaqueous solvent for injection can be, for example, propylene glycol, polyethylene glycol, a vegetable oil such as olive oil, an alcohol such as ethanol, or polysorbate 80 (pharmacopoeia name). Such a formulation may further contain a tonicity agent, a preservative, a wetting agent, an emulsifier, a dispersant, a stabilizer or a dissolution assisting agent. Such a formulation can be sterilized by filtration through a bacteria retention filter, blending with a bactericide, or radiation exposure. Alternatively, a composition obtained by dissolving or suspending an aseptic solid composition in aseptic water or an injection solvent before use can be used as the formulation.

EXAMPLES

Now, examples and test examples will be described for describing the present invention in more detail, and it is noted that the scope of the present invention is not limited to these examples.

Elution of column chromatography performed in each reference example or example was performed under observation with thin layer chromatography (TLC). In the TLC observation, the TLC plate was silica gel 60F$_{254}$ or 60NH$_2$F$_{254}$S manufactured by Merck, the developing solvent was a solvent used as an elution solvent in column chromatography, and a UV detector or a color reagent was employed as the detection method. The silica gel for a column was silica gel SK-85 manufactured by Merck, or Chromatorex NH manufactured by Fuji Silysia Chemical Ltd. In addition, an automatic purifying device manufactured by Yamazen Corporation or Biotage was used.

Abbreviations used in the reference examples and examples have the following meaning:

Me: methyl, tBu: tert-butyl, Bn: benzyl, TBDMS: tert-butyldimethylsilyl, TBDPS: tert-butyldiphenylsilyl, Cbz: benzyloxycarbonyl, Boc: tert-butoxycarbonyl, Fmoc: 9-fluorenylmethyloxycarbonyl, Ms: methanesulfonyl, Ts: p-toluenesulfonyl, PyBrop: bromotripyrrolidinophosphonium hexafluorophosphate, COMU: (1-cyano-2-ethoxy-2-oxoethylideneaminoxy)dimethylaminomorpholinocarbenium hexafluorophosphate, HATU: O-(7-azabenzotriazol-1-yl)-N,N,N',N'-tetramethyluronium hexafluorophosphate, DBU: 1,8-diazabicyclo[5.4.0]undec-7-ene.

In the examples described below, nuclear magnetic resonance (hereinafter referred to as $^1$H-NMR: 400 MHz) spectra were indicated in δ values (ppm) in terms of chemical shift values with tetramethylsilane used as standard. Splitting patterns were represented by s for singlet, d for doublet, t for triplet, q for quartet, m for multiplet and br for broad. For mass spectrometry, any one of an ESI method, an APCI method and an ESI/APCI method as an ion source was employed.

Examples

Reference Example A-1

Benzyl 4-amino-1H-indazole-1-carboxylate

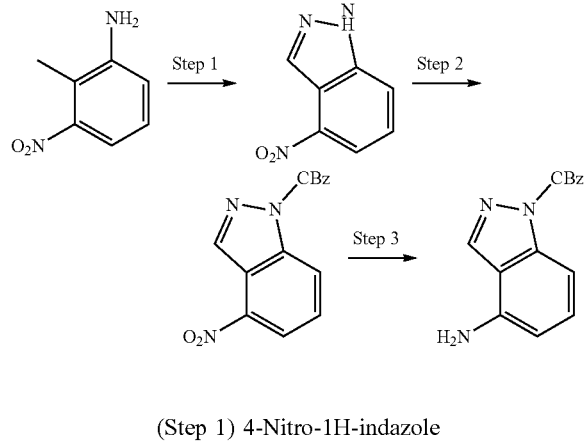

[Formula 41]

(Step 1) 4-Nitro-1H-indazole

To a solution of 2-methyl-3-nitroaniline (2.27 g) in acetic acid (60.0 mL), a solution of sodium nitrite (1.13 g) in water (5.00 mL) was added, and the mixture was stirred at room temperature for 2 hours. Ice water was added to the reaction solution, the solid thus precipitated was filtered off and dried to obtain the title compound (1.91 g) as a solid.

MS (m/z): 164 (M+H)$^+$.

(Step 2) Benzyl 4-nitro-1H-indazole-1-carboxylate

To a solution of the compound (1.91 g) obtained in Step 1 above in N,N-dimethylformamide (60.0 mL), DBU (1.92 mL) was added, the mixture was stirred at room temperature for 15 minutes, benzyl chloroformate (3.34 mL) was added thereto, and the mixture was stirred at room temperature for 4 hours. To the reaction solution, an aqueous ammonium chloride solution was added, and the mixture was extracted with ethyl acetate three times. The organic layer was washed with saturated brine, and then dried over anhydrous sodium sulfate. After filtration and concentration under reduced pressure, the residue obtained was purified by silica gel column chromatography (hexane/ethyl acetate). After concentration under reduced pressure, the solid obtained was suspended in hexane, filtered off and dried to obtain the title compound (2.68 g) as a solid.

$^1$H-NMR (CDCl$_3$) δ: 5.58 (2H, s), 7.39-7.45 (3H, m), 7.54-7.57 (2H, m), 7.70 (1H, t, J=8.2 Hz), 8.28 (1H, d, J=7.9 Hz), 8.66 (1H, d, J=8.5 Hz), 8.85 (1H, s).

(Step 3) Benzyl 4-amino-1H-indazole-1-carboxylate

To a suspension of the compound (1.00 g) obtained in Step 2 above in methanol (15.0 mL), zinc powder (1.54 g) was added under ice cooling, the mixture was stirred at the same temperature for 10 minutes, a saturated aqueous ammonium chloride solution (15.0 mL) was then added, and the mixture was stirred at room temperature for 5 and a half hours. After the reaction solution was filtered through celite, the filtrate obtained was extracted with ethyl acetate three times. The organic layer was washed with saturated brine, and dried over anhydrous sodium sulfate. After filtration and concentration under reduced pressure, the residue obtained was purified by silica gel column chromatography (chloroform/ethyl acetate) to obtain the title compound (0.841 g) as a solid.

$^1$H-NMR (DMSO-D$_6$) δ: 5.47 (2H, s), 6.14 (2H, s), 6.42 (1H, dd, J=6.7, 1.8 Hz), 7.19-7.25 (2H, m), 7.37-7.46 (3H, m), 7.51-7.54 (2H, m), 8.47 (1H, s). MS (m/z): 268 (M+H)$^+$.

Reference Example A-2 tert-Butyl 4-amino-1H-indazole-1-carboxylate

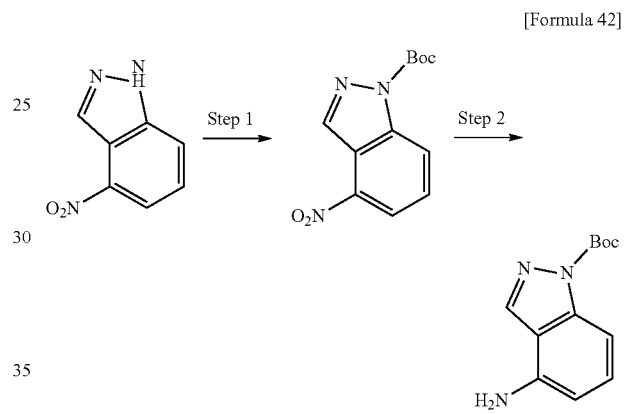

[Formula 42]

(Step 1) tert-Butyl 4-nitro-1H-indazole-1-carboxylate

To a solution of the compound (10.0 g) obtained in Step 1 of Reference Example A-1 in dichloromethane (200 mL), triethylamine (10.2 mL) and di-tert-butyl dicarbonate (14.7 g) were added, and the mixture was stirred at room temperature for 6 hours. The mixture was separated into water and dichloromethane, and the organic layer obtained was dried over anhydrous sodium sulfate. A residue obtained by concentration was purified by silica gel column chromatography (hexane/ethyl acetate) and then recrystallized (hexane/diethyl ether) to obtain the title compound (15.1 g) as a solid.

$^1$H-NMR (CDCl$_3$) δ: 1.75 (9H, s), 7.66-7.71 (1H, m), 8.27 (1H, d, J=7.9 Hz), 8.64 (1H, d, J=8.5 Hz), 8.83 1H, s).

(Step 2) tert-Butyl 4-amino-1H-indazole-1-carboxylate

The compound (15.0 g) obtained in Step 1 above was subjected to the same procedures as in Step 3 of Reference Example A-1 to obtain the title compound (12.4 g) as a solid.

$^1$H-NMR (CDCl$_3$) δ: 1.72 (9H, s), 4.18 (2H, br s), 6.52 (1H, d, J=7.3 Hz), 7.27-7.33 (1H, m), 7.54 (1H, d, J=8.5 Hz), 8.12 (1H, s).

Reference Example A-3

2-Amino-5-(2-morpholinoethoxy)benzonitrile

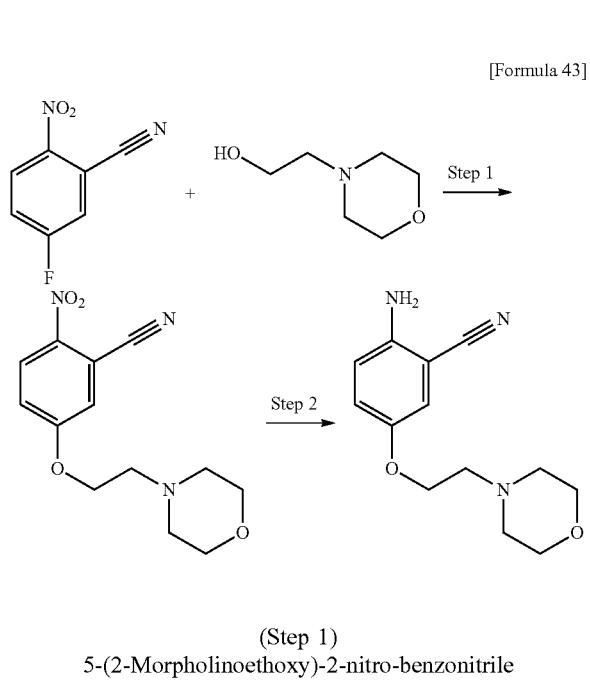

[Formula 43]

(Step 1) 5-(2-Morpholinoethoxy)-2-nitro-benzonitrile

A solution of 5-fluoro-2-nitrobenzonitrile (2.26 g) in N,N-dimethylformamide (50 mL) was allowed to cool to 0° C., N-(2-hydroxyethyl)morpholine (1.98 mL) and sodium hydride (purity>55%, 890 mg) were successively added thereto, and the mixture was stirred at room temperature for 1.1 hours. A saturated aqueous ammonium chloride solution was added thereto at 0° C., and ethyl acetate and a saturated aqueous sodium hydrogen carbonate solution were then added. The mixture was extracted with an ethyl acetate/hexane mixed solvent, washed with saturated brine, and dried over anhydrous sodium sulfate. The solvent was distilled off under reduced pressure, and the residue obtained was formed into a slurry with an ethyl acetate/hexane mixed solvent, and then filtered off to obtain the title compound (2.28 g) as a solid.
$^1$H-NMR (CDCl$_3$) δ: 2.56-2.60 (4H, m), 2.85 (2H, t, J=5.4 Hz), 3.72-3.76 (4H, m), 4.23 (2H, t, J=5.4 Hz), 7.22 (1H, dd, J=9.4, 2.7 Hz), 7.35 (1H, d, J=2.4 Hz), 8.32 (1H, d, J=9.7 Hz).

(Step 2) 2-Amino-5-(2-morpholinoethoxy)benzonitrile

To a solution of the compound (2.23 g) obtained in Step 1 above in ethanol (70 mL), 10% palladium-carbon (1.00 g) was added, and the mixture was stirred at room temperature under a hydrogen atmosphere for 30 minutes. The reaction solution was filtered through celite using dichloromethane and methanol, and the solvent was distilled off under reduced pressure. The residue obtained was subjected to silica gel column chromatography (ethyl acetate/methanol) to obtain the title compound (1.65 g) as a solid.
$^1$H-NMR (CDCl$_3$) δ: 2.53-2.58 (4H, m), 2.76 (2H, t, J=5.7 Hz), 3.71-3.76 (4H, m), 4.02 (2H, t, J=5.7 Hz), 4.08-4.15 (2H, br m), 6.69 (1H, d, J=9.1 Hz), 6.89 (1H, d, J=3.0 Hz), 6.99 (1H, dd, J=8.8, 2.7 Hz).

Reference Example A-4 tert-Butyl 5-amino-1H-indazole-1-carboxylate

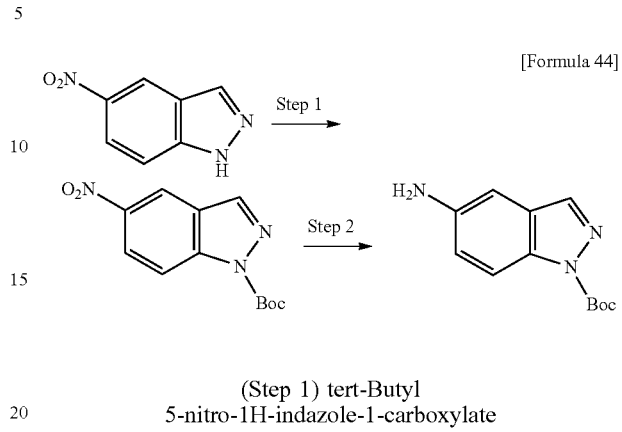

[Formula 44]

(Step 1) tert-Butyl 5-nitro-1H-indazole-1-carboxylate

A solution of 5-nitroindazole (2.00 g) in tetrahydrofuran (30 mL) was allowed to cool to 0° C., di-tert-butyl dicarbonate (3.21 g), N,N-diisopropylethylamine (3.84 mL) and 4-dimethylaminopyridine (150 mg) were added to the solution, and the mixture was stirred at room temperature for 23.8 hours. The solvent was distilled off under reduced pressure, and the residue obtained was subjected to silica gel column chromatography (hexane/ethyl acetate) to obtain the title compound (2.86 g) as a solid.
$^1$H-NMR (CDCl$_3$) δ: 1.75 (9H, s), 8.32-8.36 (2H, m), 8.43 (1H, dd, J=9.4, 2.1 Hz), 8.70 (1H, d, J=2.4 Hz).

(Step 2) tert-Butyl 5-amino-1H-indazole-1-carboxylate

The compound (2.86 g) obtained in Step 1 above was subjected to the same procedures as in Step 3 of Reference Example A-1 to obtain the title compound (2.18 g) as a solid.
$^1$H-NMR (CDCl$_3$) δ: 1.71 (9H, s), 3.73 (2H, br s), 6.91-6.97 (2H, m), 7.95-8.00 (2H, m).

Reference Example A-5 tert-Butyl (6-aminopyridin-2-yl)methylcarbamate

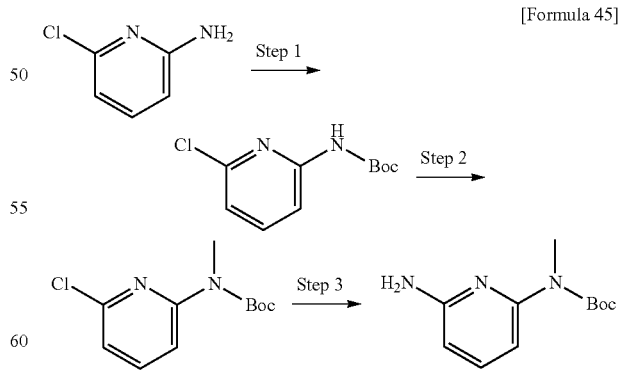

[Formula 45]

(Step 1) tert-Butyl (6-chloropyridin-2-yl)carbamate

A solution of 2-amino-6-chloropyridine (1.00 g) in tetrahydrofuran (6 mL) was allowed to cool to 0° C., sodium bis(trimethylsilyl)amide (1.0 mol/L, solution in tetrahydrofuran, 17 mL) and di-tert-butyl dicarbonate (1.87 g) were successively added to the solution, and the mixture was stirred at room temperature for 30 minutes. The solvent was distilled off under reduced pressure, and ethyl acetate and diluted hydrochloric acid were then added. The mixture was extracted with ethyl acetate, toluene was added to the organic layer obtained, and the solvent was distilled off under reduced pressure. The residue obtained was subjected to silica gel column chromatography (hexane/ethyl acetate) to obtain the title compound (1.65 g) as a solid.

$^1$H-NMR (CDCl$_3$) δ: 1.51 (9H, s), 6.97 (1H, d, J=7.9 Hz), 7.20 (1H, br s), 7.60 (1H, dd, J=7.9, 7.9 Hz), 7.85 (1H, d, J=7.9 Hz).

(Step 2) tert-Butyl (6-chloropyridin-2-yl)methylcarbamate

A solution of the compound (1.65 g) obtained in Step 1 above in N,N-dimethylformamide (20 mL) was allowed to cool to 0° C., sodium hydride (purity>55%, 378 mg) was added to the solution, and the mixture was stirred at room temperature for 10 minutes. Subsequently, iodomethane (0.898 mL) was added to the mixture at 0° C., and the mixture was stirred at room temperature for 2 hours. A saturated aqueous ammonium chloride solution was added thereto, and the mixture was extracted with an ethyl acetate/hexane mixed solvent. The resultant was washed with saturated brine and dried over anhydrous sodium sulfate. The solvent was distilled off under reduced pressure, and the residue obtained was subjected to silica gel column chromatography (hexane/ethyl acetate) to obtain the title compound (1.66 g) as an oil.

$^1$H-NMR (CDCl$_3$) δ: 1.53 (9H, s), 3.39 (3H, s), 7.01 (1H, d, J=7.9 Hz), 7.57 (1H, dd, J=7.9, 7.9 Hz), 7.70 (1H, d, J=7.9 Hz).

(Step 3) tert-Butyl (6-aminopyridin-2-yl)methylcarbamate

Tris(dibenzylideneacetone)dipalladium(0) (18.3 mg), 2-(dicyclohexylphosphino)biphenyl (16.8 mg) and the compound (243 mg) obtained in Step 2 above were mixed, and lithium bis(trimethysilyl)amide (1.17 mol/L, solution in tetrahydrofuran, 1.03 mL) was added to the mixture at room temperature under a nitrogen atmosphere. The mixture was stirred at 80° C. for 4 hours using a microwave heating synthesis apparatus. The resultant was allowed to stand still at room temperature for 6 days, tetrabutylammonium fluoride (1 mol/L, solution in tetrahydrofuran, 3.0 mL) was added thereto, and the resultant mixture was stirred at room temperature for 5 minutes. Diethyl ether was added to the mixture, and the resultant was washed with water and saturated brine, and dried over anhydrous sodium sulfate. The solvent was distilled off under reduced pressure, and the residue obtained was subjected to silica gel column chromatography (hexane/ethyl acetate) to obtain the title compound (185 mg) as a solid.

$^1$H-NMR (CDCl$_3$) δ: 1.49 (9H, s), 3.30 (3H, s), 4.32 (2H, s), 6.22 (1H, d, J=7.9 Hz), 6.92 (1H, d, J=7.9 Hz), 7.38 (1H, dd, J=7.9, 7.9 Hz).

Reference Example A-6 tert-Butyl 5-amino-1H-pyrazolo[4,3-b]pyridine-1-carboxylate

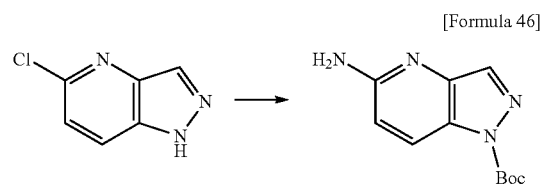 [SMILES: Clc1ccc2[nH]ncc2n1 ; CC(C)(C)OC(=O)n1ncc2nc(N)ccc21]

[Formula 46]

A mixture of 5-chloro-1H-pyrazolo[4,3-b]pyridine (14.7 g), tris(dibenzylideneacetone)dipalladium(0) (2.27 g), 2-dicyclohexylphosphino-2',4',6'-triisopropylbiphenyl (1.83 g), lithium bis(trimethylsilyl)amide (1.09 mol/L, solution in tetrahydrofuran, 200 mL) and tetrahydrofuran (100 mL) was stirred under reflux for 6.3 hours. The reaction solution was allowed to cool to room temperature and allowed to stand still for 15.8 hours. The reaction solution was then allowed to cool to 0° C., di-tert-butyl dicarbonate (22.4 g) was added thereto in small portions, and the mixture was stirred at 0° C. for 40 minutes. Tetrabutylammonium fluoride (1 mol/L, solution in tetrahydrofuran, 279 mL) was added thereto at 0° C., and the resultant was stirred at the same temperature for 1.1 hours. Water was added thereto at 0° C., the mixture was extracted with ethyl acetate, and the organic layer obtained was washed with saturated brine and dried over anhydrous sodium sulfate. The solvent was distilled off under reduced pressure, and the residue obtained was subjected to silica gel column chromatography (hexane/ethyl acetate) to obtain a slurry with a diethyl ether/hexane mixed solvent. The slurry was then filtered to obtain the title compound (16.6 g) as a solid.

$^1$H-NMR (CDCl$_3$) δ: 1.70 (9H, s), 4.60 (2H, br s), 6.70 (1H, d, J=8.5 Hz), 8.04 (1H, s), 8.21 (1H, d, J=9.1 Hz).

Reference Example A-7 tert-Butyl 4-amino-1H-benzimidazole-1-carboxylate

[Formula 47]

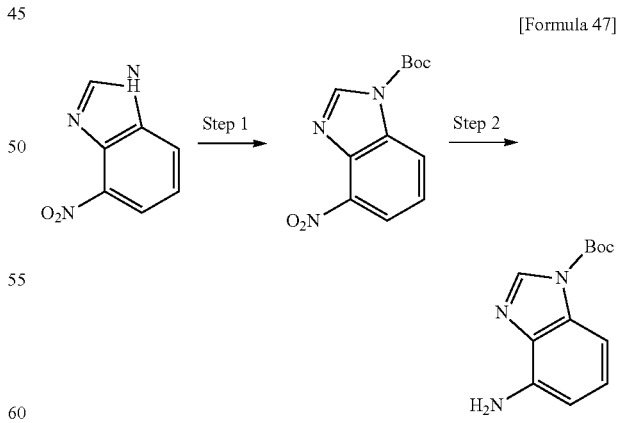

(Step 1) tert-Butyl 4-nitro-1H-benzimidazole-1-carboxylate

To a suspension of 4-nitro-1H-benzimidazole (2.65 g) in tetrahydrofuran (80.0 mL), triethylamine (3.38 mL) and di-tert-butyl dicarbonate (4.25 g) were added, and the mixture was stirred at room temperature for 1 hour. 4-Dimethylaminopyridine (0.0397 g) was then added to the mixture, and the resultant mixture was stirred at room temperature overnight. After the reaction solution was concentrated under reduced pressure, the residue obtained was purified by silica gel column chromatography (chloroform/ethyl acetate). After concentration under reduced pressure, diethyl ether was added to the solid obtained to obtain a suspension, and the suspension was filtered off and dried to obtain the title compound (3.94 g) as a solid.

$^{1}$H-NMR (CDCl$_{3}$) δ: 1.73 (9H, s), 7.53 (1H, t, J=8.2 Hz), 8.20-8.22 (1H, m), 8.39-8.41 (1H, m), 8.62 (1H, s). MS (m/z): 164 (M–CO$_{2}$tBu+H)$^{+}$.

(Step 2) tert-Butyl 4-amino-1H-benzimidazole-1-carboxylate

To a suspension of the compound (3.94 g) obtained in Step 1 above in ethanol (60.0 mL), tetrahydrofuran (30.0 mL) and 10% palladium-carbon (1.00 g) were added, and the mixture was stirred at room temperature for 2 hours under a hydrogen atmosphere. The reaction solution was replaced with nitrogen, the filtrate obtained was concentrated under reduced pressure. The residue obtained was purified by silica gel column chromatography (hexane/ethyl acetate), and further purified by amino silica gel column chromatography (hexane/ethyl acetate). After concentration under reduced pressure, the solid obtained was suspended in hexane, filtered off and dried to obtain the title compound (2.27 g) as a solid.

$^{1}$H-NMR (CDCl$_{3}$) δ: 1.69 (9H, s), 4.37 (2H, s), 6.62 (1H, d, J=7.9 Hz), 7.16 (1H, t, J=7.9 Hz), 7.32 (1H, d, J=8.5 Hz), 8.30 (1H, s). MS (m/z): 134 (M–CO$_{2}$tBu+H)$^{+}$.

Reference Example A-8 tert-Butyl 5-amino-1H-pyrrolo[3,2-b]pyridine-1-carboxylate

[Formula 48]

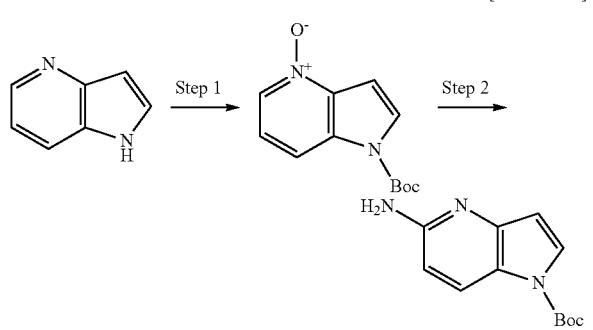

(Step 1) tert-Butyl 1H-pyrrolo[3,2-b]pyridine-1-carboxylate 4-oxide

A solution of 1H-pyrrolo[3,2-b]pyridine (24.9 g) in tetrahydrofuran (400 mL) was allowed to cool to 0° C., di-tert-butyl dicarbonate (48.3 g) was added to the solution, and the mixture was stirred at room temperature for 18.7 hours. The solvent was distilled off, the resultant was dissolved in dichloromethane (400 mL), and the resultant solution was allowed to cool to 0° C. To the solution, 3-chloroperbenzoic acid (purity≤577%, 54.6 g) was added, and the mixture was stirred at room temperature for 1.5 hours. A saturated aqueous sodium hydrogen carbonate solution and sodium thiosulfate (30 g) were then added, and the mixture was stirred and then extracted with dichloromethane and chloroform. The organic layer obtained was washed with a saturated aqueous sodium hydrogen carbonate solution, and dried over anhydrous sodium sulfate. The solvent was distilled off under reduced pressure, and the residue obtained was formed into a slurry with diisopropyl ether and then filtered off to obtain the title compound (33.5 g) as a solid.

$^{1}$H-NMR (CDCl$_{3}$) δ: 1.69 (9H, s), 7.07 (1H, d, J=3.6 Hz), 7.17 (1H, dd, J=8.5, 6.0 Hz), 7.75 (1H, d, J=4.2 Hz), 8.02-8.09 (1H, m), 8.21 (1H, d, J=6.7 Hz).

(Step 2) tert-Butyl 5-amino-1H-pyrrolo[3,2-b]pyridine-1-carboxylate

A solution of the compound (10.0 g) obtained in Step 1 above in dichloromethane (200 mL) was allowed to cool to 0° C., PyBrop (47.8 g), N,N-diisopropylethylamine (29.7 mL) and ammonia (0.5 mol/L, solution in 1,4-dioxane, 200 mL) were added to the solution, and the mixture was stirred at room temperature for 20.5 hours. The solvent was distilled off under reduced pressure, and the resultant was distributed with ethyl acetate and a saturated aqueous sodium hydrogen carbonate solution added thereto. The organic layer obtained was washed with saturated brine, and dried over anhydrous sodium sulfate. The solvent was distilled off under reduced pressure, and the residue obtained was subjected to amino silica gel column chromatography (hexane/ethyl acetate) and further to silica gel column chromatography (hexane/ethyl acetate) to obtain the title compound (1.42 g) as an oil.

$^{1}$H-NMR (CDCl$_{3}$) δ: 1.66 (9H, s), 4.36 (2H, br s), 6.46-6.50 (2H, m), 7.66 (1H, br s), 8.13 (1H, br s).

Reference Example A-9

2-Methyl-1H-pyrrolo[3,2-b]pyridin-5-amine hydrochloride

[Formula 49]

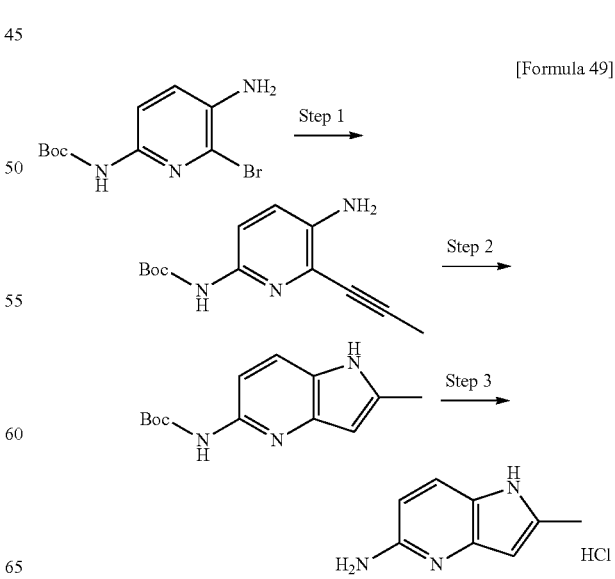

(Step 1) tert-Butyl [5-amino-6-(prop-1-yn-1-yl)pyridin-2-yl]carbamate

A mixture of tert-butyl (5-amino-6-bromopyridin-2-yl)carbamate (1.41 g), bis(triphenylphosphine)palladium(II) dichloride (0.343 g), triethylamine (2 mL), propyne (about 4%, solution in N,N-dimethylformamide, 15 mL) and copper(I) iodide (0.186 g) was stirred at 60° C. for 1 hour under a nitrogen atmosphere. The mixture was diluted with ethyl acetate, washed with water and saturated brine, and dried over anhydrous magnesium sulfate. A residue obtained by concentration was purified by silica gel column chromatography (hexane/ethyl acetate) to obtain the title compound (1.22 g) as a solid.

$^1$H-NMR (CDCl$_3$) δ: 1.49 (9H, s), 2.14 (3H, s), 3.95 (2H, s), 6.97 (1H, s), 7.05 (1H, d, J=8.5 Hz), 7.69 (1H, d, J=8.5 Hz).

(Step 2) tert-Butyl (2-methyl-1H-pyrrolo[3,2-b]pyridin-5-yl)carbamate

A mixture of the compound (1.22 g) obtained in Step 1 above, copper(I) iodide (0.470 g) and N,N-dimethylformamide (15 mL) was stirred at 80° C. for 30 minutes. The mixture was diluted with ethyl acetate, washed with water and saturated brine, and dried over anhydrous magnesium sulfate. A residue obtained by concentration was purified by silica gel column chromatography (hexane/ethyl acetate) to obtain the title compound (0.575 g) as a solid.

$^1$H-NMR (C$_6$D$_6$) δ: 1.52 (9H, s), 2.48 (3H, s), 6.22 (1H, s), 7.15 (1H, s), 7.54 (1H, d, J=8.5 Hz), 7.72 (1H, d, J=8.5 Hz), 7.87 (1H, s).

(Step 3) 2-Methyl-1H-pyrrolo[3,2-b]pyridin-5-amine hydrochloride

A mixture of the compound (233 mg) obtained in Step 2 above, hydrogen chloride (4 mol/L, solution in 1,4-dioxane, 5 mL) and dichloromethane (2 mL) was stirred at room temperature for 4 hours. The mixture was then concentrated and dried to obtain the title compound (139 mg).

$^1$H-NMR (DMSO-D$_6$) δ: 2.41 (3H, s), 6.18 (1H, s), 6.51 (1H, dd, J=8.5, 1.5 Hz), 7.38 (1H, s), 7.92 (1H, d, J=8.5 Hz).

Reference Example B-1

(4R)—N-(2-Cyanophenyl)-4-fluoro-D-prolinamide

[Formula 50]

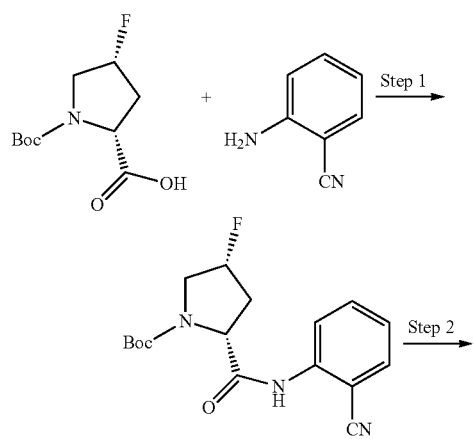

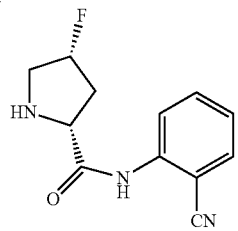

(Step 1) tert-Butyl (2R,4R)-2-[(2-cyanophenyl)carbamoyl]-4-fluoropyrrolidine-1-carboxylate Under a nitrogen atmosphere, (4R)-1-(tert-butoxycarbonyl)-4-fluoro-D-proline (1.00 g) and 2-aminobenzonitrile (0.608 g) were dissolved in pyridine (20.0 mL), cooled to −15° C. in an ice-salt bath, and then phosphoryl chloride (0.432 mL) was added dropwise and stirred at the same temperature to 0° C. for 10 hours. The reaction solution was diluted with ethyl acetate, washed with a 10% aqueous citric acid solution three times, with a saturated aqueous sodium hydrogen carbonate solution and with saturated brine, and then dried over anhydrous sodium sulfate. After filtration and concentration under reduced pressure, the residue obtained was purified by silica gel column chromatography (hexane/ethyl acetate) to obtain the title compound (0.976 g) as a solid.

$^1$H-NMR (DMSO-D$_6$, 100° C.) S: 1.41 (9H, s), 2.29-2.38 (1H, m), 2.51-2.68 (1H, m), 3.59-3.75 (2H, m), 4.48 (1H, d, J=8.5 Hz), 5.29 (1H, d, J=53.2 Hz), 7.30-7.34 (1H, m), 7.65-7.77 (3H, m), 9.67 (1H, s). MS (m/z): 234 (M−CO2tBu+H)$^+$.

(Step 2) (4R)—N-(2-Cyanophenyl)-4-fluoro-D-prolinamide

To a solution of the compound (0.960 g) obtained in Step 1 above in dichloromethane (15.0 mL), trifluoroacetic acid (5.00 mL) was added under ice-cooling and stirred at room temperature for 1 hour. The reaction solution was poured into an ice-cooled 10% aqueous sodium carbonate solution, extracted with dichloromethane three times, and the organic layer was dried over anhydrous sodium sulfate. The aqueous layer was saturated with salt, extracted with a mixed solvent of chloroform/methanol (10/1) six times, and the organic layer was dried over anhydrous magnesium sulfate. The dried organic layers were combined, filtered and then concentrated under reduced pressure, and the residue obtained was purified by amino silica gel column chromatography (hexane/ethyl acetate) to obtain the title compound (0.357 g) as a solid.

$^1$H-NMR (DMSO-D$_6$) δ: 2.15-2.36 (2H, m), 3.12-3.30 (2H, m), 3.68 (1H, s), 3.92-3.95 (1H, m), 5.27 (1H, d, J=53.8 Hz), 7.26 (1H, t, J=7.6 Hz), 7.67-7.71 (1H, m), 7.80 (1H, dd, J=7.9, 1.8 Hz), 8.25 (1H, d, J=8.5 Hz), 10.75 (1H, s). MS (m/z): 234 (M+H)$^+$.

Reference Example B-2 tert-Butyl 5-{[(4R)-4-fluoro-D-prolyl]amino}-1H-pyrazolo[4,3-b]pyridine-1-carboxylate

[Formula 51]

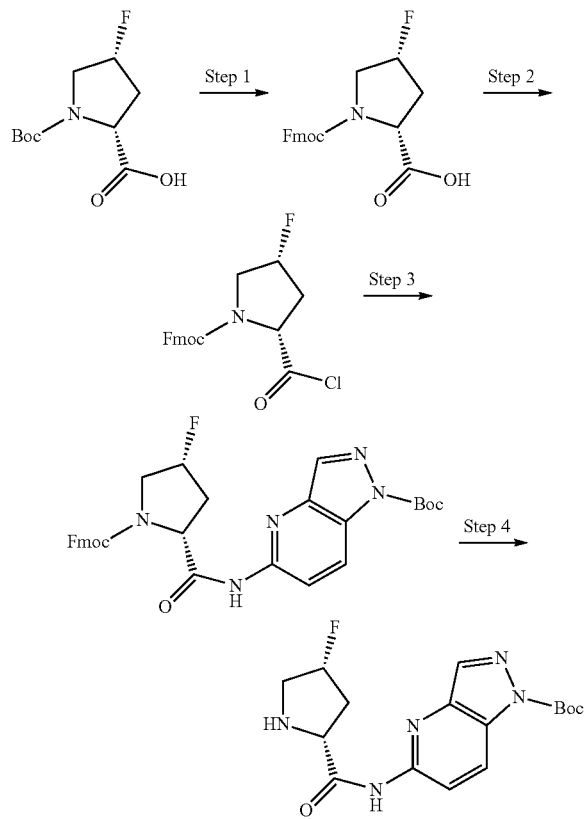

(Step 1) (4R)-1-[(9H-Fluoren-9-ylmethoxy)carbonyl]-4-fluoro-D-proline

To (4R)-1-(tert-butoxycarbonyl)-4-fluoro-D-proline (3.00 g), hydrogen chloride (4 mol/L, 1,4-dioxane solution, 30.0 mL) was added, stirred at room temperature for 4 hours, and then the mixture was concentrated under reduced pressure to obtain a solid. The solid was dissolved in water (60.0 mL) and then ice-cooled, and sodium hydrogen carbonate (5.40 g), 1,4-dioxane (60.0 mL) and 9-fluorenylmethyl chloroformate (4.00 g) were added and stirred at room temperature overnight. Water was added to the reaction solution, and the mixture was washed with diethyl ether twice and the aqueous layer was acidified by adding 1 mol/L of hydrochloric acid. The layer was extracted with chloroform three times, and the organic layer was dried over anhydrous sodium sulfate, then filtered and concentrated under reduced pressure. Water was added to the residue obtained, and the mixture was solidified by ultrasonication and allowed to stand in a refrigerator overnight. The precipitated solid was collected by filtration and dried to obtain the title compound (4.00 g) as a solid.

$^1$H-NMR (DMSO-D$_6$) δ: 2.23-2.68 (2H, m), 3.54-3.75 (2H, m), 4.18-4.51 (4H, m), 5.32 (1H, dd, J=52.9, 3.9 Hz), 7.30-7.37 (2H, m), 7.40-7.45 (2H, m), 7.63-7.70 (2H, m), 7.90 (2H, t, J=7.0 Hz), 12.73 (1H, s).

(Step 2) 9H-Fluoren-9-ylmethyl (2R,4R)-2-(chlorocarbonyl)-4-fluoropyridine-1-carboxylate To a solution of the compound (0.300 g) obtained in Step 1 above in dichloromethane (5.00 mL), thionyl chloride (0.612 mL) and N,N-dimethylformamide (0.010 mL) were added, stirred at room temperature for 3 hours and then at 40° C. for 30 minutes. After concentrating the reaction solution under reduced pressure, the residue was dissolved in dichloromethane (1.00 mL), hexane (10.0 mL) was added, and the precipitated solid was collected by filtration and dried to obtain the title compound (0.261 g) as a solid.

$^1$H-NMR (CDCl$_3$) δ: 2.32-2.54 (1H, m), 2.67-2.82 (1H, m), 3.61-3.76 (1H, m), 3.82-3.91 (1H, m), 4.19-4.29 (1H, m), 4.38-4.86 (3H, m), 5.14-5.36 (1H, m), 7.31-7.35 (2H, m), 7.38-7.44 (2H, m), 7.52-7.61 (2H, m), 7.76-7.78 (2H, m).

(Step 3) tert-Butyl 5-({(4R)-1-[(9H-fluoren-9-ylmethoxy)carbonyl]-4-fluoro-D-prolyl}amino)-1H-pyrazolo[4,3-b]pyridine-1-carboxylate To a mixture of the compound (0.162 g) obtained in Reference Example A-6, N,N-diisopropylethylamine (0.157 mL) and dichloromethane (3.00 mL), a solution of the compound (0.260 g) obtained in Step 2 above in dichloromethane (3.00 mL) was added dropwise under ice-cooling and stirred at room temperature for 1.5 hours. 1 mol/L of hydrochloric acid was added to the reaction solution, and the mixture was extracted with dichloromethane three times, and the organic layer was dried over anhydrous sodium sulfate. After filtration and concentration under reduced pressure, the residue obtained was purified by silica gel column chromatography (hexane/ethyl acetate) to obtain the title compound (0.320 g) as a solid.

$^1$H-NMR (DMSO-D$_6$, 100° C.) δ: 1.66 (9H, s), 2.32-2.41 (1H, m), 2.52-2.70 (1H, m), 3.66-3.83 (2H, m), 4.23-4.32 (3H, m), 4.67 (1H, d, J=9.7 Hz), 5.32 (1H, d, J=53.8 Hz), 7.15-7.38 (4H, m), 7.63 (2H, s), 7.81 (2H, s), 8.26-8.29 (1H, m), 8.39-8.42 (2H, m), 10.44 (1H, s). MS (m/z): 572 (M+H)$^+$.

(Step 4) tert-Butyl 5-{[(4R)-4-fluoro-D-prolyl]amino}-1H-pyrazolo[4,3-b]pyridine-1-carboxylate To a solution of the compound (0.310 g) obtained in Step 3 above in N,N-dimethylformamide (10.0 mL), piperidine (0.500 mL) was added under ice-cooling, stirred under ice-cooling for 15 minutes, and at room temperature for 15 minutes. Water was added to the reaction solution, and the mixture was extracted with ethyl acetate three times, and the organic layer was washed with saturated brine and then dried over anhydrous sodium sulfate. Further, the aqueous layers were combined, extracted with dichloromethane twice, and the organic layer was dried over anhydrous sodium sulfate. The organic layers obtained were combined, filtered, concentrated under reduced pressure, and then the residue was purified by silica gel column chromatography (ethyl acetate/methanol) to obtain the title compound (0.174 g) as a solid.

$^1$H-NMR (DMSO-D$_6$) δ: 1.66 (9H, s), 2.21-2.41 (2H, m), 3.07-3.26 (2H, m), 3.54 (1H, s), 3.92 (1H, d, J=7.3 Hz), 5.26 (1H, d, J=54.4 Hz), 8.41-8.48 (3H, m), 10.57 (1H, s). MS (m/z): 350 (M+H)$^+$.

Reference Example B-3 tert-Butyl 5-({(3S,4S)-4-fluoro-3-[(triethylsilyl)oxy]-D-prolyl}amino)-1H-pyrazolo[4,3-b]pyridine-1-carboxylate

[Formula 52]

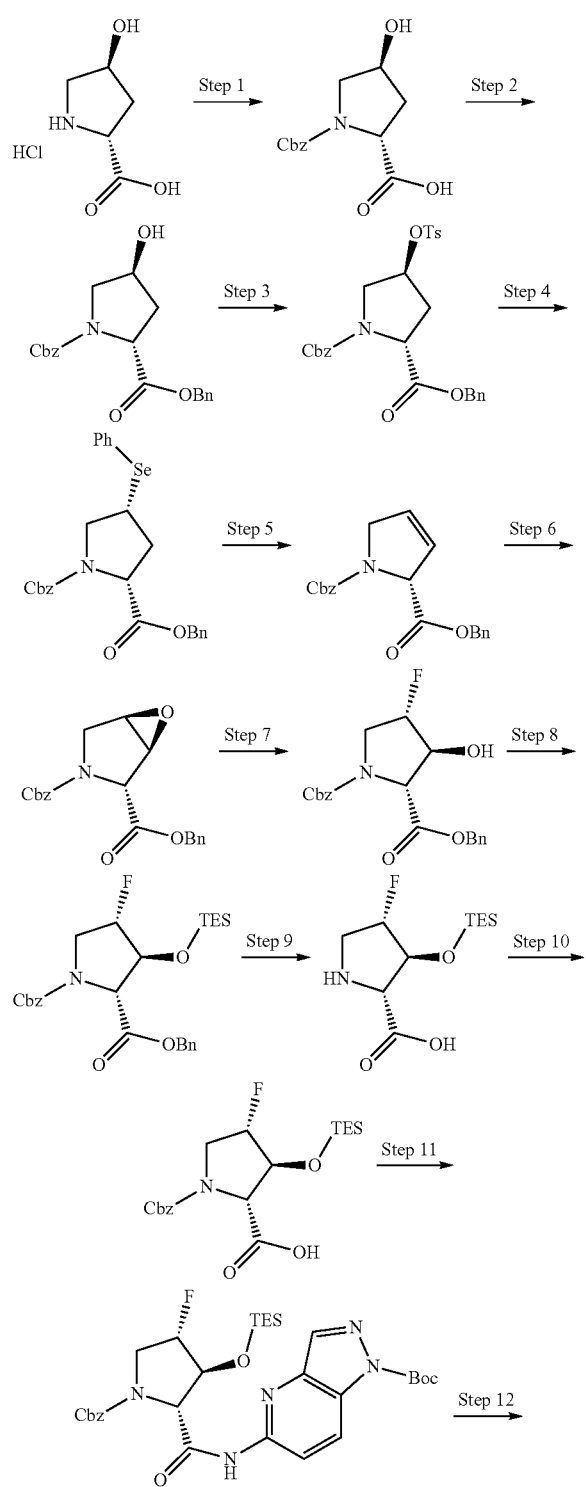

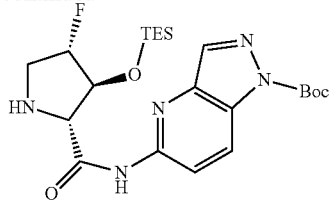

(Step 1) (4S)-1-[(Benzyloxy)carbonyl]-4-hydroxy-D-proline

Under ice-cooling, to an aqueous solution (225 mL) of sodium hydrogen carbonate (26.4 g), (4S)-4-hydroxy-D-proline hydrochloride (15.0 g), tetrahydrofuran (225 mL) and benzyl chloroformate (13.4 mL) were added and stirred at room temperature overnight. After distilling off the organic solvent under reduced pressure, the aqueous layer was washed with diethyl ether. The aqueous layer was acidified with concentrated hydrochloric acid at 0° C. and extracted with ethyl acetate. The organic layer was washed with saturated brine, dried over anhydrous sodium sulfate, and then the solvent was distilled off under reduced pressure to obtain the title compound (22.5 g) as an oil.

$^1$H-NMR (CDCl$_3$) δ: 2.10-2.42 (2H, m), 3.55-3.68 (2H, m), 4.46-4.59 (2H, m), 5.07-5.21 (2H, m), 7.27-7.39 (5H, m).

MS (m/z): 264 (M−H)$^−$.

(Step 2) Dibenzyl (2R,4S)-4-hydroxypyrrolidine-1,2-dicarboxylate

To a solution of the compound (10.0 g) obtained in Step 1 above in methanol (130 mL), an aqueous solution (5 mL) of cesium carbonate (6.16 g) cooled to 0° C. in advance was added at 0° C. and stirred at 0° C. for 5 minutes. The solvent was distilled off under reduced pressure and the residue was dried at 30° C. To a solution of the solid obtained in N,N-dimethylformamide (144 mL), benzyl bromide (4.52 mL) was added at 0° C. and stirred overnight. Ice was added to the reaction solution, and the mixture was extracted with ethyl acetate, and the organic layer was washed with water three times and with saturated brine, and dried over anhydrous sodium sulfate. The solvent was distilled off under reduced pressure, and the residue obtained was purified by silica gel column chromatography (hexane/ethyl acetate) to obtain the title compound (13.0 g) as an oil.

$^1$H-NMR (CDCl$_3$) δ: 1.77-1.86 (1H, m), 2.06-2.14 (1H, m), 2.24-2.38 (1H, m), 3.51-3.67 (1H, m), 3.67-3.74 (1H, m), 4.42-4.63 (2H, m), 4.96-5.07 (2H, m), 5.09-5.28 (2H, m), 7.16-7.43 (10H, m). MS (m/z): 356 (M+H)$^+$.

(Step 3) Dibenzyl (2R,4S)-4-{[(4-methylphenyl)sulfonyl]oxy}pyrrolidine-1,2-dicarboxylate To a solution of 1-(p-toluenesulfonyl)imidazole (6.57 g) in tetrahydrofuran (30 mL), methyl trifluoromethanesulfonate (3.36 mL) was added at 0° C. and stirred at 0° C. for 30 minutes. A solution of the compound (7.04 g) obtained in Step 2 above and 1-methylimidazole (2.36 mL) in tetrahydrofuran (30 mL) was added at 0° C. and stirred at room temperature overnight. Ice was added to the reaction solution, and the organic solvent was distilled off under reduced pressure, and the mixture was extracted with ethyl acetate. The organic layer was washed sequentially with a 5% aqueous potassium hydrogen sulfate solution, with a saturated aqueous sodium hydrogen carbonate solution, with water, and with saturated brine, and dried over anhydrous sodium sulfate. The solvent was distilled off under reduced pressure, and the residue obtained was purified by silica gel column chromatography (hexane/ethyl acetate) to obtain the title compound (9.72 g) as an oil.

$^1$H-NMR (CDCl$_3$) δ: 2.07-2.23 (1H, m), 2.40-2.62 (4H, m), 3.60-3.77 (2H, m), 4.44-4.56 (1H, m), 4.94-5.22 (5H, m), 7.15-7.40 (12H, m), 7.70-7.79 (2H, m). MS (m/z): 510 (M+H)$^+$.

(Step 4) Dibenzyl (2R,4R)-4-(phenylselanyl)pyrrolidine-1,2-dicarboxylate

To a mixture of diphenyl diselenide (8.46 g), tetrahydrofuran (60 mL) and tert-butyl alcohol (50 mL), sodium borohydride (2.06 g) was added at room temperature and stirred for 2 hours. A solution of the compound (21.9 g) obtained in Step 3 above in tetrahydrofuran (60 mL) was added at room temperature and then heated to reflux for 2 hours. The solvent was distilled off under reduced pressure, and ice was added and then the mixture was extracted with ethyl acetate. The organic layer was washed with water three times and dried over anhydrous sodium sulfate. The solvent was distilled off under reduced pressure, and the residue obtained was purified by silica gel column chromatography (hexane/ethyl acetate) to obtain the title compound (17.5 g) as an oil.

$^1$H-NMR (CDCl$_3$) δ: 2.05-2.15 (1H, m), 2.64-2.75 (1H, m), 3.46-3.68 (2H, m), 3.95-4.09 (1H, m), 4.34-4.48 (1H, m), 4.97-5.26 (4H, m), 7.20-7.38 (13H, m), 7.48-7.56 (2H, m).
MS (m/z): 496 (M+H)$^+$.

(Step 5) Dibenzyl (2R)-2,5-dihydro-1H-pyrrole-1,2-dicarboxylate

To a solution of the compound (5.01 g) obtained in Step 4 above in dichloromethane (20 mL), pyridine (1.09 mL) and aqueous hydrogen peroxide (concentration 34.5%, 2.08 mL) were added dropwise at 0° C. and stirred at room temperature for 1.5 hours. The reaction solution was extracted with dichloromethane, and the organic layer was sequentially washed with 0.5 mol/L hydrochloric acid twice, with a saturated aqueous sodium hydrogen carbonate solution, with a 10% aqueous sodium thiosulfate solution twice, and with water, and dried over anhydrous sodium sulfate. The solvent was distilled off under reduced pressure, and the residue obtained was purified by silica gel column chromatography (hexane/ethyl acetate) and then amino silica gel column chromatography (hexane/ethyl acetate) to obtain the title compound (2.46 g) as an oil.

$^1$H-NMR (CDCl$_3$) δ: 4.23-4.41 (2H, m), 5.00-5.27 (5H, m), 5.71-5.81 (1H, m), 5.93-6.04 (1H, m), 7.20-7.41 (10H, m). MS (m/z): 338 (M+H)$^+$.

(Step 6) Dibenzyl (1S,2R,5R)-6-oxa-3-azabicyclo[3.1.0]hexane-2,3-dicarboxylate

To a solution of the compound (2.45 g) obtained in Step 5 above in 1,2-dichloroethane (75 mL), 3-chloroperoxybenzoic acid (purity 577%, 1.99 g) and 4,4'-thiobis(6-tert-butyl-o-cresol) (0.156 g) were added at room temperature and stirred at 90° C. for 3 hours. The temperature was lowered to room temperature, 3-chloroperoxybenzoic acid (purity 577%, 1.63 g) and 4,4'-thiobis(6-tert-butyl-o-cresol) (0.086 g) were further added and stirred at 90° C. for 2 hours. The reaction solution was diluted with dichloromethane, sequentially washed with a 5% aqueous sodium pyrosulfite solution twice, with a saturated aqueous sodium hydrogen carbonate solution, and with saturated brine and dried over anhydrous sodium sulfate. The solvent was distilled off under reduced pressure, and the residue obtained was subjected to silica gel column chromatography (hexane/ethyl acetate, hexane/tetrahydrofuran, dichloromethane/ethyl acetate) to obtain the title compound (1.36 g) as an oil.

$^1$H-NMR (CDCl$_3$) δ: 3.50-3.61 (1H, m), 3.64-3.72 (1H, m), 3.76-3.80 (1H, m), 3.89-4.01 (1H, m), 4.65-4.80 (1H, m), 5.02-5.29 (4H, m), 7.20-7.40 (10H, m). MS (m/z): 354 (M+H)$^+$.

(Step 7) Dibenzyl (2R,3S,4S)-4-fluoro-3-hydroxypyrrolidine-1,2-dicarboxylate

To a solution of the compound (1.26 g) obtained in Step 6 above in dichloromethane (38 mL), a tetrafluoroboric acid diethyl ether complex (0.976 mL) was added at −78° C. under a nitrogen atmosphere and stirred at 0° C. for 1 hour. A saturated aqueous sodium hydrogen carbonate solution was added to the reaction solution, and the mixture was extracted with ethyl acetate. The organic layer was washed with saturated brine and dried over anhydrous sodium sulfate. The solvent was distilled off under reduced pressure, and the residue obtained was subjected to silica gel column chromatography (hexane/ethyl acetate) to obtain the title compound (0.431 g) as a solid.

$^1$H-NMR (CDCl$_3$) δ: 2.40-2.74 (1H, m), 3.74-4.03 (2H, m), 4.44-4.60 (1H, m), 4.60-4.69 (1H, m), 4.85-5.04 (1H, m), 5.04-5.31 (4H, m), 7.27-7.39 (10H, m). MS (m/z): 374 (M+H)$^+$.

(Step 8) Dibenzyl (2R,3S,4S)-4-fluoro-3-[(triethylsilyl)oxy]pyrrolidine-1,2-dicarboxylate To a solution of the compound (400 mg) obtained in Step 7 above in N,N-dimethylformamide (5 mL), imidazole (511 mg) was added at room temperature. Chlorotriethylsilane (0.726 mL) and 4-dimethylaminopyridine (2.8 mg) were added at 0° C. and stirred at room temperature for 2 days. Ice was added to the reaction solution, and the mixture was extracted with diethyl ether. The organic layer was sequentially washed with water three times and with saturated brine, and dried over anhydrous sodium sulfate. The solvent was distilled off under reduced pressure, and the residue obtained was subjected to silica gel column chromatography (hexane/ethyl acetate) and then amino silica gel column chromatography (hexane/ethyl acetate) to obtain a mixture (518 mg) containing the title compound as an oil.

MS (m/z): 488 (M+H)$^+$.

(Step 9) (3S,4S)-4-Fluoro-3-[(triethylsilyl)oxy]-D-proline

To a solution of the compound (518 mg) obtained in Step 8 above in ethanol (10 mL), 20% palladium hydroxide (202 mg) was added and stirred for 1 hour under a hydrogen atmosphere. The reaction solution was filtered through celite and the solvent was distilled off under reduced pressure to obtain a mixture (269 mg) containing the title compound as a solid.

(Step 10) (3S,4S)-1-[(Benzyloxy)carbonyl]-4-fluoro-3-[(triethylsilyl)oxy]-D-proline The compound (269 mg) obtained in Step 9 above was subjected to the same procedure as in Step 1 of Example B-3 to obtain the title compound (240 mg) as an oil.

$^1$H-NMR (CDCl$_3$) δ: 0.57-0.73 (6H, m), 0.88-1.05 (9H, m), 3.74-3.97 (2H, m), 4.31-4.47 (1H, m), 4.55-4.91 (2H, m), 5.10-5.28 (2H, m), 7.24-7.41 (5H, m). MS (m/z): 396 (M−H)$^-$.

(Step 11) tert-Butyl 5-({(3S,4S)-1-[(benzyloxy)carbonyl]-4-fluoro-3-[(triethylsilyl)oxy]-D-prolyl}amino)-1H-pyrazolo[4,3-b]pyridine-1-carboxylate To a mixture of the compound (136 mg) obtained in Step 10 above, the compound (160 mg) obtained in Reference Example A-6 and pyridine (1.7 mL), phosphoryl chloride (0.0625 mL) was added at 0° C. and stirred at 0° C. for 30 minutes. The reaction solution was diluted with diethyl ether, a 10% aqueous citric acid solution was added, and then the mixture was extracted with diethyl ether. The organic layer was sequentially washed with a 10% aqueous citric acid solution three times, with water, and with saturated brine, and dried over anhydrous sodium sulfate. The solvent was distilled off under reduced pressure, and the residue obtained was subjected to silica gel column chromatography (hexane/ethyl acetate) to obtain the title compound (132 mg) as an oil.

$^1$H-NMR (CDCl$_3$) δ: 0.69 (6H, q, J=7.8 Hz), 0.97 (9H, t, J=7.8 Hz), 1.73 (9H, s), 3.73-4.06 (2H, m), 4.28-4.99 (3H, m), 5.00-5.50 (2H, m), 7.01-7.49 (5H, m), 8.18-8.25 (1H, m), 8.38-8.53 (2H, m), 8.53-9.00 (1H, m). MS (m/z): 614 (M+H)$^+$.

(Step 12) tert-Butyl 5-({(3S,4S)-4-fluoro-3-[(triethylsilyl)oxy]-D-prolyl}amino)-1H-pyrazolo[4,3-b]pyridine-1-carboxylate The compound (269 mg) obtained in Step 11 above was subjected to the same procedure as in Step 2 of Reference Example A-3 to obtain the title compound (150 mg) as a solid.

$^1$H-NMR (CDCl$_3$) δ: 0.71 (6H, q, J=7.8 Hz), 1.01 (9H, t, J=7.8 Hz), 1.72 (9H, s), 2.43-2.55 (1H, m), 3.30-3.63 (2H, m), 3.79-3.86 (1H, m), 4.66-4.94 (2H, m), 8.22 (1H, s), 8.43 (1H, d, J=9.1 Hz), 8.55 (1H, d, J=9.1 Hz), 10.34 (1H, s). MS (m/z): 480 (M+H)$^+$.

Reference Example B-4

(3S)-3-Hydroxy-N-1H-indazol-4-yl-D-prolinamide hydrochloride

[Formula 53]

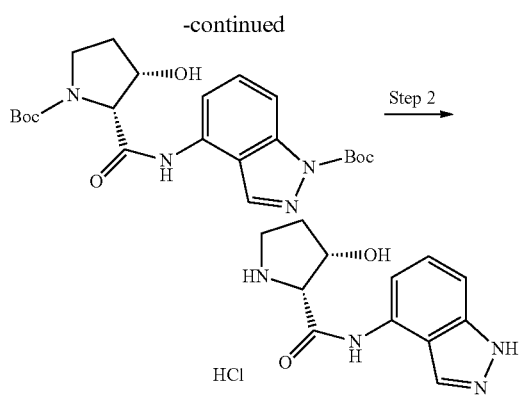

(Step 1) tert-Butyl 4-{[(3S)-1-(tert-butoxycarbonyl)-3-hydroxy-D-prolyl]amino}-1H-indazole-1-carboxylate To a mixture of (3S)-1-(tert-butoxycarbonyl)-3-hydroxy-D-proline (545 mg), the compound (500 mg) obtained in Reference Example A-2, and dichloromethane (12 mL), 1-(3-dimethylaminopropyl)-3-ethylcarbodiimide hydrochloride (453 mg) was added at 0° C. and stirred at room temperature for 16 hours. Water was added to the reaction solution, and the mixture was extracted with ethyl acetate. The organic layer was washed with saturated brine and dried over anhydrous sodium sulfate. The solvent was distilled off under reduced pressure, and the residue obtained was subjected to silica gel column chromatography (hexane/ethyl acetate) to obtain the title compound (800 mg) as a solid.

$^1$H-NMR (CDCl$_3$) δ: 1.52 (9H, s), 1.73 (9H, s), 2.12-2.28 (2H, m), 3.37-3.65 (2H, m), 4.45-4.61 (2H, m), 4.93-5.10 (1H, m), 7.47-7.53 (1H, m), 7.88-8.08 (2H, m), 8.32-8.41 (1H, m), 10.62 (1H, br s).

(Step 2) (3S)-3-Hydroxy-N-1H-indazol-4-yl-D-prolinamide hydrochloride

The compound (400 mg) obtained in Step 1 above was subjected to the same procedure as in Step 3 of Reference Example A-9 to obtain the title compound (324 mg) as a solid.

$^1$H-NMR (CD$_3$OD) δ: 2.15-2.24 (1H, m), 2.28-2.39 (1H, m), 3.45-3.54 (1H, m), 3.59-3.68 (1H, m), 4.54-4.57 (1H, m), 4.92-4.97 (1H, m), 7.39-7.51 (2H, m), 7.53-7.57 (1H, m), 8.43 (1H, s). MS (m/z): 247 (M+H—HCl)$^+$.

Reference Example B-5 tert-Butyl 5-[(N-methyl-D-alanyl)amino]-1H-pyrazolo[4,3-b]pyridine-1-carboxylate

[Formula 54]

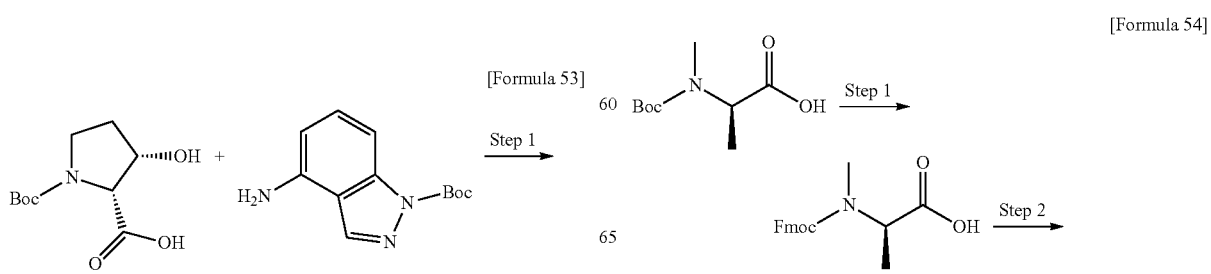

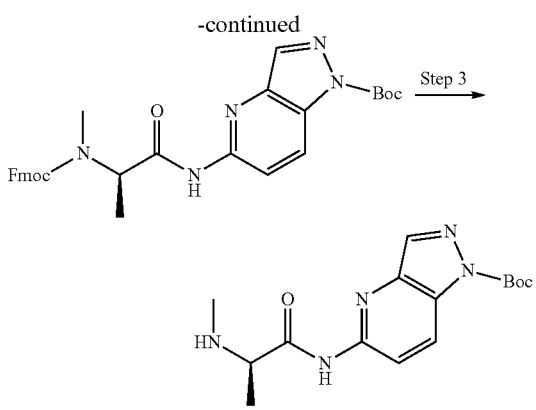

(Step 1) N-[(9H-Fluoren-9-ylmethoxy)carbonyl]-N-methyl-D-alanine

N-(tert-Butoxycarbonyl)-N-methyl-D-alanine (3.00 g) was subjected to the same procedure as in Step 1 of Reference Example B-2 to obtain the title compound (4.10 g) as a solid.

$^1$H-NMR (DMSO-D$_6$) δ: 1.29 (3H, d, J=7.3 Hz), 2.50 (3H, d, J=1.8 Hz), 4.23-4.35 (3H, m), 4.52-4.60 (1H, m), 7.29-7.44 (4H, m), 7.61-7.67 (2H, m), 7.90 (2H, d, J=7.3 Hz), 12.76-12.78 (1H, m).

(Step 2) tert-Butyl 5-({N-[(9H-fluoren-9-ylmethoxy)carbonyl]-N-methyl-D-alanyl}amino)-1H-pyrazolo[4,3-b]pyridine-1-carboxylate After ice-cooling a solution of the compound (0.200 g) obtained in Step 1 above in tetrahydrofuran (5.00 mL), 1-chloro-N,N,2-trimethyl-1-propenylamine (0.136 mL) was added and stirred at the same temperature for 2 hours. To a solution of the compound (0.120 g) obtained in Reference Example A-6 in tetrahydrofuran (10.0 mL), sodium hydrogen carbonate (0.131 g) was added and ice-cooled, and then the above reaction solution was added dropwise, stirred at the same temperature for 5 hours, and then allowed to stand in a refrigerator overnight. A 10% aqueous citric acid solution was added to the reaction solution, and the mixture was extracted with ethyl acetate three times, and the organic layer was washed with a saturated aqueous sodium hydrogen carbonate solution and with saturated brine and dried over anhydrous sodium sulfate. After filtration and concentration under reduced pressure, the residue obtained was purified by silica gel column chromatography (hexane/ethyl acetate) to obtain the title compound (0.272 g) as a solid.

$^1$H-NMR (DMSO-D$_6$, 100° C.) δ: 1.42 (3H, d, J=7.1 Hz), 1.66 (9H, s), 2.89 (3H, s), 4.24-4.28 (1H, m), 4.33-4.37 (2H, m), 4.85 (1H, q, J=7.1 Hz), 7.25 (2H, s), 7.34-7.39 (2H, m), 7.62 (2H, d, J=7.3 Hz), 7.83 (2H, d, J=7.3 Hz), 8.25 (1H, d, J=9.1 Hz), 8.37-8.41 (2H, m), 10.40 (1H, s). MS (m/z): 542 (M+H)$^+$.

(Step 3) tert-Butyl 5-[(N-methyl-D-alanyl)amino]-1H-pyrazolo[4,3-b]pyridine-1-carboxylate The compound (0.265 g) obtained in Step 2 above was subjected to the same procedure as in Step 4 of Reference Example B-2 to obtain the title compound (0.133 g) as a solid.

$^1$H-NMR (CDCl$_3$) δ: 1.42 (3H, d, J=6.9 Hz), 1.57 (1H, s), 1.73 (9H, s), 2.50 (3H, s), 3.23 (1H, q, J=6.9 Hz), 8.23 (1H, s), 8.45 (1H, d, J=9.1 Hz), 8.56 (1H, d, J=9.1 Hz), 10.03 (1H, s). MS (m/z): 320 (M+H)$^+$.

Reference Example B-6 tert-Butyl 5-{[(4R)-4-fluoro-D-prolyl]amino}-1H-pyrrolo[3,2-b]pyridine-1-carboxylate

[Formula 55]

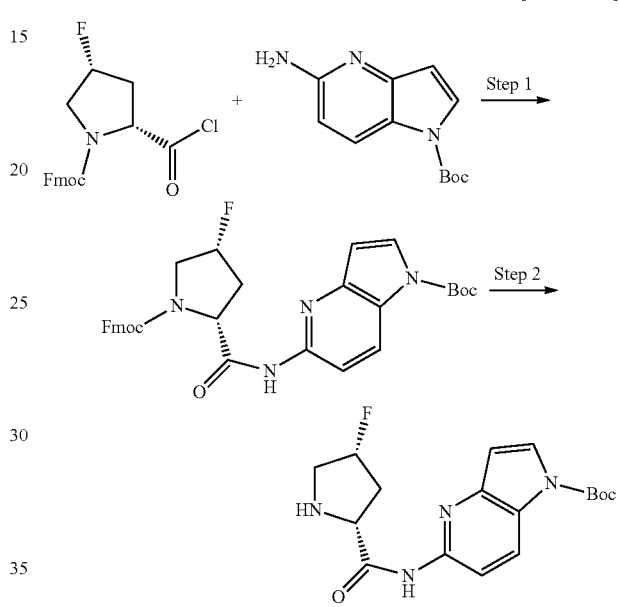

(Step 1) tert-Butyl 5-({(4R)-1-[(9H-fluoren-9-ylmethoxy)carbonyl]-4-fluoro-D-prolyl}amino)-1H-pyrrolo[3,2-b]pyridine-1-carboxylate To a solution of the compound (445 mg) obtained in Step 2 of Reference Example B-2 and N,N-diisopropylethylamine (270 μL) in dichloromethane (10 mL), the compound (292 mg) obtained in Reference Example A-8 was added and stirred at room temperature for 3 hours. Ethyl acetate was added to the residue obtained by concentrating the reaction mixture, and the resulting solid was collected by filtration to obtain the title compound (415 mg) as a solid.

$^1$H-NMR (DMSO-D$_6$) δ: 1.64 (9H, s), 2.36 (1H, dd, J=20.8, 14.6 Hz), 2.51-2.68 (1H, m), 3.65-3.84 (2H, m), 4.24 (1H, br s), 4.32 (2H, d, J=6.1 Hz), 4.65 (1H, d, J=9.8 Hz), 5.31 (1H, d, J=53.7 Hz), 6.67 (1H, d, J=3.7 Hz), 7.09-7.41 (4H, m), 7.63 (2H, d, J=6.7 Hz), 7.82 (2H, br s), 7.89 (1H, d, J=3.7 Hz), 8.03 (1H, d, J=8.5 Hz), 8.30 (1H, d, J=9.2 Hz), 10.10 (1H, br s).

MS (m/z): 571 (M+H)$^+$.

(Step 2) tert-Butyl 5-{[(4R)-4-fluoro-D-prolyl]amino}-1H-pyrrolo[3,2-b]pyridine-1-carboxylate The compound (365 mg) obtained in Step 1 above was subjected to the same procedure as in Step 4 of Reference Example B-2 to obtain the title compound (246 mg) as a solid.

¹H-NMR (CDCl₃) δ: 1.68 (9H, s), 2.25-2.46 (2H, m), 2.63 (1H, dd, J=21.4, 14.0 Hz), 3.28 (1H, ddd, J=36.0, 12.2, 3.7 Hz), 3.47 (1H, dd, J=21.4, 12.2 Hz), 4.03 (1H, d, J=10.4 Hz), 5.23 (1H, d, J=53.1 Hz), 6.63 (1H, d, J=3.7 Hz), 7.80 (1H, br s), 8.28 (1H, d, J=9.2 Hz), 8.34 (1H, br s), 10.16 (1H, br s). MS (m/z): 349 (M+H)⁺.

Reference Example B-7

Benzyl 6-{[(4R)-4-fluoro-D-prolyl]amino}-1H-pyrrolo[2,3-b]pyridine-1-carboxylate

[Formula 56]

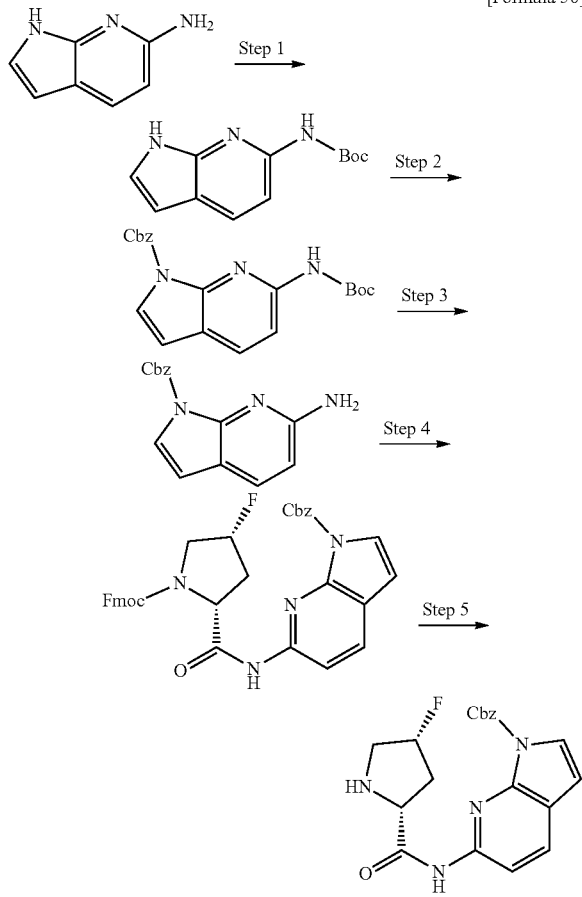

(Step 1) tert-Butyl 1H-pyrrolo[2,3-b]pyridin-6-ylcarbamate

To a mixture of 1H-pyrrolo[2,3-b]pyridin-6-amine (1.00 g), sodium carbonate (1.89 g), water (40 mL), and 1,4-dioxane (40 mL), di-tert-butyl dicarbonate (1.72 g) was added and stirred at room temperature for 84 hours. The organic layer obtained by diluting the mixed reaction solution with ethyl acetate, adding water and extracting with ethyl acetate was washed with saturated brine and dried over anhydrous sodium sulfate, and the solvent was distilled off under reduced pressure. The residue obtained was purified by silica gel column chromatography (hexane/ethyl acetate) to obtain the title compound (0.269 g) as a solid.

¹H-NMR (DMSO-D₆) δ: 1.48 (9H, s), 6.33-6.35 (1H, m), 7.24-7.27 (1H, m), 7.51 (1H, d, J=8.5 Hz), 7.86 (1H, dd, J=8.5, 2.4 Hz), 9.47 (1H, br s), 11.37 (1H, br s).
MS (m/z): 234 (M+H)⁺.

(Step 2) Benzyl 6-[(tert-butoxycarbonyl)amino]-1H-pyrrolo[2,3-b]pyridine-1-carboxylate The compound (357 mg) obtained in Step 1 above was subjected to the same procedure as in Step 2 of Reference Example A-1 to obtain the title compound (438 mg) as a solid.

¹H-NMR (CDCl₃) δ:1.50 (9H, s), 5.45 (2H, s), 6.48 (1H, d, J=3.7 Hz), 7.34-7.41 (3H, m), 7.49-7.52 (2H, m), 7.56 (2H, d, J=4.3 Hz), 7.84 (1H, d, J=8.5 Hz), 7.91 (1H, d, J=8.5 Hz). MS (m/z): 368 (M+H)⁺.

(Step 3) Benzyl 6-amino-1H-pyrrolo[2,3-b]pyridine-1-carboxylate

To the compound (437 mg) obtained in Step 2 above, hydrogen chloride (4 mol/L, 1,4-dioxane solution, 3 mL) was added at room temperature. After stirring at the same temperature for 15 hours, the mixed reaction solution was concentrated and diluted with water, and neutralized with a saturated aqueous sodium hydrogen carbonate solution. The organic layer was extracted by adding chloroform to the mixed solution, dried over sodium sulfate, and the solvent was distilled off under reduced pressure to obtain the title compound (282 mg) as a solid.

¹H-NMR (DMSO-D₆) δ: 5.43 (2H, s), 6.03 (2H, br s), 6.44 (1H, d, J=8.5 Hz), 6.46 (1H, d, J=4.3 Hz), 7.33-7.38 (2H, m), 7.43 (2H, t, J=7.6 Hz), 7.55 (2H, d, J=7.9 Hz), 7.62 (1H, d, J=8.5 Hz). MS (m/z): 268 (M+H)⁺.

(Step 4) Benzyl 6-({(4R)-1-[(9H-fluoren-9-ylmethoxy)carbonyl]-4-fluoro-D-prolyl}amino)-1H-pyrrolo[2,3-b]pyridine-1-carboxylate The compound (380 mg) obtained in Step 2 of Reference Example B-2 and the compound (285 mg) obtained in Step 3 above were subjected to the same procedure as in Step 1 of Reference Example B-6 to obtain the title compound (529 mg) as a solid.

¹H-NMR (DMSO-D₆) δ: 2.35 (1H, dd, J=21.4, 14.6 Hz), 2.52-2.71 (1H, m), 3.62-3.64 (2H, m), 3.04-3.12 (2H, m), 4.22 (1H, br s), 4.31 (2H, d, J=6.7 Hz), 4.78 (1H, br s), 5.31 (1H, d, J=53.7 Hz), 5.45 (2H, s), 6.67 (1H, d, J=4.3 Hz), 7.20 (1H, br s), 7.28-7.41 (4H, m), 7.51 (2H, d, J=6.7 Hz), 7.62 (2H, t, J=6.7 Hz), 7.69 (1H, d, J=4.3 Hz), 7.79 (2H, br s), 7.97 (1H, br s), 8.02 (1H, d, J=7.9 Hz), 10.02 (1H, s). MS (m/z): 605 (M+H)⁺.

(Step 5) Benzyl 6-{[(4R)-4-fluoro-D-prolyl]amino}-1H-pyrrolo[2,3-b]pyridine-1-carboxylate The compound (528 mg) obtained in Step 4 above was subjected to the same procedure as in Step 4 of Reference Example B-2 to obtain the title compound (232 mg) as a solid.

¹H-NMR (CDCl₃) δ: 2.25-2.43 (1H, m), 2.63 (1H, dd, J=20.8, 14.0 Hz), 2.78 (1H, br s), 3.28 (1H, ddd, J=36.6, 12.2, 3.7 Hz), 3.47 (1H, dd, J=22.0, 12.2 Hz), 4.06 (1H, dd, J=10.4, 2.4 Hz), 5.23 (1H, d, J=53.1 Hz), 5.48 (2H, d, J=3.7 Hz), 6.51 (1H, d, J=3.7 Hz), 7.34-7.45 (3H, m), 7.54 (2H, d, J=7.3 Hz), 7.61 (1H, d, J=4.3 Hz), 7.88 (1H, d, J=8.5 Hz), 8.31 (1H, d, J=8.5 Hz), 10.31 (1H, br s). MS (m/z): 383 (M+H)⁺.

Reference Example B-8 tert-Butyl 5-({O-[tert-butyl(diphenyl)silyl]-N-methyl-D-homoseryl}amino)-1H-pyrazolo[4,3-b]pyridine-1-carboxylate

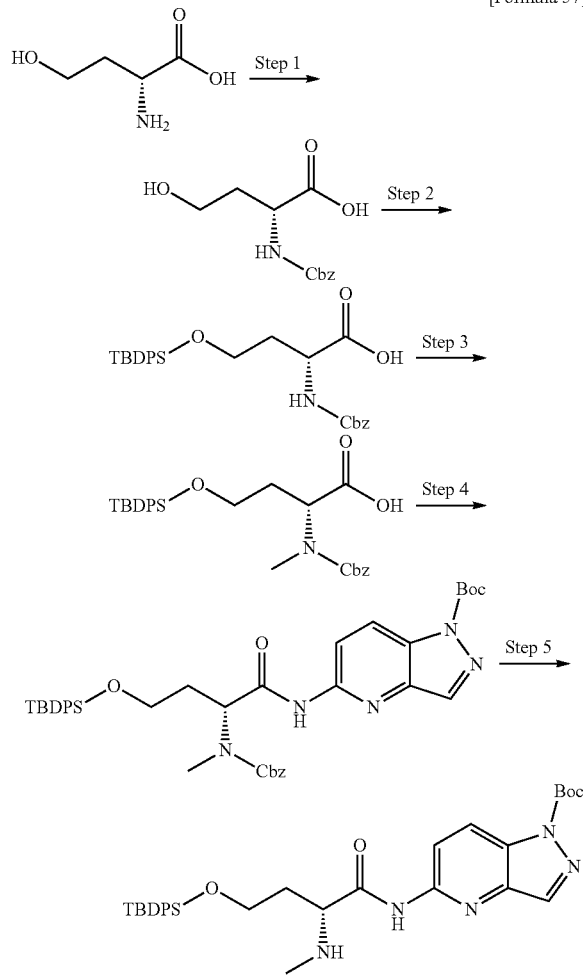

[Formula 57]

(Step 1) N-[(Benzyloxy)carbonyl]-D-homoserine

D-homoserine (10.0 g) was subjected to the same procedure as in Step 1 of Reference Example B-3 to obtain the title compound (5.33 g) as a solid.

$^1$H-NMR (CD$_3$OD) δ: 1.77-1.90 (1H, m), 1.99-2.15 (1H, m), 3.58-3.71 (2H, m), 4.26-4.36 (1H, m), 5.09 (2H, s), 7.27-7.37 (5H, m). MS (m/z): 252 (M−H)$^-$.

(Step 2) N-[(Benzyloxy)carbonyl]-O-[tert-butyl(diphenyl)silyl]-D-homoserine

To a solution of the compound (5.30 g) obtained in Step 1 above in N,N-dimethylformamide (24 mL), imidazole (5.01 g) and tert-butyldiphenylchlorosilane (5.40 mL) were added at 0° C. and stirred at room temperature overnight. Ice and a 10% aqueous citric acid solution were added to the reaction solution, and the mixture was extracted with diethyl ether. The organic layer was washed with saturated brine and dried over anhydrous sodium sulfate. The solvent was distilled off under reduced pressure, and the residue obtained was subjected to silica gel column chromatography (hexane/ethyl acetate) to obtain the title compound (7.84 g) as an oil.

$^1$H-NMR (CDCl$_3$) δ: 1.04 (9H, s), 2.00-2.23 (2H, m), 3.73-3.87 (2H, m), 4.48-4.56 (1H, m), 5.09-5.17 (2H, m), 6.11-6.16 (1H, m), 7.28-7.47 (11H, m), 7.60-7.67 (4H, m). MS (m/z): 490 (M−H)$^-$.

(Step 3) N-[(Benzyloxy)carbonyl]-O-[tert-butyl(diphenyl)silyl]-N-methyl-D-homoserine To a solution of the compound (3.32 g) obtained in Step 2 above in tetrahydrofuran (20 mL), iodomethane (4.2 mL) and sodium hydride (purity>55%, 1.62 g) were added at 0° C. and stirred at room temperature overnight. The reaction solution was acidified by adding dropwise 6 mol/L hydrochloric acid at 0° C. and extracted with diethyl ether. The organic layer was sequentially washed with water and with saturated brine and dried over anhydrous sodium sulfate. The solvent was distilled off under reduced pressure, and the residue obtained was subjected to silica gel column chromatography (dichloromethane/methanol) to obtain the title compound (3.27 g) as an oil.

$^1$H-NMR (CDCl$_3$) δ: 0.95-1.09 (9H, m), 1.87-2.09 (1H, m), 2.14-2.37 (1H, m), 2.88-2.93 (3H, m), 3.63-3.77 (2H, m), 4.84-4.91 (1H, m), 5.02-5.23 (2H, m), 7.27-7.47 (11H, m), 7.59-7.68 (4H, m). MS (m/z): 504 (M−H)$^-$.

(Step 4) tert-Butyl 5-({N-[(benzyloxy)carbonyl]-O-[tert-butyl(diphenyl)silyl]-N-methyl-D-homoseryl}amino)-1H-pyrazolo[4,3-b]pyridine-1-carboxylate The compound (689 mg) obtained in Step 3 above and the compound (638 mg) obtained in Reference Example A-6 were subjected to the same procedure as in Step 11 of Reference Example B-3 to obtain the title compound (899 mg) as a solid.

(Step 5) tert-Butyl 5-({O-[tert-butyl(diphenyl)silyl]-N-methyl-D-homoseryl}amino)-1H-pyrazolo[4,3-b]pyridine-1-carboxylate To a solution of the compound (883 mg) obtained in Step 4 above in ethanol (15 mL), 20% palladium hydroxide (511 mg) was added and stirred for 45 minutes under a hydrogen atmosphere. The residue obtained by filtering the reaction solution through celite and distilling off the solvent under reduced pressure was subjected to silica gel column chromatography (hexane/ethyl acetate) to obtain the title compound (645 mg) as a solid.

$^1$H-NMR (CDCl$_3$) δ: 1.06 (9H, s), 1.74 (9H, s), 1.83-1.96 (1H, m), 2.01-2.13 (1H, m), 2.42-2.51 (1H, m), 2.48 (3H, s), 3.25-3.34 (1H, m), 3.81-3.92 (2H, m), 7.32-7.46 (6H, m), 7.62-7.70 (4H, m), 8.24 (1H, s), 8.44 (1H, d, J=9.1 Hz), 8.55 (1H, d, J=9.1 Hz), 10.21 (1H, s). MS (m/z): 588 (M+H)$^+$.

Reference Example B-9 tert-Butyl 5-({(3R)-3-[(triethylsilyl)oxy]-D-prolyl}amino)-1H-pyrrolo[3,2-b]pyridine-1-carboxylate

[Formula 58]

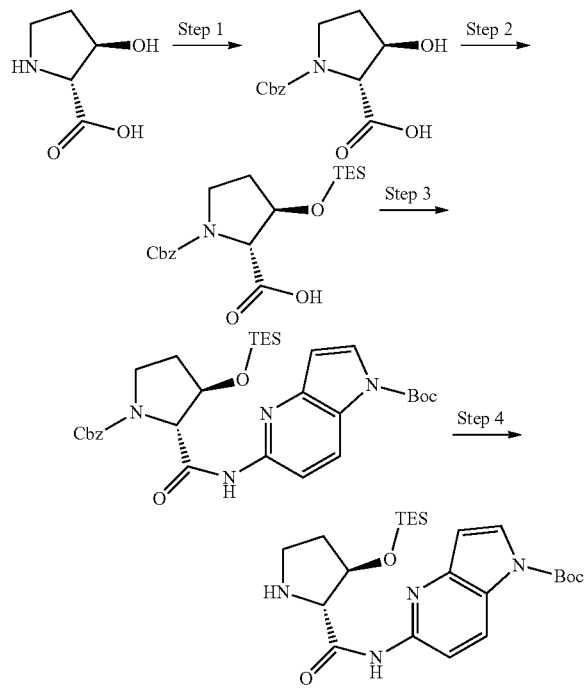

(Step 1) (3R)-1-[(Benzyloxy)carbonyl]-3-hydroxy-D-proline (3R)-3-Hydroxy-D-proline (J. Org. Chem., 61, 566-572 (1996); 1.00 g) was subjected to the same procedure as in Step 1 of Reference Example B-3 to obtain the title compound (1.72 g) as a solid.
$^1$H-NMR (CD$_3$OD) S: 1.84-1.96 (1H, m), 1.99-2.12 (1H, m), 3.55-3.69 (2H, m), 4.23-4.25 (1H, m), 4.39-4.46 (1H, m), 5.05-5.16 (2H, m), 7.24-7.42 (5H, m).

(Step 2) (3R)-1-[(Benzyloxy)carbonyl]-3-[(triethylsilyl)oxy]-D-proline

To a mixture of the compound (0.914 g) obtained in Step 1 above, imidazole (0.587 g), N,N-dimethylformamide (2.2 mL) and dichloromethane (11 mL), chlorotriethylsilane (1.46 mL) was added dropwise at 0° C. and stirred at room temperature for 16 hours. The solvent was concentrated under reduced pressure, and then ice and a 1 mol/L aqueous citric acid solution were added, and the mixture was extracted with ethyl acetate. The organic layer was sequentially washed with water and with saturated brine and dried over anhydrous sodium sulfate. The solvent was distilled off under reduced pressure, and the residue obtained was subjected to silica gel column chromatography (dichloromethane/methanol) to obtain the title compound (1.10 g) as an oil. The present compound was immediately used for the next reaction.

(Step 3) tert-Butyl 5-({(3R)-1-[(benzyloxy)carbonyl]-3-[(triethylsilyl)oxy]-D-prolyl}amino)-1H-pyrrolo[3,2-b]pyridine-1-carboxylate The compound (305 mg) obtained in Step 2 above and the compound (376 mg) obtained in Reference Example A-8 were subjected to the same procedure as in Step 11 of Reference Example B-3 to obtain the title compound (324 mg) as a solid.
$^1$H-NMR (CDCl$_3$) δ: 0.64 (6H, q, J=7.9 Hz), 0.96 (9H, t, J=7.9 Hz), 1.68 (9H, s), 1.84-1.95 (1H, m), 1.98-2.16 (1H, m), 3.53-3.88 (2H, m), 4.21-4.48 (1H, m), 4.56-4.83 (1H, m), 5.02-5.36 (2H, m), 6.55-6.65 (1H, m), 7.07-7.46 (5H, m), 7.72-7.86 (1H, m), 8.15-8.23 (1H, m), 8.29-9.07 (2H, m). MS (m/z): 595 (M+H)$^+$.

(Step 4) tert-Butyl 5-({(3R)-3-[(triethylsilyl)oxy]-D-prolyl}amino)-1H-pyrrolo[3,2-b]pyridine-1-carboxylate The compound (320 mg) obtained in Step 3 above was subjected to the same procedure as in Step 2 of Reference Example A-3 to obtain the title compound quantitatively as an oil.
$^1$H-NMR (CDCl$_3$) δ: 0.68 (6H, q, J=7.9 Hz), 1.00 (9H, t, J=7.9 Hz), 1.59-1.86 (2H, m), 1.67 (9H, s), 2.34-2.47 (1H, m), 3.09-3.18 (1H, m), 3.28-3.38 (1H, m), 3.72-3.77 (1H, m), 4.64-4.69 (1H, m), 6.59-6.65 (1H, m), 7.72-7.84 (1H, m), 8.24-8.41 (2H, m), 10.28 (1H, s). MS (m/z): 461 (M+H)$^+$.

Reference Example B-10 tert-Butyl 5-({O-[tert-butyl(diphenyl)silyl]-N—($^2$H$_3$)methyl-D-seryl}amino)-1H-pyrazolo[4,3-b]pyridine-1-carboxylate

[Formula 59]

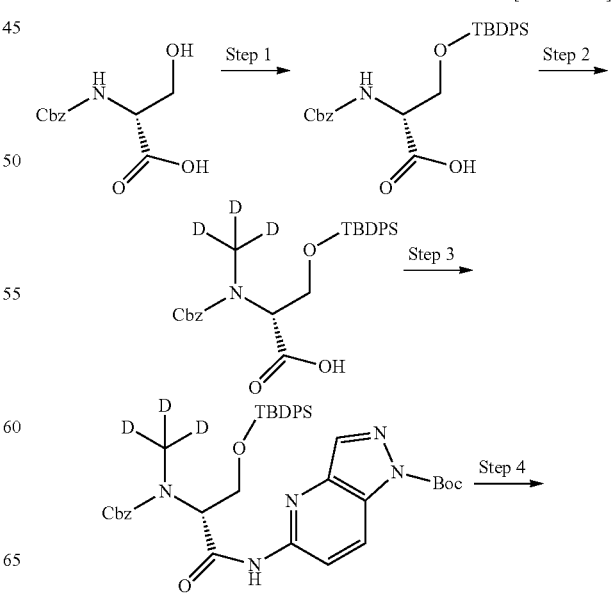

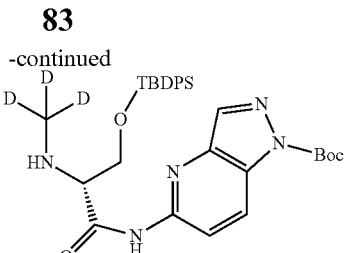

(Step 1) N-[(Benzyloxy)carbonyl]-O-[tert-butyl(diphenyl)silyl]-D-serine

N-[(Benzyloxy)carbonyl]-D-serine (4.01 g) was subjected to the same procedure as in Step 2 of Reference Example B-8 to obtain the title compound (7.54 g) as an oil.
$^1$H-NMR (CDCl$_3$) δ: 1.03 (9H, s), 3.82-3.97 (1H, m), 4.06-4.19 (1H, m), 4.41-4.55 (1H, m), 5.12 (2H, s), 5.52-5.69 (1H, m), 7.29-7.47 (11H, m), 7.55-7.66 (4H, m).
MS (m/z): 476 (M−H)$^−$.

(Step 2) N-[(Benzyloxy)carbonyl]-O-[tert-butyl(diphenyl)silyl]-N—($^2$H$_3$)methyl-D-serine To a solution of the compound (2.01 g) obtained in Step 1 above in tetrahydrofuran (28 mL), iodo($^2$H$_3$)methane (2.61 mL) was added, then sodium hydride (purity>55%, 0.921 g) was added at 0° C., and stirred at room temperature for 16 hours. The reaction solution was acidified by adding dropwise 6 mol/L hydrochloric acid at 0° C. and extracted with diethyl ether. The organic layer was sequentially washed with water and with saturated brine and dried over anhydrous sodium sulfate. The solvent was distilled off under reduced pressure, and the residue obtained was subjected to silica gel column chromatography (dichloromethane/methanol) to obtain the title compound (1.90 g) as an oil.
$^1$H-NMR (CDCl$_3$) δ: 1.03 (9H, s), 3.91-4.14 (2H, m), 4.68-4.93 (1H, m), 5.01-5.23 (2H, m), 7.27-7.48 (11H, m), 7.57-7.69 (4H, m). MS (m/z): 495 (M+H)$^+$.

(Step 3) tert-Butyl 5-({N-[(benzyloxy)carbonyl]-O-[tert-butyl(diphenyl)silyl]-N—($^2$H$_3$)methyl-D-seryl}amino)-1H-pyrazolo[4,3-b]pyridine-1-carboxylate The compound (813 mg) obtained in Step 2 above and the compound (770 mg) obtained in Reference Example A-6 were subjected to the same procedure as in Step 11 of Reference Example B-3 to obtain the title compound quantitatively as a solid.
$^1$H-NMR (CDCl$_3$) δ: 1.07 (9H, s), 1.73 (9H, s), 3.95-4.09 (1H, m), 4.20-4.34 (1H, m), 4.66-5.02 (1H, m), 5.06-5.28 (2H, m), 7.17-7.50 (11H, m), 7.57-7.75 (4H, m), 8.11-8.25 (1H, m), 8.33-8.49 (2H, m), 8.82-9.10 (1H, m). MS (m/z): 711 (M+H)$^+$.

(Step 4) tert-Butyl 5-({O-[tert-butyl(diphenyl)silyl]-N—($^2$H$_3$)methyl-D-seryl}amino)-1H-pyrazolo[4,3-b]pyridine-1-carboxylate The compound (550 mg) obtained in Step 3 above was subjected to the same procedure as in Step 5 of Reference Example B-8 to obtain the title compound (391 mg) as an oil.
$^1$H-NMR (CDCl$_3$) δ: 1.04 (9H, s), 1.73 (9H, s), 1.97-2.02 (1H, m), 3.19-3.27 (1H, m), 3.93-4.02 (2H, m), 7.33-7.48 (6H, m), 7.59-7.67 (4H, m), 8.20-8.24 (1H, m), 8.40-8.46 (1H, m), 8.49-8.55 (1H, m), 10.19 (1H, brs). MS (m/z): 577 (M+H)$^+$.

Reference Example B-11 tert-Butyl 5-({O-[tert-butyl(diphenyl)silyl]-N—($^2$H$_3$)methyl-D-seryl}amino)-1H-pyrrolo[3,2-b]pyridine-1-carboxylate

[Formula 60]

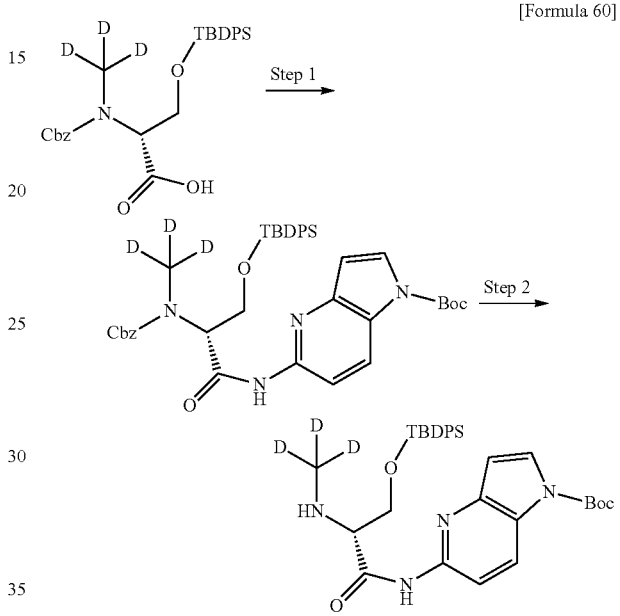

(Step 1) tert-Butyl 5-({N-[(benzyloxy)carbonyl]-O-[tert-butyl(diphenyl)silyl]-N—($^2$H$_3$)methyl-D-seryl}amino)-1H-pyrrolo[3,2-b]pyridine-1-carboxylate The compound (452 mg) obtained in Step 2 of Reference Example B-10 and the compound (427 mg) obtained in Reference Example A-8 were subjected to the same procedure as in Step 11 of Reference Example B-3 to obtain the title compound (593 mg) as a solid. Using Daicel Corporation Chiral Column IA, HPLC analysis (flow rate 1 mL/min, hexane:isopropanol=100:0 to 50:50) was carried out to confirm 99.4% ee.
$^1$H-NMR (CDCl$_3$) δ: 1.05 (9H, s), 1.67 (9H, s), 3.87-4.09 (1H, m), 4.18-4.34 (1H, m), 4.75-5.29 (3H, m), 6.52-6.67 (1H, m), 7.19-7.51 (11H, m), 7.53-7.73 (4H, m), 7.73-7.87 (1H, m), 8.03-8.19 (1H, m), 8.25-8.42 (1H, m), 8.54-8.82 (1H, m). MS (m/z): 710 (M+H)$^+$.

(Step 2) tert-Butyl 5-({O-[tert-butyl(diphenyl)silyl]-N—($^2$H3)methyl-D-seryl}amino)-1H-pyrrolo[3,2-b]pyridine-1-carboxylate The compound (590 mg) obtained in Step 1 above was subjected to the same procedure as in Step 5 of Reference Example B-8 to obtain the title compound (414 mg) as a solid.
$^1$H-NMR (CDCl$_3$) δ: 1.04 (9H, s), 1.68 (9H, s), 1.96-2.02 (1H, m), 3.21-3.26 (1H, m), 3.91-4.03 (2H, m), 6.61-6.64

(1H, m), 7.32-7.47 (6H, m), 7.60-7.67 (4H, m), 7.76-7.83 (1H, m), 8.22-8.27 (1H, m), 8.29-8.40 (1H, m), 10.02 (1H, br s). MS (m/z): 576 (M+H)⁺.

Reference Example B-12 tert-Butyl 5-({O-[tert-butyl(dimethyl)silyl]-N-methyl-D-allo-threonyl}amino)-1H-pyrazolo[4,3-b]pyridine-1-carboxylate

[Formula 61]

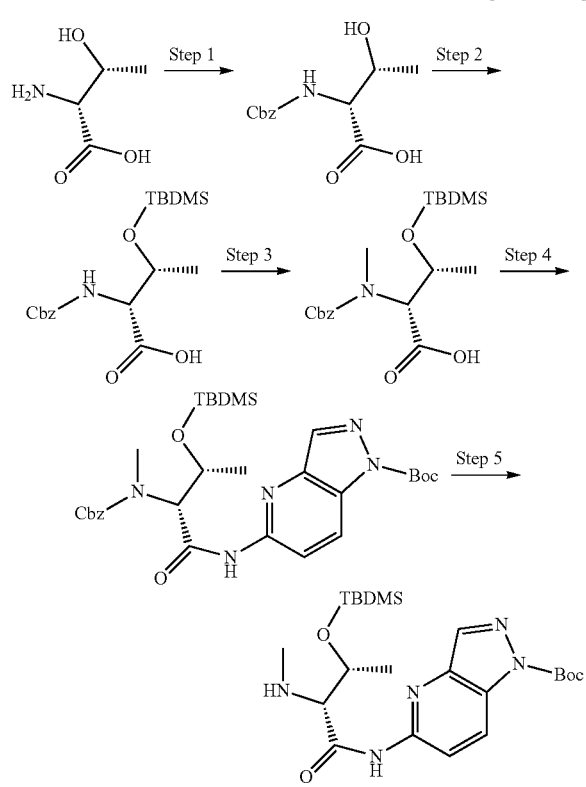

(Step 1) N-[(Benzyloxy)carbonyl]-D-allo-threonine

D-Allo-threonine (1.00 g) was subjected to the same procedure as in Step 1 of Reference Example B-3 to obtain the title compound (2.13 g) as an oil.
¹H-NMR (CDCl₃) δ: 1.29 (3H, dd, J=6.1, 4.3 Hz), 4.19 (1H, br s), 4.43 (1H, br s), 5.13 (2H, s), 5.74 (1H, br s), 7.30-7.41 (5H, m). MS (m/z): 254 (M+H)⁺.

(Step 2) N-[(Benzyloxy)carbonyl]-O-[tert-butyl(dimethyl)silyl]-D-allo-threonine

To a solution of the compound (2.13 g) obtained in Step 1 above and imidazole (1.14 g) in N,N-dimethylformamide (50 mL), tert-butyl chlorodimethylsilane (1.39 g) was added and stirred at room temperature for 65 hours. Water was added to the mixed reaction solution, and the mixture was neutralized with 1 mol/L hydrochloric acid and extracted with ethyl acetate. The combined organic layers were washed with saturated brine, dried over anhydrous sodium sulfate, and the solvent was distilled off under reduced pressure. The residue obtained was purified by silica gel column chromatography (hexane/ethyl acetate) to obtain the title compound (0.842 g) as a solid.
¹H-NMR (CDCl₃) δ: 0.04 (3H, s), 0.05 (3H, s), 0.85 (9H, s), 1.29 (3H, d, J=6.7 Hz), 2.01 (1H, s), 4.12-4.18 (1H, m), 4.34 (1H, dd, J=7.3, 3.1 Hz), 5.13 (2H, dd, J=16.5, 11.6 Hz), 5.48 (1H, d, J=7.9 Hz), 7.32-7.36 (5H, m). MS (m/z): 368 (M+H)⁺.

(Step 3) N-[(Benzyloxy)carbonyl]-O-[tert-butyl(dimethyl)silyl]-N-methyl-D-allo-threonine To a suspension of sodium hydride (purity>55%, 356 mg) in tetrahydrofuran (6 mL), the compound (300 mg) obtained in Step 2 above was added at 0° C. in small amounts. The suspension was stirred at the same temperature for 5 minutes, then iodomethane (508 μL) was added dropwise at 0° C. and stirred at room temperature for 17 hours. The mixed reaction solution was cooled again to 0° C., neutralized with 1 mol/L hydrochloric acid, and extracted with ethyl acetate. The organic layer was washed with saturated brine, dried over anhydrous sodium sulfate, and the solvent was distilled off under reduced pressure. The residue obtained was purified by silica gel column chromatography (hexane/ethyl acetate) to obtain the title compound (166 mg) as an oil.
¹H-NMR (CDCl₃) δ: 0.03-0.18 (6H, m), 0.88 (9H, s), 1.15-1.28 (3H, m), 2.97 (3H, s), 4.39-4.42 (2H, m), 5.16 (2H, d, J=2.4 Hz), 7.28-7.38 (5H, m). MS (m/z): 382 (M+H)⁺.

(Step 4) tert-Butyl 5-({N-[(benzyloxy)carbonyl]-O-[tert-butyl(dimethyl)silyl]-N-methyl-D-allo-threonyl}amino)-1H-pyrazolo[4,3-b]pyridine-1-carboxylate The compound (487 mg) obtained in Step 3 above and the compound (598 mg) obtained in Reference Example A-6 were subjected to the same procedure as in Step 11 of Reference Example B-3 to obtain the title compound (568 mg) as a solid.
¹H-NMR (DMSO-D₆) δ: −0.04 (3H, s), 0.06 (3H, s), 0.78 (9H, s), 1.16 (3H, d, J=6.1 Hz), 1.67 (9H, s), 2.98 (3H, s), 4.45 (1H, dd, J=8.5, 6.1 Hz), 4.66 (1H, d, J=8.5 Hz), 5.13 (2H, d, J=3.7 Hz), 7.25-7.38 (5H, m), 8.23 (1H, dd, J=28.7, 1.2 Hz), 8.28-8.39 (2H, m), 10.39 (1H, br s). MS (m/z): 598 (M+H)⁺.

(Step 5) tert-Butyl 5-({O-[tert-butyl(dimethyl)silyl]-N-methyl-D-allo-threonyl}amino)-1H-pyrazolo[4,3-b]pyridine-1-carboxylate The compound (558 mg) obtained in Step 4 above was subjected to the same procedure as in Step 9 of Reference Example B-3 to obtain the title compound (433 mg) as a MS (m/z): 464 (M+H)⁺.

Reference Example B-13 tert-Butyl 5-({O-[tert-butyl(dimethyl)silyl]-N-methyl-D-threonyl}amino)-1H-pyrazolo[4,3-b]pyridine-1-carboxylate

[Formula 62]

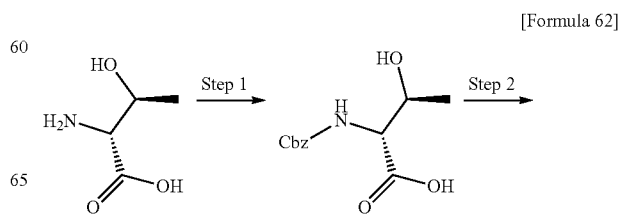

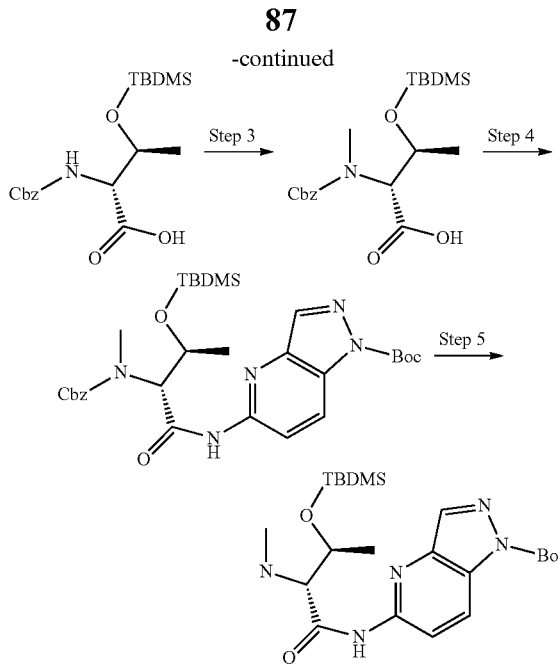

(Step 1) N-[(Benzyloxy)carbonyl]-D-threonine

D-Threonine (1.00 g) was subjected to the same procedure as in Step 1 of Reference Example B-3 to obtain the title compound (2.13 g) as an oil.

$^1$H-NMR (CDCl$_3$) δ: 1.24 (3H, d, J=6.7 Hz), 4.29-4.43 (2H, m), 5.13 (2H, s), 5.67 (1H, br s), 7.27-7.40 (5H, m).

(Step 2) N-[(Benzyloxy)carbonyl]-O-[tert-butyl(dimethyl)silyl]-D-threonine

The compound (2.13 g) obtained in Step 1 above was subjected to the same procedure as in Step 2 of Reference Example B-12 to obtain the title compound (1.41 g) as a solid.

$^1$H-NMR (CDCl$_3$) δ: 0.05-0.16 (6H, m), 0.89 (9H, s), 1.20 (3H, d, J=6.1 Hz), 1.98 (1H, s), 4.32 (1H, br s), 4.47 (1H, br s), 5.14 (2H, s), 5.52 (1H, br s), 7.30-7.40 (5H, m). MS (m/z): 368 (M+H)$^+$.

(Step 3) N-[(Benzyloxy)carbonyl]-O-[tert-butyl(dimethyl)silyl]-N-methyl-D-threonine The compound (1.41 g) obtained in Step 2 above was subjected to the same procedure as in Step 3 of Reference Example B-12 to obtain the title compound (1.09 g) as an oil.

$^1$H-NMR (CDCl$_3$) δ: 0.01-0.10 (6H, m), 0.85 (9H, s), 1.22 (3H, d, J=6.1 Hz), 1.98 (1H, s), 3.11 (3H, s), 4.46-4.62 (1H, m), 4.74-4.85 (1H, m), 5.15-5.18 (2H, m), 7.27-7.37 (5H, m). MS (m/z): 382 (M+H)$^+$.

(Step 4) tert-Butyl 5-({N-[(benzyloxy)carbonyl]-O-[tert-butyl(dimethyl)silyl]-N-methyl-D-threonyl}amino)-1H-pyrazolo[4,3-b]pyridine-1-carboxylate The compound (1.09 g) obtained in Step 3 above and the compound (1.33 g) obtained in Reference Example A-6 were subjected to the same procedure as in Step 11 of Reference Example B-3 to obtain the title compound (1.19 g) as a solid.

$^1$H-NMR (DMSO-D$_6$): −0.06 (3H, s), 0.05 (3H, s), 0.79 (9H, s), 1.21 (3H, d, J=6.7 Hz), 1.67 (9H, s), 3.14 (3H, s), 4.63 (1H, t, J=5.8 Hz), 4.89 (1H, d, J=5.5 Hz), 5.11 (2H, s), 7.23-7.36 (5H, m), 8.24 (1H, d, J=9.2 Hz), 8.36-8.39 (2H, m), 10.46 (1H, s). MS (m/z): 598 (M+H)$^+$.

(Step 5) tert-Butyl 5-({O-[tert-butyl(dimethyl)silyl]-N-methyl-D-threonyl}amino)-1H-pyrazolo[4,3-b]pyridine-1-carboxylate The compound (1.19 g) obtained in Step 4 above was subjected to the same procedure as in Step 9 of Reference Example B-3 to obtain the title compound (0.433 g) as a solid.

$^1$H-NMR (CDCl$_3$) δ: −0.01 (3H, s), 0.07 (3H, s), 0.84 (9H, s), 1.34 (3H, d, J=6.7 Hz), 1.73 (9H, s), 1.89-1.97 (1H, m), 2.65 (3H, s), 3.06-3.19 (1H, m), 4.51 (1H, br s), 8.23 (1H, s), 8.44 (1H, d, J=9.2 Hz), 8.54 (1H, d, J=9.2 Hz), 10.33 (1H, s). MS (m/z): 464 (M+H)$^+$.

Reference Example B-14 tert-Butyl 5-({[(2R,3R)-3-(methoxymethoxy)azetidin-2-yl]carbonyl}amino)-1H-pyrazolo[4,3-b]pyridine-1-carboxylate

[Formula 63]

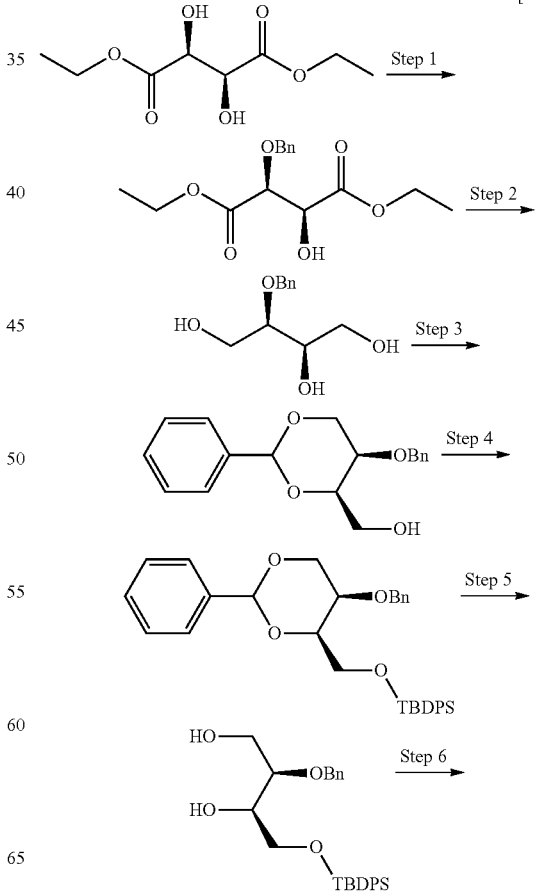

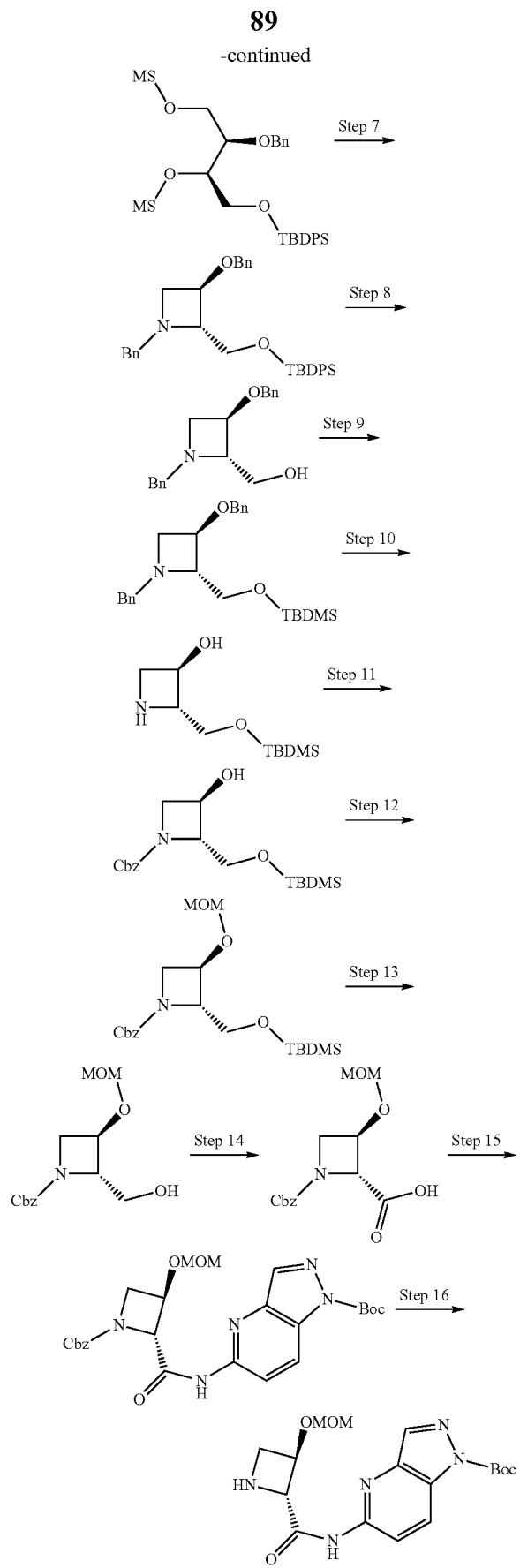

(Step 1) Diethyl (2S,3S)-2-(benzyloxy)-3-hydroxybutanedioate

To a solution of D-(−)-diethyl tartrate (24.8 g) in dichloromethane (500 mL), silver oxide(I) (41.9 g) and benzyl bromide (15.7 mL) were added, stirred at room temperature for 2 hours under shading and then allowed to stand for 14 hours. The residue obtained by filtering the reaction solution through celite and concentrating the filtrate under reduced pressure was subjected to silica gel column chromatography (hexane/ethyl acetate) to obtain the title compound (17.9 g) as an oil.

$^1$H-NMR (CDCl$_3$) δ: 1.18 (3H, t, J=7.0 Hz), 1.33 (3H, t, J=7.0 Hz), 3.12 (1H, d, J=8.5 Hz), 4.00-4.09 (1H, m), 4.18-4.35 (4H, m), 4.42 (1H, d, J=11.6 Hz), 4.56-4.60 (1H, m), 4.87 (1H, d, J=11.6 Hz), 7.24-7.39 (5H, m).

(Step 2) (2R,3R)-3-(Benzyloxy)butane-1,2,4-triol

To a suspension of lithium aluminum hydride (5.96 g) in tetrahydrofuran (200 mL), a solution of the compound (18.0 g) obtained in Step 1 above in tetrahydrofuran (50 mL) was added at 0° C., stirred at the same temperature for 30 minutes, at room temperature for 30 minutes and at 65° C. for 5 hours. The reaction solution was cooled to 0° C. and sodium sulfate decahydrate (100 g) was gradually added. The reaction mixture was diluted with tetrahydrofuran (100 mL), stirred at room temperature for 3 hours, and then allowed to stand for 16 hours. The residue obtained by filtering off insoluble matters and concentrating the filtrate under reduced pressure was subjected to silica gel column chromatography (ethyl acetate/methanol) to obtain the title compound (10.3 g) as a solid.

$^1$H-NMR (CDCl$_3$) δ: 2.25-2.35 (1H, m), 2.48-2.56 (1H, m), 2.78-2.83 (1H, m), 3.55-3.61 (1H, m), 3.63-3.81 (3H, m), 3.82-3.94 (2H, m), 4.60 (1H, d, J=11.5 Hz), 4.73 (1H, d, J=11.5 Hz), 7.30-7.42 (5H, m).

(Step 3) [(4R,5R)-5-(Benzyloxy)-2-phenyl-1,3-dioxan-4-yl]methanol

To a solution of the compound (10.2 g) obtained in Step 2 above in dichloromethane (150 mL), benzaldehyde (5.83 mL) and trifluoroacetic acid (0.517 mL) were added and stirred for 16 hours while heated to reflux. The residue obtained by concentrating the solvent under reduced pressure was subjected to silica gel column chromatography (hexane/ethyl acetate to ethyl acetate/methanol). The crude product obtained was diluted with ethyl acetate, washed sequentially with a saturated aqueous sodium hydrogen carbonate solution, with water and with saturated brine, and the solvent was distilled off under reduced pressure to obtain the title compound (8.19 g) as a solid.

$^1$H-NMR (CDCl$_3$) δ: 1.97 (1H, br s), 3.39-3.42 (1H, m), 3.65-3.77 (1H, m), 3.89-4.06 (3H, m), 4.45-4.53 (2H, m), 4.84 (1H, d, J=12.1 Hz), 5.61 (1H, s), 7.28-7.58 (10H, m). MS (m/z): 301 (M+H)$^+$.

(Step 4) {[(4R,5R)-5-(Benzyloxy)-2-phenyl-1,3-dioxan-4-yl]methoxy}(tert-butyl)diphenylsilane The compound (9.90 g) obtained in Step 3 above was subjected to the same procedure as in Step 2 of Reference Example B-8 to obtain the title compound (17.5 g) as a solid.

¹H-NMR (CDCl₃) δ: 1.06 (9H, s), 3.53-3.57 (1H, m), 3.84-4.16 (4H, m), 4.40-4.46 (1H, m), 4.59 (1H, d, J=12.1 Hz), 4.78 (1H, d, J=12.1 Hz), 5.56 (1H, s), 7.21-7.72 (20H, m).

(Step 5) (2R,3R)-2-(Benzyloxy)-4-{[tert-butyl(diphenyl)silyl]oxy}butane-1,3-diol A mixture of the compound (17.4 g) obtained in Step 4 above, acetic acid (200 mL), water (45 mL), and tetrahydrofuran (100 mL) was stirred at 40° C. for 30 minutes, then allowed to stand at room temperature for 2 days, and then stirred at 50° C. for 23 hours. The reaction solution was concentrated under reduced pressure and then neutralized by adding a 1 mol/L aqueous sodium hydroxide solution at 0° C. The reaction mixture was extracted with ethyl acetate and the organic layer was sequentially washed with a saturated aqueous sodium hydrogen carbonate solution and with saturated brine. The solvent was distilled off under reduced pressure, and the residue obtained was subjected to silica gel column chromatography (hexane/ethyl acetate) to obtain the title compound (9.37 g) as an oil.

¹H-NMR (CDCl₃) δ: 1.06 (9H, s), 2.23-2.28 (1H, m), 2.56-2.59 (1H, m), 3.66-3.91 (6H, m), 4.59 (1H, d, J=11.5 Hz), 4.68 (1H, d, J=11.5 Hz), 7.25-7.48 (11H, m), 7.62-7.68 (4H, m).

(Step 6) (2R,3R)-2-(Benzyloxy)-4-{[tert-butyl(diphenyl)silyl]oxy}-3-[(methylsulfonyl)oxy]butyl methanesulfonate To a solution of the compound (9.37 g) obtained in Step 5 above in dichloromethane (130 mL), triethylamine (11.5 mL), 4-dimethylaminopyridine (0.508 g), and methanesulfonyl chloride (4.86 mL) were added at 0° C. and stirred at room temperature for 2 hours. Ice was added to the reaction solution, and the mixture was extracted with dichloromethane. The organic layer was washed with saturated brine and dried over anhydrous sodium sulfate. The solvent was distilled off under reduced pressure, and the residue obtained was subjected to silica gel column chromatography (hexane/ethyl acetate) to obtain the title compound (12.5 g) as an oil.

¹H-NMR (CDCl₃) δ: 1.06 (9H, s), 2.94 (3H, s), 2.95 (3H, s), 3.84-3.95 (2H, m), 4.02-4.07 (1H, m), 4.28-4.34 (1H, m), 4.43-4.48 (1H, m), 4.58 (1H, d, J=11.5 Hz), 4.71 (1H, d, J=11.5 Hz), 4.75-4.80 (1H, m), 7.27-7.49 (11H, m), 7.60-7.67 (4H, m).

(Step 7) (2S,3R)-1-Benzyl-3-(benzyloxy)-2-({[tert-butyl(diphenyl)silyl]oxy}methyl)azetidine Benzylamine (65 mL) was added at 0° C. to the compound (12.5 g) obtained in Step 6 above and stirred at 100° C. for 16 hours. Ice was added to the reaction solution, and then the mixture was extracted with diethyl ether, and the organic layer was sequentially washed with water three times and with saturated brine and dried over anhydrous sodium sulfate. The solvent was distilled off under reduced pressure, and the residue obtained was subjected to silica gel column chromatography (hexane/ethyl acetate) and then amino silica gel column chromatography (hexane/ethyl acetate) to obtain the title compound (9.71 g) as an oil.

¹H-NMR (CDCl₃) δ: 1.04 (9H, s), 2.76-2.82 (1H, m), 3.29-3.35 (1H, m), 3.47-3.67 (4H, m), 3.84-3.91 (1H, m), 3.92-4.00 (1H, m), 4.40 (1H, d, J=11.5 Hz), 4.54 (1H, d, J=11.5 Hz), 7.16-7.46 (16H, m), 7.61-7.71 (4H, m). MS (m/z): 522 (M+H)⁺.

(Step 8) [(2S,3R)-1-Benzyl-3-(benzyloxy)azetidin-2-yl]methanol

To a solution of the compound (1.02 g) obtained in Step 7 above in tetrahydrofuran (20 mL), tetrabutylammonium fluoride (about 1 mol/L, tetrahydrofuran solution, 3.8 mL) was added at 0° C. and stirred at room temperature overnight. The solvent was concentrated under reduced pressure, water was added and then the mixture was extracted with ethyl acetate. The solvent was distilled off under reduced pressure, and the residue obtained was subjected to silica gel column chromatography (hexane/ethyl acetate) and then amino silica gel column chromatography (hexane/ethyl acetate) to obtain the title compound (0.476 g) as an oil.

¹H-NMR (CDCl₃) δ: 2.54-2.61 (1H, m), 2.83-2.90 (1H, m), 3.20-3.37 (3H, m), 3.53-3.59 (1H, m), 3.64 (1H, d, J=12.1 Hz), 3.71 (1H, d, J=12.1 Hz), 4.11-4.19 (1H, m), 4.45 (2H, s), 7.21-7.38 (10H, m). MS (m/z): 284 (M+H)⁺.

(Step 9) (2S,3R)-1-Benzyl-3-(benzyloxy)-2-({[tert-butyl(dimethyl)silyl]oxy}methyl)azetidine To a solution of the compound (262 mg) obtained in Step 8 above in N,N-dimethylformamide (2 mL), tert-butyl dimethylchlorosilane (176 mg) and imidazole (126 mg) were added and stirred at room temperature for 2 hours. Tert-Butyl dimethylchlorosilane (177 mg) and imidazole (128 mg) were further added and stirred at room temperature for 2 hours. Ice was added to the reaction solution, and the mixture was extracted with diethyl ether. The organic layer was sequentially washed with water and with saturated brine and dried over anhydrous sodium sulfate. The solvent was distilled off under reduced pressure, and the residue obtained was subjected to silica gel column chromatography (hexane/ethyl acetate) and then amino silica gel column chromatography (hexane/ethyl acetate) to obtain the title compound (349 mg) as an oil.

¹H-NMR (CDCl₃) δ: 0.02 (3H, s), 0.02 (3H, s), 0.88 (9H, s), 2.80-2.86 (1H, m), 3.19-3.25 (1H, m), 3.41-3.53 (2H, m), 3.56-3.62 (2H, m), 3.79-3.85 (1H, m), 3.88-3.95 (1H, m), 4.40 (1H, d, J=11.5 Hz), 4.56 (1H, d, J=11.5 Hz), 7.20-7.37 (10H, m). MS (m/z): 398 (M+H)⁺.

(Step 10) (2S,3R)-2-({[tert-Butyl(dimethyl)silyl]oxy}methyl)azetidin-3-ol

To a solution of the compound (349 mg) obtained in Step 9 above in ethanol (10 mL), 20% palladium hydroxide (201 mg) was added and stirred for 10 hours under hydrogen pressure (4.8 atm). 20% Palladium hydroxide (202 mg) was further added, stirred for 3 hours under hydrogen pressure (4.8 atm) and for 5 hours under hydrogen pressure (10 atm). The reaction solution was filtered through celite and the filtrate was concentrated under reduced pressure to obtain a mixture (211 mg) containing the title compound as an oil. The present compound was used for the next reaction without further purification.

(Step 11) Benzyl (2S,3R)-2-({[tert-butyl(dimethyl)silyl]oxy}methyl)-3-hydroxyazetidine-1-carboxylate To a mixture of the compound (191 mg) obtained in Step 10 above, tetrahydrofuran (3 mL), sodium hydrogen carbonate (186 mg), and water (3 mL), benzyl chloroformate (0.138 mL) was added at 0° C. and stirred at room temperature for 6 hours. Water was added to the reaction solution, and the mixture was extracted with ethyl acetate, and the organic layer was washed with saturated brine and dried over anhydrous sodium sulfate. The solvent was distilled off under reduced pressure, and the residue obtained was subjected to silica gel column chromatography (hexane/ethyl acetate) to obtain the title compound (178 mg) as an oil.

$^1$H-NMR (CDCl$_3$) δ: 0.01 (3H, s), 0.03 (3H, s), 0.87 (9H, s), 2.11-2.19 (1H, m), 3.71-3.76 (1H, m), 3.77-3.83 (1H, m), 3.92 (1H, br s), 4.06-4.13 (2H, m), 4.50-4.57 (1H, m), 5.09 (2H, s), 7.27-7.39 (5H, m). MS (m/z): 352 (M+H)$^+$.

(Step 12) Benzyl (2S,3R)-2-({[tert-butyl(dimethyl)silyl]oxy}methyl)-3-(methoxymethoxy)azetidine-1-carboxylate To a solution of the compound (178 mg) obtained in Step 11 above in dichloromethane (4 mL), chloromethyl methyl ether (0.057 mL) and N,N-diisopropylethylamine (0.212 mL) were added at 0° C. and stirred at room temperature for 16 hours. Chloromethyl methyl ether (0.228 mL) and N,N-diisopropylethylamine (0.848 mL) were further added at 0° C. and stirred at room temperature for 3 hours. The reaction solution was diluted with 1,2-dichloroethane (4 mL), then stirred at 60° C. for 6 hours, and allowed to stand at room temperature for 16 hours. Water was added to the reaction solution, and the mixture was extracted with ethyl acetate. The organic layer was sequentially washed with water and with saturated brine and dried over anhydrous sodium sulfate. The solvent was distilled off under reduced pressure, and the residue obtained was subjected to silica gel column chromatography (hexane/ethyl acetate) to obtain the title compound (159 mg) as an oil.

$^1$H-NMR (CDCl$_3$) δ: 0.01 (3H, s), 0.03 (3H, s), 0.87 (9H, s), 3.37 (3H, s), 3.75-3.84 (2H, m), 3.83-3.98 (1H, m), 4.04-4.11 (1H, m), 4.14-4.20 (1H, m), 4.32-4.37 (1H, m), 4.59-4.67 (2H, m), 5.10 (2H, s), 7.27-7.39 (5H, m). MS (m/z): 396 (M+H)$^+$.

(Step 13) Benzyl (2S,3R)-2-(hydroxymethyl)-3-(methoxymethoxy)azetidine-1-carboxylate The compound (159 mg) obtained in Step 12 above was subjected to the same procedure as in Step 8 of Reference Example B-14 to obtain the title compound (109 mg) as an oil.

$^1$H-NMR (CDCl$_3$) δ: 3.37 (3H, s), 3.57-3.93 (4H, m), 4.05-4.19 (2H, m), 4.29-4.42 (1H, m), 4.62 (2H, s), 5.12 (2H, s), 7.29-7.43 (5H, m). MS (m/z): 282 (M+H)$^+$.

(Step 14) (2R,3R)-1-[(Benzyloxy)carbonyl]-3-(methoxymethoxy)azetidine-2-carboxylic acid To a mixture of the compound (59.6 mg) obtained in Step 13 above, 2,2,6,6-tetramethylpiperidine 1-oxyl free radical (7.0 mg), acetonitrile (1.2 mL), and phosphate buffer (0.67 mol/L, pH 6.7, 0.89 mL), an aqueous solution (1.3 mL) of sodium chlorite (115 mg) and an aqueous solution (0.64 mL) of sodium hypochlorite (content>5%, 0.030 mL) were added dropwise simultaneously at 35° C. over a period of 30 minutes. The reaction solution was stirred at 35° C. for 4 hours and allowed to stand at room temperature for 16 hours. An aqueous solution of phosphate buffer (0.67 mol/L, pH 6.7, 0.445 mL), 2,2,6,6-tetramethylpiperidine 1-oxyl free radical (3.5 mg), and an aqueous solution (0.65 mL) of sodium chlorite (57.5 mg) and an aqueous solution (0.32 mL) of sodium hypochlorite (content>5%, 0.015 mL) were further added at 35° C. and stirred at the same temperature for 5 hours. The reaction solution was diluted with water at 0° C., and a 1 mol/L aqueous sodium hydroxide solution was used to adjust the pH to 8 to 9, and then an aqueous solution (1 mL) of sodium sulfite (64.4 mg) was added. The reaction mixture was washed with diethyl ether twice and then the aqueous layer was adjusted to pH 4 to 5 with 0.5 mol/L hydrochloric acid. The aqueous layer was extracted with diethyl ether, the organic layer was washed with saturated brine and dried over anhydrous sodium sulfate. The solvent was distilled off under reduced pressure to obtain the title compound quantitatively as an oil.

$^1$H-NMR (CDCl$_3$) δ: 3.41 (3H, s), 3.90-3.96 (1H, m), 4.14-4.24 (1H, m), 4.50-4.62 (1H, m), 4.65-4.79 (3H, m), 5.17 (2H, s), 7.29-7.43 (5H, m). MS (m/z): 296 (M+H)$^+$.

(Step 15) tert-Butyl 5-({[(2R,3R)-1-[(benzyloxy)carbonyl]-3-(methoxymethoxy)azetidin-2-yl]carbonyl}amino)-1H-pyrazolo[4,3-b]pyridine-1-carboxylate The compound (115 mg) obtained in Step 14 above and the compound (183 mg) obtained in Reference Example A-6 were subjected to the same procedure as in Step 11 of Reference Example B-3 to obtain the title compound quantitatively as an oil.

$^1$H-NMR (CDCl$_3$) δ: 1.73 (9H, s), 3.45 (3H, s), 3.96-4.02 (1H, m), 4.16-4.22 (1H, m), 4.59-4.66 (1H, m), 4.71-4.76 (1H, m), 4.79-4.87 (2H, m), 5.18 (1H, d, J=12.2 Hz), 5.27 (1H, d, J=12.2 Hz), 7.28-7.42 (5H, m), 8.25 (1H, s), 8.45 (1H, d, J=9.2 Hz), 8.50 (1H, d, J=9.2 Hz), 9.86 (1H, br s). MS (m/z): 512 (M+H)$^+$.

(Step 16) tert-Butyl 5-({[(2R,3R)-3-(methoxymethoxy)azetidin-2-yl]carbonyl}amino)-1H-pyrazolo[4,3-b]pyridine-1-carboxylate To a solution of the compound (199 mg) obtained in Step 15 above in ethanol (7 mL), 10% palladium-carbon (81 mg) was added and stirred for 4 hours under a hydrogen atmosphere. The reaction solution was filtered through celite and the filtrate was concentrated under reduced pressure. To a solution of the residue obtained in ethanol (7 mL), 10% palladium-carbon (102 mg) was added and stirred for 1 hour under a hydrogen atmosphere. The residue obtained by filtering the reaction solution through celite and concentrating the filtrate under reduced pressure was subjected to silica gel column chromatography (ethyl acetate/methanol) to obtain a mixture (145 mg) containing the title compound as an oil.

MS (m/z): 378 (M+H)$^+$.

Reference Example B-15 tert-Butyl 4-cyano-5-{[(4R)-4-fluoro-D-prolyl]amino}-1H-indazole-1-carboxylate

[Formula 64]

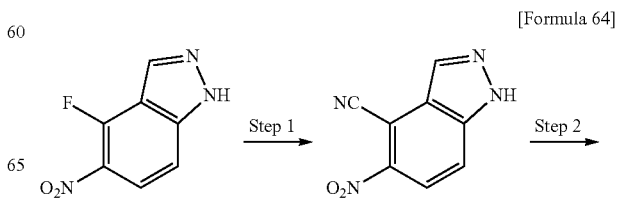

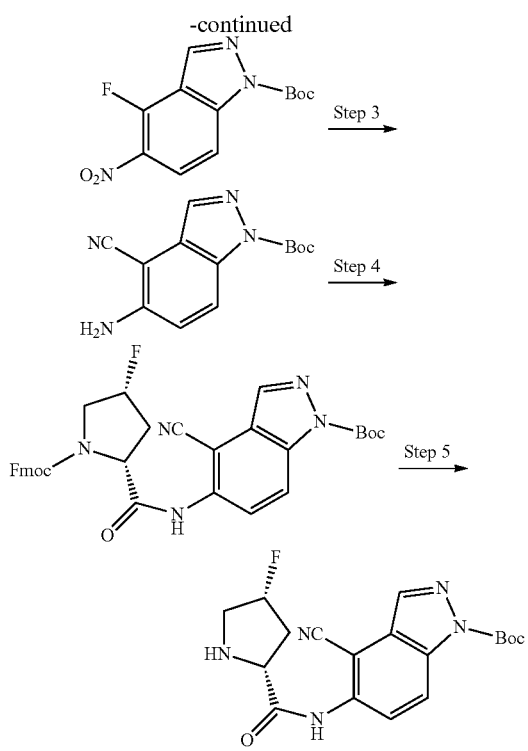

(Step 1) 5-Nitro-1H-indazole-4-carbonitrile

To a solution of 4-fluoro-5-nitro-1H-indazole (2.0 g) in dimethyl sulfoxide (20 mL), potassium cyanide (1.1 g) was added and then stirred at 60° C. for 2 hours. The reaction mixture was diluted with ethyl acetate and washed with saturated brine. The organic layer was dried over sodium sulfate, filtered, concentrated, and the residue obtained was purified by silica gel column chromatography (hexane/ethyl acetate) to obtain the title compound (970 mg) as a solid.

$^1$H-NMR (DMSO-D$_6$) δ: 8.11 (1H, d, J=9.2 Hz), 8.34 (1H, d, J=9.2 Hz), 8.61 (1H, s), 14.26 (1H, br s).

(Step 2) tert-Butyl 4-cyano-5-nitro-1H-indazole-1-carboxylate

To a solution of the compound (220 mg) obtained in Step 1 above and triethylamine (0.18 mL) in dichloromethane (4 mL), a solution of di-tert-butyl dicarbonate (281 mg) in dichloromethane (1 mL) was added and stirred at room temperature for 2 hours. After concentrating the reaction mixture, the residue obtained was purified by silica gel column chromatography (dichloromethane/ethyl acetate) to obtain the title compound (258 mg) as a solid.

$^1$H-NMR (DMSO-D$_6$) δ: 1.68 (9H, s), 8.53 (1H, d, J=9.2 Hz), 8.59 (1H, d, J=9.2 Hz), 8.89 (1H, s).

(Step 3) tert-Butyl 5-amino-4-cyano-1H-indazole-1-carboxylate

To a solution of the compound (250 mg) obtained in Step 2 above in ethyl acetate (10 mL), 10% palladium-carbon (125 mg) was added and stirred at room temperature for 1 hour under a hydrogen atmosphere. After a nitrogen purge, the reaction mixture was filtered through celite using ethyl acetate. The filtrate was concentrated to obtain the title compound (220 mg) as a solid.

$^1$H-NMR (DMSO-D$_6$) δ: 1.63 (9H, s), 6.45 (2H, s), 7.07 (1H, d, J=9.2 Hz), 8.03 (1H, d, J=9.2 Hz), 8.19 (1H, s).

(Step 4) tert-Butyl 4-cyano-5-({(4R)-1-[(9H-fluoren-9-ylmethoxy)carbonyl]-4-fluoro-D-prolyl}amino)-1H-indazole-1-carboxylate After cooling a solution of the compound (220 mg) obtained in Step 3 above and N,N-diisopropylethylamine (0.45 mL) in dichloromethane (8.8 mL) to 0° C., the compound (414 mg) obtained in Step 2 of Reference Example B-2 was added and stirred for 2 hours. The compound (64 mg) obtained in Step 2 of Reference Example B-2 was further added and stirred at 0° C. for 1 hour. The reaction mixture was diluted with dichloromethane and then washed with saturated brine. The organic layer was dried over sodium sulfate, filtered, concentrated, and the residue obtained was purified by silica gel column chromatography (hexane/ethyl acetate) to obtain the title compound (346 mg) as a solid.

$^1$H-NMR (DMSO-D$_6$) δ: 1.66 (9H, s), 2.28-2.80 (2H, m), 3.67-3.86 (2H, m), 4.17-4.43 (3H, m), 4.56-4.77 (1H, m), 5.26-5.50 (1H, m), 7.11-7.49 (4H, m), 7.57-7.79 (3H, m), 7.81-7.96 (2H, m), 8.37 (1H, d, J=9.2 Hz), 8.55 (1H, s), 10.28-10.57 (1H, m). MS (m/z): 596 (M+H)$^+$.

(Step 5) tert-Butyl 4-cyano-5-{[(4R)-4-fluoro-D-prolyl]amino}-1H-indazole-1-carboxylate After cooling a solution of the compound (340 mg) obtained in Step 4 above in tetrahydrofuran (10 mL) to 0° C., DBU (0.17 mL) was added and stirred for 1 hour. The reaction mixture was purified by silica gel column chromatography (ethyl acetate/methanol) to obtain the title compound (180 mg) as a solid.

$^1$H-NMR (DMSO-D$_6$) δ: 1.66 (9H, s), 2.18-2.38 (2H, m), 3.13-3.36 (2H, m), 3.59-3.73 (1H, m), 3.91-4.02 (1H, m), 5.18-5.38 (1H, m), 8.33-8.42 (2H, m), 8.57 (1H, s), 10.90 (1H, s). MS (m/z): 374 (M+H)$^+$.

Reference Example B-16 tert-Butyl 4-fluoro-5-{[(4R)-4-fluoro-D-prolyl]amino}-1H-indazole-1-carboxylate

[Formula 65]

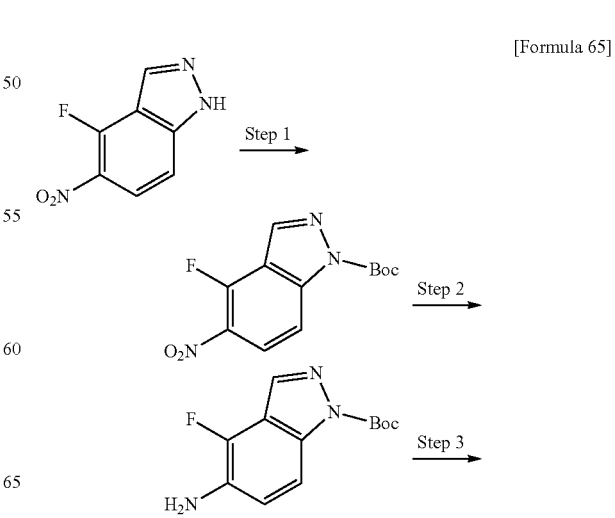

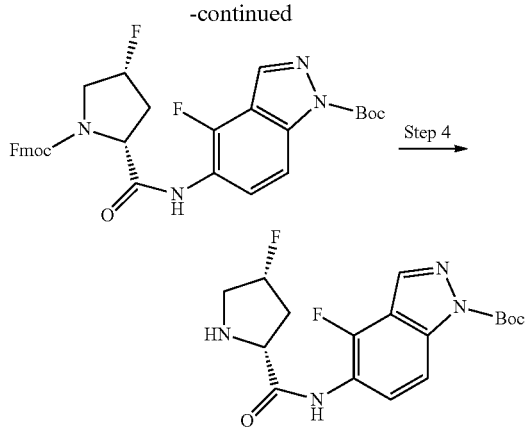

(Step 1) tert-Butyl 4-fluoro-5-nitro-1H-indazole-1-carboxylate

4-Fluoro-5-nitro-1H-indazole (1.00 g) was subjected to the same procedure as in Step 2 of Reference Example B-15 to obtain the title compound (1.41 g) as a solid.

$^1$H-NMR (DMSO-D$_6$) δ: 1.67 (9H, s), 8.03 (1H, d, J=9.2 Hz), 8.36 (1H, dd, J=9.2, 7.6 Hz), 8.85 (1H, s).

(Step 2) tert-Butyl 5-amino-4-fluoro-1H-indazole-1-carboxylate

The compound (600 mg) obtained in Step 1 above was subjected to the same procedure as in Step 3 of Reference Example B-15 to obtain the title compound (540 mg) as a solid.

$^1$H-NMR (DMSO-D$_6$) δ: 1.63 (9H, s), 5.15 (2H, s), 7.13 (1H, t, J=8.5 Hz), 7.62 (1H, d, J=8.5 Hz), 8.29 (1H, s). MS (m/z): 152 (M-CO$_2$$^t$Bu+H)$^+$.

(Step 3) tert-Butyl 5-({(4R)-1-[(9H-fluoren-9-yl-methoxy)carbonyl]-4-fluoro-D-prolyl}amino)-4-fluoro-1H-indazole-1-carboxylate The compound (530 mg) obtained in Step 2 above and the compound (867 mg) obtained in Step 2 of Reference Example B-2 were subjected to the same procedure as in Step 3 of Reference Example B-2 to obtain the title compound (1.23 g) as a solid.

$^1$H-NMR (DMSO-D$_6$) δ: 1.62-1.70 (9H, m), 2.28-2.76 (2H, m), 3.67-3.86 (2H, m), 4.15-4.25 (1H, m), 4.27-4.39 (2H, m), 4.54-4.75 (1H, m), 5.25-5.47 (1H, m), 7.13-7.25 (1H, m), 7.31-7.48 (3H, m), 7.59-7.80 (3H, m), 7.82-7.96 (3H, m), 8.56 (1H, s), 9.98 (1H, d, J=73.9 Hz). MS (m/z): 589 (M+H)$^+$.

(Step 4) tert-Butyl 4-fluoro-5-{[(4R)-4-fluoro-D-prolyl]amino}-1H-indazole-1-carboxylate The compound (600 mg) obtained in Step 3 above was subjected to the same procedure as in Step 5 of Reference Example B-15 to obtain the title compound (300 mg) as a solid.

$^1$H-NMR (DMSO-D$_6$) δ: 1.65 (9H, s), 2.20-2.41 (2H, m), 3.05-3.25 (2H, m), 3.39-3.56 (1H, m), 3.85-3.97 (1H, m), 5.15-5.37 (1H, m), 7.88 (1H, d, J=8.5 Hz), 8.15-8.23 (1H, m), 8.54 (1H, s), 10.15 (1H, br s). MS (m/z): 367 (M+H)$^+$.

Reference Example B-17

Benzyl [(5-{[(4R)-4-fluoro-D-prolyl]amino}-1H-pyrrolo[3,2-b]pyridin-2-yl)methyl]methyl carbamate

[Formula 66]

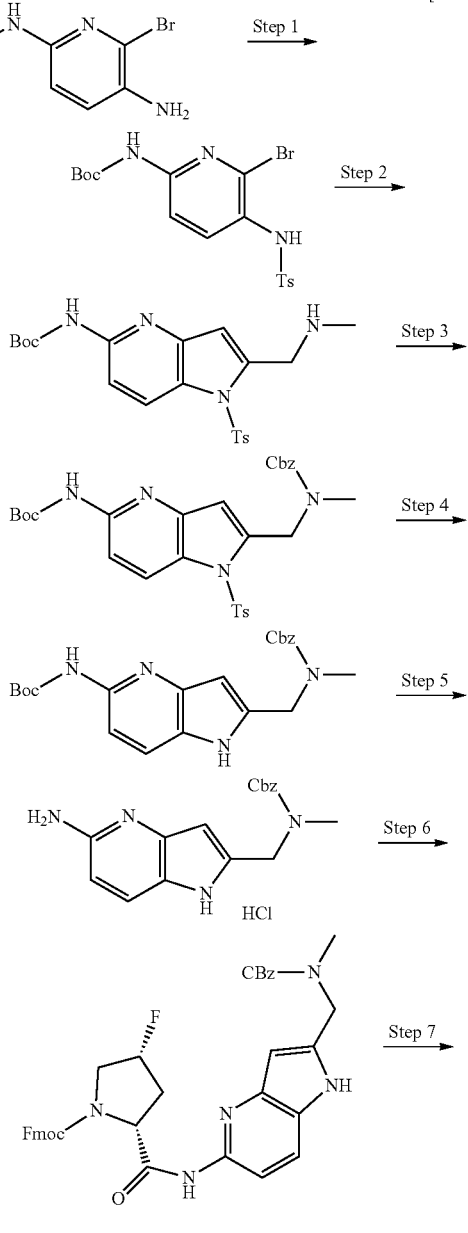

(Step 1) tert-Butyl (6-bromo-5-{[(4-methylphenyl)sulfonyl]amino}pyridin-2-yl)carbamate A solution of tert-butyl(5-amino-6-bromopyridin-2-yl)carbamate (Bioorg. Med. Chem. Lett., 16, 2270-2273 (2006); 880 mg) in pyridine (24 mL) was cooled to 0° C., p-toluenesulfonyl chloride (698 mg) was added and stirred at room temperature overnight. The reaction solution was diluted with ethyl acetate, washed with water and with saturated brine and then dried over anhydrous sodium sulfate, and the solvent was distilled off under reduced pressure. The residue obtained was purified by silica gel column chromatography (hexane/ethyl acetate) to obtain the title compound (1.43 g) as a solid.

$^1$H-NMR (DMSO-D$_6$) δ: 1.45 (9H, s), 2.38 (3H, s), 7.37 (2H, d, J=8.2 Hz), 7.52 (3H, dd, J=19.0, 8.4 Hz), 7.74 (1H, d, J=8.8 Hz), 9.88 (1H, s), 10.19 (1H, s). MS (m/z): 386 (M+H−tBu)$^+$.

(Step 2) tert-Butyl {2-[(methylamino)methyl]-1-[(4-methylphenyl)sulfonyl]-1H-pyrrolo[3,2-b]pyridin-5-yl}carbamate To a mixture of the compound (100 mg) obtained in Step 1 above, N-methylpropargylamine (57 μL), triethylamine (94 μL), and N,N-dimethylformamide (0.8 mL), bis(triphenylphosphine)palladium(II) dichloride (16 mg) and copper (I)iodide (9 mg) were added and stirred at 70° C. for 4 hours. The reaction solution was diluted with ethyl acetate, washed with water and with saturated brine and dried over anhydrous sodium sulfate, and the solvent was distilled off under reduced pressure. The residue obtained was purified by silica gel column chromatography (hexane/ethyl acetate) to obtain the title compound (82 mg) as a solid.

$^1$H-NMR (CDCl$_3$) δ: 1.48 (9H, s), 2.34 (3H, s), 2.42 (3H, s), 4.10 (2H, s), 6.63 (1H, s), 7.19 (2H, d, J=8.2 Hz), 7.63 (2H, d, J=8.5 Hz), 7.93 (1H, d, J=9.1 Hz), 8.37-8.38 (2H, m). MS (m/z): 431 (M+H)$^+$.

(Step 3) Benzyl ({5-[(tert-butoxycarbonyl)amino]-1-[(4-methylphenyl)sulfonyl]-1H-pyrrolo[3,2-b]pyridin-2-yl}methyl)methyl carbamate The compound (92 mg) obtained in Step 2 above and N,N-diisopropylethylamine (0.112 mL) were dissolved in dichloromethane (1.3 mL) and cooled to 0° C. Benzyl chloroformate (37 μL) was added and stirred at room temperature for 20 minutes. Distilled water was added to the reaction solution, and the mixture was extracted with dichloromethane and dried over anhydrous sodium sulfate, and the solvent was distilled off under reduced pressure to obtain the title compound (111 mg) as a solid.

$^1$H-NMR (CDCl$_3$) δ: 1.44 (9H, s), 2.28 (3H, s), 3.01 (3H, s), 4.93 (2H, d, J=18.5 Hz), 5.09-5.17 (2H, m), 6.40 (1H, d, J=11.2 Hz), 6.95 (1H, d, J=7.6 Hz), 7.23-7.33 (5H, m), 7.50-7.67 (2H, m), 7.93 (1H, d, J=9.1 Hz), 8.18-8.34 (2H, m). MS (m/z): 565 (M+H)$^+$.

(Step 4) Benzyl ({5-[(tert-butoxycarbonyl)amino]-1H-pyrrolo[3,2-b]pyridin-2-yl}methyl)methyl carbamate A mixture of the compound (112 mg) obtained in Step 3 above, tetrahydrofuran (2 mL), methanol (2 mL) and cesium carbonate (323 mg) was stirred at 60° C. for 2 hours. The temperature of the reaction solution was lowered to room temperature and water was added, and the mixture was extracted with ethyl acetate, washed with saturated brine and dried over anhydrous sodium sulfate. After concentrating under reduced pressure, the residue obtained was purified by reversed-phase HPLC to obtain the title compound (45 mg) as an oil.

$^1$H-NMR (CDCl$_3$) δ: 1.52 (9H, s), 2.99 (3H, s), 4.58 (2H, s), 5.17 (2H, s), 6.47 (1H, s), 7.34 (5H, s), 7.91 (2H, s), 8.43 (1H, s). MS (m/z): 411 (M+H)$^+$.

(Step 5) 2-({[(Benzyloxy)carbonyl](methyl)amino}methyl)-1H-pyrrolo[3,2-b]pyridin-5-amine hydrochloride The compound (45 mg) obtained in Step 4 above was subjected to the same procedure as in Step 3 of Reference Example A-9 to obtain the title compound (36 mg) as a solid.

$^1$H-NMR (CD$_3$OD) δ: 3.00 (3H, s), 4.65 (2H, s), 5.17 (2H, s), 6.63 (1H, d, J=8.8 Hz), 7.27-7.37 (6H, m), 7.94 (1H, d, J=8.5 Hz). MS (m/z): 311 (M+H−HCl)$^+$.

(Step 6) 9H-Fluoren-9-ylmethyl (2R,4R)-2-{[2-({[(benzyloxy)carbonyl](methyl)amino}methyl)-1H-pyrrolo[3,2-b]pyridin-5-yl]carbamoyl}-4-fluoropyrrolidine-1-carboxylate The compound (36 mg) obtained in Step 5 above and the compound (39 mg) obtained in Step 2 of Reference Example B-2 were subjected to the same procedure as in Step 3 of Reference Example B-2 to obtain the title compound (39 mg) as an oil.

MS (m/z): 648 (M+H)$^+$.

(Step 7) Benzyl [(5-{[(4R)-4-fluoro-D-prolyl]amino}-1H-pyrrolo[3,2-b]pyridin-2-yl)methyl] methyl carbamate The compound (39 mg) obtained in Step 6 above was subjected to the same procedure as in Step 5 of Reference Example B-15 to obtain the title compound (14 mg) as an oil.

MS (m/z): 426 (M+H)$^+$.

Reference Example B-18

(4R)—N-{2-({[tert-Butyl(dimethyl)silyl]oxy}methyl)-1-[(4-methylphenyl)sulfonyl]-1H-pyrrolo[3,2-b]pyridin-5-yl}-4-fluoro-D-prolinamide

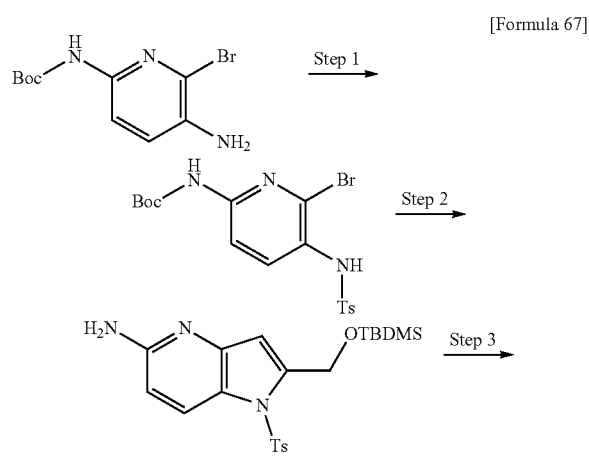

[Formula 67]

-continued

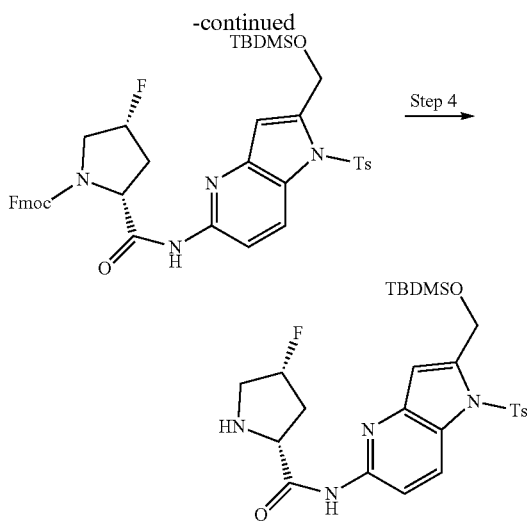

(Step 1) N-(6-Amino-2-bromopyridin-3-yl)-4-methylbenzenesulfonamide

The compound (5.00 g) obtained in Step 1 of Reference Example B-17 was dissolved in dichloromethane (60 mL), hydrogen chloride (4 mol/L, 1,4-dioxane solution, 40 mL) was added and stirred at room temperature overnight. A saturated aqueous sodium hydrogen carbonate solution was added to the reaction solution, and the mixture was extracted with ethyl acetate, dried over anhydrous sodium sulfate, and then the solvent was distilled off under reduced pressure to obtain the title compound (3.47 g) as a solid.

$^1$H-NMR (DMSO-D$_6$) δ: 2.38 (3H, s), 6.32 (1H, d, J=8.5 Hz), 6.47 (2H, s), 7.04 (1H, d, J=8.5 Hz), 7.36 (2H, d, J=7.9 Hz), 7.53 (2H, d, J=7.9 Hz), 9.42 (1H, s). MS (m/z): 342 (M+H)$^+$.

(Step 2) 2-({[tert-Butyl(dimethyl)silyl]oxy}methyl)-1-[(4-methylphenyl)sulfonyl]-1H-pyrrolo[3,2-b]pyridin-5-amine To a mixture of the compound (3.45 g) obtained in Step 1 above, triethylamine (4.19 mL), tert-butyl dimethyl(2-propynyloxy)silane (6.1 mL), and N,N-dimethylformamide (33.6 mL), bis(triphenylphosphine)palladium(II) dichloride (708 mg) and copper(I) iodide (384 mg) were added and stirred at 70° C. for 4 hours. The reaction solution was diluted with ethyl acetate, washed with water three times, dried over anhydrous sodium sulfate, and filtered, and the solvent was distilled off under reduced pressure. The residue obtained was purified by silica gel column chromatography (hexane/ethyl acetate) to obtain the title compound (3.19 g) as a solid.

$^1$H-NMR (DMSO-D$_6$) δ: 0.09 (6H, s), 0.91 (9H, s), 2.32 (3H, s), 4.99 (2H, s), 5.92 (2H, s), 6.42 (1H, d, J=9.1 Hz), 6.45 (1H, s), 7.36 (2H, d, J=7.9 Hz), 7.74 (2H, d, J=8.5 Hz), 7.96 (1H, d, J=9.1 Hz). MS (m/z): 432 (M+H)$^+$.

(Step 3) 9H-Fluoren-9-ylmethyl (2R,4R)-2-({2-({[tert-butyl(dimethyl)silyl]oxy}methyl)-1-[(4-methylphenyl)sulfonyl]-1H-pyrrolo[3,2-b]pyridin-5-yl}carbamoyl)-4-fluoropyrrolidine-1-carboxylate The compound (1.40 g) obtained in Step 2 above and the compound (1.26 g) obtained in Step 2 of Reference Example B-2 were subjected to the same procedure as in Step 3 of Reference Example B-2 to obtain the title compound (2.30 g) as a solid.

MS (m/z): 769 (M+H)$^+$.

(Step 4) (4R)—N-{2-({[tert-Butyl(dimethyl)silyl]oxy}methyl)-1-[(4-methylphenyl)sulfonyl]-1H-pyrrolo[3,2-b]pyridin-5-yl}-4-fluoro-D-prolinamide The compound (2.30 g) obtained in Step 3 above was subjected to the same procedure as in Step 5 of Reference Example B-15 to obtain the title compound (1.44 g) as a solid.

$^1$H-NMR (DMSO-D$_6$) δ: 0.10 (6H, s), 0.92 (9H, s), 2.22-2.36 (5H, m), 3.00 (1H, s), 3.16 (2H, d, J=27.6 Hz), 3.86 (1H, dd, J=9.9, 3.5 Hz), 5.05 (2H, s), 5.21 (1H, d, J=53.2 Hz), 6.68 (1H, s), 7.36 (2H, d, J=7.9 Hz), 7.74 (2H, d, J=7.9 Hz), 8.08 (1H, d, J=8.8 Hz), 8.31 (1H, d, J=9.1 Hz), 10.16 (1H, s). MS (m/z): 547 (M+H)$^+$.

Reference Example B-19 tert-Butyl 5-({O-[tert-butyl(diphenyl)silyl]-N-methyl-D-seryl}amino)-1H-pyrazolo[4,3-b]pyridine-1-carboxylate

[Formula 68]

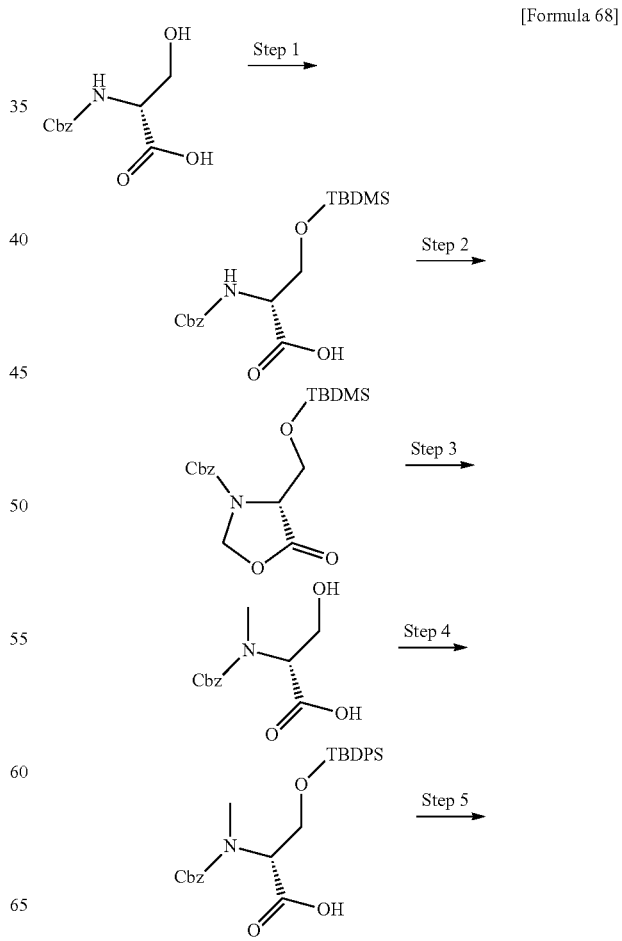

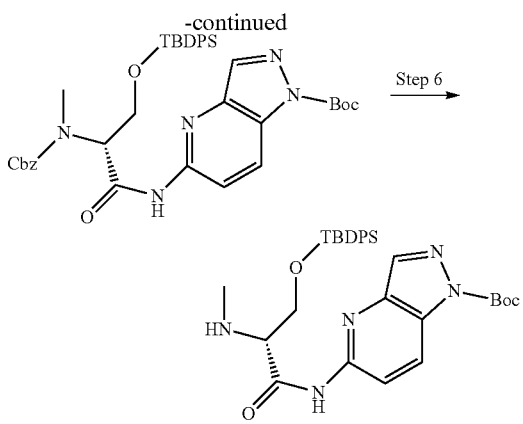

(Step 1) N-[(Benzyloxy)carbonyl]-O-[tert-butyl(dimethyl)silyl]-D-serine

To a solution of N-[(benzyloxy)carbonyl]-D-serine (10.1 g) in N,N-dimethylformamide (100 mL), imidazole (5.71 g) and tert-butyl chlorodimethylsilane (6.40 g) were added at 0° C. and stirred at room temperature for 16 hours. tert-Butyl chlorodimethylsilane (1.23 g) was added again at room temperature and stirred for 20 hours. Ice and a 10% aqueous citric acid solution were added to the reaction solution, and then the mixture was extracted with diethyl ether. The organic layer was sequentially washed with a 10% aqueous citric acid solution and with saturated brine, and dried over anhydrous sodium sulfate. The solvent was distilled off under reduced pressure, and the residue obtained was subjected to silica gel column chromatography (hexane/ethyl acetate) to obtain the title compound (12.1 g) as a solid.
$^1$H-NMR (CDCl$_3$) δ: 0.05 (6H, s), 0.87 (9H, s), 3.78-3.88 (1H, m), 4.09-4.17 (1H, m), 4.40-4.49 (1H, m), 5.14 (2H, s), 5.52-5.62 (1H, m), 7.28-7.41 (5H, m).

(Step 2) Benzyl (4R)-4-({[tert-butyl(dimethyl)silyl]oxy}methyl)-5-oxo-1,3-oxazolidine-3-carboxylate A mixture of the compound (12.1 g) obtained in Step 1 above, paraformaldehyde (6.10 g), p-toluenesulfonic acid monohydrate (0.330 g), and toluene (600 mL) was stirred for 1.5 hours while heated to reflux. After cooling to room temperature and distilling off the organic solvent under reduced pressure, water was added, and the mixture was extracted with diethyl ether. The organic layer was washed with a 5% aqueous sodium hydrogen carbonate solution, with water, and with saturated brine, and dried over anhydrous sodium sulfate. The solvent was distilled off under reduced pressure, and the residue obtained was subjected to silica gel column chromatography (hexane/ethyl acetate) to obtain the title compound (10.3 g) as an oil.
$^1$H-NMR (CDCl$_3$) δ: −0.03-0.04 (6H, m), 0.84 (9H, s), 3.94-4.34 (3H, m), 5.13-5.28 (3H, m), 5.44-5.63 (1H, m), 7.31-7.42 (5H, m).

(Step 3) N-[(Benzyloxy)carbonyl]-N-methyl-D-serine

To a solution of the compound (4.00 g) obtained in Step 2 above in chloroform (22.0 mL), trifluoroacetic acid (22.0 mL) and triethylsilane (17.4 mL) were added at room temperature and stirred at room temperature for 2 days. After distilling off the solvent under reduced pressure, a saturated aqueous sodium hydrogen carbonate solution and hexane were added to the reaction solution. The aqueous layer was washed with hexane, then acidified by adding 6 mol/L hydrochloric acid, and extracted with ethyl acetate. The organic layer was dried over anhydrous sodium sulfate, and the solvent was distilled off under reduced pressure, and then azeotropically concentrated by adding toluene to obtain the title compound (2.65 g) as an oil.
$^1$H-NMR (CDCl$_3$) δ: 3.02 (3H, s), 3.84-4.05 (1H, m), 4.05-4.17 (1H, m), 4.45-4.86 (2H, m), 5.17 (2H, s), 7.28-7.40 (5H, m).

(Step 4) N-[(Benzyloxy)carbonyl]-O-[tert-butyl(diphenyl)silyl]-N-methyl-D-serine The compound (2.14 g) obtained in Step 3 above was subjected to the same procedure as in Step 2 of Reference Example B-8 to obtain the title compound (3.02 g) as an oil.
$^1$H-NMR (CDCl$_3$) δ: 1.02 (9H, s), 2.99 (3H, s), 3.92-4.14 (2H, m), 4.71-4.95 (1H, m), 5.02-5.21 (2H, m), 7.21-7.46 (11H, m), 7.58-7.66 (4H, m).

(Step 5) tert-Butyl 5-({N-[(benzyloxy)carbonyl]-O-[tert-butyl(diphenyl)silyl]-N-methyl-D-seryl}amino)-1H-pyrazolo[4,3-b]pyridine-1-carboxylate The compound (0.300 g) obtained in Step 4 above and the compound (0.286 g) obtained in Reference Example A-6 were subjected to the same procedure as in Step 11 of Reference Example B-3 to obtain the title compound (0.410 g) as a solid. Using Daicel Corporation Chiral Column IA, HPLC analysis (flow rate 2 mL/min, hexane:isopropanol=95:5 to 50:50) was carried out to confirm 98.5% ee.
$^1$H-NMR (CDCl$_3$) δ: 1.07 (9H, s), 1.73 (9H, s), 2.91-3.01 (3H, m), 3.95-4.09 (1H, m), 4.20-4.33 (1H, m), 4.69-5.01 (1H, m), 5.07-5.26 (2H, m), 7.16-7.48 (11H, m), 7.58-7.74 (4H, m), 8.16-8.24 (1H, m), 8.33-8.47 (2H, m), 8.80-9.09 (1H, m). MS (m/z): 708 (M+H)$^+$.

(Step 6) tert-Butyl 5-({O-[tert-butyl(diphenyl)silyl]-N-methyl-D-seryl}amino)-1H-pyrazolo[4,3-b]pyridine-1-carboxylate The compound (0.400 g) obtained in Step 5 above was subjected to the same procedure as in Step 5 of Reference Example B-8 to obtain the title compound (0.297 g) as a solid.
$^1$H-NMR (CDCl$_3$) δ: 1.04 (9H, s), 1.73 (9H, s), 2.00-2.05 (1H, m), 2.49 (3H, s), 3.21-3.27 (1H, m), 3.94-4.02 (2H, m), 7.35-7.47 (6H, m), 7.61-7.67 (4H, m), 8.22-8.25 (1H, m), 8.41-8.47 (1H, m), 8.51-8.55 (1H, m), 10.20 (1H, br s). MS (m/z): 574 (M+H)$^+$.

Reference Example C-1

1-(4-Iodophenyl)cyclopentanecarboxylic acid

[Formula 69]

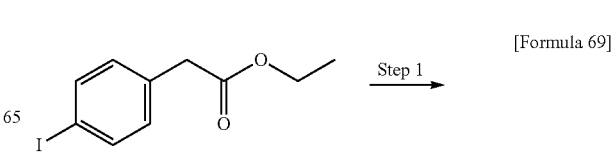

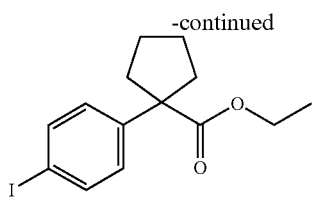

(Step 1) Ethyl 1-(4-iodophenyl)cyclopentanecarboxylate

Under a nitrogen atmosphere, a suspension of sodium hydride (purity>55%, 1.13 g) in N,N-dimethylformamide (50.0 mL) was ice-cooled, ethyl (4-iodophenyl)acetate (3.00 g) and 18-Crown-6 ether (0.273 g) were added and stirred at room temperature for 30 minutes, and then the suspension was ice-cooled again, and 1,4-dibromobutane (1.34 mL) was added and stirred at room temperature overnight. Water was added to the reaction solution, and the mixture was extracted with diethyl ether three times, and the organic layer was washed with saturated brine and then dried over anhydrous sodium sulfate. After filtration and concentration under reduced pressure, the residue obtained was purified by silica gel column chromatography (hexane/ethyl acetate) to obtain the title compound (1.74 g) as a solid.

$^1$H-NMR (CDCl$_3$) δ: 1.15 (3H, t, J=7.1 Hz), 1.68-1.76 (4H, m), 1.81-1.88 (2H, m), 2.59-2.65 (2H, m), 4.06 (2H, q, J=7.1 Hz), 7.11 (2H, d, J=8.5 Hz), 7.62 (2H, d, J=8.5 Hz). MS (m/z): 345 (M+H)$^+$.

(Step 2) 1-(4-Iodophenyl)cyclopentanecarboxylic acid

To a solution of the compound (1.74 g) obtained in Step 1 above in tetrahydrofuran (6.00 mL), methanol (6.00 mL), water (6.00 mL), and lithium hydroxide monohydrate (0.255 g) were added and stirred at room temperature overnight. To the reaction solution, a 1 mol/L aqueous sodium hydroxide solution (5.06 mL), methanol (5.00 mL), and tetrahydrofuran (15.0 mL) were added and stirred for 6 hours under heated reflux. After allowing to cool to room temperature, the organic solvent was distilled off under reduced pressure, and water was added to the residue and the mixture was washed with diethyl ether twice. The aqueous layer was acidified by adding 1 mol/L hydrochloric acid, and the precipitated solid was collected by filtration and dried to obtain the title compound (1.36 g) as a solid.

$^1$H-NMR (DMSO-D$_6$) δ: 1.59-1.79 (6H, m), 2.46-2.49 (2H, m), 7.15 (2H, d, J=8.5 Hz), 7.67 (2H, d, J=8.5 Hz), 12.36 (1H, s).

Reference Example C-2

1-{4-[(Cyclopropylsulfonyl)carbamoyl]phenyl}cyclohexanecarboxylic acid

[Formula 70]

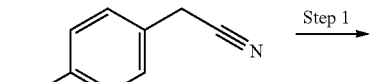

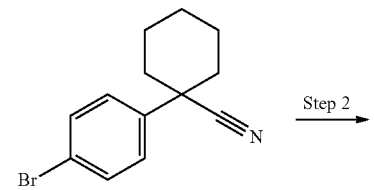

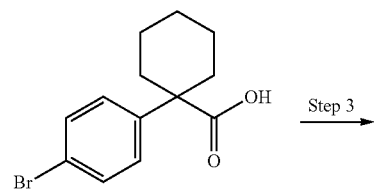

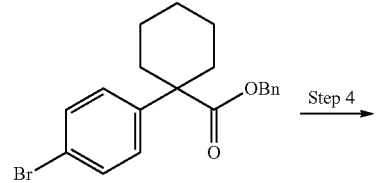

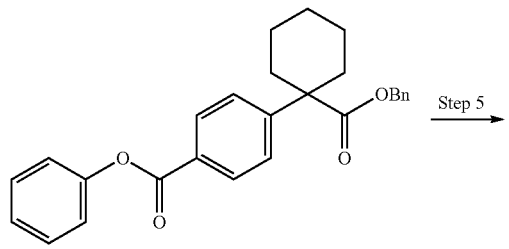

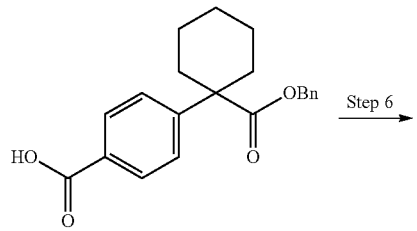

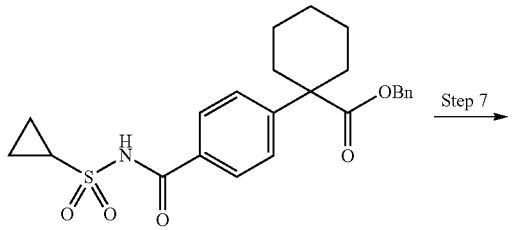

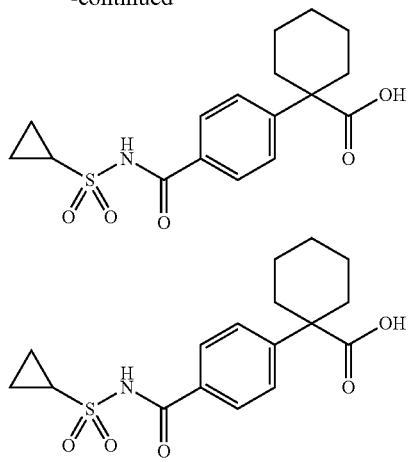

(Step 1) 1-(4-Bromophenyl)cyclohexanecarbonitrile

Under a nitrogen atmosphere, to a solution of (4-bromophenyl)acetonitrile (10.0 g) in N,N-dimethylformamide (150 mL), 1,5-dibromopentane (12.9 g) was added, then sodium hydride (purity>55%, 4.91 g) was added under ice-cooling and stirred at the same temperature for 1 hour and at room temperature for 2 hours. After ice-cooling again, water was added to the reaction solution, and the mixture was extracted with ethyl acetate three times. The organic layer was washed with saturated brine and then dried over anhydrous sodium sulfate. After concentrating under reduced pressure, the residue obtained was purified by silica gel column chromatography (chloroform) to obtain the title compound (11.1 g) as a solid.

$^1$H-NMR (CDCl$_3$) δ: 1.21-1.33 (1H, m), 1.68-1.89 (7H, m), 2.12-2.15 (2H, m), 7.37 (2H, d, J=8.5 Hz), 7.52 (2H, d, J=8.5 Hz).

(Step 2) 1-(4-Bromophenyl)cyclohexanecarboxylic acid

To a suspension of the compound (11.1 g) obtained in Step 1 above in ethylene glycol (70.0 mL), potassium hydroxide (7.20 g) was added, stirred for 8 hours under heated reflux, and allowed to stand at room temperature overnight. Water (200 mL) was added to the reaction solution, and the mixture was washed with diethyl ether twice, and the aqueous layer was acidified by adding 1 mol/L hydrochloric acid (200 mL) and stirred at room temperature for 3 hours. The precipitated solid was collected by filtration and dried to obtain the title compound (11.2 g) as a solid.

$^1$H-NMR (CDCl$_3$) δ: 1.23-1.32 (1H, m), 1.47-1.75 (7H, m), 2.41-2.44 (2H, m), 7.32 (2H, d, J=8.5 Hz), 7.46 (2H, d, J=8.5 Hz).

(Step 3) Benzyl 1-(4-bromophenyl)cyclohexanecarboxylate

To a mixture of the compound (5.00 g) obtained in Step 2 above and potassium carbonate (3.68 g), N,N-dimethylformamide (70.0 mL) and benzyl bromide (3.15 mL) were added and stirred at room temperature overnight. Water was added to the reaction solution, and the mixture was extracted with diethyl ether three times, the organic layer was washed with saturated brine and then dried over anhydrous sodium sulfate. After filtration and concentration under reduced pressure, the residue obtained was purified by silica gel column chromatography (hexane/ethyl acetate) to obtain the title compound (5.31 g) as a solid.

$^1$H-NMR (CDCl$_3$) δ: 1.21-1.31 (1H, m), 1.41-1.51 (2H, m), 1.57-1.74 (5H, m), 2.43-2.50 (2H, m), 5.07 (2H, s), 7.16-7.31 (7H, m), 7.41 (2H, d, J=9.1 Hz).

(Step 4) Phenyl 4-{1-[(benzyloxy)carbonyl]cyclohexyl}benzoate

Under a nitrogen atmosphere, to a mixture of the compound (2.01 g) obtained in Step 3 above, palladium(II) acetate (0.0368 g), and tri-tert-butylphosphonium tetrafluoroborate (0.188 g), acetonitrile (7.50 mL), triethylamine (1.49 mL), and phenyl formate (1.17 mL) were added and stirred at 80° C. overnight. After allowing to cool to room temperature, water was added to the reaction solution, and the mixture was extracted with ethyl acetate three times, and the organic layer was washed with saturated brine and then dried over anhydrous sodium sulfate. After filtration and concentration under reduced pressure, the residue obtained was purified by silica gel column chromatography (hexane/ethyl acetate) to obtain the title compound (1.38 g) as an oil.

$^1$H-NMR (CDCl$_3$) δ: 1.28-1.35 (1H, m), 1.46-1.83 (7H, m), 2.50-2.56 (2H, m), 5.10 (2H, s), 7.19-7.22 (4H, m), 7.28-7.33 (4H, m), 7.43 (2H, t, J=7.9 Hz), 7.52 (2H, d, J=8.5 Hz), 8.13 (2H, d, J=8.5 Hz).

(Step 5) 4-{1-[(Benzyloxy)carbonyl]cyclohexyl}benzoic acid

To a solution of the compound (1.38 g) obtained in Step 4 above in tetrahydrofuran (33.0 mL), methanol (10.0 mL) and a 1 mol/L aqueous sodium hydroxide solution (9.92 mL) were added and stirred at room temperature for 4.5 hours. The reaction solution was acidified by adding 1 mol/L hydrochloric acid and then extracted with ethyl acetate three times, and the organic layer was washed with saturated brine, dried over anhydrous sodium sulfate, filtered and concentrated under reduced pressure. The residue obtained was purified by silica gel column chromatography (chloroform/methanol) to obtain the title compound (0.825 g) as a solid.

$^1$H-NMR (CDCl$_3$) δ: 1.23-1.34 (1H, m), 1.44-1.83 (7H, m), 2.46-2.54 (2H, m), 5.10 (2H, s), 7.15-7.20 (2H, m), 7.23-7.31 (3H, m), 7.49 (2H, d, J=7.9 Hz), 8.04 (2H, d, J=7.9 Hz).

(Step 6) Benzyl 1-{4-[(cyclopropylsulfonyl)carbamoyl]phenyl}cyclohexanecarboxylate A mixture of the compound (0.818 g) obtained in Step 5 above, 1-(3-dimethylaminopropyl)-3-ethylcarbodiimide hydrochloride (0.696 g), and 4-dimethylaminopyridine (681 mg) was dissolved in dichloromethane (12.0 mL), then cyclopropane sulfonamide (0.453 g) was added and stirred at room temperature overnight. The reaction solution was diluted with dichloromethane and washed with 1 mol/L hydrochloric acid twice and with saturated brine once. The residue obtained by drying the organic layer over anhydrous sodium sulfate, then filtering and concentrating under reduced pressure was purified by silica gel column chromatography (chloroform/methanol) to obtain the title compound (1.05 g) as a solid.

$^1$H-NMR (CDCl$_3$) δ: 1.13-1.19 (2H, m), 1.24-1.33 (1H, m), 1.42-1.54 (4H, m), 1.60-1.80 (5H, m), 2.48-2.51 (2H, m), 3.10-3.17 (1H, m), 5.10 (2H, s), 7.17-7.20 (2H, m), 7.28-7.32 (3H, m), 7.50 (2H, d, J=8.5 Hz), 7.77 (2H, d, J=8.5 Hz), 8.52 (1H, s). MS (m/z): 442 (M+H)⁺.

(Step 7) 1-{4-[(Cyclopropylsulfonyl)carbamoyl]phenyl}cyclohexanecarboxilic acid

The compound (1.04 g) obtained in Step 6 above was subjected to the same procedure as in Step 2 of Reference Example A-3 to obtain the title compound (0.760 g) as a solid.
¹H-NMR (DMSO-D₆) δ: 1.08-1.19 (4H, m), 1.20-1.32 (1H, m), 1.41-1.49 (2H, m), 1.54-1.73 (5H, m), 2.29-2.36 (2H, m), 3.09-3.15 (1H, m), 7.53 (2H, d, J=8.5 Hz), 7.91 (2H, d, J=8.5 Hz), 12.05 (1H, s), 12.55 (1H, br s). MS (m/z): 352 (M+H)⁺.

Reference Example C-3

1-(3-Fluoro-4-methoxyphenyl)cyclohexanecarboxylic acid

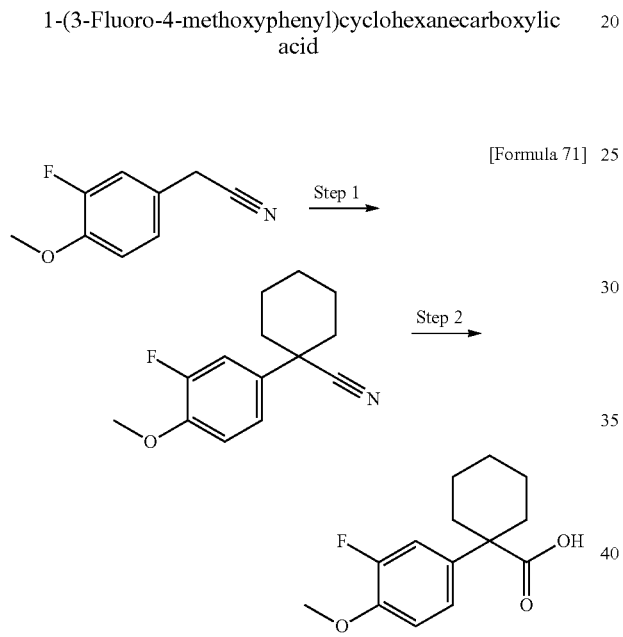

[Formula 71]

(Step 1) 1-(3-Fluoro-4-methoxyphenyl)cyclohexanecarbonitrile (3-Fluoro-4-methoxyphenyl)acetonitrile (2.20 g) and 1,5-dibromopentane (2.00 mL) were subjected to the same procedure as in Step 1 of Reference Example C-2 to obtain the title compound (2.45 g) as a solid.
¹H-NMR (CDCl₃) δ: 1.20-1.32 (1H, m), 1.65-1.73 (2H, m), 1.76-1.89 (5H, m), 2.12-2.15 (2H, m), 3.90 (3H, s), 6.96 (1H, t, J=8.8 Hz), 7.17-7.24 (2H, m). MS (m/z): 350 (M+H)⁺.

(Step 2) 1-(3-Fluoro-4-methoxyphenyl)cyclohexanecarboxylic acid

Potassium hydroxide (1.79 g) and ethylene glycol (30.0 mL) were added to the compound (2.45 g) obtained in Step 1 above and stirred for 8 hours under heated reflux. After allowing to cool to room temperature, water was added to the reaction solution, and the mixture was washed with diethyl ether twice. The aqueous layer was acidified by adding 1 mol/L hydrochloric acid and stirred at room temperature overnight. The aqueous layer was extracted with chloroform three times and the organic layer was dried over anhydrous sodium sulfate. After filtration and concentration under reduced pressure, the residue obtained was purified by silica gel column chromatography (chloroform/ethyl acetate) to obtain a mixture (0.616 g) containing the title compound as a solid.

Reference Example C-4

4,4-Difluoro-1-(4-methoxyphenyl)cyclohexanecarboxylic acid

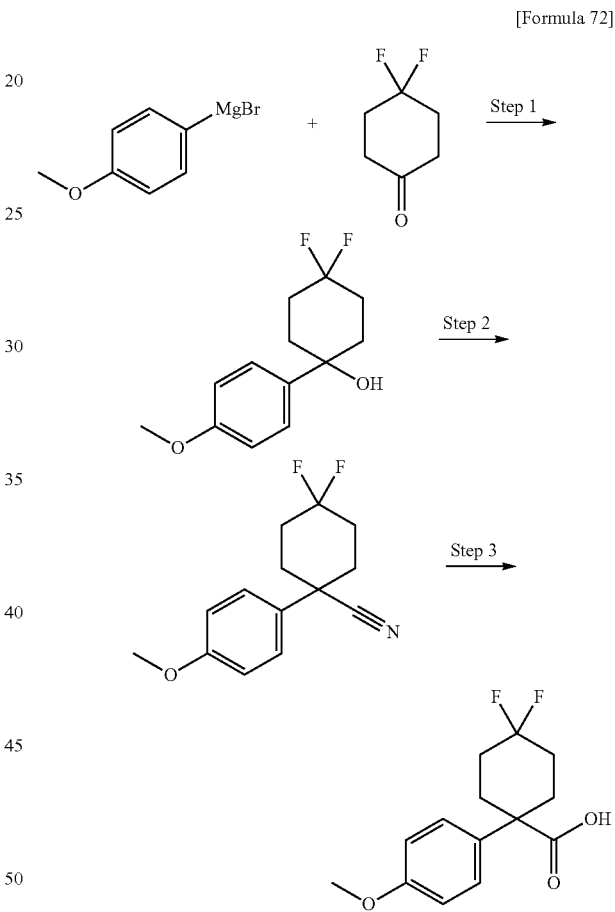

[Formula 72]

(Step 1) 4,4-Difluoro-1-(4-methoxyphenyl)cyclohexanol

A mixture of (4-methoxyphenyl)magnesium bromide (0.5 mol/L, tetrahydrofuran solution, 44 mL) and tetrahydrofuran (40 mL) was cooled to 0° C., a solution of 4,4-difluorocyclohexanone (2.68 g) in tetrahydrofuran (10 mL) was added dropwise and stirred for 1 hour while increasing the temperature to room temperature. The reaction mixture was cooled to 0° C., then 0.5 mol/L hydrochloric acid was added slowly, and the mixture was extracted with diethyl ether. The residue obtained by washing the organic layer with saturated brine, drying over anhydrous sodium sulfate, filtering and concentrating was purified by silica gel column chromatography (hexane/ethyl acetate) to obtain the title compound (3.62 g) as a solid.

¹H-NMR (CDCl₃) δ: 1.43 (1H, s), 1.83-1.94 (2H, m), 1.97-2.18 (4H, m), 2.19-2.39 (2H, m), 3.81 (3H, s), 6.86-6.93 (2H, m), 7.39-7.45 (2H, m).

(Step 2) 4,4-Difluoro-1-(4-methoxyphenyl)cyclohexanecarbonitrile

Under a nitrogen atmosphere, to a solution of indium(III) bromide (0.266 g) and trimethylsilyl cyanide (1.90 mL) in dichloromethane (15 mL), a solution of the compound (1.82 g) obtained in Step 1 above in dichloromethane (15 mL) was added dropwise and stirred for 30 minutes. The residue obtained by concentrating the reaction mixture was purified by silica gel column chromatography (hexane/ethyl acetate) to obtain the title compound (1.82 g) as an oil.

¹H-NMR (CDCl₃) δ: 2.06-2.40 (8H, m), 3.82 (3H, s), 6.90-6.96 (2H, m), 7.37-7.44 (2H, m).

(Step 3) 4,4-Difluoro-1-(4-methoxyphenyl)cyclohexanecarboxylic acid

The compound (503 mg) obtained in Step 2 above was subjected to the same procedure as in Step 2 of Reference Example C-2 to obtain the title compound (477 mg) as a solid.

¹H-NMR (CDCl₃) δ: 1.88-2.15 (6H, m), 2.47-2.62 (2H, m), 3.80 (3H, s), 6.86-6.93 (2H, m), 7.32-7.38 (2H, m). MS (m/z): 269 (M–H)⁻.

Reference Example C-5

3-(4-Methoxyphenyl)tetrahydro-2H-pyran-3-carboxylic acid

[Formula 73]

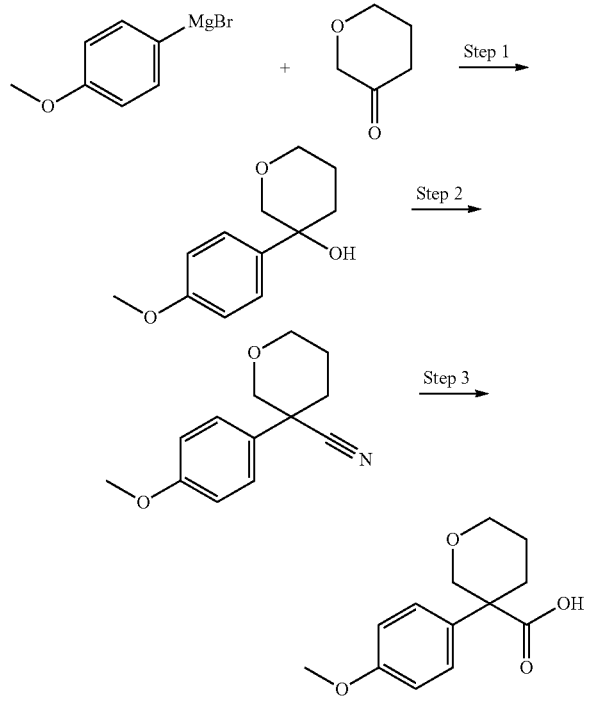

(Step 1) 3-(4-Methoxyphenyl)tetrahydro-2H-pyran-3-ol (4-Methoxyphenyl)magnesium bromide (0.5 mol/L, tetrahydrofuran solution, 88 mL) and 5,6-dihydro-2H-pyran-3(4H)-one (4.00 g) were subjected to the same procedure as in Step 1 of Reference Example C-4 to obtain the title compound (6.66 g) as a solid.

¹H-NMR (CDCl₃) δ: 1.59-1.68 (1H, m), 1.87-1.98 (1H, m), 1.99-2.14 (2H, m), 2.83 (1H, s), 3.45-3.53 (1H, m), 3.57 (1H, d, J=11.5 Hz), 3.65 (1H, dd, J=11.5, 2.4 Hz), 3.81 (3H, s), 3.97-4.04 (1H, m), 6.87-6.93 (2H, m), 7.41-7.47 (2H, m).

(Step 2) 3-(4-Methoxyphenyl)tetrahydro-2H-pyran-3-carbonitrile

The compound (5.2 g) obtained in Step 1 above was subjected to the same procedure as in Step 2 of Reference Example C-4 to obtain the title compound (4.8 g) as a solid.

¹H-NMR (CDCl₃) δ: 1.72-1.81 (1H, m), 2.03-2.12 (1H, m), 2.13-2.27 (1H, m), 2.28-2.36 (1H, m), 3.43-3.54 (2H, m), 3.82 (3H, s), 4.10 (2H, dd, J=11.5, 1.8 Hz), 6.90-6.96 (2H, m), 7.37-7.43 (2H, m).

(Step 3) 3-(4-Methoxyphenyl)tetrahydro-2H-pyran-3-carboxylic acid

The compound (434 mg) obtained in Step 2 above was subjected to the same procedure as in Step 2 of Reference Example C-2 to obtain the title compound (280 mg) as a solid.

¹H-NMR (CDCl₃) δ: 1.60-1.69 (1H, m), 1.78-1.94 (2H, m), 2.61-2.69 (1H, m), 3.42-3.52 (1H, m), 3.59 (1H, d, J=11.5 Hz), 3.79 (3H, s), 3.88-3.95 (1H, m), 4.57 (1H, d, J=10.9 Hz), 6.85-6.91 (2H, m), 7.29-7.34 (2H, m). MS (m/z): 235 (M–H)⁻.

Reference Example C-6

2-(4-Methoxyphenyl)tetrahydro-2H-pyran-2-carboxylic acid

[Formula 74]

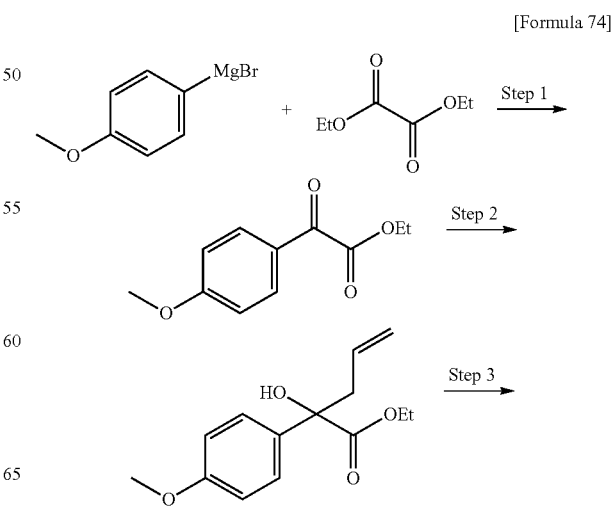

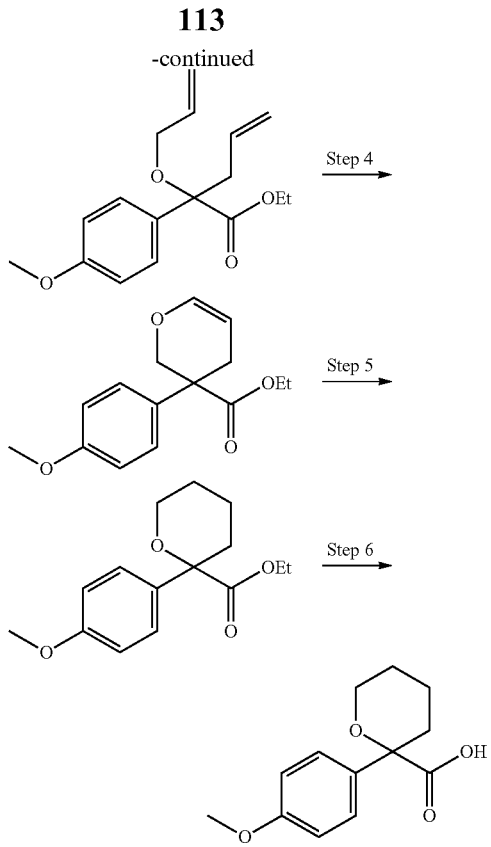

(Step 1) Ethyl (4-methoxyphenyl)(oxo)acetate

A mixed solution of diethyl oxalate (6.8 mL) in tetrahydrofuran (100 mL) and diethyl ether (100 mL) was cooled to −78° C., (4-methoxyphenyl)magnesium bromide (0.5 mol/L, tetrahydrofuran solution, 100 mL) was added dropwise and stirred at the same temperature for 2 hours. The reaction mixture was poured into 1 mol/L hydrochloric acid, ice-cooled at 0° C. and extracted with diethyl ether. The residue obtained by washing the organic layer with saturated brine, drying over anhydrous sodium sulfate, filtering and concentrating was purified by silica gel column chromatography (hexane/ethyl acetate) to obtain the title compound (8.75 g) as an oil.

$^1$H-NMR (CDCl$_3$) δ: 1.42 (3H, t, J=7.3 Hz), 3.90 (3H, s), 4.44 (2H, q, J=7.3 Hz), 6.98 (2H, d, J=8.5 Hz), 8.01 (2H, d, J=8.5 Hz). MS (m/z): 209 (M+H)$^+$.

(Step 2) Ethyl 2-hydroxy-2-(4-methoxyphenyl)pent-4-enoate

To a solution of diethylzinc (1.1 mol/L, hexane solution, 0.71 mL) in tetrahydrofuran (20 mL), ethanol (1.0 mL) was added, stirred for 30 minutes, then 2-allyl-4,4,5,5-tetramethyl-1,3,2-dioxaborolane (3.40 mL) was added, subsequently a solution of the compound (3.12 g) obtained in Step 1 above in tetrahydrofuran (5 mL) was added and stirred for 3 hours. 1 mol/L hydrochloric acid was added to the reaction mixture and stirred for 10 minutes, and then the mixture was extracted with diethyl ether, and the organic layer was sequentially washed with distilled water and with saturated brine, then dried over anhydrous sodium sulfate, filtered and concentrated. The residue obtained was purified by silica gel column chromatography (hexane/ethyl acetate) to obtain the title compound (3.50 g) as an oil.

$^1$H-NMR (CDCl$_3$) δ: 1.27 (3H, t, J=7.3 Hz), 2.74 (1H, dd, J=13.9, 6.7 Hz), 2.94 (1H, dd, J=13.9, 6.7 Hz), 3.73 (1H, s), 3.81 (3H, s), 4.13-4.31 (2H, m), 5.10-5.21 (2H, m), 5.73-5.86 (1H, m), 6.85-6.91 (2H, m), 7.49-7.55 (2H, m).

(Step 3) Ethyl 2-(4-methoxyphenyl)-2-(prop-2-en-1-yloxy)pent-4-enoate

To a solution of sodium hydride (purity>55%, 1.0 g) in 1,2-dimethoxyethane (15 mL), allyl bromide (1.6 mL) was added, then a solution of the compound (3.00 g) obtained in Step 2 above in 1,2-dimethoxyethane (30 mL) was added dropwise and stirred at 60° C. for 4 hours. A saturated aqueous ammonium chloride solution and distilled water were sequentially added to the reaction mixture, and then the mixture was extracted with diethyl ether. The organic layer was washed with saturated brine, dried over anhydrous sodium sulfate, filtered and concentrated to obtain the title compound (3.24 g) as an oil.

$^1$H-NMR (CDCl$_3$) δ: 1.23 (3H, t, J=7.3 Hz), 2.91-3.06 (2H, m), 3.79-3.85 (4H, m), 3.94-4.01 (1H, m), 4.19 (2H, q, J=7.3 Hz), 5.03-5.18 (3H, m), 5.28-5.36 (1H, m), 5.66-5.78 (1H, m), 5.89-6.00 (1H, m), 6.84-6.91 (2H, m), 7.37-7.43 (2H, m).

(Step 4) Ethyl 2-(4-methoxyphenyl)-3,6-dihydro-2H-pyran-2-carboxylate

To a solution of the compound (3.24 g) obtained in Step 3 above in dichloromethane (500 mL), Grubbs Catalyst (2nd Generation, 284 mg) was added and stirred at room temperature for 20 hours. The residue obtained by concentrating the reaction mixture was purified by silica gel column chromatography (hexane/ethyl acetate) to obtain the title compound (2.77 g) as an oil.

$^1$H-NMR (CDCl$_3$) δ: 1.20 (3H, t, J=7.3 Hz), 2.52-2.61 (1H, m), 2.99-3.08 (1H, m), 3.80 (3H, s), 4.16 (2H, q, J=7.3 Hz), 4.19-4.28 (1H, m), 4.46-4.54 (1H, m), 5.68-5.75 (1H, m), 5.85-5.93 (1H, m), 6.85-6.91 (2H, m), 7.43-7.49 (2H, m).

(Step 5) Ethyl 2-(4-methoxyphenyl)tetrahydro-2H-pyran-2-carboxylate

The compound (1.00 g) obtained in Step 4 above was subjected to the same procedure as in Step 3 of Reference Example B-15 to obtain the title compound (0.948 g) as an oil.

$^1$H-NMR (CDCl$_3$) δ: 1.18-1.24 (3H, m), 1.51-1.68 (3H, m), 1.71-1.93 (2H, m), 2.48-2.57 (1H, m), 3.72-3.83 (4H, m), 3.89-3.99 (1H, m), 4.14-4.22 (2H, m), 6.84-6.90 (2H, m), 7.42-7.48 (2H, m).

(Step 6) 2-(4-Methoxyphenyl)tetrahydro-2H-pyran-2-carboxylic acid

To a solution of the compound (560 mg) obtained in Step 5 above in methanol (20 mL), 1 mol/L aqueous sodium hydroxide solution (10 mL) was added and stirred at room temperature for 16 hours. Further, the mixture was heated to 40° C. and stirred for 4 hours. The reaction mixture was cooled to room temperature, the organic solvent was distilled off, and then the mixture was acidified with 1 mol/L hydrochloric acid. The reaction solution was extracted with Reference Example C-7

4-(4-Methoxyphenyl)tetrahydro-2H-pyran-4-carboxylic acid

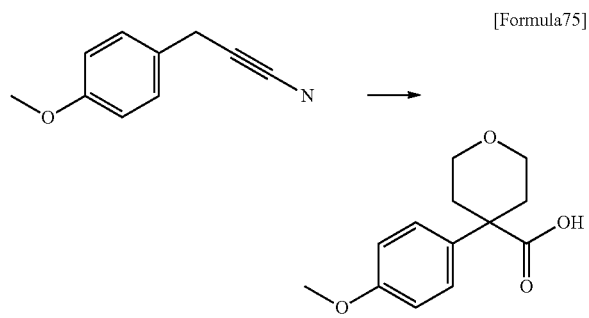
[Formula 75]

Under a nitrogen atmosphere, a suspension of sodium hydride (purity>55%, 7.51 g) in N,N-dimethylformamide (150 mL) was ice-cooled, a solution of 4-methoxyphenylacetonitrile (10.5 mL) and bis(2-bromoethyl)ether (20.2 g) in N,N-dimethylformamide (50 mL) was added dropwise over a period of 30 minutes, stirred under ice-cooling for 1 hour and at room temperature for 4 hours. After ice-cooling again, water was added to the reaction solution, and the mixture was extracted with diethyl ether three times, and the organic layer was washed with saturated brine and dried over anhydrous sodium sulfate. The organic layer was filtered and concentrated under reduced pressure to obtain crude 4-(4-methoxyphenyl)tetrahydro-2H-pyran-4-carbonitrile (22.4 g) as an oil. To this crude product (22.4 g), ethylene glycol (100 mL) and potassium hydroxide (13.01 g) were added and stirred for 8 hours under heated reflux. After allowing to cool to room temperature, water was added to the reaction solution, and the mixture was washed with diethyl ether twice. The aqueous layer was acidified by adding 1 mol/L hydrochloric acid and stirred at room temperature overnight. The precipitated solid was collected by filtration and purified by silica gel column chromatography (chloroform/methanol) to obtain the title compound (13.6 g) as a solid.

$^1$H-NMR (CDCl$_3$) δ: 1.93-2.00 (2H, m), 2.47-2.53 (2H, m), 3.58-3.64 (2H, m), 3.80 (3H, s), 3.89-3.94 (2H, m), 6.89 (2H, d, J=8.5 Hz), 7.33 (2H, d, J=8.5 Hz).

Reference Example C-8

2-(4-Methoxyphenyl)-2-methylpropionic acid

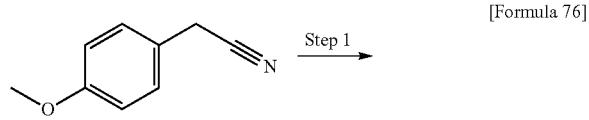
[Formula 76]

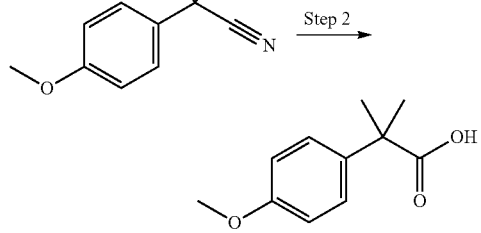

(Step 1)
2-(4-Methoxyphenyl)-2-methylpropanenitrile (4-Methoxyphenyl)acetonitrile (24.08 g) and iodomethane (22.4 mL) were subjected to the same procedure as in Step 1 of Reference Example C-2 to obtain the title compound (24.53 g) as an oil.

$^1$H-NMR (CDCl$_3$) δ: 1.70 (6H, s), 3.81 (3H, s), 6.91 (2H, d, J=9.1 Hz), 7.39 (2H, d, J=9.1 Hz).

(Step 2) 2-(4-Methoxyphenyl)-2-methylpropionic acid

The compound (24.53 g) obtained in Step 1 above was subjected to the same procedure as in Step 2 of Reference Example C-2 to obtain the title compound (15.62 g) as a solid.

$^1$H-NMR (DMSO-D$_6$) δ: 1.44 (6H, s), 3.73 (3H, s), 6.88 (2H, d, J=8.5 Hz), 7.26 (2H, d, J=8.5 Hz), 12.22 (1H, br s).

Reference Example C-9

4,4-Difluoro-1-[4-(fluoromethoxy)phenyl]cyclohexanecarboxylic acid

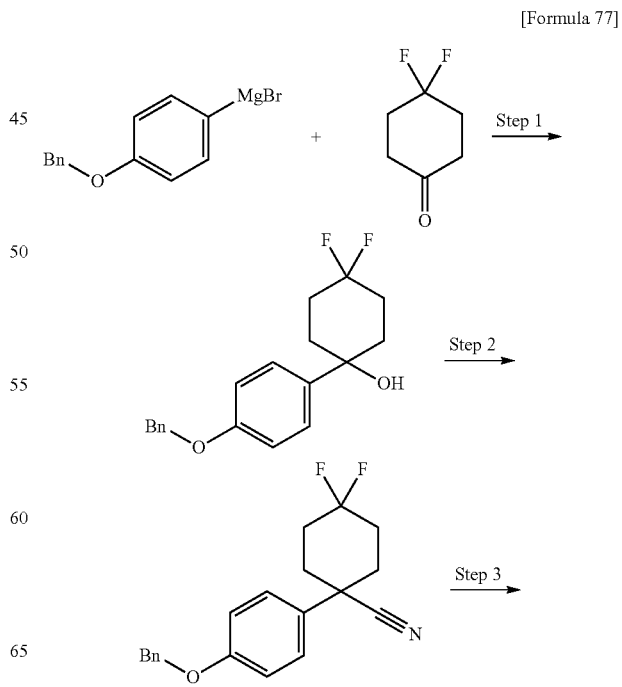
[Formula 77]

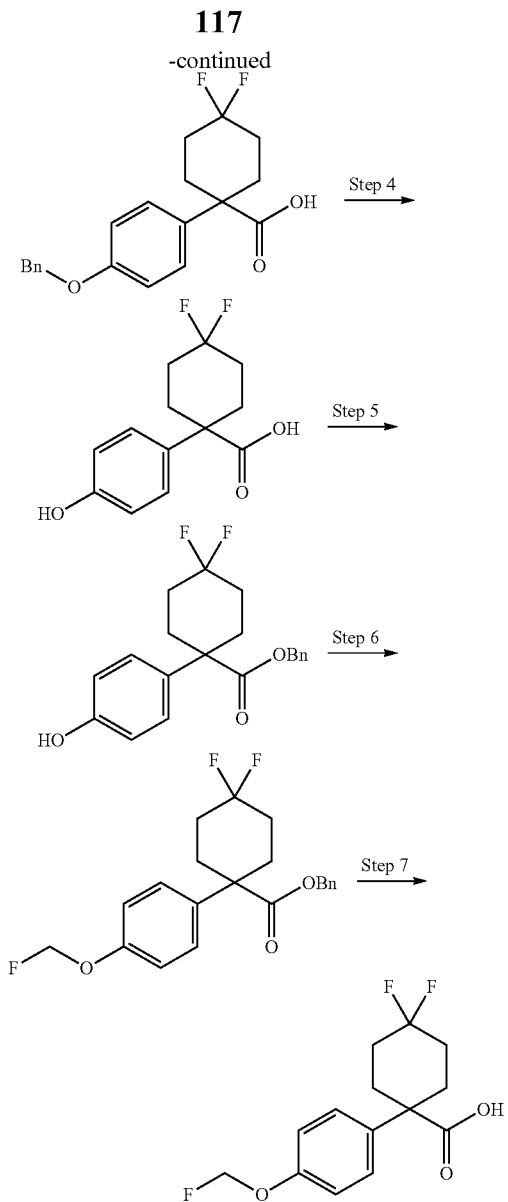

(Step 1) 1-[4-(Benzyloxy)phenyl]-4,4-difluorocyclohexanol (4-Benzyloxyphenyl)magnesium bromide (1.0 mol/L, tetrahydrofuran solution, 99.8 mL) and 4,4-difluorocyclohexanone (12.0 g) were subjected to the same procedure as in Step 1 of Reference Example C-4 to obtain the title compound (21.3 g) as a solid.
$^1$H-NMR (DMSO-D$_6$) δ: 1.68-1.78 (2H, m), 1.83-1.97 (4H, m), 2.06-2.31 (2H, m), 5.09 (3H, s), 6.95 (2H, dt, J=9.2, 3.1 Hz), 7.30-7.45 (7H, m).

(Step 2) 1-[4-(Benzyloxy)phenyl]-4,4-difluorocyclohexanecarbonitrile

To a mixture of indium(III) bromide (2.37 g), trimethylsilyl cyanide (17.3 mL), and dichloromethane (100 mL), a solution of the compound (21.3 g) obtained in Step 1 above in dichloromethane (100 mL) was added dropwise under ice-cooling and stirred for 1.5 hours while gradually increasing the temperature to room temperature. The reaction solution was washed with a saturated aqueous sodium hydrogen carbonate solution and saturated brine and then dried over anhydrous sodium sulfate. The solvent was distilled off under reduced pressure, and the residue obtained was suspended in a diethyl ether/hexane mixed solvent, stirred and collected by filtration to obtain the title compound (15.1 g) as a solid.
$^1$H-NMR (DMSO-D$_6$) δ: 1.91-2.38 (8H, m), 5.13 (2H, s), 7.08 (2H, d, J=9.2 Hz), 7.38-7.44 (7H, m).

(Step 3) 1-[4-(Benzyloxy)phenyl]-4,4-difluorocyclohexanecarboxylic acid

The compound (2.50 g) obtained in Step 2 above was subjected to the same procedure as in Step 2 of Reference Example C-2 to obtain the title compound (2.43 g) as a solid.
$^1$H-NMR (DMSO-D$_6$) δ: 1.76-2.17 (6H, m), 2.21-2.47 (2H, m), 5.09 (2H, s), 6.93-7.07 (2H, m), 7.25-7.51 (7H, m), 12.68 (1H, br s).

(Step 4) 4,4-Difluoro-1-(4-hydroxyphenyl)cyclohexanecarboxylic acid

The compound (10.0 g) obtained in Step 3 above was subjected to the same procedure as in Step 2 of Reference Example A-3 to obtain the title compound (6.41 g) as a solid.
$^1$H-NMR (DMSO-D$_6$) δ: 1.76-2.09 (6H, m), 2.37-2.46 (2H, m), 5.09 (2H, s), 6.95-7.04 (2H, m), 7.24-7.52 (7H, m), 12.68 (1H, br s).

(Step 5) Benzyl 4,4-difluoro-1-(4-hydroxyphenyl)cyclohexanecarboxylate

To a solution of the compound (2.00 g) obtained in Step 4 above in N,N-dimethylformamide (20 mL), potassium hydrogen carbonate (0.940 g) and benzyl bromide (0.97 mL) were added and stirred at room temperature for 3 hours. The reaction mixture was concentrated, diluted with ethyl acetate and then washed with 0.5 mol/L hydrochloric acid and saturated brine. The residue obtained by drying the organic layer over sodium sulfate, filtering and concentrating was purified by silica gel column chromatography (hexane/ethyl acetate) to obtain the title compound (2.63 g) as a solid.
$^1$H-NMR (DMSO-D$_6$) δ: 1.75-2.06 (6H, m), 2.38-2.48 (2H, m), 5.10 (2H, s), 6.70-6.76 (2H, m), 7.16-7.25 (4H, m), 7.29-7.35 (3H, m), 9.47 (1H, s).

(Step 6) Benzyl 4,4-difluoro-1-[4-(fluoromethoxy)phenyl]cyclohexanecarboxylate

To a solution of the compound (1.00 g) obtained in Step 5 above and fluoromethyl p-toluenesulfonate (0.710 g) in N,N-dimethylformamide (10 mL), cesium carbonate (1.9 g) was added and stirred at 60° C. for 4 hours. The reaction mixture was diluted with diethyl ether and then washed with water and saturated brine. The residue obtained by drying the organic layer over sodium sulfate, filtering and concentrating was purified by silica gel column chromatography (hexane/ethyl acetate) to obtain the title compound (0.957 g) as an oil.
$^1$H-NMR (DMSO-D$_6$) δ: 1.78-2.07 (6H, m), 2.42-2.52 (2H, m), 5.12 (2H, s), 5.86 (2H, d, J=54.3 Hz), 7.06-7.12 (2H, m), 7.19-7.25 (2H, m), 7.27-7.35 (3H, m), 7.37-7.43 (2H, m).

(Step 7) 4,4-Difluoro-1-[4-(fluoromethoxy)phenyl] cyclohexanecarboxylic acid

The compound (900 mg) obtained in Step 6 above was subjected to the same procedure as in Step 3 of Reference Example B-15 to obtain the title compound (637 mg) as a solid.

$^1$H-NMR (DMSO-D$_6$) δ: 1.80-2.09 (6H, m), 2.34-2.48 (2H, m), 5.85 (2H, d, J=54.3 Hz), 7.06-7.12 (2H, m), 7.39-7.45 (2H, m), 12.87 (1H, br s).

Reference Example C-10

1-[4-(Fluoromethoxy)phenyl]cyclopentanecarboxylic acid

[Formula 78]

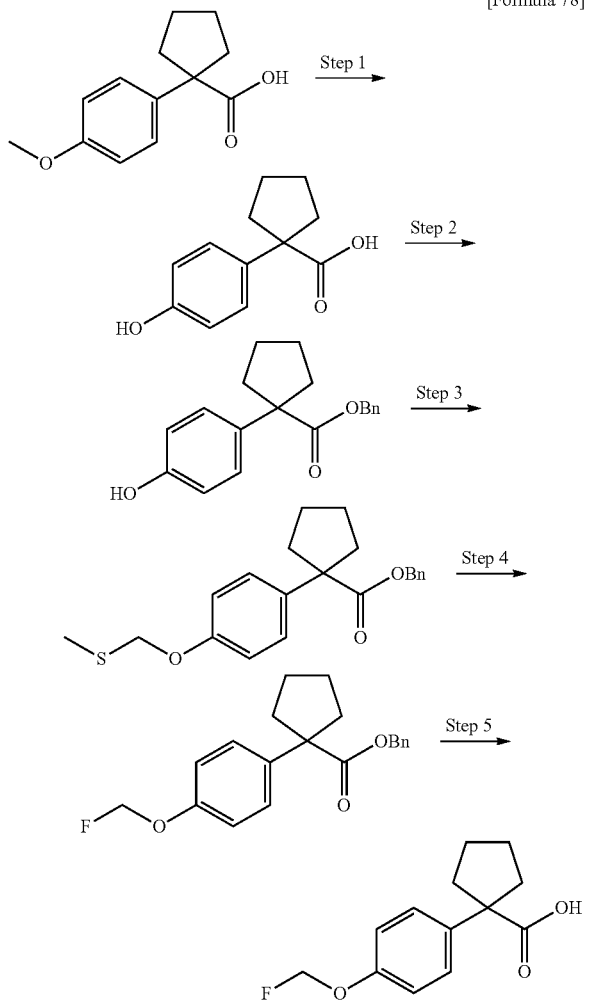

(Step 1)
1-(4-Hydroxyphenyl)cyclopentanecarboxylic acid

Under a nitrogen atmosphere, 1-(4-methoxyphenyl)cyclopentanecarboxylic acid (3.50 g) was suspended in dichloromethane (20.0 mL), cooled to −78° C., and then boron tribromide (1 mol/L, dichloromethane solution, 19.0 mL) was added dropwise and stirred at the same temperature for 1 hour and under ice-cooling for 2 hours. Iced water was poured into the reaction solution, and the mixture was extracted with ethyl acetate three times, and the organic layer was washed with saturated brine and then dried over anhydrous sodium sulfate. After filtration and concentration under reduced pressure, the solid obtained was suspended in ethyl acetate, collected by filtration and dried to obtain the title compound (1.10 g) as a solid. Further, the residue obtained by concentrating the filtrate under reduced pressure was purified by silica gel column chromatography (chloroform/methanol) to obtain the title compound (1.63 g) as a solid.

$^1$H-NMR (DMSO-D$_6$) δ: 1.61-1.73 (6H, m), 2.45-2.49 (2H, m), 6.69 (2H, d, J=8.5 Hz), 7.13 (2H, d, J=8.5 Hz), 9.29 (1H, s), 12.08 (1H, s). MS (m/z): 207 (M+H)$^+$.

(Step 2) Benzyl 1-(4-hydroxyphenyl)cyclopentanecarboxylate

The compound (1.10 g) obtained in Step 1 above was subjected to the same procedure as in Step 5 of Reference Example C-9 to obtain the title compound (1.46 g) as an oil.

$^1$H-NMR (DMSO-D$_6$) δ: 1.55-1.83 (6H, m), 2.50-2.54 (2H, m), 5.03 (2H, s), 6.69 (2H, d, J=8.5 Hz), 7.12-7.18 (4H, m), 7.30 (1H, s), 9.34 (3H, s).

(Step 3) Benzyl 1-{4-[(methylsulfanyl)methoxy] phenyl}cyclopentane-1-carboxylate Under a nitrogen atmosphere, a solution of the compound (1.40 g) obtained in Step 2 above in N,N-dimethylformamide (30.0 mL) was ice-cooled, sodium hydride (purity>55%, 0.140 g) was added and stirred at room temperature for 30 minutes, then chloromethyl methyl sulfide (0.468 mL) was added and stirred at room temperature for 2.5 hours and then at 50° C. for 3 hours. After allowing to cool to room temperature, sodium hydride (purity>55%, 0.140 g) was added, stirred for 10 minutes, and then chloromethyl methyl sulfide (0.468 mL) was added and stirred at room temperature overnight. Water was added to the reaction solution, and the mixture was extracted with diethyl ether three times, and the organic layer was washed with saturated brine and then dried over anhydrous sodium sulfate. After filtration and concentration under reduced pressure, the residue obtained was purified by silica gel column chromatography (hexane/ethyl acetate) to obtain the title compound (1.45 g) as an oil.

$^1$H-NMR (CDCl$_3$) δ: 1.66-1.74 (4H, m), 1.85-1.92 (2H, m), 2.25 (3H, s), 2.63-2.69 (2H, m), 5.04 (2H, s), 5.13 (2H, s), 6.87-6.90 (2H, m), 7.16-7.17 (2H, m), 7.26-7.32 (5H, m).

(Step 4) Benzyl 1-[4-(fluoromethoxy)phenyl]cyclopentanecarboxylate

To a solution of the compound (0.703 g) obtained in Step 3 above in dichloromethane (5.00 mL), sulfuryl chloride (0.238 mL) was added, stirred at room temperature for 2.5 hours and then concentrated under reduced pressure. The residue was dissolved in dichloromethane (5.00 mL), then ice-cooled, and tetrabutylammonium fluoride (1 mol/L, tetrahydrofuran solution, 3.90 mL) was added dropwise and stirred at room temperature for 3 hours. After concentrating the reaction solution under reduced pressure, the residue obtained was purified by silica gel column chromatography (hexane/ethyl acetate) to obtain the title compound (0.533 g) as an oil.

(Step 5) 1-[4-(Fluoromethoxy)phenyl]cyclopentan-
ecarboxylic acid

To a solution of the compound (0.524 g) obtained in Step 4 above in ethanol (10.0 mL), 10%-palladium carbon (0.105 g) was added and stirred at room temperature for 2 hours under a hydrogen atmosphere. After a nitrogen purge, 10% palladium-carbon (0.200 g) was further added and stirred at room temperature for 6 hours under a hydrogen atmosphere. After a nitrogen purge, the reaction solution was filtered and the filtrate was concentrated under reduced pressure. After dissolving the residue in ethanol (10.0 mL), 10% palladium-carbon (0.300 g) was added and stirred at room temperature for 30 minutes under a hydrogen atmosphere. After a nitrogen purge, the reaction solution was filtered and concentrated under reduced pressure. The solid obtained was suspended in hexane, collected by filtration and dried to obtain the title compound (0.329 g) as a solid.

$^1$H-NMR (CDCl$_3$) δ: 1.69-1.77 (4H, m), 1.85-1.92 (2H, m), 2.62-2.66 (2H, m), 5.69 (2H, d, J=55.0 Hz), 7.02 (2H, d, J=8.5 Hz), 7.35 (2H, d, J=8.5 Hz).

Reference Example C-11

1-(4-Methoxyphenyl)cyclobutanecarboxylic acid

[Formula 79]

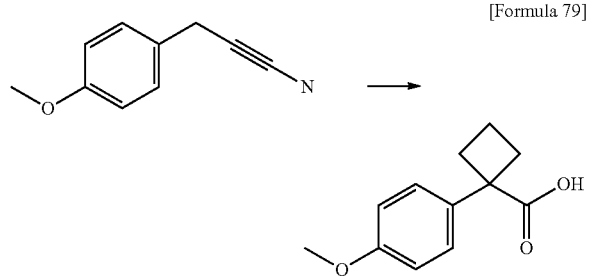

4-Methoxyphenylacetonitrile (3.27 g) and 1,3-dibromopropane (4.93 g) were subjected to the same procedure as in Step 1 of Reference Example C-2 to obtain a crude intermediate (2.40 g). The intermediate (0.374 g) was subjected to the same procedure as in C-7 to obtain the title compound (0.430 g) as a solid.

$^1$H-NMR (CDCl$_3$) δ: 1.81-1.93 (1H, m), 1.98-2.12 (1H, m), 2.43-2.54 (2H, m), 2.77-2.87 (2H, m), 3.79 (3H, s), 6.84-6.90 (2H, m), 7.21-7.25 (2H, m).

Reference Example C-12

1-(4-Methoxyphenyl)cycloheptanecarboxylic acid

[Formula 80]

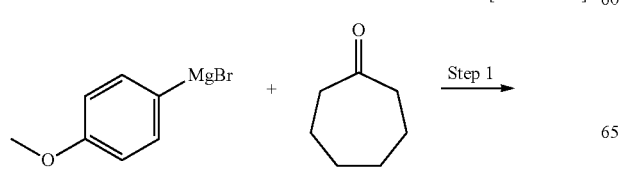

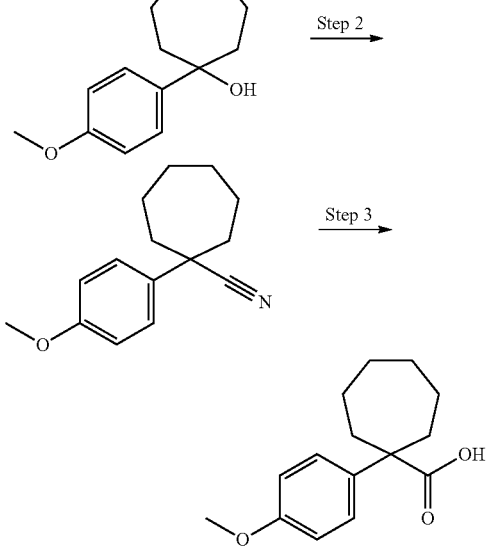

(Step 1) 1-(4-Methoxyphenyl)cycloheptanol (4-Methoxyphenyl)magnesium bromide (0.5 mol/L, tetrahydrofuran solution, 44 mL) and cycloheptanone (2.24 g) were subjected to the same procedure as in Step 1 of Reference Example C-4 to obtain the title compound (3.36 g) as an oil.

$^1$H-NMR (CDCl$_3$) δ: 1.48-1.95 (10H, m), 2.00-2.11 (2H, m), 3.80 (3H, s), 6.87 (2H, d, J=9.1 Hz), 7.42 (2H, d, J=8.5 Hz).

(Step 2) 1-(4-Methoxyphenyl)cycloheptanecarbonitrile

The compound (1.65 g) obtained in Step 1 above was subjected to the same procedure as in Step 2 of Reference Example C-4 to obtain the title compound (1.13 g) as a solid.

$^1$H-NMR (CDCl$_3$) δ: 1.56-1.69 (2H, m), 1.75-2.03 (8H, m), 2.14-2.22 (2H, m), 3.81 (3H, s), 6.86-6.92 (2H, m), 7.37-7.43 (2H, m).

(Step 3) 1-(4-Methoxyphenyl)cycloheptanecarboxylic acid

The compound (459 mg) obtained in Step 2 above was subjected to the same procedure as in Step 2 of Reference Example C-3 to obtain the title compound (128 mg) as a solid.

$^1$H-NMR (CDCl$_3$) δ: 1.47-1.70 (8H, m), 2.02-2.11 (2H, m), 2.35-2.44 (2H, m), 3.79 (3H, s), 6.84-6.89 (2H, m), 7.26-7.31 (2H, m). MS (m/z): 247 (M−H)$^-$.

Reference Example C-13

3,3-Difluoro-1-(4-methoxyphenyl)cyclobutanecarboxylic acid

[Formula 81]

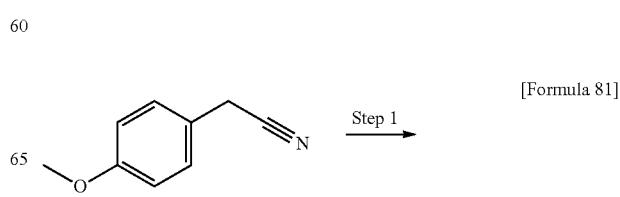

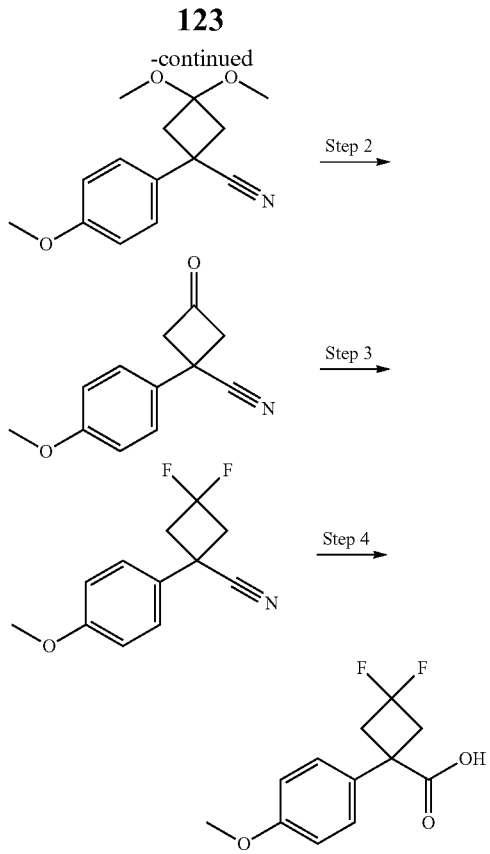

(Step 1) 3,3-Dimethoxy-1-(4-methoxyphenyl)cyclobutanecarbonitrile

To a suspension of sodium hydride (purity>55%, 1.42 g) in dimethylsulfoxide (40 mL), a solution of 4-methoxyphenylacetonitrile (2.18 g) and 1,3-dibromo-2,2-dimethoxypropane (4.27 g) in diethyl ether (10 mL) was added dropwise and stirred at room temperature for 16 hours. Isopropyl alcohol was added to the reaction mixture, and then the mixture was diluted with water and extracted with hexane. The organic layer was concentrated, then diluted with diethyl ether and washed with water. The organic layer was dried over sodium sulfate, filtered and concentrated to obtain the title compound (3.64 g) as a solid.

$^1$H-NMR (CDCl$_3$) δ: 2.65-2.72 (2H, m), 3.05-3.12 (2H, m), 3.17 (3H, s), 3.28 (3H, s), 3.82 (3H, s), 6.89-6.94 (2H, m), 7.36-7.41 (2H, m).

(Step 2) 1-(4-Methoxyphenyl)-3-oxocyclobutanecarbonitrile

To a solution of the compound (3.64 g) obtained in Step 1 above in acetone (40 mL), 6 mol/L hydrochloric acid (10 mL) was added, heated to 60° C. and stirred for 1 hour. The organic solvent was distilled off, neutralized with 5 mol/L sodium hydroxide and a saturated aqueous sodium hydrogen carbonate solution and then extracted with diethyl ether. The organic layer was washed with saturated brine and dried over sodium sulfate. The residue obtained by filtration and concentration was purified by silica gel column chromatography (hexane/ethyl acetate) to obtain the title compound (2.23 g) as an oil.

$^1$H-NMR (CDCl$_3$) δ: 3.63-3.72 (2H, m), 3.84 (3H, s), 3.99-4.07 (2H, m), 6.93-6.99 (2H, m), 7.37-7.43 (2H, m).

(Step 3) 3,3-Difluoro-1-(4-methoxyphenyl)cyclobutanecarbonitrile

A solution of the compound (2.00 g) obtained in Step 2 above in dichloromethane (20 mL) was cooled to 0° C., and a solution of (diethylamino)sulfur trifluoride (3.30 mL) in dichloromethane (10 mL) was added dropwise and stirred at room temperature for 20 hours. The reaction mixture was diluted with dichloromethane and then sequentially washed with a saturated aqueous sodium hydrogen carbonate solution and with saturated brine. The organic layer was dried over sodium sulfate, filtered and concentrated, and the residue obtained was purified by silica gel column chromatography (hexane/ethyl acetate) to obtain the title compound (1.85 g) as an oil.

$^1$H-NMR (CDCl$_3$) δ: 3.10-3.25 (2H, m), 3.43-3.55 (2H, m), 3.83 (3H, s), 6.92-6.99 (2H, m), 7.33-7.41 (2H, m).

(Step 4) 3,3-Difluoro-1-(4-methoxyphenyl)cyclobutanecarboxylic acid

A mixture of potassium hydroxide (955 mg) and ethylene glycol (7.6 mL) was heated and dissolved. The solution was cooled to room temperature, and then the compound (380 mg) obtained in Step 3 above was added and stirred at 150° C. for 5 minutes under a nitrogen atmosphere. The reaction mixture was cooled to room temperature, and then diluted with water and washed with diethyl ether. The aqueous layer was acidified with concentrated hydrochloric acid and then extracted with diethyl ether. The organic layer was dried over sodium sulfate, filtered and concentrated, and the residue obtained was purified by silica gel column chromatography (chloroform/methanol) to obtain the title compound (257 mg) as an oil.

$^1$H-NMR (CDCl$_3$) δ: 2.96-3.11 (2H, m), 3.38-3.51 (2H, m), 3.80 (3H, s), 6.86-6.93 (2H, m), 7.19-7.28 (2H, m). MS (m/z): 241 (M−H)$^-$.

Reference Example C-14

1-(4-Methoxyphenyl)-3,3-dimethylcyclobutanecarboxylic acid

[Formula 82]

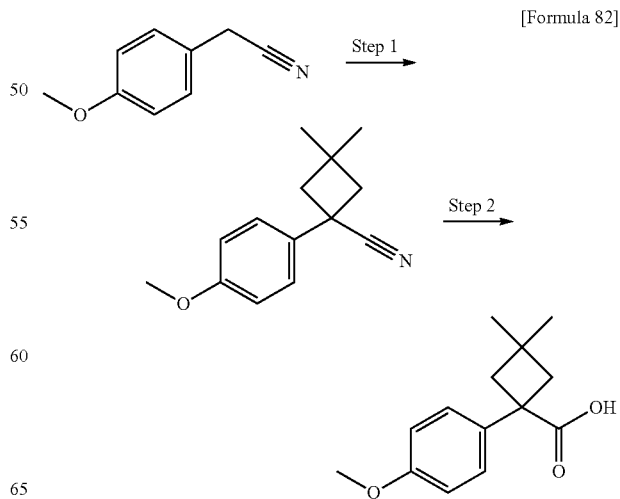

(Step 1) 1-(4-Methoxyphenyl)-3,3-dimethylcyclobutanecarbonitrile

4-Methoxyphenylacetonitrile (2.30 g) and 1,3 dibromo-2,2-dimethylpropane (4.00 g) were subjected to the same procedure as in Step 1 of Reference Example C-13 to obtain the title compound (3.55 g) as an oil.
$^1$H-NMR (CDCl$_3$) δ: 1.13 (3H, s), 1.47 (3H, s), 2.40-2.48 (2H, m), 2.67-2.74 (2H, m), 3.81 (3H, s), 6.87-6.94 (2H, m), 7.27-7.33 (2H, m).

(Step 2) 1-(4-Methoxyphenyl)-3,3-dimethylcyclobutanecarboxylic acid

The compound (3.00 g) obtained in Step 1 above was subjected to the same procedure as in Step 2 of Reference Example C-2 to obtain the title compound (2.77 g) as a solid.
$^1$H-NMR (CDCl$_3$) δ: 0.99 (3H, s), 1.15 (3H, s), 2.33 (2H, d, J=12.1 Hz), 2.73 (2H, d, J=12.1 Hz), 3.79 (3H, s), 6.82-6.88 (2H, m), 7.21-7.28 (2H, m).

Reference Example C-15

2-Methyl-2-[4-(trifluoromethoxy)phenyl]propionic acid

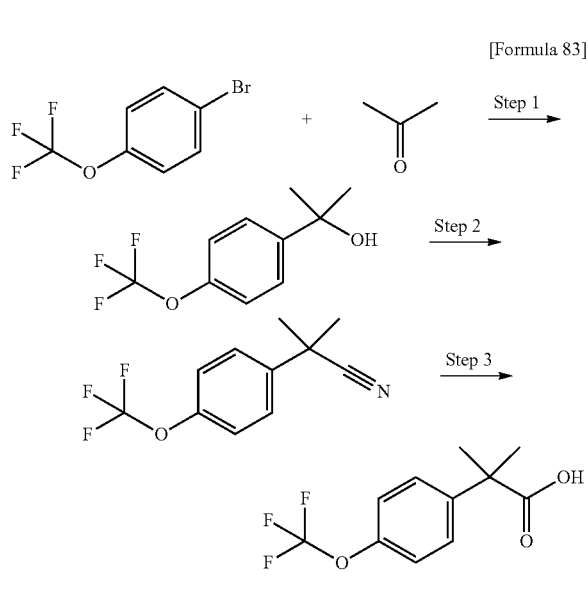

[Formula 83]

(Step 1) 2-[4-(Trifluoromethoxy)phenyl]propan-2-ol

To a suspension of magnesium (1.26 g) in tetrahydrofuran (70 mL), 1-bromo-4-(trifluoromethoxy)benzene (1.60 mL) was added and stirred at 50° C. for 30 minutes. 1-Bromo-4-(trifluoromethoxy)benzene (4.98 mL) was added, stirred at room temperature for 1 hour, and then acetone (2.00 g) was added. The reaction solution was stirred at room temperature for 2.5 hours, and then 1 mol/L hydrochloric acid was added, and the mixture was extracted with ethyl acetate. The organic layer was washed with saturated brine and dried over anhydrous magnesium sulfate. The residue obtained by concentration was purified by silica gel column chromatography (hexane/ethyl acetate) to obtain the title compound (6.55 g) as an oil.

$^1$H-NMR (CDCl$_3$) δ: 1.59 (6H, s), 7.18 (2H, d, J=8.5 Hz), 7.51 (2H, d, J=8.5 Hz).

(Step 2) 2-Methyl-2-[4-(trifluoromethoxy)phenyl]propanenitrile

The compound (2.00 g) obtained in Step 1 above was subjected to the same procedure as in Step 2 of Reference Example C-4 to obtain the title compound (1.81 g) as an oil.
$^1$H-NMR (CDCl$_3$) δ: 1.96 (6H, s), 7.31-7.41 (4H, m).

(Step 3) 2-Methyl-2-[4-(trifluoromethoxy)phenyl]propionic acid

The compound (1.81 g) obtained in Step 2 above was subjected to the same procedure as in Step 2 of Reference Example C-2 to obtain the title compound (1.76 g) as a solid.
$^1$H-NMR (CDCl$_3$) δ: 1.61 (6H, s), 7.18 (2H, d, J=7.9 Hz), 7.41-7.44 (2H, m).

Reference Example C-16

1-[4-(Trifluoroacetyl)phenyl]cyclohexanecarboxylic acid

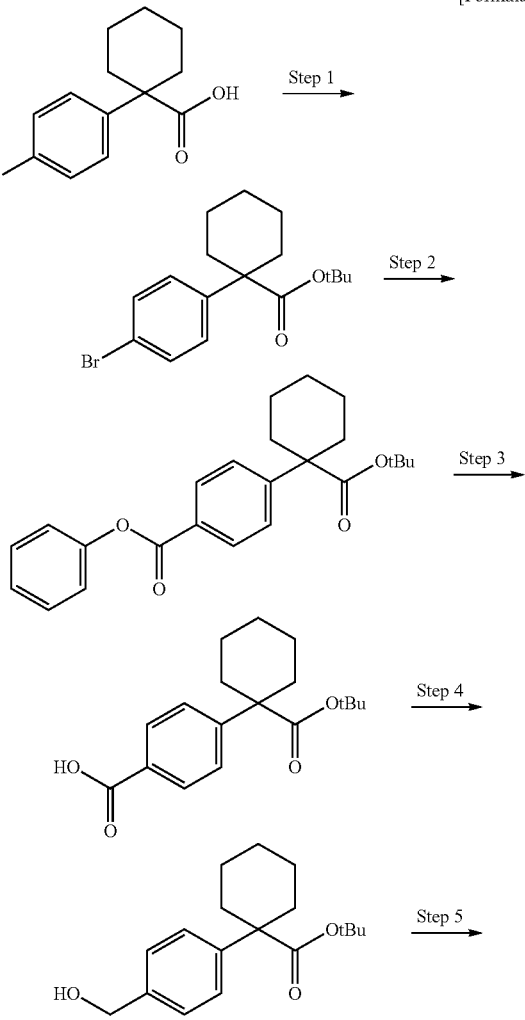

[Formula 84]

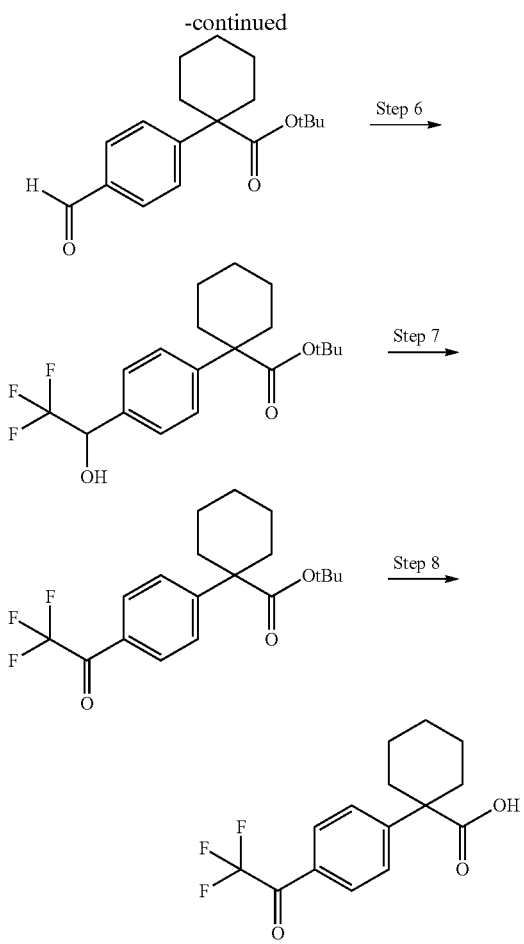

(Step 1) tert-Butyl 1-(4-bromophenyl)cyclohexanecarboxylate

To a suspension of 1-(4-bromophenyl)cyclohexanecarboxylic acid (11.5 g) in dichloromethane (200 mL), thionyl chloride (5.6 mL) and N,N-dimethylformamide (0.100 mL) were added, stirred at 40° C. for 4 hours and then concentrated under reduced pressure. The procedure of adding toluene to the residue and concentrating under reduced pressure was carried out twice to obtain a crude acid chloride. To a solution of the crude acid chloride in tetrahydrofuran (200 mL), potassium tert-butoxide (1.0 mol/L, tetrahydrofuran solution, 50 mL) was added dropwise at 0° C. and stirred at room temperature overnight. After concentrating the reaction solution under reduced pressure, a 10% aqueous citric acid solution was added to the residue, and the mixture was extracted with ethyl acetate three times. The organic layer was sequentially washed with a saturated aqueous sodium hydrogen carbonate solution and with saturated brine and then dried over anhydrous sodium sulfate. After filtration and concentration under reduced pressure, the residue obtained was purified by silica gel column chromatography (hexane/ethyl acetate) to obtain the title compound (10.9 g) as a solid.

$^1$H-NMR (CDCl$_3$) δ: 1.19-1.29 (1H, m), 1.36 (9H, s), 1.45-1.68 (7H, m), 2.35-2.41 (2H, m), 7.27 (3H, d, J=8.5 Hz), 7.43 (2H, d, J=8.5 Hz).

(Step 2) Phenyl 4-[1-(tert-butoxycarbonyl)cyclohexyl]benzoate

Under a nitrogen atmosphere, the compound (10.9 g) obtained in Step 1 above was subjected to the same procedure as in Step 4 of Reference Example C-2 to obtain the title compound (8.62 g) as a solid.

$^1$H-NMR (CDCl$_3$) δ: 1.24-1.33 (1H, m), 1.38 (9H, s), 1.49-1.58 (2H, m), 1.64-1.73 (5H, m), 2.44-2.47 (2H, m), 7.19-7.29 (3H, m), 7.40-7.45 (2H, m), 7.55 (2H, d, J=8.5 Hz), 8.15 (2H, d, J=8.5 Hz).

(Step 3) 4-[1-(tert-Butoxycarbonyl)cyclohexyl]benzoic acid

The compound (8.62 g) obtained in Step 2 above was subjected to the same procedure as in Step 5 of Reference Example C-2 to obtain the title compound (6.82 g) as a solid.

$^1$H-NMR (CDCl$_3$) δ: 8.06 (2H, d, J=8.5 Hz), 7.51 (2H, d, J=8.5 Hz), 2.47-2.40 (2H, m), 1.72-1.62 (5H, m), 1.58-1.46 (2H, m), 1.37 (9H, s), 1.31-1.21 (1H, m).

MS (m/z): 303 (M−H)$^-$.

(Step 4) tert-Butyl 1-[4-(hydroxymethyl)phenyl]cyclohexanecarboxylate

To a solution of the compound (1.00 g) obtained in Step 3 above in tetrahydrofuran (15.0 mL), triethylamine (0.687 mL) was added, ice-cooled, and then isobutyl chloroformate (0.518 mL) was added and stirred at the same temperature for 30 minutes. After separating insoluble matters by filtration, the filtrate was ice-cooled, and sodium borohydride (0.620 g) and water (3.00 mL) were added, stirred at the same temperature for 15 minutes and at room temperature for 1 hour. A saturated aqueous ammonium chloride solution was added to the reaction solution, and the mixture was extracted with ethyl acetate three times, and the organic layer was washed with saturated brine and then dried over anhydrous sodium sulfate. After filtration and concentration under reduced pressure, the residue obtained was purified by silica gel column chromatography (hexane/ethyl acetate) to obtain the title compound (0.861 g) as a solid.

$^1$H-NMR (CDCl$_3$) δ: 1.21-1.29 (1H, m), 1.37 (9H, s), 1.44-1.54 (2H, m), 1.60-1.71 (6H, m), 2.39-2.45 (2H, m), 4.67 (2H, d, J=5.4 Hz), 7.31 (2H, d, J=8.5 Hz), 7.39 (2H, d, J=8.5 Hz).

(Step 5) tert-Butyl 1-(4-formylphenyl)cyclohexanecarboxylate

To a suspension of Dess-Martin periodinane (4.56 g) in dichloromethane (24.0 mL), a solution of the compound (2.08 g) obtained in Step 4 above in dichloromethane (35.0 mL) was added and stirred at room temperature for 3.5 hours. To the reaction solution, diethyl ether, a saturated aqueous sodium hydrogen carbonate solution and sodium thiosulfate pentahydrate (18.9 g) were added, stirred at room temperature for 1 hour and then the liquid was separated. The aqueous layer was extracted with diethyl ether twice, and the organic layers were combined, washed with saturated brine and then dried over anhydrous sodium sulfate. After filtration and concentration under reduced pressure, the residue obtained was purified by silica gel column chromatography (hexane/ethyl acetate) to obtain the title compound (1.39 g) as an oil.

¹H-NMR (CDCl₃) δ: 1.24-1.37 (10H, m), 1.48-1.57 (2H, m), 1.62-1.72 (5H, m), 2.44 (2H, d, J=11.5 Hz), 7.57 (2H, d, J=8.5 Hz), 7.84 (2H, d, J=8.5 Hz), 10.00 (1H, s).

(Step 6) tert-Butyl 1-[4-(2,2,2-trifluoro-1-hydroxyethyl)phenyl]cyclohexanecarboxylate Under a nitrogen atmosphere, to a solution of the compound (1.39 g) obtained in Step 5 above in N,N-dimethylformamide (25.0 mL), (trifluoromethyl)trimethylsilane (0.855 mL) and potassium carbonate (0.0120 g) were added, stirred at room temperature for 4 hours, and then potassium carbonate (0.0530 g) was added and stirred at room temperature for 2.5 hours. (Trifluoromethyl)trimethylsilane (1.07 mL) and potassium carbonate (0.0650 mg) were further added and stirred at room temperature for 1.5 hours. After ice-cooling the reaction solution, tetrabutylammonium fluoride (1 mol/L, tetrahydrofuran solution, 19.5 mL) was added and stirred at room temperature for 30 minutes. Water and saturated brine were added to the reaction solution, and the mixture was extracted with diethyl ether three times, and the organic layer was washed with saturated brine, then dried over anhydrous sodium sulfate, filtered and concentrated under reduced pressure. The residue was purified by silica gel column chromatography (hexane/ethyl acetate) to obtain the title compound (1.65 g) as an oil.

¹H-NMR (CDCl₃) δ: 1.21-1.29 (1H, m), 1.37 (9H, s), 1.46-1.70 (7H, m), 2.43 (2H, d, J=10.9 Hz), 2.53-2.58 (1H, m), 4.97-5.03 (1H, m), 7.40-7.45 (4H, m).

(Step 7) tert-Butyl 1-[4-(trifluoroacetyl)phenyl]cyclohexanecarboxylate

To a solution of the compound (1.65 g) obtained in Step 6 above in dichloromethane (25.0 mL), manganese(IV) oxide (2.35 g) was added and stirred at room temperature overnight. Manganese(IV) oxide (2.35 g) was further added and stirred at room temperature overnight. After stirring at 40° C. for 8 hours, the reaction solution was filtered through celite, the filtrate was concentrated under reduced pressure, and then the residue obtained was purified by silica gel column chromatography (chloroform) to obtain the title compound (1.50 g) as an oil.

¹H-NMR (CDCl₃) δ: 1.21-1.34 (1H, m), 1.38 (9H, s), 1.48-1.58 (2H, m), 1.61-1.73 (5H, m), 2.42-2.45 (2H, m), 7.58 (2H, d, J=8.5 Hz), 8.03 (2H, d, J=8.5 Hz).

(Step 8) 1-[4-(Trifluoroacetyl)phenyl]cyclohexanecarboxylic acid

To a solution of the compound (1.50 g) obtained in Step 7 above in dichloromethane (20.0 mL), trifluoroacetic acid (20.0 mL) was added under ice-cooling and stirred at room temperature for 2 hours. After concentrating the reaction solution under reduced pressure, dichloromethane was added to the residue, and the mixture was washed with water, and then the organic layer was dried over anhydrous sodium sulfate. After filtration and concentration under reduced pressure, the solid obtained was suspended in hexane, collected by filtration and dried to obtain the title compound (1.11 g) as a solid.

¹H-NMR (CDCl₃) δ: 1.26-1.35 (1H, m), 1.52-1.72 (5H, m), 1.77-1.84 (2H, m), 2.46-2.49 (2H, m), 7.63 (2H, d, J=8.5 Hz), 8.05 (2H, d, J=8.5 Hz).

Reference Example C-17

1-(3,5-Difluoro-4-methoxyphenyl)-4,4-difluorocyclohexanecarboxylic acid

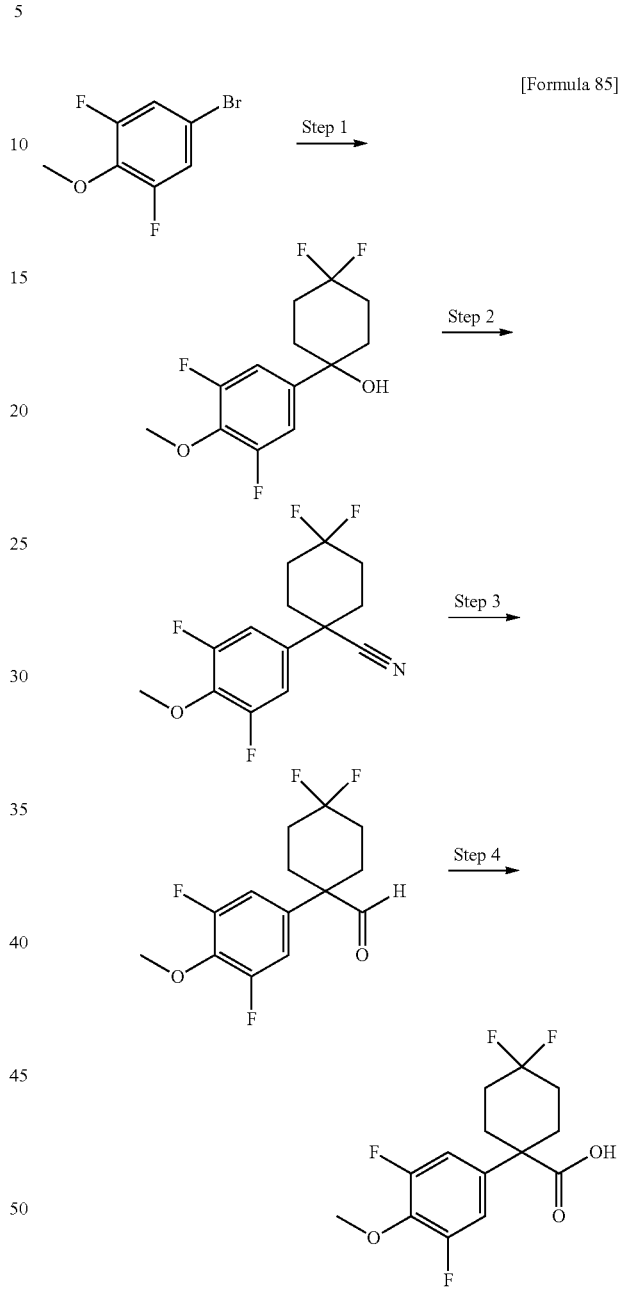

[Formula 85]

(Step 1) 1-(3,5-Difluoro-4-methoxyphenyl)-4,4-difluorocyclohexanol

Under ice-cooling, to a solution of 4-bromo-2,6-difluoroanisole (5.00 g) in tetrahydrofuran (50 mL), isopropyl magnesium chloride-lithium chloride (1.3 mol/L, tetrahydrofuran solution, 19 mL) was added and stirred for 1 hour. 4,4-Difluorocyclohexanone (3.61 g) was added and stirred at the same temperature for 1 hour, then 1 mol/L hydrochloric acid was added, and the mixture was extracted with ethyl acetate, washed with saturated brine and dried over anhydrous magnesium sulfate. The residue obtained by concentration was purified by silica gel column chromatography (hexane/ethyl acetate) to obtain the title compound (3.88 g) as a solid.

$^1$H-NMR (CDCl$_3$) δ: 1.81-1.85 (2H, m), 2.02-2.11 (4H, m), 2.17-2.35 (2H, m), 3.99 (3H, s), 7.01-7.05 (2H, m).

(Step 2) 1-(3,5-Difluoro-4-methoxyphenyl)-4,4-difluorocyclohexanecarbonitrile

The compound (3.88 g) obtained in Step 1 above was subjected to the same procedure as in Step 2 of Reference Example C-4 to obtain the title compound (3.13 g) as a solid.

$^1$H-NMR (CDCl$_3$) δ: 2.03-2.11 (2H, m), 2.18-2.36 (6H, m), 4.02 (3H, s), 7.02-7.09 (2H, m).

(Step 3) 1-(3,5-Difluoro-4-methoxyphenyl)-4,4-difluorocyclohexanecarboaldehyde

To a solution of the compound (1.00 g) obtained in Step 2 above in toluene (10 mL), diisobutylaluminium hydride (0.97 mol/L, toluene solution, 5.2 mL) was added. After stirring for 20 minutes, a saturated aqueous L-(+)-potassium sodium tartrate solution was added and stirred at room temperature for 5 minutes. The mixture was extracted with ethyl acetate, and the organic layer was washed with 1 mol/L hydrochloric acid and with saturated brine. The organic layer was dried over anhydrous magnesium sulfate and concentrated to obtain the crude title compound (0.982 g) as an oil.

$^1$H-NMR (CDCl$_3$) δ: 1.85-2.08 (6H, m), 2.34-2.38 (2H, m), 4.01 (3H, s), 6.81-6.88 (2H, m), 9.35 (1H, s).

(Step 4) 1-(3,5-Difluoro-4-methoxyphenyl)-4,4-difluorocyclohexanecarboxylic acid Under ice-cooling, to a mixture of the compound (982 mg) obtained in Step 3 above, tert-butyl alcohol (15 mL) and water (3 ml), 2-methyl-2-butene (1.8 mL), sodium dihydrogenphosphate (812 mg), and sodium chlorite (612 mg) were sequentially added and stirred at room temperature for 3 hours. 1 mol/L hydrochloric acid was added, and the mixture was extracted with ethyl acetate, and the organic layer was washed with saturated brine and dried over anhydrous magnesium sulfate. The residue obtained by concentration was purified by silica gel column chromatography (hexane/ethyl acetate) to obtain the title compound (603 mg) as a solid.

$^1$H-NMR (CDCl$_3$) δ: 1.90-2.18 (6H, m), 2.51-2.53 (2H, m), 4.00 (3H, s), 6.96-7.01 (2H, m).

Reference Example C-18

1-(6-Methoxypyridin-3-yl)cyclohexanecarboxylic acid

[Formula 86]

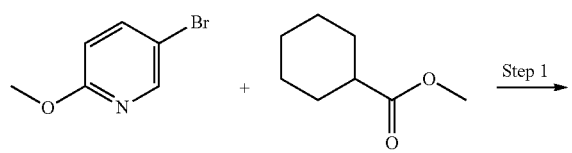

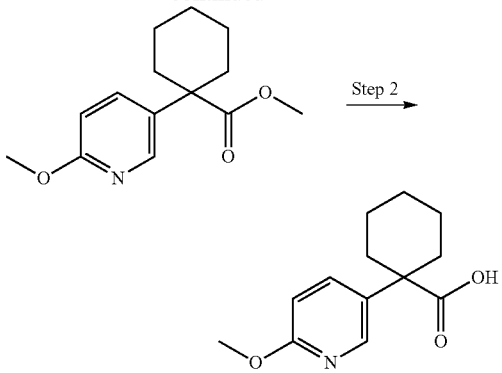

(Step 1) Methyl 1-(6-methoxypyridin-3-yl)cyclohexanecarboxylate

Under a nitrogen atmosphere, a solution of dicyclohexylamine (3.5 mL) in toluene (150 mL) was ice-cooled, n-butyllithium (1.6 mol/l, hexane solution, 11 mL) was added and stirred at room temperature for 30 minutes. Methyl cyclohexanecarboxylate (3.0 mL) was added at room temperature, stirred for 15 minutes, and then 5-bromo-2-methoxy-pyridine (1.9 mL), tris(dibenzylideneacetone)dipalladium(0) (735 mg) and tri-tert-butylphosphonium tetrafluoroborate (461 mg) were added and stirred at room temperature overnight. 1 mol/L hydrochloric acid was added to the reaction solution, and insoluble matter was filtered off. The filtrate was extracted with ethyl acetate three times, and the organic layer was washed with saturated brine and then dried over anhydrous sodium sulfate. After filtration and concentration under reduced pressure, the residue obtained was purified by silica gel column chromatography (hexane/ethyl acetate) and then purified again by amino silica gel column chromatography (hexane/ethyl acetate) to obtain the title compound (1.61 g) as an oil.

$^1$H-NMR (CDCl$_3$) δ: 1.24-1.33 (1H, m), 1.41-1.52 (2H, m), 1.56-1.75 (5H, m), 2.42-2.47 (2H, m), 3.64 (3H, s), 3.92 (3H, s), 6.70 (1H, d, J=8.8 Hz), 7.60 (1H, dd, J=8.8, 2.7 Hz), 8.18 (1H, d, J=2.7 Hz). MS (m/z): 250 (M+H)$^+$.

(Step 2) 1-(6-Methoxypyridin-3-yl)cyclohexanecarboxylic acid

The compound (1.60 g) obtained in Step 1 above was subjected to the same procedure as in Step 5 of Reference Example C-2 to obtain the title compound (1.17 g) as a solid.

$^1$H-NMR (CDCl$_3$) δ: 1.25-1.34 (1H, m), 1.48-1.78 (7H, m), 2.42-2.45 (2H, m), 3.92 (3H, s), 6.72 (1H, d, J=9.1 Hz), 7.66 (1H, d, J=9.1 Hz), 8.23 (1H, s). MS (m/z): 236 (M+H)$^+$.

Reference Example C-19

1-(2-Methoxypyrimidin-5-yl)cyclopentanecarboxylic acid

[Formula 87]

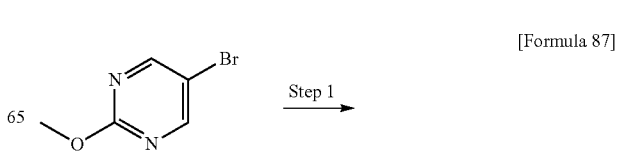

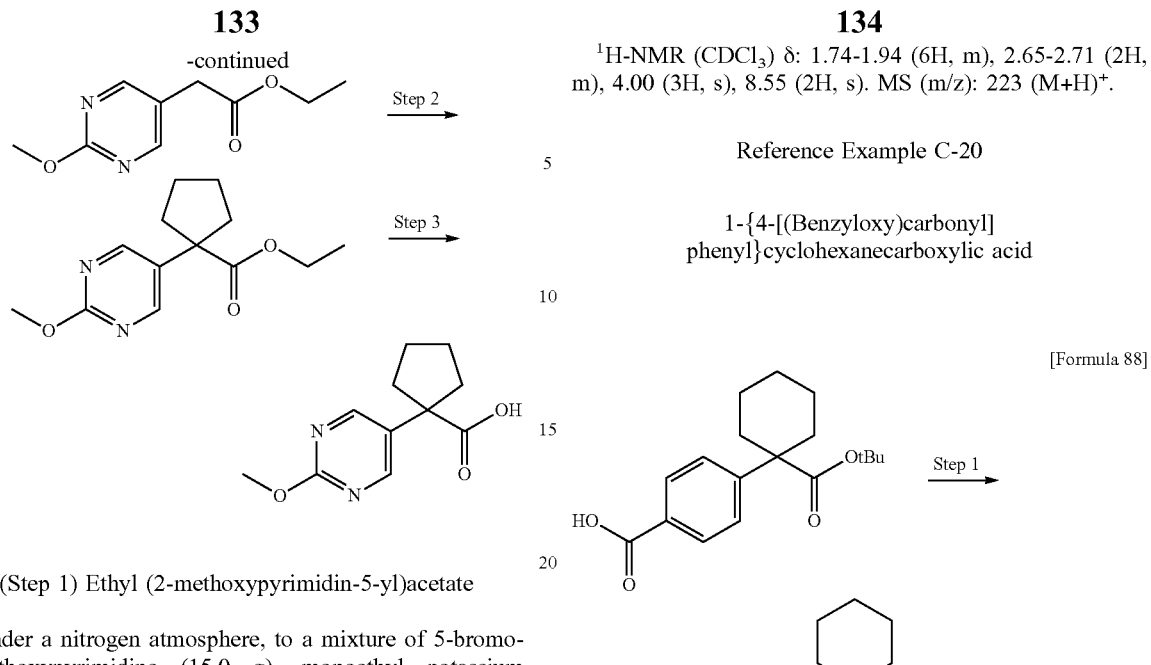

(Step 1) Ethyl (2-methoxypyrimidin-5-yl)acetate

Under a nitrogen atmosphere, to a mixture of 5-bromo-2-methoxypyrimidine (15.0 g), monoethyl potassium malonate (20.3 g), allyl palladium(II) chloride dimer (0.581 g), 2-dicyclohexylphosphino-2',6'-diisopropoxybiphenyl (2.22 g) and 4-dimethylaminopyridine (0.970 g), 1,3,5-trimethylbenzene (150 mL) was added and stirred at 140° C. overnight. After allowing to cool to room temperature, the reaction solution was concentrated under reduced pressure, and ethyl acetate and water were added to the residue obtained, and the mixture was filtered through celite. The filtrate was extracted with ethyl acetate three times, and the organic layer was washed with saturated brine and then dried over anhydrous sodium sulfate. After filtration and concentration under reduced pressure, the residue obtained was purified by silica gel column chromatography (hexane/ethyl acetate) to obtain the title compound (8.53 g) as a solid.

$^1$H-NMR (CDCl$_3$) δ: 1.27 (3H, t, J=7.0 Hz), 3.55 (2H, s), 4.01 (3H, s), 4.18 (2H, q, J=7.0 Hz), 8.45 (2H, s). MS (m/z): 197 (M+H)$^+$.

(Step 2) Ethyl 1-(2-methoxypyrimidin-5-yl)cyclopentanecarboxylate

The compound (5.00 g) obtained in Step 1 above and 1,4-dibromobutane (3.31 mL) were subjected to the same procedure as in Step 1 of Reference Example C-2 to obtain the title compound (3.08 g) as an oil.

$^1$H-NMR (CDCl$_3$) δ: 1.19 (3H, t, J=7.1 Hz), 1.72-1.79 (4H, m), 1.83-1.92 (2H, m), 2.63-2.70 (2H, m), 4.01 (3H, s), 4.09 (2H, q, J=7.1 Hz), 8.51 (2H, s). MS (m/z): 251 (M+H)$^+$.

(Step 3) 1-(2-Methoxypyrimidin-5-yl)cyclopentanecarboxylic acid

To a solution of the compound (1.00 g) obtained in Step 2 above in tetrahydrofuran (24.0 mL), methanol (12.0 mL) and 1 mol/L aqueous sodium hydroxide solution (12.0 mL) were added and stirred at 50° C. for 5 hours. After allowing to cool to room temperature, the organic solvent was distilled off under reduced pressure and the residue was acidified by adding 1 mol/L hydrochloric acid. The precipitated solid was collected by filtration and dried to obtain the title compound (0.774 g) as a solid.

$^1$H-NMR (CDCl$_3$) δ: 1.74-1.94 (6H, m), 2.65-2.71 (2H, m), 4.00 (3H, s), 8.55 (2H, s). MS (m/z): 223 (M+H)$^+$.

Reference Example C-20

1-{4-[(Benzyloxy)carbonyl]phenyl}cyclohexanecarboxylic acid

[Formula 88]

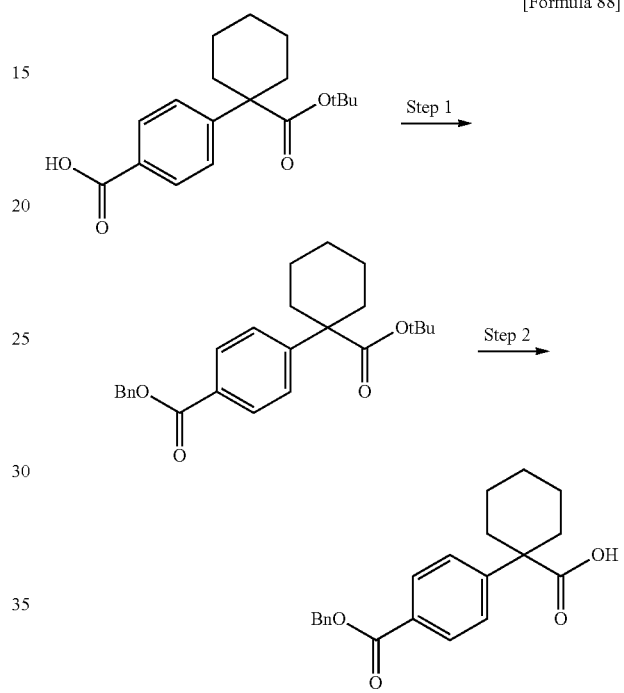

(Step 1) Benzyl 4-[1-(tert-butoxycarbonyl)cyclohexyl]benzoate

The compound (4.01 g) obtained in Step 3 of Reference Example C-16 was subjected to the same procedure as in Step 3 of Reference Example C-2 to obtain the title compound (5.11 g) as a solid.

$^1$H-NMR (CDCl$_3$) δ: 1.21-1.30 (1H, m), 1.35 (9H, s), 1.46-1.57 (2H, m), 1.60-1.72 (5H, m), 2.38-2.45 (2H, m), 5.35 (2H, s), 7.48-7.32 (7H, m), 8.02 (2H, d, J=8.5 Hz).

(Step 2) 1-{4-[(Benzyloxy)carbonyl]phenyl}cyclohexanecarboxylic acid

The compound (5.10 g) obtained in Step 1 above was subjected to the same procedure as in Step 8 of Reference Example C-16 to obtain the title compound (3.89 g) as a solid.

$^1$H-NMR (CDCl$_3$) δ: 1.24-1.33 (1H, m), 1.50-1.80 (7H, m), 2.42-2.49 (2H, m), 5.35 (2H, s), 7.31-7.44 (5H, m), 7.51 (2H, d, J=8.5 Hz), 8.04 (2H, d, J=8.5 Hz).

Reference Example C-21

1-[4-(Benzyloxy)phenyl]cyclohexanecarboxylic acid

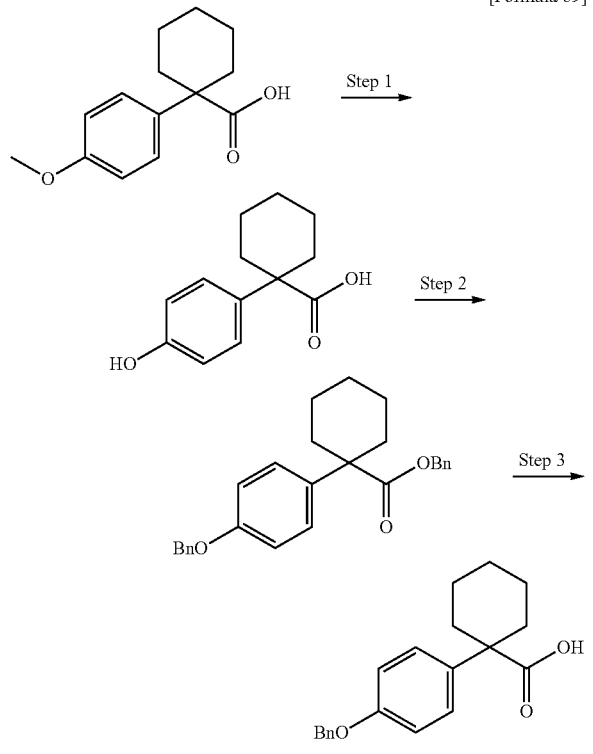

[Formula 89]

(Step 1)
1-(4-Hydroxyphenyl)cyclohexanecarboxylic acid 1-(4-Methoxyphenyl)cyclohexanecarboxylic acid (5.00 g) was subjected to the same procedure as in Step 1 of Reference Example C-10 to obtain the title compound (4.60 g) as a solid.

$^1$H-NMR (DMSO-D$_6$) δ: 1.17-1.63 (8H, m), 2.29 (2H, d, J=11.0 Hz), 6.70 (2H, d, J=8.5 Hz), 7.17 (2H, d, J=8.5 Hz), 9.26 (1H, s).

(Step 2) Benzyl 1-[4-(benzyloxy)phenyl]cyclohexanecarboxylate

The compound (1.00 g) obtained in Step 1 above was subjected to the same procedure as in Step 3 of Reference Example C-2 to obtain the title compound (1.24 g) as a solid.

$^1$H-NMR (DMSO-D$_6$) δ: 1.18-1.70 (8H, m), 2.33-2.39 (2H, m), 5.05-5.09 (4H, m), 6.96 (2H, d, J=9.2 Hz), 7.17-7.45 (12H, m).

(Step 3) 1-[4-(Benzyloxy)phenyl]cyclohexanecarboxylic acid

The compound (1.20 g) obtained in Step 2 above was subjected to the same procedure as in Step 2 of Reference Example C-3 to obtain the title compound (0.898 g) as a solid.

$^1$H-NMR (DMSO-D$_6$) δ: 1.15-1.31 (1H, m), 1.33-1.48 (2H, m), 1.50-1.66 (5H, m), 2.24-2.36 (2H, m), 5.08 (2H, s), 6.96 (2H, d, J=8.5 Hz), 7.25-7.48 (7H, m), 12.20 (1H, br s).

Reference Example C-22

1-[4-(Difluoromethoxy)phenyl]-4,4-difluorocyclohexanecarboxylic acid

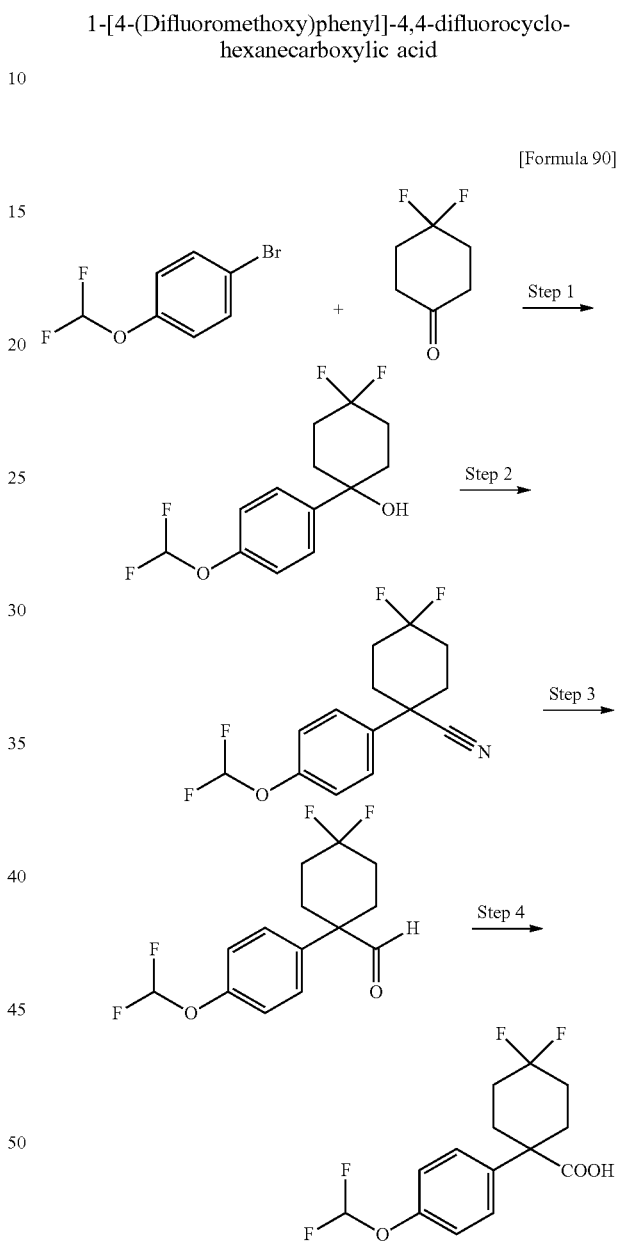

[Formula 90]

(Step 1) 1-[4-(Difluoromethoxy)phenyl]-4,4-difluorocyclohexanol

1-Bromo-4-(difluoromethoxy)benzene (5.00 g) and 4,4-difluorocyclohexanone (2.50 g) were subjected to the same procedure as in Step 1 of Reference Example C-17 to obtain the title compound (3.56 g) as an oil.

$^1$H-NMR (CDCl$_3$) δ: 1.49 (1H, s), 1.82-1.91 (2H, m), 2.00-2.40 (6H, m), 6.51 (1H, t, J=73.9 Hz), 7.09-7.15 (2H, m), 7.47-7.52 (2H, m).

(Step 2) 1-[4-(Difluoromethoxy)phenyl]-4,4-difluorocyclohexanecarbonitrile

The compound (4.40 g) obtained in Step 1 above was subjected to the same procedure as in Step 2 of Reference Example C-4 to obtain the title compound (1.30 g) as a solid.
$^1$H-NMR (CDCl$_3$) δ: 2.17-2.31 (8H, m), 6.54 (1H, t, J=73.5 Hz), 7.17 (2H, dt, J=9.5, 2.6 Hz), 7.50 (2H, dt, J=9.5, 2.6 Hz).

(Step 3) 1-[4-(Difluoromethoxy)phenyl]-4,4-difluorocyclohexanecarboaldehyde

Under a nitrogen atmosphere, the compound (1.19 g) obtained in Step 2 above was subjected to the same procedure as in Step 3 of Reference Example C-17 at −78° C. to obtain the title compound (1.03 g) as an oil.
$^1$H-NMR (CDCl$_3$) δ: 1.86-2.16 (6H, m), 2.40-2.43 (2H, m), 6.52 (1H, t, J=73.4 Hz), 7.16 (2H, dd, J=11.7, 2.9 Hz), 7.30 (2H, dt, J=9.5, 2.6 Hz), 9.38 (1H, s).

(Step 4) 1-[4-(Difluoromethoxy)phenyl]-4,4-difluorocyclohexanecarboxylic acid

The compound (1.03 g) obtained in Step 3 above was subjected to the same procedure as in Step 4 of Reference Example C-17 to obtain the title compound (1.03 g) as a solid.
$^1$H-NMR (DMSO-D$_6$) δ: 1.90-2.04 (6H, m), 2.43-2.45 (2H, m), 7.05-7.42 (3H, m), 7.48 (2H, dd, J=6.7, 2.1 Hz), 12.88 (1H, br s). MS (m/z): 305 (M−H)$^-$.

Reference Example C-23

4,4-Difluoro-1-[3-fluoro-4-(fluoromethoxy)phenyl]cyclohexanecarboxylic acid

[Formula 91]

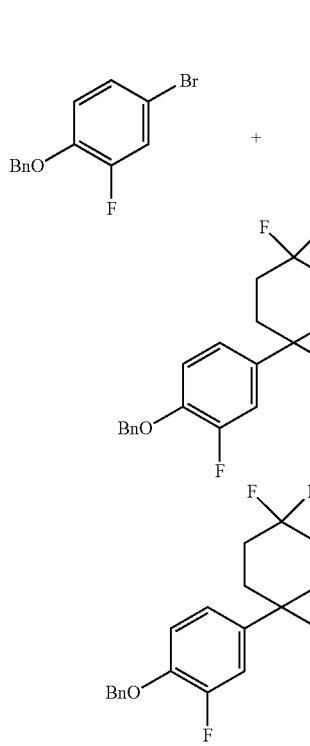

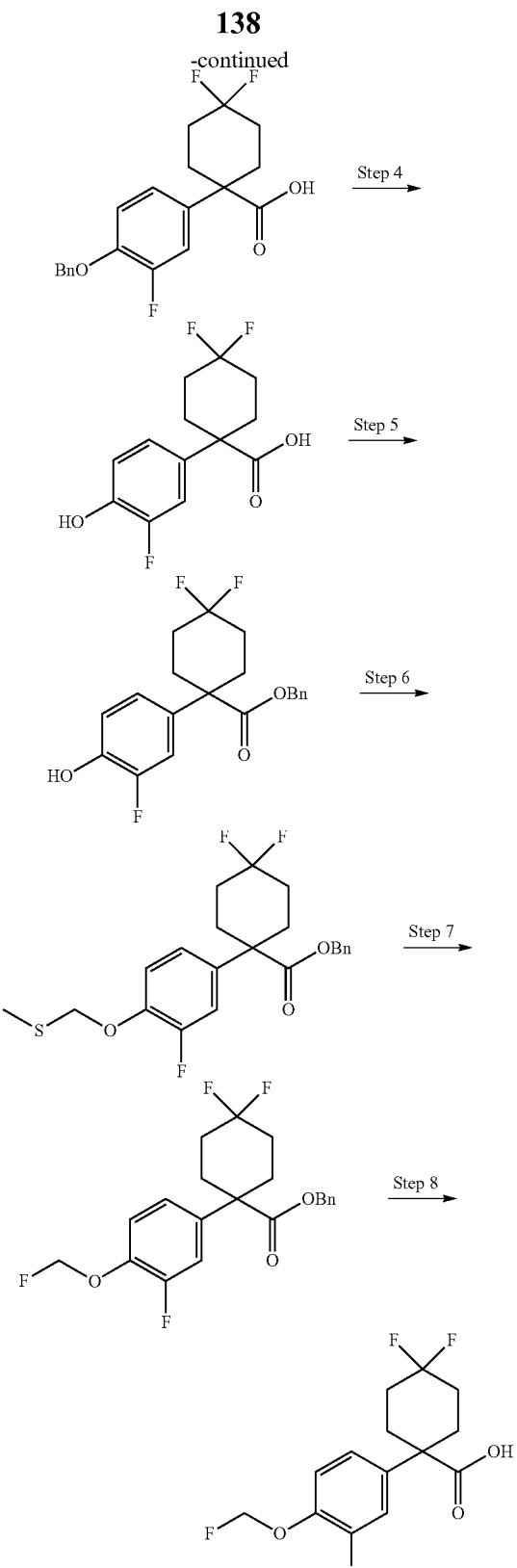

(Step 1) 1-[4-(Benzyloxy)-3-fluorophenyl]-4,4-difluorocyclohexanol

Benzyl 4-bromo-2-fluorophenyl ether (6.29 g) and 4,4-difluorocyclohexanone (2.50 g) were subjected to the same procedure as in Step 1 of Reference Example C-17 to obtain the title compound (4.40 g) as a solid.

¹H-NMR (CDCl₃) δ: 1.45 (1H, s), 1.83-1.87 (2H, m), 2.04-2.36 (6H, m), 5.14 (2H, s), 6.97 (1H, t, J=8.5 Hz), 7.13 (1H, dd, J=8.5, 0.9 Hz), 7.23-7.45 (6H, m). MS (m/z): 319 (M−H₂O+H)⁺.

(Step 2) 1-[4-(Benzyloxy)-3-fluorophenyl]-4,4-difluorocyclohexanecarbonitrile

The compound (4.40 g) obtained in Step 1 above was subjected to the same procedure as in Step 2 of Reference Example C-4 to obtain the title compound (2.50 g) as a solid.

¹H-NMR (CDCl₃) δ: 2.14-2.24 (8H, m), 5.16 (2H, s), 7.02 (1H, t, J=8.5 Hz), 7.16-7.23 (2H, m), 7.32-7.45 (5H, m).

(Step 3) 1-[4-(Benzyloxy)-3-fluorophenyl]-4,4-difluorocyclohexanecarboxylic acid The compound (2.51 g) obtained in Step 2 above was subjected to the same procedure as in Step 2 of Reference Example C-2 to obtain the title compound (2.12 g) as a solid.

¹H-NMR (CDCl₃) δ: 1.98-2.03 (6H, m), 2.51-2.54 (2H, m), 5.13 (2H, s), 6.98 (1H, t, J=8.7 Hz), 7.09 (1H, dd, J=5.5, 4.3 Hz), 7.20 (1H, dd, J=12.8, 2.4 Hz), 7.30-7.52 (5H, m). MS (m/z): 363 (M−H)⁻.

(Step 4) 4,4-Difluoro-1-(3-fluoro-4-hydroxyphenyl)cyclohexanecarboxylic acid

The compound (2.12 g) obtained in Step 3 above was subjected to the same procedure as in Step 2 of Reference Example A-3 to obtain the title compound (2.04 g) as a solid.
MS (m/z): 273 (M−H)⁻.

(Step 5) Benzyl 4,4-difluoro-1-(3-fluoro-4-hydroxyphenyl)cyclohexanecarboxylate

The compound (1.60 g) obtained in Step 4 above was subjected to the same procedure as in Step 5 of Reference Example C-9 to obtain the title compound (1.76 g) as a solid.

¹H-NMR (CDCl₃) δ: 1.81-2.08 (6H, m), 2.53-2.56 (2H, m), 5.10 (2H, s), 5.22 (1H, d, J=2.7 Hz), 6.94 (1H, t, J=8.8 Hz), 7.01-7.04 (1H, m), 7.09 (1H, dd, J=12.3, 2.3 Hz), 7.17-7.20 (2H, m), 7.30-7.34 (3H, m). MS (m/z): 363 (M−H)⁻.

(Step 6) Benzyl 4,4-difluoro-1-{3-fluoro-4-[(methylsulfanyl)methoxy]phenyl}cyclohexane-1-carboxylate Under a nitrogen atmosphere, a solution of sodium hydride (purity>55%, 253 mg) in N,N-dimethylformamide (10 mL) was ice-cooled, and a solution of the compound (1.76 g) obtained in Step 5 above in N,N-dimethylformamide (20 mL) was added and stirred at room temperature for 20 minutes. Chloromethyl methyl sulfide (0.478 mL) was added and stirred at room temperature for 2 hours. Water was added to the reaction solution, and the mixture was extracted with diethyl ether three times, and the organic layer was washed with saturated brine and then dried over anhydrous sodium sulfate. The residue obtained by concentration under reduced pressure was purified by silica gel column chromatography (hexane/ethyl acetate) to obtain the title compound (2.03 g) as an oil.

¹H-NMR (CDCl₃) δ: 1.81-2.11 (6H, m), 2.27 (3H, s), 2.56-2.58 (2H, br m), 5.11 (2H, s), 5.21 (2H, s), 6.98 (1H, t, J=8.5 Hz), 7.05-7.20 (4H, m), 7.31 (3H, dd, J=5.2, 1.8 Hz). MS (m/z): 425 (M+H)⁺.

(Step 7) Benzyl 4,4-difluoro-1-[3-fluoro-4-(fluoromethoxy)phenyl]cyclohexanecarboxylate The compound (2.03 g) obtained in Step 6 above was subjected to the same procedure as in Step 4 of Reference Example C-10 to obtain the title compound (1.55 g) as an oil.

¹H-NMR (CDCl₃) δ: 1.86-2.11 (6H, m), 2.54-2.57 (2H, m), 5.11 (2H, s), 5.70 (2H, d, J=53.8 Hz), 7.07-7.21 (5H, m), 7.29-7.36 (3H, m).

(Step 8) 4,4-Difluoro-1-[3-fluoro-4-(fluoromethoxy)phenyl]cyclohexanecarboxylic acid The compound (900 mg) obtained in Step 7 above was subjected to the same procedure as in Step 5 of Reference Example B-8 to obtain the title compound (691 mg) as an oil.
MS (m/z): 305 (M−H)⁻.

Reference Example C-24

3,3-Difluoro-1-[3-fluoro-4-(fluoromethoxy)phenyl]cyclobutanecarboxylic acid

[Formula 92]

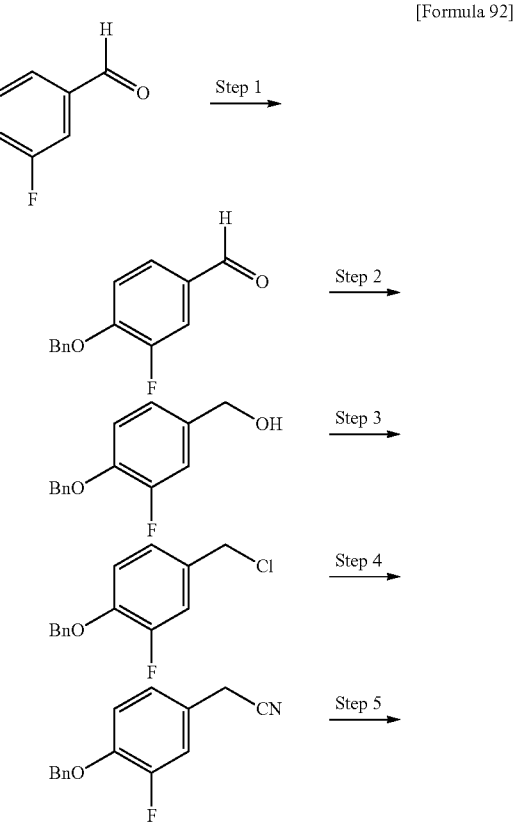

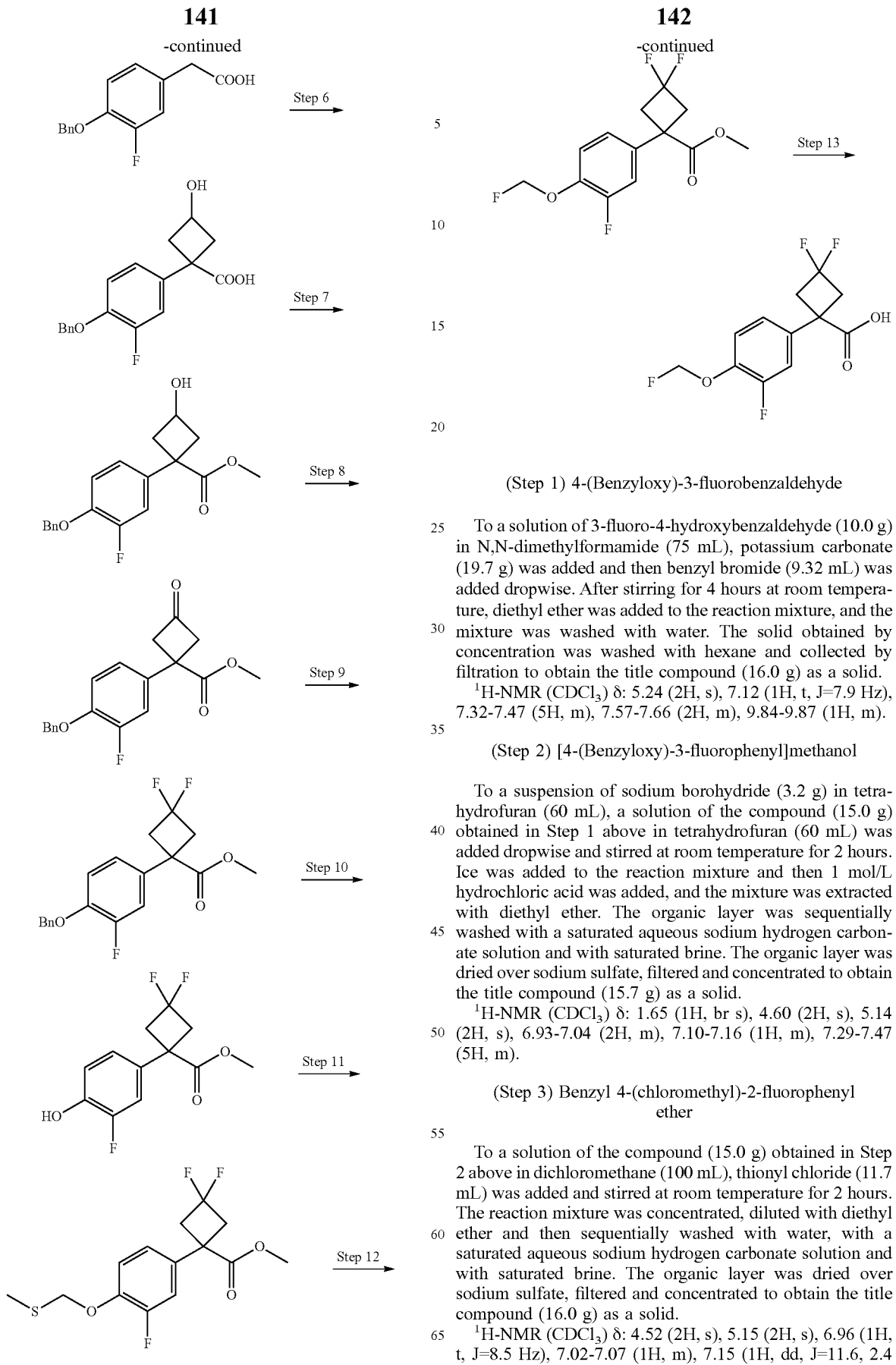

(Step 1) 4-(Benzyloxy)-3-fluorobenzaldehyde

To a solution of 3-fluoro-4-hydroxybenzaldehyde (10.0 g) in N,N-dimethylformamide (75 mL), potassium carbonate (19.7 g) was added and then benzyl bromide (9.32 mL) was added dropwise. After stirring for 4 hours at room temperature, diethyl ether was added to the reaction mixture, and the mixture was washed with water. The solid obtained by concentration was washed with hexane and collected by filtration to obtain the title compound (16.0 g) as a solid.

$^1$H-NMR (CDCl$_3$) δ: 5.24 (2H, s), 7.12 (1H, t, J=7.9 Hz), 7.32-7.47 (5H, m), 7.57-7.66 (2H, m), 9.84-9.87 (1H, m).

(Step 2) [4-(Benzyloxy)-3-fluorophenyl]methanol

To a suspension of sodium borohydride (3.2 g) in tetrahydrofuran (60 mL), a solution of the compound (15.0 g) obtained in Step 1 above in tetrahydrofuran (60 mL) was added dropwise and stirred at room temperature for 2 hours. Ice was added to the reaction mixture and then 1 mol/L hydrochloric acid was added, and the mixture was extracted with diethyl ether. The organic layer was sequentially washed with a saturated aqueous sodium hydrogen carbonate solution and with saturated brine. The organic layer was dried over sodium sulfate, filtered and concentrated to obtain the title compound (15.7 g) as a solid.

$^1$H-NMR (CDCl$_3$) δ: 1.65 (1H, br s), 4.60 (2H, s), 5.14 (2H, s), 6.93-7.04 (2H, m), 7.10-7.16 (1H, m), 7.29-7.47 (5H, m).

(Step 3) Benzyl 4-(chloromethyl)-2-fluorophenyl ether

To a solution of the compound (15.0 g) obtained in Step 2 above in dichloromethane (100 mL), thionyl chloride (11.7 mL) was added and stirred at room temperature for 2 hours. The reaction mixture was concentrated, diluted with diethyl ether and then sequentially washed with water, with a saturated aqueous sodium hydrogen carbonate solution and with saturated brine. The organic layer was dried over sodium sulfate, filtered and concentrated to obtain the title compound (16.0 g) as a solid.

$^1$H-NMR (CDCl$_3$) δ: 4.52 (2H, s), 5.15 (2H, s), 6.96 (1H, t, J=8.5 Hz), 7.02-7.07 (1H, m), 7.15 (1H, dd, J=11.6, 2.4 Hz), 7.30-7.46 (5H, m).

(Step 4) [4-(Benzyloxy)-3-fluorophenyl]acetonitrile

To a mixture of the compound (12.0 g) obtained in Step 3 above, N,N-dimethylformamide (120 mL) and water (12 mL), potassium cyanide (4.68 g) was added and stirred at 90° C. for 2 hours. The reaction mixture was concentrated, diluted with ethyl acetate and then sequentially washed with water and with saturated brine. The organic layer was dried over sodium sulfate, filtered and concentrated to obtain the title compound (10.3 g) as a solid.

$^1$H-NMR (CDCl$_3$) δ: 3.96 (2H, s), 5.18 (2H, s), 7.09-7.14 (1H, m), 7.21-7.30 (2H, m), 7.31-7.48 (5H, m).

(Step 5) [4-(Benzyloxy)-3-fluorophenyl]acetic acid

To a mixture of the compound (8.0 g) obtained in Step 4 above, ethanol (40 mL) and water (10 mL), potassium hydroxide (4.4 g) was added and stirred for 3 hours while heated to reflux. The reaction mixture was cooled to room temperature, and then the organic layer was distilled off under reduced pressure. The organic layer was diluted with water, acidified with 6 mol/L hydrochloric acid, and the resulting solid was collected by filtration and dried. The solid obtained was dispersed with ethyl acetate to form a slurry and then the solid was collected by filtration and dried to obtain the title compound (4.9 g) as a solid. Additionally, the filtrate was concentrated and then purified by silica gel column chromatography (dichloromethane/methanol) to obtain the title compound (1.9 g) as a solid.

$^1$H-NMR (DMSO-D$_6$) δ: 3.51 (2H, s), 5.16 (2H, s), 6.99 (1H, d, J=7.9 Hz), 7.07-7.21 (2H, m), 7.29-7.49 (5H, m), 12.34 (1H, s).

(Step 6) 1-[4-(Benzyloxy)-3-fluorophenyl]-3-hydroxycyclobutanecarboxylic acid

Under a nitrogen atmosphere, isopropylmagnesium chloride (2.0 mol/L, tetrahydrofuran solution, 25 mL) was cooled to 0° C., a solution of the compound (5.80 g) obtained in Step 5 above in tetrahydrofuran (12.0 mL) was added dropwise and stirred at room temperature for 1 hour. Epichlorohydrin (3.3 mL) was added dropwise and stirred at 40° C. for 2 hours. To the reaction mixture, isopropylmagnesium chloride (2.0 mol/L, tetrahydrofuran solution, 25 mL) was added dropwise at room temperature and stirred again at 40° C. for 8 hours. 1 mol/L hydrochloric acid was added slowly to the reaction mixture, and then the mixture was extracted with ethyl acetate. The organic layer was washed with 1 mol/L hydrochloric acid, then dried over sodium sulfate, filtered and concentrated. Diethyl ether was added to the residue obtained, and the solid was collected by filtration and dried to obtain the title compound (4.97 g) as a solid.

$^1$H-NMR (DMSO-D$_6$) δ: 2.41-2.49 (2H, m), 2.66-2.75 (2H, m), 3.79-3.89 (1H, m), 5.10-5.19 (3H, m), 7.08-7.13 (1H, m), 7.16-7.23 (2H, m), 7.31-7.48 (5H, m), 12.30 (1H, br s).

(Step 7) Methyl 1-[4-(benzyloxy)-3-fluorophenyl]-3-hydroxycyclobutanecarboxylate To a suspension of the compound (4.90 g) obtained in Step 6 above in methanol (49 mL), sulfuric acid (0.17 mL) was added and then stirred for 6 hours under heated reflux. The reaction mixture was concentrated, diluted with toluene and ethyl acetate and then washed with a saturated aqueous sodium hydrogen carbonate solution. The organic layer was dried over sodium sulfate, filtered and concentrated. The residue obtained was diluted with dichloromethane, then hexane was added, and the resulting solid was collected by filtration and dried to obtain the title compound (4.60 g) as a solid.

$^1$H-NMR (DMSO-D$_6$) δ: 2.42-2.53 (2H, m), 2.70-2.80 (2H, m), 3.54 (3H, s), 3.81-3.93 (1H, m), 5.13-5.23 (3H, m), 7.08-7.14 (1H, m), 7.17-7.25 (2H, m), 7.31-7.49 (5H, m).
MS (m/z): 331 (M+H)$^+$.

(Step 8) Methyl 1-[4-(benzyloxy)-3-fluorophenyl]-3-oxocyclobutanecarboxylate

The compound (500 mg) obtained in Step 7 above was subjected to the same procedure as in Step 5 of Reference Example C-16 to obtain the title compound (441 mg) as a solid.

$^1$H-NMR (DMSO-D$_6$) δ: 3.54-3.64 (5H, m), 3.72-3.81 (2H, m), 5.20 (2H, s), 7.10-7.15 (1H, m), 7.21-7.31 (2H, m), 7.32-7.49 (5H, m).

(Step 9) Methyl 1-[4-(benzyloxy)-3-fluorophenyl]-3,3-difluorocyclobutanecarboxylate The compound (430 mg) obtained in Step 8 above was subjected to the same procedure as in Step 3 of Reference Example C-13 to obtain the title compound (378 mg) as an oil.

$^1$H-NMR (DMSO-D$_6$) δ: 3.07-3.21 (2H, m), 3.28-3.43 (2H, m), 3.61 (3H, s), 5.18 (2H, s), 7.08-7.13 (1H, m), 7.21-7.28 (2H, m), 7.32-7.49 (5H, m).

(Step 10) Methyl 3,3-difluoro-1-(3-fluoro-4-hydroxyphenyl)cyclobutanecarboxylate The compound (330 mg) obtained in Step 9 above was subjected to the same procedure as in Step 3 of Reference Example B-15 to obtain the title compound (247 mg) as an oil.

$^1$H-NMR (DMSO-D$_6$) δ: 3.01-3.18 (2H, m), 3.26-3.41 (2H, m), 3.61 (3H, s), 6.89-7.00 (2H, m), 7.09-7.17 (1H, m), 9.97 (1H, br s).

(Step 11) Methyl 3,3-difluoro-1-{3-fluoro-4-[(methylsulfanyl)methoxy]phenyl}cyclobutene-1-carboxylate The compound (247 mg) obtained in Step 10 above was subjected to the same procedure as in Step 6 of Reference Example C-23 to obtain the title compound (195 mg) as an oil.

$^1$H-NMR (DMSO-D$_6$) δ: 2.18 (3H, s), 3.08-3.22 (2H, m), 3.29-3.43 (2H, m), 3.62 (3H, s), 5.37 (2H, s), 7.08-7.16 (1H, m), 7.22-7.31 (2H, m).

(Step 12) Methyl 3,3-difluoro-1-[3-fluoro-4-(fluoromethoxy)phenyl]cyclobutanecarboxylate The compound (190 mg) obtained in Step 11 above was subjected to the same procedure as in Step 4 of Reference Example C-10 to obtain the title compound (116 mg) as a solid.

$^1$H-NMR (DMSO-D$_6$) δ: 3.10-3.24 (2H, m), 3.29-3.45 (2H, m), 3.62 (3H, s), 5.90 (2H, d, J=53.1 Hz), 7.16-7.22 (1H, m), 7.30-7.39 (2H, m).

(Step 13) 3,3-Difluoro-1-[3-fluoro-4-(fluoromethoxy)phenyl]cyclobutanecarboxylic acid A mixture of the compound (100 mg) obtained in Step 12 above, tetrahydrofuran (0.5 mL) and water (0.5 mL) was cooled to 0° C., then lithium hydroxide monohydrate (16 mg) and methanol (1 drop) were added and stirred at room temperature for 1 hour. The reaction mixture was diluted with saturated ammonium chloride water and then extracted with ethyl acetate. The organic layers were combined, washed with saturated brine, then dried over sodium sulfate, filtered and concentrated to obtain the title compound (105 mg) as a solid.
$^1$H-NMR (DMSO-D$_6$) δ: 2.82-2.99 (2H, m), 3.19-3.46 (2H, m), 5.86 (2H, d, J=53.7 Hz), 7.07-7.14 (1H, m), 7.20-7.29 (2H, m).

Reference Example C-25

3,3-Difluoro-1-[3-fluoro-4-(2,2,2-trifluoroethoxy)phenyl]cyclobutanecarboxylic acid

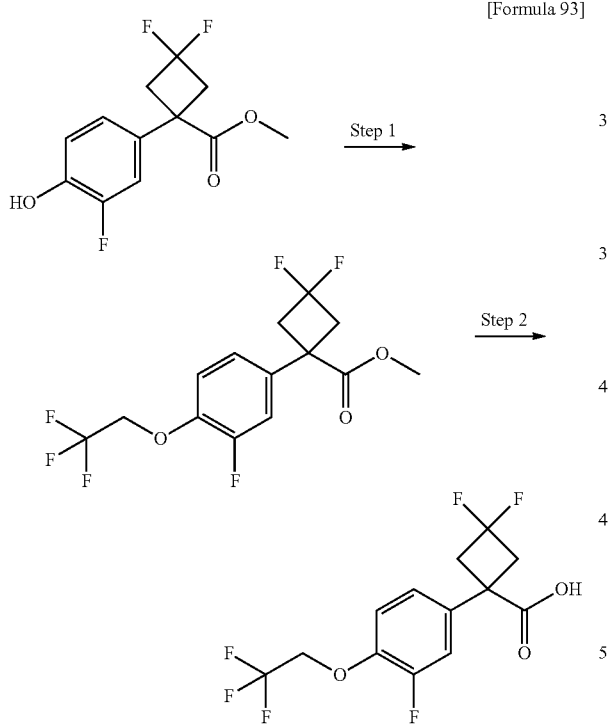

[Formula 93]

(Step 1) Methyl 3,3-difluoro-1-[3-fluoro-4-(2,2,2-trifluoroethoxy)phenyl]cyclobutanecarboxylate To a solution of the compound (200 mg) obtained in Step 10 of Reference Example C-24 in acetone (4 mL), potassium carbonate (319 mg) and 2,2,2-trifluoroethyl trifluoromethanesulfonate (144 μL) were added and stirred at room temperature for 12 hours. Ethyl acetate was added to the reaction mixture and then the mixture was filtered through celite, and the filtrate was concentrated. The residue obtained was diluted with ethyl acetate, sequentially washed with water and with saturated brine, and then the organic layer was dried over sodium sulfate, filtered and concentrated to obtain the title compound (243 mg) as an oil.
$^1$H-NMR (DMSO-D$_6$) δ: 3.09-3.23 (2H, m), 3.26-3.44 (2H, m), 3.61 (3H, s), 4.87 (2H, q, J=8.7 Hz), 7.14-7.20 (1H, m), 7.26-7.36 (2H, m).

(Step 2) 3,3-Difluoro-1-[3-fluoro-4-(2,2,2-trifluoroethoxy)phenyl]cyclobutanecarboxylic acid The compound (240 mg) obtained in Step 1 above was subjected to the same procedure as in Step 13 of Reference Example C-24 to obtain the title compound (240 mg) as an oil.
$^1$H-NMR (DMSO-D$_6$) δ: 3.02-3.18 (2H, m), 3.25-3.41 (2H, m), 4.86 (2H, q, J=9.0 Hz), 7.12-7.18 (1H, m), 7.26-7.33 (2H, m), 13.03 (1H, br s).

Reference Example C-26

1-(4-Ethoxy-3-fluorophenyl)-3,3-difluorocyclobutanecarboxylic acid

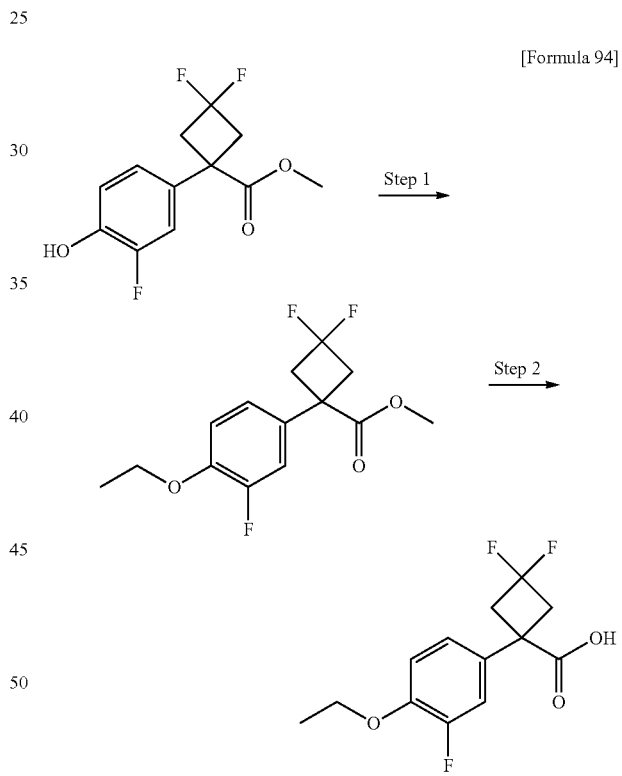

[Formula 94]

(Step 1) Methyl 1-(4-ethoxy-3-fluorophenyl)-3,3-difluorocyclobutanecarboxylate

To a solution of the compound (200 mg) obtained in Step 10 of Reference Example C-24 in acetone (4 mL), potassium carbonate (319 mg) and iodoethane (80 μL) were added and stirred at room temperature for 12 hours. The reaction mixture was diluted with ethyl acetate and then sequentially washed with water and with saturated brine. The organic layer was dried over sodium sulfate, filtered and concentrated to obtain the title compound (199 mg) as an oil.

$^1$H-NMR (DMSO-D$_6$) δ: 1.34 (3H, t, J=7.1 Hz), 3.06-3.20 (2H, m), 3.28-3.43 (2H, m), 3.61 (3H, s), 4.10 (2H, q, J=7.1 Hz), 7.07-7.18 (2H, m), 7.22 (1H, dd, J=12.8, 2.4 Hz).

(Step 2) 1-(4-Ethoxy-3-fluorophenyl)-3,3-difluoro-cyclobutanecarboxylic acid

The compound (195 mg) obtained in Step 1 above was subjected to the same procedure as in Step 13 of Reference Example C-24 to obtain the title compound (185 mg) as a solid.

$^1$H-NMR (DMSO-D$_6$) δ: 1.34 (3H, t, J=6.9 Hz), 2.99-3.16 (2H, m), 3.22-3.40 (2H, m), 4.10 (2H, q, J=6.9 Hz), 7.05-7.25 (3H, m), 12.91 (1H, br s).

Reference Example C-27

1-[4-(Difluoromethoxy)-3-fluorophenyl]-4,4-difluorocyclohexanecarboxylic acid sodium sulfate, filtered and concentrated. The residue obtained was purified by silica gel column chromatography (hexane/ethyl acetate) to obtain the title compound (372 mg) as an oil.

$^1$H-NMR (CDCl$_3$) δ: 1.80-2.12 (6H, m), 2.50-2.63 (2H, m), 5.12 (2H, s), 6.54 (1H, t, J=73.2 Hz), 7.08-7.13 (1H, m), 7.14-7.21 (4H, m), 7.29-7.33 (3H, m).

(Step 2) 1-[4-(Difluoromethoxy)-3-fluorophenyl]-4,4-difluorocyclohexanecarboxylic acid The compound (360 mg) obtained in Step 1 above was subjected to the same procedure as in Step 3 of Reference Example B-15 to obtain the title compound (281 mg) as a solid.

$^1$H-NMR (DMSO-D$_6$) δ: 1.79-2.10 (6H, m), 2.35-2.48 (2H, m), 7.05-7.49 (4H, m), 13.10 (1H, br s).

Reference Example C-28

1-[4-(Difluoromethoxy)phenyl]-3,3-difluorocyclobutanecarboxylic acid

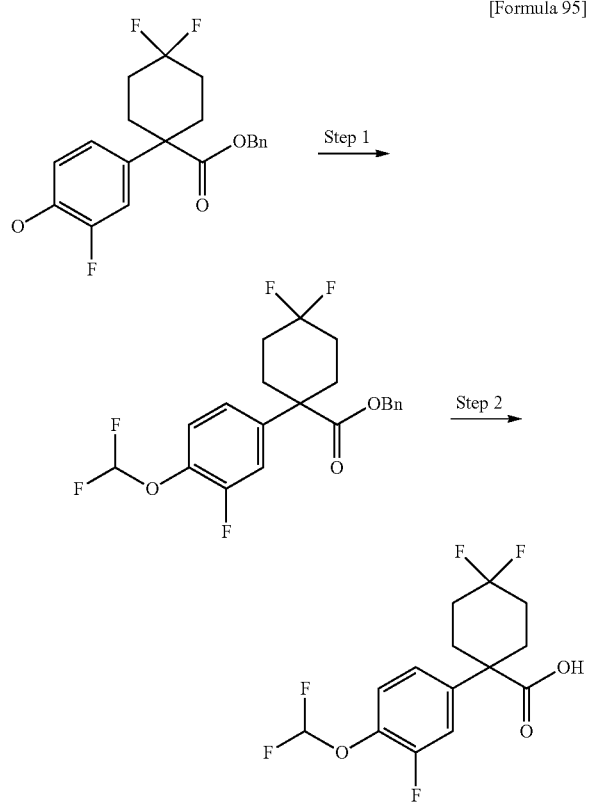

[Formula 95]

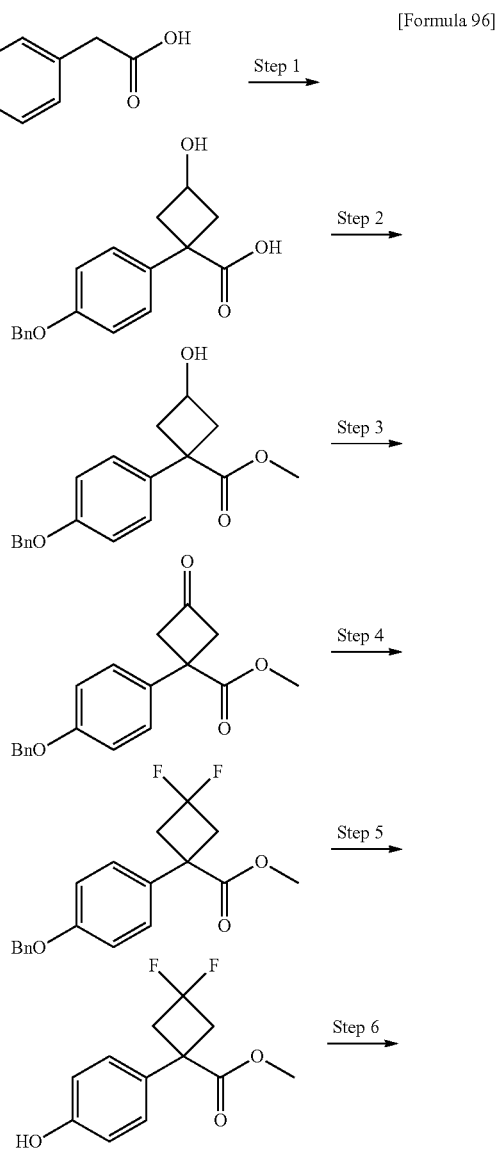

[Formula 96]

(Step 1) Benzyl 1-[4-(difluoromethoxy)-3-fluorophenyl]-4,4-difluorocyclohexanecarboxylate A solution of the compound (364 mg) obtained in Step 5 of Reference Example C-23 in acetonitrile (2 mL) was vigorously stirred under ice-cooling, during which an aqueous solution (2 mL) of potassium hydroxide (673 mg) cooled to 0° C. and subsequently diethyl (bromodifluoromethyl)phosphonate (0.53 mL) were added. The mixture was stirred at the same temperature for 5 minutes, then diluted with water and extracted with diethyl ether. The organic layer was washed with saturated brine, then dried over

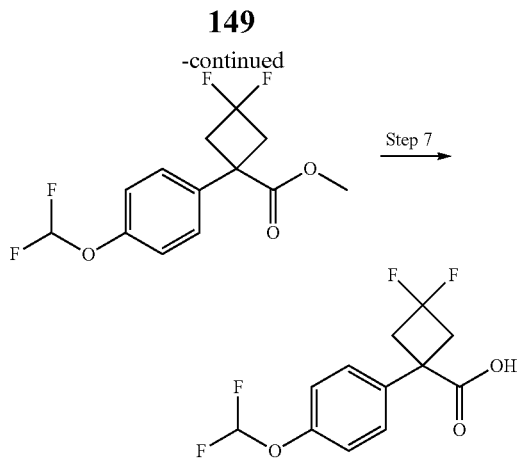

(Step 1) 1-[4-(Benzyloxy)phenyl]-3-hydroxycyclobutanecarboxylic acid

[4-(Benzyloxy)phenyl]acetic acid (12.1 g) was subjected to the same procedure as in Step 6 of Reference Example C-24 to obtain the title compound (5.50 g) as a solid.
$^1$H-NMR (DMSO-D$_6$) δ: 2.40-2.55 (2H, m), 2.64-2.76 (2H, m), 3.77-3.91 (1H, m), 5.01-5.19 (3H, m), 6.93-7.02 (2H, m), 7.15-7.49 (7H, m), 12.14 (1H, br s). MS (m/z): 299 (M+H)$^+$.

(Step 2) Methyl 1-[4-(benzyloxy)phenyl]-3-hydroxycyclobutanecarboxylate

The compound (5.0 g) obtained in Step 1 above was subjected to the same procedure as in Step 7 of Reference Example C-24 to obtain the title compound (5.1 g) as a solid.
$^1$H-NMR (DMSO-D$_6$) δ: 2.42-2.54 (2H, m), 2.69-2.79 (2H, m), 3.53 (3H, s), 3.81-3.92 (1H, m), 5.09 (2H, s), 6.93-7.02 (2H, m), 7.16-7.48 (7H, m). MS (m/z): 313 (M+H)$^+$.

(Step 3) Methyl 1-[4-(benzyloxy)phenyl]-3-oxocyclobutanecarboxylate

The compound (5.0 g) obtained in Step 2 above was subjected to the same procedure as in Step 5 of Reference Example C-16 to obtain the title compound (3.7 g) as a solid.
$^1$H-NMR (DMSO-D$_6$) δ: 3.51-3.64 (5H, m), 3.74-3.84 (2H, m), 5.11 (2H, s), 7.02 (2H, d, J=8.5 Hz), 7.27-7.48 (7H, m). MS (m/z): 311 (M+H)$^+$.

(Step 4) Methyl 1-[4-(benzyloxy)phenyl]-3,3-difluorocyclobutanecarboxylate

The compound (3.6 g) obtained in Step 3 above was subjected to the same procedure as in Step 3 of Reference Example C-13 to obtain the title compound (3.0 g) as a solid.
$^1$H-NMR (DMSO-D$_6$) δ: 3.03-3.18 (2H, m), 3.30-3.44 (2H, m), 3.59 (3H, s), 5.10 (2H, s), 6.98-7.05 (2H, m), 7.24-7.48 (7H, m). MS (m/z): 333 (M+H)$^+$.

(Step 5) Methyl 3,3-difluoro-1-(4-hydroxyphenyl)cyclobutanecarboxylate

The compound (3.0 g) obtained in Step 4 above was subjected to the same procedure as in Step 3 of Reference Example B-15 to obtain the title compound (2.2 g) as an oil.
$^1$H-NMR (DMSO-D$_6$) δ: 2.98-3.13 (2H, m), 3.26-3.42 (2H, m), 3.59 (3H, s), 6.71-6.78 (2H, m), 7.10-7.17 (2H, m), 9.54 (1H, s).

(Step 6) Methyl 1-[4-(difluoromethoxy)phenyl]-3,3-difluorocyclobutanecarboxylate The compound (1.2 g) obtained in Step 5 above was subjected to the same procedure as in Step 1 of Reference Example C-27 to obtain the title compound (1.1 g) as an oil.
$^1$H-NMR (DMSO-D$_6$) δ: 3.08-3.22 (2H, m), 3.32-3.48 (2H, m), 3.61 (3H, s), 7.06-7.47 (5H, m).

(Step 7) 1-[4-(Difluoromethoxy)phenyl]-3,3-difluorocyclobutanecarboxylic acid

The compound (1.0 g) obtained in Step 6 above was subjected to the same procedure as in Step 13 of Reference Example C-24 to obtain the title compound (0.88 g) as an oil.
$^1$H-NMR (DMSO-D$_6$) δ: 3.00-3.17 (2H, m), 3.28-3.42 (2H, m), 7.05-7.46 (5H, m), 13.02 (1H, br s).

Reference Example C-29

4,4-Difluoro-1-{3-fluoro-4-[($^2$H$_3$)methyloxy]phenyl}cyclohexanecarboxylic acid

[Formula 97]

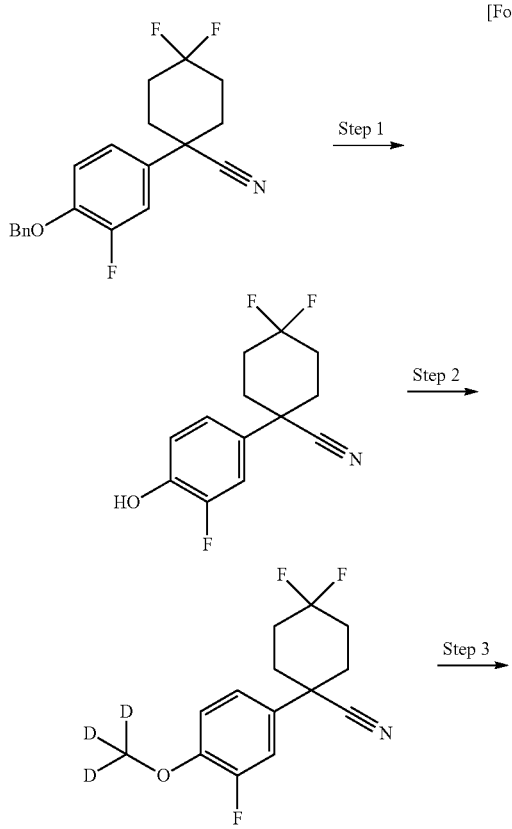

-continued

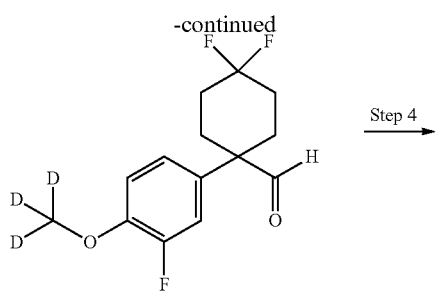

(Step 1) 4,4-Difluoro-1-(3-fluoro-4-hydroxyphenyl)cyclohexanecarbonitrile

The compound (2.00 g) obtained in Step 2 of Reference Example C-23 was subjected to the same procedure as in Step 2 of Reference Example A-3 to obtain the title compound (1.46 g) as a solid.

$^1$H-NMR (DMSO-D$_6$) δ: 1.99-2.35 (8H, m), 6.99 (1H, t, J=9.0 Hz), 7.19 (1H, dt, J=8.5, 1.2 Hz), 7.35 (1H, dd, J=12.8, 2.4 Hz), 10.20 (1H, br s). MS (m/z): 254 (M-H)$^-$.

(Step 2) 4,4-Difluoro-1-{3-fluoro-4-[($^2$H$_3$)methyloxy]phenyl}cyclohexanecarbonitrile The compound (400 mg) obtained in Step 1 above was dissolved in acetone (1 mL), potassium carbonate (433 mg) and iodo($^2$H$_3$)methane (194 μL) were added and stirred at 60° C. for 4 hours. The residue obtained by filtering the reaction solution and concentrating the filtrate under reduced pressure was purified by silica gel column chromatography (hexane/ethyl acetate) to obtain the title compound (435 mg) as a solid.

$^1$H-NMR (DMSO-D$_6$) δ: 1.99-2.32 (8H, m), 7.23 (1H, t, J=8.8 Hz), 7.34-7.36 (1H, m), 7.46 (1H, dd, J=12.8, 2.4 Hz).

(Step 3) 4,4-Difluoro-1-{3-fluoro-4-[($^2$H$_3$)methyloxy]phenyl}cyclohexanecarboaldehyde The compound (480 mg) obtained in Step 2 above was subjected to the same procedure as in Step 3 of Reference Example C-17 at −78° C. to obtain the title compound (424 mg) as an oil.

$^1$H-NMR (DMSO-D$_6$) δ: 1.65-2.36 (8H, m), 6.86-7.29 (3H, m), 9.42 (1H, s).

(Step 4) 4,4-Difluoro-1-{3-fluoro-4-[($^2$H$_3$)methyloxy]phenyl}cyclohexanecarboxylic acid The compound (450 mg) obtained in Step 3 above was subjected to the same procedure as in Step 4 of Reference Example C-17 to obtain the title compound (306 mg) as a solid.

$^1$H-NMR (DMSO-D$_6$) δ: 1.78-2.09 (6H, m), 2.39-2.41 (2H, m), 6.89-7.27 (3H, m), 12.83 (1H, br s). MS (m/z): 290 (M-H)$^-$.

Reference Example C-30

4,4-Difluoro-1-(3-methoxyphenyl)cyclohexanecarboxylic acid

[Formula 98]

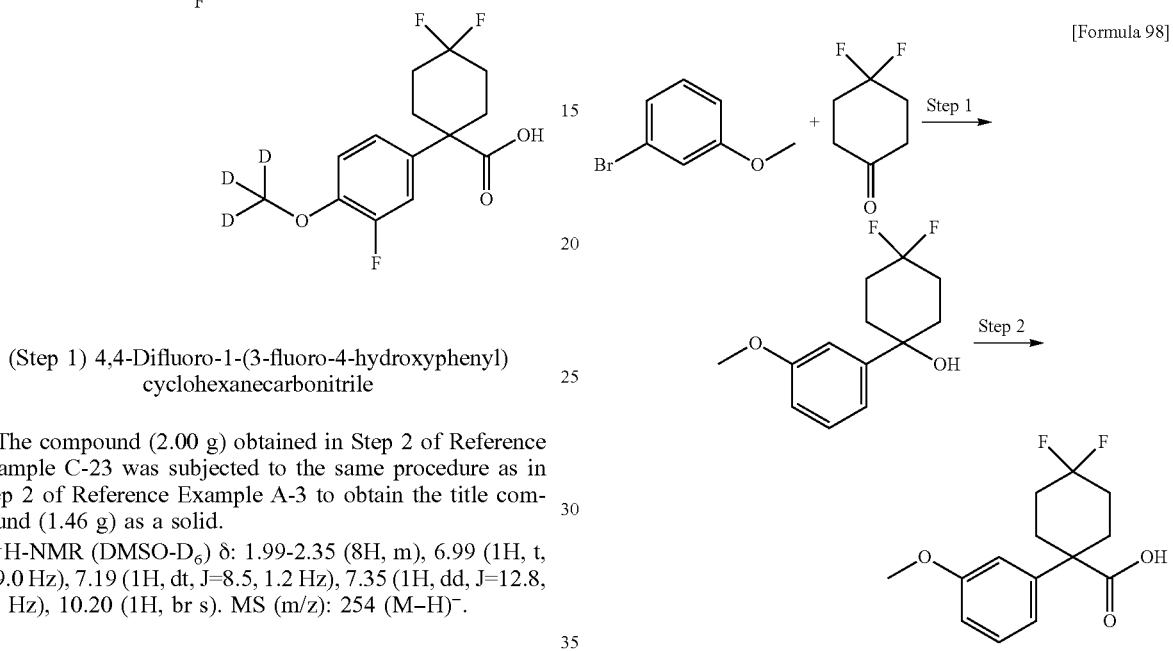

(Step 1) 4,4-Difluoro-1-(3-methoxyphenyl)cyclohexanol

3-Bromoanisole (2.09 g) and 4,4-difluorocyclohexanone (1.00 g) were subjected to the same procedure as in Step 1 of Reference Example C-15 to obtain the title compound (1.41 g) as a solid.

$^1$H-NMR (CDCl$_3$) δ: 1.87 (2H, d, J=12.2 Hz), 2.00-2.39 (6H, m), 3.82 (3H, s), 6.81-6.84 (1H, m), 7.05 (1H, d, J=7.9 Hz), 7.26 (1H, s), 7.29 (1H, t, J=8.2 Hz).

(Step 2) 4,4-Difluoro-1-(3-methoxyphenyl)cyclohexanecarboxylic acid

Under a nitrogen atmosphere, to a mixed solution of trimethylsilyl cyanide (1.15 g) and indium(III) bromide (205 mg) in dichloromethane (30 mL), a solution of the compound (1.40 g) obtained in Step 1 above in dichloromethane (10 mL) was added dropwise at 0° C. The mixture was stirred at room temperature for 3 hours, and then the mixed reaction solution was concentrated. The residue obtained was purified by silica gel column chromatography (hexane/ethyl acetate) to obtain an intermediate (604 mg) as an oil. The intermediate was dissolved in ethylene glycol (10 mL), and potassium hydroxide (404 mg) was added and stirred at 170° C. for 18 hours. The mixed reaction solution was cooled to room temperature, water was added, and the aqueous layer was washed with diethyl ether. The aqueous layer was adjusted to be acidic with 2 mol/L hydrochloric acid, and the resulting organic product was extracted with chloroform. The organic layer was washed with saturated brine, dried over anhydrous sodium sulfate, and the solvent was distilled off under reduced pressure. The residue obtained was purified by silica gel column chromatography (ethyl acetate/hexane) to obtain the title compound (322 mg) as a solid.

$^1$H-NMR (DMSO-D$_6$) δ: 1.83-2.08 (6H, m), 2.39-2.46 (2H, m), 3.75 (3H, s), 6.87 (1H, dd, J=8.2, 2.1 Hz), 6.92 (1H, t, J=1.8 Hz), 6.99 (1H, d, J=7.9 Hz), 7.30 (1H, t, J=8.2 Hz), 12.81 (1H, br s). MS (m/z): 269 (M−H)$^−$.

Reference Example C-31

4,4-Difluoro-1-(2-fluorobiphenyl-4-yl)cyclohexanecarboxylic acid

[Formula 99]

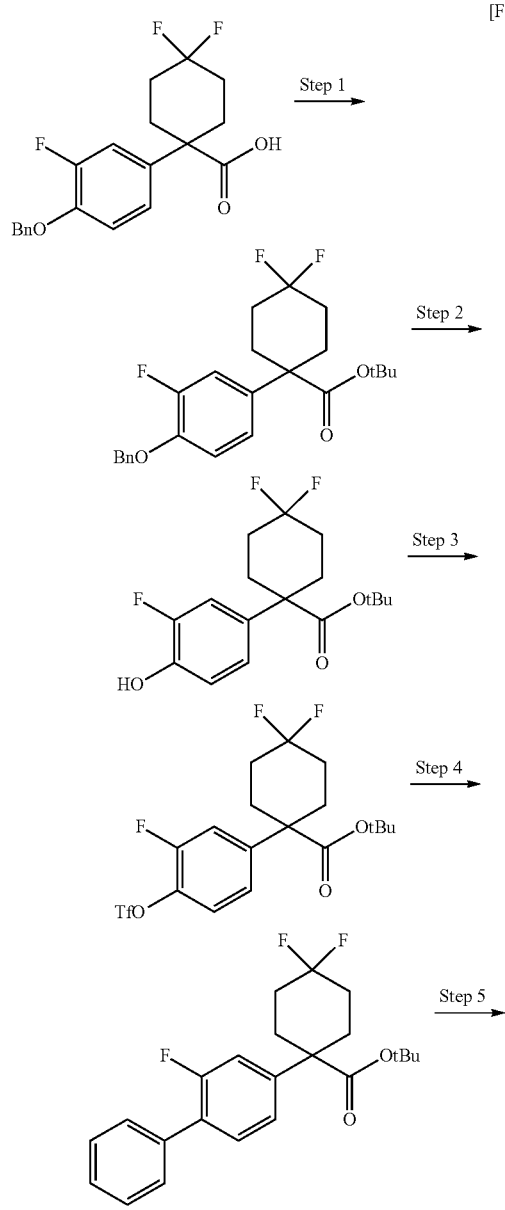

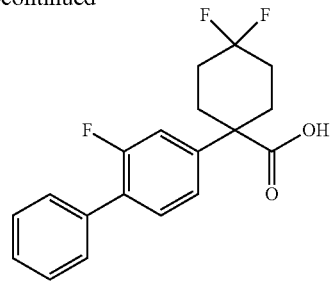

(Step 1) tert-Butyl 1-[4-(benzyloxy)-3-fluorophenyl]-4,4-difluorocyclohexanecarboxylate To a solution of the compound (381 mg) obtained in Step 3 of Reference Example C-23 in dichloromethane (10 mL), thionyl chloride (91.0 μL) and N,N-dimethylformamide (12.0 μL) were added at 0° C. The mixture was stirred at room temperature for 1 hour and then at 50° C. for 30 minutes. The mixed reaction solution was cooled to 0° C., potassium tert-butoxide (1 mol/L, tetrahydrofuran solution, 1.2 mL) was added and stirred at room temperature for 12 hours. The mixed reaction solution was cooled again to 0° C., potassium tert-butoxide (1 mol/L, tetrahydrofuran solution, 0.523 mL) was added and stirred at 50° C. for 3 hours. The mixed reaction solution was concentrated under reduced pressure, a 10% aqueous citric acid solution was added and extracted with ethyl acetate. The organic layer was washed with saturated brine, dried over sodium sulfate, and the solvent was distilled off under reduced pressure. The residue obtained was purified by silica gel column chromatography (hexane/ethyl acetate) to obtain the title compound (188 mg) as a solid.

$^1$H-NMR (CDCl$_3$) δ: 1.38 (9H, s), 1.87-2.00 (4H, m), 2.03-2.10 (2H, m), 2.44-2.51 (2H, m), 5.13 (2H, s), 6.95 (1H, t, J=8.5 Hz), 7.04 (1H, dd, J=8.5, 2.4 Hz), 7.14 (1H, dd, J=12.8, 2.4 Hz), 7.31-7.45 (5H, m).

(Step 2) tert-Butyl 4,4-difluoro-1-(3-fluoro-4-hydroxyphenyl)cyclohexanecarboxylate The compound (345 mg) obtained in Step 1 above was subjected to the same procedure as in Step 2 of Reference Example A-3 to obtain the title compound (268 mg) as an oil.

$^1$H-NMR (CDCl$_3$) δ: 1.38 (9H, s), 1.88-2.00 (4H, m), 2.03-2.11 (2H, m), 2.44-2.50 (2H, m), 6.96 (1H, t, J=8.9 Hz), 7.05 (1H, ddd, J=8.9, 2.4, 1.2 Hz), 7.12 (1H, dd, J=12.5, 2.1 Hz). MS (m/z): 329 (M−H)$^−$.

(Step 3) tert-Butyl 4,4-difluoro-1-(3-fluoro-4-{[(trifluoromethyl)sulfonyl]oxy}phenyl)cyclohexanecarboxylate To a solution of the compound (266 mg) obtained in Step 2 above and 4-dimethylaminopyridine (14.8 mg) in dichloromethane (8 mL), triethylamine (167 μL) and trifluoromethanesulfonic anhydride (203 μL) were added at 0° C. After stirring at room temperature for 30 minutes, water was added to the mixed reaction solution, and the mixture was extracted with chloroform. The organic layer was washed with saturated brine, dried over anhydrous sodium sulfate, and the solvent was distilled off under reduced pressure. The residue obtained was purified by silica gel column chromatography (hexane/ethyl acetate) to obtain the title compound (141 mg) as an oil.

$^1$H-NMR (CDCl$_3$) δ: 1.40 (9H, s), 1.86-2.00 (4H, m), 2.03-2.17 (2H, m), 2.49-2.55 (2H, m), 7.23 (1H, d, J=9.2 Hz), 7.28-7.34 (2H, m).

(Step 4) tert-Butyl 4,4-difluoro-1-(2-fluorobiphenyl-4-yl)cyclohexanecarboxylate A suspension of the compound (119 mg) obtained in Step 3 above, sodium benzenesulfinate (50.7 mg), tris(dibenzylideneacetone)dipalladium(0) (23.6 mg), 4,5-bis(diphenylphosphino)-9,9-dimethylxanthene (7.50 mg), cesium carbonate (126 mg) and tetrabutylammonium chloride (85.8 mg) in toluene (2.5 mL) was stirred at 120° C. for 5 hours under a nitrogen atmosphere. Water was added to the mixed reaction solution, and the mixture was extracted with ethyl acetate. The combined organic layers were washed with saturated brine, dried over sodium sulfate, and the solvent was distilled off under reduced pressure. The residue obtained was purified by silica gel column chromatography (hexane/ethyl acetate) to obtain the title compound (60.2 mg) as a solid.

$^1$H-NMR (CDCl$_3$) δ: 1.42 (9H, s), 1.88-2.00 (2H, m), 2.03-2.16 (4H, m), 2.45-2.58 (2H, m), 7.19 (1H, dd, J=12.8, 1.8 Hz), 7.23 (1H, dd, J=7.9, 1.8 Hz), 7.29-7.47 (4H, m), 7.55 (2H, d, J=7.3 Hz).

(Step 5) 4,4-Difluoro-1-(2-fluorobiphenyl-4-yl)cyclohexanecarboxylic acid

A solution of the compound (60.0 mg) obtained in Step 4 above in dichloromethane (0.3 mL) was cooled to 0° C., and trifluoroacetic acid (0.3 mL) was added. After stirring at room temperature for 2 hours, the reaction mixture was concentrated under reduced pressure, and the residue obtained was purified by silica gel column chromatography (hexane/ethyl acetate) to obtain the title compound (51.4 mg) as a solid.

$^1$H-NMR (DMSO-D$_6$) δ: 1.82-2.11 (6H, m), 2.38-2.49 (2H, m), 7.31-7.72 (8H, m), 13.02 (1H, br s).

Reference Example C-32

4,4-Difluoro-1-[4-(methylsulfonyl)phenyl]cyclohexanecarboxylic acid

[Formula 100]

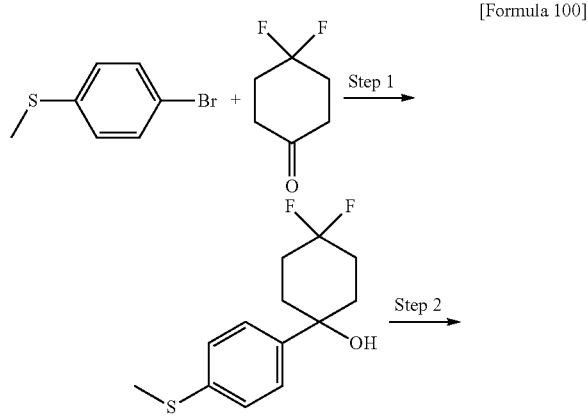

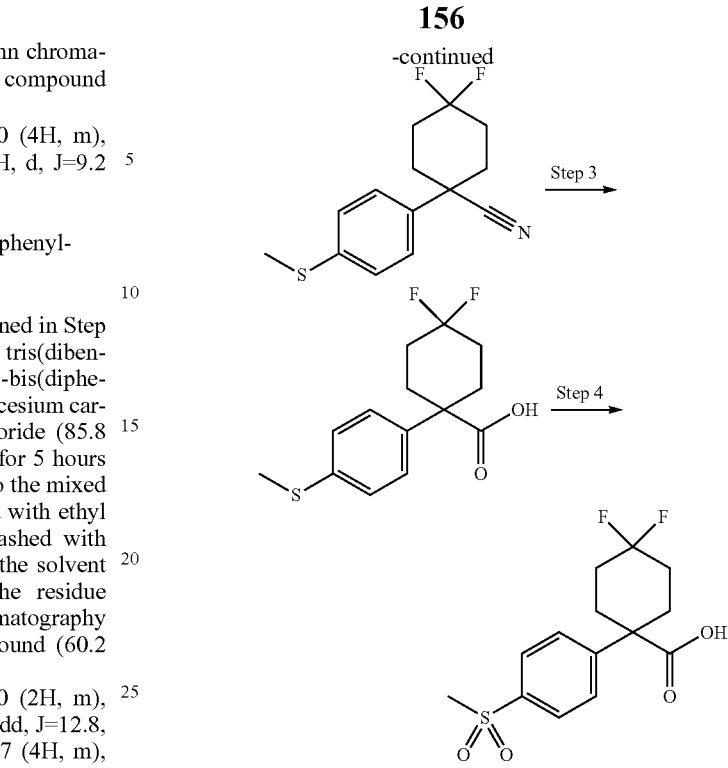

(Step 1) 4,4-Difluoro-1-[4-(methylsulfanyl)phenyl]cyclohexanol

1-Bromo-4-(methylsulfamoyl)benzene (3.81 mL) and 4,4-difluorocyclohexanone (2.50 g) were subjected to the same procedure as in Step 1 of Reference Example C-15 to obtain the title compound (2.94 g) as an oil.

MS (m/z): 259 (M+H)$^+$.

(Step 2) 4,4-Difluoro-1-[4-(methylsulfanyl)phenyl]cyclohexanecarbonitrile

The compound (2.94 g) obtained in Step 1 above was subjected to the same procedure as in Step 2 of Reference Example C-4 to obtain the title compound (1.12 g) as a solid.

$^1$H-NMR (CDCl$_3$) δ: 2.10-2.35 (8H, m), 2.49 (3H, s), 7.28 (2H, d, J=8.5 Hz), 7.40 (2H, d, J=8.5 Hz).

(Step 3) 4,4-Difluoro-1-[4-(methylsulfanyl)phenyl]cyclohexanecarboxylic acid

The compound (1.12 g) obtained in Step 2 above was subjected to the same procedure as in Step 2 of Reference Example C-3 to obtain the title compound (0.944 g) as a solid.

$^1$H-NMR (DMSO-D$_6$) δ: 1.82-2.09 (6H, m), 2.37-2.44 (2H, m), 2.46 (3H, s), 7.25 (2H, d, J=8.5 Hz), 7.36 (2H, d, J=8.5 Hz), 12.80 (1H, br s). MS (m/z): 285 (M–H)$^-$.

(Step 4) 4,4-Difluoro-1-[4-(methylsulfonyl)phenyl]cyclohexanecarboxylic acid

To a solution of the compound (400 mg) obtained in Step 3 above in acetic acid (4 mL), hydrogen peroxide water (concentration 35%, 0.575 mL) was added at 0° C. After stirring at 50° C. for 7 hours, the mixed reaction solution was diluted with water, and the resulting solid was collected by filtration to obtain the title compound (208 mg) as a solid.

$^1$H-NMR (DMSO-D$_6$) δ: 1.87-2.10 (6H, m), 2.40-2.49 (2H, m), 3.25 (3H, s), 7.71 (2H, d, J=8.5 Hz), 7.93 (2H, d, J=8.5 Hz).

Reference Example C-33

1-(4-{5-[(Benzyloxy)carbonyl]-1-methyl-4-oxo-1,4-dihydropyridin-3-yl}phenyl)cyclopentanecarboxylic acid

[Formula 101]

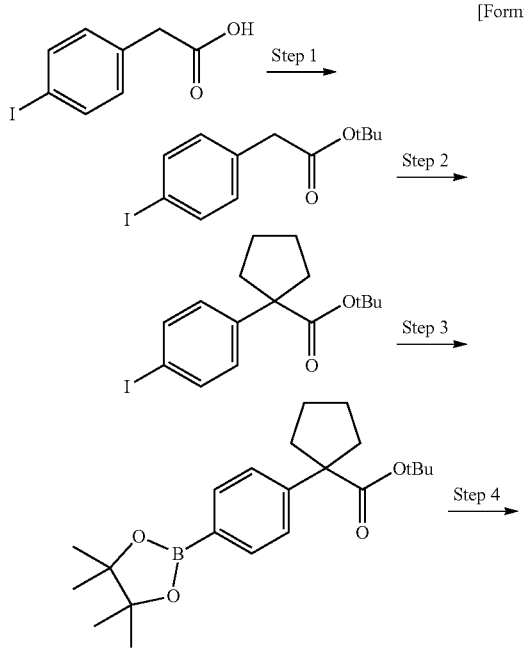

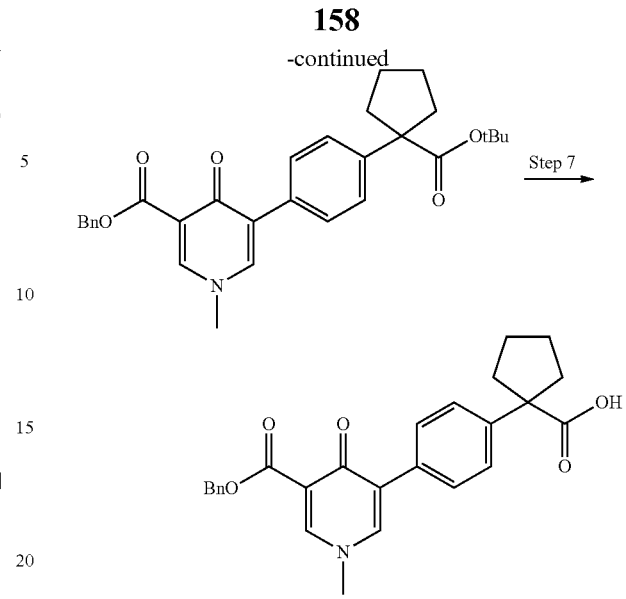

(Step 1) tert-Butyl (4-iodophenyl)acetate

To a solution of (4-iodophenyl)acetic acid (5.00 g) in tert-butyl alcohol (40.0 mL), 4-dimethylaminopyridine (0.699 g) and di-tert-butyl dicarbonate (8.33 g) were added and stirred at room temperature for 3 hours. After concentrating the reaction solution under reduced pressure, the residue was purified by silica gel column chromatography (hexane/chloroform) to obtain the title compound (5.48 g) as an oil.

$^1$H-NMR (CDCl$_3$) δ: 1.43 (9H, s), 3.46 (2H, s), 7.02 (2H, d, J=8.5 Hz), 7.64 (2H, d, J=8.5 Hz).

(Step 2) tert-Butyl 1-(4-iodophenyl)cyclopentanecarboxylate

The compound (5.48 g) obtained in Step 1 above and 1,4-dibromobutane (2.30 mL) were subjected to the same procedure as in Step 1 of Reference Example C-1 to obtain the title compound (3.32 g) as a solid.

$^1$H-NMR (CDCl$_3$) δ: 1.33 (9H, s), 1.70-1.79 (6H, m), 2.54-2.60 (2H, m), 7.10 (2H, d, J=8.5 Hz), 7.61 (2H, d, J=8.5 Hz).

(Step 3) tert-Butyl 1-[4-(4,4,5,5-tetramethyl-1,3,2-dioxaborolan-2-yl)phenyl]cyclopentanecarboxylate Under a nitrogen atmosphere, to a mixture of the compound (1.00 g) obtained in Step 2 above, bis(pinacolato)diboron (0.754 g), potassium acetate (0.799 g), and a [1,1'-bis(diphenylphosphino)ferrocene]palladium(II) dichloromethane complex (0.109 g), degassed dimethyl sulfoxide (15.0 mL) was added and stirred at 55° C. for 2.5 hours. After allowing to cool to room temperature, water was added to the reaction solution, and the mixture was extracted with diethyl ether three times. The organic layer was washed with saturated brine and then dried over anhydrous sodium sulfate. After filtration and concentration under reduced pressure, the residue obtained was purified by silica gel column chromatography (hexane/ethyl acetate) to obtain the title compound (0.852 g) as a solid.

¹H-NMR (CDCl₃) δ: 1.32 (9H, s), 1.34 (12H, s), 1.70-1.75 (4H, m), 1.80-1.85 (2H, m), 2.57-2.62 (2H, m), 7.36 (2H, d, J=8.5 Hz), 7.74 (2H, d, J=8.5 Hz).

(Step 4) Ethyl 5-{4-[1-(tert-butoxycarbonyl)cyclopentyl]phenyl}-1-methyl-4-oxo-1,4-dihydropyridine-3-carboxylate Under a nitrogen atmosphere, to a mixture of ethyl 5-iodo-1-methyl-4-oxo-1,4-dihydropyridine-3-carboxylate (0.632 g), the compound (0.845 g) obtained in Step 3 above, a [1,1'-bis(diphenylphosphino)ferrocene]palladium(II) dichloromethane complex (1:1) (0.171 g), and cesium carbonate (2.05 g), 1,4-dioxane (20.0 mL) and water (4.00 mL) were added and stirred at 80° C. for 4 hours. After allowing to cool to room temperature, water was added and the mixture was extracted with ethyl acetate three times, the organic layer was washed with saturated brine and then dried over anhydrous sodium sulfate. After filtration and concentration under reduced pressure, the residue obtained was purified by silica gel column chromatography (ethyl acetate/methanol) to obtain the title compound (0.445 g) as a solid.

¹H-NMR (CDCl₃) δ: 1.35 (9H, s), 1.38 (3H, t, J=7.3 Hz), 1.68-1.75 (4H, m), 1.79-1.88 (2H, m), 2.56-2.63 (2H, m), 3.75 (3H, s), 4.37 (2H, q, J=7.3 Hz), 7.34-7.38 (3H, m), 7.53 (2H, d, J=7.9 Hz), 8.12 (1H, d, J=2.4 Hz).
MS (m/z) m/z: 426 (M+H)⁺.

(Step 5) 5-{4-[1-(tert-Butoxycarbonyl)cyclopentyl]phenyl}-1-methyl-4-oxo-1,4-dihydropyridine-3-carboxylic acid The compound (0.440 g) obtained in Step 4 above was subjected to the same procedure as in Step 5 of Reference Example C-2 to obtain the title compound (0.405 g) as a solid.

¹H-NMR (CDCl₃) δ: 1.36 (9H, s), 1.52-1.89 (6H, m), 2.58-2.65 (2H, m), 3.93 (3H, s), 7.43-7.62 (5H, m), 8.50 (1H, s). MS (m/z): 398 (M+H)⁺.

(Step 6) Benzyl 5-{4-[1-(tert-butoxycarbonyl)cyclopentyl]phenyl}-1-methyl-4-oxo-1,4-dihydropyridine-3-carboxylate The compound (0.400 g) obtained in Step 5 above was subjected to the same procedure as in Step 3 of Reference Example C-2 to obtain the title compound (0.326 g) as a solid.

¹H-NMR (CDCl₃) δ: 1.35 (9H, s), 1.71-1.87 (6H, m), 2.57-2.62 (2H, m), 3.72 (3H, s), 5.37 (2H, s), 7.29-7.38 (6H, m), 7.48-7.53 (4H, m), 8.11 (1H, d, J=2.4 Hz). MS (m/z): 488 (M+H)⁺.

(Step 7) 1-(4-{5-[(Benzyloxy)carbonyl]-1-methyl-4-oxo-1,4-dihydropyridin-3-yl}phenyl)cyclopentanecarboxylic acid The compound (0.321 mg) obtained in Step 6 above was subjected to the same procedure as in Step 8 of Reference Example C-16 to obtain the title compound (0.272 g) as a solid.

¹H-NMR (DMSO-D₆) δ: 1.61-1.71 (4H, m), 1.79-1.86 (2H, m), 2.49-2.57 (2H, m), 3.75 (3H, s), 5.26 (2H, s), 7.30-7.41 (5H, m), 7.47-7.49 (2H, m), 7.53 (2H, d, J=8.5 Hz), 7.88 (1H, d, J=2.4 Hz), 8.31 (1H, d, J=2.4 Hz). MS (m/z): 432 (M+H)⁺.

Reference Example D-1

1-{[1-(4-Methoxyphenyl)cyclopentyl]carbonyl}-D-proline

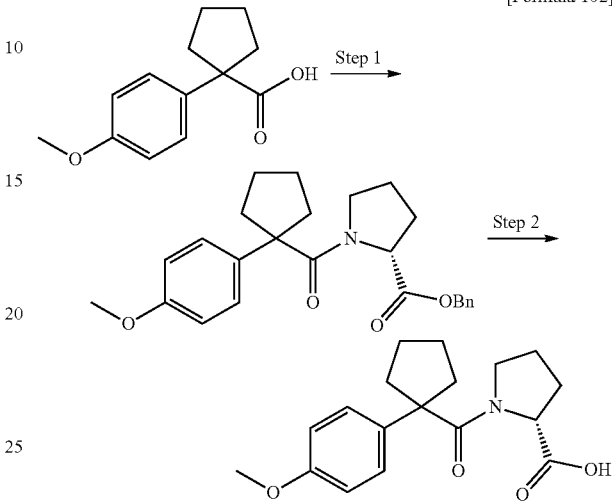

[Formula 102]

(Step 1) Benzyl 1-{[1-(4-methoxyphenyl)cyclopentyl]carbonyl}-D-prolinate

To a mixture of 1-(4-methoxyphenyl)cyclopentane carboxylic acid (8.20 g) and toluene (100 mL), thionyl chloride (5.69 mL) and N,N-dimethylformamide (1 drop) were added at room temperature, and the mixture was heated under reflux for 45 minutes. The reaction solution was concentrated under reduced pressure, and the residue obtained was dissolved in dichloromethane (30 mL). The resultant solution was added, under ice cooling, in a dropwise manner to a mixture of D-proline benzyl ester hydrochloride (11.9 g), N,N-diisopropylethylamine (26 mL) and dichloromethane (70 mL), and the resultant mixture was stirred for 16 hours while being allowed to gradually restore to room temperature. The reaction solution was washed with 1 mol/L hydrochloric acid, a saturated aqueous sodium hydrogen carbonate solution and saturated brine, and dried over anhydrous sodium sulfate. The solvent was distilled off under reduced pressure, and the residue obtained was subjected to silica gel column chromatography (hexane/ethyl acetate) to obtain the title compound (13.7 g) as an oil.

¹H-NMR (CDCl₃) δ: 1.53-2.13 (8H, m), 2.30-2.45 (2H, m), 2.95-3.00 (2H, m), 3.21-3.25 (1H, m), 3.67-3.71 (1H, m), 3.78 (3H, s), 4.53 (1H, dd, J=8.5, 4.8 Hz), 5.13 (1H, d, J=12.7 Hz), 5.25 (1H, d, J=12.7 Hz), 6.75-6.80 (2H, m), 7.12-7.17 (2H, m), 7.29-7.38 (5H, m).

(Step 2) 1-{[1-(4-Methoxyphenyl)cyclopentyl]carbonyl}-D-proline

The compound (13.7 g) obtained in Step 1 above was subjected to the same procedures as in Step 2 of Reference Example A-3 to obtain the title compound (8.78 g) as a solid.

¹H-NMR (DMSO-D₆) δ: 1.44-2.07 (10H, m), 2.22-2.32 (2H, m), 2.84-2.95 (2H, m), 3.73 (3H, s), 4.22 (1H, dd, J=9.1, 4.8 Hz), 6.84-6.90 (2H, m), 7.12-7.18 (2H, m), 12.29 (1H, br s).

Reference Example D-2

(4S)-3-{[1-(4-Methoxyphenyl)cyclohexyl]carbonyl}-1,3-thiazolidine-4-carboxylic acid 1,1-dioxide

[Formula 103]

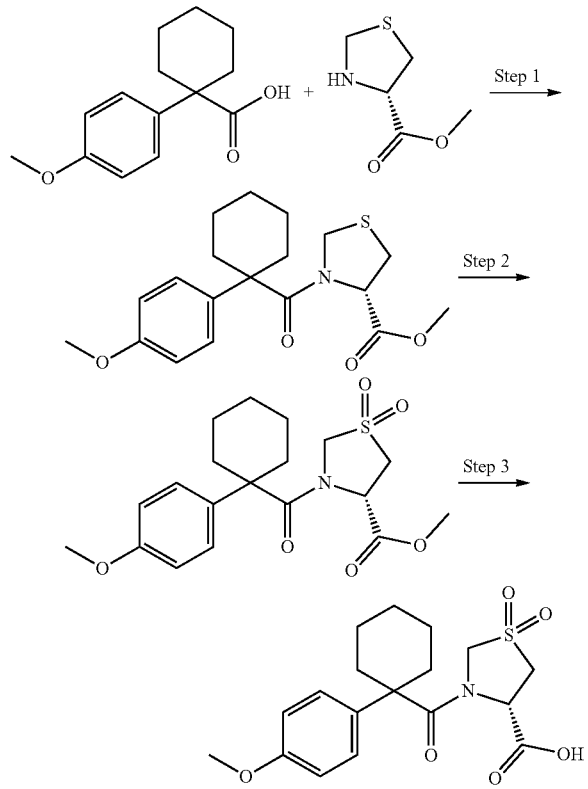

(Step 1) Methyl (4S)-3-{[1-(4-methoxyphenyl)cyclohexyl]carbonyl}-1,3-thiazolidine-4-carboxylate To a solution of 1-(4-methoxyphenyl)cyclohexane carboxylic acid (406 mg) in 1,2-dichloroethane (8 mL), oxalyl chloride (0.297 mL) and N,N-dimethylformamide (2 drops) were added, and the mixture was stirred at room temperature for 25 minutes. To the reaction solution, oxalyl chloride (0.297 mL) and N,N-dimethylformamide (1 drop) were further added, and the mixture was stirred at room temperature for 50 minutes, and then at 75° C. for 45 minutes. A residue obtained by distilling off the solvent under reduced pressure was dissolved in 1,2-dichloroethane (4 mL), and a solution of methyl (4S)-thiazoridine-4-carboxylate (232 mg) in 1,2-dichloroethane (6 mL), pyridine (0.635 mL) and 4-dimethylaminopyridine (23 mg) were added thereto, and the resultant mixture was stirred at 75° C. for 3.3 hours. The resultant was allowed to cool to room temperature, and a saturated aqueous ammonium chloride solution was added thereto. The resultant was extracted with dichloromethane, washed with a 10% aqueous citric acid solution and saturated brine, and dried over anhydrous sodium sulfate. A residue obtained by distilling off the solvent under reduced pressure was subjected to amino silica gel column chromatography (hexane/ethyl acetate), and further to silica gel column chromatography (hexane/ethyl acetate) to obtain the title compound (328 mg) as an oil.

$^1$H-NMR (CDCl$_3$) δ: 1.20-2.37 (10H, m), 2.97 (1H, dd, J=11.8, 5.7 Hz), 3.14 (1H, br s), 3.76 (3H, s), 3.80 (3H, s), 4.03 (1H, br s), 4.17 (1H, br s), 5.05 (1H, br s), 6.85-6.91 (2H, m), 7.17-7.24 (2H, m).

(Step 2) Methyl (4S)-3-{[1-(4-methoxyphenyl)cyclohexyl]carbonyl}-1,3-thiazolidine-4-carboxylate 1,1-dioxide To a solution of the compound (118 mg) obtained in Step 1 above in dichloromethane (5 mL), 3-chloroperbenzoic acid (purity 577%, 140 mg) was added, and the mixture was stirred at room temperature for 6.4 hours. The mixture was diluted with ethyl acetate, and water was added thereto. The resultant was extracted with ethyl acetate, washed with saturated brine, and dried over anhydrous sodium sulfate. A residue obtained by distilling off the solvent under reduced pressure was subjected to silica gel column chromatography (hexane/ethyl acetate) to obtain the title compound (68 mg) as a solid.

$^1$H-NMR (CDCl$_3$) δ: 1.24-1.81 (8H, m), 2.17-2.27 (2H, m), 3.22 (1H, dd, J=13.3, 5.4 Hz), 3.38 (1H, br s), 3.71-3.78 (1H, m), 3.80 (3H, s), 3.81 (3H, s), 4.25 (1H, br s), 5.39 (1H, br s), 6.89-6.94 (2H, m), 7.16-7.21 (2H, m).

(Step 3) (4S)-3-{[1-(4-Methoxyphenyl)cyclohexyl]carbonyl}-1,3-thiazolidine-4-carboxylic acid 1,1-dioxide A solution of the compound (28 mg) obtained in Step 2 above in tetrahydrofuran (2 mL) was allowed to cool to 0° C., water (1 mL) and lithium hydroxide monohydrate (9 mg) were added to the solution, and the mixture was stirred at room temperature for 24.5 hours. The organic solvent was distilled off under reduced pressure, and 1 mol/L hydrochloric acid was added thereto to obtain about pH 2. The resultant was extracted with ethyl acetate, washed with saturated brine, and dried over anhydrous sodium sulfate. A residue obtained by distilling off the solvent under reduced pressure was formed into a slurry with diisopropyl ether, and the resultant was filtered off to obtain the title compound (25 mg) as a solid.

$^1$H-NMR (DMSO-D$_6$) δ: 1.16-1.87 (8H, m), 2.12-2.26 (2H, m), 3.39 (1H, dd, J=13.6, 6.3 Hz), 3.73 (1H, br s), 3.74 (3H, s), 4.01-4.08 (1H, br m), 4.12 (1H, br s), 5.08 (1H, br s), 6.89-6.94 (2H, m), 7.16-7.21 (2H, m), 13.27 (1H, br s).

Example 1

N-1H-Indazol-4-yl-1-{[1-(4-methoxyphenyl)cyclopentyl]carbonyl}-D-prolinamide

[Formula 104]

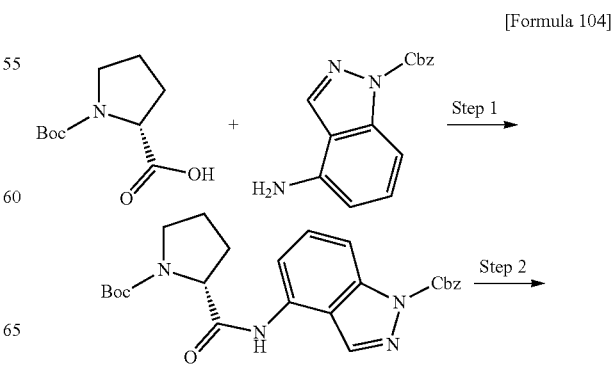

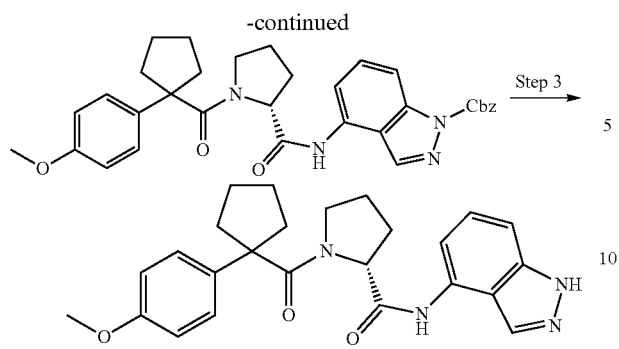

(Step 1) Benzyl 4-{[1-(tert-butoxycarbonyl)-D-prolyl]amino}-1H-indazole-1-carboxylate To a solution of 1-(tert-butoxycarbonyl)-D-proline (0.216 g) in N,N-dimethylformamide (5 mL), the compound obtained in Reference Example A-1 (0.282 g), HATU (0.420 g) and N,N-diisopropylethylamine (0.277 mL) were added, and the mixture was stirred at room temperature for 5 days. To the reaction solution, 1 mol/L hydrochloric acid was added, and the mixture was extracted with ethyl acetate three times. The organic layer was washed with a saturated aqueous sodium hydrogen carbonate solution, and with saturated brine, and then dried over anhydrous sodium sulfate. After filtration and concentration under reduced pressure, the residue obtained was purified by silica gel column chromatography (chloroform/ethyl acetate) to obtain the title compound (0.302 g) as a solid.

$^1$H-NMR (DMSO-D$_6$) δ: 1.35 (9H, s), 1.83-2.03 (3H, m), 2.25 (1H, s), 3.36-3.49 (2H, m), 4.41-4.44 (1H, m), 5.52 (2H, s), 7.36-7.45 (3H, m), 7.51-7.56 (3H, m), 7.71 (1H, d, J=7.3 Hz), 7.86 (1H, d, J=8.5 Hz), 8.51 (1H, s), 10.09 (1H, s). MS (m/z): 465 (M+H)$^+$.

(Step 2) Benzyl 4-[(1-{[1-(4-methoxyphenyl)cyclopentyl]carbonyl}-D-prolyl)amino]-1H-indazole-1-carboxylate To a suspension of (1-(4-methoxyphenyl)cyclopentanecarboxylic acid (0.168 g) in dichloromethane (5 mL), thionyl chloride (0.111 mL) and N,N-dimethylformamide (0.0100 mL) were added, and the mixture was stirred at 40° C. for 4 hours. After allowing to cool to room temperature, the reaction solution was concentrated under reduced pressure to obtain the crude acid chloride as an oil. Hydrogen chloride (4 mol/L, 1,4-dioxane solution, 5 mL) was added to the compound (0.295 g) obtained in Step 1 above, and the mixture was stirred at room temperature for 3 hours, and then concentrated under reduced pressure to obtain the crude amine intermediate. The intermediate was dissolved in dichloromethane (5 mL), and a solution of the acid chloride prepared previously in dichloromethane (5 mL) was added. After ice-cooling, N,N-diisopropylethylamine (0.332 mL) was added, and the mixture was stirred at room temperature overnight. To the reaction solution, 1 mol/L hydrochloric acid was added, and the mixture was extracted with dichloromethane. The organic layer was washed with a saturated aqueous sodium hydrogen carbonate solution, and then dried over anhydrous sodium sulfate. After filtration and concentration under reduced pressure, the residue obtained was purified by silica gel column chromatography (chloroform/methanol) to obtain the title compound (0.353 g) as a solid.

$^1$H-NMR (DMSO-D$_6$) δ: 1.55-1.66 (5H, m), 1.72-1.94 (4H, m), 2.07-2.13 (1H, m), 2.27-2.36 (2H, m), 2.99 (2H, t, J=5.4 Hz), 3.74 (3H, s), 4.60 (1H, dd, J=8.5, 5.4 Hz), 5.52 (2H, s), 6.90 (2H, d, J=9.1 Hz), 7.19 (2H, d, J=9.1 Hz), 7.38-7.48 (3H, m), 7.55-7.59 (3H, m), 7.82-7.88 (2H, m), 8.62 (1H, s), 10.36 (1H, s). MS (m/z): 567 (M+H)$^+$.

(Step 3) N-1H-Indazol-4-yl-1-{[1-(4-methoxyphenyl)cyclopentyl]carbonyl}-D-prolinamide To a solution of the compound (0.345 g) obtained in Step 2 above in tetrahydrofuran (1 mL), methanol (5 mL) and potassium carbonate (0.252 g) were added, and the mixture was stirred at room temperature for 2 hours. To the reaction solution, 1 mol/L hydrochloric acid was added, and the mixture was extracted with ethyl acetate three times. The organic layer was washed with a saturated aqueous sodium hydrogen carbonate solution and with saturated brine, and then dried over anhydrous sodium sulfate. After filtration and concentration under reduced pressure, the residue obtained was purified by silica gel column chromatography (hexane/ethyl acetate) to obtain the title compound (0.197 g) as a solid.

$^1$H-NMR (DMSO-D$_6$) δ: 1.53-1.68 (5H, m), 1.73-1.95 (4H, m), 2.05-2.11 (1H, m), 2.28-2.36 (2H, m), 2.97-3.00 (2H, m), 3.75 (3H, s), 4.64-4.68 (1H, m), 6.90 (2H, d, J=8.5 Hz), 7.19-7.30 (4H, m), 7.66 (1H, d, J=7.9 Hz), 8.29 (1H, s), 10.08 (1H, s), 13.07 (1H, s). MS (m/z): 433 (M+H)$^+$.

Example 2

N-[2-(1H-Indazol-4-ylamino)-2-oxoethyl]-1-(4-methoxyphenyl)-N-methylcyclohexanecarboxamide

[Formula 105]

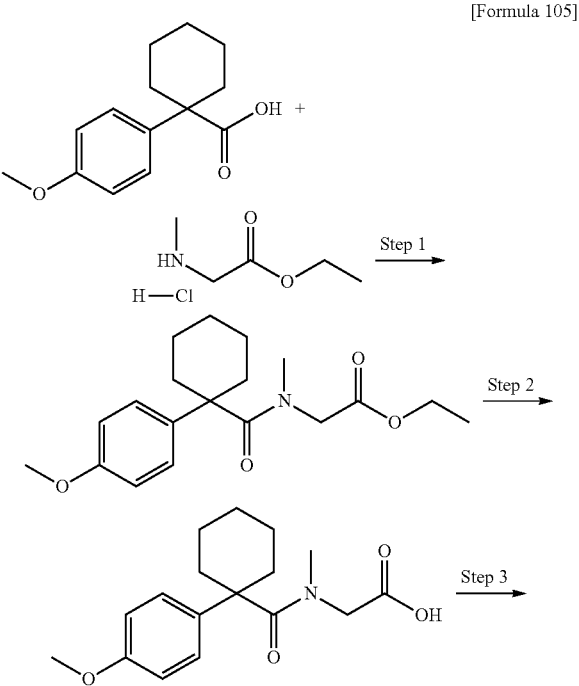

165
-continued

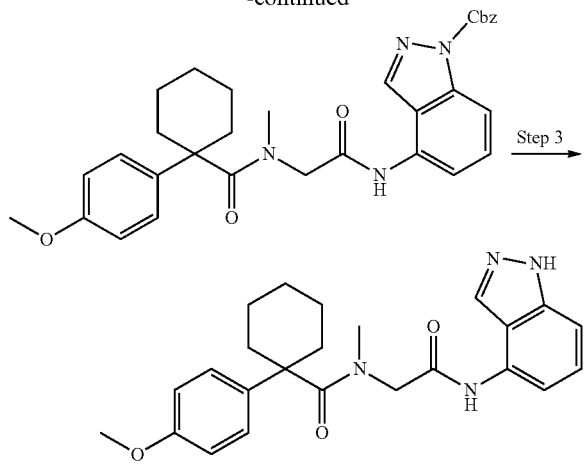

(Step 1) Ethyl N-{[1-(4-methoxyphenyl)cyclohexyl]carbonyl}-N-methylglycinate 1-(4-Methoxyphenyl)cyclopentanecarboxylic acid (0.370 g) and sarcosine ethyl ester hydrochloride (0.261 g) were subjected to the same procedure as in Step 1 of Example 1 to obtain the title compound (0.272 g) as an oil.
$^1$H-NMR (CDCl$_3$) δ: 1.20-1.78 (10H, m), 2.28-2.39 (2H, m), 2.57-2.71 (2H, m), 3.80 (3H, s), 3.92-4.04 (2H, m), 4.12-4.26 (2H, m), 6.88 (2H, d, J=8.5 Hz), 7.23 (2H, d, J=8.5 Hz).

(Step 2) N-{[1-(4-Methoxyphenyl)cyclohexyl]carbonyl}-N-methylglycine

A mixture of the compound (0.272 g) obtained in Step 1 above, 4 mol/L aqueous lithium hydroxide solution (3 mL) and methanol (9 mL) was stirred at room temperature for 2 hours. To the resultant, 1 mol/L hydrochloric acid was added, and the mixture was extracted with ethyl acetate. The organic layer was washed with saturated brine, and dried over anhydrous magnesium sulfate. Then the solvent was distilled off under reduced pressure, and the residue was dried to obtain the title compound (0.231 g) as a solid.
$^1$H-NMR (CDCl$_3$) δ: 1.20-1.34 (1H, m), 1.61-1.73 (7H, m), 2.28-2.35 (2H, m), 2.64-2.72 (3H, m), 3.80 (3H, s), 3.97-4.05 (2H, m), 6.86-6.89 (2H, m), 7.19-7.23 (2H, m). MS (m/z): 306 (M+H)$^+$.

(Step 3) Benzyl 4-[(N-{[1-(4-methoxyphenyl)cyclohexyl]carbonyl}-N-methylglycyl)amino]-1H-indazole-1-carboxylate The compound (0.139 g) obtained in Step 2 above and the compound obtained in Reference Example A-1 (0.152 g) were subjected to the same procedure as in Step 1 of Example 1 to obtain the title compound (0.139 g) as an oil.
$^1$H-NMR (CDCl$_3$) δ: 1.25-1.34 (1H, m), 1.65-1.75 (7H, m), 2.35-2.41 (2H, m), 2.75 (3H, s), 3.71 (3H, s), 4.09-4.14 (2H, m), 5.56 (2H, s), 6.71-6.75 (2H, m), 7.08-7.12 (2H, m), 7.36-7.45 (3H, m), 7.49-7.57 (3H, m), 7.88-7.99 (2H, m), 8.41 (1H, s), 9.89 (1H, s).

(Step 4) N-[2-(1H-Indazol-4-ylamino)-2-oxoethyl]-1-(4-methoxyphenyl)-N-methylcyclohexanecarboxamide The compound (0.139 g) obtained in Step 3 above was subjected to the same procedure as in Step 2 of Example 2 to obtain the title compound (0.024 g) as a solid.
MS (m/z): 421 (M+H)$^+$.

Example 3

1-{[1-(4-Methoxyphenyl)cyclohexyl]carbonyl}-N-(1-methyl-1H-indazol-4-yl)prolinamide

[Formula 106]

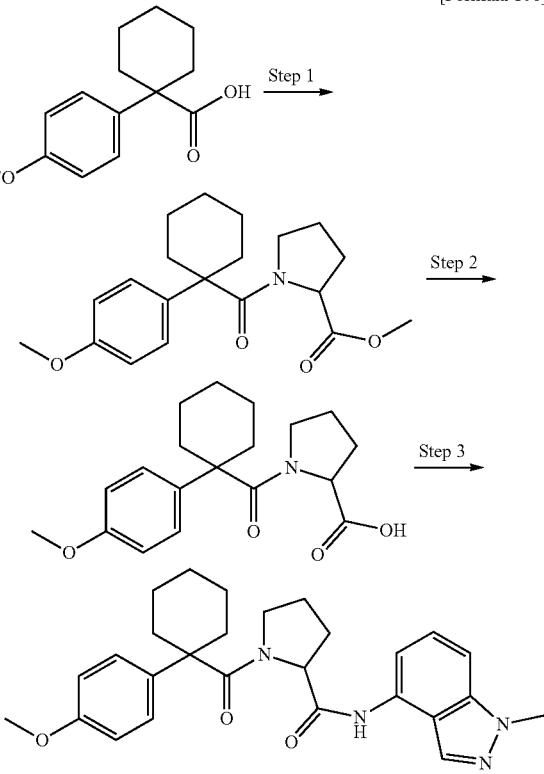

(Step 1) Methyl 1-{[1-(4-methoxyphenyl)cyclohexyl]carbonyl}prolinate 1-(4-Methoxyphenyl)cyclohexanecarboxylic acid (0.242 g) and methyl prolinate (0.199 g) were subjected to the same procedure as in Step 1 of Example 1 to obtain the title compound (0.287 g) as an oil.
$^1$H-NMR (CDCl$_3$) δ: 1.20-1.32 (1H, m), 1.47-1.84 (10H, m), 1.98-2.10 (1H, m), 2.29-2.39 (2H, m), 2.98-3.07 (2H, m), 3.75 (3H, s), 3.80 (3H, s), 4.45-4.50 (1H, m), 6.85-6.88 (2H, m), 7.23 (2H, d, J=9.1 Hz). MS (m/z): 346 (M+H)$^+$.

(Step 2) 1-{[1-(4-Methoxyphenyl)cyclohexyl]carbonyl}proline

The compound (0.287 g) obtained in Step 1 above was subjected to the same procedure as in Step 2 of Example 2 to obtain the title compound (0.282 g) as a solid.
$^1$H-NMR (CDCl$_3$) δ: 1.23-1.37 (1H, m), 1.46-1.94 (10H, m), 2.15-2.25 (1H, m), 2.31-2.39 (2H, m), 2.90-3.06 (2H, m), 3.80 (3H, s), 4.59-4.67 (1H, m), 6.87 (2H, d, J=8.5 Hz), 7.18 (2H, d, J=8.5 Hz). MS (m/z): 332 (M+H)$^+$.

(Step 3) 1-{[1-(4-Methoxyphenyl)cyclohexyl]carbonyl}-N-(1-methyl-1H-indazol-4-yl)prolinamide The compound (0.040 g) obtained in Step 2 above and 1-methyl-1H-indazole-4-amine were subjected to the same procedure as in Step 1 of Example 1 to obtain the title compound (0.030 g) as a solid.
MS (m/z): 461 (M+H)+.

Example 4

4-(1-{[(2R)-2-(1H-Indazol-4-ylcarbamoyl)pyrrolidin-1-yl]carbonyl}cyclopentyl)benzoic acid

[Formula 107]

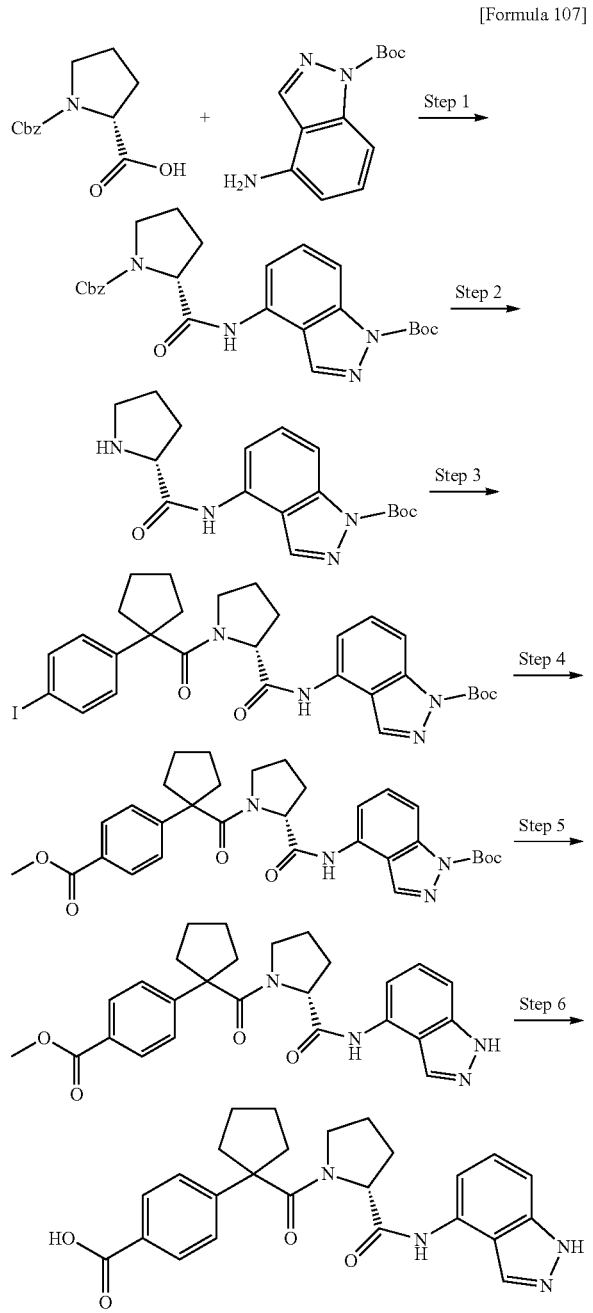

(Step 1) tert-Butyl 4-({1-[(benzyloxy)carbonyl]-D-prolyl}amino)-1H-indazole-1-carboxylate To a solution of 1-[(benzyloxy)carbonyl]-D-proline (3.00 g) in N,N-dimethylformamide (60 mL), COMU (5.67 g) and N,N-diisopropylethylamine (2.73 mL) were added, and the mixture was stirred at room temperature for 15 minutes. The compound obtained in Reference Example A-2 (2.81 g) was then added, and the mixture was stirred at room temperature overnight. A saturated aqueous ammonium chloride solution was added to the reaction solution, and the mixture was extracted with ethyl acetate three times. The organic layer was washed with a saturated aqueous sodium hydrogen carbonate solution, and with saturated brine, and then dried over anhydrous sodium sulfate. After filtration and concentration under reduced pressure, the residue obtained was purified by silica gel column chromatography (chloroform/ethyl acetate, then hexane/ethyl acetate) to obtain the title compound (4.06 g) as a solid.
$^1$H-NMR (DMSO-$D_6$) δ: 1.65 (9H, s), 1.85-2.08 (3H, m), 2.23-2.39 (1H, m), 3.44-3.59 (2H, m), 4.52-4.61 (1H, m), 4.97-5.14 (2H, m), 7.06-7.39 (5H, m), 7.55 (1H, td, J=8.2, 2.8 Hz), 7.81 (2H, dd, J=14.8, 8.2 Hz), 8.52 (1H, d, J=32.0 Hz), 10.36 (1H, s). MS (m/z): 465 (M+H)+.

(Step 2) tert-Butyl 4-(D-prolylamino)-1H-indazole-1-carboxylate

To a solution of the compound (3.60 g) obtained in Step 1 above in ethanol (70 mL), a 10% palladium-carbon catalyst (1.50 g) was added, and the mixture was stirred under a hydrogen atmosphere at room temperature for 3 hours. The reaction solution was filtered and concentrated under reduced pressure, and diethyl ether and hexane were added to the solid obtained for suspension. The solid was collected by filtration and dried to obtain the title compound (2.05 g) as a solid.
$^1$H-NMR (CDCl$_3$) δ: 1.73 (9H, s), 1.77-1.89 (2H, m), 2.07-2.15 (1H, m), 2.23-2.36 (2H, m), 3.03-3.09 (1H, m), 3.13-3.19 (1H, m), 3.97 (1H, s), 7.50 (1H, t, J=8.2 Hz), 7.90 (1H, d, J=8.5 Hz), 7.96 (1H, d, J=7.9 Hz), 8.21 (1H, s), 10.35 (1H, s). MS (m/z): 331 (M+H)+.

(Step 3) tert-Butyl 4-[(1-{[1-(4-iodophenyl)cyclopentyl]carbonyl}-D-prolyl)amino]-1H-indazole-1-carboxylate To a suspension of the compound obtained in Reference Example C-1 (0.421 g) in dichloromethane (15 mL), thionyl chloride (0.176 mL) and N,N-dimethylformamide (0.0100 mL) were added, and the mixture obtained was stirred at 40° C. for 2 hours. After allowing to cool to room temperature, the reaction solution was concentrated under reduced pressure to obtain the crude acid chloride.
To a solution of the compound (0.400 g) obtained in Step 2 above in dichloromethane (10 mL), N,N-diisopropylethylamine (0.422 mL) was added, and after ice-cooling, a solution of the acid chloride obtained above in dichloromethane (5 mL) was added, and the mixture was stirred at room temperature for 45 minutes. To the reaction solution, 1 moL/L hydrochloric acid was added, and the mixture was extracted with dichloromethane three times. The organic layer was washed with a saturated aqueous sodium hydrogen carbonate solution, and dried over anhydrous sodium sulfate. After filtration and concentration under reduced pressure, the residue obtained was purified by amino silica gel column chromatography (hexane/ethyl acetate) to obtain the title compound (0.801 g) as a solid.
$^1$H-NMR (CDCl$_3$) δ: 1.64-1.79 (15H, m), 1.85-1.96 (2H, m), 2.07-2.14 (1H, m), 2.26-2.33 (1H, m), 2.52-2.59 (2H, m), 2.98 (2H, t, J=7.0 Hz), 4.95 (1H, dd, J=7.9, 2.4 Hz), 6.93 (2H, d, J=8.5 Hz), 7.48 (1H, t, J=7.9 Hz), 7.59 (2H, d, J=7.9

Hz), 7.89 (1H, d, J=8.5 Hz), 8.04 (1H, d, J=7.9 Hz), 8.47 (1H, s), 10.63 (1H, s). MS (m/z): 528 (M-CO₂tBu+H)⁺.

(Step 4) tert-Butyl 4-{[1-({1-[4-(methoxycarbonyl)phenyl]cyclopentyl}carbonyl)-D-prolyl]amino}-1H-indazole-1-carboxylate A mixture of the compound (0.760 g) obtained in Step 3 above, N,N-dimethylformamide (12 mL), methanol (6 mL), triethylamine (0.355 mL), palladium acetate(II), and 1,3-bis(diphenylphosphino)propane (0.120 g) was stirred under a carbon monoxide atmosphere at 60° C. for 7 hours. To the reaction solution, saturated brine was added, and the mixture was extracted with ethyl acetate three times. The organic layer was dried over anhydrous sodium sulfate. After filtration and concentration under reduced pressure, the residue obtained was purified by silica gel column chromatography (hexane/ethyl acetate) to obtain the title compound (0.267 g) as a solid.

¹H-NMR (DMSO-D₆) δ: 1.50-1.82 (16H, m), 1.91-1.98 (2H, m), 2.07-2.16 (1H, m), 2.34-2.42 (2H, m), 2.92 (2H, t, J=6.3 Hz), 3.85 (3H, s), 4.64 (1H, dd, J=8.5, 4.8 Hz), 7.44 (2H, d, J=8.5 Hz), 7.56 (1H, t, J=8.2 Hz), 7.84 (2H, t, J=7.3 Hz), 7.95 (2H, d, J=8.5 Hz), 8.60 (1H, s), 10.36 (1H, s). MS (m/z): 561 (M+H)⁺.

(Step 5) Methyl 4-(1-{[(2R)-2-(1H-indazol-4-ylcarbamoyl)pyrrolidin-1-yl]carbonyl}cyclopentyl)benzoate To a solution of the compound (0.260 g) obtained in Step 4 above in dichloromethane (5 mL), trifluoroacetic acid (5 mL) was added under ice-cooling, and the mixture was stirred at room temperature for 2 hours. After the reaction solution was concentrated under reduced pressure, a saturated aqueous sodium hydrogen carbonate solution was added to the residue obtained. The mixture was extracted with dichloromethane three times, and the organic layer was dried over anhydrous sodium sulfate. After filtration and concentration under reduced pressure, the residue obtained was purified by silica gel column chromatography (hexane/ethyl acetate) to obtain the title compound (0.218 g) as a solid.

¹H-NMR (CDCl₃) δ: 1.57-2.01 (8H, m), 2.15-2.22 (1H, m), 2.35-2.42 (1H, m), 2.48-2.57 (1H, m), 2.62-2.69 (1H, m), 2.91-3.00 (2H, m), 3.90 (3H, s), 4.99 (1H, dd, J=7.9, 3.0 Hz), 7.22-7.30 (3H, m), 7.36 (1H, t, J=8.2 Hz), 7.90 (1H, d, J=7.3 Hz), 7.96 (2H, d, J=8.5 Hz), 8.35 (1H, s), 10.44 (2H, s). MS (m/z): 461 (M+H)⁺.

(Step 6) 4-(1-{[(2R)-2-(1H-Indazol-4-ylcarbamoyl)pyrrolidin-1-yl]carbonyl}cyclopentyl)benzoic acid The compound (0.210 g) obtained in Step 5 above was subjected to the same procedure as in Step 5 of Reference Example C-2 to obtain the title compound (0.172 g) as a solid.

¹H-NMR (DMSO-D₆) δ: 1.51-1.82 (7H, m), 1.89-2.01 (2H, m), 2.05-2.14 (1H, m), 2.33-2.43 (2H, m), 2.88-2.98 (2H, m), 4.68 (1H, dd, J=8.2, 5.1 Hz), 7.24-7.30 (2H, m), 7.41 (2H, d, J=8.5 Hz), 7.66 (1H, d, J=6.7 Hz), 7.92 (2H, d, J=8.5 Hz), 8.30 (1H, s), 10.10 (1H, s), 12.99 (2H, s). MS (m/z): 447 (M+H)⁺.

Example 5

(4R)-4-Hydroxy-N-1H-indazol-4-yl-1-{[1-(4-methoxyphenyl)cyclopentyl]carbonyl}-D-prolinamide

[Formula 108]

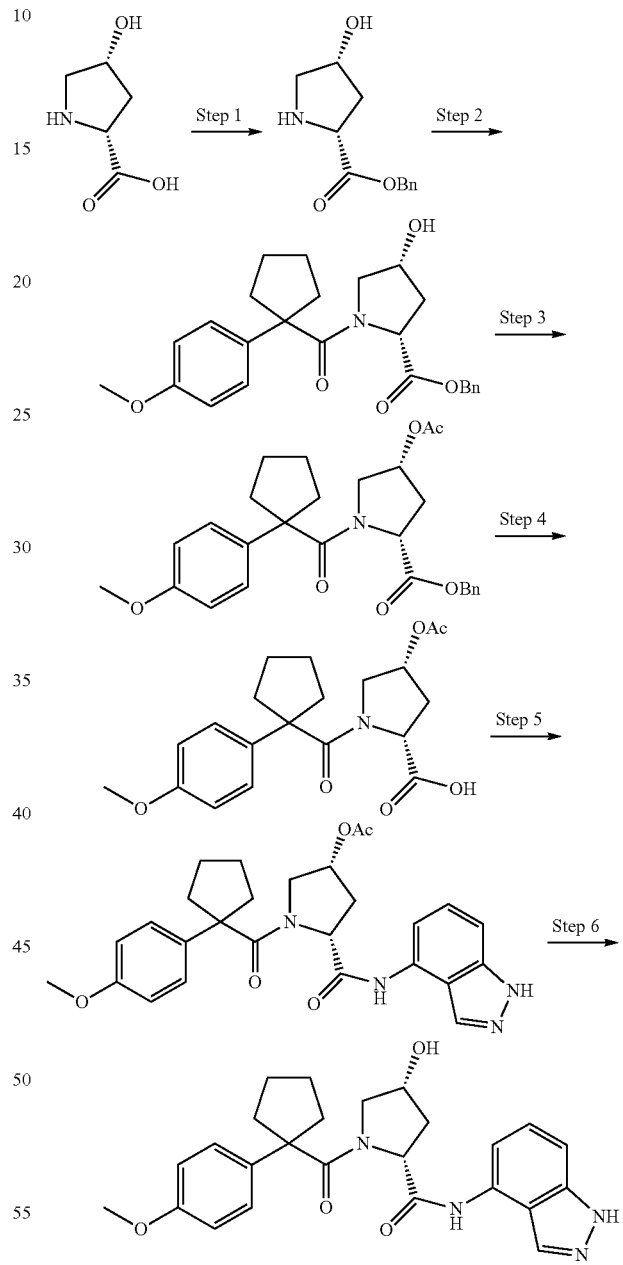

(Step 1) Benzyl (4R)-4-hydroxy-D-prolinate

A mixture of (4R)-4-hydroxy-D-proline (1.50 g), benzyl alcohol (9 mL), p-toluenesulfonic acid hydrate (2.20 g) and benzene (9 mL) was stirred at 120° C. for 17 hours. The solvent was distilled off under reduced pressure, and then a saturated aqueous sodium hydrogen carbonate solution was added to the residue obtained. The mixture was extracted with a mixed solvent of chloroform/isopropyl alcohol (3/1), and the organic layer was dried over anhydrous sodium sulfate. The solvent was distilled off under reduced pressure, and the residue obtained was purified by amino silica gel column chromatography (hexanes/ethyl acetate and ethyl acetate/methanol) to afford the title compound (1.59 g) as an oil.

$^1$H-NMR (CDCl$_3$) δ: 1.51-2.21 (2H, m), 2.01-2.09 (1H, m), 2.21-2.33 (1H, m), 2.95-3.03 (1H, m), 3.09-3.16 (1H, m), 3.83-3.91 (1H, m), 4.30-4.40 (1H, m), 5.14-5.24 (2H, m), 7.33-7.45 (5H, m).

(Step 2) Benzyl (4R)-4-Hydroxy-1-{[1-(4-methoxyphenyl)cyclopentyl]carbonyl}-D-prolinate 1-(4-Methoxyphenyl)cyclopentanecarboxylic acid (0.700 g) and the compound (0.738 g) obtained in Step 1 above were subjected to the same procedure as in Step 1 of Example 4 to obtain the title compound (1.24 g) as a solid.

$^1$H-NMR (CDCl$_3$) δ: 1.63-1.80 (4H, m), 1.86-1.92 (1H, m), 1.92-2.03 (2H, m), 2.09-2.19 (1H, m), 2.29-2.46 (2H, m), 2.88-2.95 (1H, m), 3.25-3.33 (2H, m), 3.78 (3H, s), 4.05-4.14 (1H, m), 4.49-4.56 (1H, m), 5.19 (1H, d, J=12.1 Hz), 5.33 (1H, d, J=12.1 Hz), 6.79-6.85 (2H, m), 7.12-7.18 (2H, m), 7.31-7.43 (5H, m).

(Step 3) Benzyl (4R)-4-(acetyloxy)-1-{[1-(4-methoxyphenyl)cyclopentyl]carbonyl}-D-prolinate To a mixture of the compound (0.556 g) obtained in Step 2 above, pyridine (0.317 mL) and dichloromethane (5 mL), acetic anhydride (0.372 mL) was added at 0° C., and the mixture was stirred at room temperature for 4 hours. After ethanol was added to the reaction solution, the solvent was distilled off under reduced pressure. 0.3 mol/L Hydrochloric acid was added to the residue obtained, and the mixture was extracted with ethyl acetate. The organic layer was washed with a saturated aqueous sodium hydrogen carbonate solution, with water and with saturated brine, and then dried over anhydrous sodium sulfate. The solvent was distilled off under reduced pressure to obtain the title compound (0.610 g) as an oil.

$^1$H-NMR (CDCl$_3$) δ: 1.58-2.11 (7H, m), 1.78 (3H, s), 2.27-2.43 (3H, m), 3.04-3.12 (1H, m), 3.14-3.21 (1H, m), 3.77-3.79 (3H, m), 4.72-4.79 (1H, m), 4.89-4.96 (1H, m), 5.12 (1H, d, J=12.4 Hz), 5.27 (1H, d, J=12.4 Hz), 6.75-6.80 (2H, m), 7.13-7.17 (2H, m), 7.29-7.42 (5H, m).

MS (m/z): 466 (M+H)$^+$.

(Step 4) (4R)-4-(Acetyloxy)-1-{[1-(4-methoxyphenyl)cyclopentyl]carbonyl}-D-proline The compound (0.610 g) obtained in Step 3 above was subjected to the same procedure as in Step 2 of Example 4 to obtain quantitatively the title compound as an oil.
$^1$H-NMR (CDCl$_3$) δ: 1.64-1.85 (4H, m), 1.86-2.00 (1H, m), 1.94 (3H, s), 2.02-2.15 (1H, m), 2.15-2.28 (1H, m), 2.28-2.49 (3H, m), 3.08-3.20 (2H, m), 3.80 (3H, s), 4.67-4.77 (1H, m), 4.90-4.98 (1H, m), 6.86 (2H, d, J=8.5 Hz), 7.16 (2H, d, J=8.5 Hz). MS (m/z): 376 (M+H)$^+$.

(Step 5) (3R,5R)-5-(1H-Indazol-4-ylcarbamoyl)-1-{[1-(4-methoxyphenyl)cyclopentyl]carbonyl}pyrrolidin-3-yl acetate To a solution of the compound (0.491 g) obtained in Step 4 above in N,N-dimethylformamide (6 mL), COMU (0.616 g) and N,N-diisopropylamine (0.296 mL) were added at 0° C., and the mixture was stirred at room temperature for 5 minutes. The compound obtained in Reference Example A-2 (0.397 g) was then added at 0° C., and the mixture was stirred at room temperature overnight. Ice was added to the reaction solution, and the mixture was extracted with ethyl acetate. The organic layer was washed with water three times, and with saturated brine, and then dried over anhydrous sodium sulfate. The solvent was distilled off under reduced pressure, and the residue obtained was purified by amino silica gel column chromatography (hexane/ethyl acetate) to obtain an intermediate. To a solution of the intermediate obtained in dichloromethane (7 mL), hydrogen chloride (4 mol/L, 1,4-dioxane solution, 10 mL) was added, and the mixture was stirred at 50° C. for 2 hours. Ice was added at room temperature, and then the mixture was extracted with ethyl acetate. The organic layer was washed with 6 mol/L hydrochloric acid, with water, and with saturated brine, and then dried over anhydrous sodium sulfate. The solvent was distilled off under reduced pressure, and the residue obtained was purified by silica gel column chromatography (hexane/ethyl acetate) to obtain the title compound (0.157 g) as a solid.

$^1$H-NMR (CDCl$_3$) δ: 1.64-2.37 (8H, m), 1.95 (3H, s), 2.52-2.64 (1H, m), 2.78-2.88 (1H, m), 3.08-3.17 (1H, m), 3.27-3.37 (1H, m), 3.79 (3H, s), 4.89-4.98 (1H, m), 4.98-5.06 (1H, m), 6.81-6.87 (2H, m), 7.10-7.16 (2H, m), 7.22-7.26 (1H, m), 7.32-7.39 (1H, m), 7.83-7.91 (1H, m), 8.28 (1H, s), 10.00-10.77 (2H, m).

(Step 6) (4R)-4-Hydroxy-N-1H-indazol-4-yl-1-{[1-(4-methoxyphenyl)cyclopentyl]carbonyl}-D-prolinamide The compound obtained in Step 5 above (0.153 g) was dissolved in methanol (4 mL) and water (1.5 mL), then sodium carbonate (0.066 g) was added at room temperature, and the mixture was stirred at room temperature for 4 hours. Water was added to the reaction solution, and the mixture was extracted with ethyl acetate. The organic layer was washed with saturated brine, and dried over anhydrous sodium sulfate. The solvent was distilled off under reduced pressure, and the residue was purified by silica gel column chromatography (hexane/ethyl acetate then ethyl acetate/methanol) to obtain the title compound (0.124 g) as a solid.

$^1$H-NMR (CDCl$_3$) δ: 1.59-1.81 (4H, m), 1.87-2.06 (2H, m), 2.11-2.22 (1H, m), 2.23-2.35 (1H, m), 2.40-2.49 (1H, m), 2.50-2.61 (1H, m), 2.92-3.00 (1H, m), 3.18-3.26 (1H, m), 3.78 (3H, s), 4.20-4.28 (1H, m), 4.61-4.66 (1H, m), 5.06-5.12 (1H, m), 6.79-6.84 (2H, m), 7.09-7.13 (2H, m), 7.29 (1H, d, J=8.5 Hz), 7.38 (1H, dd, J=8.5, 7.3 Hz), 7.78 (1H, d, J=7.3 Hz), 8.34 (1H, s), 10.26-10.45 (2H, m). MS (m/z): 449 (M+H)$^+$.

Example 6

(4R)—N-1H-Indazol-4-yl-4-methoxy-1-{[1-(4-methoxyphenyl)cyclopentyl]carbonyl}-D-prolinamide

[Formula 109]

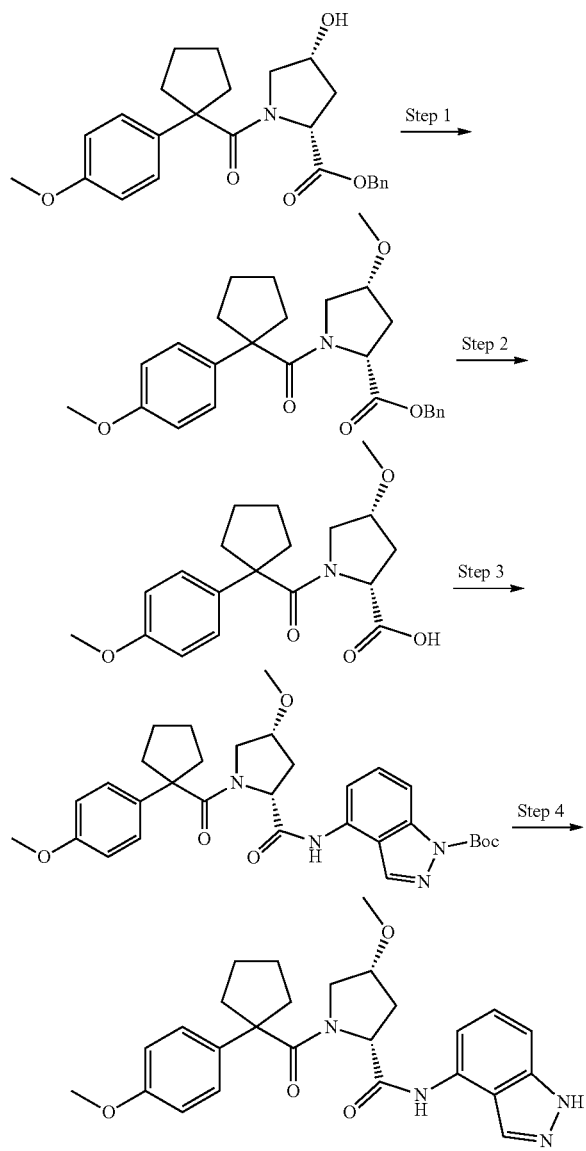

(Step 1) Benzyl (4R)-4-methoxy-1-{[1-(4-methoxyphenyl)cyclopentyl]carbonyl}-D-prolinate To a solution of the compound (620 mg) obtained in Step 2 of Example 5 in acetone (10 mL), iodomethane (5.47 mL) and silver(I) oxide (20.4 g) were added at room temperature under an argon atmosphere, and the mixture was stirred overnight. The reaction solution was filtered and concentrated, then the residue obtained was purified by silica gel column chromatography (hexane/ethyl acetate) to obtain quantitatively the title compound as a solid.

$^1$H-NMR (CDCl$_3$) δ: 1.59-1.78 (4H, m), 1.82-2.04 (3H, m), 2.12-2.23 (1H, m), 2.32-2.44 (2H, m), 2.92-3.01 (1H, m), 3.04 (3H, s), 3.07-3.14 (1H, m), 3.61-3.70 (1H, m), 3.77 (3H, s), 4.66-4.72 (1H, m), 5.14 (1H, d, J=12.4 Hz), 5.21 (1H, d, J=12.4 Hz), 6.73-6.78 (2H, m), 7.11-7.17 (2H, m), 7.28-7.40 (5H, m). MS (m/z): 438 (M+H)$^+$.

(Step 2) (4R)-4-Methoxy-1-{[1-(4-methoxyphenyl)cyclopentyl]carbonyl}-D-proline

The compound (640 mg) obtained in Step 1 above was subjected to the same procedure as in Step 2 of Example 4 to obtain quantitatively the title compound as an oil.

$^1$H-NMR (CDCl$_3$) δ: 1.58-1.85 (4H, m), 1.85-2.19 (3H, m), 2.28-2.53 (3H, m), 2.93-3.05 (1H, m), 3.07-3.19 (1H, m), 3.12 (3H, s), 3.64-3.71 (1H, m), 3.80 (3H, s), 4.59-4.71 (1H, m), 6.87 (2H, d, J=8.5 Hz), 7.14 (2H, d, J=8.5 Hz).

(Step 3) tert-Butyl 4-{[(4R)-4-methoxy-1-{[1-(4-methoxyphenyl)cyclopentyl]carbonyl}-D-prolyl]amino}-1H-indazole-1-carboxylate The compound (505 mg) obtained in Step 2 above and the compound obtained in Reference Example A-2 (441 mg) were subjected to the same procedure as in Step 1 of Example 4 to obtain the title compound (556 mg) as an oil.

$^1$H-NMR (CDCl$_3$) δ: 1.56-1.82 (4H, m), 1.74 (9H, s), 1.95-2.10 (3H, m), 2.30-2.47 (2H, m), 2.53-2.63 (1H, m), 3.08-3.15 (1H, m), 3.14 (3H, s), 3.30-3.37 (1H, m), 3.71-3.81 (1H, m), 3.77 (3H, s), 4.73-4.82 (1H, m), 6.75-6.80 (2H, m), 7.10-7.15 (2H, m), 7.47-7.53 (1H, m), 7.85-7.92 (1H, m), 7.96-8.02 (1H, m), 8.21 (1H, s), 9.55 (1H, s).

(Step 4) (4R)—N-1H-Indazol-4-yl-4-methoxy-1-{[1-(4-methoxyphenyl)cyclopentyl]carbonyl}-D-prolinamide To a solution of the compound (556 mg) obtained in Step 3 above in dichloromethane (7 mL), hydrogen chloride (4 mol/L, 1,4-dioxane solution, 20 mL) was added at room temperature, and the mixture was stirred at 50° C. for 2 hours. The reaction solution was diluted with ethyl acetate, then ice was added, and then the mixture was extracted with ethyl acetate. The organic layer was washed with water, and with saturated brine, and then dried over anhydrous sodium sulfate. The solvent was distilled off under reduced pressure, and the residue obtained was purified by silica gel column chromatography (hexane/ethyl acetate) to obtain the title compound (325 mg) as a solid.

$^1$H-NMR (CDCl$_3$) δ: 1.55-1.83 (4H, m), 1.95-2.12 (3H, m), 2.34-2.46 (2H, m), 2.51-2.61 (1H, m), 3.11-3.19 (1H, m), 3.14 (3H, s), 3.32-3.39 (1H, m), 3.75-3.80 (1H, m), 3.77 (3H, s), 4.70-4.81 (1H, m), 6.75-6.81 (2H, m), 7.12-7.18 (2H, m), 7.20-7.25 (1H, m), 7.35-7.41 (1H, m), 7.88-7.93 (1H, m), 8.03-8.06 (1H, m), 9.35 (1H, s), 10.13 (1H, br s). MS (m/z): 463 (M+H)$^+$.

Example 7

(4S)-4-Fluoro-N-1H-indazol-4-yl-1-{[1-(4-methoxyphenyl)cyclopentyl]carbonyl}-D-prolinamide

[Formula 110]

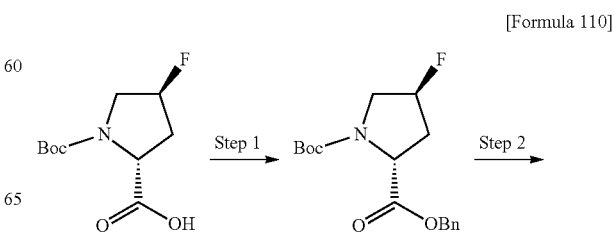

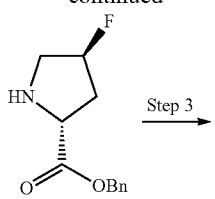

Step 3 →

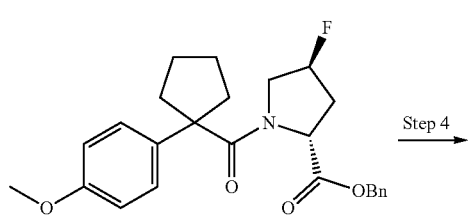

(Step 1) 2-Benzyl 1-tert-butyl (2R,4S)-4-fluoropyrrolidine-1,2-dicarboxylate (4S)-1-(tert-Butoxycarbonyl)-4-fluoro-D-proline (500 mg) was subjected to the same procedure as in Step 2 of Reference Example B-3 to obtain the title compound (680 mg) as an oil.

$^1$H-NMR (CDCl$_3$) δ: 1.32-1.48 (9H, m), 1.96-2.20 (1H, m), 2.49-2.68 (1H, m), 3.51-3.70 (1H, m), 3.75-3.99 (1H, m), 4.41-4.57 (1H, m), 5.08-5.15 (1H, m), 5.15-5.18 (1H, m), 5.22-5.32 (1H, m), 7.29-7.40 (5H, m).

(Step 2) Benzyl (4S)-4-fluoro-D-prolinate

A mixture of the compound (680 mg) obtained in Step 1 above and hydrogen chloride (4 mol/L, 1,4-dioxane solution, 15 mL) was stirred at room temperature for 4 hours. After the solvent was distilled off under reduced pressure, a saturated aqueous sodium hydrogen carbonate solution was added. The mixture was extracted with a mixed solvent of chloroform/isopropyl alcohol (3/1), and the organic layer was dried over anhydrous sodium sulfate. The solvent was distilled off under reduced pressure to obtain the title compound (460 mg) as an oil.

$^1$H-NMR (CDCl$_3$) δ: 1.96-2.17 (1H, m), 2.23-2.35 (1H, m), 2.35-2.53 (1H, m), 3.07-3.34 (2H, m), 4.03-4.13 (1H, m), 5.14-5.32 (1H, m), 5.17 (2H, s), 7.29-7.41 (5H, m).

(Step 3) Benzyl (4S)-4-fluoro-1-{[1-(4-methoxyphenyl)cyclopentyl]carbonyl}-D-prolinate 1-(4-Methoxyphenyl)cyclopentanecarboxylic acid (483 mg) and the compound (460 mg) obtained in Step 2 above were subjected to the same procedure as in Step 1 of Example 4 to obtain the title compound (810 mg) as a solid.

$^1$H-NMR (CDCl$_3$) δ: 1.60-1.96 (6H, m), 2.05-2.16 (1H, m), 2.22-2.33 (1H, m), 2.41-2.55 (2H, m), 2.82-2.97 (1H, m), 3.39-3.50 (1H, m), 3.77 (3H, s), 4.67-4.75 (1H, m), 4.89-5.06 (1H, m), 5.14 (1H, d, J=12.4 Hz), 5.29 (1H, d, J=12.4 Hz), 6.75-6.80 (2H, m), 7.10-7.16 (2H, m), 7.29-7.41 (5H, m). MS (m/z): 426 (M+H)$^+$.

(Step 4) (4S)-4-Fluoro-1-{[1-(4-methoxyphenyl)cyclopentyl]carbonyl}-D-proline

The compound (807 mg) obtained in Step 3 above was subjected to the same procedure as in Step 2 of Example 4 to obtain quantitatively the title compound as an oil.

$^1$H-NMR (CDCl$_3$) δ: 1.62-1.93 (5H, m), 2.02-2.37 (3H, m), 2.41-2.56 (2H, m), 2.87-3.03 (1H, m), 3.46-3.58 (1H, m), 3.79 (3H, s), 4.65-4.75 (1H, m), 4.90-5.10 (1H, m), 6.83-6.88 (2H, m), 7.15-7.20 (2H, m). MS (m/z): 336 (M+H)$^+$.

(Step 5) (4S)-4-Fluoro-N-1H-indazol-4-yl-1-{[1-(4-methoxyphenyl)cyclopentyl]carbonyl}-D-prolinamide The compound (636 mg) obtained in Step 4 above and the compound obtained in Reference Example A-2 (575 mg) were subjected to the same procedure as in Step 5 of Example 5 to obtain the title compound (390 mg) as a solid.

$^1$H-NMR (CDCl$_3$) δ: 1.66-1.84 (4H, m), 1.91-2.01 (1H, m), 2.06-2.15 (1H, m), 2.21-2.38 (1H, m), 2.41-2.54 (2H, m), 2.76-2.99 (2H, m), 3.63-3.74 (1H, m), 3.76 (3H, s), 4.96-5.14 (1H, m), 5.15-5.22 (1H, m), 6.77-6.82 (2H, m), 7.07-7.12 (2H, m), 7.23 (1H, d, J=8.5 Hz), 7.34 (1H, dd, J=7.9, 3.9 Hz), 7.84 (1H, d, J=7.3 Hz), 8.38 (1H, s), 10.34 (1H, br s), 10.50 (1H, s). MS (m/z): 449 (M−H)$^−$.

The compound obtained in Reference Example D-1 was subjected to the same procedure as in Step 1 of Example 4 to obtain the following compounds.

TABLE 1

| Example No. | Name and Structure | Equipment data |
|---|---|---|
| 8 | 1-{[1-(4-Methoxyphenyl)cyclopentyl]carbonyl}-N-phenyl-D-prolinamide | ¹H-NMR (CDCl₃) δ: 1.53-2.14 (9H, m), 2.28-2.49 (3H, m), 2.94-3.07 (2H, m), 3.79 (3H, s), 4.79-4.85 (1H, m), 6.83 (2H, d, J = 9.1 Hz), 7.06-7.16 (3H, m), 7.31 (2H, dd, J = 8.2, 8.2 Hz), 7.54 (2H, d, J = 7.9 Hz), 9.39 (1H, s). MS (m/z): 393 (M + H)⁺. |
| 9 | 1-{[1-(4-Methoxyphenyl)cyclopentyl]carbonyl}-N-(3-methylphenyl)-D-prolinamide | ¹H-NMR (CDCl₃) δ: 1.53-2.13 (8H, m), 2.29-2.50 (4H, m), 2.34 (3H, s), 3.00 (2H, dd, J = 54.4, 27.2 Hz), 3.79 (3H, s), 4.81 (1H, d, J = 4.8 Hz), 6.83 (2H, d, J = 8.5 Hz), 6.90 (1H, d, J = 7.3 Hz), 7.13 (2H, d, J = 9.1 Hz), 7.19 (1H, dd, J = 7.9, 7.9 Hz), 7.30 (1H, d, J = 7.9 Hz), 7.41 (1H, s), 9.34 (1H, s). MS (m/z): 407 (M + H)⁺. |
| 10 | N-(2-Methoxyphenyl)-1-{[1-(4-methoxyphenyl)cyclopentyl]carbonyl}-D-prolinamide | ¹H-NMR (CDCl₃) δ: 1.53-2.53 (12H, m), 2.96-3.07 (2H, m), 3.79 (3H, s), 3.90 (3H, s), 4.73-4.81 (1H, m), 6.83 (2H, d, J = 8.5 Hz), 6.88 (1H, dd, J = 8.2, 1.5 Hz), 6.95 (1H, ddd, J = 7.9, 7.9, 1.2 Hz), 7.04 (1H, ddd, J = 7.7, 7.7, 1.4 Hz), 7.17 (2H, d, J = 9.1 Hz), 8.35 (1H, d, J = 7.3 Hz), 9.00 (1H, s). MS (m/z): 423 (M + H)⁺. |
| 11 | 1-{[1-(4-Methoxyphenyl)cyclopentyl]carbonyl}-N-pyridin-4-yl-D-prolinamide | ¹H-NMR (CDCl₃) δ: 1.58-2.00 (8H, m), 2.07-2.17 (1H, m), 2.26-2.49 (3H, m), 2.95-3.09 (2H, m), 3.79 (3H, s), 4.76-4.85 (1H, m), 6.83 (2H, d, J = 8.5 Hz), 7.08-7.14 (2H, m), 7.46 (2H, d, J = 6.0 Hz), 8.44-8.49 (2H, m), 9.94 (1H, br s). MS (m/z): 394 (M + H)⁺. |
| 12 | N-[4-(Benzyloxy)phenyl]-1-{[1-(4-methoxyphenyl)cyclopentyl]carbonyl}-D-prolinamide | ¹H-NMR (CDCl₃) δ: 1.53-2.13 (9H, m), 2.27-2.48 (3H, m), 2.92-3.08 (2H, m), 3.79 (3H, s), 4.77-4.83 (1H, m), 5.05 (2H, s), 6.83 (2H, d, J = 8.5 Hz), 6.93 (2H, d, J = 9.1 Hz), 7.09-7.15 (2H, m), 7.29-7.49 (7H, m), 9.22 (1H, br s). MS (m/z): 497 (M − H)⁻. |

TABLE 1-continued

| Example No. | Name and Structure | Equipment data |
| --- | --- | --- |
| 13 | 1-{[1-(4-Methoxyphenyl)cyclopentyl]carbonyl}-N-naphthalen-1-yl-D-prolinamide | $^1$H-NMR (CDCl$_3$) δ: 1.53-2.64 (12H, m), 3.05 (2H, t, J = 6.7 Hz), 3.77 (3H, s), 5.01-5.08 (1H, m), 6.81 (2H, d, J = 8.5 Hz), 7.12-7.17 (2H, m), 7.44-7.60 (3H, m), 7.66 (1H, d, J = 8.5 Hz), 7.87 (1H, d, J = 7.9 Hz), 8.16 (2H, dd, J = 7.9, 4.2 Hz), 9.99 (1H, br s). MS (m/z): 443 (M + H)$^+$. |
| 14 | 1-{[1-(4-Methoxyphenyl)cyclopentyl]carbonyl}-N-quinolin-8-yl-D-prolinamide | $^1$H-NMR (CDCl$_3$) δ: 1.54-2.67 (12H, m), 3.02-3.29 (2H, m), 3.80 (3H, s), 4.80-4.87 (1H, m), 6.86 (2H, d, J = 8.5 Hz), 7.25 (2H, d, J = 8.5 Hz), 7.46 (1H, dd, J = 7.9, 4.2 Hz), 7.49-7.57 (2H, m), 8.17 (1H, dd, J = 8.5, 1.8 Hz), 8.77 (1H, d, J = 6.0 Hz), 8.80 (1H, d, J = 3.0 Hz), 10.31 (1H, br s). MS (m/z): 444 (M + H)$^+$. |
| 15 | N-(6-Aminopyridin-2-yl)-1-{[1-(4-methoxyphenyl)cyclopentyl]carbonyl}-D-prolinamide | $^1$H-NMR (CDCl$_3$) δ: 1.51-2.47 (12H, m), 2.95-3.11 (2H, m), 3.79 (3H, s), 4.28-4.35 (2H, m), 4.66-4.72 (1H, m), 6.24 (1H, d, J = 7.9 Hz), 6.85 (2H, d, J = 7.9 Hz), 7.18 (2H, d, J = 8.5 Hz), 7.42 (1H, dd, J = 7.9, 7.9 Hz), 7.48 (1H, d, J = 7.3 Hz), 8.72 (1H, br s). MS (m/z): 409 (M + H)$^+$. |
| 16 | N-1H-Indol-4-yl-1-{[1-(4-methoxyphenyl)cyclopentyl]carbonyl}-D-prolinamide | $^1$H-NMR (CDCl$_3$) δ: 1.64-2.00 (8H, m), 2.09-2.15 (1H, m), 2.30-2.36 (1H, m), 2.51-2.59 (2H, m), 2.94-3.05 (2H, m), 3.77 (3H, s), 5.00 (1H, dd, J = 7.9, 2.4 Hz), 6.78-6.80 (3H, m), 7.11-7.21 (5H, m), 7.92 (1H, t, J = 4.3 Hz), 8.29 (1H, s), 10.06 (1H, s). MS (m/z): 432 (M + H)$^+$. |

TABLE 1-continued

| Example No. | Name and Structure | Equipment data |
|---|---|---|
| 17 | N-1H-Indol-5-yl-1-{[1-(4-methoxyphenyl)cyclopentyl]carbonyl}-D-prolinamide<br>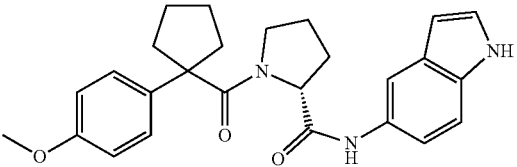 [SMILES: COc1ccc(C2(C(=O)N3CCC[C@@H]3C(=O)Nc3ccc4[nH]ccc4c3)CCCC2)cc1] | $^1$H-NMR (CDCl$_3$) δ: 1.58-1.91 (7H, m), 1.96-2.11 (2H, m), 2.33-2.48 (3H, m), 2.95-3.08 (2H, m), 3.78 (3H, s), 4.85-4.87 (1H, m), 6.50-6.52 (1H, m), 6.83 (2H, d, J = 9.1 Hz), 7.15 (2H, d, J = 9.1 Hz), 7.19 (1H, t, J = 2.7 Hz), 7.24-7.26 (1H, m), 7.31-7.33 (1H, m), 7.91 (1H, s), 8.20 (1H, s), 9.21 (1H, s). MS (m/z): 432 (M + H)$^+$. |
| 18 | 1-{[1-(4-Methoxyphenyl)cyclopentyl]carbonyl}-N-(2-oxo-1,2,3,4-tetrahydroquinolin-6-yl)-D-prolinamide<br>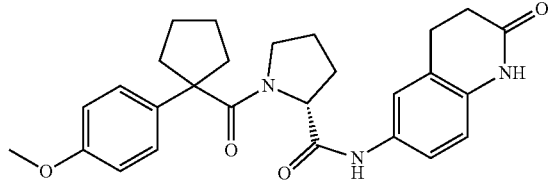 [SMILES: COc1ccc(C2(C(=O)N3CCC[C@@H]3C(=O)Nc3ccc4c(c3)CCC(=O)N4)CCCC2)cc1] | $^1$H-NMR (DMSO-D$_6$) δ: 1.93-1.47 (9H, m), 2.04-1.97 (1H, m), 2.33-2.24 (2H, m), 2.44-2.40 (2H, m), 2.86-2.83 (2H, m), 2.96-2.92 (2H, m), 3.74 (3H, s), 4.41-4.37 (1H, m), 6.78 (1H, d, J = 8.5 Hz), 6.89 (2H, d, J = 8.5 Hz), 7.17 (2H, d, J = 8.5 Hz), 7.29 (1H, dd, J = 8.5, 2.4 Hz), 7.49 (1H, d, J = 2.4 Hz), 9.86 (1H, s), 10.02 (1H, s). MS (m/z): 462 (M + H)$^+$. |
| 19 | 1-{[1-(4-Methoxyphenyl)cyclopentyl]carbonyl}-N-(2-oxo-2,3-dihydro-1H-benzimidazol-5-yl)-D-prolinamide<br>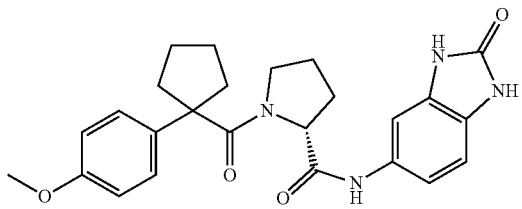 [SMILES: COc1ccc(C2(C(=O)N3CCC[C@@H]3C(=O)Nc3ccc4[nH]c(=O)[nH]c4c3)CCCC2)cc1] | $^1$H-NMR (CDCl$_3$) δ: 1.53-2.50 (12H, m), 3.00-3.14 (2H, m), 3.77 (3H, s), 4.74-4.80 (1H, m), 6.75-6.86 (3H, m), 7.00-7.09 (1H, m), 7.16 (2H, d, J = 9.1 Hz), 7.33-7.42 (1H, br m), 9.25-9.61 (2H, br m), 9.64 (1H, br s). MS (m/z): 449 (M + H)$^+$. |
| 20 | 1-{[1-(4-Methoxyphenyl)cyclopentyl]carbonyl}-N-pyrimidin-2-yl-D-prolinamide<br>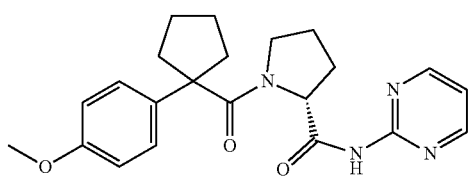 [SMILES: COc1ccc(C2(C(=O)N3CCC[C@@H]3C(=O)Nc3ncccn3)CCCC2)cc1] | $^1$H-NMR (CDCl$_3$) δ: 1.57-2.48 (12H, m), 2.95-3.09 (2H, m), 3.79 (3H, s), 4.90-5.01 (1H, m), 6.84 (2H, d, J = 8.5 Hz), 7.01 (1H, dd, J = 4.8, 4.8 Hz), 7.17 (2H, d, J = 8.5 Hz), 8.63 (2H, d, J = 4.8 Hz), 9.59 (1H, br s). MS (m/z): 395 (M + H)$^+$. |

TABLE 1-continued

| Example No. | Name and Structure | Equipment data |
|---|---|---|
| 21 | N-(3-Chloro-4-hydroxy-phenyl)-1-{[1-(4-methoxyphenyl)cyclopentyl]carbonyl}-D-prolinamide | ¹H-NMR (CDCl₃) δ: 1.51-2.12 (9H, m), 2.27-2.47 (3H, m), 2.93-3.09 (2H, m), 3.79 (3H, s), 4.74-4.81 (1H, m), 5.44 (1H, s), 6.80-6.86 (2H, m), 6.91-6.97 (1H, m), 7.09-7.14 (2H, m), 7.15-7.21 (1H, m), 7.74 (1H, br s), 9.39 (1H, br s). MS (m/z): 443 (M + H)⁺. |
| 22 | 1-{[1-(4-Methoxyphenyl)cyclopentyl]carbonyl}-N-(1-methyl-1H-pyrazol-3-yl)-D-prolinamide | ¹H-NMR (CDCl₃) δ: 1.53-2.47 (12H, m), 2.92-3.07 (2H, m), 3.79 (3H, s), 3.81 (3H, s), 4.74 (1H, br s), 6.60 (1H, d, J = 1.8 Hz), 6.85 (2H, d, J = 8.5 Hz), 7.15 (2H, d, J = 8.5 Hz), 7.23 (1H, d, J = 2.4 Hz), 9.10 (1H, br s). MS (m/z): 397 (M + H)⁺. |
| 23 | N-{2-Cyano-4-[2-(morpholin-4-yl)ethoxy]phenyl}-1-{[1-(4-methoxyphenyl)cyclopentyl]carbonyl}-D-prolinamide | ¹H-NMR (CDCl₃) δ: 1.55-1.97 (8H, m), 2.12-2.21 (1H, m), 2.23-2.33 (1H, m), 2.34-2.44 (1H, m), 2.44-2.54 (1H, m), 2.54-2.61 (4H, m), 2.80 (2H, t, J = 5.5 Hz), 2.95-3.14 (2H, m), 3.74 (4H, t, J = 4.6 Hz), 3.80 (3H, s), 4.10 (2H, t, J = 5.5 Hz), 4.75-4.83 (1H, m), 6.81-6.87 (2H, m), 7.11 (1H, dd, J = 14.6, 3.0 Hz), 7.14-7.19 (3H, m), 8.06 (1H, d, J = 9.1 Hz), 9.18 (1H, br s). MS (m/z): 547 (M + H)⁺. |

Example 24

N-1H-Indazol-5-yl-1-{[1-(4-methoxyphenyl)cyclopentyl]carbonyl}-D-prolinamide

[Formula 111]

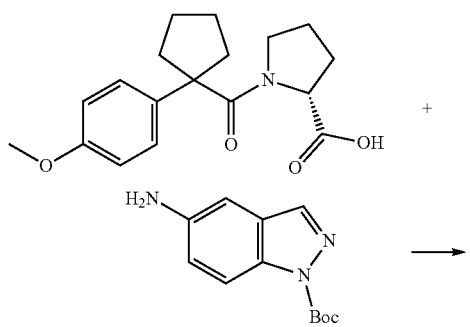

+

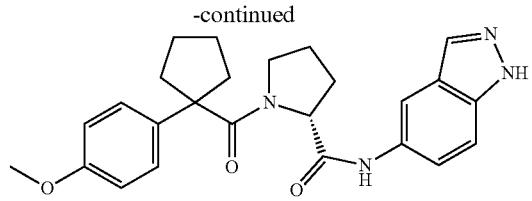

→

A solution of the compound (500 mg) obtained in Reference Example D-1 in N,N-dimethylformamide (20 mL) was cooled to 0° C. Then, the compound (441 mg) obtained in Reference Example A-4, COMU (810 mg) and N,N-diisopropylethylamine (0.412 mL) were added, and the mixture was stirred at room temperature for 16.3 hours. Then, water and saturated brine were added in this order, and the mixture was extracted with a mixed solvent of ethyl acetate/hexane. The resultant was washed with saturated brine, and then dried over anhydrous sodium sulfate. The solvent was distilled off under reduced pressure, then the residue obtained was subjected to silica gel column chromatography (hexane/ethyl acetate). Hydrogen chloride (4 mol/L, dioxane solution, 30 mL) was added at 0° C. to the compound obtained, and the mixture was stirred at room temperature for 17.8 hours. Toluene was added, and the mixture was concentrated under reduced pressure. Then, the resultant was subjected to amino silica gel column chromatography (hexane/ethyl acetate). The solid obtained was slurried with ethyl acetate and hexane, then filtered to obtain the title compound (355 mg) as a solid.

$^1$H-NMR (CDCl$_3$) δ: 1.44-2.15 (9H, m), 2.31-2.52 (3H, m), 2.96-3.10 (2H, m), 3.79 (3H, s), 4.81-4.91 (1H, m), 6.83 (2H, d, J=8.5 Hz), 7.11-7.17 (2H, m), 7.36-7.44 (2H, m), 8.02 (1H, s), 8.12 (1H, s), 9.52 (1H, br s).

Example 25

(5R)—N-1H-Indazol-4-yl-1-{[1-(4-methoxyphenyl)cyclopentyl]carbonyl}-5-methyl-D-prolinamide

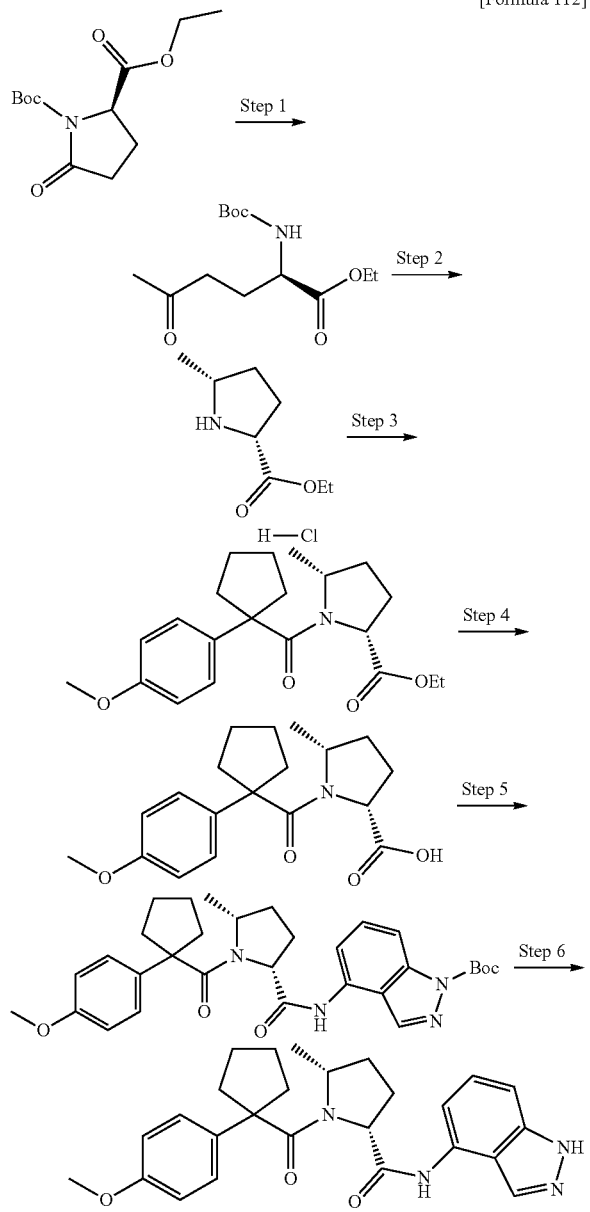

[Formula 112]

(Step 1) Ethyl N-(tert-butoxycarbonyl)-5-oxo-D-norleucinate

A solution of 1-tert-butyl 2-ethyl (2R)-5-oxopyrrolidine-1,2-dicarboxylate (5.00 g) in tetrahydrofuran (60 mL) was cooled to −40° C. Then, methylmagnesium bromide (0.97 mol/L, tetrahydrofuran solution, 26 mL) was added dropwise, and the mixture was stirred at the same temperature for 2.5 hours. Then, an aqueous saturated ammonium chloride solution was added, then the mixture was extracted with ethyl acetate. The organic layer was washed with saturated brine, then dried over anhydrous magnesium sulfate. The resultant was concentrated, then the residue obtained was purified by silica gel column chromatography (hexane/ethyl acetate) to obtain the title compound (4.63 g) as an oil.

$^1$H-NMR (CDCl$_3$) δ: 1.29 (3H, t, J=7.0 Hz), 1.45 (9H, s), 1.84-1.93 (1H, m), 2.08-2.22 (4H, m), 2.49-2.63 (2H, m), 4.14-4.27 (3H, m), 5.06-5.17 (1H, m).

(Step 2) Ethyl (5R)-5-methyl-D-prolinate hydrochloride

A mixture of the compound (3.75 g) obtained in Step 1 above, trifluoroacetic acid (8 mL) and dichloromethane (15 mL) was stirred at room temperature for 30 minutes. The resultant was concentrated, and azeotropically concentrated with toluene to obtain the crude imine. The imine was dissolved in methanol (50 mL), then 10% palladium-carbon (0.65 g) was added. Under a hydrogen atmosphere, the mixture was stirred at room temperature for 3 hours. The resultant was filtered with celite, and concentrated to obtain the crude amine (2.16 g) as an oil. To a solution of the crude amine (2.16 g) in tetrahydrofuran (30 mL), di-tert-butyl dicarbonate (5.46 g) and 1 mol/L aqueous sodium hydroxide solution (30 mL) were added, and the mixture was stirred at room temperature for 45 minutes. The resultant was diluted with ethyl acetate, then washed with water and with saturated brine, and then dried over anhydrous magnesium sulfate. The resultant was concentrated, then the residue obtained was purified by silica gel column chromatography (dichloromethane/methanol) to obtain the Boc compound (3.15 g). A mixture of the Boc compound (3.15 g), hydrogen chloride (4 mol/L, 1,4-dioxane solution, 8 mL) and dichloromethane (10 mL) was stirred at room temperature for 1.5 hours, and concentrated. To the residue obtained, ethyl acetate was added, then the precipitated solid was filtered, and dried to obtain the title compound (1.50 g) as a solid.

$^1$H-NMR (DMSO-D$_6$) δ: 1.25 (3H, t, J=7.3 Hz), 1.32 (3H, d, J=6.7 Hz), 1.53-1.63 (1H, m), 2.03-2.16 (2H, m), 2.20-2.31 (1H, m), 3.54-3.65 (1H, m), 4.16-4.29 (2H, m), 4.37-4.45 (1H, m), 8.57-9.09 (1H, m), 10.00-10.61 (1H, m).

(Step 3) Ethyl (5R)-1-{[1-(4-methoxyphenyl)cyclopentyl]carbonyl}-5-methyl-D-prolinate A mixture of 1-(4-methoxyphenyl)cyclopentanecarboxylic acid (0.300 g), oxalyl chloride (0.27 mL), N,N-dimethylformamide (50 μL) and dichloromethane (10 mL) was stirred at room temperature for 1 hour. The resultant was concentrated, and azeotropically concentrated with toluene to obtain the crude acid chloride. A mixture of the crude acid chloride, 4-dimethylaminopyridine (12.6 mg), pyridine (0.42 mL) and the compound (0.200 g) obtained in Step 2 above was stirred at room temperature for 72 hours. The resultant was diluted with dichloromethane, then washed with water and with saturated aqueous sodium hydrogen carbonate solution, and then dried over anhydrous magnesium sulfate. The resultant was concentrated, then the residue obtained was purified by silica gel column chromatography (hexane/ethyl acetate) to obtain the title compound (0.395 g) as an oil.

$^1$H-NMR (CDCl$_3$) δ: 0.67 (3/2H, d, J=6.0 Hz), 1.24-1.31 (3H, m), 1.38-2.48 (12H, m), 1.46 (3/2H, d, J=6.0 Hz), 3.79 (3H, s), 3.80-3.85 (1H, m), 4.01 (1H, q, J=7.3 Hz), 4.15-4.53 (2H, m), 6.80-6.88 (2H, m), 7.09-7.18 (2H, m).

(Step 4) (5R)-1-{[1-(4-Methoxyphenyl)cyclopentyl]carbonyl}-5-methyl-D-proline

The compound (0.395 g) obtained in Step 3 above was subjected to the same procedure as in Step 5 of Reference Example C-2 to obtain the title compound (0.188 g) as an oil.

$^1$H-NMR (CDCl$_3$) δ: 0.65 (3H, d, J=6.7 Hz), 1.30-2.11 (9H, m), 2.30-2.40 (2H, m), 2.51-2.66 (1H, m), 3.80 (3H, s), 3.89-3.98 (1H, m), 4.54-4.61 (1H, m), 6.85-6.88 (2H, m), 7.08-7.12 (2H, m).

(Step 5) tert-Butyl 4-{[(5R)-1-{[1-(4-methoxyphenyl)cyclopentyl]carbonyl}-5-methyl-D-prolyl]amino}-1H-indazole-1-carboxylate The compound (0.188 g) obtained in Step 4 above and the compound (0.172 g) obtained in Reference Example A-2 were subjected to the same procedure as in Step 1 of Example 4 to obtain the title compound (0.245 g) as a solid.

$^1$H-NMR (CDCl$_3$) δ: 0.68 (3H, d, J=6.0 Hz), 1.28-2.16 (9H, m), 1.74 (9H, s), 2.28-2.51 (2H, m), 2.75-2.87 (1H, m), 3.78 (3H, s), 3.92-3.98 (1H, m), 4.88-4.94 (1H, m), 6.82 (2H, d, J=8.5 Hz), 7.09 (2H, d, J=8.5 Hz), 7.48-7.53 (1H, m), 7.89 (1H, d, J=8.5 Hz), 8.07 (1H, d, J=7.9 Hz), 8.51 (1H, s), 11.03 (1H, s).

(Step 6) (5R)—N-1H-Indazol-4-yl-1-{[1-(4-methoxyphenyl)cyclopentyl]carbonyl}-5-methyl-D-prolinamide The compound (0.245 g) obtained in Step 5 above was subjected to the same procedure as in Step 5 of Example 4 to obtain the title compound (0.116 g) as a solid.

$^1$H-NMR (CDCl$_3$) δ: 0.70 (3H, d, J=6.0 Hz), 1.29-2.17 (9H, m), 2.32-2.41 (1H, m), 2.46-2.54 (1H, m), 2.75-2.88 (1H, m), 3.78 (4H, s), 3.93-3.98 (1H, m), 4.89-4.96 (1H, m), 6.83 (2H, d, J=7.9 Hz), 7.12 (3H, d, J=8.5 Hz), 7.35-7.40 (1H, m), 7.92-7.96 (1H, m), 8.36 (1H, s), 10.84 (1H, s). MS 447 (M+H)$^+$.

Example 26

(4R)-4-(Acetylamino)-N-1H-indazol-4-yl-1-{[1-(4-methoxyphenyl)cyclopentyl]carbonyl}-D-prolinamide

[Formula 113]

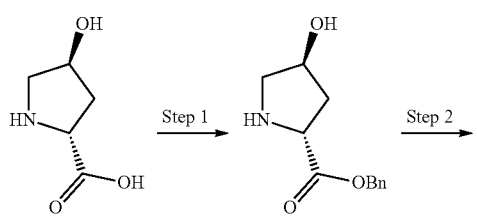

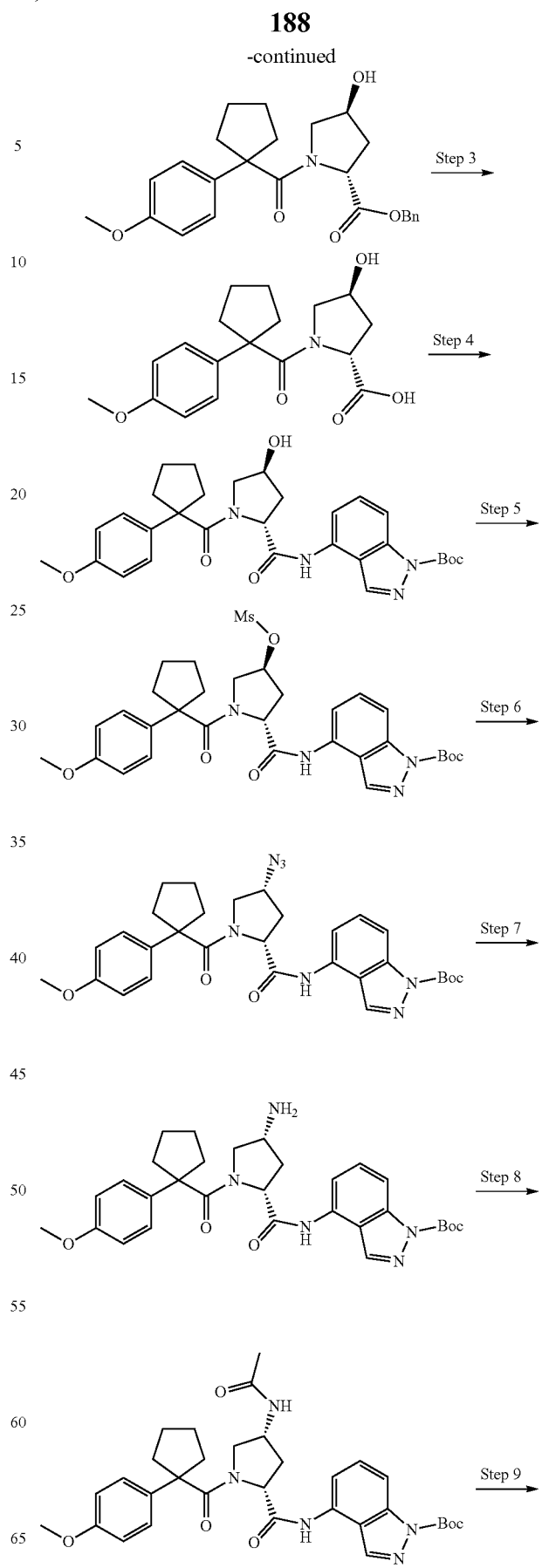

-continued

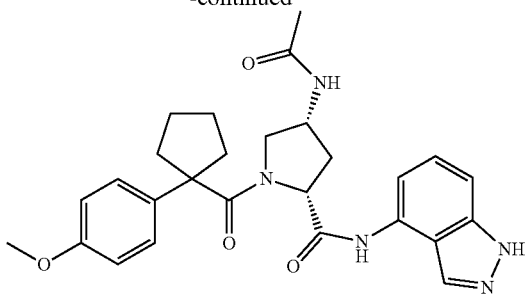

(Step 1) Benzyl (4S)-4-hydroxy-D-prolinate (4S)-4-Hydroxy-D-proline (1.00 g) was subjected to the same procedure as in Step 1 of Example 5 using toluene (6 mL) as a solvent to obtain the title compound (1.03 g) as an oil.
$^1$H-NMR (CDCl$_3$) δ: 1.98-2.09 (1H, m), 2.13-2.22 (1H, m), 2.15-2.45 (2H, m), 2.89-2.98 (1H, m), 3.10-3.17 (1H, m), 3.98-4.08 (1H, m), 4.36-4.45 (1H, m), 5.16 (2H, s), 7.29-7.40 (5H, m).

(Step 2) Benzyl (4S)-4-hydroxy-1-{[1-(4-methoxyphenyl)cyclopentyl]carbonyl}-D-prolinate 1-(4-Methoxyphenyl)cyclopentanecarboxylic acid (0.765 g) and the compound (0.807 g) obtained in Step 1 above were subjected to the same procedure as in Step 1 of Example 4 to obtain the title compound (1.18 g) as a solid.
$^1$H-NMR (CDCl$_3$) δ: 1.23-1.29 (1H, m), 1.63-1.79 (4H, m), 1.81-1.94 (2H, m), 1.94-2.03 (1H, m), 2.11-2.21 (1H, m), 2.33-2.46 (2H, m), 3.00-3.06 (1H, m), 3.07-3.13 (1H, m), 3.77 (3H, s), 4.21-4.29 (1H, m), 4.66-4.73 (1H, m), 5.13 (1H, d, J=12.1 Hz), 5.27 (1H, d, J=12.1 Hz), 6.75-6.81 (2H, m), 7.11-7.18 (2H, m), 7.30-7.40 (5H, m).

(Step 3) (4S)-4-Hydroxy-1-{[1-(4-methoxyphenyl)cyclopentyl]carbonyl}-D-proline

The compound (0.400 g) obtained in Step 2 above was subjected to the same procedure as in Step 2 of Example 4 to obtain the title compound quantitatively as a solid.
$^1$H-NMR (CDCl$_3$) δ: 1.63-1.80 (4H, m), 1.91-2.06 (2H, m), 2.08-2.20 (1H, m), 2.20-2.31 (1H, m), 2.31-2.44 (2H, m), 2.95-3.03 (1H, m), 3.17-3.24 (1H, m), 3.75-3.81 (1H, m), 3.78 (3H, s), 4.22-4.30 (1H, m), 4.69-4.79 (1H, m), 6.85 (2H, d, J=9.1 Hz), 7.16 (2H, d, J=9.1 Hz). MS (m/z): 333 [M]$^-$.

(Step 4) tert-Butyl 4-{[(4S)-4-hydroxy-1-{[1-(4-methoxyphenyl)cyclopentyl]carbonyl}-D-prolyl]amino}-1H-indazole-1-carboxylate The compound (0.310 g) obtained in Step 3 above and the compound (0.282 g) obtained in Reference Example A-2 were subjected to the same procedure as in Step 1 of Example 4 to obtain the title compound (0.389 g) as a solid.
$^1$H-NMR (CDCl$_3$) δ: 1.61-2.10 (8H, m), 1.74 (9H, s), 2.32-2.42 (1H, m), 2.46-2.57 (2H, m), 3.03-3.10 (1H, m), 3.23-3.31 (1H, m), 3.77 (3H, s), 4.29-4.37 (1H, m), 5.07-5.14 (1H, m), 6.80-6.86 (2H, m), 7.13-7.18 (2H, m), 7.28-7.36 (1H, m), 7.71-7.79 (1H, m), 7.98 (1H, d, J=7.9 Hz), 8.50 (1H, s), 10.54 (1H, s).

(Step 5) tert-Butyl 4-{[(4S)-1-{[1-(4-methoxyphenyl)cyclopentyl]carbonyl}-4-[(methylsulfonyl)oxy]-D-prolyl}amino)-1H-indazole-1-carboxylate To a mixture of the compound (0.200 g) obtained in Step 4 above, triethylamine (0.157 mL) and dichloromethane (2 mL), methanesulfonyl chloride (0.029 mL) was added at 0° C., and the mixture was stirred at 0° C. for 5 minutes, and then at room temperature for 3 hours. Ice was added to the reaction solution, then the mixture was extracted with ethyl acetate. The organic layer was washed with a saturated aqueous sodium hydrogen carbonate solution, water and saturated brine sequentially, and then dried over anhydrous sodium sulfate. The solvent was distilled off under reduced pressure to obtain the title compound (0.231 g) as a solid.
$^1$H-NMR (CDCl$_3$) δ: 1.53-1.79 (4H, m), 1.74 (9H, s), 1.97-2.11 (2H, m), 2.24-2.37 (2H, m), 2.43-2.52 (1H, m), 2.82 (3H, s), 2.94-3.05 (1H, m), 3.05-3.12 (1H, m), 3.65-3.73 (1H, m), 3.77 (3H, s), 5.05-5.11 (1H, m), 5.11-5.18 (1H, m), 6.80-6.84 (2H, m), 7.08-7.13 (2H, m), 7.47 (1H, dd, J=8.5, 7.9 Hz), 7.91 (1H, d, J=8.5 Hz), 7.97 (1H, d, J=7.9 Hz), 8.49 (1H, s), 10.55 (1H, br s).

(Step 6) tert-Butyl 4-{[(4R)-4-azido-1-{[1-(4-methoxyphenyl)cyclopentyl]carbonyl}-D-prolyl]amino}-1H-indazole-1-carboxylate A mixture of the compound (0.228 g) obtained in Step 5 above, sodium azide (0.071 g) and dimethylsulfoxide (5 mL) was stirred at 80° C. for 4 hours. The mixture was returned to room temperature, then ice was added, and the mixture was extracted with ethyl acetate. The organic layer was dried with water, saturated brine, and anhydrous sodium sulfate. The solvent was distilled off under reduced pressure, then the residue obtained was purified by silica gel column chromatography (hexane/ethyl acetate) to obtain the title compound (0.121 g) as an oil.
$^1$H-NMR (CDCl$_3$) δ: 1.63-1.79 (4H, m), 1.74 (9H, s), 1.85-1.94 (1H, m), 2.13-2.29 (3H, m), 2.50-2.60 (1H, m), 2.74-2.83 (1H, m), 2.92-2.99 (1H, m), 3.26-3.33 (1H, m), 3.74-3.84 (1H, m), 3.79 (3H, s), 4.95-5.01 (1H, m), 6.82-6.87 (2H, m), 7.07-7.13 (2H, m), 7.49 (1H, dd, J=8.5, 7.9 Hz), 7.90 (1H, d, J=8.5 Hz), 8.03 (1H, d, J=7.9 Hz), 8.41 (1H, s), 10.35 (1H, br s). MS (m/z): 572 (M–H)$^-$.

(Step 7) tert-Butyl 4-{[(4R)-4-amino-1-{[1-(4-methoxyphenyl)cyclopentyl]carbonyl}-D-prolyl]amino}-1H-indazole-1-carboxylate The compound (0.120 g) obtained in Step 6 above was subjected to the same procedure as in Step 2 of Example 4 to obtain the title compound (0.110 g) as a solid.
$^1$H-NMR (CD$_3$OD) δ: 1.65-1.84 (4H, m), 1.73 (9H, s), 1.93-2.02 (1H, m), 2.04-2.14 (2H, m), 2.30-2.47 (2H, m), 2.58-2.68 (1H, m), 3.37-3.41 (2H, m), 3.72-3.79 (1H, m), 3.79 (3H, s), 4.78-4.83 (1H, m), 6.91-6.98 (2H, m), 7.20-7.25 (2H, m), 7.56-7.66 (2H, m), 8.02 (1H, d, J=8.5 Hz), 8.46 (1H, s). MS (m/z): 548 (M+H)$^+$.

(Step 8) tert-Butyl 4-{[(4R)-4-(acetylamino)-1-{[1-(4-methoxyphenyl)cyclopentyl]carbonyl}-D-prolyl]amino}-1H-indazole-1-carboxylate To a mixture of the compound (0.030 g) obtained in Step 7 above, N,N-diisopropylamine (0.029 mL) and dichloromethane (1 mL), acetic anhydride (0.010 mL) was added at 0° C., and the mixture was stirred at room temperature for 2 hours. Methanol, then water were added, and then the mixture was extracted with ethyl acetate. The organic layer was washed with water and with saturated brine sequentially, and then dried over anhydrous sodium sulfate. The solvent was distilled off under reduced pressure, then the residue obtained was purified by silica gel column chromatography (ethyl acetate/methanol) to obtain the title compound (0.026 g) as a solid.

$^1$H-NMR (CDCl$_3$) δ: 1.57-1.79 (4H, m), 1.75 (9H, s), 1.87 (3H, s), 1.88-1.98 (1H, m), 1.98-2.10 (1H, m), 2.13-2.22 (2H, m), 2.30-2.37 (1H, m), 2.45-2.55 (1H, m), 3.05-3.12 (1H, m), 3.13-3.19 (1H, m), 3.79 (3H, s), 4.30-4.38 (1H, m), 5.02-5.08 (1H, m), 6.82 (2H, d, J=8.5 Hz), 7.07 (2H, d, J=8.5 Hz), 7.38-7.44 (1H, m), 7.45-7.52 (1H, m), 7.89-7.96 (2H, m), 8.48 (1H, s), 10.67 (1H, br s).

(Step 9) (4R)-4-(Acetylamino)-N-1H-indazol-4-yl-1-{[1-(4-methoxyphenyl)cyclopentyl]carbonyl}-D-prolinamide The compound (0.026 g) obtained in Step 8 above was subjected to the same procedure as in Step 4 of Example 6 to obtain the title compound (0.020 g) as a solid.

$^1$H-NMR (CDCl$_3$) δ: 1.53-1.81 (4H, m), 1.87-1.97 (1H, m), 1.88 (3H, s), 1.98-2.09 (1H, m), 2.14-2.21 (2H, m), 2.33-2.41 (1H, m), 2.50-2.60 (1H, m), 3.05-3.17 (2H, m), 3.79 (3H, s), 4.30-4.39 (1H, m), 5.07-5.12 (1H, m), 6.79-6.84 (2H, m), 7.07-7.11 (2H, m), 7.28-7.31 (1H, m), 7.37-7.43 (1H, m), 7.46-7.51 (1H, m), 7.79-7.82 (1H, m), 8.35 (1H, s), 10.25 (1H, br s), 10.58 (1H, s). MS (m/z): 490 (M+H)$^+$.

Example 27

(2R)—N-(2-Cyanophenyl)-1-{[1-(4-methoxyphenyl)cyclopentyl]carbonyl}azepan-2-carboxamide

[Formula 114]

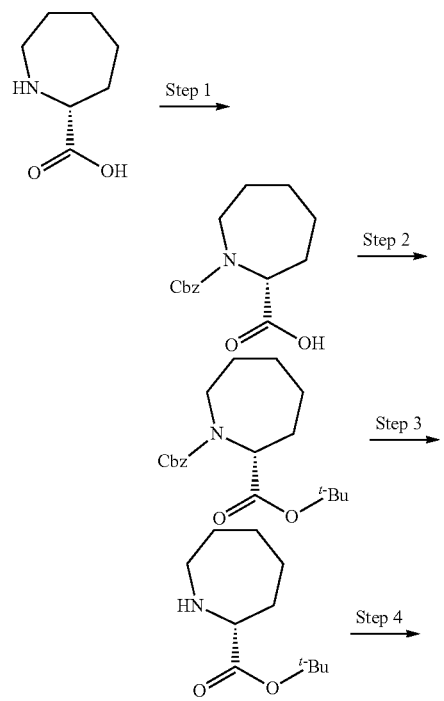

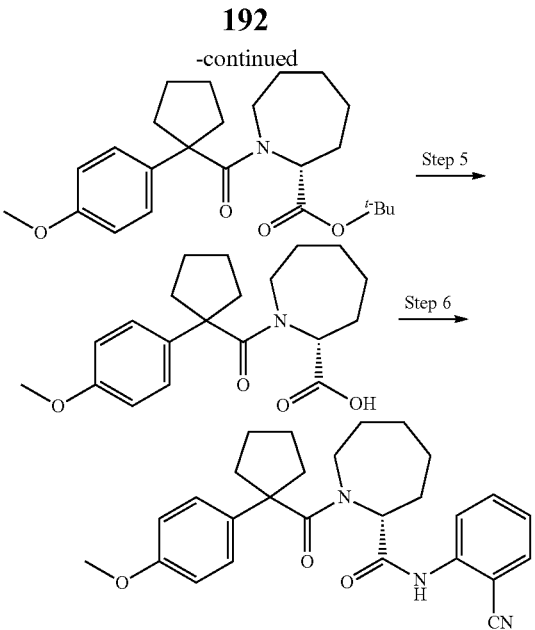

(Step 1) (2R)-1-[(Benzyloxy)carbonyl]azepan-2-carboxylic acid (2R)-Azepan-2-carboxylic acid (0.440 g) synthesized by the method described in the literature (J. Med. Chem., 46, 2057-2073 (2003)) was subjected to the same procedure as in Step 1 of Reference Example B-3 to obtain the title compound (0.823 g) as an oil.

$^1$H-NMR (CDCl$_3$) δ: 1.24-1.58 (3H, m), 1.66-1.95 (4H, m), 2.31-2.42 (1H, m), 2.96-3.07 (1H, m), 3.92-4.10 (1H, m), 4.56-4.70 (1H, m), 5.14-5.22 (2H, m), 7.24-7.39 (5H, m).

(Step 2) 1-Benzyl 2-tert-butyl (2R)-azepan-1,2-dicarboxylate

Under a nitrogen atmosphere, to a mixture of the compound (0.400 g) obtained in Step 1 above, dichloromethane (5 mL) and cyclohexane (3 mL), boron trifluoride diethyl ether complex (0.00906 mL) was added at 0° C. Then, tert-butyl 2,2,2-trichloroacetimidate (0.517 mL) was added dropwise over 30 minutes. Then, while gradually warmed to room temperature, the mixture was stirred at room temperature overnight. A saturated aqueous sodium hydrogen carbonate solution was added to the reaction solution, and the mixture was extracted with dichloromethane three times. The organic layer was washed with saturated brine, then dried over anhydrous sodium sulfate. The resultant was filtered, and concentrated under reduced pressure, then the residue obtained was purified by silica gel column chromatography (hexane/ethyl acetate) to obtain the title compound (0.346 g) as an oil.

$^1$H-NMR (DMSO-D$_6$) δ: 1.21-1.38 (12H, m), 1.56-1.84 (4H, m), 2.13-2.24 (1H, m), 2.97-3.07 (1H, m), 3.77-3.87 (1H, m), 4.29-4.37 (1H, m), 4.97-5.14 (2H, m), 7.28-7.40 (5H, m).

(Step 3) tert-Butyl (2R)-azepan-2-carboxylate

The compound (0.335 g) obtained in Step 2 above was subjected to the same procedure as in Step 2 of Example 4 to obtain the title compound (0.141 g) as an oil.

¹H-NMR (CDCl₃) δ: 1.46 (9H, s), 1.52-1.81 (8H, m), 2.02-2.09 (1H, m), 2.65-2.72 (1H, m), 3.02-3.08 (1H, m), 3.39 (1H, dd, J=9.1, 4.5 Hz).

(Step 4) tert-Butyl (2R)-1-{[1-(4-methoxyphenyl)cyclopentyl]carbonyl}azepan-2-carboxylate 1-(4-Methoxyphenyl)cyclopentanecarboxylic acid (0.164 g) and the compound (0.135 g) obtained in Step 3 above were subjected to the same procedure as in Step 3 of Example 4 to obtain the title compound (0.264 g) as a solid.

¹H-NMR (DMSO-D₆) δ: 0.53-0.62 (0.4H, m), 0.79-0.89 (0.6H, m), 1.10-1.19 (1.4H, m), 1.23-1.43 (11.4H, m), 1.47-1.73 (5.6H, m), 1.80-2.01 (3H, m), 2.22-2.39 (1.6H, m), 2.61-2.67 (0.4H, m), 3.04-3.10 (0.6H, m), 3.25-3.30 (0.6H, m), 3.72-3.73 (3H, m), 4.04-4.18 (1.4H, m), 6.87-6.91 (2H, m), 7.09-7.16 (2H, m). MS (m/z): 402 (M+H)⁺.

(Step 5) (2R)-1-{[1-(4-Methoxyphenyl)cyclopentyl]carbonyl}azepan-2-carboxylic acid The compound (0.255 g) obtained in Step 4 above was subjected to the same procedure as in Step 2 of Example 7 to obtain the title compound (0.076 g) as a solid.

¹H-NMR (DMSO-D₆) δ: 0.44-0.53 (0.4H, m), 0.78-0.85 (0.6H, m), 1.09-1.72 (10.4H, m), 1.80-2.02 (2.6H, m), 2.07-2.14 (0.4H, m), 2.22-2.44 (1.6H, m), 2.61-2.67 (0.4H, m), 3.01-3.06 (0.6H, m), 3.29-3.34 (0.6H, m), 3.73 (3.0H, s), 4.04-4.15 (0.8H, m), 4.28 (0.6H, dd, J=10.9, 4.2 Hz), 6.85-6.93 (2.0H, m), 7.10-7.17 (2.0H, m), 12.24 (1.0H, br s). MS (m/z): 346 (M+H)⁺.

(Step 6) (2R)—N-(2-Cyanophenyl)-1-{[1-(4-methoxyphenyl)cyclopentyl]carbonyl}azepan-2-carboxamide Under a nitrogen atmosphere, the compound (0.0700 g) obtained in Step 5 above and 2-aminobenzonitrile (0.0287 g) were dissolved in pyridine (2 mL), and the resultant was cooled in an ice salt bath. Then, phosphoryl chloride (0.0200 mL) was added, and the mixture was stirred at the same temperature for 6 hours. The reaction solution was diluted with ethyl acetate, then washed with 10% aqueous citric acid solution three times, with saturated sodium hydrogen carbonate and with saturated brine. Then, the organic layer was dried over anhydrous sodium sulfate, filtered, and concentrated under reduced pressure. The residue obtained was purified by silica gel column chromatography (hexane/ethyl acetate) to obtain the title compound (0.0386 g) as a solid.

¹H-NMR (DMSO-D₆) δ: 0.61-0.84 (1.0H, m), 1.11-1.92 (12.0H, m), 2.07-2.35 (3.0H, m), 2.80 (0.5H, t, J=13.3 Hz), 3.01-3.07 (0.5H, m), 3.45-3.50 (0.5H, m), 3.65-3.72 (3.0H, m), 4.14-4.18 (0.5H, m), 4.33-4.38 (0.5H, m), 4.57-4.61 (0.5H, m), 6.87 (2.0H, d, J=8.5 Hz), 7.16 (2.0H, d, J=8.5 Hz), 7.32-7.38 (1.5H, m), 7.58 (0.5H, d, J=8.5 Hz), 7.64-7.72 (1.0H, m), 7.78-7.81 (1.0H, m), 9.77 (0.5H, s), 10.13 (0.5H, s). MS (m/z): 446 (M+H)⁺.

Example 28

(4S)—N-(1H-Indazol-4-yl)-3-{[1-(4-methoxyphenyl)cyclopentyl]carbonyl}-1,3-thiazolidin-4-carboxamide 1-oxide (Low Polarity Isomer) and (High Polarity Isomer)

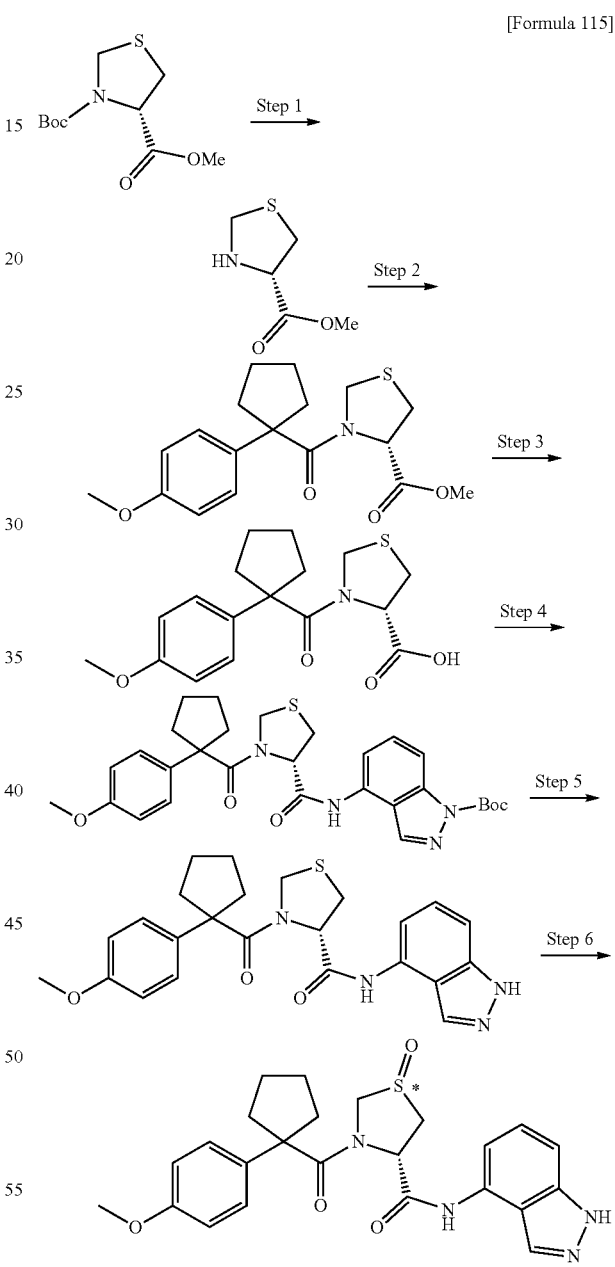

[Formula 115]

(Step 1) Methyl (4S)-1,3-thiazolidine-4-carboxylate 3-tert-Butyl 4-methyl(4S)-1,3-thiazolidine-3,4-dicarboxylate (2.00 g) was subjected to the same procedure as in Step 2 of Example 7 to obtain the title compound (1.05 g) as an oil.

¹H-NMR (CDCl₃) δ: 2.44 (1H, br s), 2.89 (1H, dd, J=10.3, 7.6 Hz), 3.26 (1H, dd, J=10.3, 7.6 Hz), 3.79 (3H, s), 3.87 (1H, t, J=7.6 Hz), 4.13 (1H, d, J=9.7 Hz), 4.38 (1H, d, J=9.7 Hz).

(Step 2) Methyl (4S)-3-{[1-(4-methoxyphenyl)cyclopentyl]carbonyl}-1,3-thiazolidine-4-carboxylate To a solution of (1-(4-methoxyphenyl)cyclopentanecarboxylic acid (1.73 g) in 1,2-dichloroethane (40 mL), oxalyl chloride (1.35 mL) and N,N-dimethylformamide (0.100 mL) were added at room temperature, and the mixture was stirred at 75° C. for 2 hours. Oxalyl chloride (2.70 mL) was added at room temperature, and the mixture was stirred at 75° C. until the reactants disappeared. The solvent was distilled off under reduced pressure, and azeotropically concentrated with 1,2-dichloroethane two times to obtain the crude acid chloride. To a solution of the crude acid chloride in 1,2-dichloroethane (20 mL), a solution of the compound (1.05 g) obtained in Step 1 above in 1,2-dichloroethane (20 mL), pyridine (2.87 mL) and 4-dimethylaminopyridine (0.105 g) were added at 0° C., and the mixture was stirred at 75° C. for 2 hours. To the reaction solution, ice was added, and the organic solvent was distilled off under reduced pressure, and the reaction solution was extracted with ethyl acetate. The organic layer was washed with 1 mol/L hydrochloric acid, a saturated aqueous sodium hydrogen carbonate solution, and saturated brine, and then dried over anhydrous sodium sulfate. The solvent was distilled off under reduced pressure, then the residue obtained was purified by silica gel column chromatography (hexane/ethyl acetate), then by amino silica gel column chromatography (hexane/ethyl acetate) to obtain the title compound (1.77 g) as an oil.
¹H-NMR (CDCl₃) δ: 1.49-2.08 (6H, m), 2.24-2.54 (2H, m), 2.89-3.06 (1H, m), 3.08-3.24 (1H, m), 3.54-3.98 (7H, m), 4.02-4.23 (1H, m), 4.94-5.14 (1H, m), 6.74-6.93 (2H, m), 7.02-7.22 (2H, m).

(Step 3) (4S)-3-{[1-(4-Methoxyphenyl)cyclopentyl]carbonyl}-1,3-thiazolidine-4-carboxylic acid To a mixture of the compound (0.500 g) obtained in Step 2 above, methanol (5 mL) and tetrahydrofuran (5 mL), lithium hydroxide monohydrate (0.090 g) was added, and the mixture was stirred at room temperature for 2 days. Lithium hydroxide monohydrate (0.090 g) and water (1 mL) were added at 0° C., and the mixture was stirred at room temperature for 3 hours. After neutralization by the addition of 1 mol/L hydrochloric acid at 0° C., the reaction solution was extracted with ethyl acetate, and the organic layer was dried over anhydrous sodium sulfate. The solvent was distilled off under reduced pressure, then the residue obtained was purified by silica gel column chromatography (ethyl acetate/methanol) to obtain the title compound (0.470 g) as a solid.
¹H-NMR (CDCl₃) δ: 1.67-1.86 (4H, m), 1.95-2.07 (2H, m), 2.33-2.50 (2H, m), 3.10-3.29 (2H, m), 3.80 (3H, s), 3.88-4.00 (1H, m), 4.14-4.24 (1H, m), 4.94-5.11 (1H, m), 6.87 (2H, d, J=8.5 Hz), 7.17 (2H, d, J=8.5 Hz).

(Step 4) tert-Butyl 4-({[(4S)-3-{[1-(4-methoxyphenyl)cyclopentyl]carbonyl}-1,3-thiazolidin-4-yl]carbonyl}amino)-1H-indazole-1-carboxylate The compound (0.469 g) obtained in Step 3 above and the compound (0.408 g) obtained in Reference Example A-2 were subjected to the same procedure as in Step 1 of Example 4 to obtain the title compound (0.462 g) as an oil.
¹H-NMR (CDCl₃) δ: 1.69-1.82 (4H, m), 1.75 (9H, s), 1.95-2.16 (2H, m), 2.35-2.44 (1H, m), 2.47-2.56 (1H, m), 3.06-3.14 (1H, m), 3.56-3.67 (1H, m), 3.77 (3H, s), 3.93-4.01 (1H, m), 4.32-4.40 (1H, m), 5.23-5.32 (1H, m), 6.80-6.85 (2H, m), 7.06-7.12 (2H, m), 7.32-7.42 (1H, m), 7.76-7.86 (1H, m), 7.93-8.01 (1H, m), 8.35-8.42 (1H, m), 10.08 (1H, br s).

(Step 5) (4S)—N-(1H-Indazol-4-yl)-3-{[1-(4-methoxyphenyl)cyclopentyl]carbonyl}-1,3-thiazolidine-4-carboxamide To a solution of the compound (0.230 g) obtained in Step 4 above in dichloromethane (1 mL), hydrogen chloride (4 mol/L, 1,4-dioxane solution, 5 mL) was added at room temperature, and the mixture was stirred at room temperature for 3 hours. The reaction solution was concentrated under reduced pressure, and water was added, then the mixture was extracted with ethyl acetate. The organic layer was washed with a saturated aqueous sodium hydrogen carbonate solution and with saturated brine, and then dried over anhydrous sodium sulfate. The solvent was distilled off under reduced pressure, then the residue obtained was purified by silica gel column chromatography (hexane/ethyl acetate) to obtain the title compound (0.167 g) as a solid.
¹H-NMR (CDCl₃) δ: 1.67-1.84 (4H, m), 2.00-2.10 (2H, m), 2.37-2.47 (1H, m), 2.47-2.56 (1H, m), 3.04-3.13 (1H, m), 3.68-3.78 (1H, m), 3.76 (3H, s), 3.88-3.96 (1H, m), 4.33-4.42 (1H, m), 5.26-5.34 (1H, m), 6.80 (2H, d, J=9.1 Hz), 7.11 (2H, d, J=9.1 Hz), 7.24-7.27 (1H, m), 7.34-7.39 (1H, m), 7.81-7.87 (1H, m), 8.25 (1H, s), 9.74-10.00 (1H, m), 10.13-10.35 (1H, m). MS (m/z): 449 (M−H)⁻.

(Step 6) (4S)—N-(1H-Indazol-4-yl)-3-{[1-(4-methoxyphenyl)cyclopentyl]carbonyl}-1,3-thiazolidin-4-carboxamide 1-oxide (low polarity isomer) and (high polarity isomer)

To a solution of the compound (0.114 g) obtained in Step 5 above in dichloromethane (6 mL), a solution of 3-chloroperoxybenzoic acid (purity 577%, 0.057 g) in dichloromethane (2 mL) was added at 0° C., and the mixture was stirred at the same temperature for 1.5 hours. To the reaction solution, ice and a saturated aqueous sodium hydrogen carbonate solution were added sequentially, and the mixture was extracted with a mixed solvent of chloroform:isopropyl alcohol=3:1, and the organic layer was dried over anhydrous sodium sulfate. The solvent was distilled off under reduced pressure, then the residue obtained was subjected to amino silica gel column chromatography (hexane/ethyl acetate to ethyl acetate/methanol), then subjected to silica gel column chromatography (hexane/ethyl acetate to ethyl acetate/methanol). The obtained crude product was purified with a chiral column (Daicel Corporation, CHIRALPAK IA, hexane/isopropyl alcohol) to obtain the title compound (low polarity isomer)(0.041 g, >95% d.e.) as a solid, and the title compound (high polarity isomer)(0.017 g, 86% d.e.) as a solid.

28a (Low Polarity Isomer)

¹H-NMR (DMSO-D₆) δ: 1.57-1.76 (5H, m), 2.15-2.22 (2H, m), 2.42-2.48 (1H, m), 2.92-3.00 (1H, m), 3.44-3.53 (1H, m), 3.75 (3H, s), 3.75-3.80 (1H, m), 4.47-4.55 (1H, m), 5.37-5.45 (1H, m), 6.87-6.94 (2H, m), 7.18-7.33 (4H, m), 7.66-7.72 (1H, m), 8.33 (1H, s), 10.32 (1H, s), 13.11 (1H, s). MS (m/z): 467 (M+H)+.

28b (High Polarity Isomer)

¹H-NMR (DMSO-D₆) δ: 1.47-1.73 (5H, m), 1.78-1.89 (1H, m), 1.95-2.06 (1H, m), 2.16-2.27 (1H, m), 2.30-2.40 (1H, m), 3.50-3.64 (1H, m), 3.72 (3H, s), 4.21-4.39 (2H, m), 4.81-4.90 (1H, m), 6.77-6.83 (2H, m), 7.11-7.17 (2H, m), 7.20-7.34 (2H, m), 7.67-7.74 (1H, m), 8.06 (1H, s), 10.24 (1H, br s), 13.09 (1H, br s). MS (m/z): 467 (M+H)+.

Example 29

4-[1-({(2R,4R)-2-[(2-Cyanophenyl)carbamoyl]-4-fluoropyrrolidin-1-yl}carbonyl)cyclopentyl] benzoic acid

[Formula 116]

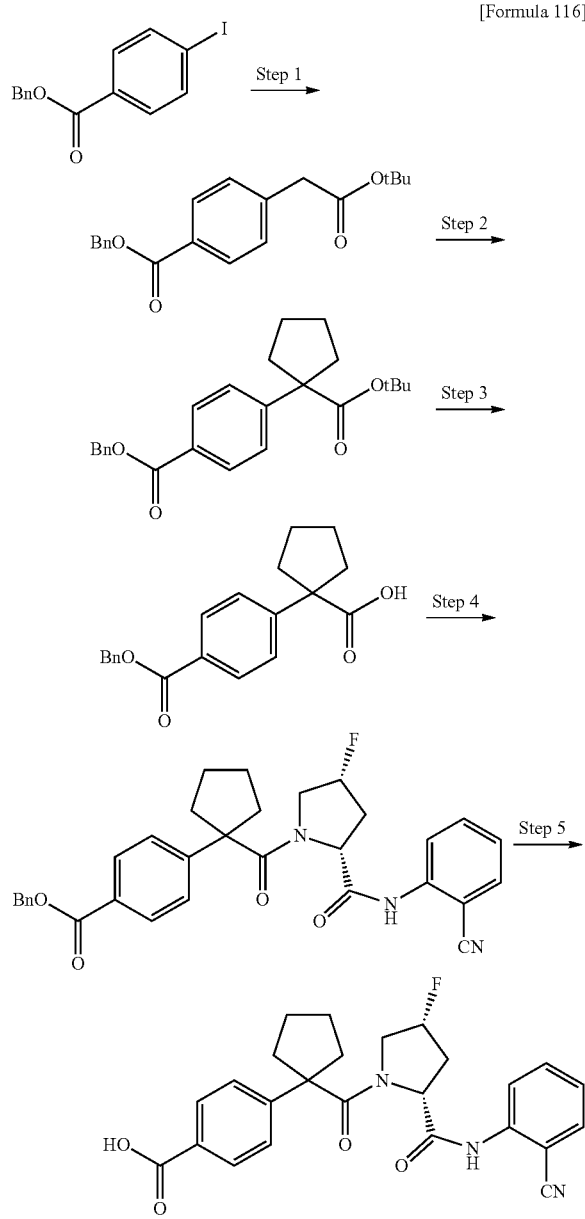

(Step 1) Benzyl 4-(2-tert-butoxy-2-oxoethyl)benzoate

Under a nitrogen atmosphere, benzyl 4-iodobenzoate (described in WO2009/74590A1, 2009; 3.40 g), picolinic acid (0.124 g), copper(I) iodide (0.0957 g) and cesium carbonate (9.83 g), 1,4-dioxane (20 mL) and tert-butyl acetoacetate (3.28 mL) were added, and the mixture was stirred at 70° C. for 48 hours, then left at room temperature overnight. To the reaction solution, a saturated aqueous ammonium chloride solution was added, and the mixture was extracted with diethyl ether three times. The organic layer was washed with saturated brine, and then dried over anhydrous sodium sulfate. The resultant was filtered, and concentrated under reduced pressure, then the residue obtained was purified by silica gel column chromatography (hexane/ethyl acetate) to obtain the title compound (2.06 g) as an oil.

¹H-NMR (CDCl₃) δ: 1.42 (9H, s), 3.58 (2H, s), 5.36 (2H, s), 7.33-7.46 (7H, m), 8.03 (2H, d, J=8.5 Hz).

(Step 2) Benzyl 4-[1-(tert-butoxycarbonyl)cyclopentyl]benzoate

Under a nitrogen atmosphere, to a solution of the compound (2.06 g) obtained in Step 1 above in N,N-dimethylformamide (60.0 mL) was added 1,4-dibromobutane (0.819 mL), and the mixture was cooled with ice. Then, sodium hydride (purity>55%, 0.661 g) was added, and the mixture was stirred overnight while being gradually warmed to room temperature. Water was added to the reaction solution, then the mixture was extracted with ethyl acetate three times. The organic layer was washed with saturated brine, and dried over anhydrous sodium sulfate. The resultant was filtered, and concentrated under reduced pressure, then the residue obtained was purified by silica gel column chromatography (hexane/ethyl acetate) to obtain the title compound (0.755 g) as an oil.

¹H-NMR (CDCl₃) δ: 1.32 (9H, s), 1.71-1.74 (4H, m), 1.80-1.85 (2H, m), 2.59-2.64 (2H, m), 5.36 (2H, s), 7.34-7.46 (7H, m), 8.00 (2H, d, J=9.1 Hz).

(Step 3) 1-{4-[(Benzyloxy)carbonyl]phenyl}cyclopentanecarboxylic acid

The compound (0.750 g) obtained in Step 2 above was subjected to the same procedure as in Step 5 of Example 4 to obtain the title compound (0.621 g) as a solid.

¹H-NMR (CDCl₃) δ: 1.73-1.78 (4H, m), 1.88-1.97 (2H, m), 2.64-2.68 (2H, m), 5.35 (2H, s), 7.32-7.47 (7H, m), 8.02 (2H, d, J=8.5 Hz).

(Step 4) Benzyl 4-[1-({(2R,4R)-2-[(2-Cyanophenyl)carbamoyl]-4-fluoropyrrolidin-1-yl}carbonyl)cyclopentyl] benzoate The compound (0.184 g) obtained in Step 3 above and the compound (0.110 g) obtained in Reference Example B-1 were subjected to the same procedure as in Step 3 of Example 4 to obtain the title compound (0.234 g) as a solid.

¹H-NMR (DMSO-D₆) δ: 1.64-1.69 (4H, m), 1.91-2.01 (2H, m), 2.09-2.21 (1H, m), 2.33-2.46 (3H, m), 3.08-3.19 (2H, m), 4.73 (1H, d, J=7.9 Hz), 5.09 (1H, d, J=53.8 Hz), 5.34 (2H, s), 7.32-7.48 (8H, m), 7.69-7.74 (2H, m), 7.82 (1H, d, J=7.9 Hz), 7.92-7.97 (2H, m), 10.05 (1H, s). MS (m/z): 540 (M+H)+.

(Step 5) 4-[1-({(2R,4R)-2-[(2-Cyanophenyl)carbamoyl]-4-fluoropyrrolidin-1-yl}carbonyl)cyclopentyl]benzoic acid To a mixture of the compound (0.230 g) obtained in Step 3 above, ethanol (5 mL) and tetrahydrofuran (5 mL), 10% palladium-carbon (0.0400 g) was added, and the mixture was stirred under a hydrogen atmosphere at room temperature for 45 minutes. After purging with nitrogen, the reaction solution was filtered, then the filtrate was concentrated under reduced pressure. The residue obtained was purified by silica gel column chromatography (chloroform/methanol). The resultant was concentrated under reduced pressure, then diethyl ether was added to the residue obtained. The mixture was solidified, filtered and dried to obtain the title compound (0.134 g) as a solid.

$^1$H-NMR (DMSO-D$_6$) δ: 1.52-1.78 (4H, m), 1.89-2.04 (2H, m), 2.10-2.20 (1H, m), 2.33-2.48 (3H, m), 3.08-3.21 (2H, m), 4.72-4.75 (1H, m), 5.10 (1H, d, J=53.8 Hz), 7.29-7.44 (3H, m), 7.68-7.75 (2H, m), 7.83 (1H, d, J=7.9 Hz), 7.91 (2H, d, J=8.5 Hz), 10.05 (1H, s), 12.89 (1H, s). MS (m/z): 450 (M+H)$^+$.

Example 30

1-{[1-(4-Methoxyphenyl)cyclopentyl]carbonyl}-N-[6-(methylamino)pyridin-2-yl]-D-prolinamide

[Formula 117]

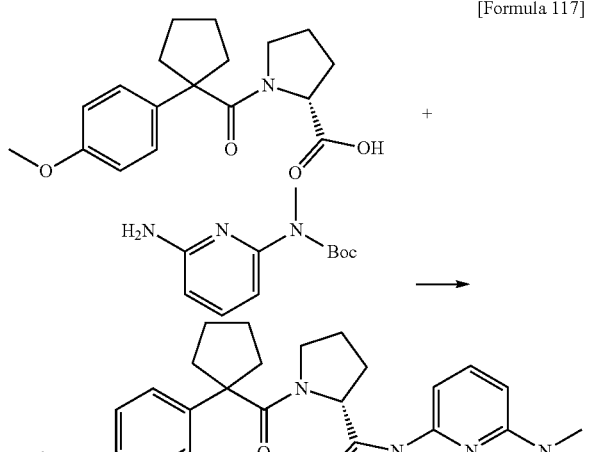

A solution of the compound (0.200 g) obtained in Reference Example D-1 and the compound (0.169 g) obtained in Reference Example A-5 in pyridine (5 mL) was cooled to 0° C., and phosphoryl chloride (0.075 mL) was added, and the mixture was stirred at 0° C. for 1.2 hours. The resultant was diluted with ethyl acetate, then washed with 10% aqueous citric acid solution three times, with a saturated aqueous sodium hydrogen carbonate solution and with saturated brine, and then dried over anhydrous sodium sulfate. The solvent was distilled off under reduced pressure, then the residue obtained was purified by silica gel column chromatography (hexane/ethyl acetate), then by amino silica gel column chromatography (hexane/ethyl acetate) to obtain the intermediate as an oil. To this intermediate, hydrogen chloride (4 mol/L, 1,4-dioxane solution, 10 mL) was added, and the mixture was stirred at room temperature for 4 hours. The resultant was concentrated under reduced pressure, then the residue obtained was subjected to amino silica gel column chromatography (hexane/ethyl acetate). The solid obtained was slurried with diethyl ether and hexane, then filtered to obtain the title compound (0.073 g) as a solid.

$^1$H-NMR (CDCl$_3$) δ: 1.55-2.23 (10H, m), 2.37-2.46 (2H, m), 2.89 (3H, d, J=5.4 Hz), 2.97-3.08 (2H, m), 3.79 (3H, s), 4.37-4.43 (1H, m), 4.67-4.73 (1H, m), 6.13 (1H, dd, J=7.3, 1.2 Hz), 6.85 (2H, d, J=8.5 Hz), 7.19 (2H, d, J=8.5 Hz), 7.37-7.46 (2H, m), 8.71 (1H, br s).

Example 31

(4R)-4-Hydroxy-N-1H-indazol-4-yl-1-{[1-(4-methoxyphenyl)cyclopentyl]carbonyl}-4-methyl-D-prolinamide

[Formula 118]

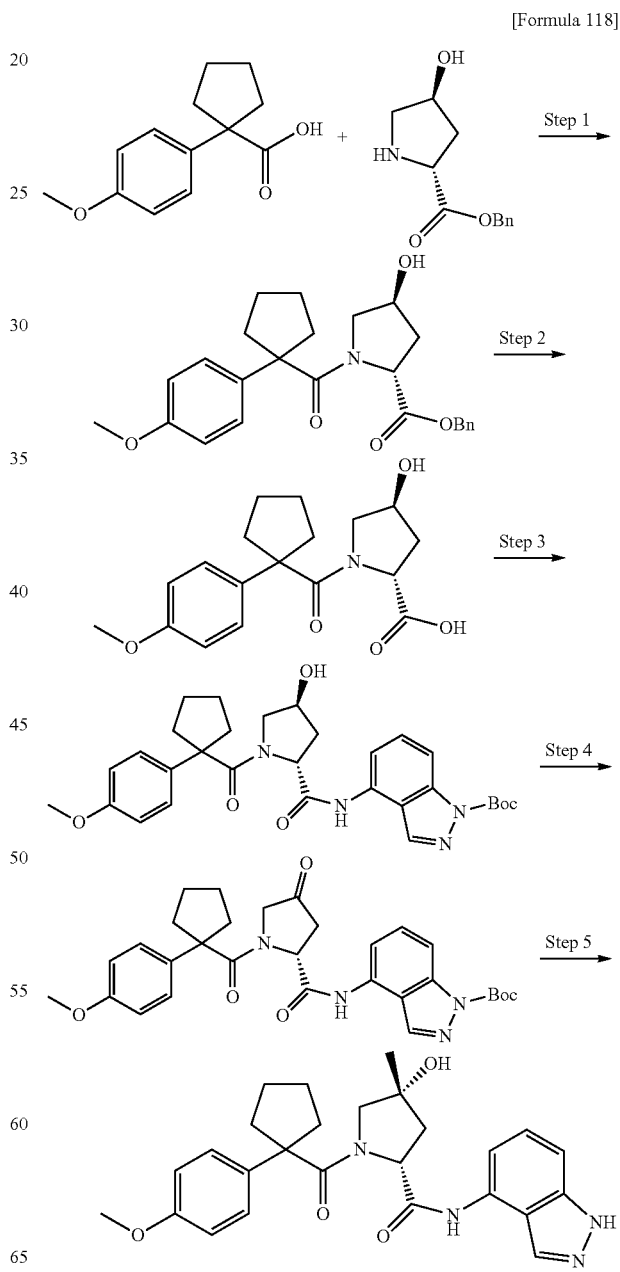

(Step 1) Benzyl (4S)-4-hydroxy-1-{[1-(4-methoxyphenyl)cyclopentyl]carbonyl}-D-prolinate 1-(4-Methoxyphenyl)cyclopentanecarboxylic acid (0.765 g) and the compound (0.807 g) obtained in Step 1 of Example 26 were subjected to the same procedure as in Step 1 of Example 4 to obtain the title compound (1.18 g) as a solid.

$^1$H-NMR (CDCl$_3$) δ: 1.23-1.29 (1H, m), 1.63-1.79 (4H, m), 1.81-1.94 (2H, m), 1.94-2.03 (1H, m), 2.11-2.21 (1H, m), 2.33-2.46 (2H, m), 3.00-3.06 (1H, m), 3.07-3.13 (1H, m), 3.77 (3H, s), 4.21-4.29 (1H, m), 4.66-4.73 (1H, m), 5.13 (1H, d, J=12.1 Hz), 5.27 (1H, d, J=12.1 Hz), 6.75-6.81 (2H, m), 7.11-7.18 (2H, m), 7.30-7.40 (5H, m).

(Step 2) (4S)-4-Hydroxy-1-{[1-(4-methoxyphenyl)cyclopentyl]carbonyl}-D-proline The compound (0.400 g) obtained in Step 1 above was subjected to the same procedure as in Step 2 of Example 4 to obtain the title compound quantitatively as a solid.

$^1$H-NMR (CDCl$_3$) δ: 1.63-1.80 (4H, m), 1.91-2.06 (2H, m), 2.08-2.20 (1H, m), 2.20-2.31 (1H, m), 2.31-2.44 (2H, m), 2.95-3.03 (1H, m), 3.17-3.24 (1H, m), 3.75-3.81 (1H, m), 3.78 (3H, s), 4.22-4.30 (1H, m), 4.69-4.79 (1H, m), 6.85 (2H, d, J=9.1 Hz), 7.16 (2H, d, J=9.1 Hz). MS (m/z): 333 (M)$^-$.

(Step 3) tert-Butyl 4-{[(4S)-4-hydroxy-1-{[1-(4-methoxyphenyl)cyclopentyl]carbonyl}-D-prolyl]amino}-1H-indazole-1-carboxylate The compound (0.310 g) obtained in Step 2 above and the compound (0.282 g) obtained in Reference Example A-2 were subjected to the same procedure as in Step 1 of Example 4 to obtain the title compound (0.389 g) as a solid.

$^1$H-NMR (CDCl$_3$) δ: 1.61-2.10 (8H, m), 1.74 (9H, s), 2.32-2.42 (1H, m), 2.46-2.57 (2H, m), 3.03-3.10 (1H, m), 3.23-3.31 (1H, m), 3.77 (3H, s), 4.29-4.37 (1H, m), 5.07-5.14 (1H, m), 6.80-6.86 (2H, m), 7.13-7.18 (2H, m), 7.28-7.36 (1H, m), 7.71-7.79 (1H, m), 7.98 (1H, d, J=7.9 Hz), 8.50 (1H, s), 10.54 (1H, s).

(Step 4) tert-Butyl 4-[(1-{[1-(4-methoxyphenyl)cyclopentyl]carbonyl}-4-oxo-D-prolyl]amino]-1H-indazole-1-carboxylate The compound (0.062 g) obtained in Step 3 above was subjected to the same procedure as in Step 5 of Reference Example C-16 to obtain the title compound (0.038 g) as an oil.

$^1$H-NMR (CDCl$_3$) δ: 1.50-2.57 (9H, m), 1.74 (9H, s), 3.23 (2H, dd, J=18.7, 6.0 Hz), 3.55-3.63 (1H, m), 3.76 (3H, s), 5.48-5.53 (1H, m), 6.73-6.79 (2H, m), 7.00-7.06 (2H, m), 7.51 (1H, dd, J=8.2, 8.2 Hz), 7.91-7.99 (2H, m), 8.45 (1H, s), 10.15 (1H, br s).

(Step 5) (4R)-4-Hydroxy-N-1H-indazol-4-yl-1-{[1-(4-methoxyphenyl)cyclopentyl]carbonyl}-4-methyl-D-prolinamide Under a nitrogen atmosphere, a solution of the compound (0.094 g) obtained in Step 4 above in tetrahydrofuran (5 mL) was cooled to −15° C. Then, methylmagnesium bromide (0.97 mol/L, tetrahydrofuran solution, 1.8 mL) was added, and the mixture was stirred at room temperature for 2.3 hours. The resultant was cooled to 0° C., and methylmagnesium bromide (0.97 mol/L, tetrahydrofuran solution, 0.89 mL) was further added, and the mixture was stirred at room temperature for 30 minutes, and then stirred at 50° C. for 2.7 hours. A saturated aqueous ammonium chloride solution was added, then the mixture was extracted with ethyl acetate. The resultant was washed with water and with saturated brine, and dried over anhydrous sodium sulfate. The solvent was distilled off under reduced pressure, then the residue obtained was subjected to silica gel column chromatography (hexane/ethyl acetate), and further purified by amino silica gel column chromatography (hexane/ethyl acetate) to obtain the title compound (0.008 g) as an oil.

$^1$H-NMR (CDCl$_3$) δ: 1.21 (3H, s), 1.62-2.53 (10H, m), 2.81 (1H, d, J=11.5 Hz), 3.34 (1H, d, J=10.9 Hz), 3.79 (3H, s), 4.99 (1H, d, J=9.7 Hz), 5.29 (1H, s), 6.86 (2H, d, J=20.6 Hz), 7.15 (2H, d, J=18.7 Hz), 7.24 (1H, dd, J=7.9, 7.9 Hz), 7.34 (1H, dd, J=7.9, 7.9 Hz), 7.88 (1H, d, J=7.3 Hz), 8.43 (1H, s), 10.52 (1H, s), 11.52 (1H, br s). MS (m/z): 463 (M+H)$^+$.

Example 32

(4S)—N-(2-Chlorophenyl)-4-ethynyl-4-hydroxy-1-{[1-(4-methoxyphenyl)cyclopentyl]carbonyl}-D-prolinamide

[Formula 119]

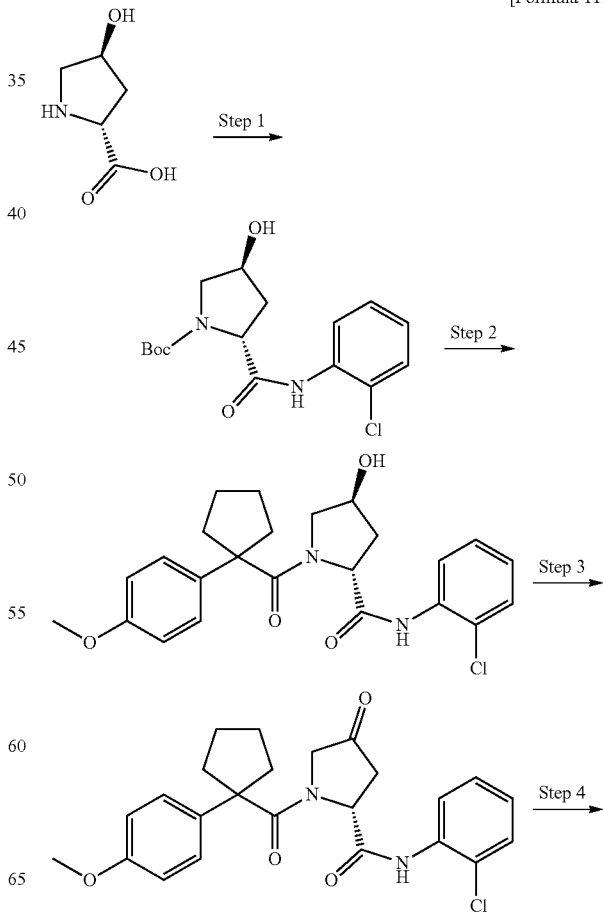

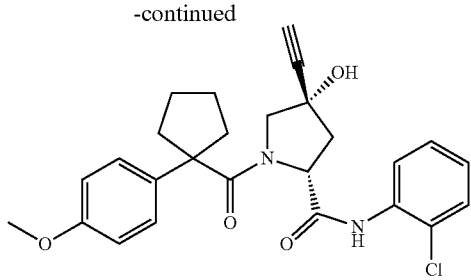

(Step 1) tert-Butyl (2R,4S)-2-[(2-chlorophenyl)carbamoyl]-4-hydroxypyrrolidine-1-carboxylate A solution of trans-4-hydroxy-D-proline (2.00 g) in 1,4-dioxane (16 mL) was cooled to 0° C., and 1 mol/L aqueous sodium hydroxide solution (16 mL) and di-tert-butyl dicarbonate (3.66 g) were added, then the mixture was stirred at a temperature from 0° C. to room temperature for 18.8 hours. To the resultant, 1 mol/L hydrochloric acid (15 mL) was added to about pH 2, and the mixture was extracted with ethyl acetate. The organic layer obtained was washed with saturated brine, and dried over anhydrous sodium sulfate. The solvent was distilled off under reduced pressure, and a solution of the residue obtained in N,N-dimethylformamide (30 mL) was cooled to 0° C. Then, o-chloroaniline (3.30 mL), COMU (8.11 g) and N,N-diisopropylamine (6.87 mL) were added, and the mixture was stirred at room temperature for 20 hours. Water and saturated brine were added, and the mixture was extracted with a mixed solvent of ethyl acetate/hexane. The organic layer was washed with saturated brine, and dried over anhydrous sodium sulfate. The solvent was distilled off under reduced pressure, then the residue obtained was subjected to amino silica gel column chromatography (hexane/ethyl acetate) to obtain the title compound (2.18 g) as a solid.

$^1$H-NMR (CDCl$_3$) δ: 1.46 (9H, br s), 1.71-1.78 (1H, br m), 2.10-2.74 (2H, br m), 3.43-3.86 (2H, br m), 4.30-4.74 (2H, br m), 7.02-7.09 (1H, br m), 7.24-7.31 (1H, br m), 7.34-7.40 (1H, br m), 8.33-8.42 (1H, br m), 9.19 (1H, br s).

(Step 2) (4S)—N-(2-Chlorophenyl)-4-hydroxy-1-{[1-(4-methoxyphenyl)cyclopentyl]carbonyl}-D-prolinamide To a solution of the compound (2.18 g) obtained in Step 1 above in 1,4-dioxane (5 mL), hydrogen chloride (4 mol/L, 1,4-dioxane solution, 20 mL) was added, and the mixture was stirred at room temperature for 1.3 hours. The resultant was concentrated under reduced pressure, then the residue obtained was dissolved in N,N-dimethylformamide (30 mL). The solution was cooled to 0° C., and then 1-(4-methoxyphenyl)cyclopentanecarboxylic acid (1.30 g), COMU (3.03 g) and N,N-diisopropylamine (2.57 mL) were added sequentially, then the mixture was stirred at room temperature for 15.5 hours. Water and saturated brine were added, and the mixture was extracted with a mixed solvent of ethyl acetate/hexane. The resultant was washed with saturated brine, and dried over anhydrous sodium sulfate. The solvent was distilled off under reduced pressure, then the residue obtained was purified by amino silica gel column chromatography (hexane/ethyl acetate), then by silica gel column chromatography (hexane/ethyl acetate) to obtain the title compound (1.90 g) as a solid.

$^1$H-NMR (CDCl$_3$) δ: 1.01-1.05 (1H, br m), 1.55-1.81 (4H, br m), 1.88-2.15 (3H, m), 2.28-2.37 (1H, m), 2.47-2.57 (2H, m), 3.06-3.30 (2H, m), 3.78 (3H, s), 4.29-4.34 (1H, m), 4.94-5.00 (1H, m), 6.82-6.88 (2H, m), 7.05 (1H, ddd, J=7.7, 7.7, 1.4 Hz), 7.17-7.22 (2H, m), 7.23-7.29 (1H, m), 7.38 (1H, dd, J=7.9, 1.2 Hz), 8.33 (1H, dd, J=8.2, 1.5 Hz), 9.25 (1H, br s).

(Step 3) N-(2-Chlorophenyl)-1-{[1-(4-methoxyphenyl)cyclopentyl]carbonyl}-4-oxo-D-prolinamide The compound (1.90 g) obtained in Step 2 above was subjected to the same procedure as in Step 4 of Example 31 to obtain the title compound (0.810 g) as a solid.

$^1$H-NMR (CDCl$_3$) δ: 1.50-2.55 (9H, m), 2.99-3.08 (1H, br m), 3.26-3.35 (1H, br m), 3.51-3.61 (1H, br m), 3.77 (3H, s), 5.43-5.49 (1H, br m), 6.78-6.83 (2H, m), 7.06-7.13 (3H, m), 7.24-7.30 (1H, m), 7.41 (1H, dd, J=7.9, 1.2 Hz), 8.26 (1H, dd, J=8.2, 1.5 Hz), 9.24 (1H, br s).

(Step 4) (4S)—N-(2-Chlorophenyl)-4-ethynyl-4-hydroxy-1-{[1-(4-methoxyphenyl)cyclopentyl]carbonyl}-D-prolinamide Under a nitrogen atmosphere, a solution of trimethylsilylacetylene (0.235 mL) in tetrahydrofuran (5 mL) was cooled to −78° C., then n-butyl lithium (1.55 mol/L, hexane solution, 1.08 mL) was added, and then the mixture was stirred at −78° C. for 10 minutes. To the resultant, a solution of the compound (0.147 g) obtained in Step 3 above in tetrahydrofuran (3 mL) was added at −78° C., and the mixture was stirred at 0° C. for 3.5 hours. To the resultant, a saturated aqueous ammonium chloride solution was added, and the mixture was extracted with ethyl acetate. The organic layer was washed with saturated brine, and dried over anhydrous sodium sulfate. The solvent was distilled off under reduced pressure, then the residue obtained was subjected to amino silica gel column chromatography (hexane/ethyl acetate) to obtain the intermediate as an oil. The intermediate was dissolved in tetrahydrofuran (5 mL), and cooled to 0° C., and tetrabutylammonium fluoride (1 mol/L, tetrahydrofuran solution, 0.23 mL) was added, and the mixture was stirred at 0° C. for 10 minutes. To the resultant, a saturated aqueous ammonium chloride solution was added, and the mixture was extracted with ethyl acetate. The organic layer was washed with saturated brine, then dried over anhydrous sodium sulfate. The resultant was concentrated, then the residue obtained was subjected to silica gel column chromatography (hexane/ethyl acetate) to obtain the title compound (0.045 g) as a solid.

$^1$H-NMR (CDCl$_3$) δ: 1.58-2.11 (6H, m), 2.31-2.42 (3H, m), 2.43 (1H, s), 2.54 (1H, d, J=13.9 Hz), 3.12 (1H, d, J=10.9 Hz), 3.46 (1H, d, J=11.5 Hz), 3.80 (3H, s), 4.85 (1H, d, J=9.1 Hz), 5.13 (1H, s), 6.83-6.88 (2H, m), 7.06-7.16 (3H, m), 7.25-7.31 (1H, m), 7.38-7.42 (1H, m), 8.28 (1H, d, J=8.5 Hz), 9.05 (1H, br s).

Example 33

5-[4-(1-{[(2R)-2-(1H-Indazol-4-ylcarbamoyl)pyrrolidin-1-yl]carbonyl}cyclopentyl)phenyl]-1-methyl-4-oxo-1,4-dihydropyridine-3-carboxylic acid

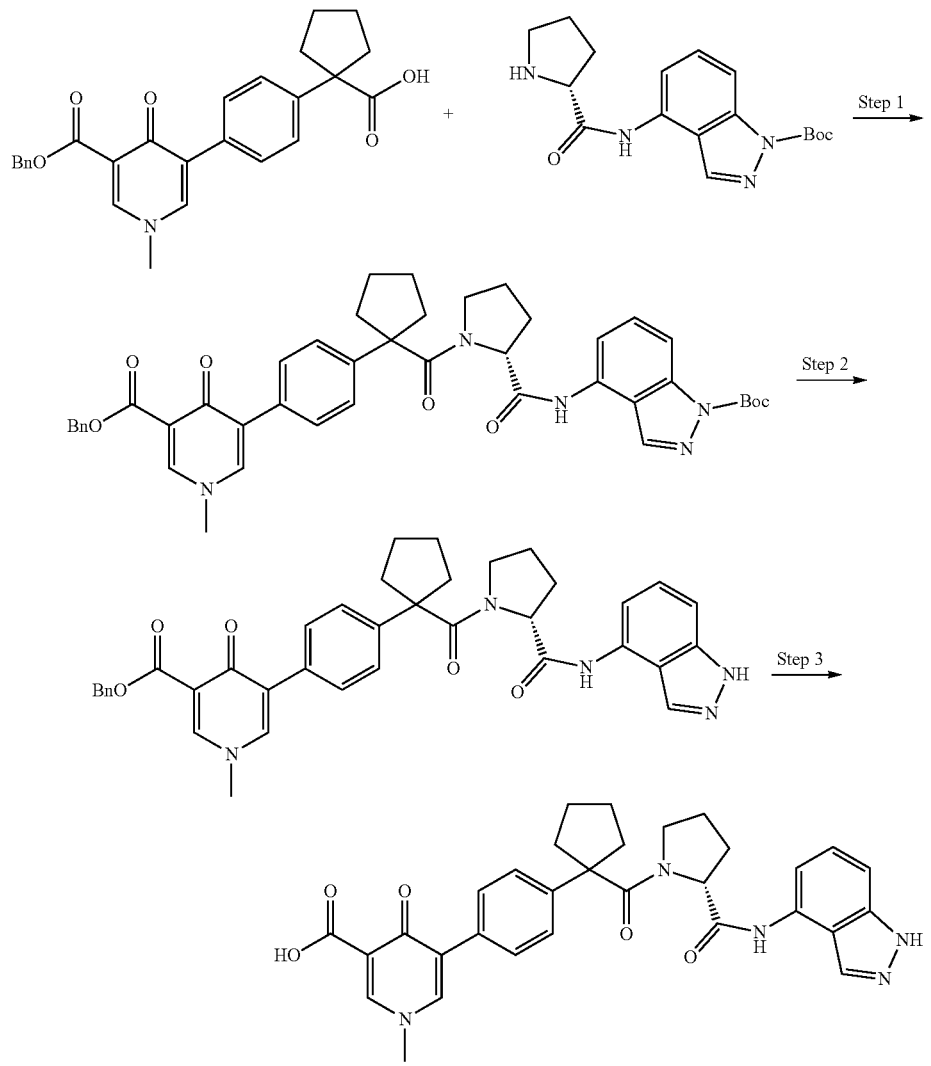

[Formula 120]

(Step 1) tert-Butyl 4-[(1-{[1-(4-{5-[(benzyloxy)carbonyl]-1-methyl-4-oxo-1,4-dihydropyridin-3-yl}phenyl)cyclopentyl]carbonyl}-D-prolyl)amino]-1H-indazole-1-carboxylate The compound (0.267 g) obtained in Reference Example C-33 and the compound (0.204 g) obtained in Step 2 of Example 4 were subjected to the same procedure as in Step 3 of Example 4 to obtain the title compound (0.121 g) as a solid.

$^1$H-NMR (CDCl$_3$) t: 1.61-1.90 (16H, m), 1.95-2.05 (1H, m), 2.13-2.20 (1H, m), 2.32-2.39 (1H, m), 2.48-2.57 (2H, m), 3.01-3.07 (2H, m), 3.72 (3H, s), 4.97-5.00 (1H, m), 5.36 (2H, s), 7.19 (2H, d, J=8.5 Hz), 7.30-7.38 (4H, m), 7.44-7.53 (5H, n), 7.87 (1H, d, J=7.9 Hz), 8.03 (1H, d, J=7.9 Hz), 8.10 (1H, d, J=2.4 Hz), 8.48 (1H, s), 10.69 (1H, s). MS (m/z): 744 (M+H)$^+$.

(Step 2) Benzyl 5-[4-(1-{[(2R)-2-(1H-indazol-4-ylcarbamoyl)pyrrolidin-1-yl]carbonyl}cyclopentyl)phenyl]-1-methyl-4-oxo-1,4-dihydropyridine-3-carboxylate The compound (0.116 g) obtained in Step 1 above was subjected to the same procedure as in Step 5 of Example 4 to obtain the title compound (0.074 g) as a solid.

$^1$H-NMR (CDCl$_3$) δ: 1.62-1.91 (7H, m), 2.00-2.07 (1H, m), 2.11-2.20 (1H, m), 2.34-2.43 (1H, m), 2.47-2.60 (2H, m), 2.97-3.09 (2H, m), 3.71 (3H, s), 4.98-5.01 (1H, m), 5.36 (2H, s), 7.20-7.23 (3H, m), 7.29-7.37 (5H, m), 7.46-7.53

(4H, m), 7.88 (1H, d, J=7.3 Hz), 8.11 (1H, d, J=3.0 Hz), 8.33 (1H, s), 10.38 (1H, br s), 10.48 (1H, s).
MS (m/z): 644 (M+H)⁺.

(Step 3) 5-[4-(1-{[(2R)-2-(1H-Indazol-4-ylcarbamoyl)pyrrolidin-1-yl]carbonyl}cyclopentyl)phenyl]-1-methyl-4-oxo-1,4-dihydropyridine-3-carboxylic acid The compound (0.705 g) obtained in Step 2 above was subjected to the same procedure as in Step 2 of Example 4 to obtain the title compound (0.337 g) as a solid.
¹H-NMR (DMSO-D₆) δ: 1.56-1.72 (5H, m), 1.75-1.84 (2H, m), 1.91-2.02 (2H, m), 2.06-2.16 (1H, m), 2.33-2.43 (2H, m), 3.00-3.05 (2H, m), 3.96 (3H, s), 4.68-4.72 (1H, m), 7.23-7.30 (2H, m), 7.39 (2H, d, J=8.5 Hz), 7.66-7.71 (3H, m), 8.31 (1H, s), 8.36 (1H, s), 8.72 (1H, s), 10.12 (1H, s), 13.08 (1H, s). MS (m/z): 554 (M+H)⁺.

Example 34

(4S)—N-(2-Cyanophenyl)-3-{[1-(4-methoxyphenyl)cyclohexyl]carbonyl}-1,3-thiazolidine-4-carboxamide

[Formula 121]

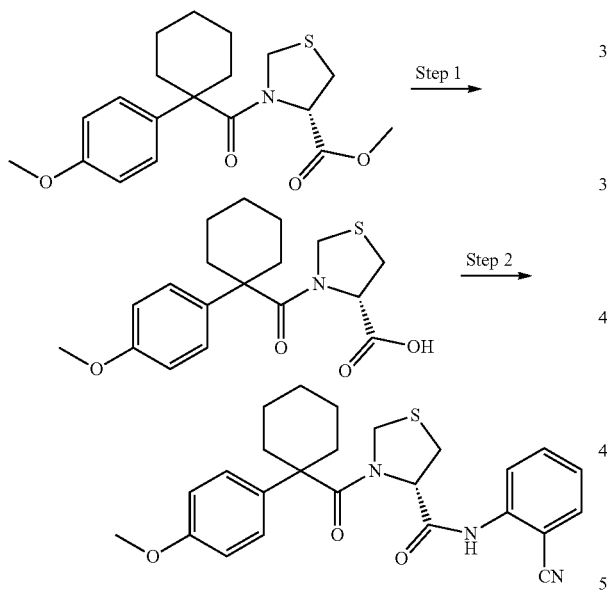

(Step 1) (4S)-3-{[1-(4-Methoxyphenyl)cyclohexyl]carbonyl}-1,3-thiazolidine-4-carboxylic acid To a mixture of the compound (1.15 g) obtained in Step 1 of Reference Example D-2, methanol (10 mL) and tetrahydrofuran (10 mL), an aqueous solution (5 mL) of lithium hydroxide monohydrate (0.406 g) was added, and the mixture was stirred at room temperature for 5 hours. Further, water (10 mL) was added, and the mixture was stirred overnight. Lithium hydroxide monohydrate (0.406 g) was added at 0° C., and the mixture was stirred at room temperature for 1.5 hours. The mixture was acidified by the addition of 6 mol/L hydrochloric acid at 0° C., then the mixture was extracted with ethyl acetate. The organic layer was washed with 0.5 mol/L hydrochloric acid, and dried over anhydrous sodium sulfate. The solvent was distilled off under reduced pressure, then the solid obtained was suspended in diethyl ether, and filtered to obtain the title compound (1.01 g) as a solid.
¹H-NMR (CDCl₃) δ: 1.21-1.38 (1H, m), 1.46-1.91 (7H, m), 2.18-2.37 (2H, m), 2.98-3.25 (2H, m), 3.81 (3H, s), 3.87-4.03 (1H, m), 4.13-4.38 (1H, m), 4.91-5.07 (1H, m), 6.88 (2H, d, J=8.5 Hz), 7.20 (2H, d, J=8.5 Hz). MS (m/z): 348 (M−H)⁻.

(Step 2) (4S)—N-(2-Cyanophenyl)-3-{[1-(4-methoxyphenyl)cyclohexyl]carbonyl}-1,3-thiazolidine-4-carboxamide To a mixture of the compound (0.501 g) obtained in Step 2, 2-aminobenzonitrile (0.507 g) and pyridine (10 mL), phosphoryl chloride (0.393 mL) was added dropwise at 0° C., and the mixture was stirred at the same temperature for 1 hour, and then at room temperature for 5 hours. Ice was added to the reaction solution, and the mixture was extracted with ethyl acetate. The organic layer was washed with 10% aqueous citric acid solution five times, with water and with saturated brine sequentially, then dried over anhydrous sodium sulfate. The solvent was distilled off under reduced pressure, then the residue obtained was purified by silica gel column chromatography (hexane/ethyl acetate) to obtain the title compound (0.460 g) as a solid.
¹H-NMR (CDCl₃) δ: 1.25-1.37 (1H, m), 1.45-1.97 (7H, m), 2.30-2.43 (2H, m), 3.00-3.08 (1H, m), 3.33-3.41 (1H, m), 3.80 (3H, s), 4.12-4.19 (1H, m), 4.25-4.34 (1H, m), 5.14-5.25 (1H, m), 6.84-6.90 (2H, m), 7.17-7.25 (3H, m), 7.56-7.64 (2H, m), 8.33-8.39 (1H, m), 8.79 (1H, s). LC-MS (m/z): 448 (M−H)⁻.

Example 35

(4R)-4-Fluoro-1-{[1-(4-methoxyphenyl)cyclohexyl]carbonyl}-N-1H-pyrazolo[4,3-b]pyridin-5-yl-D-prolinamide

[Formula 122]

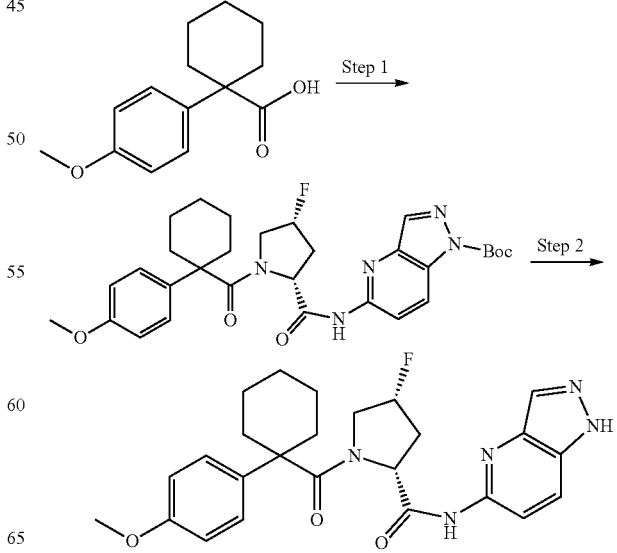

(Step 1) tert-Butyl 5-{[(4R)-4-fluoro-1-{[1-(4-methoxyphenyl)cyclohexyl]carbonyl}-D-prolyl]amino}-1H-pyrazolo[4,3-b]pyridine-1-carboxylate To a solution of 1-(4-methoxyphenyl)cyclohexanecarboxylic acid (100 mg) in dichloromethane (3 mL), thionyl chloride (0.0619 mL) and N,N-dimethylformamide (1 drop) were added, and the mixture was stirred at 40° C. for 30 minutes. The reaction mixture was concentrated under reduced pressure to obtain the crude acid chloride. A solution of the compound (163 mg) obtained in Step 3 of Reference Example B-2 in tetrahydrofuran (10 mL) was cooled to 0° C., and DBU (0.0851 mL) was added, and the mixture was stirred at 0° C. for 15 minutes. Then, a solution of the acid chloride obtained above in dichloromethane (5 mL) was added, and the mixture was stirred for 15 minutes. To the resultant, a saturated aqueous ammonium chloride solution was added, and the mixture was extracted with ethyl acetate. The organic layer was washed with saturated brine, and dried over anhydrous sodium sulfate. The solvent was distilled off under reduced pressure, then the residue obtained was subjected to silica gel column chromatography (hexane/ethyl acetate), and further purified by amino silica gel column chromatography (hexane/ethyl acetate) to obtain the title compound (114 mg) as an oil.

$^1$H-NMR (CDCl$_3$) δ: 1.23-3.59 (14H, m), 1.73 (9H, s), 3.82 (3H, s), 4.75-5.13 (2H, m), 6.88-6.96 (2H, m), 7.21-7.30 (2H, m), 8.23 (1H, s), 8.42 (1H, d, J=9.1 Hz), 8.49 (1H, d, J=9.1 Hz), 8.69 (1H, br s).

(Step 2) (4R)-4-Fluoro-1-{[1-(4-methoxyphenyl)cyclohexyl]carbonyl}-N-1H-pyrazolo[4,3-b]pyridin-5-yl-D-prolinamide To a solution of the compound (2.96 g) obtained in Step 1 above in dichloromethane (30 mL), trifluoroacetic acid (30 mL) was added, and the mixture was stirred at room temperature for 1 hour. The resultant was concentrated under reduced pressure, and a saturated aqueous sodium hydrogen carbonate solution was added to the residue obtained, then the mixture was extracted with ethyl acetate. The resultant was washed with saturated brine, and dried over anhydrous sodium sulfate. The solvent was distilled off under reduced pressure, then the residue obtained was purified by silica gel column chromatography (hexane/ethyl acetate) to obtain the title compound (1.90 g) as a solid.

$^1$H-NMR (CDCl$_3$) δ: 1.21-2.59 (12H, m), 2.87-3.69 (2H, br m), 3.81 (3H, s), 4.58-5.18 (2H, m), 6.88-6.98 (2H, m), 7.21-7.32 (2H, m), 7.80 (1H, d, J=9.1 Hz), 8.12 (1H, s), 8.30 (1H, d, J=9.1 Hz), 8.56 (1H, s), 10.74 (1H, br s). MS (m/z): 466 (M+H)$^+$.

The elemental analysis value as C$_{25}$H$_{28}$N$_5$O$_3$F$_3$ is calculated value: C: 64.50%, H: 6.06%, N: 15.04%, F: 4.08%.

found value: C: 64.30%, H: 6.16%, N: 14.88%, F: 4.12%.

The powder X-ray diffraction of the solid obtained in Step 2 is shown in FIG. 1.

Table 2 shows peaks of relative intensity of 13 or more when the maximum peak intensity is set to 100 in the diffraction pattern of powder X-ray diffraction (CuKα, λ=1.54 angstroms, scanning speed=20°/min) in FIG. 1.

TABLE 2

| Peak number | 2θ | d value | Relative intensity |
|---|---|---|---|
| 1 | 7.08 | 12.48 | 96 |
| 2 | 10.86 | 8.14 | 23 |
| 3 | 12.46 | 7.10 | 31 |
| 4 | 12.74 | 6.94 | 13 |
| 5 | 16.56 | 5.35 | 32 |
| 6 | 19.18 | 4.62 | 100 |
| 7 | 19.50 | 4.55 | 31 |
| 8 | 20.22 | 4.39 | 15 |
| 9 | 21.20 | 4.19 | 15 |
| 10 | 21.88 | 4.06 | 14 |

Example 36

(4R)-1-[(1-{4-[(Cyclopropylsulfonyl)carbamoyl]phenyl}cyclohexyl)carbonyl]-4-fluoro-N-1H-indazol-4-yl-D-prolinamide

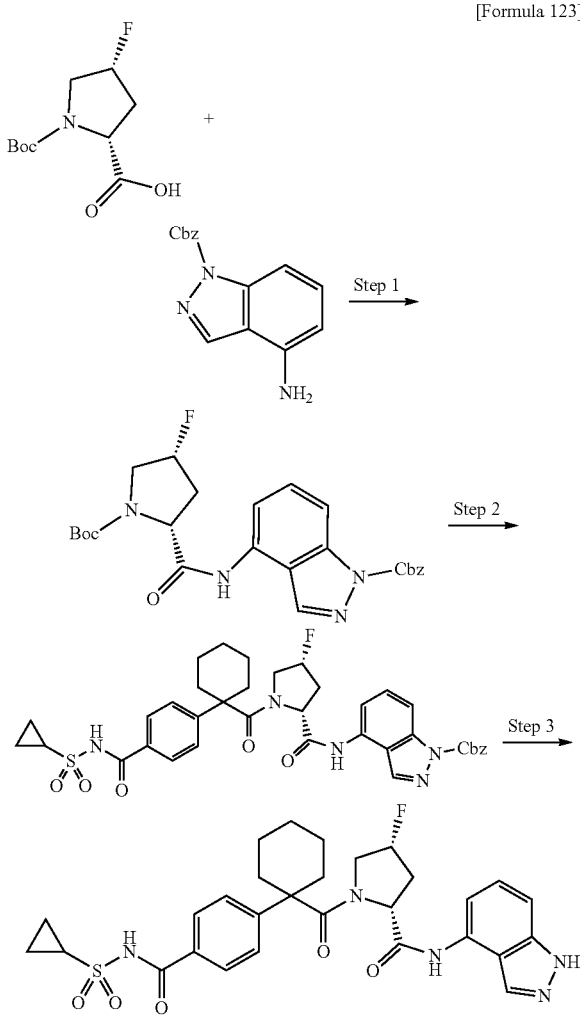

[Formula 123]

(Step 1) Benzyl 4-{[(4R)-1-(tert-butoxycarbonyl)-4-fluoro-D-prolyl]amino}-1H-indazole-1-carboxylate Under a nitrogen atmosphere, (4R)-1-(tert-butoxycarbonyl)-4-fluoro-D-proline (1.03 g) and the compound (1.24 g)

obtained in Reference Example A-1 were subjected to the same procedure as in Step 6 of Example 27 to obtain the title compound (0.897 g) as a solid.

$^1$H-NMR (DMSO-D$_6$, 100° C.) δ: 1.39 (9H, s), 2.31-2.41 (1H, m), 2.52-2.70 (1H, m), 3.65-3.76 (2H, m), 4.54 (1H, d, J=9.7 Hz), 5.31 (1H, d, J=54.4 Hz), 5.52 (2H, s), 7.36-7.46 (3H, m), 7.52-7.57 (3H, m), 7.62-7.64 (1H, m), 7.87 (1H, d, J=8.5 Hz), 8.42 (1H, s), 10.08 (1H, s). MS (m/z): 483 (M+H)$^+$.

(Step 2) Benzyl 4-({(4R)-1-[(1-{4-[(cyclopropylsulfonyl)carbamoyl]phenyl}cyclohexyl)carbonyl]-4-fluoro-D-prolyl}amino)-1H-indazole-1-carboxylate To the compound (0.350 g) obtained in Step 1 above, hydrogen chloride (4 mol/L, 1,4-dioxane solution, 10.0 mL) was added, and the mixture was stirred at room temperature for 1.5 hours, and then concentrated under reduced pressure to obtain the crude amine. A mixture of the compound (0.303 g) obtained in Reference Example C-2 and COMU (0.370 g) was dissolved in N,N-dimethylformamide (5 mL), and then N,N-diisopropylethylamine (0.632 mL) was added. The mixture was stirred at room temperature for 1 hour, then a suspension of the crude amine obtained above in N,N-dimethylformamide (5 mL) was added, and the mixture was stirred at room temperature overnight. To the reaction solution, 1 mol/L hydrochloric acid was added, and the mixture was extracted with ethyl acetate three times. The organic layer was washed with water and with saturated brine, then dried over anhydrous sodium sulfate. The resultant was filtered, and concentrated under reduced pressure, then the residue obtained was purified by silica gel column chromatography (chloroform/methanol), and concentrated under reduced pressure. Then, the residue was purified by high performance liquid chromatography (acetonitrile/water/0.1% formic acid). The fractions were collected, and the organic solvent was distilled off under reduced pressure, and the residue was extracted with ethyl acetate three times. The organic layer was washed with saturated brine in that order, and dried over anhydrous sodium sulfate. The resultant was filtered, and concentrated under reduced pressure to obtain the title compound (0.205 g) as a solid.

MS (m/z): 716 (M+H)$^+$.

(Step 3) (4R)-1-[(1-{4-[(Cyclopropylsulfonyl)carbamoyl]phenyl}cyclohexyl)carbonyl]-4-fluoro-N-1H-indazol-4-yl-D-prolinamide The compound (0.195 g) obtained in Step 2 above was subjected to the same procedure as in Step 3 of Example 1 to obtain the title compound (0.102 g) as a solid.

$^1$H-NMR (DMSO-D$_6$, 80° C.) δ: 0.97-1.13 (4H, m), 1.24-1.33 (1H, m), 1.53-1.81 (7H, m), 2.07-2.17 (1H, m), 2.23-2.38 (3H, m), 3.02-3.44 (3H, m), 4.82 (1H, s), 5.06 (1H, d, J=55.0 Hz), 7.25-7.29 (2H, m), 7.41-7.52 (3H, m), 7.94 (2H, d, J=7.9 Hz), 8.17 (1H, s), 9.77 (1H, s), 11.83 (1H, s), 12.90 (1H, s). MS (m/z): 582 (M+H)$^+$.

Example 37

(4R)-4-Fluoro-1-{[1-(3-fluoro-4-methoxyphenyl)cyclohexyl]carbonyl}-N-1H-pyrazolo[4,3-b]pyridin-5-yl-D-prolinamide

[Formula 124]

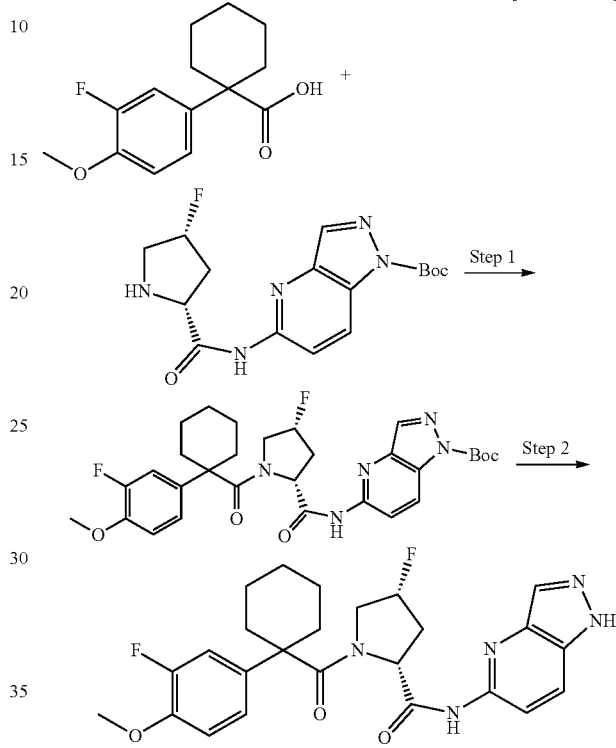

(Step 1) tert-Butyl 5-{[(4R)-4-fluoro-1-{[1-(3-fluoro-4-methoxyphenyl)cyclohexyl]carbonyl}-D-prolyl]amino}-1H-pyrazolo[4,3-b]pyridine-1-carboxylate The compound (0.200 g) obtained in Reference Example C-3 and the compound (0.166 g) obtained in Reference Example B-2 were subjected to the same procedure as in Step 3 of Example 4 to obtain the title compound (0.256 g) as a solid.

$^1$H-NMR (DMSO-D$_6$) δ: 1.26 (1H, s), 1.50-1.62 (6H, m), 1.66 (9H, s), 1.70-1.82 (1H, m), 2.01-2.35 (4H, m), 3.14-3.30 (2H, m), 3.84 (3H, s), 4.76-4.80 (1H, m), 5.08 (1H, d, J=53.8 Hz), 7.10-7.20 (3H, m), 8.35-8.46 (2H, m), 8.50 (1H, s), 10.68 (1H, s). MS (m/z): 584 (M+H)$^+$.

(Step 2) (4R)-4-Fluoro-1-{[1-(3-fluoro-4-methoxyphenyl)cyclohexyl]carbonyl}-N-1H-pyrazolo[4,3-b]pyridin-5-yl-D-prolinamide The compound (0.248 g) obtained in Step 1 above was subjected to the same procedure as in Step 2 of Example 35 to obtain the title compound (0.186 g) as a solid.

$^1$H-NMR (CDCl$_3$) δ: 1.23-1.37 (1H, m), 1.60-1.82 (7H, m), 2.07-2.59 (4H, m), 3.22 (1H, br s), 3.58 (1H, s), 3.91 (3H, s), 4.84 (1H, s), 5.06 (1H, d, J=52.6 Hz), 6.99-7.13 (3H, m), 7.82 (1H, d, J=9.1 Hz), 8.12 (1H, s), 8.33 (1H, d, J=9.1 Hz), 8.52 (1H, s), 10.50 (1H, s). MS (m/z): 484 (M+H)$^+$.

Using the same method, the following compounds were synthesized.

TABLE 3

| Example No. | Intermediate | Name and Structure | Equipment data |
|---|---|---|---|
| 38 | C-4<br><br>B-3 | (3S, 4S)-1-{[4,4-Difluoro-1-(4-methoxyphenyl)cyclohexyl]carbonyl}-4-fluoro-3-hydroxy-N-1H-pyrazolo[4,3-b]pyridin-5-yl-D-prolinamide | $^1$H-NMR (DMSO-D$_6$) δ: 1.57-1.75 (1H, m), 1.86-2.57 (7H, m), 3.04-3.44 (2H, m), 3.77 (3H, s), 4.08-4.25 (1H, m), 4.52-4.83 (2H, m), 5.70-5.83 (1H, m), 6.97 (2H, d, J = 8.5 Hz), 7.27 (2H, d, J = 8.5 Hz), 7.99-8.18 (3H, m), 10.56 (1H, s), 13.29 (1H, s). LC-MS (m/z): 518 (M + H)$^+$. |

Example 39

(3S)-3-Hydroxy-N-1H-indazol-4-yl-1-{[1-(4-methoxyphenyl)cyclopentyl]carbonyl}-D-prolinamide

[Formula 125]

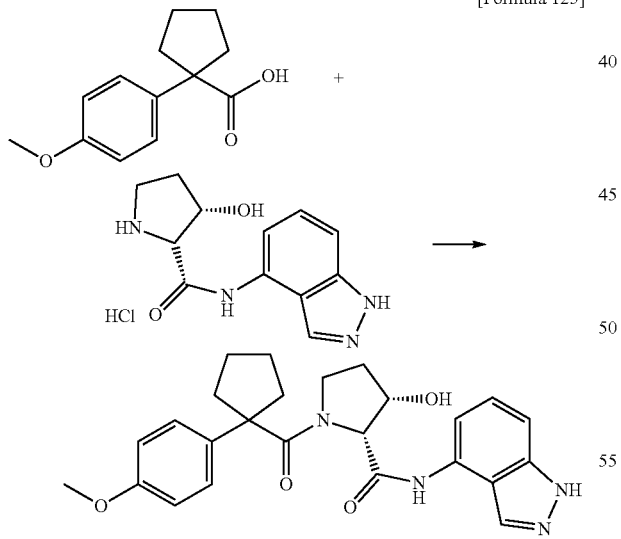

To a solution of 1-(4-methoxyphenyl)cyclopentanecarboxylic acid (43 mg) in dichloromethane (2 mL), thionyl chloride (26 μL) and N,N-dimethylformamide (10 μL) were added at 0° C., and the mixture was stirred at 40° C. for 4.5 hours. The solvent was distilled off under reduced pressure, then the residue was azeotropically concentrated with dichloromethane to obtain the crude acid chloride. To a mixture of the compound (63.9 mg) obtained in Reference Example B-4, a saturated aqueous sodium hydrogen carbonate solution (3 mL) and tetrahydrofuran (1 mL), a solution of the crude acid chloride in tetrahydrofuran (2 mL) was added at 0° C., and the mixture was stirred at room temperature overnight. Water was added to the reaction solution, then the mixture was extracted with ethyl acetate. The organic layer was washed with saturated brine, and dried over anhydrous sodium sulfate. The solvent was distilled off under reduced pressure, then the residue obtained was purified by silica gel column chromatography (hexane/ethyl acetate to ethyl acetate/methanol) to obtain the title compound (34 mg) as a solid.

$^1$H-NMR (CDCl$_3$) δ: 1.51-1.85 (5H, m), 1.88-2.07 (2H, m), 2.10-2.24 (1H, m), 2.26-2.41 (1H, m), 2.48-2.61 (1H, m), 3.10-3.30 (2H, m), 3.78 (3H, s), 4.36-4.47 (1H, m), 4.80-5.03 (2H, m), 6.77-6.86 (2H, m), 7.08-7.14 (2H, m), 7.23-7.29 (1H, m), 7.31-7.39 (1H, m), 7.77-7.84 (1H, m), 8.30 (1H, s), 10.37 (1H, br s), 10.57 (1H, s). MS (m/z): 449 (M+H)$^+$.

Example 40

(4S)-3-{[1-(4-Methoxyphenyl)cyclohexyl]carbonyl}-N-(1H-pyrazolo[4,3-b]pyridin-5-yl)-1,3-thiazolidin-4-carboxamide 1,1-dioxide

[Formula 126]

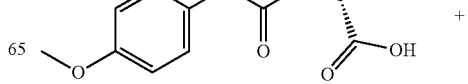

-continued

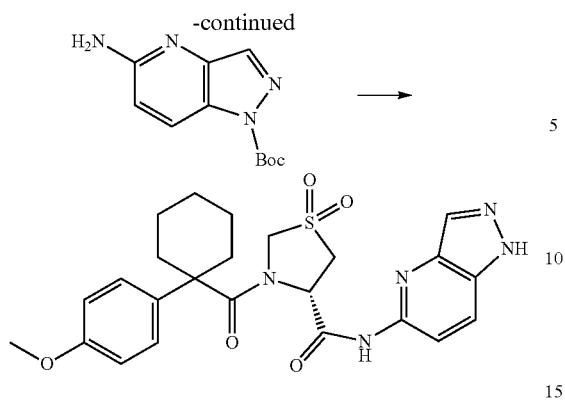

A suspension of the compound (400 mg) obtained in Reference Example D-2 and the compound (491 mg) obtained in Reference Example A-6 in pyridine (6 mL) was cooled to 0° C., and phosphoryl chloride (0.288 mL) was added, then the mixture was stirred at a temperature from 0° C. to room temperature for 19.2 hours. The resultant was diluted with ethyl acetate, then washed with 10% aqueous citric acid solution three times, with a saturated aqueous sodium hydrogen carbonate solution and with saturated brine, then dried over anhydrous sodium sulfate. The solvent was distilled off under reduced pressure, then the residue obtained was purified by silica gel column chromatography (hexane/ethyl acetate), then by amino silica gel column chromatography (hexane/ethyl acetate) to obtain the intermediate as an oil. This intermediate was dissolved in dichloromethane (6 mL), then trifluoroacetic acid (6 mL) was added, and the mixture was stirred at room temperature for 2.3 hours. The resultant was concentrated under reduced pressure, then ethyl acetate and a saturated aqueous sodium hydrogen carbonate solution were added to the residue obtained, and the mixture was extracted with ethyl acetate. The organic layer was washed with saturated brine, and dried over anhydrous sodium sulfate. The solvent was distilled off under reduced pressure, then the residue obtained was purified by silica gel column chromatography (hexane/ethyl acetate) to obtain the title compound (168 mg) as a solid.

$^1$H-NMR (DMSO-D$_6$) δ: 1.23-2.37 (10H, m), 3.24-3.36 (1H, br m), 3.70-3.78 (2H, m), 3.77 (3H, s), 4.41-4.52 (1H, br m), 5.62-5.71 (1H, br m), 6.85 (2H, d, J=8.5 Hz), 7.19 (2H, d, J=8.5 Hz), 7.88 (1H, d, J=9.1 Hz), 8.16-8.26 (2H, m), 9.17 (1H, br s), 10.43 (1H, br s). MS (m/z): 498 (M+H)$^+$.

Example 41

(4R)-4-Fluoro-N-1H-indazol-4-yl-1-{[3-(4-methoxyphenyl)tetrahydro-2H-pyran-3-yl]carbonyl}-D-prolinamide

[Formula 127]

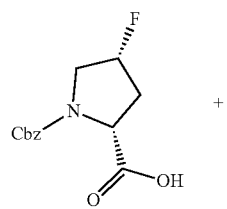

+

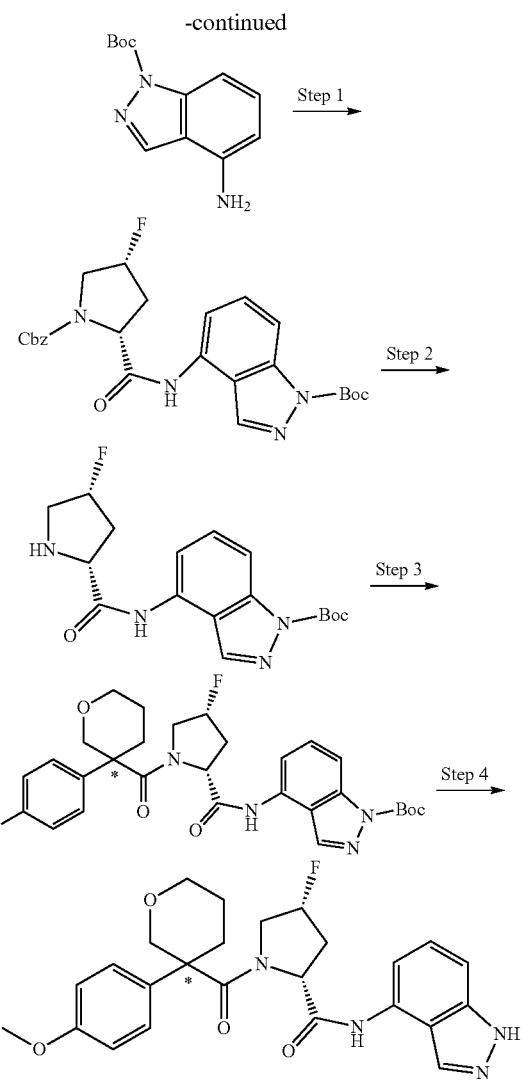

(Step 1) tert-Butyl 4-({[(4R)-1-[(benzyloxy)carbonyl]-4-fluoro-D-prolyl}amino)-1H-indazole-1-carboxylate A solution of (4R)-1-[(benzyloxy)carbonyl]-4-fluoro-D-proline (1.00 g) and the compound (1.10 g) obtained in Reference Example A-2 in pyridine (20 mL) was cooled to 0° C., and phosphoryl chloride (0.750 g) was added dropwise, and then the mixture was stirred at the same temperature for 1 hour. The reaction mixture was diluted with ethyl acetate, and washed with 10% aqueous citric acid solution, a saturated aqueous sodium hydrogen carbonate solution, and saturated brine sequentially. The organic layer was dried over sodium sulfate, filtered and concentrated, and then the residue obtained was purified by silica gel chromatography (hexane/ethyl acetate) to obtain the title compound (0.925 g) as a solid.

$^1$H-NMR (DMSO-D$_6$, 100° C.) δ: 1.66 (9H, s), 2.30-2.47 (2H, m), 3.70-3.90 (2H, m), 4.63-4.70 (1H, m), 5.05-5.20 (2H, m), 5.25-5.44 (1H, m), 7.15-7.43 (5H, m), 7.48-7.61 (2H, m), 7.84 (1H, d, J=7.9 Hz), 8.33 (1H, s), 10.05 (1H, br s). MS (m/z): 383 (M-CO$_2$tBu+H)$^+$.

(Step 2) tert-Butyl 4-{[(4R)-4-fluoro-D-prolyl]amino}-1H-indazole-1-carboxylate The compound (0.925 g) obtained in Step 1 above was subjected to the same procedure as in Step 3 of Reference Example B-15 to obtain the title compound (0.660 g) as a solid.

$^1$H-NMR (CDCl$_3$) δ: 1.73 (9H, s), 2.27-2.48 (2H, m), 2.57-2.72 (1H, m), 3.23-3.42 (1H, m), 3.44-3.58 (1H, m), 4.03-4.16 (1H, m), 5.17-5.36 (1H, m), 7.45-7.54 (1H, m), 7.83-7.94 (2H, m), 8.21 (1H, s), 10.11 (1H, br s). MS (m/z): 249 (M-CO$_2$tBu+H)$^+$.

(Step 3) tert-Butyl 4-{[(4R)-4-fluoro-1-{[3-(4-methoxyphenyl)tetrahydro-2H-pyran-3-yl]carbonyl}-D-prolyl]amino}-1H-indazole-1-carboxylate (low polarity isomer, high polarity isomer)

To a solution of the compound (45 mg) obtained in Reference Example C-5 in dichloromethane (1 mL), thionyl chloride (25 µL) and N,N-dimethylformamide (5 µL) were added, then the mixture was heated to 40° C., and stirred for 2 hours. After being allowed to cool to room temperature, the reaction mixture was concentrated to obtain the acid chloride as an oil. Under ice-cooling, to a solution of the compound (60 mg) obtained in Step 2 above and N,N-diisopropylethylamine (90 µL) in dichloromethane (2 mL), a solution of the acid chloride obtained above in dichloromethane (1 mL) was added dropwise, and the mixture was stirred for 1 hour. To the reaction mixture, a saturated aqueous sodium hydrogen carbonate solution was added, then the mixture was extracted with dichloromethane. The organic layer was dried over sodium sulfate, filtered, and concentrated, then purified by PTLC (hexane/ethyl acetate: methanol). The isomer mixture obtained was purified with a chiral column (Daicel Corporation, CHIRALFLASH IC, hexane/ethanol) to obtain the title compound (low polarity isomer) (41 mg) as an oil and the title compound (high polarity isomer) (39 mg) as an oil.

(Low Polarity Isomer)
$^1$H-NMR (CDCl$_3$) δ: 1.53-1.80 (10H, m), 1.90-2.23 (2H, m), 2.51-2.66 (1H, m), 2.77-3.00 (1H, m), 3.14-3.47 (2H, m), 3.52-3.90 (7H, m), 4.28-4.50 (1H, m), 4.90-5.25 (2H, m), 6.85 (2H, d, J=8.5 Hz), 7.08-7.26 (2H, m), 7.49 (1H, t, J=8.2 Hz), 7.84-8.08 (2H, m), 8.39 (1H, s), 9.73 (1H, br s). MS (m/z): 565 (M−H)$^−$.

(High Polarity Isomer)
$^1$H-NMR (CDCl$_3$) δ: 1.49-1.62 (1H, m), 1.66-1.86 (10H, m), 1.98-2.19 (2H, m), 2.56-2.69 (1H, m), 2.74-3.07 (2H, m), 3.51-3.67 (2H, m), 3.80 (4H, s), 4.01-4.14 (1H, m), 4.49 (1H, d, J=11.5 Hz), 4.92-5.20 (2H, m), 6.88 (2H, d, J=8.5 Hz), 7.18 (2H, d, J=8.5 Hz), 7.49 (1H, t, J=8.2 Hz), 7.82-7.97 (2H, m), 8.36 (1H, s), 9.23 (1H, br s). MS (m/z): 565 (M−H)$^−$.

(Step 4) (4R)-4-Fluoro-N-1H-indazol-4-yl-1-{[3-(4-methoxyphenyl)tetrahydro-2H-pyran-3-yl]carbonyl}-D-prolinamide The low polarity isomer (41 mg) obtained in Step 3 above was subjected to the same procedure as in Step 5 of Example 4 to obtain the title compound (33 mg) as a solid.

$^1$H-NMR (CDCl$_3$) δ: 1.50-1.87 (2H, m), 1.94-2.28 (2H, m), 2.53-2.67 (1H, m), 2.77-2.95 (1H, m), 3.12-3.51 (2H, m), 3.53-3.64 (1H, m), 3.65-3.77 (1H, m), 3.77-3.94 (4H, m), 4.31-4.51 (1H, m), 4.87-5.23 (2H, m), 6.86 (2H, d, J=9.1 Hz), 7.17-7.29 (3H, m), 7.36 (1H, t, J=7.9 Hz), 7.86 (1H, br s), 8.25 (1H, s), 9.52 (1H, br s), 10.33 (1H, br s). MS (m/z): 467 (M+H)$^+$.

Example 42

(4R)-4-Fluoro-N-1H-indazol-4-yl-1-{[3-(4-methoxyphenyl)tetrahydro-2H-pyran-3-yl]carbonyl}-D-prolinamide

[Formula 128]

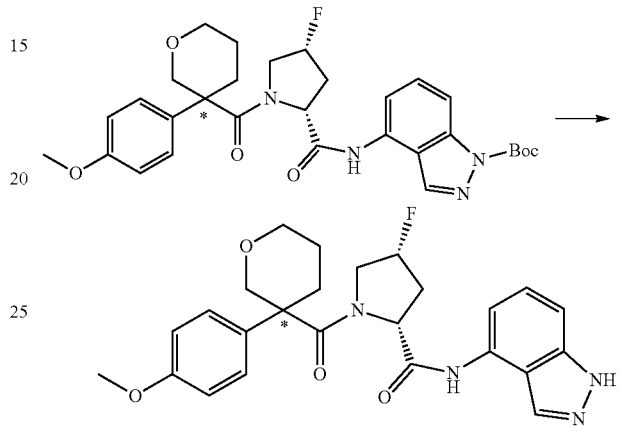

The high polarity isomer (40 mg) obtained in Step 3 of Example 41 was subjected to the same procedure as in Step 5 of Example 4 to obtain the title compound (32 mg) as a solid.

$^1$H-NMR (CDCl$_3$) δ: 1.46-1.73 (1H, m), 1.79-1.92 (1H, m), 1.97-2.20 (2H, m), 2.59-2.69 (1H, m), 2.74-2.90 (1H, m), 2.92-3.14 (1H, m), 3.50-3.69 (2H, m), 3.76-3.86 (4H, m), 4.00-4.16 (1H, m), 4.48 (1H, d, J=11.5 Hz), 4.91-5.21 (2H, m), 6.88 (2H, d, J=8.5 Hz), 7.20 (2H, d, J=8.5 Hz), 7.24-7.29 (1H, m), 7.36 (1H, t, J=7.9 Hz), 7.75 (1H, d, J=7.3 Hz), 8.23 (1H, s), 9.11 (1H, s), 10.14 (1H, s). MS (m/z): 467 (M+H)$^+$.

Example 43

(4R)-4-Fluoro-N-1H-indazol-4-yl-1-{[2-(4-methoxyphenyl)tetrahydro-2H-pyran-2-yl]carbonyl}-D-prolinamide

[Formula 129]

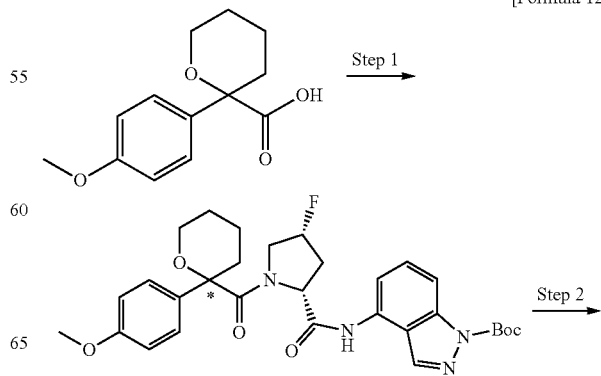

-continued

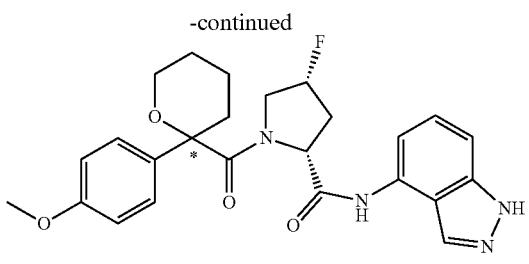

(Step 1) tert-Butyl 4-{[(4R)-4-fluoro-1-{[2-(4-methoxyphenyl)tetrahydro-2H-pyran-2-yl]carbonyl}-D-prolyl]amino}-1H-indazole-1-carboxylate (low polarity isomer, high polarity isomer)

A solution of the compound (49 mg) obtained in Reference Example C-6 and N,N-dimethylformamide (3 μL) in dichloromethane (1 mL) was cooled to 0° C., and oxalyl chloride (22 μL) was added, then the mixture was stirred at room temperature for 30 minutes. The reaction mixture was concentrated to obtain the acid chloride as an oil.

A solution of the acid chloride obtained above in dichloromethane (1 mL) was added dropwise to a solution of the compound (60 mg) obtained in Step 2 of Example 41 and N,N-diisopropylamine (90 μL) in dichloromethane (2 mL) at 0° C., and the mixture was stirred at the same temperature for 1 hour. The reaction mixture was diluted with ethyl acetate, and then washed with a saturated aqueous sodium hydrogen carbonate solution and with saturated brine. The organic layer was dried over sodium sulfate, filtered, and concentrated. Then, the residue obtained was purified by silica gel column chromatography (hexane/ethyl acetate) and by PTLC (chloroform/methanol) to obtain the title compound (low polarity isomer) (38 mg) as an oil and the title compound (high polarity isomer) (34 mg) as a solid.
(Low Polarity Isomer)
$^1$H-NMR (CDCl$_3$) δ: 1.38-1.50 (2H, m), 1.52-1.81 (12H, m), 1.82-2.02 (1H, m), 2.66 (1H, d, J=13.3 Hz), 3.02 (1H, t, J=16.3 Hz), 3.21-3.40 (1H, m), 3.41-3.51 (1H, m), 3.82 (3H, s), 3.98-4.16 (2H, m), 4.95-5.17 (2H, m), 6.89 (2H, d, J=8.5 Hz), 7.35 (2H, d, J=9.1 Hz), 7.50 (1H, t, J=7.9 Hz), 7.90 (1H, d, J=8.5 Hz), 8.07 (1H, d, J=7.9 Hz), 8.45 (1H, s), 10.16 (1H, br s). MS (m/z): 565 (M−H)$^−$.
(High Polarity Isomer)
$^1$H-NMR (CDCl$_3$) δ: 1.38-1.49 (1H, m), 1.54-1.81 (12H, m), 1.84-2.00 (1H, m), 2.11-2.32 (1H, m), 2.60 (1H, d, J=13.3 Hz), 2.83 (1H, t, J=16.3 Hz), 3.46 (1H, t, J=10.9 Hz), 3.56-3.71 (4H, m), 3.76-4.16 (2H, m), 4.99 (1H, d, J=9.7 Hz), 5.24 (1H, d, J=53.2 Hz), 6.61 (2H, d, J=8.5 Hz), 7.22-7.30 (2H, m), 7.48 (1H, t, J=8.2 Hz), 7.76 (1H, d, J=7.9 Hz), 7.92 (1H, d, J=7.9 Hz), 8.05 (1H, s), 8.94 (1H, br s). MS (m/z): 565 (M−H)$^−$.

(Step 2) (4R)-4-Fluoro-N-1H-indazol-4-yl-1-{[2-(4-methoxyphenyl)tetrahydro-2H-pyran-2-yl]carbonyl}-D-prolinamide The low polarity isomer (38 mg) obtained in Step 1 above was subjected to the same procedure as in Step 5 of Example 4 to obtain the title compound (27 mg) as a solid.
$^1$H-NMR (CDCl$_3$) δ: 1.38-1.50 (2H, m), 1.53-2.03 (3H, m), 2.65-2.74 (1H, m), 2.93-3.07 (1H, m), 3.23-3.39 (1H, m), 3.45-3.76 (2H, m), 3.82 (3H, s), 3.98-4.14 (2H, m), 4.95-5.16 (2H, m), 6.89 (2H, d, J=8.5 Hz), 7.20-7.27 (1H, m), 7.28-7.40 (3H, m), 7.93 (1H, d, J=7.9 Hz), 8.31 (1H, s), 9.96 (1H, br s), 10.21 (1H, br s). MS (m/z): 467 (M+H)$^+$.

Example 44

(4R)-4-Fluoro-N-1H-indazol-4-yl-1-{[2-(4-methoxyphenyl)tetrahydro-2H-pyran-2-yl]carbonyl}-D-prolinamide

[Formula 130]

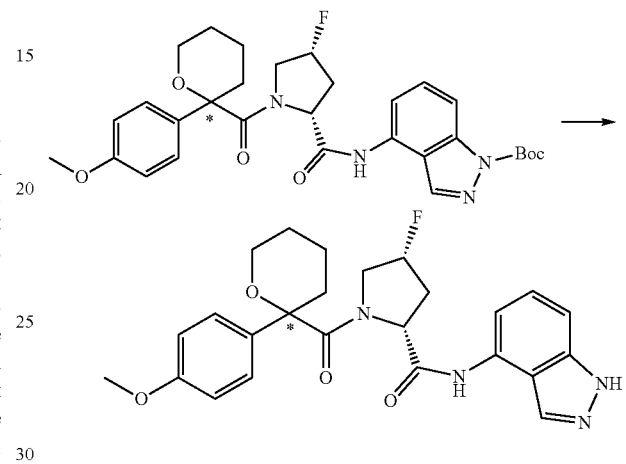

The high polarity isomer (34 mg) obtained in Step 1 of Example 43 was subjected to the same procedure as in Step 5 of Example 4 to obtain the title compound (27 mg) as a solid.
$^1$H-NMR (CDCl$_3$) δ: 1.35-1.82 (4H, m), 1.86-2.01 (1H, m), 2.15-2.36 (1H, m), 2.57-2.66 (1H, m), 2.70-2.85 (1H, m), 3.39-3.54 (1H, m), 3.58-3.84 (4H, m), 3.86-4.03 (1H, m), 4.06-4.16 (1H, m), 4.97 (1H, d, J=10.3 Hz), 5.14-5.35 (1H, m), 6.61 (2H, d, J=8.5 Hz), 7.21-7.41 (4H, m), 7.70 (1H, d, J=7.3 Hz), 7.82 (1H, s), 8.62 (1H, br s), 10.12 (1H, br s). MS (m/z): 467 (M+H)$^+$.

Example 45

(4R)-4-Fluoro-1-{[4-(4-methoxyphenyl)tetrahydro-2H-pyran-4-yl]carbonyl}-N-1H-pyrazolo[4,3-b]pyridin-5-yl-D-prolinamide

[Formula 131]

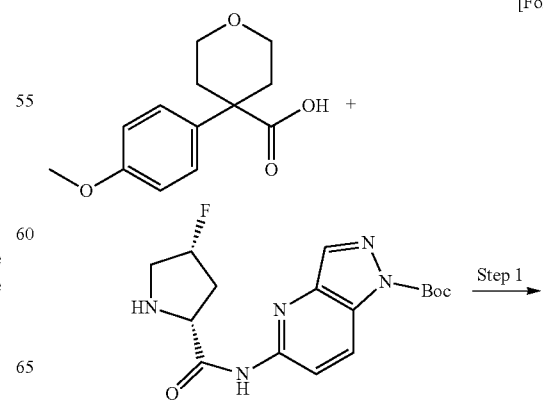

-continued

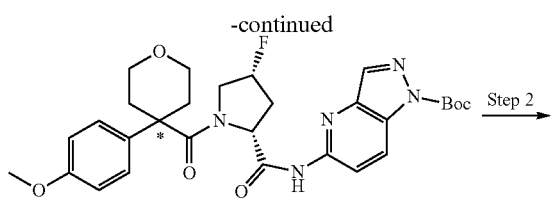

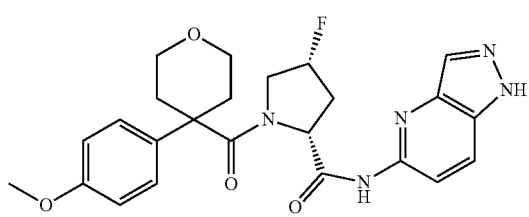

(Step 1) tert-Butyl 5-{[(4R)-4-fluoro-1-{[4-(4-methoxyphenyl)tetrahydro-2H-pyran-4-yl]carbonyl}-D-prolyl]amino}-1H-pyrazolo[4,3-b]pyridine-1-carboxylate To a suspension of the compound (0.180 g) obtained in Reference Example C-7 in dichloromethane (5 mL), oxalyl chloride (0.318 mL) and N,N-dimethylformamide (0.0100 mL) were added, and the mixture was stirred at room temperature for 1 hour. Then, the mixture was concentrated under reduced pressure to obtain the crude acid chloride as an oil. To a solution of the compound (0.175 g) obtained in Reference Example B-2 in dichloromethane (5 mL), N,N-diisopropylethylamine (0.262 mL) was added. Then, the mixture was cooled with ice, then a solution of the acid chloride obtained above in dichloromethane (5 mL) was added, and the mixture was stirred at room temperature for 30 minutes. To the reaction solution, a saturated aqueous ammonium chloride solution was added, and the mixture was extracted with dichloromethane three times. The organic layer was washed with a saturated aqueous sodium hydrogen carbonate solution, and then dried over anhydrous sodium sulfate. The resultant was filtered, and concentrated under reduced pressure, then the residue obtained was purified by silica gel column chromatography (ethyl acetate/methanol) to obtain the title compound (0.305 g) as a solid.
MS (m/z): 568 (M+H)$^+$.

(Step 2) (4R)-4-Fluoro-1-{[4-(4-methoxyphenyl)tetrahydro-2H-pyran-4-yl]carbonyl}-N-1H-pyrazolo[4,3-b]pyridin-5-yl-D-prolinamide The compound (0.300 g) obtained in Step 1 above was subjected to the same procedure as in Step 3 of Example 1 to obtain the title compound (0.103 g) as a solid.
$^1$H-NMR (DMSO-D$_6$, 100° C.) δ: 1.83-2.38 (6H, m), 3.22-3.36 (2H, m), 3.67-3.76 (7H, m), 4.77 (1H, d, J=9.1 Hz), 5.05 (1H, d, J=53.2 Hz), 6.95 (2H, d, J=8.5 Hz), 7.26 (2H, d, J=8.5 Hz), 7.98-8.08 (3H, m), 9.91 (1H, s), 13.03 (1H, s). MS (m/z): 468 (M+H)$^+$.

The intermediates described below were subjected to the same procedure as above to synthesize the following compounds.

TABLE 4

| Example No. | Intermediate | Name and Structure | Equipment data |
|---|---|---|---|
| 46 | ![intermediate structure] B-5 | 1-(4-Methoxyphenyl)-N-methyl-N-[(2R)-1-oxo-1-(1H-pyrazolo[4,3-b]pyridin-5-ylamino)propan-2-yl]cyclohexanecarboxamine ![product structure] | $^1$H-NMR (DMSO-D$_6$, 100° C.) δ: 1.28 (4H, d, J = 6.7 Hz), 1.46-1.77 (7H, m), 2.25-2.32 (2H, m), 2.60 (3H, s), 3.66 (3H, s), 4.93 (1H, s), 6.83 (2H, d, J = 7.9 Hz), 7.19 (2H, d, J = 7.9 Hz), 7.96-8.02 (2H, m), 8.09 (1H, s), 9.53 (1H, s), 13.06 (1H, s). MS (m/z): 436 (M + H)$^+$. |

TABLE 4-continued

| Example No. | Intermediate | Name and Structure | Equipment data |
|---|---|---|---|
| 47 | 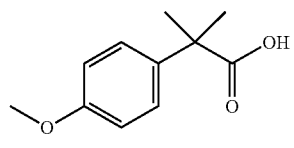 C-8<br><br>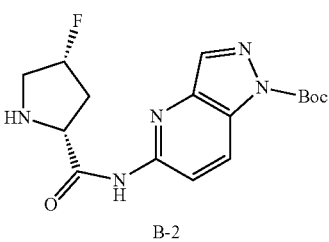 B-2 | (4R)-4-Fluoro-1-[2-(4-methoxyphenyl)-2-methylpropanoyl]-N-1H-pyrazolo-[4,3-b]pyridin-5-yl-D-prolinamide | $^1$H-NMR (DMSO-D$_6$, 100° C.) δ: 2.05-2.16 (1H, m), 2.27-2.43 (1H, m), 3.02-3.39 (2H, m), 3.75 (3H, s), 4.74 (1H, d, J = 8.5 Hz), 5.07 (1H, d, J = 54.4 Hz), 6.79 (6H, s), 6.93 (2H, d, J = 8.5 Hz), 7.26 (2H, d, J = 8.5 Hz), 7.97-8.10 (3H, m), 9.86 (1H, s), 13.03 (1H, s). MS (m/z): 426 (M + H)$^+$. |
| 48 | 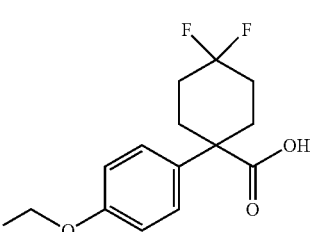 C-9<br><br>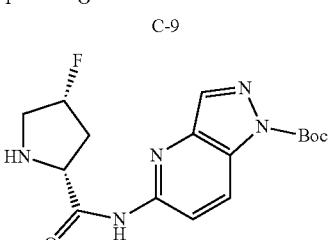 B-2 | (4R)-1-({4,4-Difluoro-1-[4-(fluoromethoxy)phenyl]cyclohexyl}carbonyl)-4-fluoro-N-1H-pyrazolo[4,3-b]pyridin-5-yl-D-prolinamide | $^1$H-NMR (DMSO-D$_6$, 100° C.) δ: 1.75-2.50 (10H, m), 3.14-3.45 (2H, m), 4.75-4.86 (1H, m), 4.95-5.18 (1H, m), 5.80 (2H, d, J = 54.3 Hz), 7.12 (2H, d, J = 9.2 Hz), 7.36 (2H, d, J = 8.5 Hz), 7.94-8.07 (3H, m), 9.97 (1H, s), 12.96 (1H, br s). MS (m/z): 520 (M + H)$^+$. |

//

TABLE 4-continued

| Example No. | Intermediate | Name and Structure | Equipment data |
|---|---|---|---|
| 49 | 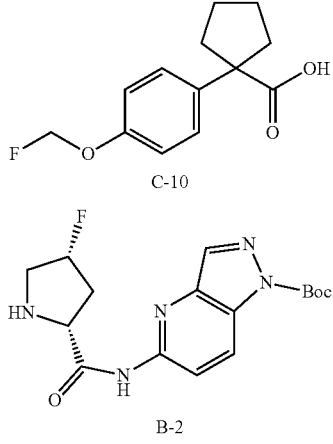 C-10 <br> B-2 | (4R)-4-Fluoro-1-({1-[4-(fluoromethoxy)phenyl]cyclopentyl}carbonyl)-N-1H-pyrazolo[4,3-b]pyridin-5-yl-D-prolinamide <br> 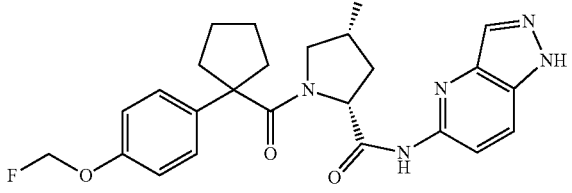 | $^1$H-NMR (DMSO-D$_6$, 100° C.) δ: 1.66 (4H, s), 1.88-2.00 (2H, m), 2.13 (1H, t, J = 18.1 Hz), 2.29-2.44 (3H, m), 3.20-3.39 (2H, m), 4.74 (1H, d, J = 7.9 Hz), 5.10 (1H, d, J = 55.0 Hz), 5.80 (2H, d, J = 54.4 Hz), 7.08 (2H, d, J = 7.9 Hz), 7.31 (2H, d, J = 7.9 Hz), 7.97-8.09 (3H, m), 9.87 (1H, s), 13.04 (1H, s). MS (m/z): 470 (M + H)$^+$. |
| 50 | 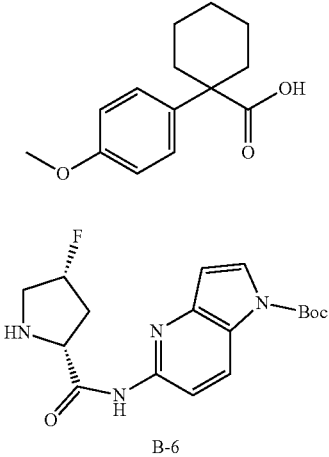 <br> B-6 | (4R)-4-Fluoro-1-{[1-(4-methoxyphenyl)cyclohexyl]carbonyl}-N-1H-pyrrolo[3,2-b]pyridin-5-yl-D-prolinamide <br> 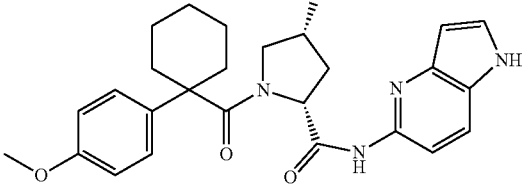 | $^1$H-NMR (DMSO-D$_6$) δ: 1.21-1.31 (1H, m), 1.46-1.83 (7H, m), 1.97-2.07 (1H, m), 2.17-2.44 (3H, m), 3.02-3.30 (2H, m), 3.76 (3H, s), 4.72 (1H, d, J = 9.2 Hz), 5.03 (1H, d, J = 53.1 Hz), 6.41 (1H, s), 6.94 (2H, d, J = 8.5 Hz), 7.26 (2H, d, J = 7.9 Hz), 7.59 (1H, br s), 7.77 (1H, d, J = 9.2 Hz), 7.91 (1H, d, J = 9.2 Hz), 9.90 (1H, t, J = 3.1 Hz), 11.26 (1H, s). MS (m/z): 465 (M + H)$^+$. |

TABLE 4-continued

| Example No. | Intermediate | Name and Structure | Equipment data |
|---|---|---|---|
| 51 | 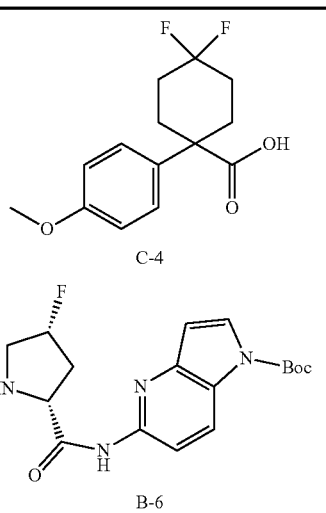 C-4<br><br>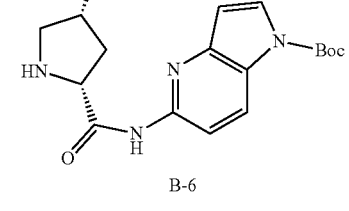 B-6 | (4R)-1-{[4,4-Difluoro-1-(4-methoxyphenyl)cyclohexyl]carbonyl}-4-fluoro-N-1H-pyrrolo[3,2-b]pyridin-5-yl-D-prolinamide<br><br>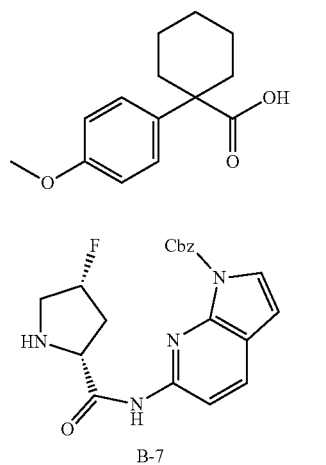 | $^1$H-NMR (DMSO-D$_6$) δ: 1.60-1.71 (1H, m), 1.87-2.13 (4H, m), 2.15-2.49 (5H, m), 3.01 (1H, ddd, J = 29.3, 11.6, 4.9 Hz), 3.25-3.33 (1H, m), 3.76 (3H, s), 4.78 (1H, dd, J = 9.8, 3.7 Hz), 5.04 (1H, d, J = 53.7 Hz), 6.42 (1H, br s), 6.96 (2H, d, J = 8.5 Hz), 7.29 (2H, d, J = 9.2 Hz), 7.59 (1H, t, J = 2.7 Hz), 7.78 (1H, d, J = 9.2 Hz), 7.88 (1H, d, J = 8.5 Hz), 10.19 (1H, s), 11.27 (1H, s). MS (m/z): 501 (M + H)$^+$. |
| 52 | 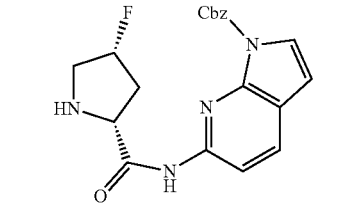 B-7 | (4R)-4-Fluoro-1-{[1-(4-methoxyphenyl)cyclohexyl]carbonyl}-N-1H-pyrrolo[2,3-b]pyridin-6-yl-D-prolinamide | $^1$H-NMR (DMSO-D$_6$) δ: 1.27 (1H, br s), 1.48-1.82 (7H, m), 1.98-2.10 (1H, m), 2.17-2.38 (2H, m), 3.03-3.29 (2H, m), 3.33-3.37 (1H, m), 3.75 (3H, s), 4.74 (1H, d, J = 8.5 Hz), 5.03 (1H, d, J = 54.1 Hz), 6.40 (1H, dd, J = 3.6, 1.8 Hz), 6.95 (2H, d, J = 8.5 Hz), 7.26 (2H, d, J = 8.5 Hz), 7.34 (1H, t, J = 3.0 Hz), 7.85 (1H, d, J = 7.3 Hz), 7.93 (1H, d, J = 8.5 Hz), |

TABLE 4-continued

| Example No. | Intermediate | Name and Structure | Equipment data |
|---|---|---|---|
| | | | 9.91 (1H, s), 11.42 (1H, s). MS (m/z): 465 (M + H)$^+$. |

Example 53

N-1H-Indazol-4-yl-1-{[1-(4-methoxyphenyl)cyclobutyl]carbonyl}-D-prolinamide

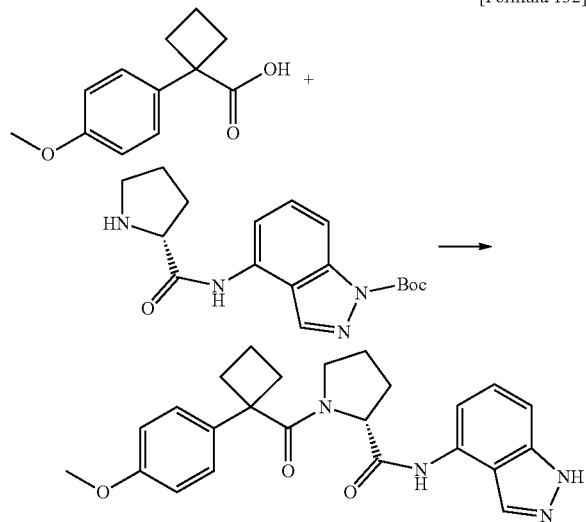

[Formula 132]

A solution of the compound (24 mg) obtained in Reference Example C-11 and N,N-dimethylformamide (3 µL) in dichloromethane (1 mL) was cooled to 0° C., and oxalyl chloride (13 µL) was added. The mixture was stirred at room temperature for 30 minutes, then the reaction mixture was concentrated to obtain the acid chloride as an oil. Under ice-cooling, to a mixture of the compound (30 mg) obtained in Step 2 of Example 4, N,N-diisopropylamine (47 µL) and dichloromethane (2 mL), a solution of the acid chloride obtained above in dichloromethane (1 mL) was added dropwise, and the mixture was stirred for 1 hour. The reaction mixture was concentrated, then the residue obtained was diluted with dichloromethane (1.0 mL). Then, trifluoroacetic acid (0.5 mL) was added at 0° C., and the mixture was stirred at room temperature for 1 hour. The reaction mixture was concentrated, then diluted with ethyl acetate, and then washed with a saturated aqueous sodium hydrogen carbonate solution. The organic layer was dried over sodium sulfate, filtered, and concentrated. The residue obtained was purified by silica gel column chromatography (chloroform/methanol) to obtain the title compound (26 mg) as a solid.

$^1$H-NMR (CDCl$_3$) δ: 1.67-1.79 (2H, m), 1.79-2.05 (3H, m), 2.32-2.49 (2H, m), 2.53-2.63 (1H, m), 2.73-2.84 (1H, m), 2.87-3.07 (3H, m), 3.77 (3H, s), 4.91-4.98 (1H, m), 6.82 (2H, d, J=9.1 Hz), 7.20-7.31 (3H, m), 7.36 (1H, t, J=7.9 Hz), 7.90 (1H, d, J=7.9 Hz), 8.40 (1H, s), 10.12 (1H, br s), 10.63 (1H, s). MS (m/z): 419 (M+H)$^+$.

The compound described in the intermediate and the compounds obtained in Step 2 of Example 4 were subjected to the same procedure as above to obtain the following compounds.

TABLE 5

| Example No. | Intermediate | Name and Structure | Equipment data |
|---|---|---|---|
| 54 | C-12 | N-1H-indazol-4-yl-{[1-(4-methoxyphenyl)cycloheptyl]carbonyl}-D-prolinamide | $^1$H-NMR (CDCl$_3$) δ: 1.38-1.92 (12H, m), 2.09-2.21 (1H, m), 2.22-2.33 (1H, m), 2.44-2.55 (2H, m), 2.82-2.99 (2H, m), 3.78 (3H, s), 4.95-5.04 (1H, m), 6.76-6.84 (2H, m), 7.06-7.14 (2H, m), 7.19-7.30 (1H, m), 7.32-7.40 (1H, m), 7.90 (1H, d, J = 7.9 Hz), |

TABLE 5-continued

| Example No. | Intermediate | Name and Structure | Equipment data |
|---|---|---|---|
| | | | 8.36 (1H, s), 10.16 (1H, br s), 10.49 (1H, s). MS (m/z): 459 (M + H)+. |
| 55 | C-4 | 1-{[4,4-Difluoro-1-(4-methoxyphenyl)cyclohexyl]carbonyl}-N-1H-indazol-4-yl-D-prolinamide | 1H-NMR (CDCl3) δ: 1.52-1.63 (1H, m), 1.78-1.95 (3H, m), 1.98-2.22 (4H, m), 2.27-2.55 (4H, m), 2.95-3.08 (2H, m), 3.78 (3H, s), 4.92-5.01 (1H, m), 6.84 (2H, d, J = 8.5 Hz), 7.17 (2H, d, J = 8.5 Hz), 7.22-7.28 (1H, m), 7.35 (1H, t, J = 7.9 Hz), 7.82 (1H, d, J = 7.3 Hz), 8.30 (1H, s), 10.01 (1H, br s). MS (m/z): 483 (M + H)+. |

Example 56

(4R)-1-{[3,3-Difluoro-1-(4-methoxyphenyl)cyclobutyl]carbonyl}-4-fluoro-N-1H-pyrazolo[4,3-b]pyridin-5-yl-D-prolinamide

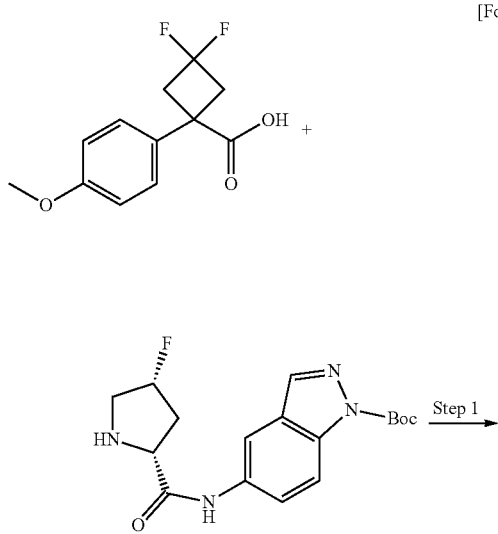

[Formula 133]

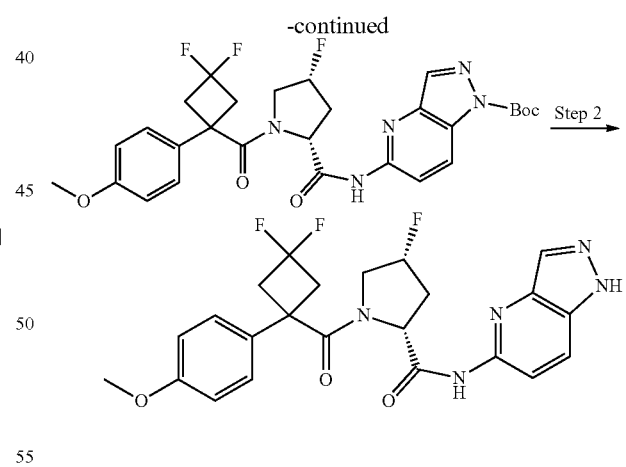

(Step 1) tert-Butyl 5-{[(4R)-1-{[3,3-difluoro-1-(4-methoxyphenyl)cyclobutyl]carbonyl}-4-fluoro-D-prolyl]amino}-1H-pyrazolo[4,3-b]pyridine-1-carboxylate The compound (173 mg) obtained in Reference Example C-13 and the compound (250 mg) obtained in Reference Example B-2 were subjected to the same procedure as in Step 1 of Example 4 to obtain the title compound (323 mg) as a solid.

1H-NMR (CDCl3) δ: 1.73 (9H, s), 2.11-2.34 (1H, m), 2.69-2.87 (1H, m), 2.93-3.15 (2H, m), 3.17-3.51 (3H, m), 3.53-3.68 (1H, m), 3.82 (3H, s), 4.89-4.98 (1H, m), 5.06-5.26 (1H, m), 6.95 (2H, d, J=7.9 Hz), 7.33 (2H, d, J=8.5 Hz), 8.26 (1H, s), 8.38-8.48 (2H, m), 8.82 (1H, br s). MS (m/z): 574 (M+H)$^+$.

(Step 2) (4R)-1-{[3,3-Difluoro-1-(4-methoxyphenyl)cyclobutyl]carbonyl}-4-fluoro-N-1H-pyrazolo[4,3-b]pyridin-5-yl-D-prolinamide The compound (315 mg) obtained in Step 1 above was subjected to the same procedure as in Step 5 of Example 4 to obtain the title compound (157 mg) as a solid.

$^1$H-NMR (DMSO-D$_6$, 100° C.) δ: 2.14-2.28 (1H, m), 2.30-2.52 (1H, m), 2.93-3.10 (2H, m), 3.19-3.57 (4H, m), 3.75 (3H, s), 4.66-4.87 (1H, m), 5.07-5.27 (1H, m), 6.94 (2H, d, J=7.9 Hz), 7.36 (2H, d, J=7.9 Hz), 7.92-8.08 (3H, m), 9.85 (1H, br s), 12.95 (1H, br s). MS (m/z): 474 (M+H)$^+$.

The intermediates described below were subjected to the same procedure as above to synthesize the following compounds.

TABLE 6

| Example No. | Intermediate | Name and Structure | Equipment data |
|---|---|---|---|
| 57 | 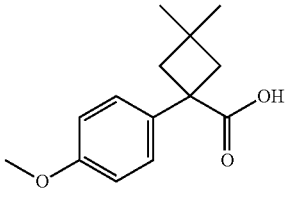 C-14 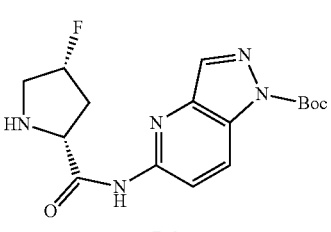 B-2 | (4R)-4-Fluoro-1-{[1-(4-methoxyphenyl)-3,3-dimethylcyclobutyl]carbonyl}-N-1H-pyrazolo[4,3-b]pyridin-5-yl-D-prolinamide 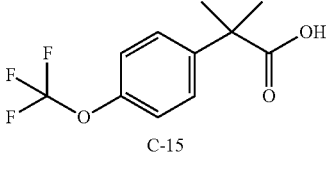 | $^1$H-NMR (DMSO-D$_6$, 100° C.) δ: 1.03-1.15 (6H, m), 2.11-2.45 (4H, m), 2.63-2.77 (2H, m), 3.26-3.48 (2H, m), 3.72 (3H, s), 4.72 (1H, d, J = 8.5 Hz), 5.14 (1H, d, J = 53.5 Hz), 6.89 (2H, d, J = 7.9 Hz), 7.29 (2H, d, J = 8.5 Hz), 7.91-8.10 (3H, m), 9.64 (1H, br s), 12.95 (1H, br s). MS (m/z): 466 (M + H)$^+$. |
| 58 | 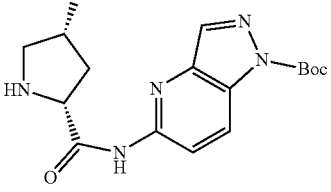 C-15 B-2 | (4R)-4-Fluoro-1-{2-methyl-2-[4-(trifluoromethoxy)phenyl]propanoyl}-N-1H-pyrazolo[4,3-b]pyridin-5-yl-D-prolinamide | $^1$H-NMR (DMSO-D$_6$) δ: 1.48 (3H, s), 1.50 (3H, s), 2.11 (1H, t, J = 17.8 Hz), 2.35-2.41 (1H, m), 3.09-3.12 (2H, m), 4.76 (1H, d, J = 8.2 Hz), 5.08 (1H, d, J = 54.1 Hz), 7.32 (2H, d, J = 8.5 Hz), 7.49 (2H, d, J = 8.5 Hz), 8.00-8.08 (3H, m), 10.00 (1H, s), 13.04 (1H, s). MS (m/z): 480 (M + H)$^+$. |

TABLE 6-continued

| Example No. | Intermediate | Name and Structure | Equipment data |
|---|---|---|---|
| 59 | 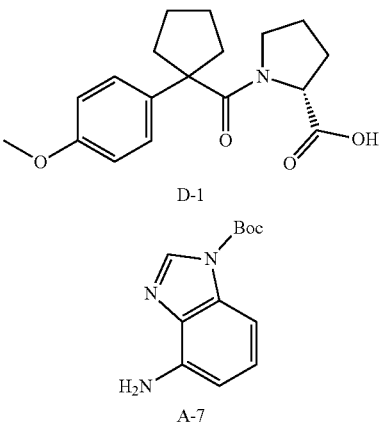<br>D-1<br><br>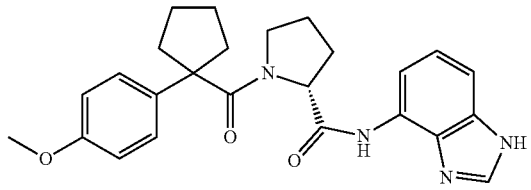<br>A-7 | N-1H-Benzimidazol-4-yl-1-{[1-(4-methoxyphenyl)cyclopentyl]carbonyl}-D-prolinamide<br><br>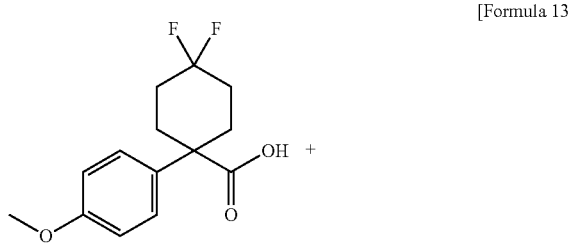 | $^1$H-NMR (DMSO-D$_6$) δ: 1.50-1.87 (8H, m), 1.93-1.99 (1H, m), 2.06-2.13 (1H, m), 2.27-2.41 (2H, m), 3.00 (2H, t, J = 6.3 Hz), 3.74 (3H, s), 4.67 (1H, s), 6.90 (2H, d, J = 9.1 Hz), 7.13-7.29 (4H, m), 7.87 (1H, s), 8.23 (1H, s), 9.74 (1H, br s), 12.50 (1H, br s). MS (m/z): 433 (M + H)$^+$. |

Example 60

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide

[Formula 134]

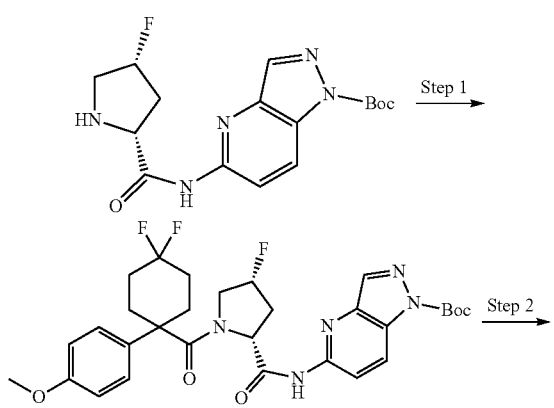

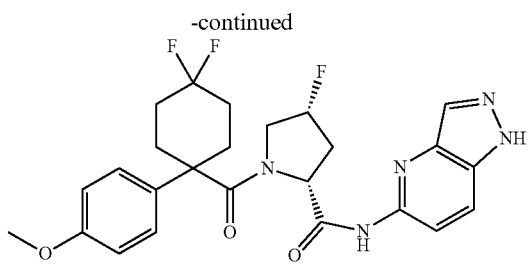

(Step 1) tert-Butyl 5-{[(4R)-1-{[4,4-difluoro-1-(4-methoxyphenyl)cyclohexyl]carbonyl}-4-fluoro-D-prolyl]amino}-1H-pyrazolo[4,3-b]pyridine-1-carboxylate A mixture of the compound (193 mg) obtained in Reference Example C-4, the compound (250 mg) obtained in Reference Example B-2, N,N-diisopropylethylamine (0.25 mL) and N,N-dimethylformamide (7 mL) was cooled to 0° C., then COMU (368 mg) was added, and the mixture was stirred at room temperature for 24 hours. The reaction mixture was concentrated, and diluted with ethyl acetate, and then washed with saturated brine. The organic layer was dried over anhydrous magnesium sulfate, filtered, and concentrated. Then, the residue obtained was purified by silica gel column chromatography (hexane/ethyl acetate) to obtain the title compound (362 mg) as a solid.

$^1$H-NMR (CDCl$_3$) δ: 1.73 (9H, s), 1.87-2.65 (8H, m), 2.91-3.22 (1H, m), 3.37-3.60 (1H, m), 3.83 (3H, s), 4.77-5.16 (2H, m), 5.04 (2H, d, J=52.8 Hz), 6.91-6.98 (2H, m), 7.21-7.29 (2H, m), 8.23 (1H, s), 8.39-8.51 (2H, m), 8.64 (1H, br s). MS (m/z): 602 (M+H)$^+$.

(Step 2) (4R)-1-{[4,4-Difluoro-1-(4-methoxyphenyl)cyclohexyl]carbonyl}-4-fluoro-N-1H-pyrazolo[4,3-b]pyridin-5-yl-D-prolinamide To a solution of the compound (355 mg) obtained in Step 1 above in dichloromethane (6 mL), trifluoroacetic acid (3 mL) was added, and the mixture was stirred at room temperature for 2 hours. The reaction solution was concentrated, then a saturated aqueous sodium hydrogen carbonate solution was added to the residue obtained, and the mixture was extracted with ethyl acetate. The organic layer was dried over anhydrous sodium sulfate, filtered, and concentrated. The residue obtained was purified by silica gel column chromatography (hexane/ethyl acetate). To the residue obtained by concentration, methanol (1 mL) and water (50 mL) were added, then the solid obtained was filtered to obtain the title compound (247 mg) as a solid.

$^1$H-NMR (DMSO-D$_6$, 100° C.) δ: 1.74-1.86 (1H, m), 1.88-2.53 (9H, m), 3.19-3.42 (2H, m), 3.76 (3H, s), 4.74-4.84 (1H, m), 4.94-5.15 (1H, m), 6.90-6.98 (2H, m), 7.22-7.31 (2H, m), 7.93-8.09 (3H, m), 9.91 (1H, br s), 12.95 (1H, br s).
MS (m/z): 502 (M+H)$^+$.

(Step 2') (4R)-1-{[4,4-Difluoro-1-(4-methoxyphenyl)cyclohexyl]carbonyl}-4-fluoro-N-1H-pyrazolo[4,3-b]pyridin-5-yl-D-prolinamide (Fr1)

To a solution of the compound (32.3 g) obtained in Step 2 above in dichloromethane (100 mL), trifluoroacetic acid (20.0 mL) was added, and the mixture was stirred at room temperature for 2 hours. The reaction solution was concentrated, then a saturated aqueous sodium hydrogen carbonate solution was added to the residue obtained, and the mixture was extracted with ethyl acetate. The organic layer was dried over anhydrous sodium sulfate, filtered, and concentrated. The residue obtained was purified by amino silica gel column chromatography (ethyl acetate). The resultant was concentrated, then the solid obtained was washed with hexane, then dried to obtain the title compound (22.3 g) as a solid.

$^1$H-NMR (DMSO-D$_6$, 100° C.) δ: 1.74-1.85 (1H, m), 1.89-2.43 (9H, m), 2.91-2.97 (1H, m), 3.24-3.38 (1H, m), 3.76 (3H, s), 4.75-4.82 (1H, m), 5.04 (1H, d, J=55.9 Hz), 6.94 (2H, d, J=8.5 Hz), 7.27 (2H, d, J=8.5 Hz), 7.95-8.06 (3H, m), 9.90 (1H, br s), 13.00 (1H, br s). MS (m/z): 502 (M+H)$^+$.

The elemental analysis value as $C_{25}H_{26}N_5O_3F_3$ is
calculated value: C: 59.87%, H: 5.23%, N: 13.97%, F: 11.37%.
found value: C: 59.68%, H: 5.41%, N: 13.84%, F: 11.45%.

Figure 2:
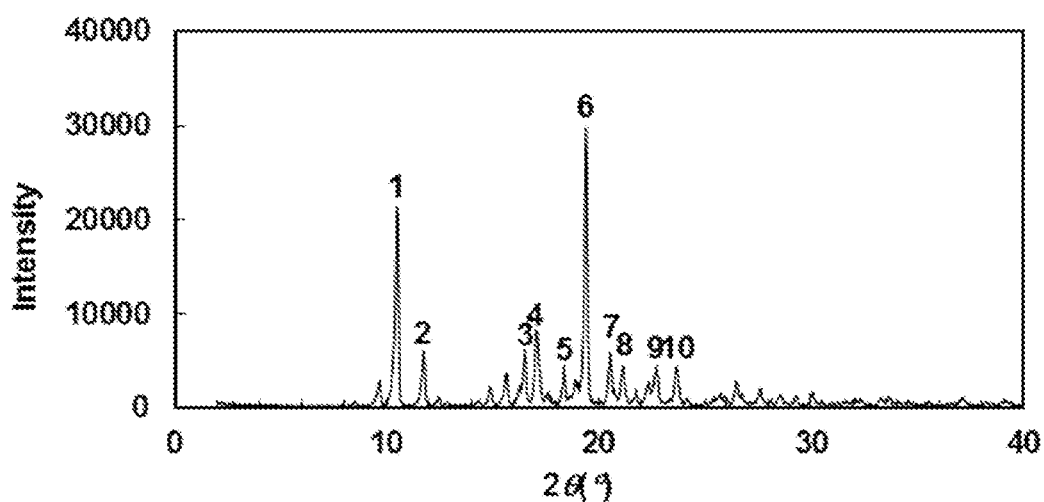
FIG. 2 is a powder X-ray diffraction diagram of a crystal obtained in Step 2' of Example 60. The ordinate indicates diffraction intensity (Intensity) in counts/sec (cps), and the abscissa indicates a value of the diffraction angle 2θ.

The powder X-ray diffraction of the solid obtained in Step 2' is shown in FIG. 2.

Figure 5:
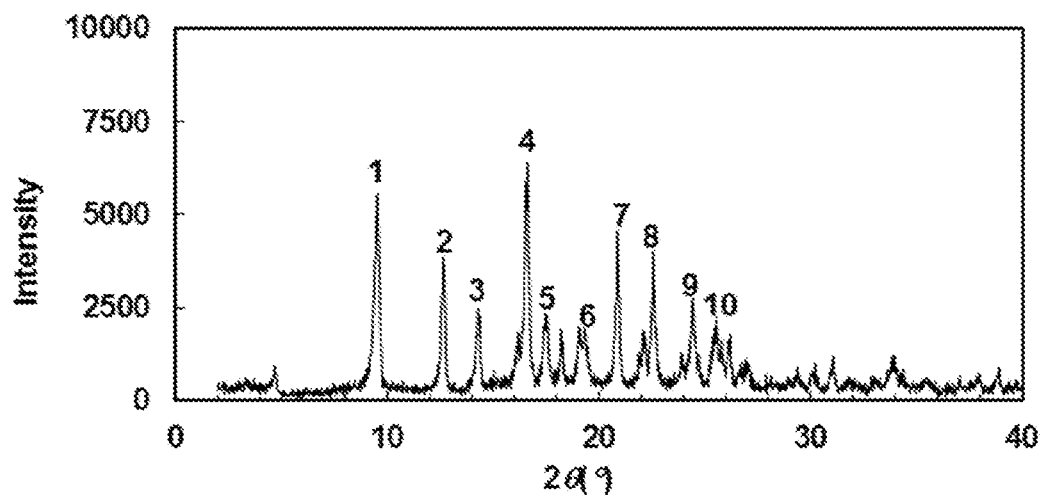
FIG. 5 is a powder X-ray diffraction diagram of a crystal obtained in Example 109. The ordinate indicates diffraction intensity (Intensity) in counts/sec (cps), and the abscissa indicates a value of the diffraction angle 2θ.

Table 7 shows peaks of relative intensity of 15 or more when the maximum peak intensity is set to 100 in the diffraction pattern of powder X-ray diffraction (CuKα, λ=1.54 angstroms, scanning speed=20°/min) in FIG. 5.

TABLE 7

| Peak number | 2θ | d value | Relative intensity |
|---|---|---|---|
| 1 | 10.48 | 8.43 | 74 |
| 2 | 11.72 | 7.54 | 21 |
| 3 | 16.50 | 5.37 | 21 |

TABLE 7-continued

| Peak number | 2θ | d value | Relative intensity |
|---|---|---|---|
| 4 | 17.06 | 5.19 | 31 |
| 5 | 18.34 | 4.83 | 15 |
| 6 | 19.38 | 4.58 | 100 |
| 7 | 20.52 | 4.32 | 20 |
| 8 | 21.12 | 4.20 | 17 |
| 9 | 22.70 | 3.91 | 16 |
| 10 | 23.64 | 3.76 | 17 |

(Step 2") (4R)-1-{[4,4-Difluoro-1-(4-methoxyphenyl)cyclohexyl]carbonyl}-4-fluoro-N-1H-pyrazolo[4,3-b]pyridin-5-yl-D-prolinamide (Fr2)

To the compound (301.13 mg) obtained in Step 2 above, water (3011 μL) was added at room temperature. The mixture was stirred at 40° C. for about 24 hours, and then at room temperature for about 30 minutes to obtain a precipitated solid. The solid was then dried at room temperature overnight to obtain the title compound (267.65 mg).

The elemental analysis value as $C_{25}H_{26}N_5O_3F_3$ is
calculated value: C: 59.87%, H: 5.23%, N: 13.96%, F: 11.36%.
found value: C: 59.69%, H: 5.30%, N: 13.91%, F: 11.54%.

Figure 3:
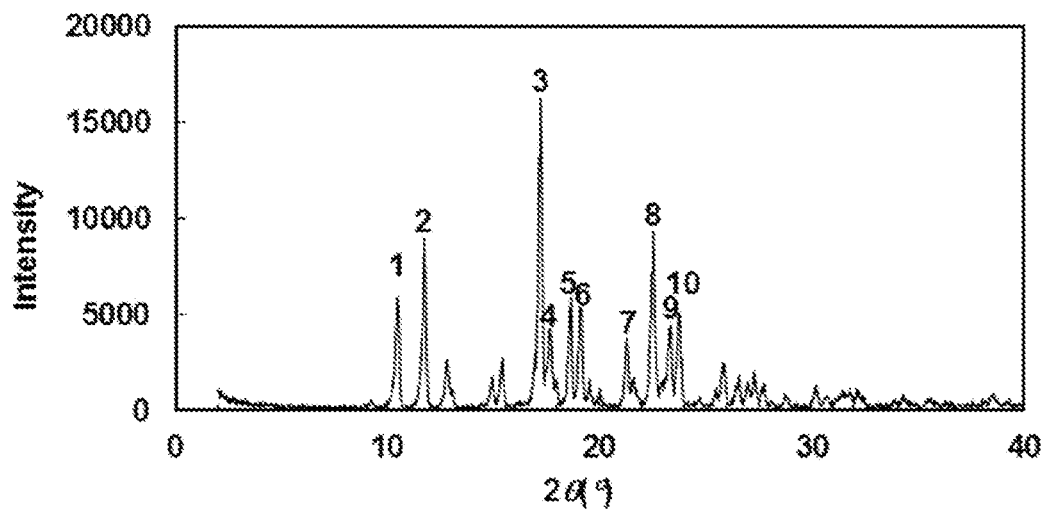
FIG. 3 is a powder X-ray diffraction diagram of a crystal obtained in Step 2" of Example 60. The ordinate indicates diffraction intensity (Intensity) in counts/sec (cps), and the abscissa indicates a value of the diffraction angle 2θ.

The powder X-ray diffraction of the solid obtained in Step 2" is shown in FIG. 3.

Table 8 shows peaks of relative intensity of 25 or more when the maximum peak intensity is set to 100 in the diffraction pattern of powder X-ray diffraction (CuKα, λ=1.54 angstroms, scanning speed=20°/min) in FIG. 3.

TABLE 8

| Peak number | 2θ | d value | Relative intensity |
|---|---|---|---|
| 1 | 10.48 | 8.43 | 40 |
| 2 | 11.74 | 7.53 | 57 |
| 3 | 17.20 | 5.15 | 100 |
| 4 | 17.66 | 5.02 | 29 |
| 5 | 18.62 | 4.76 | 37 |
| 6 | 19.10 | 4.64 | 38 |
| 7 | 21.28 | 4.17 | 25 |
| 8 | 22.50 | 3.95 | 56 |
| 9 | 23.30 | 3.81 | 29 |
| 10 | 23.74 | 3.74 | 34 |

Example 61

(4R)-4-Fluoro-N-1H-pyrazolo[4,3-b]pyridin-5-yl-1-({1-[4-(trifluoroacetyl)phenyl]cyclohexyl}carbonyl)-D-prolinamide

[Formula 135]

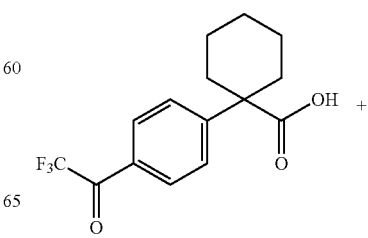

239
-continued

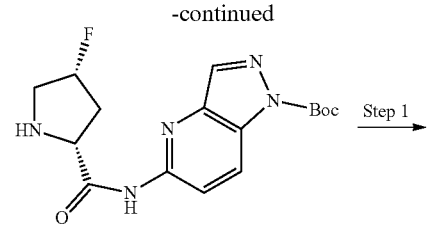

Step 1 →

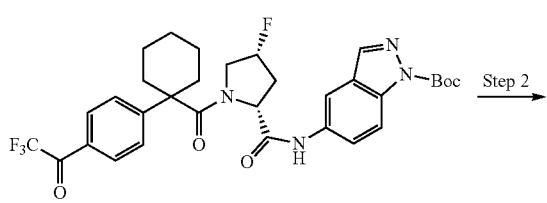

Step 2 →

240

(Step 1) tert-Butyl 5-{[(4R)-4-fluoro-1-({1-[4-(trifluoroacetyl)phenyl]cyclohexyl}carbonyl)-D-prolyl]amino}-1H-pyrazolo[4,3-b]pyridine-1-carboxylate The compound (0.180 g) obtained in Reference Example C-16 and the compound (0.175 g) obtained in Reference Example B-2 were subjected to the same procedure as in Step 1 of Example 45 to obtain the title compound (0.260 g) as a solid.

$^1$H-NMR (DMSO-D$_6$, 100° C.) δ: 1.32 (1H, s), 1.52-1.84 (16H, m), 2.04-2.14 (1H, m), 2.28-2.41 (3H, m), 3.24-3.42 (2H, m), 4.79-4.81 (1H, m), 5.07 (1H, d, J=54.4 Hz), 7.66 (2H, d, J=7.9 Hz), 8.04 (2H, d, J=7.9 Hz), 8.24-8.30 (1H, m), 8.38-8.40 (2H, m), 10.28 (1H, s). MS (m/z): 632 (M+H)$^+$.

(Step 2) (4R)-4-Fluoro-N-1H-pyrazolo[4,3-b]pyridin-5-yl-1-({1-[4-(trifluoroacetyl)phenyl]cyclohexyl}carbonyl)-D-prolinamide The compound (0.255 g) obtained in Step 1 above was subjected to the same procedure as in Step 5 of Example 4 to obtain the title compound (0.149 g) as a solid.

$^1$H-NMR (CDCl$_3$) δ: 1.35 (1H, s), 1.68-1.92 (7H, m), 2.18-2.57 (4H, m), 3.09-3.59 (2H, m), 4.84 (1H, s), 5.06 (1H, d, J=52.0 Hz), 7.60 (2H, d, J=8.5 Hz), 7.84 (1H, d, J=9.7 Hz), 8.14-8.19 (3H, m), 8.34 (1H, d, J=9.1 Hz), 8.44 (1H, s), 10.60 (1H, s). MS (m/z): 532 (M+H)$^+$.

The intermediates described below were subjected to the same procedure as above to synthesize the following compounds.

TABLE 9

| Example No. | Intermediate | Name and Structure | Equipment data |
|---|---|---|---|
| 62 | C-17<br>B-2 | (4R)-1-{[1-(3,5-Difluoro-4-methoxyphenyl)-4,4-difluorocyclohexyl]carbonyl}-4-fluoro-N-1H-pyrazolo[4,3-b]pyridin-5-yl-D-prolinamide | $^1$H-NMR (DMSO-D$_6$) δ: 1.80-2.20 (6H, m), 2.23-2.47 (4H, m), 3.38 (2H, d, J = 24.3 Hz), 3.92 (3H, s), 4.82 (1H, d, J = 7.9 Hz), 5.12 (1H, d, J = 54.1 Hz), 7.08 (2H, d, J = 9.7 Hz), 7.95-8.06 (3H, m), 10.04 (1H, s), 12.89 (1H, br s). MS (m/z): 538 (M + H)$^+$. |

TABLE 9-continued

| Example No. | Intermediate | Name and Structure | Equipment data |
|---|---|---|---|
| 63 | 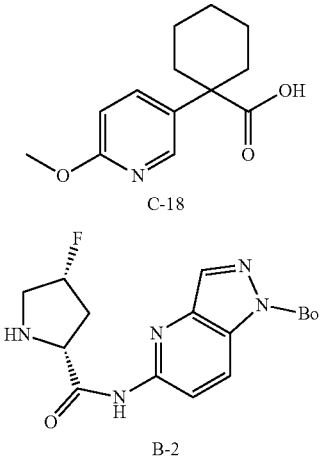 C-18<br><br>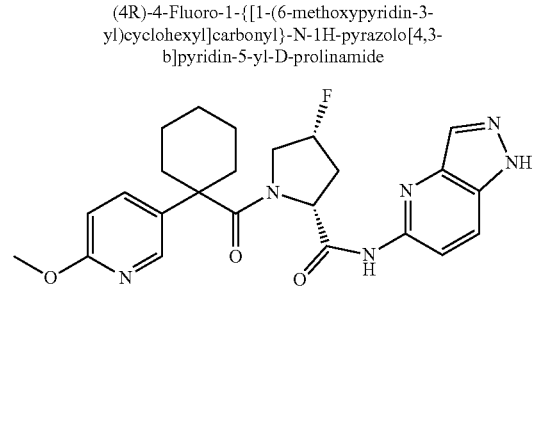 [SMILES: COc1ccc(C2(C(=O)N3C[C@H](F)C[C@@H]3C(=O)Nc3ccc4[nH]ncc4n3)CCCCC2)cn1] B-2 | (4R)-4-Fluoro-1-{[1-(6-methoxypyridin-3-yl)cyclohexyl]carbonyl}-N-1H-pyrazolo[4,3-b]pyridin-5-yl-D-prolinamide<br><br>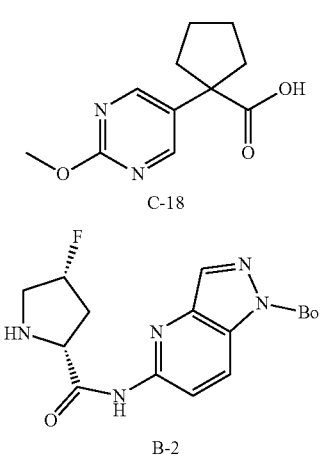 | $^1$H-NMR (DMSO-D$_6$, 100° C.) δ: 1.24-2.40 (12H, m), 3.04-3.53 (2H, m), 3.85 (3H, s), 4.74-4.83 (1H, m), 5.09 (1H, d, J = 53.8 Hz), 6.75-6.79 (1H, m), 7.59-7.64 (1H, m), 7.96-8.17 (4H, m), 10.00 (1H, s), 13.06 (1H, S). MS (m/z): 467 (M + H)$^+$. |
| 64 | 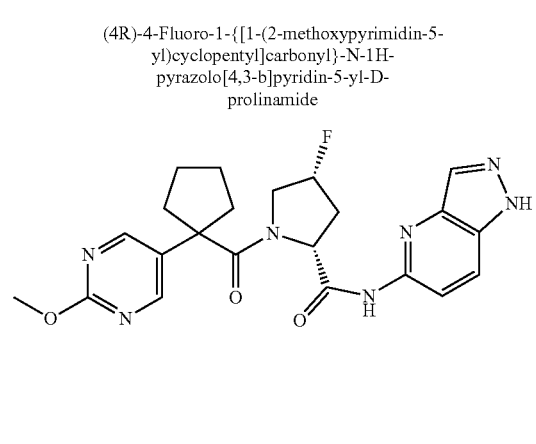 [SMILES: COc1ncc(C2(C(=O)N3C[C@H](F)C[C@@H]3C(=O)Nc3ccc4[nH]ncc4n3)CCCC2)cn1] C-18<br><br>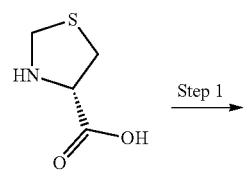 B-2 | (4R)-4-Fluoro-1-{[1-(2-methoxypyrimidin-5-yl)cyclopentyl]carbonyl}-N-1H-pyrazolo[4,3-b]pyridin-5-yl-D-prolinamide | $^1$H-NMR (DMSO-D$_6$, 50° C.) δ: 1.56-1.87 (7H, m), 2.03-2.33 (3H, m), 3.36-3.63 (2H, m), 3.93 (3H, s), 4.72-4.85 (1H, m), 5.15 (1H, d, J = 53.2 Hz), 7.96-8.20 (3H, m), 8.59 (2H, s), 10.48 (1H, s), 13.18 (1H, s). MS (m/z): 454 (M + H)$^+$. |

Example 65

(4S)-3-{[1-(4-Methoxyphenyl)cyclopentyl]carbonyl}-N-(1H-pyrrolo[3,2-b]pyridin-5-yl)-1,3-thiazolidine-4-carboxamide 1,1-dioxide

[Formula 136]

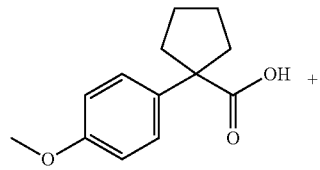

-continued

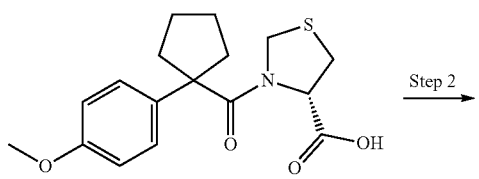

243

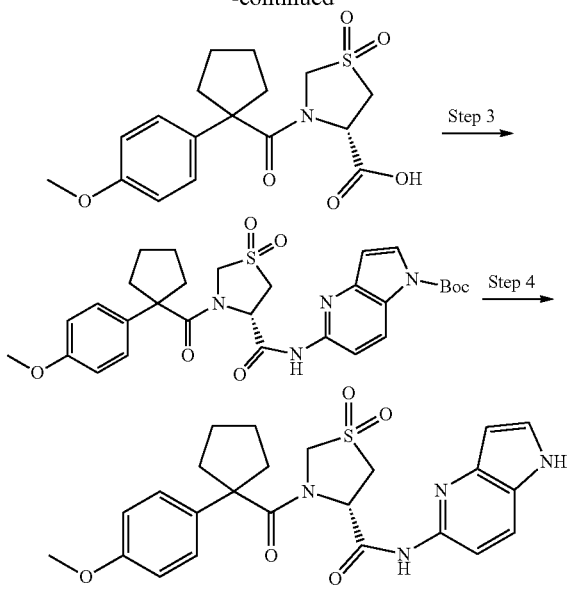

(Step 1) (4S)-3-{[1-(4-Methoxyphenyl)cyclopentyl]carbonyl}-1,3-thiazolidine-4-carboxylic acid To a mixture of 1-(4-methoxyphenyl)cyclopentanecarboxylic acid (2.50 g) and toluene (50.0 mL), thionyl chloride (2.60 mL) and N,N-dimethylformamide (1 drop) were added at room temperature, and the mixture was heated and stirred at 60° C. for 1 hour. The reaction solution was concentrated under reduced pressure, then the residue obtained was dissolved in tetrahydrofuran (10.0 mL). Under ice-cooling, the above solution was added to a mixture of (4S)-1,3-thiazolidin-4-carboxylic acid (1.96 g), a saturated aqueous sodium hydrogen carbonate solution (40.0 mL) and tetrahydrofuran (30.0 mL), and the mixture was stirred for 22 hours while gradually returning to room temperature. The reaction solution was diluted with water, and acidified by the addition of 6 mol/L hydrochloric acid under ice-cooling, and then the mixture was extracted with ethyl acetate. The organic layer obtained was washed with saturated brine, and dried over anhydrous sodium sulfate. The solvent was distilled off under reduced pressure, then the residue obtained was suspended in diethyl ether, and filtered to obtain the title compound (3.04 g) as a solid.

$^1$H-NMR (DMSO-D$_6$) δ: 1.51-1.74 (4H, m), 1.77-2.05 (2H, m), 2.21-2.35 (2H, m), 2.94 (1H, dd, J=11.5, 4.8 Hz), 3.20-3.37 (1H, m), 3.74 (3H, s), 3.87-3.97 (1H, m), 4.05-4.17 (1H, m), 4.75-4.86 (1H, m), 6.90 (2H, d, J=8.5 Hz), 7.16 (2H, d, J=7.9 Hz), 12.80 (1H, br s). MS (m/z): 336 (M+H)$^+$.

(Step 2) (4S)-3-{[1-(4-Methoxyphenyl)cyclopentyl]carbonyl}-1,3-thiazolidine-4-carboxylic acid 1,1-dioxide To a suspension of the compound (3.04 g) obtained in Step 1 above in acetic acid (20.0 mL), hydrogen peroxide (34.5%, 3.73 mL) was added at room temperature, and the mixture was stirred for 1 hour, and then heated and stirred at 50° C. for 8 hours. The reaction solution was diluted with water, and then the precipitated solid was filtered to obtain the title compound (2.47 g) as a solid.

244

$^1$H-NMR (DMSO-D$_6$) δ: 1.55-1.72 (4H, m), 1.82-2.05 (2H, m), 2.17-2.36 (2H, m), 3.40-3.49 (1H, m), 3.71-3.91 (5H, m), 4.22-4.32 (1H, m), 5.05-5.15 (1H, m), 6.86-6.94 (2H, m), 7.13-7.21 (2H, m), 13.32 (1H, br s). MS (m/z): 366 (M–H)$^-$.

(Step 3) tert-Butyl 5-({[(4S)-3-{[1-(4-methoxyphenyl)cyclopentyl]carbonyl}-1,1-dioxide-1,3-thiazolidin-4-yl]carbonyl}amino)-1H-pyrrolo[3,2-b]pyridine-1-carboxylate The compound (0.200 g) obtained in Step 2 above and the compound (0.254 g) obtained in Reference Example A-8 were subjected to the same procedure as in Step 6 of Example 27 to obtain the title compound (0.291 g) as a solid.

$^1$H-NMR (DMSO-D$_6$) δ: 1.62-1.90 (14H, m), 2.21-2.38 (2H, m), 2.56-2.66 (1H, m), 3.26-3.41 (1H, m), 3.55-3.68 (1H, m), 3.75 (3H, s), 3.81-3.91 (1H, m), 4.38-4.54 (1H, m), 5.56-5.68 (1H, m), 6.67 (1H, d, J=3.6 Hz), 6.81 (2H, d, J=8.5 Hz), 7.12 (2H, d, J=9.1 Hz), 7.79-7.88 (1H, m), 8.07 (1H, d, J=9.1 Hz), 8.30-8.45 (1H, m), 8.93 (1H, br s). MS (m/z): 583 (M+H)$^+$.

(Step 4) (4S)-3-{[1-(4-Methoxyphenyl)cyclopentyl]carbonyl}-N-(1H-pyrrolo[3,2-b]pyridin-5-yl)-1,3-thiazolidine-4-carboxamide 1,1-dioxide The compound (0.280 g) obtained in Step 3 above was subjected to the same procedure as in Step 5 of Example 4 to obtain the title compound (0.177 g) as a solid.

$^1$H-NMR (CDCl$_3$) δ: 1.54-1.89 (5H, m), 2.17-2.39 (2H, m), 2.54-2.67 (1H, m), 3.24-3.44 (1H, m), 3.55-3.86 (5H, m), 4.33-4.56 (1H, m), 5.52-5.69 (1H, m), 6.63-6.67 (1H, m), 6.83 (2H, d, J=8.5 Hz), 7.14 (2H, d, J=8.5 Hz), 7.45-7.49 (1H, m), 7.73 (1H, d, J=9.1 Hz), 7.98 (1H, d, J=8.5 Hz), 8.34 (1H, s), 8.94 (1H, br s). MS (m/z): 483 (M+H)$^+$.

Example 66

(4R)-4-Fluoro-1-{[1-(4-methoxyphenyl)cyclohexyl]carbonyl}-N-(2-oxo-2,3-dihydro-1H-pyrrolo[3,2-b]pyridin-5-yl)-D-prolinamide

[Formula 137]

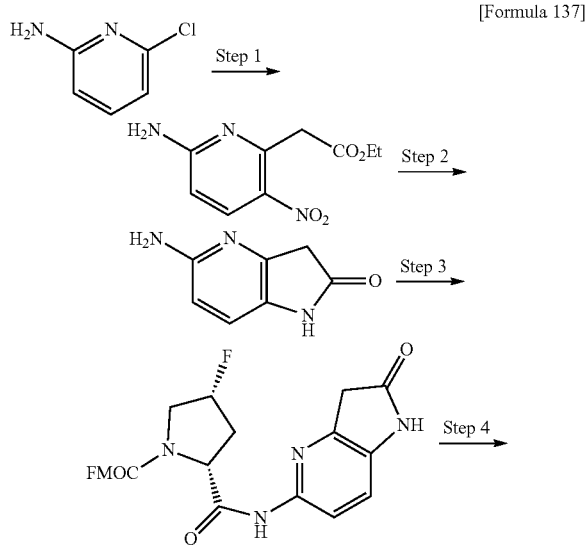

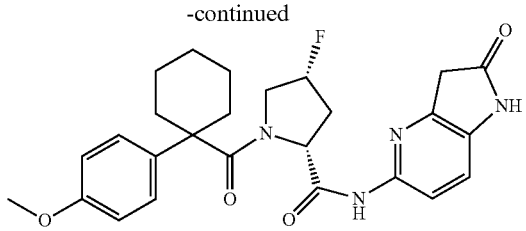

(Step 1) Ethyl 2-(6-amino-3-nitro-2-pyridinyl)acetate

2-Amino-6-chloropyridine (26.5 g) was dissolved in sulfuric acid (160 mL) at 0° C., and the mixture was stirred for 15 minutes. Nitric acid (13.0 mL) was slowly added dropwise at the same temperature, and the mixture was stirred for 10 minutes, and then stirred at 55° C. for 1.7 hours. The reaction solution was poured into ice, then ammonia water was added to about pH 9 while maintaining the temperature at 0° C. The solid obtained by filtration was washed with water, and dissolved in ethyl acetate. The resultant was washed with water and with saturated brine, and then dried over anhydrous sodium sulfate. The solvent was distilled off under reduced pressure, and the residue was azeotropically concentrated with toluene to obtain the nitro compound (28.4 g) as a solid.

A solution of sodium hydride (purity>55%, 10.6 g) in N,N-dimethylformamide (200 mL) was cooled to 0° C., then tert-butyl ethyl malonate (45.4 mL) was added, then the mixture was stirred at 50° C. for 15 minutes. While maintained at 50° C., a solution of the intermediate (12.0 g) obtained above in N,N-dimethylformamide (200 mL) was added over 30 minutes, and the mixture was stirred at 50° C. for 6.8 hours. After leaving the resultant at room temperature overnight, ice and a saturated aqueous ammonium chloride solution were added, and a saturated aqueous sodium hydrogen carbonate solution was added to about pH 8. The mixture was extracted with ethyl acetate, then the organic layer was washed with saturated brine, and dried over anhydrous sodium sulfate. The solvent was distilled off under reduced pressure, then dichloromethane (200 mL) was added to the residue obtained. Trifluoroacetic acid (200 mL) was added thereto, and the mixture was stirred at room temperature for 15 hours, then concentrated. Toluene was further added, then the mixture was concentrated. The residue obtained was partitioned by the addition of ethyl acetate and a saturated aqueous sodium hydrogen carbonate solution. The organic layer was washed with saturated brine, then dried over anhydrous sodium sulfate. Diatomaceous earth was added, and the mixture was stirred well. The solvent was distilled off under reduced pressure, then the residue obtained was subjected to silica gel column chromatography (hexane/ethyl acetate) to obtain the title compound (4.20 g) as a solid.

$^1$H-NMR (DMSO-D$_6$) δ: 1.16 (3H, t, J=7.0 Hz), 3.98 (2H, s), 4.08 (2H, q, J=7.1 Hz), 6.48 (1H, d, J=9.7 Hz), 7.51 (2H, br s), 8.17 (1H, d, J=9.1 Hz).

(Step 2) 5-Amino-1,3-dihydropyrrolo[3,2-b]pyridin-2-one

A solution of the compound (4.00 g) obtained in Step 1 above in ethanol (80 mL) was cooled to 0° C., and zinc powder (11.6 g) and acetic acid (10.2 mL) were slowly added, and the mixture was stirred at room temperature for 30 minutes. The reaction solution was filtered through celite, then the filtrate was concentrated. Water (10 mL) was added, and the mixture was cooled to 0° C., then ammonia water (28%, 50 mL) was added, and the mixture was stirred at room temperature for 1 hour. Air was blown into the reaction solution for 2 hours to remove ammonia, then toluene was added, and the mixture was concentrated. Methanol and diatomaceous earth were added, and the mixture was stirred well, and the solvent was distilled off under reduced pressure. The residue obtained was purified by silica gel column chromatography (hexane/ethyl acetate) to obtain the title compound (1.45 g) as a solid.

$^1$H-NMR (DMSO-D$_6$) δ: 5.46 (2H, br s), 6.25 (1H, d, J=8.5 Hz), 6.88 (1H, d, J=8.5 Hz), 9.96 (1H, br s). MS (m/z): 150 (M+H)$^+$.

(Step 3) 9H-Fluoren-9-ylmethyl (2R,4R)-4-fluoro-2-[(2-oxo-2,3-dihydro-1H-pyrrolo[3,2-b]pyridin-5-yl)carbamoyl]pyrrolidine-1-carboxylate The compound (400 mg) obtained in Step 2 of Reference Example B-2 and the compound (168 mg) obtained in Step 2 above were subjected to the same procedure as in Step 3 of Reference Example B-2 to obtain the title compound (422 mg) as a solid.

$^1$H-NMR (DMSO-D$_6$) δ: 2.32 (1H, dd, J=20.1, 14.6 Hz), 2.50-2.66 (1H, m), 3.51 (2H, s), 3.64-3.81 (2H, m), 4.19-4.34 (3H, m), 4.59 (1H, d, J=9.8 Hz), 5.29 (1H, d, J=53.7 Hz), 7.15 (1H, d, J=8.5 Hz), 7.23 (2H, br s), 7.33-7.40 (2H, m), 7.62 (2H, d, J=7.3 Hz), 7.80-7.86 (3H, m), 9.88 (1H, br s), 10.20 (1H, s). MS (m/z): 487 (M+H)$^+$.

(Step 4) (4R)-4-Fluoro-1-{[1-(4-methoxyphenyl)cyclohexyl]carbonyl}-N-(2-oxo-2,3-dihydro-1H-pyrrolo[3,2-b]pyridin-5-yl)-D-prolinamide To a solution of 1-(4-methoxyphenyl)cyclohexanecarboxylic acid (246 mg) in dichloromethane (5 mL), oxalyl chloride (180 μL) and N,N-dimethylformamide (15 mL) were added, and the mixture was stirred at room temperature for 30 minutes, then the reaction mixture solution was concentrated to obtain the crude acid chloride. DBU was added to a solution of the compound (421 mg) obtained in Step 3 above in tetrahydrofuran (5 mL), then the mixture was stirred at room temperature for 1 hour. To the resultant, a solution of the crude acid chloride obtained above in dichloromethane (5 mL) was added at 0° C., and the mixture was stirred at room temperature for 3 hours. The reaction mixture solution was concentrated, then the residue obtained was purified by silica gel column chromatography (ethyl acetate/chloroform) to obtain the title compound (74 mg) as a solid.

$^1$H-NMR (DMSO-D$_6$) δ: 1.20-1.31 (1H, m), 1.47-1.80 (8H, m), 2.18-2.38 (3H, m), 3.04-3.27 (2H, m), 3.57 (2H, s), 3.75 (3H, s), 4.68 (1H, d, J=9.2 Hz), 5.01 (1H, d, J=54.3 Hz), 6.93 (2H, d, J=8.5 Hz), 7.17 (1H, d, J=8.5 Hz), 7.25 (2H, d, J=8.5 Hz), 7.89 (1H, d, J=8.5 Hz), 9.97 (1H, s), 10.46 (1H, s). MS (m/z): 481 (M+H)$^+$.

Example 67

(4R)-4-Fluoro-1-{[1-(4-methoxyphenyl)cyclohexyl]carbonyl}-N-(3-oxo-3,4-dihydro-2H-pyrido[3,2-b][1,4]oxazin-6-yl)-D-prolinamide

[Formula 138]

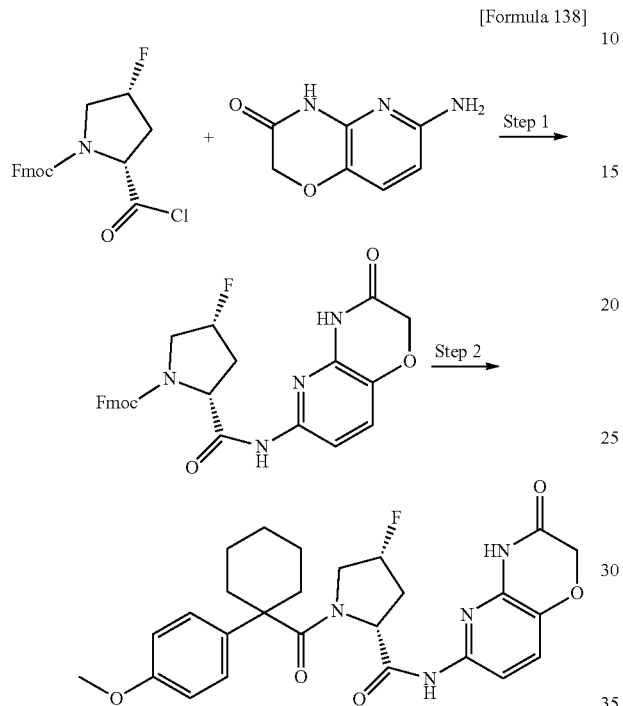

(Step 1) 9H-Fluoren-9-ylmethyl (2R,4R)-4-fluoro-2-[(3-oxo-3,4-dihydro-2H-pyrido[3,2-b][1,4]oxazin-6-yl)carbamoyl]pyrrolidine-1-carboxylate The compound (400 mg) obtained in Step 2 of Reference Example B-2 and 6-amino-2H-pyrido[3,2-b][1,4]oxazine-3(4H)-one (212 mg) were subjected to the same procedure as in Step 3 of Reference Example B-2 to obtain the title compound (378 mg) as a solid.

$^1$H-NMR (DMSO-D$_6$) δ: 2.31 (1H, dd, J=20.8, 16.5 Hz), 2.50-2.66 (1H, m), 3.61-3.81 (2H, m), 4.18-4.26 (1H, m), 4.31 (2H, d, J=6.7 Hz), 4.58 (2H, s), 4.62 (1H, d, J=9.8 Hz), 5.29 (1H, d, J=53.7 Hz), 7.23 (2H, br s), 7.33 (1H, d, J=8.5 Hz), 7.37 (2H, t, J=6.7 Hz), 7.56 (1H, d, J=8.5 Hz), 7.61 (2H, d, J=6.7 Hz), 7.80-7.85 (2H, m), 9.72 (1H, s), 10.83 (1H, s). MS (m/z): 503 (M+H)$^+$.

(Step 2) (4R)-4-Fluoro-1-{[1-(4-methoxyphenyl)cyclohexyl]carbonyl}-N-(3-oxo-3,4-dihydro-2H-pyrido[3,2-b][1,4]oxazin-6-yl)-D-prolinamide 1-(4-Methoxyphenyl)cyclohexanecarboxylic acid (210 mg) and the compound (377 mg) obtained in Step 1 above were subjected to the same procedure as in Step 4 of Example 66 to obtain the title compound (103 mg) as a solid.

$^1$H-NMR (DMSO-D$_6$) δ: 1.16-1.31 (1H, m), 1.46-1.77 (7H, m), 1.89-2.03 (1H, m), 2.15-2.38 (3H, m), 3.00-3.26 (2H, m), 3.75 (3H, s), 4.61 (2H, s), 4.68-4.77 (1H, m), 5.01 (1H, d, J=53.7 Hz), 6.93 (2H, d, J=7.9 Hz), 7.24 (2H, d, J=7.9 Hz), 7.36 (1H, d, J=8.5 Hz), 7.62 (1H, d, J=8.5 Hz), 9.93 (1H, s), 11.15 (1H, s). MS (m/z): 497 (M+H)$^+$.

Example 68

(4S)-3-{[4,4-Difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide

[Formula 139]

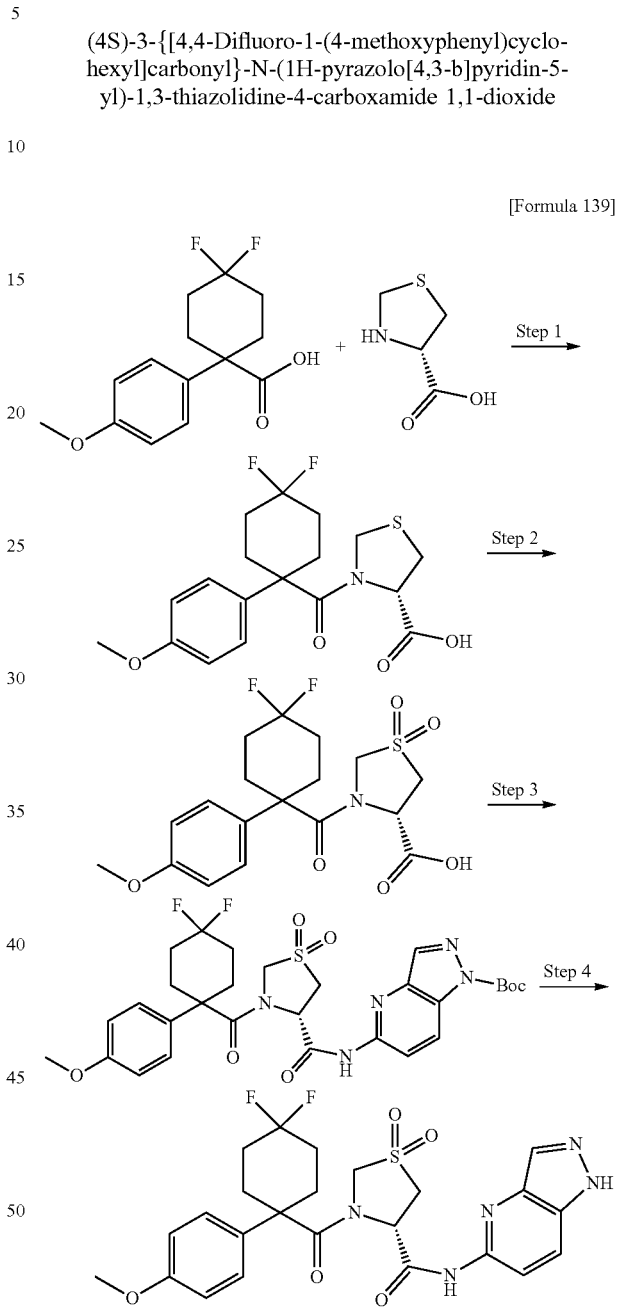

(Step 1) (4S)-3-{[4,4-Difluoro-1-(4-methoxyphenyl)cyclohexyl]carbonyl}-1,3-thiazolidine-4-carboxylic acid The compound (700 mg) obtained in Reference Example C-4 and (4S)-1,3-thiazolidine-4-carboxylic acid (448 mg) were subjected to the same procedure as in Step 1 of Example 65 to obtain the title compound (948 mg) as a solid.

$^1$H-NMR (DMSO-D$_6$) δ: 1.43-1.61 (1H, m), 1.88-2.47 (7H, m), 2.93 (1H, dd, J=11.6, 6.7 Hz), 3.22-3.50 (1H, m), 3.75 (3H, s), 3.96-4.09 (1H, m), 4.17 (1H, d, J=9.2 Hz), 4.73-4.89 (1H, m), 6.94 (2H, d, J=8.5 Hz), 7.21 (2H, d, J=8.5 Hz), 12.95 (1H, br s). MS (m/z): 386 (M+H)⁺.

(Step 2) (4S)-3-{[4,4-Difluoro-1-(4-methoxyphenyl)cyclohexyl]carbonyl}-1,3-thiazolidine-4-carboxylic acid 1,1-dioxide The compound (800 mg) obtained in Step 1 above was subjected to the same procedure as in Step 2 of Example 65 to obtain the title compound (770 mg) as a solid.
¹H-NMR (DMSO-D₆) δ: 1.51-1.66 (1H, m), 1.91-2.46 (7H, m), 3.45 (1H, dd, J=13.7, 7.0 Hz), 3.72-3.85 (4H, m), 3.99-4.10 (1H, m), 4.20-4.30 (1H, m), 5.05-5.15 (1H, m), 6.95 (2H, d, J=8.5 Hz), 7.22 (2H, d, J=9.2 Hz), 13.43 (1H, br s). MS (m/z): 416 (M−H)⁻.

(Step 3) tert-Butyl 5-({[(4S)-3-{[4,4-difluoro-1-(4-methoxyphenyl)cyclohexyl]carbonyl}-1,1-dioxide-1,3-thiazolidin-4-yl]carbonyl}amino)-1H-pyrazolo[4,3-b]pyridine-1-carboxylate The compound (250 mg) obtained in Step 2 above and the compound (280 mg) obtained in Reference Example A-6 were subjected to the same procedure as in Step 6 of Example 27 to obtain the title compound (370 mg) as a solid.
¹H-NMR (CDCl₃) δ: 1.74 (9H, s), 1.98-2.45 (8H, m), 3.67-3.75 (1H, m), 3.76-3.86 (4H, m), 4.33-4.43 (1H, m), 5.60-5.69 (1H, m), 6.87 (2H, d, J=8.5 Hz), 7.16 (2H, d, J=9.2 Hz), 8.26-8.34 (2H, m), 8.49 (1H, d, J=9.2 Hz), 9.13 (1H, br s). MS (m/z): 634 (M+H)⁺.

(Step 4) (4S)-3-{[4,4-Difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide The compound (365 mg) obtained in Step 3 above was subjected to the same procedure as in Step 5 of Example 4 to obtain the title compound (278 mg) as a solid.
¹H-NMR (DMSO-D₆) δ: 1.54-1.66 (1H, m), 1.87-2.48 (7H, m), 3.40-3.50 (1H, m), 3.45 (2H, dd, J=13.7, 8.9 Hz), 3.71-3.87 (4H, m), 4.14 (1H, d, J=11.6 Hz), 4.38 (1H, d, J=11.6 Hz), 5.22 (1H, t, J=8.9 Hz), 6.97 (2H, d, J=8.5 Hz), 7.24 (2H, d, J=8.5 Hz), 8.05-8.21 (3H, m), 11.02 (1H, s), 13.34 (1H, s). MS (m/z): 534 (M+H)⁺.

Example 69

4,4-Difluoro-N-[(2R)-4-hydroxy-1-oxo-1-(1H-pyrazolo[4,3-b]pyridin-5-ylamino)butan-2-yl]-1-(4-methoxyphenyl)-N-methylcyclohexanecarboxamide

[Formula 140]

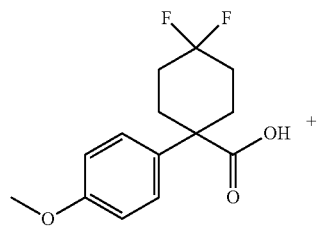

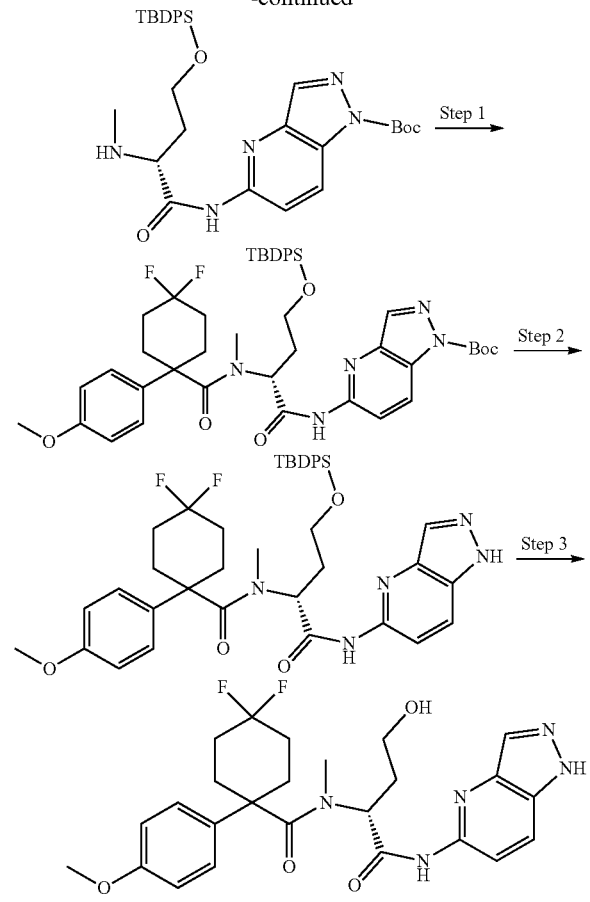

(Step 1) tert-Butyl 5-[(O-[tert-butyl(diphenyl)silyl]-N-{[4,4-difluoro-1-(4-methoxyphenyl)cyclohexyl]carbonyl}-N-methyl-D-homoseryl)amino]-1H-pyrazolo[4,3-b]pyridine-1-carboxylate The compound (228 mg) obtained in Reference Example C-4 and the compound (450 mg) obtained in Reference Example B-8 were subjected to the same procedure as in Step 1 of Reference Example D-2 to obtain the title compound (290 mg) as a solid.
¹H-NMR (CDCl₃) δ: 1.08 (9H, s), 1.22-2.09 (5H, m), 1.74 (9H, s), 2.14-2.64 (8H, m), 3.63-3.71 (5H, m), 5.48-5.62 (1H, m), 6.61-6.71 (2H, m), 7.15-7.21 (2H, m), 7.29-7.48 (6H, m), 7.60-7.70 (4H, m), 8.27-8.34 (2H, m), 8.39-8.47 (1H, m), 9.24 (1H, s). MS (m/z): 840 (M+H)⁺.

(Step 2) N-[(2R)-4-{[tert-Butyl(diphenyl)silyl]oxy}-1-oxo-1-(1H-pyrazolo[4,3-b]pyridin-5-ylamino)butan-2-yl]-4,4-difluoro-1-(4-methoxyphenyl)-N-methylcyclohexanecarboxamide The compound (50 mg) obtained in Step 1 above was subjected to the same procedure as in Step 5 of Example 4 to obtain the title compound (44 mg) as an oil.
¹H-NMR (CDCl₃) δ: 1.08 (9H, s), 1.21-2.10 (5H, m), 2.16-2.66 (8H, m), 3.59-3.72 (5H, m), 5.50-5.60 (1H, m), 6.64-6.74 (2H, m), 7.16-7.23 (2H, m), 7.30-7.48 (6H, m), 7.60-7.69 (4H, m), 7.80-7.87 (1H, m), 8.17-8.25 (2H, m), 9.14 (1H, s), 10.27 (1H, br s). MS (m/z): 740 (M+H)⁺.

(Step 3) 4,4-Difluoro-N-[(2R)-4-hydroxy-1-oxo-1-(1H-pyrazolo[4,3-b]pyridin-5-ylamino)butan-2-yl]-1-(4-methoxyphenyl)-N-methylcyclohexanecarboxamide To a solution of the compound (188 mg) obtained in Step 2 above in tetrahydrofuran (3.2 mL), hydrogen fluoride pyridine (purity 70%, 390 μL) was added at 0° C., and the mixture was stirred at room temperature for 2.5 hours. Ice and a saturated aqueous sodium carbonate solution were added to the reaction solution, and the mixture was extracted with ethyl acetate. The organic layer was washed with a saturated aqueous sodium hydrogen carbonate solution two times, with 10% aqueous citric acid solution three times, with water and with saturated brine, and then dried over anhydrous sodium sulfate. The solvent was distilled off under reduced pressure, then the residue obtained was purified by silica gel column chromatography (hexane/ethyl acetate) to obtain the title compound (109 mg) as a solid.

$^1$H-NMR (CD$_3$OD) δ: 1.65-2.72 (13H, m), 3.37-3.82 (5H, m), 5.20-5.31 (1H, m), 6.81 (2H, d, J=8.5 Hz), 7.25 (2H, d, J=8.5 Hz), 7.94-8.05 (1H, m), 8.05-8.21 (2H, m). MS (m/z): 502 (M+H)$^+$.

Example 70

(4R)-4-Fluoro-1-{[1-(4-methoxyphenyl)cyclohexyl]carbonyl}-N-pyrazolo[1,5-a]pyridin-2-yl-D-prolinamide

[Formula 141]

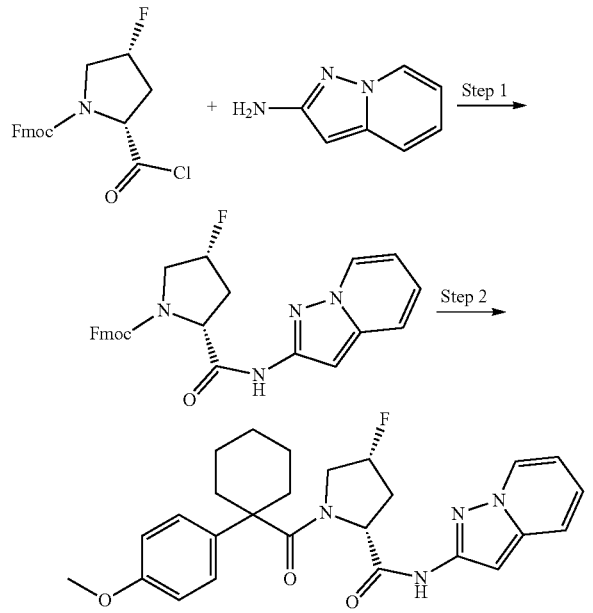

(Step 1) 9H-Fluoren-9-ylmethyl (2R,4R)-4-fluoro-2-(pyrazolo[1,5-a]pyridin-2-ylcarbamoyl)pyrrolidine-1-carboxylate The compound (500 mg) obtained in Step 2 of Reference Example B-2 and pyrazolo[1,5-a]pyridine-2-amine (214 mg) were subjected to the same procedure as in Step 1 of Reference Example B-6 to obtain the title compound (587 mg) as a solid.

$^1$H-NMR (DMSO-D$_6$) δ: 2.34 (1H, dd, J=20.1, 14.6 Hz), 2.51-2.69 (1H, m), 3.08 (1H, s), 3.66-3.83 (2H, m), 4.17-4.35 (3H, m), 4.63 (1H, d, J=7.9 Hz), 5.31 (1H, d, J=53.7 Hz), 6.77 (1H, td, J=7.0, 1.4 Hz), 6.82 (1H, br s), 7.13-7.18 (1H, m), 7.14-7.29 (1H, m), 7.35 (2H, br s), 7.54 (1H, d, J=8.5 Hz), 7.63 (2H, d, J=6.1 Hz), 7.82 (2H, d, J=6.7 Hz), 8.44 (1H, d, J=6.7 Hz), 10.48 (1H, br s). MS (m/z): 471 (M+H)$^+$.

(Step 2) (4R)-4-Fluoro-1-{[1-(4-methoxyphenyl)cyclohexyl]carbonyl}-N-pyrazolo[1,5-a]pyridin-2-yl-D-prolinamide 1-(4-Methoxyphenyl)cyclohexanecarboxylic acid (398 mg) and the compound (585 mg) obtained in Step 1 above were subjected to the same procedure as in Step 4 of Example 66 to obtain the title compound (87 mg) as a solid.

$^1$H-NMR (DMSO-D$_6$) δ: 1.17-1.31 (1H, m), 1.46-1.80 (6H, m), 1.93-2.05 (1H, m), 2.17-2.42 (3H, m), 3.04-3.30 (2H, m), 3.42 (1H, br s), 3.76 (3H, s), 4.71 (1H, dd, J=9.8, 3.1 Hz), 5.02 (1H, d, J=53.7 Hz), 6.78-6.84 (2H, m), 6.94 (2H, d, J=8.5 Hz), 7.18 (1H, dd, J=8.5, 6.1 Hz), 7.25 (2H, d, J=8.5 Hz), 7.57 (1H, d, J=9.2 Hz), 8.53 (1H, d, J=6.7 Hz), 10.60 (1H, s). MS (m/z): 465 (M+H)$^+$.

Example 71

(4S)-4-Hydroxy-1-{[1-(4-methoxyphenyl)cyclohexyl]carbonyl}-N-1H-pyrazolo[4,3-b]pyridin-5-yl-D-prolinamide

[Formula 142]

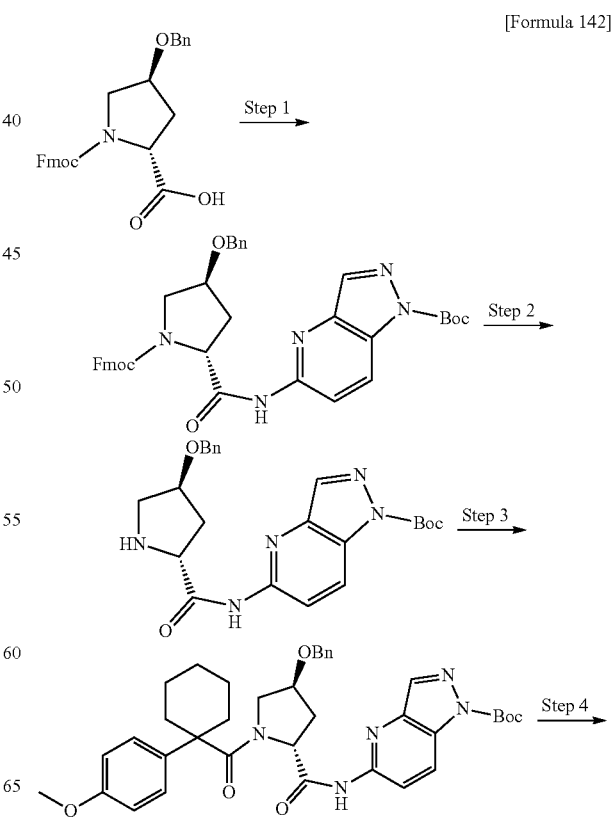

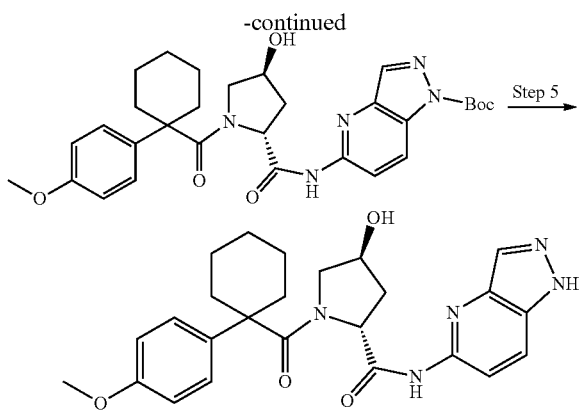

(Step 1) tert-Butyl 5-({(4S)-4-(benzyloxy)-1-[(9H-fluoren-9-ylmethoxy)carbonyl]-D-prolyl}amino)-1H-pyrazolo[4,3-b]pyridine-1-carboxylate (4S)-4-(Benzyloxy)-1-[(9H-fluoren-9-ylmethoxy)carbonyl]-D-proline (1.00 g) and the compound (0.581 g) obtained in Reference Example A-6 were subjected to the same procedure as in Step 1 of Example 45 to obtain the title compound (1.37 g) as a solid.
MS (m/z): 660 (M+H)⁺.

(Step 2) tert-Butyl 5-{[(4S)-4-(benzyloxy)-D-prolyl]amino}-1H-pyrazolo[4,3-b]pyridine-1-carboxylate The compound (1.37 g) obtained in Step 1 above was subjected to the same procedure as in Step 5 of Reference Example B-15 to obtain the title compound (0.762 g) as a solid.
$^1$H-NMR (DMSO-D$_6$) δ: 1.66 (9H, s), 1.87-1.94 (1H, m), 2.27-2.34 (1H, m), 2.92 (1H, dd, J=12.1, 3.6 Hz), 3.12 (1H, d, J=12.1 Hz), 3.96-4.01 (1H, m), 4.10-4.14 (1H, m), 4.49 (2H, s), 7.26-7.38 (5H, m), 8.40-8.49 (3H, m), 10.56 (1H, s).

(Step 3) tert-Butyl 5-{[(4S)-4-(benzyloxy)-1-{[1-(4-methoxyphenyl)cyclohexyl]carbonyl}-D-prolyl]amino}-1H-pyrazolo[4,3-b]pyridine-1-carboxylate 1-(4-Methoxyphenyl)cyclohexanecarboxylic acid (0.520 g) and the compound (0.762 g) obtained in Step 2 above were subjected to the same procedure as in Step 1 of Example 45 to obtain the title compound (1.02 g) as a solid.
MS (m/z): 654 (M+H)⁺.

(Step 4) tert-Butyl 5-{[(4S)-1-{[1-(4-methoxyphenyl)cyclohexyl]carbonyl}-4-hydroxy-D-prolyl]amino}-1H-pyrazolo[4,3-b]pyridine-1-carboxylate A mixture of the compound (1.02 g) obtained in Step 3 above, 10% palladium-carbon (0.22 g), ethanol (30 mL), ethyl acetate (5 mL) and 1 mol/L hydrochloric acid (3 mL) was stirred at room temperature under a hydrogen atmosphere for 5 hours. The resultant was filtered through celite, and concentrated, then a saturated aqueous sodium hydrogen carbonate solution was added to the residue obtained. Then, the mixture was extracted with ethyl acetate three times. The organic layer obtained was washed with saturated brine, and dried over anhydrous magnesium sulfate. The resultant was concentrated, then the solid obtained was slurry washed with a mixed solvent of ethyl acetate/hexane to obtain the title compound (0.681 g) as a solid.
$^1$H-NMR (DMSO-D$_6$) δ: 1.19-1.28 (1H, m), 1.44-1.78 (8H, m), 1.66 (9H, s), 1.95-2.01 (1H, m), 2.16-2.31 (2H, m), 2.90 (1H, d, J=10.3 Hz), 3.06 (1H, dd, J=10.3, 3.9 Hz), 3.74 (3H, s), 4.07-4.11 (1H, m), 4.70-4.81 (2H, m), 6.89 (2H, d, J=9.1 Hz), 7.21 (2H, d, J=9.1 Hz), 8.36-8.52 (3H, m), 10.87 (1H, s).

(Step 5) (4S)-4-Hydroxy-1-{[1-(4-methoxyphenyl)cyclohexyl]carbonyl-N-1H-pyrazolo[4,3-b]pyridin-5-yl-D-prolinamide The compound (0.681 g) obtained in Step 4 above was subjected to the same procedure as in Step 5 of Example 4 to obtain the title compound (0.293 g) as a solid.
$^1$H-NMR (DMSO-D$_6$) δ: 1.15-1.31 (1H, m), 1.44-2.04 (9H, m), 2.13-2.34 (2H, m), 2.82-3.10 (2H, m), 3.74 (3H, s), 3.99-4.12 (1H, m), 4.64-4.85 (2H, m), 6.89 (2H, d, J=9.1 Hz), 7.21 (2H, d, J=9.1 Hz), 7.99-8.23 (3H, m), 10.60 (1H, s), 13.26 (1H, s).

Example 72

4,4-Difluoro-N-(2-hydroxyethyl)-1-(4-methoxyphenyl)-N-[2-oxo-2-(1H-pyrazolo[4,3-b]pyridin-5-ylamino)ethyl]cyclohexanecarboxamide

[Formula 143]

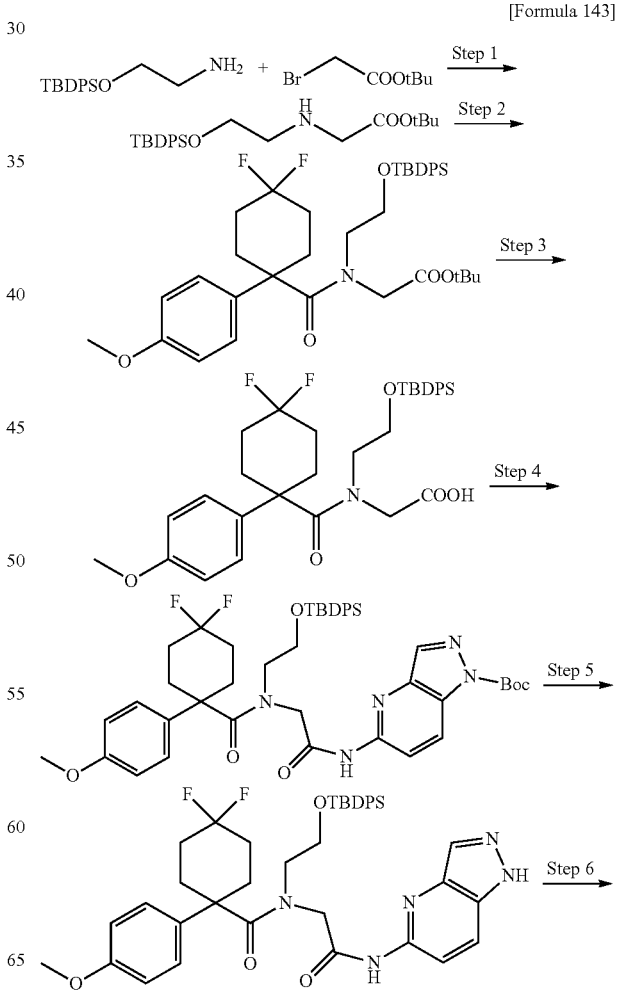

-continued

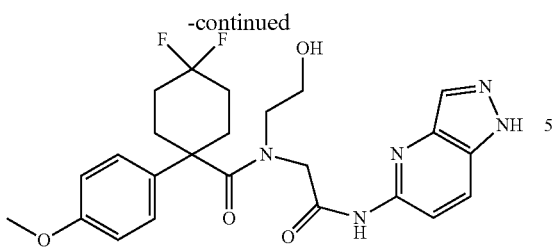

(Step 1) tert-Butyl N-(2-{[tert-butyl(diphenyl)silyl]oxy}ethyl)glycinate

To a mixture of 2-{[tert-butyl(diphenyl)silyl]oxy}ethanamine (Tetrahedron, 68, 6329-6337 (2012); 5.50 g), triethylamine (3.60 mL) and tetrahydrofuran (16 mL), tert-butyl bromoacetate (2.70 mL) was added at 0° C. Then, the mixture was stirred at room temperature for 3 days. Ice was added to the reaction solution, and the mixture was extracted with ethyl acetate. The organic layer was washed with saturated brine, and dried over anhydrous sodium sulfate. The solvent was distilled off under reduced pressure, then the residue obtained was purified by silica gel column chromatography (hexane/ethyl acetate) to obtain the title compound (6.20 g).

$^1$H-NMR (CDCl$_3$) δ: 1.06 (9H, s), 1.48 (9H, s), 1.89-2.09 (1H, m), 2.76 (2H, t, J=5.2 Hz), 3.33 (2H, s), 3.76 (2H, t, J=5.2 Hz), 7.35-7.45 (6H, m), 7.65-7.71 (4H, m). MS (m/z): 414 (M+H)$^+$.

(Step 2) tert-Butyl N-(2-{[tert-butyl(diphenyl)silyl]oxy}ethyl)-N-{[4,4-difluoro-1-(4-methoxyphenyl)cyclohexyl]carbonyl}glycinate The compound (334 mg) obtained in Reference Example C-4 and the compound (501 mg) obtained in Step 1 above were subjected to the same procedure as in Example 39 to obtain the title compound (700 mg) as a solid.

$^1$H-NMR (CDCl$_3$) δ: 0.98 (9H, s), 1.35-1.47 (9H, m), 1.81-2.11 (4H, m), 2.11-2.36 (4H, m), 3.11-3.99 (9H, m), 6.76-6.90 (2H, m), 7.12-7.23 (2H, m), 7.34-7.48 (6H, m), 7.50-7.62 (4H, m). MS (m/z): 666 (M+H)$^+$.

(Step 3) N-(2-{[tert-Butyl(diphenyl)silyl]oxy}ethyl)-N-{[4,4-difluoro-1-(4-methoxyphenyl)cyclohexyl]carbonyl}glycine To a mixture of the compound (386 mg) obtained in Step 2 above, 2,6-lutidine (271 μL) and dichloromethane (6 mL), trimethylsilyl trifluoromethanesulfonate (315 μL) was added dropwise at 0° C. for 5 minutes, then the mixture was stirred at 0° C. for 1 hour. Ice and 0.25 mol/L hydrochloric acid were added to the reaction solution, and the mixture was extracted with diethyl ether. The organic layer was washed with saturated brine, and dried over anhydrous sodium sulfate. The solvent was concentrated under reduced pressure, then the residue obtained was purified by silica gel column chromatography (hexane/ethyl acetate) to obtain the title compound (321 mg) as an oil.

$^1$H-NMR (CDCl$_3$) δ: 0.98 (9H, s), 1.80-2.45 (8H, m), 3.10-4.23 (9H, m), 6.72-6.90 (2H, m), 7.07-7.25 (2H, m), 7.32-7.47 (6H, m), 7.48-7.63 (4H, m). MS (m/z): 608 (M−H)$^−$.

(Step 4) tert-Butyl 5-{[N-(2-{[tert-butyl(diphenyl)silyl]oxy}ethyl)-N-{[4,4-difluoro-1-(4-methoxyphenyl)cyclohexyl]carbonyl}glycyl]amino}-1H-pyrazolo[4,3-b]pyridine-1-carboxylate The compound (320 mg) obtained in Step 3 above and the compound (246 mg) obtained in Reference Example A-6 were subjected to the same procedure as in Step 6 of Example 27 to obtain the title compound (391 mg) as a solid.

$^1$H-NMR (CDCl$_3$) δ: 0.97 (9H, s), 1.74 (9H, s), 1.87-2.42 (8H, m), 3.10-3.81 (7H, m), 4.14-4.26 (2H, m), 6.78-6.83 (2H, m), 7.14-7.22 (2H, m), 7.32-7.46 (6H, m), 7.49-7.60 (4H, m), 8.15-8.66 (4H, m). MS (m/z): 826 (M+H)$^+$.

(Step 5) N-(2-{[tert-Butyl(diphenyl)silyl]oxy}ethyl)-4,4-difluoro-1-(4-methoxyphenyl)-N-[2-oxo-2-(1H-pyrazolo[4,3-b]pyridin-5-ylamino)ethyl]cyclohexanecarboxamide The compound (290 mg) obtained in Step 4 above was subjected to the same procedure as in Step 5 of Example 4 to obtain the title compound (177 mg) as a solid.

$^1$H-NMR (CDCl$_3$) δ: 0.97 (9H, s), 1.86-2.08 (4H, m), 2.15-2.43 (4H, m), 3.07-3.81 (7H, m), 4.15-4.25 (2H, m), 6.82 (2H, d, J=9.2 Hz), 7.20 (2H, d, J=9.2 Hz), 7.32-7.47 (6H, m), 7.49-7.59 (4H, m), 7.78-7.87 (1H, m), 8.13 (1H, s), 8.19-8.43 (2H, m), 10.54 (1H, s). MS (m/z): 726 (M+H)$^+$.

(Step 6) 4,4-Difluoro-N-(2-hydroxyethyl)-1-(4-methoxyphenyl)-N-[2-oxo-2-(1H-pyrazolo[4,3-b]pyridin-5-ylamino)ethyl]cyclohexanecarboxamide The compound (177 mg) obtained in Step 5 above was subjected to the same procedure as in Step 3 of Example 69 to obtain the title compound (91 mg) as a solid.

$^1$H-NMR (DMSO-D$_6$) δ: 1.79-2.04 (5H, m), 2.11-2.42 (5H, m), 3.11-3.38 (2H, m), 3.72 (3H, s), 4.06-4.19 (2H, m), 4.41-4.48 (1H, m), 6.91 (2H, d, J=8.5 Hz), 7.23 (2H, d, J=8.5 Hz), 7.91-8.09 (3H, m), 10.24 (1H, s), 13.04 (1H, s). MS (m/z): 488 (M+H)$^+$.

Example 73

(4R)-1-{[4,4-Difluoro-1-(4-methoxyphenyl)cyclohexyl]carbonyl}-4-fluoro-N-(2-oxo-2,3-dihydro-1H-pyrrolo[3,2-b]pyridin-5-yl)-D-prolinamide

[Formula 144]

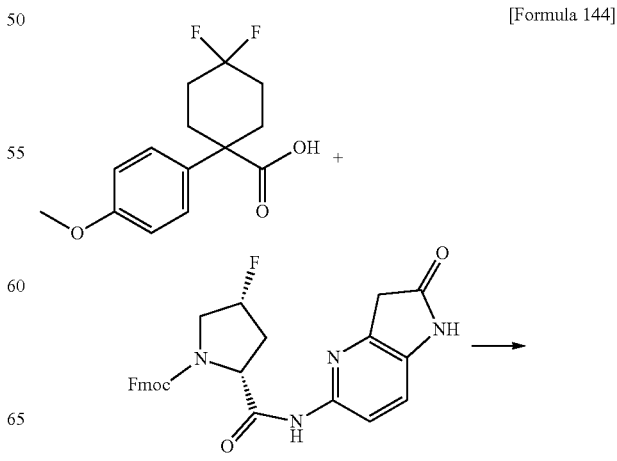

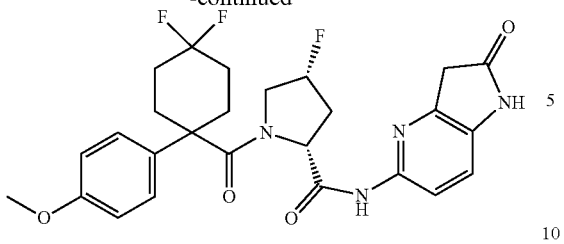

To a solution of the compound (555 mg) obtained in Reference Example C-4 in dichloromethane (10 mL), thionyl chloride (0.3 mL) and N,N-dimethylformamide (7 μL) were added. Then, the mixture was stirred at 40° C. for 1 hour. The reaction mixture was concentrated, and toluene was added, then the mixture was concentrated again, and dried. Tetrahydrofuran (5 mL) was added to the residue obtained to obtain a solution of the acid chloride in tetrahydrofuran. Separately, a solution of the compound (250 mg) obtained in Step 3 of Example 66 in tetrahydrofuran (10 mL) was cooled to 0° C., and then DBU (0.153 mL) was added. The mixture was stirred for 15 minutes, then a saturated aqueous sodium hydrogen carbonate solution (10 mL) was added, and the solution of the acid chloride in tetrahydrofuran obtained above was added thereto portionwise. Water was added to the reaction mixture, then the mixture was extracted with ethyl acetate. The organic layer was washed with water and with saturated brine sequentially, and then dried over anhydrous sodium sulfate, filtered, and concentrated. The residue obtained was purified by silica gel column chromatography (chloroform/methanol) to obtain the title compound (52 mg) as a solid.

$^1$H-NMR (DMSO-D$_6$) δ: 1.60-1.73 (1H, m), 1.86-2.48 (9H, m), 2.92-3.09 (1H, m), 3.21-3.35 (1H, m), 3.57 (2H, s), 3.76 (3H, s), 4.69-4.78 (1H, m), 4.92-5.14 (1H, m), 6.95 (2H, d, J=8.5 Hz), 7.17 (1H, d, J=8.5 Hz), 7.27 (2H, d, J=8.5 Hz), 7.87 (1H, d, J=8.5 Hz), 10.24 (1H, s), 10.46 (1H, s). MS (m/z): 517 (M+H)$^+$.

Example 74

(3R)-1-{[4,4-Difluoro-1-(4-methoxyphenyl)cyclohexyl]carbonyl}-3-hydroxy-N-1H-pyrrolo[3,2-b]pyridin-5-yl-D-prolinamide

[Formula 145]

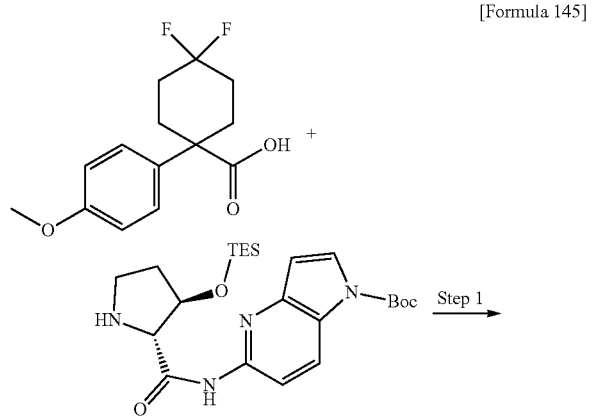

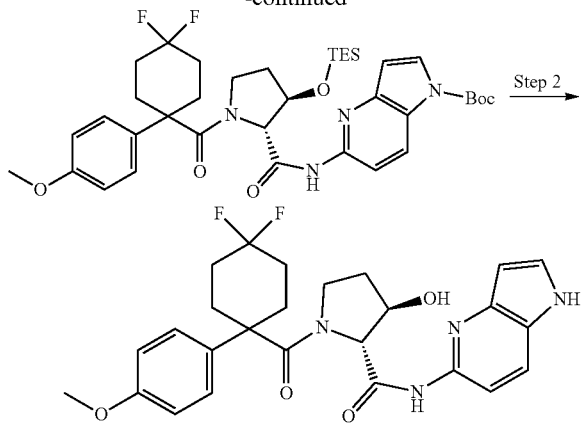

(Step 1) tert-Butyl 5-({(3R)-1-{[4,4-difluoro-1-(4-methoxyphenyl)cyclohexyl]carbonyl}-3-[(triethylsilyl)oxy]-D-prolyl}amino)-1H-pyrrolo[3,2-b]pyridine-1-carboxylate The compound (189 mg) obtained in Reference Example C-4 and the compound (248 mg) obtained in Reference Example B-9 were subjected to the same procedure as in Step 1 of Reference Example D-2 to obtain the title compound (333 mg) as a solid.

$^1$H-NMR (CDCl$_3$) δ: 0.58 (6H, q, J=7.9 Hz), 0.91 (9H, t, J=7.9 Hz), 1.62-2.14 (6H, m), 1.68 (9H, s), 2.15-2.42 (2H, m), 2.43-2.57 (2H, m), 3.04-3.21 (2H, m), 3.81 (3H, s), 4.47-4.54 (1H, m), 4.55-4.60 (1H, m), 6.62-6.65 (1H, m), 6.90 (2H, d, J=8.5 Hz), 7.26 (2H, d, J=8.5 Hz), 7.75-7.83 (1H, m), 8.08-8.15 (1H, m), 8.26-8.40 (1H, m), 8.81 (1H, s). MS (m/z): 713 (M+H)$^+$.

(Step 2) (3R)-1-{[4,4-Difluoro-1-(4-methoxyphenyl)cyclohexyl]carbonyl}-3-hydroxy-N-1H-pyrrolo[3,2-b]pyridin-5-yl-D-prolinamide The compound (317 mg) obtained in Step 1 above was subjected to the same procedure as in Step 5 of Example 4 to obtain the title compound (186 mg) as a solid.

$^1$H-NMR (DMSO-D$_6$) δ: 1.45-1.57 (1H, m), 1.66-2.45 (9H, m), 2.89-2.99 (1H, m), 3.11-3.19 (1H, m), 3.76 (3H, s), 4.07-4.14 (1H, m), 4.45-4.51 (1H, m), 5.13-5.18 (1H, m), 6.41-6.45 (1H, m), 6.95 (2H, d, J=7.9 Hz), 7.26 (2H, d, J=7.9 Hz), 7.58-7.62 (1H, m), 7.78 (1H, d, J=8.5 Hz), 7.86 (1H, d, J=8.5 Hz), 10.28 (1H, s), 11.26 (1H, s).

MS (m/z): 499 (M+H)$^+$.

Example 75

1-{[4,4-Difluoro-1-(4-methoxyphenyl)cyclohexyl]carbonyl}-4-oxo-N-1H-pyrrolo[3,2-b]pyridin-5-yl-D-prolinamide

[Formula 146]

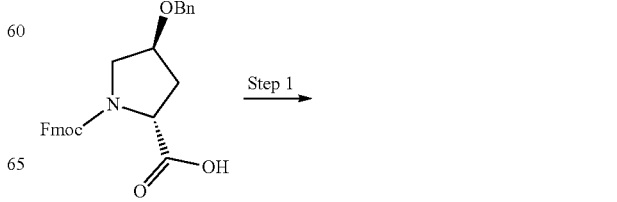

-continued

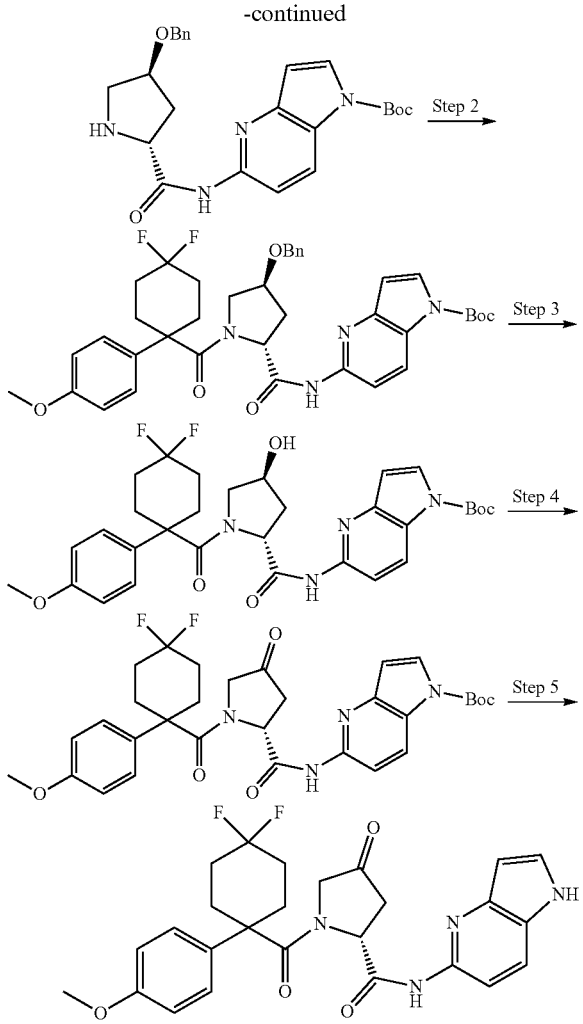

(Step 1) tert-Butyl 5-{[(4S)-4-(benzyloxy)-D-prolyl]amino}-1H-pyrrolo[3,2-b]pyridine-1-carboxylate A solution of (4S)-4-(benzyloxy)-1-[(9H-fluoren-9-ylmethoxy)carbonyl]-D-proline (1.00 g) in dichloromethane (6 mL) was cooled to 0° C., and thionyl chloride (0.590 mL) and N,N-dimethylformamide (0.010 mL) were added, then the mixture was stirred at the same temperature for 1.5 hours. The solvent was distilled off under reduced pressure, and toluene was added to the residue. Then, the solvent was distilled off under reduced pressure to obtain the crude acid chloride. To a solution of the crude acid chloride in dichloromethane (13.2 mL), N,N-diisopropylethylamine (1.18 mL) was added under ice-cooling, subsequently a solution of the compound (0.551 g) obtained in Reference Example A-8 in dichloromethane (7 mL) was added dropwise. Then, the mixture was stirred for 1.5 hours. To the reaction solution, 1 mol/L hydrochloric acid was added, and the mixture was extracted with ethyl acetate. Then, the extract was washed with saturated brine, and dried over anhydrous sodium sulfate. The solvent was distilled off under reduced pressure, then the residue was roughly purified by silica gel column chromatography (hexane/ethyl acetate) to obtain the intermediate.

A solution of the intermediate in tetrahydrofuran (38 mL) was cooled to 0° C., and DBU (0.680 mL) was added, then the mixture was stirred for 20 minutes. The reaction solution was purified by silica gel column chromatography (ethyl acetate/methanol) to obtain the title compound (0.842 g) as a solid.

$^1$H-NMR (CDCl$_3$) δ: 1.68 (9H, s), 2.01-2.08 (1H, m), 2.57 (2H, dd, J=14.3, 8.8 Hz), 2.89 (1H, dd, J=12.6, 3.5 Hz), 3.26 (1H, d, J=12.8 Hz), 4.13 (2H, t, J=8.5 Hz), 4.51 (2H, dd, J=25.1, 11.7 Hz), 6.62 (1H, d, J=3.6 Hz), 7.26-7.38 (5H, m), 7.80 (1H, s), 8.27 (1H, d, J=8.8 Hz), 8.34 (1H, s), 10.28 (1H, s).

(Step 2) tert-Butyl 5-{[(4S)-4-(benzyloxy)-1-{[4,4-difluoro-1-(4-methoxyphenyl)cyclohexyl]carbonyl}-D-prolyl]amino}-1H-pyrrolo[3,2-b]pyridine-1-carboxylate The compound (210 mg) obtained in Reference Example C-4 and the compound (317 mg) obtained in Step 1 above were subjected to the same procedure as in Step 1 of Example 45 to obtain the title compound (521 mg) as a solid.

$^1$H-NMR (CDCl$_3$) δ: 1.68-1.73 (10H, m), 1.99 (1H, s), 2.09-2.46 (9H, m), 3.15 (1H, dd, J=11.4, 3.5 Hz), 3.47 (1H, d, J=11.5 Hz), 3.91 (3H, dt, J=52.8, 9.3 Hz), 4.89 (1H, t, J=7.9 Hz), 6.62 (1H, d, J=3.9 Hz), 6.82 (2H, d, J=8.8 Hz), 7.10 (2H, d, J=7.0 Hz), 7.25 (2H, t, J=2.7 Hz), 7.29-7.34 (3H, m), 7.80 (1H, s), 8.13 (1H, d, J=9.1 Hz), 8.33 (1H, s), 8.83 (1H, s). MS (m/z): 689 (M+H)$^+$.

(Step 3) tert-Butyl 5-{[(4S)-1-{[4,4-difluoro-1-(4-methoxyphenyl)cyclohexyl]carbonyl}-4-hydroxy-D-prolyl]amino}-1H-pyrrolo[3,2-b]pyridine-1-carboxylate The compound (521 mg) obtained in Step 2 above was subjected to the same procedure as in Step 4 of Example 71 to obtain the title compound (499 mg) as a solid.

MS (m/z): 599 (M+H)$^+$.

(Step 4) tert-Butyl 5-[(1-{[4,4-difluoro-1-(4-methoxyphenyl)cyclohexyl]carbonyl}-4-oxo-D-prolyl)amino]-1H-pyrrolo[3,2-b]pyridine-1-carboxylate The compound (347 mg) obtained in Step 3 above was subjected to the same procedure as in Step 4 of Example 31 to obtain the title compound (109 mg) as an oil.

$^1$H-NMR (CDCl$_3$) δ: 1.68 (9H, s), 1.82-2.49 (8H, m), 2.50-2.63 (1H, m), 2.83-2.93 (1H, m), 3.33-3.47 (2H, m), 3.79 (3H, s), 5.34-5.45 (1H, m), 6.62-6.66 (1H, m), 6.83-6.87 (2H, m), 7.14-7.20 (2H, m), 7.79-7.85 (1H, m), 8.00-8.08 (1H, m), 8.36 (1H, s), 9.06 (1H, s). MS (m/z): 597 (M+H)$^+$.

(Step 5) 1-{[4,4-Difluoro-1-(4-methoxyphenyl)cyclohexyl]carbonyl}-4-oxo-N-1H-pyrrolo[3,2-b]pyridin-5-yl-D-prolinamide To a solution of the compound (109 mg) obtained in Step 4 above in dichloromethane (4 mL), trifluoroacetic acid (2 mL) was added at 0° C., and the mixture was stirred at room temperature for 1 hour. Trifluoroacetic acid (2 mL) was added at room temperature, and the mixture was stirred until the reactants disappeared. The reaction solution was concentrated under reduced pressure, then a saturated aqueous sodium hydrogen carbonate solution was added to the residue obtained. Then, the mixture was extracted with ethyl acetate. The organic layer was washed with a saturated aqueous sodium hydrogen carbonate solution, with water

Example 76

4,4-Difluoro-N-[(2R)-3-hydroxy-1-oxo-1-(1H-pyrazolo[4,3-b]pyridin-5-ylamino)propan-2-yl]-1-(4-methoxyphenyl)-N—(²H₃)methylcyclohexanecarboxamide

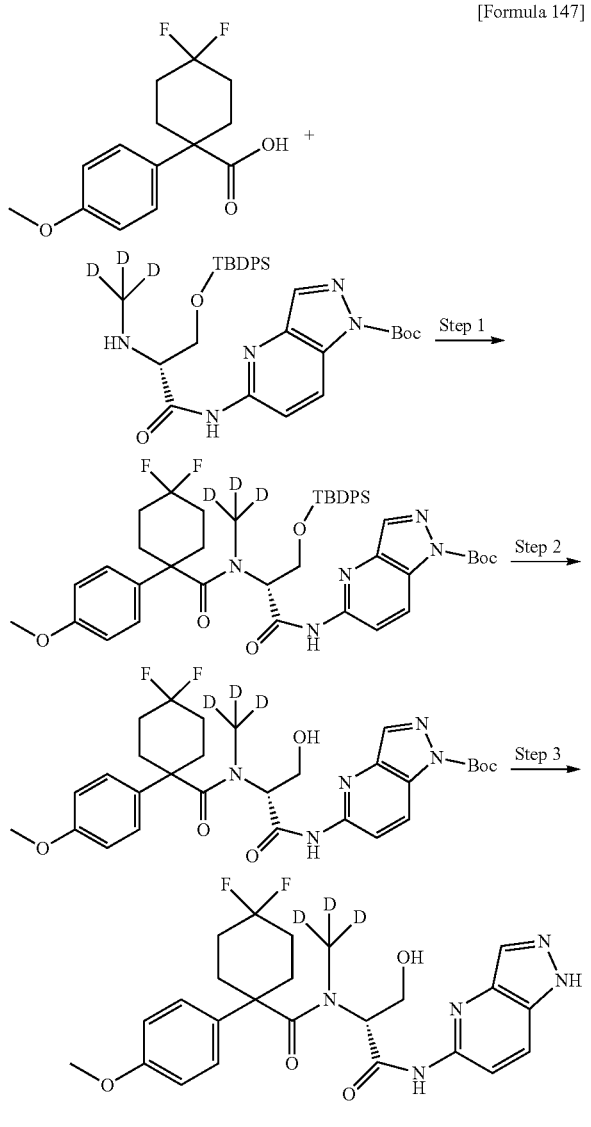

[Formula 147]

(Step 1) tert-Butyl 5-({O-[tert-butyl(diphenyl)silyl]-N-{[4,4-difluoro-1-(4-methoxyphenyl)cyclohexyl]carbonyl}-N—(²H₃)methyl-D-seryl}amino)-1H-pyrazolo[4,3-b]pyridine-1-carboxylate The compound (806 mg) obtained in Reference Example C-4 and the compound (391 mg) obtained in Reference Example B-10 were subjected to the same procedure as in Step 1 of Reference Example D-2 to obtain the title compound quantitatively as an oil.

¹H-NMR (CDCl₃) δ: 1.09 (9H, s), 1.70-2.57 (8H, m), 1.73 (9H, s), 3.71 (3H, s), 3.90-4.02 (1H, m), 4.16-4.29 (1H, m), 5.03-5.15 (1H, m), 6.75 (2H, d, J=8.5 Hz), 7.19 (2H, d, J=8.5 Hz), 7.34-7.50 (6H, m), 7.61-7.72 (4H, m), 8.25 (1H, s), 8.31 (1H, d, J=9.4 Hz), 8.41 (1H, d, J=9.4 Hz), 9.37 (1H, s). MS (m/z): 829 (M+H)⁺.

(Step 2) tert-Butyl 5-{[N-{[4,4-difluoro-1-(4-methoxyphenyl)cyclohexyl]carbonyl}-N—(²H₃)methyl-D-seryl]amino}-1H-pyrazolo[4,3-b]pyridine-1-carboxylate The compound (559 mg) obtained in Step 1 above was subjected to the same procedure as in Step 3 of Example 69 to obtain the title compound (380 mg) as an oil.

¹H-NMR (CDCl₃) δ: 1.73 (9H, s), 1.76-2.59 (8H, m), 3.73 (3H, s), 3.84-4.01 (1H, m), 4.16-4.27 (1H, m), 4.90-5.15 (1H, m), 6.85 (2H, d, J=8.5 Hz), 7.26 (2H, d, J=8.5 Hz), 8.26 (1H, s), 8.35 (1H, d, J=9.2 Hz), 8.44 (1H, d, J=9.2 Hz), 9.09 (1H, br s). MS (m/z): 591 (M+H)⁺.

(Step 3) 4,4-Difluoro-N-[(2R)-3-hydroxy-1-oxo-1-(1H-pyrazolo[4,3-b]pyridin-5-ylamino)propan-2-yl]-1-(4-methoxyphenyl)-N—(²H₃)methylcyclohexanecarboxamide The compound (380 mg) obtained in Step 2 above was subjected to the same procedure as in Step 5 of Example 4 to obtain the title compound (240 mg) as a solid.

¹H-NMR (CDCl₃) δ: 1.75-2.58 (8H, m), 2.70-3.00 (1H, m), 3.74 (3H, s), 3.82-3.99 (1H, m), 4.16-4.29 (1H, m), 4.91-5.09 (1H, m), 6.87 (2H, d, J=8.5 Hz), 7.28 (2H, d, J=8.5 Hz), 7.86 (1H, d, J=9.2 Hz), 8.18 (1H, s), 8.24 (1H, d, J=9.2 Hz), 8.98 (1H, br s), 10.44 (1H, br s). MS (m/z): 491 (M+H)⁺.

Example 77

4,4-Difluoro-N-[(2R)-3-hydroxy-1-oxo-1-(1H-pyrrolo[3,2-b]pyridin-5-ylamino)propan-2-yl]-1-(4-methoxyphenyl)-N—(²H₃)methylcyclohexanecarboxamide

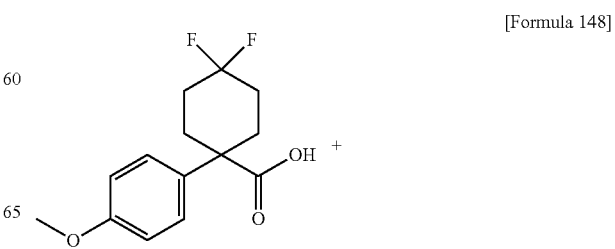

[Formula 148]

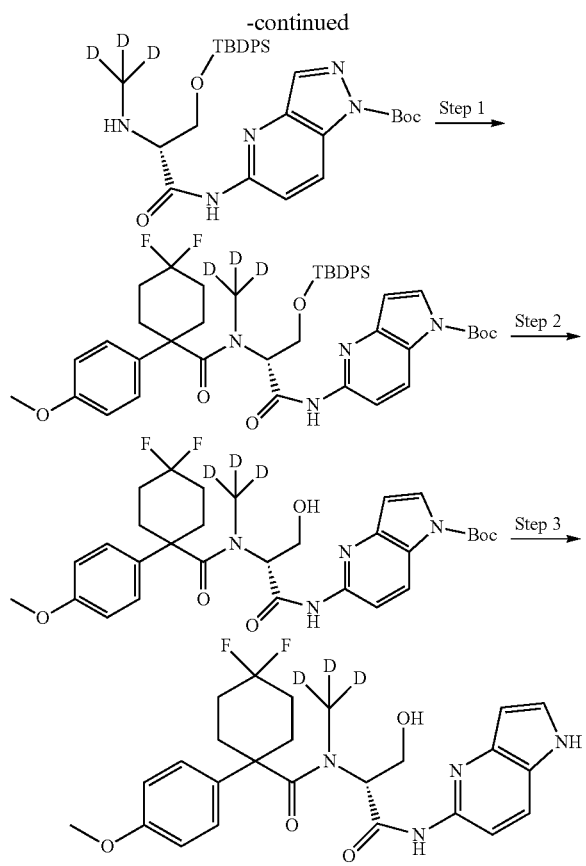

(Step 1) tert-Butyl 5-({0-[tert-butyl(diphenyl)silyl]-N-{[4,4-difluoro-1-(4-methoxyphenyl)cyclohexyl]carbonyl}-N—($^2$H$_3$)methyl-D-seryl}amino)-1H-pyrrolo[3,2-b]pyridine-1-carboxylate To a suspension of the compound (213 mg) obtained in Reference Example C-4 in toluene (4 mL), thionyl chloride (171 μL) and N,N-dimethylformamide (10 μL) were added at 0° C., then the mixture obtained was stirred at 75° C. for 1 hour. The solvent was distilled off under reduced pressure to obtain the crude acid chloride. The compound (411 mg) obtained in Reference Example B-11 was dissolved in dichloromethane (8 mL), then a solution of the crude acid chloride obtained above in dichloromethane (2 mL) was added at 0° C. Subsequently, pyridine (230 μL) and 4-dimethylaminopyridine (8.9 mg) were added, and the mixture was stirred at room temperature for 16 hours. With the compound (637 mg) obtained in Reference Example C-4, toluene (12 mL), thionyl chloride (513 μL) and N,N-dimethylformamide (10 μL), the crude acid chloride was prepared again. To the reaction solution, a solution of the acid chloride in dichloromethane (2 mL) was added at 0° C. Pyridine (690 μL) and 4-dimethylaminopyridine (26.3 mg) were further added, and the mixture was stirred at room temperature for 5 hours. Ice was added to the reaction solution, and the mixture was extracted with diethyl ether. The organic layer was washed with 10% aqueous citric acid solution three times, with saturated aqueous sodium hydrogen carbonate solution and with saturated brine, then dried over anhydrous sodium sulfate. The solvent was distilled off under reduced pressure, then the residue obtained was purified by silica gel column chromatography (hexane/ethyl acetate), then by amino silica gel column chromatography (hexane/ethyl acetate) to obtain the title compound (460 mg) as a solid.

$^1$H-NMR (CDCl$_3$) δ: 1.08 (9H, s), 1.67 (9H, s), 1.70-2.62 (8H, m), 3.70 (3H, s), 3.92-4.06 (1H, m), 4.15-4.27 (1H, m), 5.12-5.26 (1H, m), 6.60-6.67 (1H, m), 6.75 (2H, d, J=8.8 Hz), 7.21 (2H, d, J=8.8 Hz), 7.32-7.49 (6H, m), 7.59-7.72 (4H, m), 7.76-7.85 (1H, m), 8.02 (1H, d, J=9.1 Hz), 8.24-8.37 (1H, m), 9.09 (1H, s). MS (m/z): 828 (M+H)$^+$.

(Step 2) tert-Butyl 5-{[N-{[4,4-difluoro-1-(4-methoxyphenyl)cyclohexyl]carbonyl}-N—($^2$H$_3$)methyl-D-seryl]amino}-1H-pyrrolo[3,2-b]pyridine-1-carboxylate The compound (457 mg) obtained in Step 1 above was subjected to the same procedure as in Step 3 of Example 69 to obtain the title compound quantitatively as a solid.

$^1$H-NMR (CDCl$_3$) δ: 1.68 (9H, s), 1.72-2.59 (8H, m), 2.69-2.99 (1H, m), 3.73 (3H, s), 3.80-4.01 (1H, m), 4.14-4.27 (1H, m), 4.92-5.18 (1H, m), 6.62-6.67 (1H, m), 6.86 (2H, d, J=8.5 Hz), 7.28 (2H, d, J=8.5 Hz), 7.74-7.88 (1H, m), 8.07 (1H, d, J=9.1 Hz), 8.26-8.42 (1H, m), 8.85 (1H, br s). MS (m/z): 590 (M+H)$^+$.

(Step 3) 4,4-Difluoro-N-[(2R)-3-hydroxy-1-oxo-1-(1H-pyrrolo[3,2-b]pyridin-5-ylamino)propan-2-yl]-1-(4-methoxyphenyl)-N—($^2$H$_3$)methylcyclohexanecarboxamide The compound (325 mg) obtained in Step 2 above was subjected to the same procedure as in Step 5 of Example 4 to obtain the title compound (206 mg) as a solid.

$^1$H-NMR (DMSO-D$_6$) δ: 1.55-2.47 (8H, m), 3.65-3.80 (1H, m), 3.73 (3H, s), 3.87-3.99 (1H, m), 4.88-5.04 (1H, m), 5.11-5.23 (1H, m), 6.38-6.46 (1H, m), 6.90 (2H, d, J=7.9 Hz), 7.25 (2H, d, J=7.9 Hz), 7.54-7.65 (1H, m), 7.70-7.88 (2H, m), 9.92 (1H, s), 11.26 (1H, s). MS (m/z): 490 (M+H)$^+$.

Example 78

4,4-Difluoro-N-[(2R,3R)-3-hydroxy-1-oxo-1-(1H-pyrazolo[4,3-b]pyridin-5-ylamino)butan-2-yl]-1-(4-methoxyphenyl)-N-methylcyclohexanecarboxamide

[Formula 149]

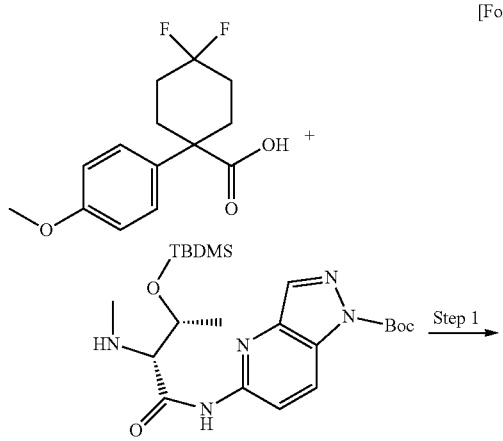

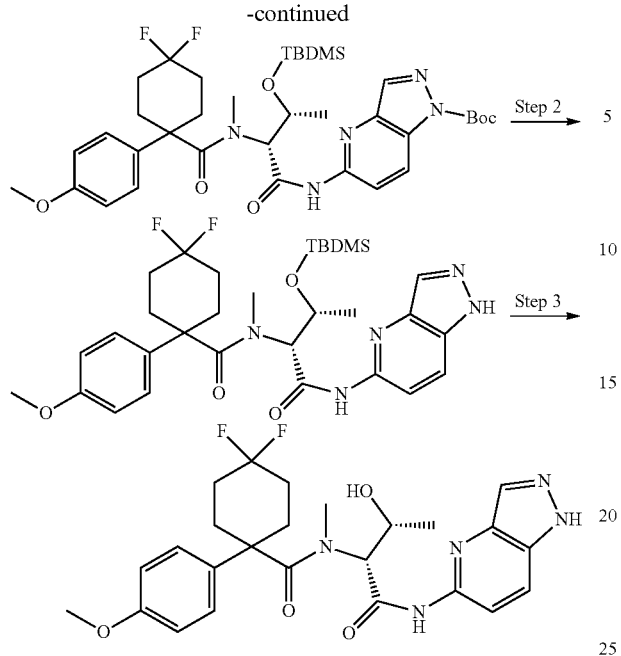

(Step 1) tert-Butyl 5-[(O-[tert-butyl(dimethyl)silyl]-N-{[4,4-difluoro-1-(4-methoxyphenyl)cyclohexyl]carbonyl}-N-methyl-D-allothreonyl)amino]-1H-pyrazolo[4,3-b]pyridine-1-carboxylate The compound obtained in Reference Example C-4 (609 mg) and the compound (455 mg) obtained in Reference Example B-12 were subjected to the same procedure as in Step 1 of Example 45 to obtain the title compound (238 mg) as a solid.

$^1$H-NMR (DMSO-D$_6$) δ: −0.02 (3H, s), 0.07 (3H, s), 0.80 (9H, s), 1.12 (3H, d, J=6.1 Hz), 1.67 (9H, s), 1.74-1.85 (1H, m), 1.89-2.14 (5H, m), 2.35-2.45 (2H, m), 2.62 (3H, s), 3.68 (3H, s), 4.43 (1H, dd, J=8.5, 6.1 Hz), 4.87 (1H, d, J=8.5 Hz), 6.82 (2H, d, J=9.2 Hz), 7.18 (2H, d, J=8.5 Hz), 8.19-8.23 (1H, m), 8.38 (2H, d, J=9.2 Hz), 9.91 (1H, s). MS (m/z): 716 (M+H)$^+$.

(Step 2) N-[(2R,3R)-3-{[tert-Butyl(dimethyl)silyl]oxy}-1-oxo-1-(1H-pyrazolo[4,3-b]pyridin-5-ylamino)butan-2-yl]-4,4-difluoro-1-(4-methoxyphenyl)-N-methylcyclohexanecarboxamide The compound (282 mg) obtained in Step 1 above was subjected to the same procedure as in Step 3 of Example 1 to obtain the title compound (242 mg) as a solid.

$^1$H-NMR (DMSO-D$_6$) δ: 0.00 (3H, s), 0.08 (3H, s), 0.81 (9H, s), 1.11 (3H, d, J=6.1 Hz), 1.80 (1H, td, J=13.4, 3.7 Hz), 1.88-2.26 (5H, m), 2.36-2.46 (2H, m), 2.61 (3H, s), 3.67 (3H, s), 4.43 (1H, dt, J=14.4, 6.1 Hz), 4.85 (1H, d, J=8.5 Hz), 6.81 (2H, d, J=7.9 Hz), 7.19 (2H, d, J=8.5 Hz), 7.95-8.08 (2H, m), 8.19 (1H, d, J=1.8 Hz), 9.57 (1H, s), 13.01 (1H, br s). MS (m/z): 616 (M+H)$^+$.

(Step 3) 4,4-Difluoro-N-[(2R,3R)-3-hydroxy-1-oxo-1-(1H-pyrazolo[4,3-b]pyridin-5-ylamino)butan-2-yl]-1-(4-methoxyphenyl)-N-methylcyclohexanecarboxamide To the compound (242 mg) obtained in Step 2 above, tetrabutylammonium fluoride (1 mol/L, tetrahydrofuran solution, 3.93 mL) was added at 0° C. The mixture was stirred at room temperature for 3 hours, then the reaction solution was concentrated. To the residue obtained, water and a saturated aqueous sodium hydrogen carbonate solution were added, and the mixture was extracted with chloroform. The organic layer was dried over sodium sulfate, and the solvent was distilled off under reduced pressure. The residue obtained was purified by silica gel column chromatography (hexane/ethyl acetate) to obtain the title compound (109 mg) as a solid.

$^1$H-NMR (DMSO-d$_6$) δ: 1.09 (3H, d, J=5.5 Hz), 1.80-2.06 (4H, m), 2.12-2.32 (2H, m), 2.43 (2H, d, J=14.0 Hz), 2.59 (3H, s), 3.71 (3H, s), 4.23-4.31 (1H, m), 4.62 (1H, d, J=8.5 Hz), 5.43 (1H, d, J=5.5 Hz), 6.88 (2H, d, J=9.2 Hz), 7.23 (2H, d, J=8.5 Hz), 7.98 (1H, d, J=9.2 Hz), 8.04-8.10 (2H, m), 10.00 (1H, s), 12.98 (1H, br s). MS (m/z): 502 (M+H)$^+$.

Example 79

(4S)-3-{[4,4-Difluoro-1-(4-methoxyphenyl)cyclohexyl]carbonyl}-N-(2-methyl-1H-pyrrolo[3,2-b]pyridin-5-yl)-1,3-thiazolidine-4-carboxamide 1,1-dioxide

[Formula 150]

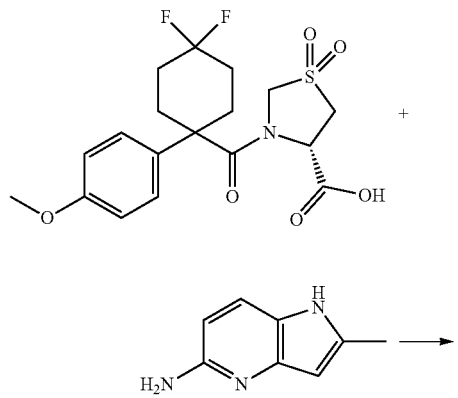

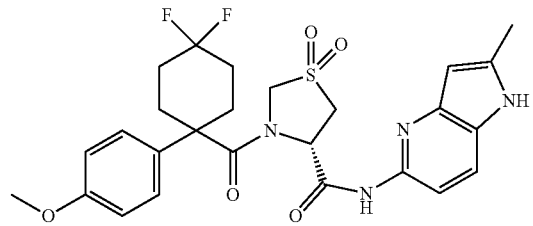

The compound (175 mg) obtained in Step 2 of Example 68 and the compound (139 mg) obtained in Reference Example A-9 were subjected to the same procedure as in Step 1 of Example 41 to obtain the title compound (175 mg) as a solid.

$^1$H-NMR (CDCl$_3$) δ: 1.75-2.64 (10H, m), 2.86-3.06 (1H, m), 3.33-3.52 (1H, m), 4.80-4.90 (1H, m), 4.94-5.14 (1H, m), 7.46-7.62 (5H, m), 7.94-7.98 (2H, m), 8.00-8.04 (2H, m), 8.27 (1H, s), 8.42-8.49 (3H, m). MS (m/z): 712 (M+H)$^+$.

Example 80

4,4-Difluoro-N-[(2R,3S)-3-hydroxy-1-oxo-1-(1H-pyrazolo[4,3-b]pyridin-5-ylamino)butan-2-yl]-1-(4-methoxyphenyl)-N-methylcyclohexanecarboxamide

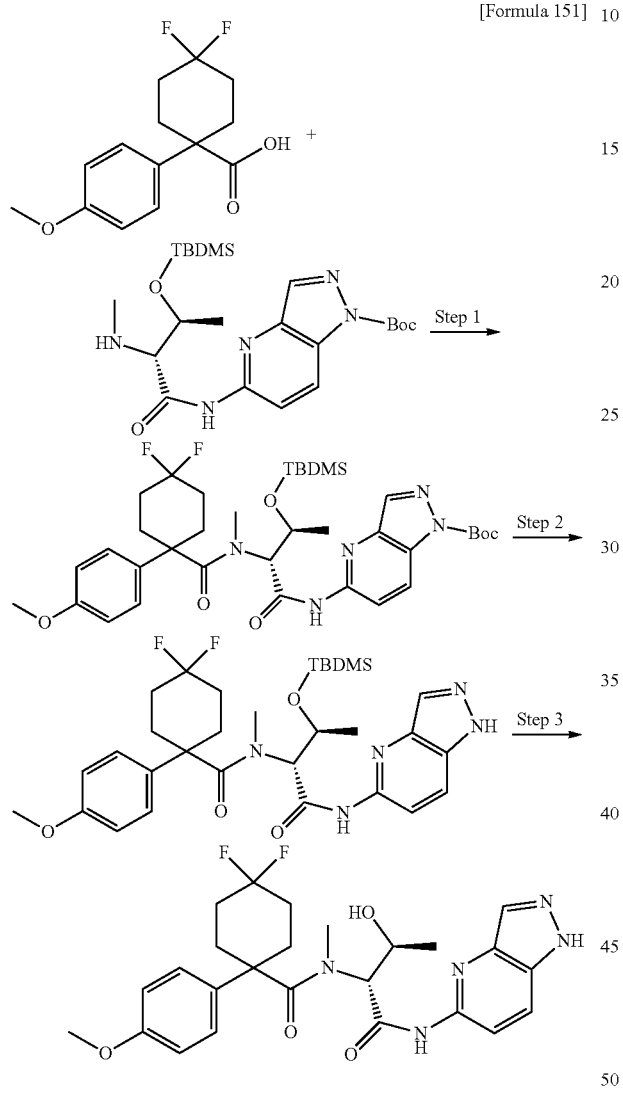

(Step 1) tert-Butyl 5-[(O-[tert-butyl(dimethyl)silyl]-N-{[4,4-difluoro-1-(4-methoxyphenyl)cyclohexyl]carbonyl}-N-methyl-D-threonyl)amino]-1H-pyrazolo[4,3-b]pyridine-1-carboxylate The compound (1.29 g) obtained in Reference Example C-4 and the compound (0.967 g) obtained in Reference Example B-13 were subjected to the same procedure as in Step 1 of Example 45 to obtain the title compound (1.38 g) as a solid.

$^1$H-NMR (DMSO-D$_6$) δ: −0.13 (3H, s), 0.01 (3H, d, J=1.8 Hz), 0.73 (9H, d, J=3.0 Hz), 1.12 (3H, br s), 1.67 (9H, d, J=2.4 Hz), 1.75-2.20 (6H, m), 2.43 (2H, d, J=12.1 Hz), 2.90 (3H, s), 3.61-3.77 (3H, m), 4.65-4.73 (1H, m), 5.16 (1H, br s), 6.83-6.88 (2H, m), 7.19 (2H, dd, J=9.1, 2.4 Hz), 8.17-8.23 (1H, m), 8.34-8.40 (2H, m), 10.18 (1H, br s). MS (m/z): 716 (M+H)$^+$.

(Step 2) N-[(2R,3S)-3-{[tert-Butyl(dimethyl)silyl]oxy}-1-oxo-1-(1H-pyrazolo[4,3-b]pyridin-5-ylamino)butan-2-yl]-4,4-difluoro-1-(4-methoxyphenyl)-N-methylcyclohexanecarboxamide The compound (1.31 g) obtained in Step 1 above was subjected to the same procedure as in Step 3 of Example 1 to obtain the title compound (1.07 g) as a solid. MS (m/z): 616 (M+H)$^+$.

(Step 3) 4,4-Difluoro-N-[(2R,3S)-3-hydroxy-1-oxo-1-(1H-pyrazolo[4,3-b]pyridin-5-ylamino)butan-2-yl]-1-(4-methoxyphenyl)-N-methylcyclohexanecarboxamide The compound (1.07 g) obtained in Step 2 above was subjected to the same procedure as in Step 3 of Example 78 to obtain the title compound (86.4 mg) as a solid.

$^1$H-NMR (DMSO-D$_6$) δ: 1.18 (3H, d, J=6.1 Hz), 1.67-1.76 (1H, m), 1.92-2.46 (7H, m), 2.75 (3H, s), 3.66 (3H, s), 4.23 (1H, dd, J=13.4, 6.1 Hz), 4.69 (1H, dd, J=5.5, 1.8 Hz), 4.91 (1H, d, J=7.3 Hz), 6.80 (2H, d, J=9.2 Hz), 7.21 (2H, d, J=9.2 Hz), 7.96 (2H, s), 8.09 (1H, br s), 9.61 (1H, br s), 12.99 (1H, br s). MS (m/z): 502 (M+H)$^+$.

Example 81

(4R)-4-Fluoro-1-({1-[4-(2-hydroxypropan-2-yl)phenyl]cyclohexyl}carbonyl)-N-1H-pyrazolo[4,3-b]pyridin-5-yl-D-prolinamide (81a) and methyl 4-(1-{[(2R,4R)-4-Fluoro-2-(1H-pyrazolo[4,3-b]pyridin-5-ylcarbamoyl)pyrrolidin-1-yl]carbonyl}cyclohexyl)benzoate (81b)

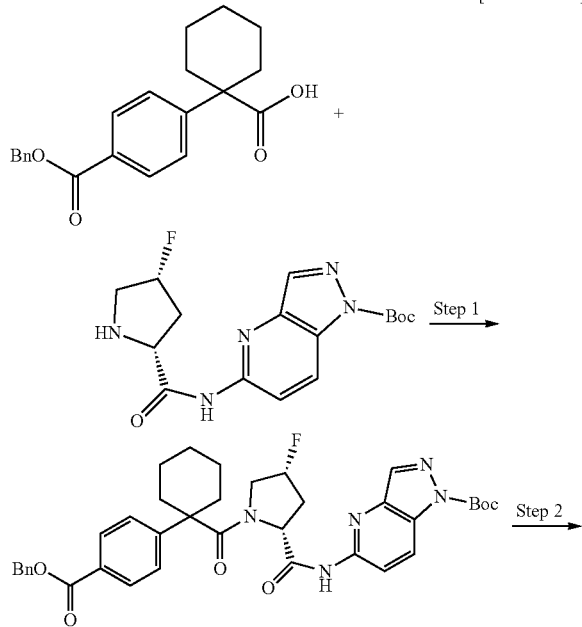

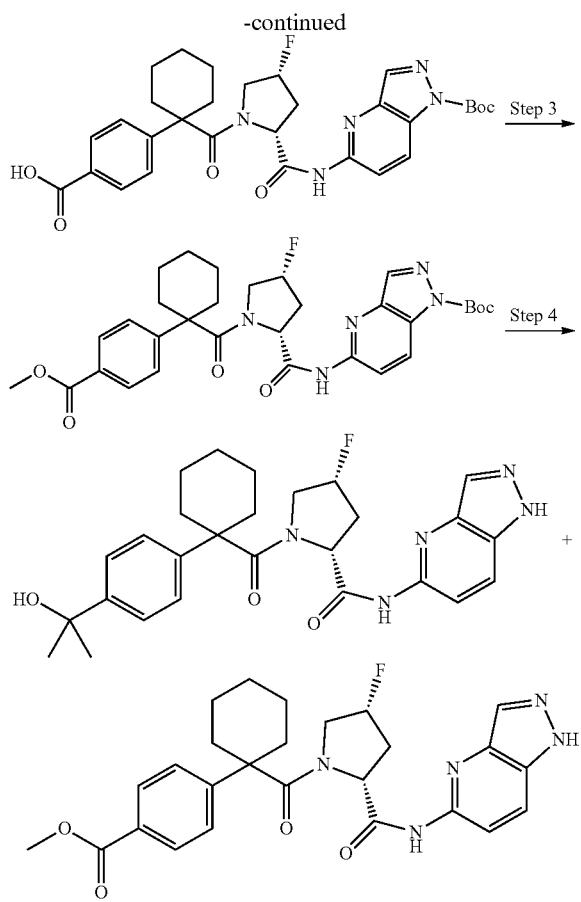

(Step 1) tert-Butyl 5-({(4R)-1-[(1-{4-[(benzyloxy)carbonyl]phenyl}cyclohexyl)carbonyl]-4-fluoro-D-prolyl}amino)-1H-pyrazolo[4,3-b]pyridine-1-carboxylate The compound (100 mg) obtained in Reference Example C-20 and the compound (103 mg) obtained in Reference Example B-2 were subjected to the same procedure as in Step 1 of Example 4 to obtain the title compound (132 mg) as a solid.

$^1$H-NMR (DMSO-D$_6$) δ: 1.22-1.34 (1H, m), 1.49-1.65 (5H, m), 1.67 (9H, s), 1.70-1.83 (2H, m), 2.09 (1H, dd, J=21.4, 13.4 Hz), 2.23-2.41 (3H, m), 3.20-3.40 (2H, m), 4.77 (1H, d, J=10.4 Hz), 5.04 (1H, d, J=56.2 Hz), 5.33 (2H, s), 7.32-7.52 (7H, m), 7.97 (2H, d, J=8.5 Hz), 8.25 (1H, d, J=9.2 Hz), 8.34-8.40 (2H, m), 10.06 (1H, s). MS (m/z): 670 (M+H)$^+$.

(Step 2) 4-(1-{[(2R,4R)-2-{[1-(tert-Butoxycarbonyl)-1H-pyrazolo[4,3-b]pyridin-5-yl]carbamoyl}-4-fluoropyrrolidin-1-yl]carbonyl}cyclohexyl)benzoic acid The compound (328 mg) obtained in Step 1 above was subjected to the same procedure as in Step 2 of Example 4 to obtain the title compound (260 mg) as a solid.

$^1$H-NMR (DMSO-D$_6$) δ: 1.25-1.36 (1H, m), 1.50-1.64 (4H, m), 1.67 (9H, s), 1.68-1.84 (3H, m), 2.04-2.15 (1H, m), 2.24-2.43 (3H, m), 3.17-3.37 (2H, m), 4.78 (1H, dd, J=9.2, 2.4 Hz), 5.04 (1H, d, J=54.3 Hz), 7.46 (2H, d, J=8.5 Hz), 7.93 (2H, d, J=8.5 Hz), 8.26 (1H, d, J=9.2 Hz), 8.37-8.41 (2H, m), 10.05 (1H, s). MS (m/z): 580 (M+H)$^+$.

(Step 3) tert-Butyl 5-{[(4R)-4-fluoro-1-({1-[4-(methoxycarbonyl)phenyl]cyclohexyl}carbonyl)-D-prolyl]amino}-1H-pyrazolo[4,3-b]pyridine-1-carboxylate To a solution of the compound (260 mg) obtained in Step 2 above and potassium carbonate (186 mg) in N,N-dimethylformamide (5 mL), iodomethane (43.9 μL) was added at 0° C., and the mixture was stirred at room temperature for 4 hours. The reaction solution was partitioned by the addition of water and ethyl acetate. The organic layer was dried over sodium sulfate, and the solvent was distilled off under reduced pressure. The residue obtained was purified using silica gel column chromatography (hexane/ethyl acetate) to obtain the title compound (227 mg) as a solid.

$^1$H-NMR (DMSO-D$_6$) δ: 1.22-1.36 (1H, m), 1.51-1.65 (4H, m), 1.67 (9H, s), 1.69-1.84 (3H, m), 2.09 (1H, dd, J=20.8, 14.6 Hz), 2.25-2.38 (3H, m), 3.21-3.37 (2H, m), 3.83 (3H, s), 4.78 (1H, d, J=7.9 Hz), 5.04 (1H, d, J=53.7 Hz), 7.48 (2H, d, J=8.5 Hz), 7.93 (2H, d, J=8.5 Hz), 8.25 (1H, d, J=9.2 Hz), 8.37 (1H, s), 8.38 (1H, d, J=9.2 Hz), 10.05 (1H, br s). MS (m/z): 594 (M+H)$^+$.

(Step 4) (4R)-4-Fluoro-1-({1-[4-(2-hydroxypropan-2-yl)phenyl]cyclohexyl}carbonyl)-N-1H-pyrazolo[4,3-b]pyridin-5-yl-D-prolinamide (81a) and methyl 4-(1-{[(2R,4R)-4-fluoro-2-(1H-pyrazolo[4,3-b]pyridin-5-ylcarbamoyl)pyrrolidin-1-yl]carbonyl}cyclohexyl)benzoate (81b)

Under a nitrogen atmosphere, to a solution of the compound (226 mg) obtained in Step 3 above in tetrahydrofuran (3.5 mL), methylmagnesium chloride (3 mol/L, tetrahydrofuran solution, 0.570 mL) was added dropwise at −78° C. The mixture was stirred at −30° C. for 30 minutes, followed by at 0° C. for 1 hour, and then at room temperature for 15 minutes. The reaction solution was diluted with tetrahydrofuran, and neutralized with a saturated aqueous ammonium chloride solution, and then extracted with ethyl acetate. The organic layer was washed with saturated brine, then dried over anhydrous sodium sulfate, and the solvent was distilled off under reduced pressure. The residue obtained was purified by silica gel column chromatography (hexane/ethyl acetate) to obtain 81a (34 mg) and 81b (58 mg) as solids.

81a $^1$H-NMR (DMSO-D$_6$) δ: 1.44 (6H, s), 1.51-1.81 (1H, m), 1.56-1.77 (7H, m), 2.10 (1H, dd, J=20.8, 14.6 Hz), 2.22-2.36 (3H, m), 3.21-3.35 (2H, m), 4.59 (1H, d, J=1.8 Hz), 4.75 (1H, dd, J=10.4, 3.7 Hz), 5.01 (1H, d, J=53.7 Hz), 7.26 (2H, d, J=8.5 Hz), 7.46 (2H, d, J=8.5 Hz), 7.97 (1H, d, J=9.2 Hz), 8.05 (1H, s), 8.07 (1H, d, J=9.2 Hz), 9.68 (1H, s), 12.96 (1H, br s). MS (m/z): 494 (M+H)$^+$.

81b $^1$H-NMR (DMSO-D$_6$) δ: 1.25-1.36 (1H, m), 1.54-1.84 (7H, m), 2.10 (1H, dd, J=21.4, 14.6 Hz), 2.23-2.39 (3H, m), 3.22-3.35 (2H, m), 3.84 (3H, s), 4.75 (1H, dd, J=9.8, 2.4 Hz), 5.04 (1H, d, J=53.7 Hz), 7.49 (2H, d, J=8.5 Hz), 7.94 (2H, d, J=8.5 Hz), 7.96-7.99 (1H, m), 8.03-8.07 (2H, m), 9.73 (1H, s), 12.96 (1H, br s). MS (m/z): 494 (M+H)$^+$.

Example 82

(4R)-4-Fluoro-1-{[1-(4-hydroxyphenyl)cyclohexyl]carbonyl}-N-1H-pyrazolo[4,3-b]pyridin-5-yl-D-prolinamide

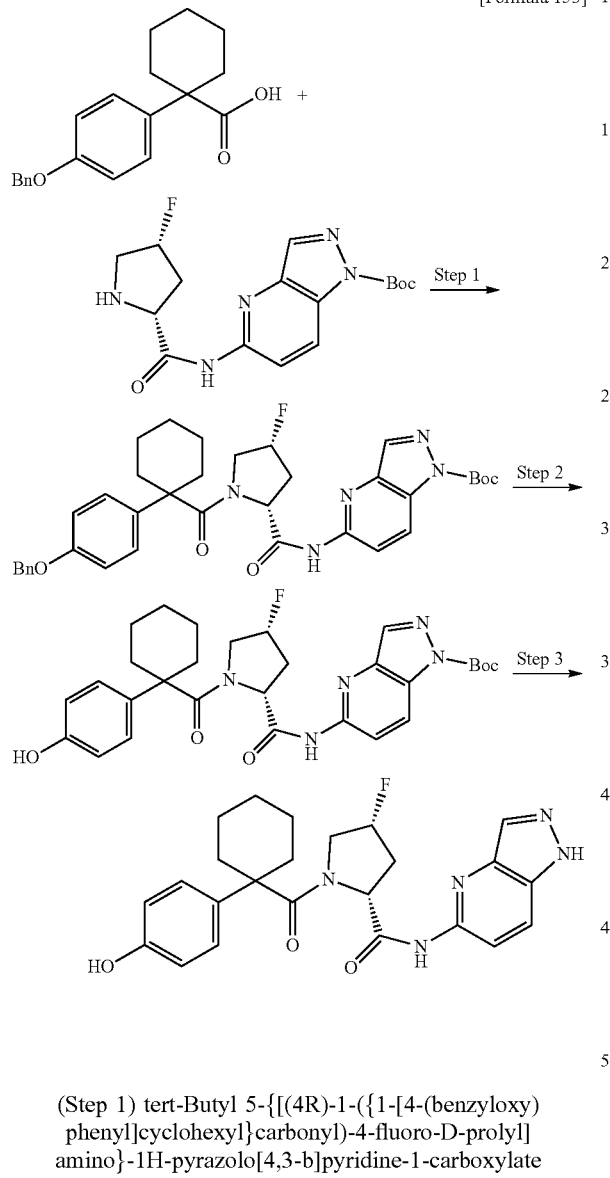

[Formula 153]

(Step 1) tert-Butyl 5-{[(4R)-1-({1-[4-(benzyloxy)phenyl]cyclohexyl}carbonyl)-4-fluoro-D-prolyl]amino}-1H-pyrazolo[4,3-b]pyridine-1-carboxylate The compound (0.600 g) obtained in Reference Example C-21 and the compound (0.675 g) obtained in Reference Example B-2 were subjected to the same procedure as in Step 3 of Example 4 to obtain the title compound (1.18 g) as a solid.

$^1$H-NMR (CDCl$_3$) δ: 1.25-1.39 (1H, m), 1.50-1.89 (17H, m), 2.29-2.47 (2H, m), 2.50-2.64 (1H, m), 2.97-3.31 (1H, m), 3.40-3.61 (1H, m), 4.71-5.12 (4H, m), 7.00 (2H, d, J=8.5 Hz), 7.22-7.28 (2H, m), 7.30-7.46 (5H, m), 8.21 (1H, s), 8.41 (1H, d, J=9.2 Hz), 8.48 (1H, d, J=9.2 Hz), 8.69 (1H, s). MS (m/z): 642 (M+H)$^+$.

(Step 2) tert-Butyl 5-{[(4R)-4-fluoro-1-{[1-(4-hydroxyphenyl)cyclohexyl]carbonyl}-D-prolyl]amino}-1H-pyrazolo[4,3-b]pyridine-1-carboxylate The compound (1.18 g) obtained in Step 1 above was subjected to the same procedure as in Step 3 of Reference Example B-15 to obtain the title compound (0.960 g) as a solid.

$^1$H-NMR (DMSO-D$_6$) δ: 1.20-1.32 (1H, m), 1.44-1.83 (16H, m), 2.01-2.46 (4H, m), 3.05-3.34 (2H, m), 4.69-4.81 (1H, m), 4.93-5.16 (1H, m), 6.76 (2H, d, J=7.9 Hz), 7.13 (2H, d, J=8.5 Hz), 8.33-8.53 (3H, m), 9.34 (1H, s), 10.51 (1H, s). MS (m/z): 552 (M+H)$^+$.

(Step 3) (4R)-4-Fluoro-1-{[1-(4-hydroxyphenyl)cyclohexyl]carbonyl}-N-1H-pyrazolo[4,3-b]pyridin-5-yl-D-prolinamide The compound (0.150 g) obtained in Step 2 above was subjected to the same procedure as in Step 2 of Example 35 to obtain the title compound (0.120 g) as a solid.

$^1$H-NMR (DMSO-D$_6$) δ: 1.15-1.35 (1H, m), 1.42-1.83 (7H, m), 1.93-2.45 (4H, m), 3.04-3.36 (2H, m), 4.63-4.82 (1H, m), 4.91-5.17 (1H, m), 6.76 (2H, d, J=8.5 Hz), 7.13 (2H, d, J=7.9 Hz), 7.99-8.22 (3H, m), 9.34 (1H, s), 10.18 (1H, s), 13.26 (1H, s). MS (m/z): 452 (M+H)$^+$.

Example 83

(4R)-1-{[1-(4-Acetylphenyl)cyclohexyl]carbonyl}-4-fluoro-N-1H-pyrazolo[4,3-b]pyridin-5-yl-D-prolinamide

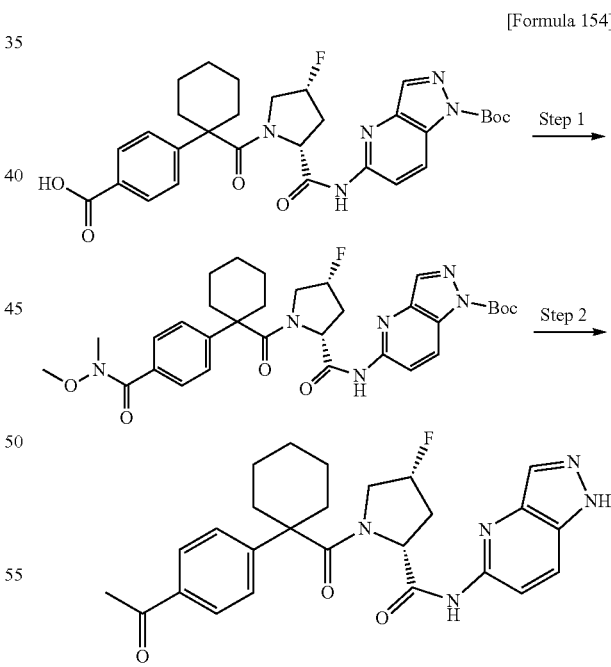

[Formula 154]

(Step 1) tert-Butyl 5-({(4R)-4-fluoro-1-[(1-{4-[methoxy(methyl)carbamoyl]phenyl}cyclohexyl)carbonyl]-D-prolyl}amino)-1H-pyrazolo[4,3-b]pyridine-1-carboxylate To a solution of the compound (300 mg) obtained in Step 2 of Example 81, 1H-benzotriazole (91 mg) and WSC hydrochloride (129 mg) in N,N-dimethylformamide (5 mL), N,O-dimethylhydroxylamine hydrochloride (61 mg) and N,N-diisopropylethylamine (225 μL) were added at 0° C. The mixture was stirred at room temperature for 14 hours, then water was added, and the mixture was extracted with ethyl acetate. The organic layer was washed with saturated brine, then dried over anhydrous sodium sulfate, and the solvent was distilled off under reduced pressure. The residue obtained was purified by silica gel column chromatography (hexane/ethyl acetate) to obtain the title compound (296 mg) as a solid.

$^1$H-NMR (DMSO-D$_6$) δ: 1.25-1.40 (1H, m), 1.50-1.64 (4H, m), 1.67 (9H, s), 1.70-1.86 (3H, m), 2.10 (1H, dd, J=20.8, 14.6 Hz), 2.24-2.42 (3H, m), 3.19-3.35 (2H, m), 3.24 (3H, s), 3.53 (3H, s), 4.78 (1H, dd, J=9.5, 2.7 Hz), 5.04 (1H, d, J=53.7 Hz), 7.42 (2H, d, J=8.5 Hz), 7.61 (2H, d, J=8.5 Hz), 8.26 (1H, d, J=9.2 Hz), 8.38 (1H, s), 8.39 (1H, d, J=9.8 Hz), 10.04 (1H, br s). MS (m/z): 623 (M+H)$^+$.

(Step 2) (4R)-1-{[1-(4-Acetylphenyl)cyclohexyl]carbonyl}-4-fluoro-N-1H-pyrazolo[4,3-b]pyridin-5-yl-D-prolinamide Under a nitrogen atmosphere, to a solution of the compound (295 mg) obtained in Step 1 above in tetrahydrofuran (4 mL), methylmagnesium chloride (3 mol/L, tetrahydrofuran solution, 0.470 mL) was added dropwise at 0° C. The mixture was stirred at room temperature for 30 minutes, then the mixture was cooled to 0° C. again, and methylmagnesium chloride (3 mol/L, tetrahydrofuran solution, 0.160 mL) was added dropwise. The mixture was stirred at room temperature for 60 hours, then the mixture was cooled to 0° C. again, and methylmagnesium chloride (3 mol/L, tetrahydrofuran solution, 0.160 mL) was added thereto, and the mixture was stirred at room temperature for 2 hours. The reaction mixture solution was diluted with tetrahydrofuran, and neutralized with a saturated aqueous ammonium chloride solution, and then extracted with ethyl acetate. The combined organic layer was washed with saturated brine, and dried over anhydrous sodium sulfate, then the solvent was distilled off under reduced pressure. The residue obtained was purified by silica gel column chromatography (hexane/ethyl acetate) to obtain the title compound (61 mg) as a solid.

$^1$H-NMR (DMSO-D$_6$) δ: 1.24-1.36 (1H, m), 1.52-1.83 (7H, m), 2.10 (1H, dd, J=21.4, 14.6 Hz), 2.23-2.39 (3H, m), 2.53 (3H, s), 3.21-3.37 (2H, m), 4.76 (1H, dd, J=9.8, 3.1 Hz), 5.04 (1H, d, J=53.7 Hz), 7.49 (2H, d, J=7.9 Hz), 7.93 (2H, d, J=7.9 Hz), 7.97 (1H, d, J=9.2 Hz), 8.05 (1H, s), 8.05 (1H, d, J=9.2 Hz), 9.76 (1H, s), 12.96 (1H, br s). MS (m/z): 478 (M+H)$^+$.

Example 84

(4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolinamide

[Formula 155]

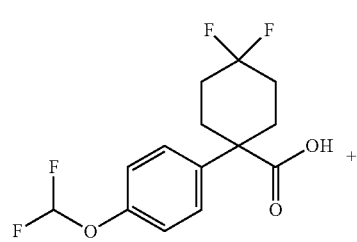

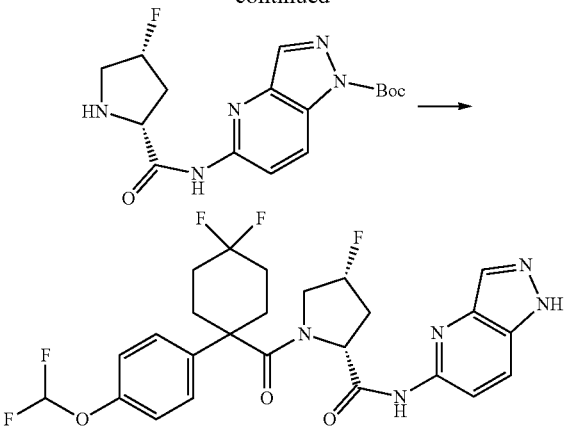

A mixture of the compound (175 mg) obtained in Reference Example C-22, the compound (200 mg) obtained in Reference Example B-2, N,N-diisopropylethylamine (0.200 mL) and N,N-dimethylformamide (5.70 mL) was cooled with ice, then COMU (294 mg) was added, and the mixture was stirred at room temperature for 43 hours. The reaction solution was concentrated, diluted with ethyl acetate, washed with saturated brine, and dried over anhydrous sodium sulfate. The resultant was concentrated under reduced pressure, then the residue obtained was roughly purified by silica gel column chromatography (hexane/ethyl acetate) to obtain the intermediate (101 mg) as a solid.

A solution of the above intermediate in methanol (1.6 mL) was cooled with ice, and potassium carbonate (44 mg) was added, then the mixture was stirred at the same temperature for 1 hour. Water was added to the reaction solution, then the mixture was extracted with ethyl acetate, washed with saturated brine, and dried over anhydrous sodium sulfate. The resultant was concentrated under reduced pressure, then the residue obtained was subjected to silica gel column chromatography (hexane/ethyl acetate) to obtain the title compound (64 mg) as a solid.

$^1$H-NMR (DMSO-D$_6$) δ: 1.65-1.77 (1H, m), 1.90-2.54 (9H, m), 2.96-3.12 (1H, m), 3.23-3.37 (1H, m), 4.76-4.86 (1H, m), 4.96-5.17 (1H, m), 7.07-7.49 (5H, m), 8.01-8.18 (3H, m), 10.59 (1H, br s), 13.28 (1H, br s). MS (m/z): 538 (M+H)$^+$.

Example 84A (4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolinamide

[Formula 156]

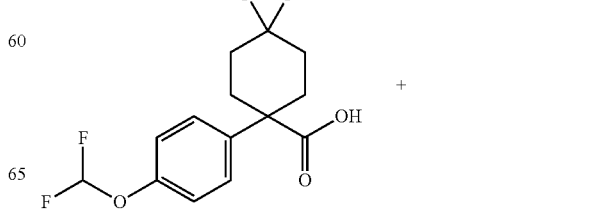

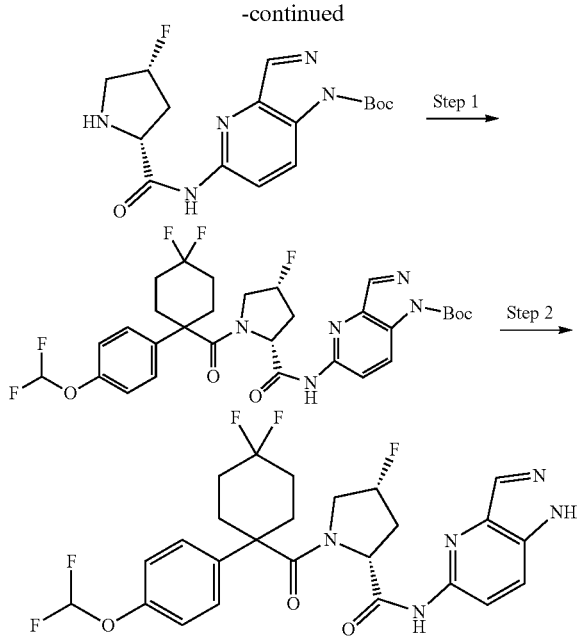

(Step 1) tert-Butyl 5-{[(4R)-1-({1-[4-(difluoromethoxy)phenyl]-4,4-difluorocyclohexyl}carbonyl)-4-fluoro-D-prolyl]amino}-1H-pyrazolo[4,3-b]pyridine-1-carboxylate A mixture of the compound (0.800 g) obtained in Reference Example C-22, the compound (1.01 g) obtained in Reference Example B-2, N,N-diisopropylethylamine (0.910 mL) and N,N-dimethylformamide (26 mL) was cooled with ice, then COMU (1.35 g) was added, and then the mixture was stirred at room temperature for 48 hours. Water was added to the reaction solution, then the mixture was extracted with ethyl acetate three times. The organic layer was washed with saturated brine, and dried over anhydrous sodium sulfate. The resultant was concentrated under reduced pressure, then the residue obtained was purified by silica gel column chromatography (hexane/ethyl acetate), and recrystallized from ethyl acetate/hexane to obtain the title compound (0.967 g) as a solid.

$^1$H-NMR (CDCl$_3$) δ: 1.73 (9H, s), 1.96-2.63 (10H, m), 2.99-3.19 (1H, m), 3.40-3.56 (1H, m), 4.80-4.92 (1H, m), 5.07 (1H, d, J=52.8 Hz), 6.55 (1H, t, J=73.5 Hz), 7.20 (2H, d, J=8.5 Hz), 7.35 (2H, d, J=9.1 Hz), 8.23 (1H, s), 8.43-8.56 (3H, m).

(Step 2) (4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolinamide A mixture of the compound (1.25 g) obtained in Step 1 above, potassium carbonate (0.542 g), methanol (30 mL) and THF (10 mL) was stirred at 0° C. for 2.5 hours. A saturated aqueous ammonium chloride solution was added to the reaction solution, and the mixture was extracted with ethyl acetate. The organic layer was washed with saturated brine, and dried over anhydrous sodium sulfate. The resultant was concentrated under reduced pressure, then the residue obtained was subjected to silica gel column chromatography (hexane/ethyl acetate) then to amino silica gel column chromatography (hexane/ethyl acetate) to obtain the title compound (0.965 g) as a solid.

$^1$H-NMR (DMSO-D$_6$) δ: 1.67-1.78 (1H, m), 1.94-2.47 (9H, m), 2.98-3.12 (1H, m), 3.23-3.31 (1H, m), 4.77-4.85 (1H, m), 4.98-5.15 (1H, m), 7.21 (2H, d, J=8.5 Hz), 7.28 (1H, t, J=74.1 Hz), 7.44 (2H, d, J=8.5 Hz), 8.03-8.16 (3H, m), 10.58 (1H, s), 13.28 (1H, s). MS (m/z): 538 (M+H)$^+$.

The elemental analysis value as $C_{25}H_{24}N_5O_3F_5$ is calculated value: C: 55.86%, H: 4.50%, N: 13.03%, F: 17.67%.

found value: C: 55.75%, H: 4.64%, N: 12.99%, F: 17.87%.

Figure 4:
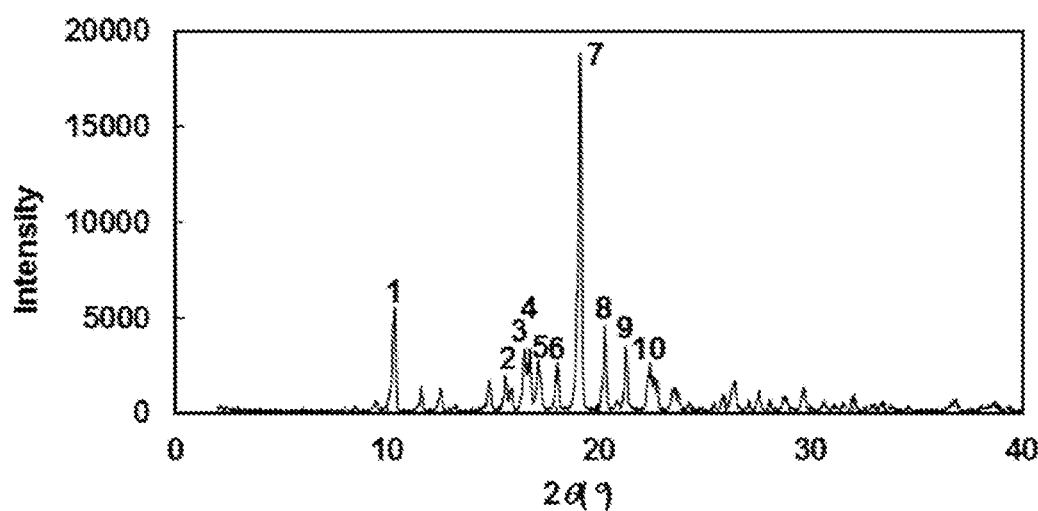
FIG. 4 is a powder X-ray diffraction diagram of a crystal obtained in Example 84A. The ordinate indicates diffraction intensity (Intensity) in counts/sec (cps), and the abscissa indicates a value of the diffraction angle 2θ.

The powder X-ray diffraction of the obtained solid is shown in FIG. 4.

Table 10 shows peaks of relative intensity of 11 or more when the maximum peak intensity is set to 100 in the diffraction pattern of powder X-ray diffraction (CuKα, λ=1.54 angstroms, scanning speed=20°/min) in FIG. 4.

TABLE 10

| Peak number | 2θ | d value | Relative intensity |
|---|---|---|---|
| 1 | 10.34 | 8.55 | 31 |
| 2 | 15.60 | 5.68 | 11 |
| 3 | 16.48 | 5.37 | 19 |
| 4 | 16.74 | 5.29 | 18 |
| 5 | 17.16 | 5.16 | 16 |
| 6 | 18.04 | 4.91 | 15 |
| 7 | 19.12 | 4.64 | 100 |
| 8 | 20.30 | 4.37 | 24 |
| 9 | 21.30 | 4.17 | 19 |
| 10 | 22.38 | 3.97 | 14 |

Example 85

(4R)-1-({4,4-Difluoro-1-[3-fluoro-4-(fluoromethoxy)phenyl]cyclohexyl}carbonyl)-4-fluoro-N-1H-pyrazolo[4,3-b]pyridin-5-yl-D-prolinamide

[Formula 157]

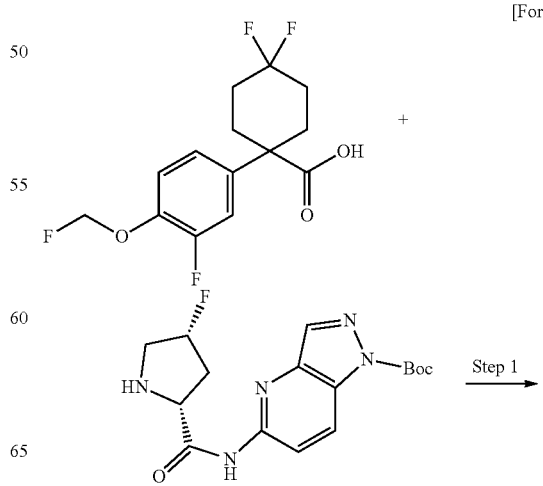

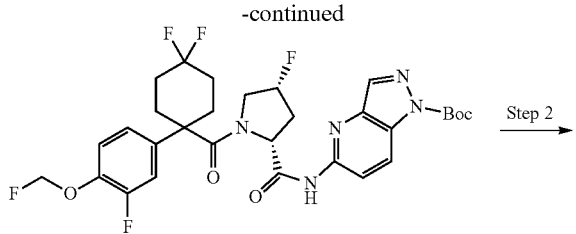

Example B-2 were subjected to the same procedure as in Step 1 of Example 4 to obtain the title compound (172 mg) as a solid.

MS (m/z): 638 (M+H)$^+$.

(Step 2) (4R)-1-({4,4-Difluoro-1-[3-fluoro-4-(fluoromethoxy)phenyl]cyclohexyl}carbonyl)-4-fluoro-N-1H-pyrazolo[4,3-b]pyridin-5-yl-D-prolinamide To a solution of the compound (170 mg) obtained in Step 1 above in methanol (2.5 mL), potassium carbonate (74 mg) was added under ice-cooling, then the mixture was stirred at the same temperature for 1 hour. Water was added to the reaction solution, then the mixture was extracted with ethyl acetate three times. The organic layer was washed with saturated brine, dried over anhydrous sodium sulfate, filtered, and concentrated under reduced pressure. The residue obtained was purified by silica gel column chromatography (hexane/ethyl acetate) to obtain the title compound (66 mg) as a solid.

$^1$H-NMR (DMSO-D$_6$) δ: 1.74-1.77 (1H, m), 2.05-2.37 (9H, m), 3.11-3.26 (2H, m), 4.84-5.12 (2H, m), 5.92 (2H, d, J=53.5 Hz), 7.15-7.37 (3H, m), 8.05-8.14 (3H, m), 10.60 (1H, s), 13.28 (1H, s). MS (m/z): 538 (M+H)$^+$.

(Step 1) tert-Butyl 5-{[(4R)-1-({4,4-difluoro-1-[3-fluoro-4-(fluoromethoxy)phenyl]cyclohexyl}carbonyl)-4-fluoro-D-prolyl]amino}-1H-pyrazolo[4,3-b]pyridine-1-carboxylate The compound (175 mg) obtained in Reference Example C-23 and the compound (200 mg) obtained in Reference Example B-2 were subjected to the same procedure as above to synthesize the following compounds.

The intermediates described below were subjected to the same procedure as above to synthesize the following compounds.

TABLE 11

| Example No. | Intermediate | Name and Structure | Equipment data |
|---|---|---|---|
| 86 | C-24, B-2 | (4R)-1-({3,3-Difluoro-1-[3-fluoro-4-(fluoromethoxy)phenyl]cyclobutyl}carbonyl)-4-fluoro-N-1H-pyrazolo[4,3-b]pyridin-5-yl-D-prolinamide | $^1$H-NMR (DMSO-D$_6$, 100° C.) δ: 2.14-2.28 (1H, m), 2.36-2.55 (1H, m), 2.92-3.59 (6H, m), 4.68-4.90 (1H, m), 5.08-5.31 (1H, m), 5.82 (2H, d, J = 53.7 Hz), 7.20-7.45 (3H, m), 7.90-8.09 (3H, m), 9.96 (1H, br s), 12.96 (1H, br s). MS (m/z): 510(M + H)$^+$. |

TABLE 11-continued

| Example No. | Intermediate | Name and Structure | Equipment data |
|---|---|---|---|
| 87 | 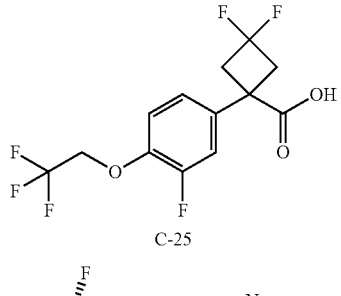C-25<br>B-2 | (4R)-1-({3,3-Difluoro-1-[3-fluoro-4-(2,2,2-trifluoroethoxy)phenyl]cyclobutyl}carbonyl)-4-fluoro-N-1H-pyrazolo[4,3-b]pyridin-5-yl-D-prolinamide<br>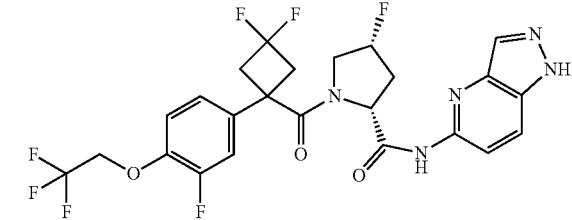 | $^1$H-NMR (DMSO-D$_6$, 100° C.) δ: 2.14-2.28 (1H, m), 2.36-2.54 (1H, m), 2.91-3.59 (6H, m), 4.62-4.89 (3H, m), 5.09-5.29 (1H, m), 7.20-7.39 (3H, m), 7.92-8.07 (3H, m), 9.96 (1H, s), 12.96 (1H, s). MS (m/z): 560 (M + H)$^+$. |
| 88 | 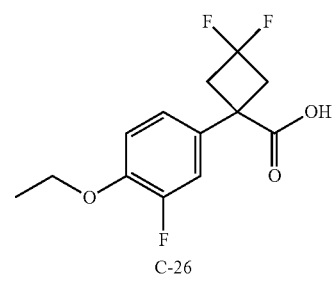C-26<br>B-2 | (4R)-1-{[1-(4-Ethoxy-3-fluorophenyl)-3,3-difluorocyclobutyl]carbonyl}-4-fluoro-N-1H-pyrazolo[4,3-b]pyridin-5-yl-D-prolinamide<br>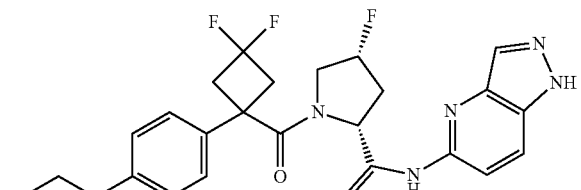 | $^1$H-NMR (DMSO-D$_6$) δ: 1.21-1.40 (3H, m), 2.12-2.50 (2H, m), 2.90-3.16 (2H, m), 3.19-3.58 (4H, m), 3.96-4.23 (2H, m), 4.67-4.87 (1H, m), 5.08-5.29 (1H, m), 6.99-7.29 (3H, m), 7.89-8.09 (3H, m), 9.91 (1H, br s), 12.96 (1H, br s). MS (m/z): 506 (M + H)$^+$. |
| 89 | 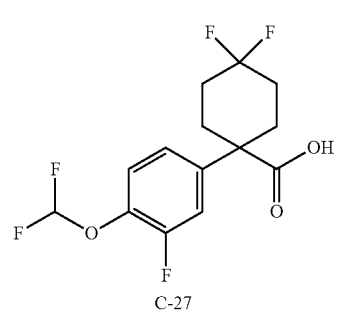C-27<br>B-2 | (4R)-1-({1-[4-(Difluoromethoxy)-3-fluorophenyl]-4,4-difluorocyclohexyl}carbonyl)-4-fluoro-N-1H-pyrazolo[4,3-b]pyridin-5-yl-D-prolinamide<br>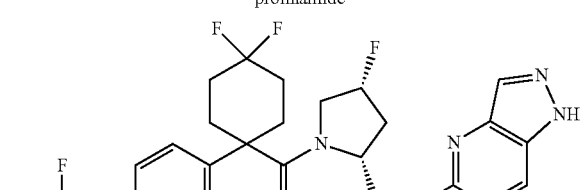 | $^1$H-NMR (DMSO-D$_6$) δ: 1.69-1.83 (1H, m), 1.89-2.56 (9H, m), 3.03-3.19 (1H, m), 3.23-3.38 (1H, m), 4.76-4.87 (1H, m), 4.98-5.20 (1H, m), 7.07-7.50 (4H, m), 8.00-8.20 (3H, m), 10.63 (1H, s), 13.28 (1H, s). MS (m/z): 556 (M + H)$^+$. |

TABLE 11-continued

| Example No. | Intermediate | Name and Structure | Equipment data |
|---|---|---|---|
| 90 | 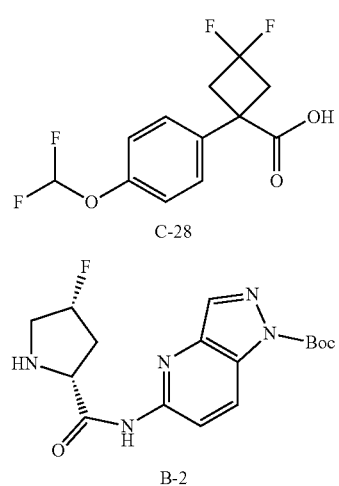<br>C-28<br><br>B-2 | (4R)-1-({1-[4-(Difluoromethoxy)phenyl]-3,3-difluorocyclobutyl}carbonyl)-4-fluoro-N-1H-pyrazolo[4,3-b]pyridin-5-yl-D-prolinamide<br>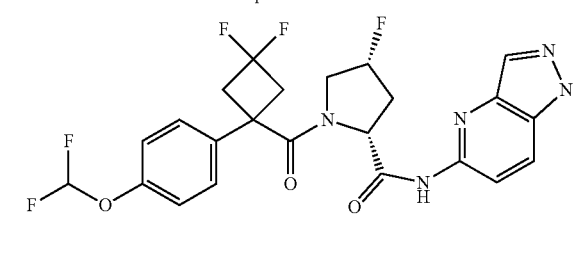 | $^1$H-NMR (DMSO-D$_6$, 100° C.) δ: 2.13-2.56 (2H, m), 2.91-3.61 (6H, m), 4.66-4.90 (1H, m), 5.08-5.28 (1H, m), 6.89-7.36 (3H, m), 7.46-7.56 (2H, m), 7.92-8.07 (3H, m), 9.95 (1H, s), 12.97 (1H, br s). MS (m/z): 510 (M + H)$^+$. |

Example 91

(4R)-1-[(4,4-Difluoro-1-{3-fluoro-4-[($^2$H$_3$)methyloxy]phenyl}cyclohexyl)carbonyl]-4-fluoro-N-1H-pyrazolo[4,3-b]pyridin-5-yl-D-prolinamide

[Formula 158]

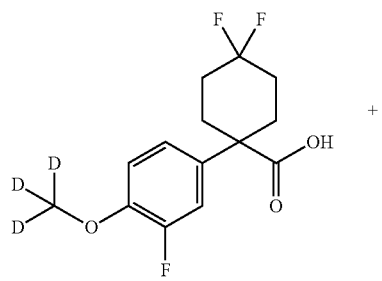

+

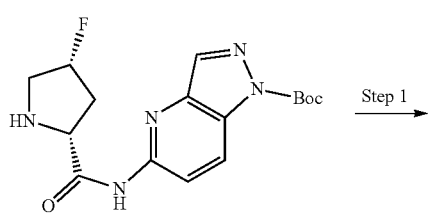

Step 1 →

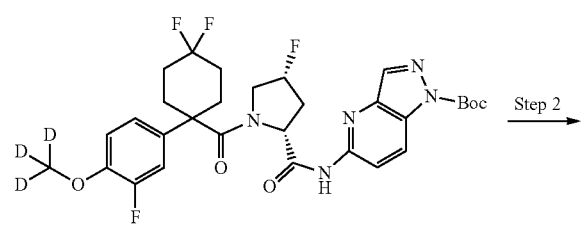

Step 2 →

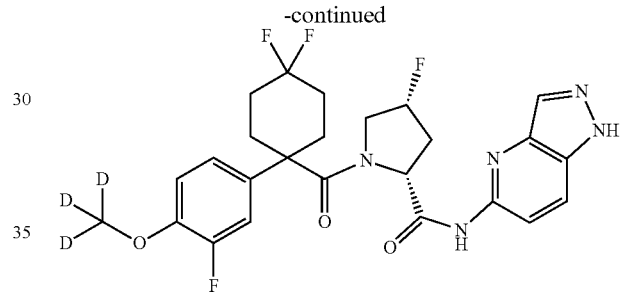

(Step 1) tert-Butyl 5-({(4R)-1-[(4,4-difluoro-1-{3-fluoro-4-[($^2$H$_3$)methoxy]phenyl}cyclohexyl)carbonyl]-4-fluoro-D-prolyl}amino)-1H-pyrazolo[4,3-b]pyridine-1-carboxylate The compound (300 mg) obtained in Reference Example C-29 and the compound (210 mg) obtained in Reference Example B-2 were subjected to the same procedure as in Step 3 of Example 4 to obtain the title compound (351 mg) as a solid.

MS (m/z): 623 (M+H)$^+$.

(Step 2) (4R)-1-[(4,4-Difluoro-1-{3-fluoro-4-[(H$_3$)methyloxy]phenyl}cyclohexyl)carbonyl]-4-fluoro-N-1H-pyrazolo[4,3-b]pyridin-5-yl-D-prolinamide The compound (340 mg) obtained in Step 1 above was subjected to the same procedure as in Step 3 of Example 1 to obtain the title compound (193 mg) as a solid.

$^1$H-NMR (DMSO-D$_6$) δ: 1.72-2.42 (10H, m), 3.08 (1H, dd, J=28.1, 10.2 Hz), 3.30-3.32 (1H, m), 4.81 (1H, d, J=9.4 Hz), 5.02-5.15 (1H, m), 7.13-7.24 (3H, m), 8.06-8.11 (3H, m), 10.58 (1H, s), 13.28 (1H, s). MS (m/z): 523 (M+H)$^+$.

Example 92

(4R)-1-[(4,4-Difluoro-1-{4-[($^2$H$_3$)methyloxy]phenyl}cyclohexyl)carbonyl]-4-fluoro-N-1H-pyrazolo[4,3-b]pyridin-5-yl-D-prolinamide

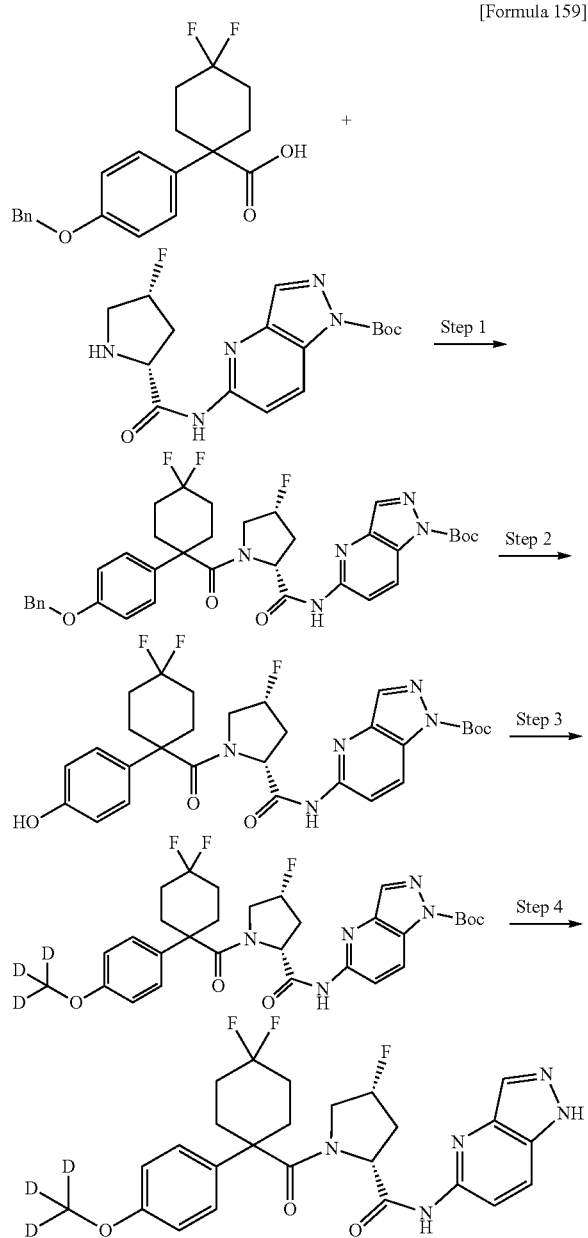

[Formula 159]

(Step 1) tert-Butyl 5-{[(4R)-1-({1-[4-(benzyloxy)phenyl]-4,4-difluorocyclohexyl}carbonyl)-4-fluoro-D-prolyl]amino}-1H-pyrazolo[4,3-b]pyridine-1-carboxylate The compound (400 mg) obtained in Step 3 of Reference Example C-9 and the compound (423 mg) obtained in Reference Example B-2 were subjected to the same procedure as in Step 1 of Example 4 to obtain the title compound (527 mg) as a solid.

$^1$H-NMR (DMSO-D$_6$) δ: 1.66 (9H, s), 1.69-2.47 (10H, m), 3.00-3.07 (1H, m), 3.28-3.31 (1H, m), 4.89-5.03 (4H, m), 7.05 (2H, d, J=8.8 Hz), 7.35-7.42 (7H, m), 8.34-8.51 (3H, m), 10.84 (1H, s). MS (m/z): 678 (M+H)$^+$.

(Step 2) tert-Butyl 5-{[(4R)-1-{[4,4-difluoro-1-(4-hydroxyphenyl)cyclohexyl]carbonyl}-4-fluoro-D-prolyl]amino}-1H-pyrazolo[4,3-b]pyridine-1-carboxylate The compound (527 mg) obtained in Step 1 above was subjected to the same procedure as in Step 2 of Example 4 to obtain the title compound (492 mg) as a solid.

$^1$H-NMR (DMSO-D$_6$) δ: 1.67 (11H, s), 1.95-2.40 (8H, m), 2.99-3.06 (1H, m), 3.29 (1H, d, J=12.5 Hz), 4.81 (1H, d, J=10.0 Hz), 5.07 (1H, d, J=53.8 Hz), 6.79 (2H, d, J=8.5 Hz), 7.15 (2H, d, J=8.8 Hz), 8.34-8.51 (3H, m), 9.51 (1H, s), 10.77 (1H, s). MS (m/z): 588 (M+H)$^+$.

(Step 3) tert-Butyl 5-({(4R)-1-[(4,4-difluoro-1-{4-[($^2$H$_3$)methyloxy]phenyl}cyclohexyl)carbonyl]-4-fluoro-D-prolyl}amino)-1H-pyrazolo[4,3-b]pyridine-1-carboxylate A mixture of the compound (250 mg) obtained in Step 2 above, potassium carbonate (118 mg), iodo($^2$H$_3$)methane (53 μL) and acetone (2.1 mL) was stirred at room temperature for 4 hours, then warmed to 60° C. and stirred for 4 hours. Iodo ($^2$H$_3$) methane (50 μL) was further added to the reaction solution, then the mixture was stirred at 60° C. overnight. The reaction solution was diluted with ethyl acetate, washed with saturated brine, and dried over anhydrous sodium sulfate. The resultant was concentrated under reduced pressure, then the solid obtained was dissolved in ethyl acetate, and hexane was added, then the solid obtained was filtered, and dried to obtain the title compound (188 mg) as a solid.

$^1$H-NMR (DMSO-D$_6$) δ: 1.65-1.67 (10H, m), 2.06-2.37 (9H, m), 2.96-3.07 (1H, m), 3.27-3.37 (1H, m), 4.82 (1H, d, J=8.2 Hz), 5.06 (1H, d, J=54.1 Hz), 6.96 (2H, d, J=8.8 Hz), 7.29 (2H, d, J=8.8 Hz), 8.33-8.51 (3H, m), 10.82 (1H, s). MS (m/z): 605 (M+H)$^+$.

(Step 4) (4R)-1-[(4,4-Difluoro-1-{4-[($^2$H$_3$)methyloxy]phenyl}cyclohexyl)carbonyl]-4-fluoro-N-1H-pyrazolo[4,3-b]pyridin-5-yl-D-prolinamide The compound (180 mg) obtained in Step 3 above was subjected to the same procedure as in Step 2 of Example 85 to obtain the title compound (111 mg) as a solid.

$^1$H-NMR (DMSO-D$_6$) δ: 1.67 (1H, t, J=12.9 Hz), 1.91-2.10 (4H, m), 2.20-2.47 (5H, m), 2.96-3.07 (1H, m), 3.27-3.37 (1H, m), 4.80 (1H, d, J=8.8 Hz), 5.05 (1H, d, J=54.4 Hz), 6.96 (2H, d, J=8.8 Hz), 7.28 (2H, d, J=8.5 Hz), 8.03-8.15 (3H, m), 10.53 (1H, s), 13.28 (1H, s).

MS (m/z): 505 (M+H)$^+$.

Example 93

(4R)-1-{[4,4-Difluoro-1-(3-methoxyphenyl)cyclohexyl]carbonyl}-4-fluoro-N-1H-pyrazolo[4,3-b]pyridin-5-yl-D-prolinamide

[Formula 160]

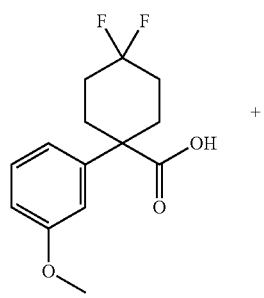

+

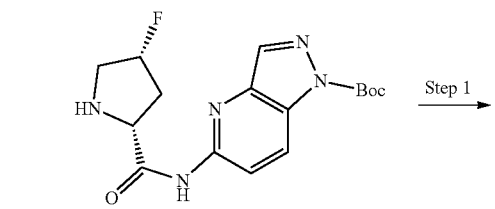

Step 1 →

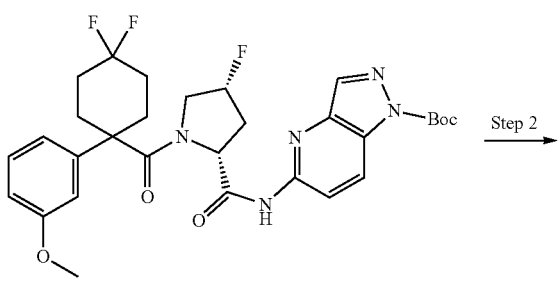

Step 2 →

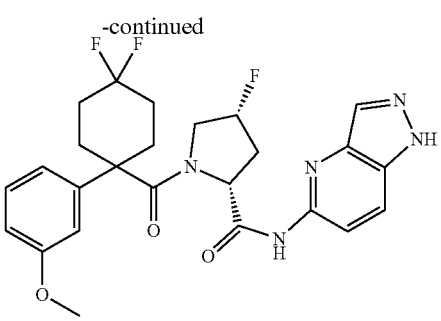

(Step 1) tert-Butyl 5-{[(4R)-1-{[4,4-difluoro-1-(3-methoxyphenyl)cyclohexyl]carbonyl}-4-fluoro-D-prolyl]amino}-1H-pyrazolo[4,3-b]pyridine-1-carboxylate To a solution of the compound (320 mg) obtained in Example C-30 in tetrahydrofuran (5 mL), 1-chloro-N,N,2-trimethyl-1-propenylamine (235 µL) was added dropwise under ice-cooling. The reaction mixture solution was stirred at room temperature for 30 minutes, then cooled again to 0° C., then the compound (103 mg) obtained in Example B-2 and triethylamine (164 µL) were added. The reaction solution was stirred at the same temperature for 30 minutes, then diluted with water and ethyl acetate, and extracted with ethyl acetate. The organic layer was washed with saturated brine, then dried over anhydrous sodium sulfate, and the solvent was distilled off under reduced pressure. The residue obtained was purified by silica gel column chromatography (hexane/ethyl acetate) to obtain the title compound (672 mg) as a solid.

$^1$H-NMR (DMSO-D$_6$) δ: 1.67 (9H, s), 1.78-2.17 (5H, m), 2.21-2.45 (3H, m), 2.80-3.08 (2H, m), 3.31 (2H, d, J=23.2 Hz), 3.78 (3H, s), 4.82 (1H, d, J=10.4 Hz), 5.06 (1H, d, J=53.7 Hz), 6.84-6.95 (3H, m), 7.31 (1H, t, J=7.9 Hz), 8.24 (1H, d, J=9.2 Hz), 8.38 (1H, s), 8.39 (1H, d, J=9.2 Hz), 10.29 (1H, s). MS (m/z): 602 (M+H)$^+$.

(Step 2) (4R)-1-{[4,4-Difluoro-1-(3-methoxyphenyl)cyclohexyl]carbonyl}-4-fluoro-N-1H-pyrazolo[4,3-b]pyridin-5-yl-D-prolinamide The compound (670 mg) obtained in Step 1 above was subjected to the same procedure as in Step 5 of Example 4 to obtain the title compound (268 mg) as a solid.

$^1$H-NMR (DMSO-D$_6$) δ: 1.85 (1H, td, J=12.8, 3.1 Hz), 1.90-2.08 (2H, m), 2.08-2.46 (5H, m), 2.89-3.18 (2H, m), 3.31 (2H, d, J=22.0 Hz), 3.78 (3H, s), 4.80 (1H, dd, J=9.2, 3.1 Hz), 5.05 (1H, d, J=54.3 Hz), 6.86 (1H, dd, J=7.9, 2.4 Hz), 6.89 (1H, br s), 6.93 (1H, d, J=8.5 Hz), 7.31 (1H, t, J=7.9 Hz), 7.96-8.06 (3H, m), 9.99 (1H, s), 12.97 (1H, br s). MS (m/z): 502 (M+H)$^+$.

The intermediates described below were subjected to the same procedure as above to synthesize the following compounds.

TABLE 12

| Example No. | Intermediate | Name and Structure | Equipment data |
|---|---|---|---|
| 94 | 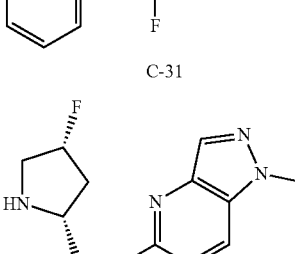 C-31<br><br>B-6 | (4R)-1-{[4,4-Difluoro-1-(2-fluoro[biphenyl]-4-yl)cyclohexyl]carbonyl}-4-fluoro-N-1H-pyrazolo[4,3-b]pyridin-5-yl-D-prolinamide<br><br>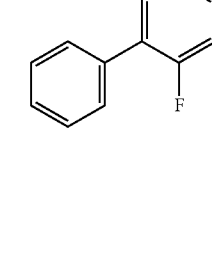 | $^1$H-NMR (DMSO-D$_6$) δ: 1.83-2.46 (10H, m), 3.42 (2H, d, J = 24.4 Hz), 4.84 (1H, d, J = 7.3 Hz), 5.11 (1H, d, J = 56.2 Hz), 7.25-7.32 (2H, m), 7.39 (1H, d, J = 7.3 Hz), 7.45 (2H, t, J = 7.6 Hz), 7.51-7.60 (3H, m), 7.96 (1H, d, J = 9.2 Hz), 8.00-8.06 (2H, m), 10.03 (1H, s). MS (m/z): 566 (M + H)$^+$. |
| 95 | 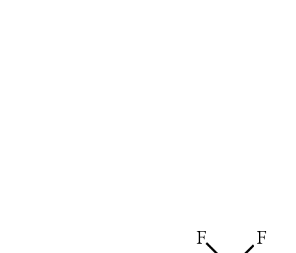 C-22<br><br>B-3 | (3S,4S)-1-({1-[4-(Difluoromethoxy)phenyl]-4,4-difluorocyclohexyl}carbonyl)-4-fluoro-3-hydroxy-N-1H-pyrazolo[4,3-b]pyridin-5-yl-D-prolinamide<br><br> | $^1$H-NMR (DMSO-D$_6$) δ: 1.58-2.43 (8H, m), 3.00-3.31 (2H, m), 4.10-4.25 (1H, m), 4.52-4.85 (2H, m), 5.78 (1H, d, J = 4.9 Hz), 7.08-7.51 (5H, m), 8.01-8.19 (3H, m), 10.64 (1H, s), 13.29 (1H, s). MS (m/z): 554 (M + H)$^+$. |

Example 96

(2R,3R)-1-{[4,4-Difluoro-1-(4-methoxyphenyl)cyclohexyl]carbonyl}-3-(methoxymethoxy)-N-(1H-pyrazolo[4,3-b]pyridin-5-yl)azetidine-2-carboxamide

[Formula 161]

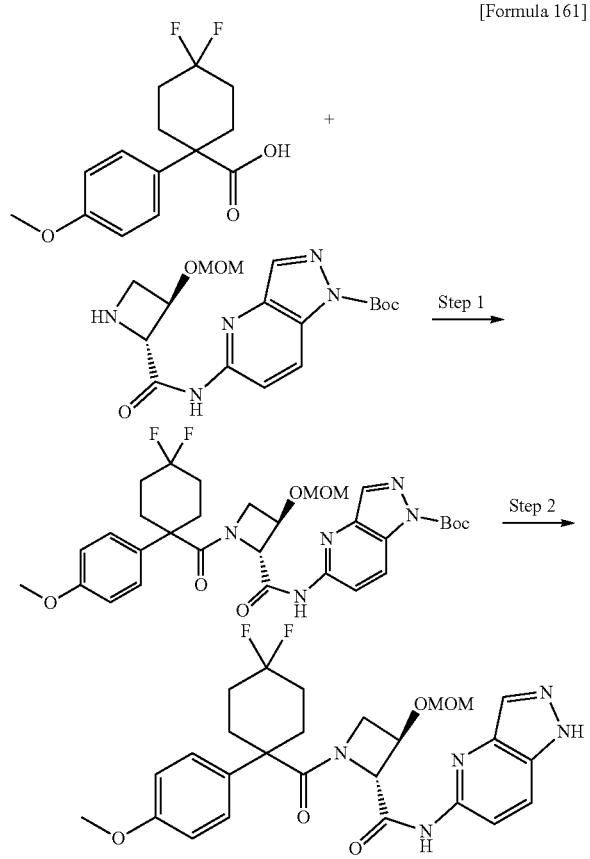

(Step 1) tert-Butyl 5-({[(2R,3R)-1-{[4,4-difluoro-1-(4-methoxyphenyl)cyclohexyl]carbonyl}-3-(methoxymethoxy)azetidin-2-yl]carbonyl}amino)-1H-pyrazolo[4,3-b]pyridine-1-carboxylate The compound obtained in Reference Example C-4 (136 mg) and the compound (145 mg) obtained in Reference Example B-14 were subjected to the same procedure as in Step 1 of Reference Example D-2 to obtain the title compound (200 mg) as a solid.

$^{1}$H-NMR (CDCl$_3$) δ: 1.57-2.58 (8H, m), 1.73 (9H, s), 3.17-3.28 (1H, m), 3.33 (3H, s), 3.82 (3H, s), 3.86-3.94 (1H, m), 4.42-4.50 (1H, m), 4.61 (1H, d, J=6.7 Hz), 4.68 (1H, d, J=6.7 Hz), 4.83-4.92 (1H, m), 6.90-6.96 (2H, m), 7.24-7.31 (2H, m), 8.27 (1H, s), 8.39-8.47 (2H, m), 9.99 (1H, br s). MS (m/z): 630 (M+H)$^{+}$.

(Step 2) (2R,3R)-1-{[4,4-Difluoro-1-(4-methoxyphenyl)cyclohexyl]carbonyl}-3-(methoxymethoxy)-N-(1H-pyrazolo[4,3-b]pyridin-5-yl)azetidine-2-carboxamide To a mixture of the compound (66 mg) obtained in Step 1 above, ethanol (2.5 mL) and tetrahydrofuran (2.5 mL), potassium carbonate (15 mg) was added at 0° C., and the mixture was stirred at room temperature for 1 hour. Methanol (2.5 mL) was added, then potassium carbonate (44 mg) was added at 0° C., and the mixture was stirred at room temperature for 1 hour. Ethyl acetate and water were added to the reaction solution, then the mixture was extracted with ethyl acetate. The organic layer was washed with saturated brine, then dried over anhydrous sodium sulfate. The solvent was distilled off under reduced pressure, then the residue obtained was purified by silica gel column chromatography (hexane/ethyl acetate) two times to obtain the title compound (43 mg) as a solid.

$^{1}$H-NMR (CDCl$_3$) δ: 1.51-2.60 (8H, m), 3.15-3.31 (1H, m), 3.34 (3H, s), 3.82 (3H, s), 3.87-3.97 (1H, m), 4.35-4.49 (1H, m), 4.61 (1H, d, J=7.3 Hz), 4.68 (1H, d, J=7.3 Hz), 4.80-4.90 (1H, m), 6.89-6.96 (2H, m), 7.27-7.32 (2H, m), 7.81-7.85 (1H, m), 8.17 (1H, s), 8.25-8.30 (1H, m), 9.67 (1H, br s), 10.38 (1H, br s). MS (m/z): 530 (M+H)$^{+}$.

Example 97

(4R)-1-{[4,4-Difluoro-1-(4-methoxyphenyl)cyclohexyl]carbonyl}-4-fluoro-N-(2-methyl-1H-pyrrolo[3,2-b]pyridin-5-yl)-D-prolinamide

[Formula 162]

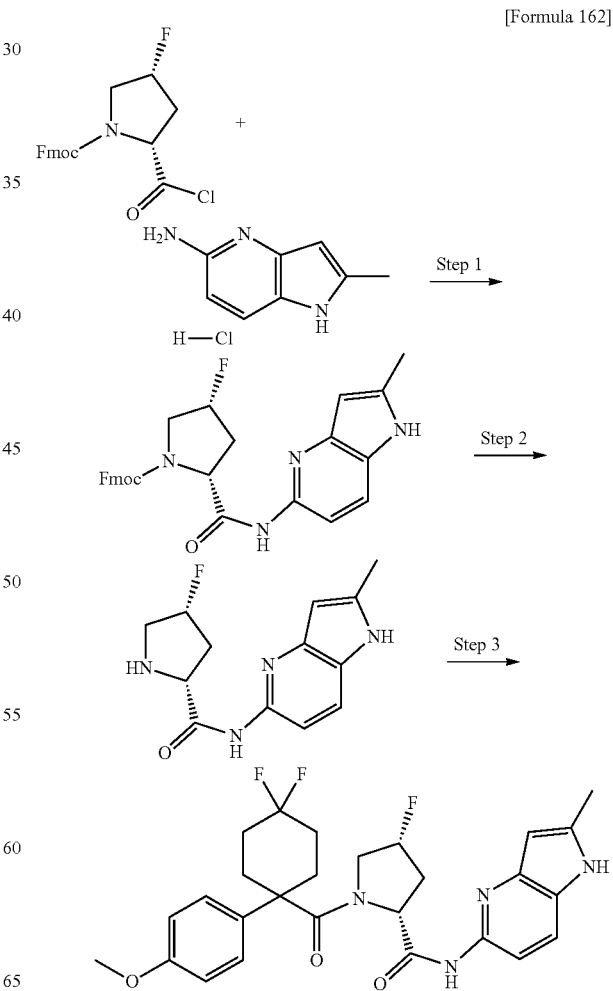

(Step 1) (4R)-1-[(9H-Fluoren-9-ylmethoxy)carbonyl]-4-fluoro-N-(2-methyl-1H-pyrrolo[3,2-b]pyridin-5-yl)-D-prolinamide The compound (345 mg) obtained in Step 2 of Reference Example B-2 and the compound (186 mg) obtained in Reference Example A-9 were subjected to the same procedure as in Step 3 of Reference Example B-2 to obtain the title compound (402 mg) as a solid.

$^1$H-NMR (DMSO-D$_6$) δ: 2.27-2.45 (4H, m), 2.57-2.73 (1H, m), 3.72-3.81 (2H, m), 4.16-4.35 (3H, m), 4.65 (1H, dd, J=74.3, 9.6 Hz), 5.33 (1H, d, J=53.8 Hz), 6.14 (1H, s), 7.04 (1H, dt, J=32.0, 7.5 Hz), 7.29-7.44 (3H, m), 7.58-7.93 (6H, m), 10.16 (1H, d, J=113.6 Hz), 11.12 (1H, s). MS (m/z): 485 (M+H)$^+$.

(Step 2) (4R)-4-Fluoro-N-(2-methyl-1H-pyrrolo[3,2-b]pyridin-5-yl)-D-prolinamide

The compound (386 mg) obtained in Step 1 above was subjected to the same procedure as in Step 5 of Reference Example B-15 to obtain the title compound (172 mg) as a solid.

$^1$H-NMR (DMSO-D$_6$) δ: 2.24-2.34 (2H, m), 2.40 (3H, s), 3.07-3.23 (2H, m), 3.46 (1H, s), 3.82 (1H, d, J=6.7 Hz), 5.24 (1H, d, J=54.7 Hz), 6.11 (1H, s), 7.62 (1H, d, J=8.5 Hz), 7.86 (1H, d, J=8.8 Hz), 10.11 (1H, s), 11.11 (1H, s). MS (m/z): 263 (M+H)$^+$.

(Step 3) (4R)-1-{[4,4-Difluoro-1-(4-methoxyphenyl)cyclohexyl]carbonyl}-4-fluoro-N-(2-methyl-1H-pyrrolo[3,2-b]pyridin-5-yl)-D-prolinamide The compound (85 mg) obtained in Reference Example C-4 and the compound (82 mg) obtained in Step 2 above were subjected to the same procedure as in Step 1 of Example 93 to obtain the title compound (100 mg) as a solid.

$^1$H-NMR (DMSO-D$_6$) δ: 2.03-2.37 (13H, m), 2.98-3.04 (1H, m), 3.26-3.38 (1H, m), 3.76 (3H, s), 4.76 (1H, d, J=7.3 Hz), 5.03 (1H, d, J=53.5 Hz), 6.14 (1H, s), 6.96 (2H, d, J=8.8 Hz), 7.28 (2H, d, J=8.8 Hz), 7.62 (1H, d, J=8.8 Hz), 7.77 (1H, d, J=8.8 Hz), 10.09 (1H, s), 11.10 (1H, s). MS (m/z): 515 (M+H)$^+$.

Example 98

(4R)-1-({4,4-Difluoro-1-[4-(2-hydroxypropan-2-yl)phenyl]cyclohexyl}carbonyl)-4-fluoro-N-1H-pyrazolo[4,3-b]pyridin-5-yl-D-prolinamide

[Formula 163]

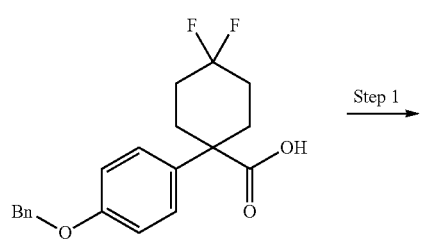

-continued

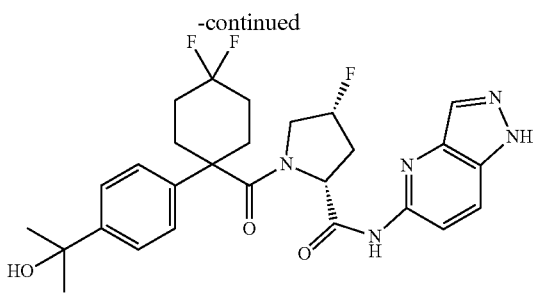

(Step 1) 4,4-Difluoro-1-(4-hydroxyphenyl)cyclohexanecarboxylic acid

The compound (10.0 g) obtained in Step 3 of Reference Example C-9 was subjected to the same procedure as in Step 2 of Example 4 to obtain the title compound (6.51 g) as a solid.

$^1$H-NMR (DMSO-D$_6$) δ: 1.80-2.05 (6H, m), 2.31-2.45 (2H, m), 6.73 (2H, d, J=8.5 Hz), 7.20 (2H, d, J=8.5 Hz), 9.42 (1H, s), 12.69 (1H, br s).

(Step 2) Benzyl 4,4-difluoro-1-(4-hydroxyphenyl)cyclohexanecarboxylate

The compound (350 mg) obtained in Step 1 above was subjected to the same procedure as in Step 5 of Reference Example C-9 to obtain the title compound (397 mg) as a solid.

$^1$H-NMR (CDCl$_3$) δ: 1.80-2.11 (6H, m), 2.56 (2H, d, J=14.0 Hz), 4.90 (1H, d, J=19.5 Hz), 5.10 (2H, s), 6.78 (2H, d, J=9.2 Hz), 7.16-7.19 (2H, m), 7.24 (2H, d, J=9.2 Hz), 7.28-7.32 (3H, m).

(Step 3) Benzyl 4,4-difluoro-1-(4-{[(trifluoromethyl)sulfonyl]oxy}phenyl)cyclohexanecarboxylate The compound (1.70 g) obtained in Step 2 above was subjected to the same procedure as in Step 3 of Reference Example C-31 to obtain the title compound (2.44 g) as a solid.

$^1$H-NMR (CDCl$_3$) δ: 1.83-2.13 (6H, m), 2.57-2.64 (2H, m), 5.12 (2H, s), 7.15 (2H, dd, J=6.1, 3.1 Hz), 7.22 (2H, d, J=9.2 Hz), 7.28-7.32 (3H, m), 7.43 (2H, d, J=9.2 Hz).

(Step 4) Methyl 4-{1-[(benzyloxy)carbonyl]-4,4-difluorocyclohexyl}benzoate

To a mixed solution of the compound (2.00 g) obtained in Step 3 above and [1,1'-bis(diphenylphosphino)ferrocene]palladium(II) dichloride dichloromethane adduct (171 mg) in N,N-dimethylformamide (30 mL), triethylamine (1.16 mL) and methanol (15 mL) were added, and the mixture was stirred at 80° C. for 9 hours under a carbon monoxide atmosphere. The reaction solution was returned to room temperature, then a saturated aqueous ammonium chloride solution was added, and then the mixture was extracted with ethyl acetate. The combined organic layer was washed with saturated brine, and dried over anhydrous sodium sulfate, then the solvent was distilled off under reduced pressure. The residue obtained was purified using silica gel column chromatography (hexane/ethyl acetate) to obtain the title compound (1.60 g) as a solid.

$^1$H-NMR (CDCl$_3$) δ: 1.82-1.98 (2H, m), 2.03-2.13 (4H, m), 2.60 (2H, d, J=14.0 Hz), 3.92 (3H, s), 5.11 (2H, s), 7.17 (2H, dd, J=6.4, 3.4 Hz), 7.30 (3H, t, J=3.4 Hz), 7.43 (2H, d, J=8.5 Hz), 7.98 (2H, d, J=8.5 Hz).

(Step 5) 4,4-Difluoro-1-[4-(methoxycarbonyl)phenyl]cyclohexanecarboxylic acid

The compound (1.19 g) obtained in Step 4 above was subjected to the same procedure as in Step 2 of Example 4 to obtain the title compound (0.881 g) as a solid.

$^1$H-NMR (DMSO-D$_6$) δ: 1.86-2.07 (6H, m), 2.40-2.49 (2H, m), 3.85 (3H, s), 7.59 (2H, d, J=8.5 Hz), 7.96 (2H, d, J=8.5 Hz), 13.02 (1H, s).

(Step 6) tert-Butyl 5-{[(4R)-1-({4,4-difluoro-1-[4-(methoxycarbonyl)phenyl]cyclohexyl}carbonyl)-4-fluoro-D-prolyl]amino}-1H-pyrazolo[4,3-b]pyridine-1-carboxylate The compound (65 mg) obtained in Step 5 above and the compound (76 mg) obtained in Reference Example B-2 were subjected to the same procedure as in Step 1 of Example 93 to obtain the title compound (123 mg) as a solid.

$^1$H-NMR (DMSO-D$_6$) δ: 1.68 (9H, s), 1.83-2.39 (10H, m), 3.18-3.38 (2H, m), 3.84 (3H, s), 4.79-4.87 (1H, m), 5.05 (1H, d, J=53.7 Hz), 7.51 (2H, d, J=8.5 Hz), 7.96 (2H, d, J=8.5 Hz), 8.19-8.25 (1H, m), 8.37-8.40 (2H, m), 10.28 (1H, s). MS (m/z): 630 (M+H)$^+$.

(Step 7) (4R)-1-({4,4-Difluoro-1-[4-(2-hydroxypropan-2-yl)phenyl]cyclohexyl}carbonyl)-4-fluoro-N-1H-pyrazolo[4,3-b]pyridin-5-yl-D-prolinamide The compound (121 mg) obtained in Step 6 above was subjected to the same procedure as in Step 4 of Example 81 to obtain the title compound (123 mg) as a solid.

$^1$H-NMR (DMSO-D$_6$) δ: 1.44 (6H, s), 1.79-2.45 (10H, m), 3.13-3.42 (2H, m), 4.63 (1H, s), 4.77-4.83 (1H, m), 5.03 (1H, d, J=54.3 Hz), 7.28 (2H, d, J=8.5 Hz), 7.49 (2H, d, J=8.5 Hz), 7.97 (1H, d, J=9.2 Hz), 8.04 (1H, d, J=9.2 Hz), 8.05 (1H, s), 9.95 (1H, s), 12.97 (1H, br s). MS (m/z): 530 (M+H)$^+$.

Example 99

(4R)—N-(4-Cyano-1H-indazol-5-yl)-1-({4,4-difluoro-1-[4-(methylsulfonyl)phenyl]cyclohexyl}carbonyl)-4-fluoro-D-prolinamide

[Formula 164]

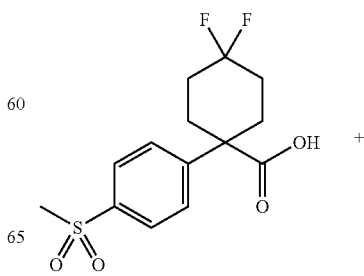

-continued

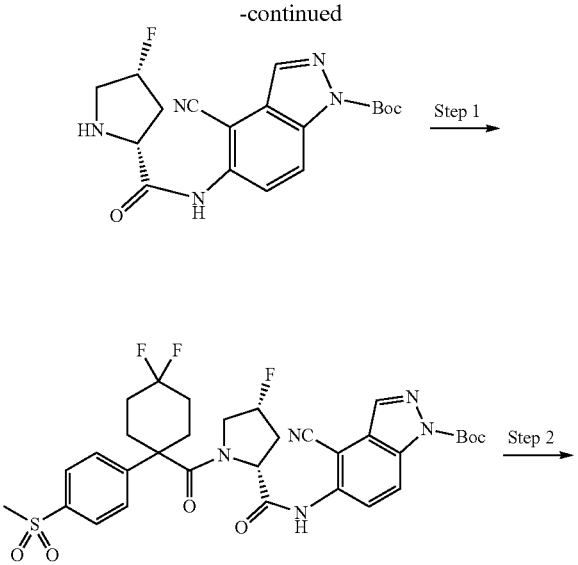

(Step 1) tert-Butyl 4-cyano-5-{[(4R)-1-({4,4-difluoro-1-[4-(methylsulfonyl)phenyl]cyclohexyl}carbonyl)-4-fluoro-D-prolyl]amino}-1H-indazole-1-carboxylate The compound (90 mg) obtained in Reference Example C-32 and the compound (88 mg) obtained in Reference Example B-15 were subjected to the same procedure as in Step 1 of Example 93 to obtain the title compound (157 mg) as a solid.

$^1$H-NMR (DMSO-D$_6$) δ: 1.67 (9H, s), 1.75-1.89 (1H, m), 1.93-2.61 (10H, m), 2.97-3.16 (1H, m), 3.23 (3H, s), 4.78-4.90 (1H, m), 4.99-5.24 (1H, m), 7.67 (2H, d, J=8.5 Hz), 7.81 (1H, d, J=8.5 Hz), 7.94 (2H, d, J=8.5 Hz), 8.39 (1H, d, J=9.2 Hz), 8.56 (1H, s), 10.53 (1H, br s). MS (m/z): 696 (M+Na)$^+$.

(Step 2) (4R)—N-(4-Cyano-1H-indazol-5-yl)-1-({4,4-difluoro-1-[4-(methylsulfonyl)phenyl]cyclohexyl}carbonyl)-4-fluoro-D-prolinamide The compound (155 mg) obtained in Step 1 above was subjected to the same procedure as in Step 2 of Example 85 to obtain the title compound (92 mg) as a solid.

$^1$H-NMR (DMSO-D$_6$, 100° C.) δ: 1.83-2.08 (4H, m), 2.12-2.55 (6H, m), 3.16 (3H, s), 3.22-3.43 (2H, m), 4.66-4.82 (1H, m), 4.98-5.19 (1H, m), 7.51 (1H, d, J=8.5 Hz), 7.64 (2H, d, J=8.5 Hz), 7.83-7.95 (3H, m), 8.14 (1H, s), 9.92 (1H, br s), 13.40 (1H, br s). MS (m/z): 574 (M+H)$^+$.

Using the same method, the following compounds were synthesized.

TABLE 13

| Example No. | Intermediate | Name and Structure | Equipment data |
|---|---|---|---|
| 100 | C-4, B-16 | (4R)-1-{[4,4-Difluoro-1-(4-methoxyphenyl)cyclohexyl]carbonyl}-4-fluoro-N-(4-fluoro-1H-indazol-5-yl)-D-prolinamide | $^1$H-NMR (DMSO-D$_6$, 100° C.) δ: 1.74-2.52 (10H, m), 3.27-3.43 (2H, m), 3.75 (3H, s), 4.65-4.75 (1H, m), 4.95-5.16 (1H, m), 6.92 (2H, d, J = 8.5 Hz), 7.25 (2H, d, J = 8.5 Hz), 7.31 (1H, d, J = 8.5 Hz), 7.51 (1H, t, J = 7.9 Hz), 8.09 (1H, s), 9.19 (1H, br s), 13.07 (1H, br s). MS (m/z): 519 (M + H)$^+$. |

Example 101

(4R)-1-({1-[4-(acetylamino)phenyl]-4,4-difluorocyclohexyl}carbonyl)-4-fluoro-N-1H-pyrazolo[4,3-b]pyridin-5-yl-D-prolinamide

[Formula 165]

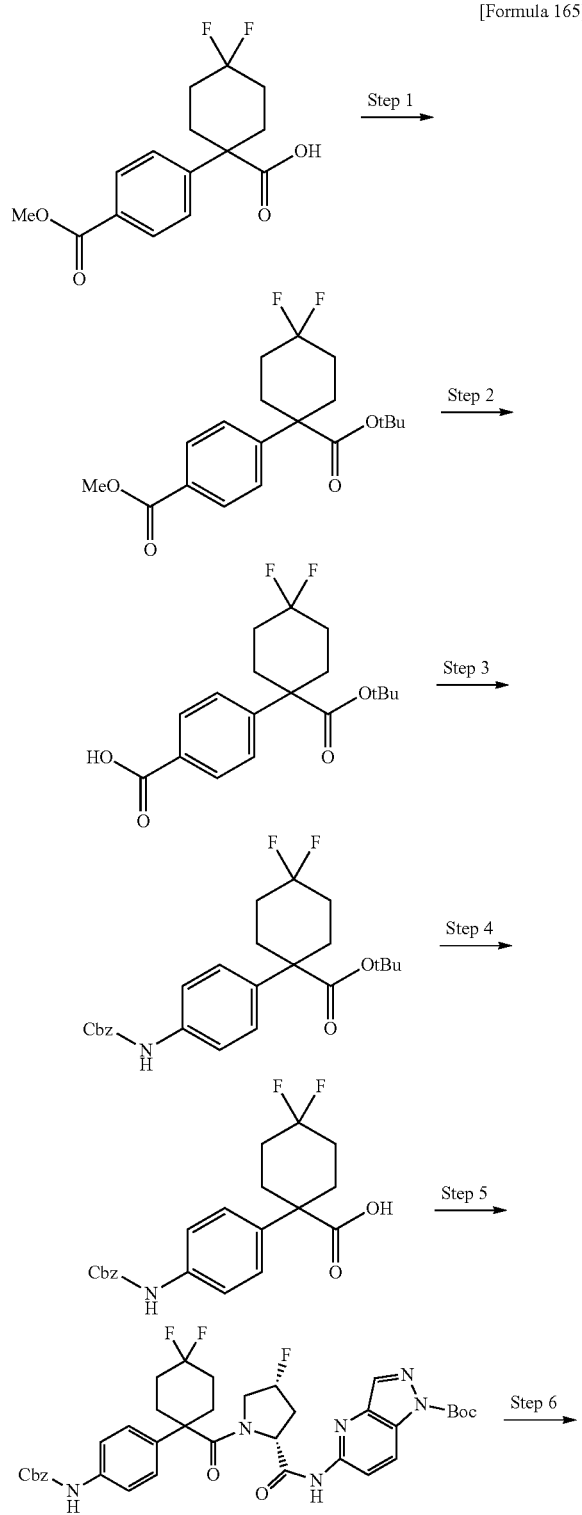

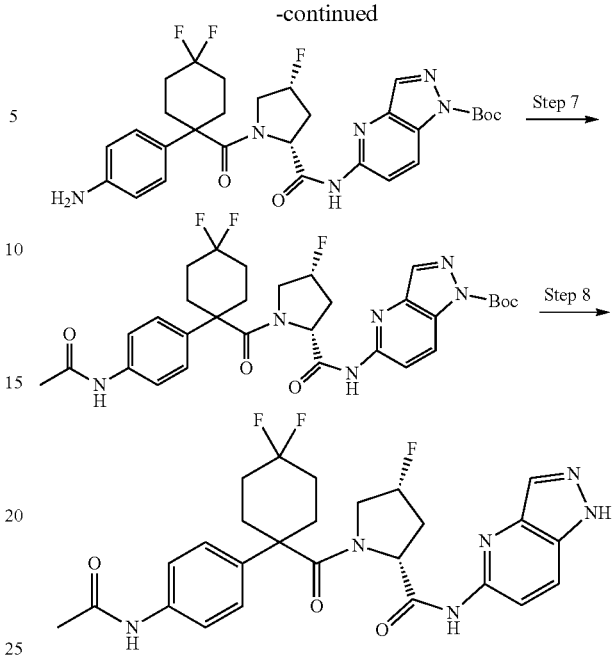

(Step 1) Methyl 4-[1-(tert-butoxycarbonyl)-4,4-difluorocyclohexyl]benzoate

To a solution of the compound (881 mg) obtained in Step 5 of Example 98 in tetrahydrofuran (15 mL), 1-chloro-N,N,2-trimethyl-1-propenylamine (586 μL) was added dropwise under ice-cooling. Then, the reaction solution was stirred at room temperature for 30 minutes, and cooled again to 0° C., then potassium tert-butoxide (1 mol/L tetrahydrofuran solution, 3.54 mL) and triethylamine (491 μL) were added. The reaction mixture solution was stirred at the same temperature for 30 minutes, then water was added, and then the mixture was extracted with ethyl acetate. The combined organic layer was washed with saturated brine, and dried over anhydrous sodium sulfate, and then the solvent was distilled off under reduced pressure. The residue obtained was purified by silica gel column chromatography (hexane/ethyl acetate) to obtain the title compound (500 mg) as a solid.

$^1$H-NMR (CDCl$_3$) δ: 1.37 (9H, s), 1.88-2.14 (6H, m), 2.50-2.57 (2H, m), 3.92 (3H, s), 7.46 (2H, d, J=8.5 Hz), 8.01 (2H, d, J=8.5 Hz).

(Step 2) 4-1-(tert-Butoxycarbonyl)-4,4-difluorocyclohexyl]benzoic acid

The compound (498 mg) obtained in Step 1 above was subjected to the same procedure as in Step 5 of Reference Example C-2 to obtain the title compound (376 mg) as a solid.

$^1$H-NMR (CDCl$_3$) δ: 1.38 (9H, s), 1.88-2.17 (6H, m), 2.54 (2H, s), 7.50 (2H, d, J=7.9 Hz), 8.08 (2H, d, J=7.9 Hz).

(Step 3) tert-Butyl 1-(4-{[(benzyloxy)carbonyl]amino}phenyl)-4,4-difluorocyclohexanecarboxylate To a solution of the compound (225 mg) obtained in Step 2 above and triethylamine (183 μL) in toluene (4 mL), diphenylphosphoryl azide (199 μL) was added at room temperature, then the mixture was stirred at 100° C. for 2 hours. The reaction solution was returned to room temperature, then benzyl alcohol (0.400 mL) was added, and then the mixture was heated to 100° C. again, and stirred for 2 hours. The reaction solution was returned to room temperature, then a saturated aqueous sodium sulfate solution was added, and then the mixture was extracted with ethyl acetate. The combined organic layer was washed with saturated brine, and dried over anhydrous sodium sulfate, then the solvent was distilled off under reduced pressure. The residue obtained was purified using silica gel column chromatography (hexane/ethyl acetate) to obtain the title compound (214 mg) as an oil.

$^1$H-NMR (CDCl$_3$) δ: 1.36 (9H, s), 1.87-2.10 (6H, m), 2.44-2.53 (2H, m), 5.20 (2H, s), 6.61 (1H, s), 7.30-7.42 (9H, m).

(Step 4) 1-(4-{[(Benzyloxy)carbonyl]amino}phenyl)-4,4-difluorocyclohexanecarboxylic acid The compound (212 mg) obtained in Step 3 above was subjected to the same procedure as in Step 8 of Reference Example C-16 to obtain the title compound (136 mg) as a solid.

$^1$H-NMR (CDCl$_3$) δ: 1.89-2.12 (6H, m), 2.49-2.60 (2H, m), 5.19 (2H, s), 6.80 (1H, br s), 7.31-7.46 (9H, m). MS (m/z): 388 (M−H)$^−$.

(Step 5) tert-Butyl 5-{[(4R)-1-{[1-(4-{[(benzyloxy)carbonyl]amino}phenyl)-4,4-difluorocyclohexyl]carbonyl}-4-fluoro-D-prolyl]amino}-1H-pyrazolo[4,3-b]pyridine-1-carboxylate The compound (134 mg) obtained in Step 4 above and the compound obtained in Reference Example B-2 were subjected to the same procedure as in Step 1 of Example 93 to obtain the title compound (214 mg) as a solid.

$^1$H-NMR (DMSO-D$_6$) δ: 1.66 (9H, s), 1.76-2.20 (7H, m), 2.21-2.44 (3H, m), 3.19-3.37 (2H, m), 4.81 (1H, d, J=7.9 Hz), 5.05 (1H, d, J=55.5 Hz), 5.15 (2H, s), 7.26 (2H, d, J=8.5 Hz), 7.29-7.42 (5H, m), 7.49 (2H, d, J=8.5 Hz), 8.23 (1H, d, J=9.2 Hz), 8.37-8.40 (2H, m), 9.46 (1H, s), 10.16 (1H, s). MS (m/z): 721 (M+H)$^+$.

(Step 6) tert-Butyl 5-{[(4R)-1-{[1-(4-aminophenyl)-4,4-difluorocyclohexyl]carbonyl}-4-fluoro-D-prolyl]amino}-1H-pyrazolo[4,3-b]pyridine-1-carboxylate The compound (231 mg) obtained in Step 5 above was subjected to the same procedure as in Step 2 of Example 4 to obtain the title compound (163 mg) as a solid.

$^1$H-NMR (DMSO-D$_6$) δ: 1.67 (9H, s), 1.73-2.45 (10H, m), 3.34 (2H, d, J=23.8 Hz), 4.80 (1H, dd, J=9.8, 3.4 Hz), 5.06 (1H, d, J=54.3 Hz), 6.63 (2H, d, J=8.5 Hz), 7.01 (2H, d, J=8.5 Hz), 8.24 (1H, d, J=9.2 Hz), 8.39 (1H, s), 8.39 (1H, d, J=9.2 Hz), 10.14 (1H, s). MS (m/z): 587 (M+H)$^+$.

(Step 7) tert-Butyl 5-{[(4R)-1-({1-[4-(acetylamino)phenyl]-4,4-difluorocyclohexyl}carbonyl)-4-fluoro-D-prolyl]amino}-1H-pyrazolo[4,3-b]pyridine-1-carboxylate To a solution of the compound (80 mg) obtained in Step 6 above in 1,2-dichloroethane (1.5 mL), acetic anhydride (20 μL) and 4-dimethylaminopyridine (2 mg) were added. The mixture was stirred at room temperature for 64 hours. Then the reaction solution was purified using silica gel column chromatography (methanol/chloroform) to obtain the title compound (56 mg) as a solid.

$^1$H-NMR (DMSO-D$_6$) δ: 1.67 (9H, s), 1.77-2.00 (4H, m), 2.02 (3H, s), 2.03-2.23 (3H, m), 2.27-2.46 (3H, m), 3.22-3.37 (2H, m), 4.81 (1H, d, J=7.3 Hz), 5.06 (1H, d, J=53.7 Hz), 7.26 (2H, d, J=8.5 Hz), 7.59 (2H, d, J=8.5 Hz), 8.24 (1H, d, J=9.2 Hz), 8.39 (1H, d, J=9.2 Hz), 8.39 (1H, s), 9.63 (1H, s), 10.18 (1H, s). MS (m/z): 629 (M+H)$^+$.

(Step 8) (4R)-1-({1-[4-(Acetylamino)phenyl]-4,4-difluorocyclohexyl}carbonyl)-4-fluoro-N-1H-pyrazolo[4,3-b]pyridin-5-yl-D-prolinamide The compound (55 mg) obtained in Step 7 above was subjected to the same procedure as in Step 5 of Example 4 to obtain the title compound (35 mg) as a solid.

$^1$H-NMR (DMSO-D$_6$) δ: 1.73-2.00 (4H, m), 2.09-2.42 (6H, m), 2.97 (3H, d, J=1.2 Hz), 3.18-3.37 (2H, m), 4.79 (1H, d, J=6.7 Hz), 5.05 (1H, d, J=53.7 Hz), 7.27 (2H, d, J=8.5 Hz), 7.59 (2H, d, J=8.5 Hz), 7.94-8.09 (3H, m), 9.64 (1H, s), 9.90 (1H, s), 12.96 (1H, s). MS (m/z): 529 (M+H)$^+$.

Example 102

(4R)-1-[(4,4-Difluoro-1-{4-[(methylsulfonyl)amino]phenyl}cyclohexyl)carbonyl]-4-fluoro-N-1H-pyrazolo[4,3-b]pyridin-5-yl-D-prolinamide

[Formula 166]

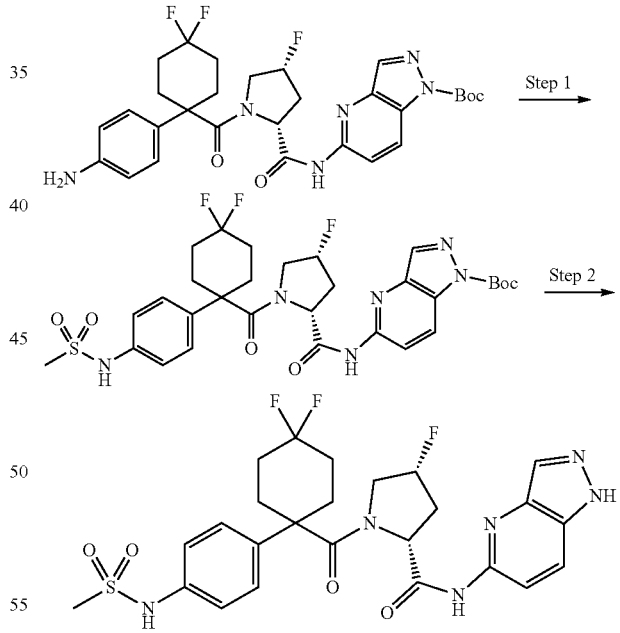

(Step 1) tert-Butyl 5-({(4R)-1-[(4,4-difluoro-1-{4-[(methylsulfonyl)amino]phenyl}cyclohexyl)carbonyl]-4-fluoro-D-prolyl}amino)-1H-pyrazolo[4,3-b]pyridine-1-carboxylate To a solution of the compound (80 mg) obtained in Step 6 of Example 101 and pyridine (24 μL) in dichloromethane (1.5 mL), methanesulfonyl chloride (22 mg) was added dropwise at 0° C. The mixture was stirred at the same temperature for 2 hours, then reaction solution was diluted with dichloromethane and purified using silica gel column chromatography (methanol/chloroform) to obtain the title compound (65 mg) as a solid.

$^1$H-NMR (DMSO-D$_6$) δ: 1.67 (9H, s), 1.78-2.16 (6H, m), 2.20-2.45 (4H, m), 2.96 (3H, s), 3.30 (2H, d, J=24.4 Hz), 4.81 (1H, d, J=8.5 Hz), 5.07 (1H, d, J=54.3 Hz), 7.25 (2H, d, J=8.5 Hz), 7.32 (2H, d, J=8.5 Hz), 8.24 (1H, d, J=9.2 Hz), 8.40 (1H, d, J=9.2 Hz), 8.39 (1H, s), 9.47 (1H, s), 10.20 (1H, s). MS (m/z): 665 (M+H)$^+$.

(Step 2) (4R)-1-[(4,4-Difluoro-1-{4-[(methylsulfonyl)amino]phenyl}cyclohexyl)carbonyl]-4-fluoro-N-1H-pyrazolo[4,3-b]pyridin-5-yl-D-prolinamide The compound (64 mg) obtained in Step 1 above was subjected to the same procedure as in Step 5 of Example 4 to obtain the title compound (18 mg) as a solid.

$^1$H-NMR (DMSO-D$_6$) δ: 1.81-2.43 (10H, m), 2.95 (3H, s), 3.23-3.37 (2H, m), 4.78 (1H, d, J=9.2 Hz), 5.06 (1H, d, J=54.3 Hz), 7.25 (2H, t, J=4.3 Hz), 7.31 (2H, t, J=4.3 Hz), 7.96-8.07 (3H, m), 9.46-9.67 (1H, m), 9.91 (1H, br s), 13.00 (1H, br s). MS (m/z): 565 (M+H)$^+$.

Example 103

(4R)-1-({1-[4-(Difluoromethoxy)phenyl]-4,4-difluorocyclohexyl}carbonyl)-4-fluoro-N-{2-[(methylamino)methyl]-1H-pyrrolo[3,2-b]pyridin-5-yl}-D-prolinamide

[Formula 167]

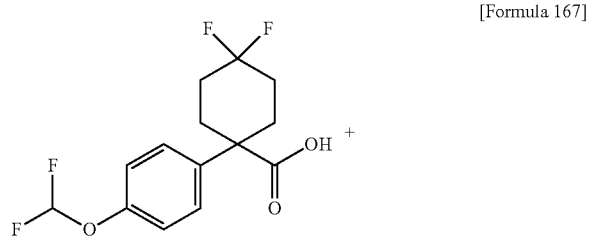

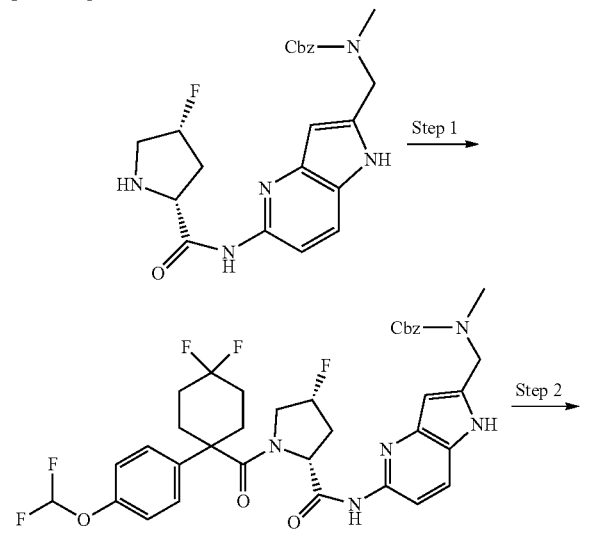

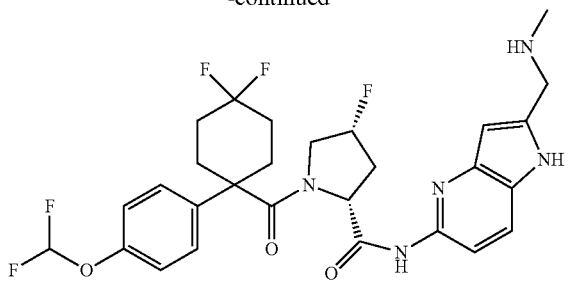

(Step 1) Benzyl [(5-{[(4R)-1-({1-[4-(difluoromethoxy)phenyl]-4,4-difluorocyclohexyl}carbonyl)-4-fluoro-D-prolyl]amino}-1H-pyrrolo[3,2-b]pyridin-2-yl)methyl] methyl carbamate The compound (9 mg) obtained in Reference Example C-22 and the compound (13 mg) obtained in Reference Example B-17 were subjected to the same procedure as in Step 1 of Example 4 to obtain the title compound (20 mg) as a solid.

MS (m/z): 714 (M+H)$^+$.

(Step 2) (4R)-1-({1-[4-(Difluoromethoxy)phenyl]-4,4-difluorocyclohexyl}carbonyl)-4-fluoro-N-{2-[(methylamino)methyl]-1H-pyrrolo[3,2-b]pyridin-5-yl}-D-prolinamide The compound (20 mg) obtained in Step 1 above was subjected to the same procedure as in Step 2 of Reference Example A-3 to obtain the title compound (5 mg) as a solid.

MS (m/z): 580 (M+H)$^+$.

Example 104

(4R)-1-[(4,4-Difluoro-1-{4-[(phenylsulfonyl)amino]phenyl}cyclohexyl)carbonyl]-4-fluoro-N-1H-pyrazolo[4,3-b]pyridin-5-yl-D-prolinamide

[Formula 168]

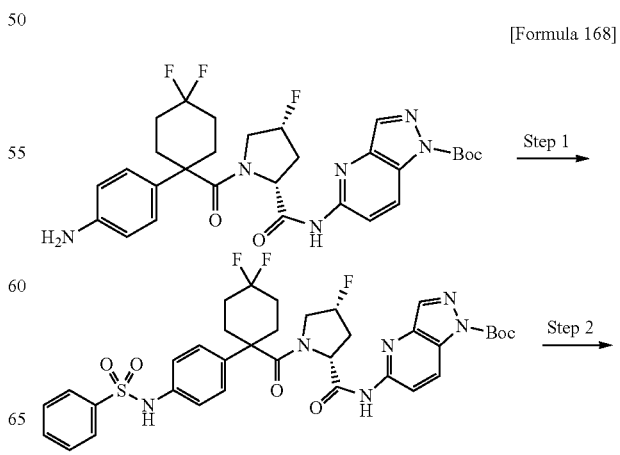

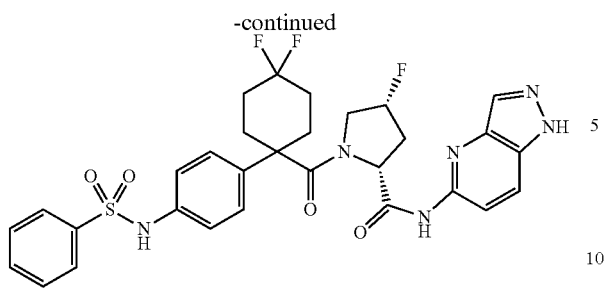

(Step 1) tert-Butyl 5-({(4R)-1-[(4,4-difluoro-1-{4-[(phenylsulfonyl)amino]phenyl}cyclohexyl)carbonyl]-4-fluoro-D-prolyl}amino)-1H-pyrazolo[4,3-b]pyridine-1-carboxylate The compound (190 mg) obtained in Step 6 of Example 101 and benzenesulfonyl chloride (89 mg) were subjected to the same procedure as in Step 1 of Example 102 to obtain the title compound (214 mg) as a solid.

$^1$H-NMR (DMSO-D$_6$) δ: 1.67 (9H, s), 1.69-2.19 (6H, m), 2.23-2.42 (4H, m), 3.08-3.24 (2H, m), 4.77 (1H, d, J=9.8 Hz), 4.99 (1H, d, J=54.3 Hz), 7.13 (2H, d, J=8.5 Hz), 7.22 (2H, d, J=8.5 Hz), 7.47 (2H, t, J=7.3 Hz), 7.55 (1H, t, J=7.6 Hz), 7.73 (2H, d, J=7.3 Hz), 8.23 (1H, d, J=9.2 Hz), 8.38 (1H, s), 8.39 (1H, d, J=9.2 Hz), 9.95 (1H, s), 10.19 (1H, br s). MS (m/z): 727 (M+H)$^+$.

(Step 2) (4R)-1-[(4,4-Difluoro-1-{4-[(phenylsulfonyl)amino]phenyl}cyclohexyl)carbonyl]-4-fluoro-N-1H-pyrazolo[4,3-b]pyridin-5-yl-D-prolinamide The compound (214 mg) obtained in Step 1 above was subjected to the same procedure as in Step 5 of Example 4 to obtain the title compound (122 mg) as a solid.

$^1$H-NMR (DMSO-D$_6$) δ: 1.70-2.02 (4H, m), 2.06-2.41 (6H, m), 3.01-3.23 (2H, m), 4.75 (1H, d, J=9.2 Hz), 4.98 (1H, d, J=54.3 Hz), 7.14 (2H, d, J=8.5 Hz), 7.22 (2H, d, J=8.5 Hz), 7.47 (2H, t, J=7.3 Hz), 7.55 (1H, t, J=7.3 Hz), 7.71-7.75 (2H, m), 7.97 (1H, d, J=9.2 Hz), 8.03 (1H, d, J=9.2 Hz), 8.06 (1H, s), 9.89 (1H, s), 9.94 (1H, s), 12.97 (1H, br s). MS (m/z): 627 (M+H)$^+$.

Example 105

(4R)-1-({1-[4-(Difluoromethoxy)phenyl]-4,4-difluorocyclohexyl}carbonyl)-4-fluoro-N-[2-(methoxymethyl)-1H-pyrrolo[3,2-b]pyridin-5-yl]-D-prolinamide

[Formula 169]

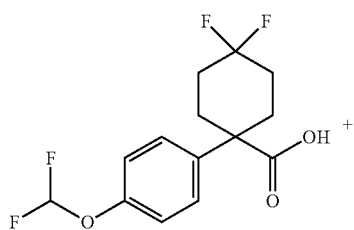

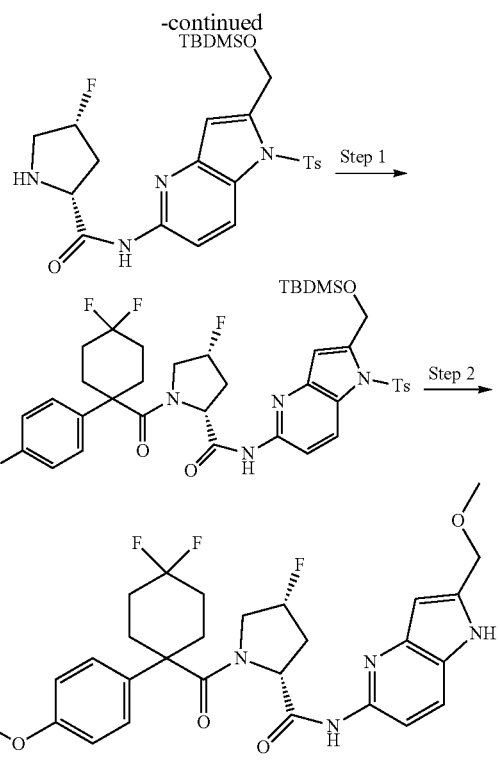

(Step 1) (4R)-1-({1-[4-(Difluoromethoxy)phenyl]-4,4-difluorocyclohexyl}carbonyl)-4-fluoro-N-{2-(hydroxymethyl)-1-[(4-methylphenyl)sulfonyl]-1H-pyrrolo[3,2-b]pyridin-5-yl}-D-prolinamide The compound (0.550 g) obtained in Reference Example C-22 and the compound (1.18 g) obtained in Reference Example B-18 were subjected to the same procedure as in Step 1 of Example 4 to obtain the title compound (0.154 g) as a solid and (4R)—N-{2-({[tert-butyl(dimethyl)silyl]oxy}methyl)-1-[(4-methylphenyl)sulfonyl]-1H-pyrrolo[3,2-b]pyridin-5-yl}-1-({1-[4-(difluoromethoxy)phenyl]-4,4-difluorocyclohexyl}carbonyl)-4-fluoro-D-prolinamide (0.771 g) as a solid.

(4R)-1-({1-[4-(Difluoromethoxy)phenyl]-4,4-difluorocyclohexyl}carbonyl)-4-fluoro-N-{2-(hydroxymethyl)-1-[(4-methylphenyl)sulfonyl]-1H-pyrrolo[3,2-b]pyridin-5-yl}-D-prolinamide $^1$H-NMR (DMSO-D$_6$) δ: 1.81-2.43 (13H, m), 3.27-3.30 (2H, m), 4.76 (1H, s), 4.88 (2H, d, J=5.8 Hz), 5.04 (1H, d, J=26.9 Hz), 5.37 (1H, t, J=5.5 Hz), 6.70 (1H, s), 6.96-7.33 (3H, m), 7.37-7.41 (4H, m), 7.78 (2H, d, J=8.5 Hz), 7.98 (1H, d, J=9.1 Hz), 8.32 (1H, d, J=9.1 Hz), 10.16 (1H, s). MS (m/z): 721 (M+H)$^+$.

(4R)—N-{2-({[tert-Butyl(dimethyl)silyl]oxy}methyl)-1-[(4-methylphenyl)sulfonyl]-1H-pyrrolo[3,2-b]pyridin-5-yl}-1-({1-[4-(difluoromethoxy)phenyl]-4,4-difluorocyclohexyl}carbonyl)-4-fluoro-D-prolinamide (OTBS Compound)

$^1$H-NMR (DMSO-D$_6$) δ: 0.11 (6H, s), 0.93 (9H, s), 1.96-2.30 (13H, m), 3.06-3.26 (2H, m), 4.78 (1H, s), 5.02-5.09 (3H, m), 6.69 (1H, s), 6.96-7.33 (3H, m), 7.37-7.42 (4H, m), 7.77 (2H, d, J=8.2 Hz), 8.00 (1H, d, J=9.1 Hz), 8.32 (1H, d, J=9.1 Hz), 10.10 (1H, s). MS (m/z): 835 (M+H)$^+$.

(Step 2) (4R)-1-({1-[4-(Difluoromethoxy)phenyl]-4,4-difluorocyclohexyl}carbonyl)-4-fluoro-N-[2-(methoxymethyl)-1H-pyrrolo[3,2-b]pyridin-5-yl]-D-prolinamide To a solution of (4R)-1-({1-[4-(Difluoromethoxy)phenyl]-4,4-difluorocyclohexyl}carbonyl)-4-fluoro-N-{2-(hydroxymethyl)-1-[(4-methylphenyl)sulfonyl]-1H-pyrrolo[3,2-b]pyridin-5-yl}-D-prolinamide (137 mg) in dichloromethane (3.8 mL) obtained in Step 1 above, thionyl chloride (69 µL) was added dropwise, and the mixture was stirred at room temperature for 1 hour. The reaction solution was concentrated, then methanol (1.9 mL) and sodium methoxide (28% methanol solution, 0.38 mL) were added to the residue, and the mixture was stirred at 50° C. for 1 hour. The reaction solution was returned to room temperature, diluted with ethyl acetate, washed with water and with saturated brine, and then dried over anhydrous sodium sulfate. The resultant was concentrated under reduced pressure, then the residue was purified by silica gel column chromatography (hexane/ethyl acetate) to obtain the title compound (42 mg) as a solid.

$^1$H-NMR (DMSO-D$_6$) δ: 1.81-2.45 (10H, m), 3.05 (3H, s), 3.15-3.37 (3H, m), 4.56 (2H, s), 4.77 (1H, s), 5.05 (1H, d, J=53.8 Hz), 6.35 (1H, s), 6.96-7.33 (3H, m), 7.42 (2H, d, J=8.8 Hz), 7.68 (1H, d, J=8.8 Hz), 7.78 (1H, d, J=8.8 Hz), 9.76 (1H, s). MS (m/z): 581 (M+H)$^+$.

Example 106

(4R)-1-({1-[4-(Difluoromethoxy)phenyl]-4,4-difluorocyclohexyl}carbonyl)-4-fluoro-N-[2-(hydroxymethyl)-1H-pyrrolo[3,2-b]pyridin-5-yl]-D-prolinamide

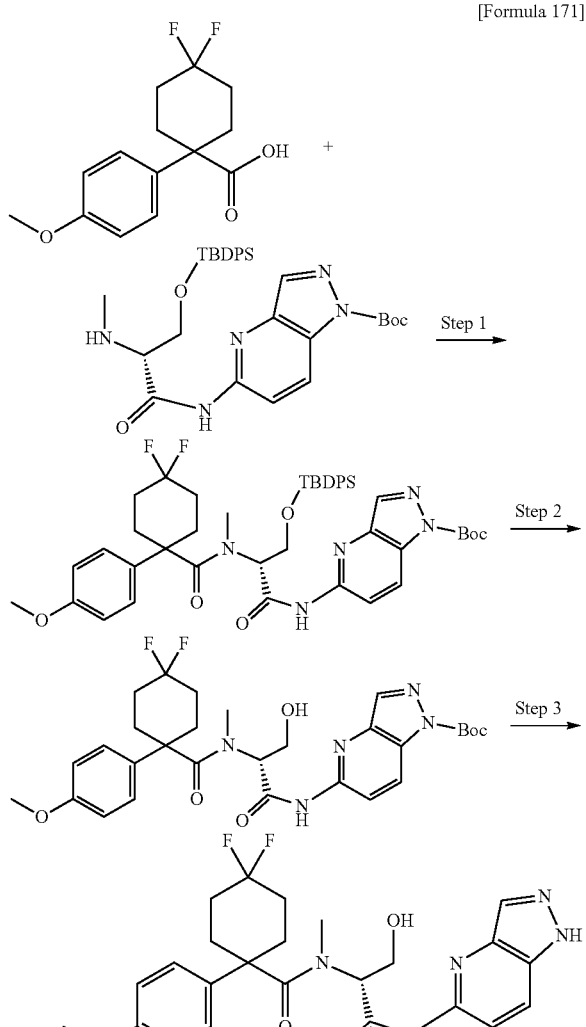

[Formula 170]

A mixture of the OTBS compound (0.728 g) obtained in Step 1 of Example 105, tetrahydrofuran (8.7 mL), methanol (8.7 mL), and cesium carbonate (1.42 g) was stirred at 60° C. for 4 hours. The reaction solution was returned to room temperature, then water was added, and then the mixture was extracted with ethyl acetate three times. The extract was washed with saturated brine, dried over anhydrous sodium sulfate, then concentrated under reduced pressure. The residue was purified by silica gel column chromatography (ethyl acetate/methanol) to obtain the title compound (0.160 g) as a solid.

$^1$H-NMR (DMSO-D$_6$) δ: 1.79-2.45 (10H, m), 3.28-3.33 (2H, m), 4.65 (2H, d, J=5.5 Hz), 4.76 (1H, d, J=7.6 Hz), 5.02-5.07 (2H, m), 6.27 (1H, d, J=1.2 Hz), 6.94-7.31 (3H, m), 7.42 (2H, t, J=4.4 Hz), 7.65 (1H, d, J=8.8 Hz), 7.74 (1H, d, J=8.5 Hz), 9.65 (1H, s), 10.87 (1H, s). MS (m/z): 567 (M+H)$^+$.

Example 107

4,4-Difluoro-N-[(2R)-3-hydroxy-1-oxo-1-(1H-pyrazolo[4,3-b]pyridin-5-ylamino)propan-2-yl]-1-(4-methoxyphenyl)-N-methylcyclohexanecarboxamide

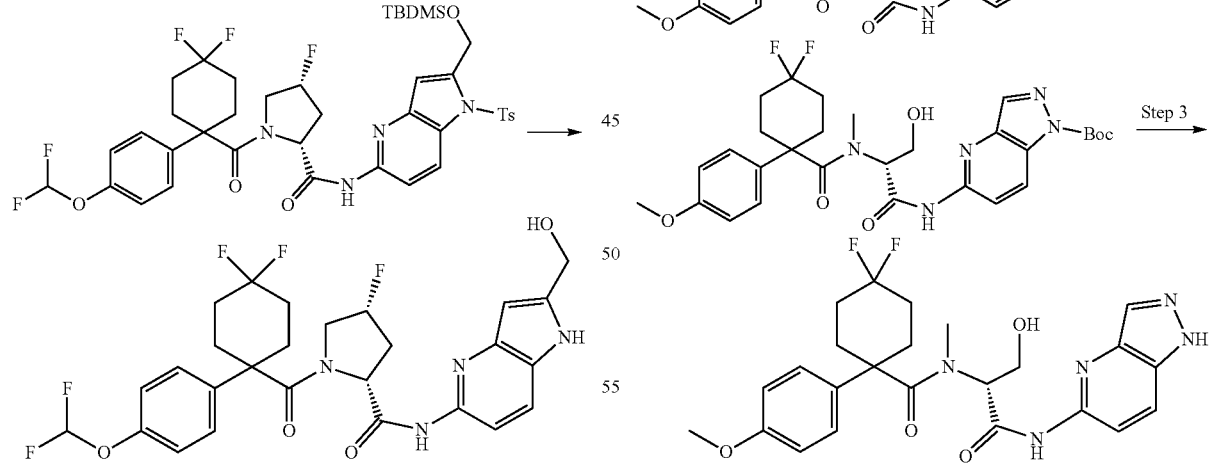

[Formula 171]

(Step 1) tert-Butyl 5-[(O-[tert-butyl(diphenyl)silyl]-N-{[4,4-difluoro-1-(4-methoxyphenyl)cyclohexyl]carbonyl}-N-methyl-D-seryl)amino]-1H-pyrazolo[4,3-b]pyridine-1-carboxylate The compound (233 mg) obtained in Reference Example C-4 and the compound (450 mg) obtained in Reference Example B-19 were subjected to the same procedure as in Step 1 of Reference Example D-2 to obtain the title compound (420 mg) as an oil.

$^1$H-NMR (CDCl$_3$) δ: 1.10 (9H, s), 1.70-2.66 (8H, m), 1.73 (9H, s), 2.57 (3H, s), 3.71 (3H, s), 3.91-4.02 (1H, m), 4.17-4.30 (1H, m), 5.03-5.16 (1H, m), 6.75 (2H, d, J=8.5 Hz), 7.19 (2H, d, J=8.5 Hz), 7.35-7.50 (6H, m), 7.62-7.72 (4H, m), 8.25 (1H, s), 8.31 (1H, d, J=9.1 Hz), 8.41 (1H, d, J=9.1 Hz), 9.38 (1H, s). MS (m/z): 826 (M+H)$^+$.

(Step 2) tert-Butyl 5-[(N-{[4,4-difluoro-1-(4-methoxyphenyl)cyclohexyl]carbonyl}-N-methyl-D-seryl)amino]-1H-pyrazolo[4,3-b]pyridine-1-carboxylate The compound (420 mg) obtained in Step 1 above was subjected to the same procedure as in Step 3 of Example 69 to obtain the title compound (295 mg) as an oil.

$^1$H-NMR (CDCl$_3$) δ: 1.74 (9H, s), 1.76-2.59 (8H, m), 2.71 (3H, s), 3.73 (3H, s), 3.83-4.02 (1H, m), 4.17-4.29 (1H, m), 4.93-5.13 (1H, m), 6.85 (2H, d, J=8.5 Hz), 7.27 (2H, d, J=8.5 Hz), 8.27 (1H, s), 8.35 (1H, d, J=9.1 Hz), 8.44 (1H, d, J=9.1 Hz), 9.05 (1H, br s). MS (m/z): 588 (M+H)$^+$.

(Step 3) 4,4-Difluoro-N-[(2R)-3-hydroxy-1-oxo-1-(1H-pyrazolo[4,3-b]pyridin-5-ylamino)propan-2-yl]-1-(4-methoxyphenyl)-N-methylcyclohexanecarboxamide The compound (295 mg) obtained in Step 2 above was subjected to the same procedure as in Step 5 of Example 4 to obtain the title compound (225 mg) as a solid.

$^1$H-NMR (CDCl$_3$) δ: 1.77-2.61 (8H, m), 2.72 (3H, s), 2.77-2.96 (1H, m), 3.74 (3H, s), 3.79-4.00 (1H, m), 4.17 4.29 (1H, m), 4.91-5.14 (1H, m), 6.87 (2H, d, J=8.5 Hz), 7.28 (2H, d, J=8.5 Hz), 7.86 (1H, d, J=9.1 Hz), 8.19 (1H, s), 8.25 (1H, d, J=9.1 Hz), 8.98 (1H, s), 10.42 (1H, s). MS (m/z): 488 (M+H)$^+$.

Example 108

[6-(1H-Indazol-4-ylmethyl)-1,4-oxazepan-4-yl][1-(4-methoxyphenyl)cyclopentyl]methanone

[Formula 172]

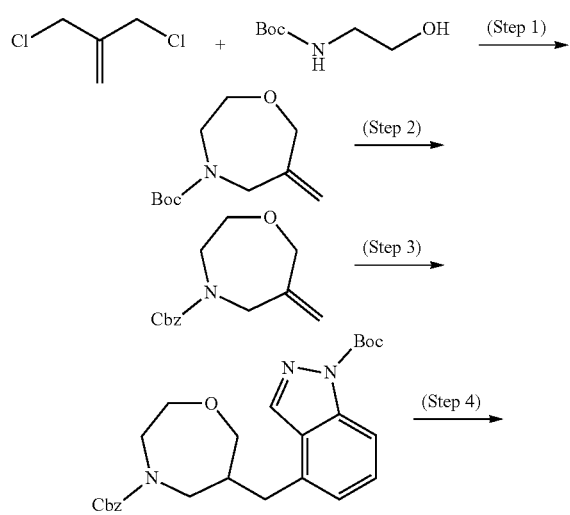

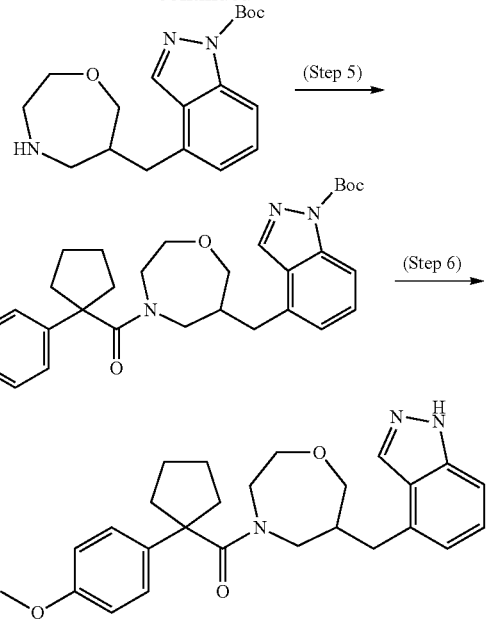

(Step 1) tert-Butyl 6-methylidyne-1,4-oxazepan-4-carboxylate

To a suspension of sodium hydride (purity>55%, 11.4 g) in N,N-dimethylformamide (150 mL), 3-chloro-2-chloromethyl-1-propene (12.7 mL) was added under ice-cooling, and the mixture was stirred at the same temperature for 10 minutes. Then, a solution of 2-(tert-butoxycarbonylamino)-1-ethanol (19.3 g) in tetrahydrofuran (150 mL) was added dropwise over 1.5 hours, and the mixture was stirred at room temperature for 2.5 hours. The reaction solution was cooled with ice, then water was added, and then the mixture was extracted with diethyl ether three times. The organic layer was washed with saturated brine, then dried over anhydrous sodium sulfate. The resultant was filtered, and concentrated under reduced pressure, then the residue obtained was purified by silica gel column chromatography (hexane/ethyl acetate) to obtain the title compound (16.0 g) as an oil.

$^1$H-NMR (CDCl$_3$) δ: 5.06-4.95 (2H, m), 4.19-4.06 (4H, m), 3.76-3.69 (2H, m), 3.54-3.48 (2H, m), 1.46 (9H, s). MS (m/z): 114 (M-CO$_2$tBu+H)$^+$.

(Step 2) Benzyl 6-methylidyne-1,4-oxazepan-4-carboxylate

To the compound (5.00 g) obtained in Step 1 above, hydrogen chloride (2 mol/L, methanol solution, 100 mL) was added, and the mixture was stirred at room temperature overnight. Hydrogen chloride (4 mol/L, 1,4-dioxane solution, 20 mL) was added, and the mixture was stirred at room temperature for 3 hours. The reaction solution was concentrated under reduced pressure. Then, to a suspension of the residue obtained in dichloromethane (80 mL), N,N-diisopropylethylamine (10.2 mL) and benzyl chloroformate (3.67 mL) were added under ice-cooling, and the mixture was stirred at the same temperature for 30 minutes. To the reaction solution, 1 mol/L hydrochloric acid was added. Then, the mixture was extracted with dichloromethane three times, and the organic layer was dried over anhydrous sodium sulfate. The resultant was filtered, and concentrated under reduced pressure, then the residue obtained was purified by silica gel column chromatography (hexane/ethyl acetate) to obtain the title compound (5.70 g) as an oil.

$^1$H-NMR (CDCl$_3$) δ: 7.38-7.29 (5H, m), 5.15 (2H, s), 5.10-4.99 (2H, m), 4.21-4.16 (4H, m), 3.77-3.69 (2H, m), 3.62-3.56 (2H, m).

(Step 3) tert-Butyl 4-({4-[(benzyloxy)carbonyl]-1,4-oxazepan-6-yl}methyl)-1H-indazole-1-carboxylate To the compound (5.63 g) obtained in Step 2 above, 9-borabicyclo[3.3.1]nonane (0.50 mol/L, tetrahydrofuran solution, 46 mL) was added under a nitrogen atmosphere. Then, under reflux, the mixture was stirred for 3 hours, then allowed to cool to room temperature. To the reaction solution, N,N-dimethylformamide (92 mL), water (9.2 mL), potassium carbonate (3.93 g), tert-butyl 4-bromoindazole-1-carboxylate (5.64 g) and [1,1'-bis(diphenylphosphino)ferrocene]palladium(II) dichloride dichloromethane complex (0.775 g) were added, and the mixture was stirred at 65° C. for 4 hours. Then, the reaction solution was allowed to cool to room temperature, and water was added. The mixture was extracted with ethyl acetate three times. The organic layer was washed with saturated brine, then dried over anhydrous sodium sulfate, filtered, and concentrated under reduced pressure. The residue was purified by silica gel column chromatography (hexane/ethyl acetate), then by amino silica gel column chromatography (hexane/ethyl acetate) to obtain the title compound (7.53 g) as an oil.

$^1$H-NMR (DMSO-D$_6$, 100° C.) δ: 8.41 (1H, s), 7.92 (1H, d, J=8.5 Hz), 7.45 (1H, t, J=7.9 Hz), 7.33-7.14 (6H, m), 5.02 (2H, s), 3.71-3.61 (5H, m), 3.44 (2H, dd, J=12.4, 7.0 Hz), 3.27 (1H, dd, J=14.2, 8.2 Hz), 2.93-2.81 (2H, m), 2.33-2.27 (1H, m), 1.66 (9H, s). MS (m/z): 366 (M-CO$_2$tBu+H)$^+$.

(Step 4) tert-Butyl 4-(1,4-oxazepan-6-ylmethyl)-1H-indazole-1-carboxylate

The compound (7.53 g) obtained in Step 3 above was subjected to the same procedure as in Step 2 of Reference Example A-3 to obtain the title compound (5.02 g) as an oil.

$^1$H-NMR (CDCl$_3$) δ: 8.22 (1H, s), 8.03 (1H, d, J=8.5 Hz), 7.44 (1H, dd, J=8.5, 7.3 Hz), 7.11 (1H, d, J=7.3 Hz), 3.86 (1H, dd, J=12.4, 5.1 Hz), 3.78-3.68 (2H, m), 3.60-3.53 (1H, m), 3.02-2.90 (5H, m), 2.72-2.67 (1H, m), 2.35-2.25 (1H, m), 1.73 (9H, s). MS (m/z): 332 (M+H)$^+$.

(Step 5) tert-Butyl 4-[(4-{[1-(4-methoxyphenyl)cyclopentyl]carbonyl}-1,4-oxazepan-6-yl)methyl]-1H-indazole-1-carboxylate The compound (2.00 g) obtained in Step 4 above and 1-(4-methoxyphenyl)cyclopentanecarboxylic acid (1.73 g) were subjected to the same procedure as in Step 1 of Example 1 to obtain the title compound (2.65 g) as a solid.

$^1$H-NMR (DMSO-D$_6$, 100° C.) δ: 8.32 (1H, s), 7.95 (1H, d, J=8.5 Hz), 7.48 (1H, td, J=7.9, 2.6 Hz), 7.06 (1H, d, J=5.4 Hz), 6.95 (2H, d, J=7.9 Hz), 6.78 (2H, d, J=8.5 Hz), 3.71-3.28 (9H, m), 3.19-3.13 (1H, m), 2.91 (1H, br s), 2.77-2.61 (2H, m), 2.29-2.18 (2H, m), 1.97 (1H, br s), 1.85-1.82 (1H, m), 1.71-1.67 (10H, m), 1.57-1.55 (4H, m). MS (m/z): 534 (M+H)$^+$.

(Step 6) [6-(1H-Indazol-4-ylmethyl)-1,4-oxazepan-4-yl][1-(4-methoxyphenyl)cyclopentyl]methanone The compound (2.65 g) obtained in Step 5 above was subjected to the same procedure as in Step 2 of Example 7 to obtain the title compound (2.11 g) as a solid.

$^1$H-NMR (DMSO-D$_6$, 100° C.) δ: 12.77 (1H, s), 7.97 (1H, s), 7.37 (1H, d, J=8.5 Hz), 7.22 (1H, t, J=7.6 Hz), 6.98 (2H, d, J=7.9 Hz), 6.82-6.76 (3H, m), 3.72 (3H, s), 3.68-3.54 (2H, m), 3.45-3.27 (4H, m), 3.20-3.14 (1H, m), 2.93-2.87 (1H, m), 2.70-2.60 (2H, m), 2.33-2.25 (1H, m), 2.20-2.04 (2H, m), 1.86-1.72 (2H, m), 1.60-1.50 (4H, m).

MS (m/z): 434 (M+H)$^+$.

The obtained compound (600 mg) was optically resolved under the following condition to obtain (108a, first peak, 281 mg) as a solid and (108b, second peak, 282 mg) as a solid.
Resolution condition:
Column: Daicel Corporation, CHIRALPAK IA, 20×250 mm
Eluting solvent: hexane/ethanol=70/30
Flow Rate: 20 mL/min
Temperature: 40° C.
108a (first peak)
Optical purity: 99.8% ee or higher
$[α]_D^{20}$ −38.861° (c=1.004, MeOH)
108b (second peak)
Optical purity: 99.3% ee
$[α]_D^{20}$ 37.941° (c=1.009, MeOH)

Example 109

(4R)-4-Fluoro-1-{[1-(4-methoxyphenyl)cyclohexyl]carbonyl}-N-1H-pyrazolo[4,3-b]pyridin-5-yl-D-prolinamide hydrochloride To (4R)-4-fluoro-1-{[1-(4-methoxyphenyl)cyclohexyl]carbonyl}-N-1H-pyrazolo[4,3-b]pyridin-5-yl-D-prolinamide (19.76 mg) as described in Example 35, ethanol (375 μL), 5.788 mol/L aqueous hydrochloric acid solution (7.58 μL) and water (12.2 μL) were added at room temperature. The mixture was stirred at 40° C. for about 24 hours, then the solvent was removed by concentration under reduced pressure to obtain a solid. The solid was then dried at room temperature overnight to obtain the title compound.

The powder X-ray diffraction of the solid obtained is shown in FIG. 5.

Table 14 shows peaks of relative intensity of 31 or more when the maximum peak intensity is set to 100 in the diffraction pattern of powder X-ray diffraction (CuKα, λ=1.54 angstroms, scanning speed=20°/min) in FIG. 5.

TABLE 14

| Peak number | 2θ | d value | Relative intensity |
|---|---|---|---|
| 1 | 9.54 | 9.26 | 87 |
| 2 | 12.66 | 6.99 | 62 |
| 3 | 14.32 | 6.18 | 39 |
| 4 | 16.60 | 5.34 | 100 |
| 5 | 17.50 | 5.06 | 39 |
| 6 | 19.34 | 4.59 | 31 |
| 7 | 20.88 | 4.25 | 65 |
| 8 | 22.56 | 3.94 | 53 |
| 9 | 24.44 | 3.64 | 42 |
| 10 | 25.54 | 3.48 | 33 |

Example 110

(4R)-4-Fluoro-1-{[1-(3-fluoro-4-methoxyphenyl)cyclohexyl]carbonyl}-N-1H-pyrazolo[4,3-b]pyridin-5-yl-D-prolinamide hydrochloride To (4R)-4-fluoro-1-{[1-(3-fluoro-4-methoxyphenyl)cyclohexyl]carbonyl}-N-1H-pyrazolo[4,3-b]pyridin-5-yl-D- prolinamide (20.33 mg) described in Example 37, ethanol (386 μL), 5.788 mol/L aqueous hydrochloric acid solution (7.51 μL) and water (12.8 μL) were added at room temperature. The mixture was stirred at 40° C. for about 24 hours, then the solvent was removed by concentration under reduced pressure to obtain a solid. The solid was then dried at room temperature overnight to obtain the title compound.

Figure 6:
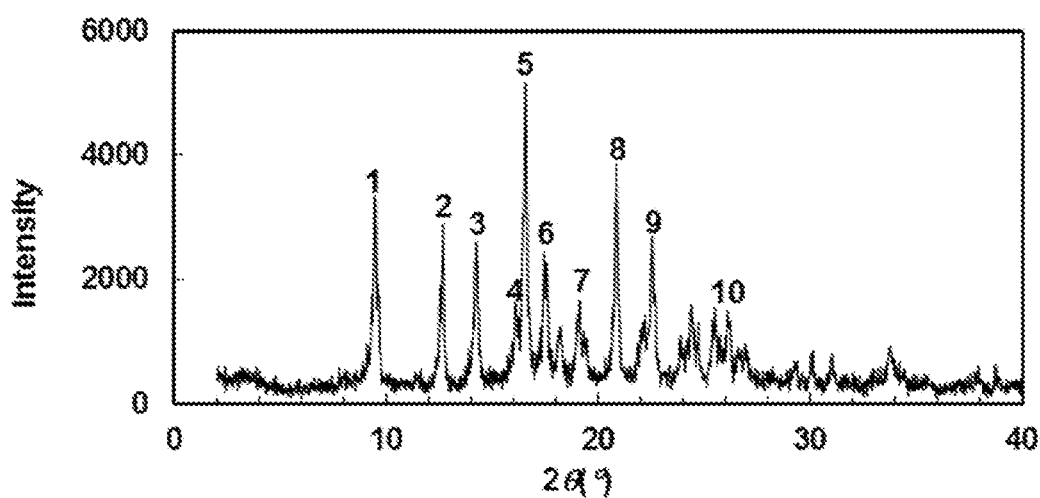
FIG. 6 is a powder X-ray diffraction diagram of a crystal obtained in Example 110. The ordinate indicates diffraction intensity (Intensity) in counts/sec (cps), and the abscissa indicates a value of the diffraction angle 2θ.

The powder X-ray diffraction of the solid obtained is shown in FIG. 6.

Table 15 shows peaks of relative intensity of 33 or more when the maximum peak intensity is set to 100 in the diffraction pattern of powder X-ray diffraction (CuKα, λ=1.54 angstroms, scanning speed=20°/min) in FIG. 6.

TABLE 15

| Peak number | 2θ | d value | Relative intensity |
| --- | --- | --- | --- |
| 1 | 9.48 | 9.32 | 64 |
| 2 | 12.66 | 6.99 | 54 |
| 3 | 14.26 | 6.21 | 54 |
| 4 | 16.14 | 5.49 | 35 |
| 5 | 16.58 | 5.34 | 100 |
| 6 | 17.52 | 5.06 | 50 |
| 7 | 19.10 | 4.64 | 34 |
| 8 | 20.86 | 4.25 | 76 |
| 9 | 22.56 | 3.94 | 54 |
| 10 | 24.42 | 3.64 | 33 |

Example 111

(4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolinamide hydrochloride To (4R)-1-({1-[4-(difluoromethoxy)phenyl]-4,4-difluorocyclohexyl}carbonyl)-4-fluoro-N-1H-pyrazolo[4,3-b]pyridin-5-yl-D-prolinamide (20.49 mg) described in Example 84, ethanol (389 μL), 5.788 mol/L aqueous hydrochloric acid solution (6.81 μL) and water (13.7 μL) were added at room temperature. The mixture was stirred at 40° C. for about 24 hours and then at room temperature for about 30 minutes to obtain a precipitated solid. The solid was then dried at room temperature overnight to obtain 6.10 mg of the title compound.

Figure 7:
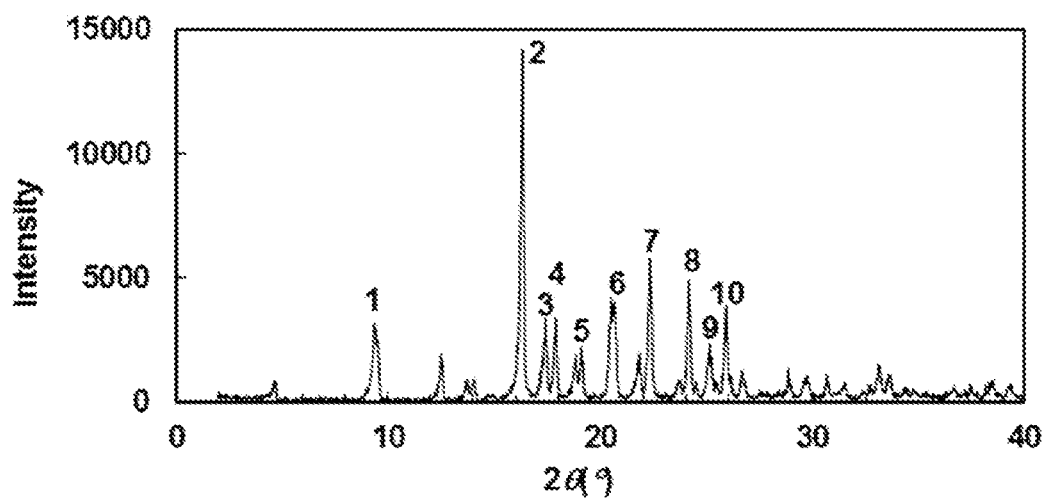
FIG. 7 is a powder X-ray diffraction diagram of a crystal obtained in Example 111. The ordinate indicates diffraction intensity (Intensity) in counts/sec (cps), and the abscissa indicates a value of the diffraction angle 2θ.

The powder X-ray diffraction of the solid obtained is shown in FIG. 7.

Table 16 shows peaks of relative intensity of 15 or more when the maximum peak intensity is set to 100 in the diffraction pattern of powder X-ray diffraction (CuKα, λ=1.54 angstroms, scanning speed=20°/min) in FIG. 7.

TABLE 16

| Peak number | 2θ | d value | Relative intensity |
| --- | --- | --- | --- |
| 1 | 9.40 | 9.40 | 25 |
| 2 | 16.32 | 5.43 | 100 |
| 3 | 17.40 | 5.09 | 24 |
| 4 | 17.88 | 4.96 | 24 |
| 5 | 19.10 | 4.64 | 15 |
| 6 | 20.60 | 4.31 | 33 |
| 7 | 22.34 | 3.98 | 42 |
| 8 | 24.18 | 3.68 | 36 |
| 9 | 25.16 | 3.54 | 17 |
| 10 | 25.92 | 3.43 | 28 |

Example 112

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide hydrochloride To a suspension of (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (49.0 g) in THF (466 mL) described in Example 60, water (7.35 mL) followed by 6 mol/L hydrochloric acid (17.1 mL) were added dropwise at room temperature over 5 minutes. The mixture was stirred at the same temperature for 1 hour, then concentrated to obtain a solid. Ethyl acetate (466 mL) was added to the solid obtained, and the mixture was stirred for 3 hours. Then, the resultant was suction filtered with a Kiriyama funnel, and dried to obtain the title compound (52.0 g) as a solid.

$^1$H-NMR (DMSO-D$_6$) δ: 1.62-1.74 (1H, m), 1.91-2.13 (4H, m), 2.17-2.56 (5H, m), 2.94-3.08 (1H, m), 3.26-3.37 (1H, m), 3.76 (3H, s), 4.74-4.85 (1H, m), 4.98-5.14 (1H, m), 6.96 (2H, d, J=9.2 Hz), 7.29 (2H, d, J=9.2 Hz), 8.05-8.18 (3H, m), 10.57-10.63 (1H, m). MS (m/z): 502 (M+H)$^+$.

The elemental analysis value as $C_{25}H_{26}N_5O_3F_3$·HCl is
calculated value: C: 55.81%, H: 5.06%, N: 13.02%, F: 10.60%, Cl: 6.59%.
found value: C: 55.62%, H: 5.17%, N: 12.76%, F: 10.59%, Cl: 6.70%.

Figure 8:
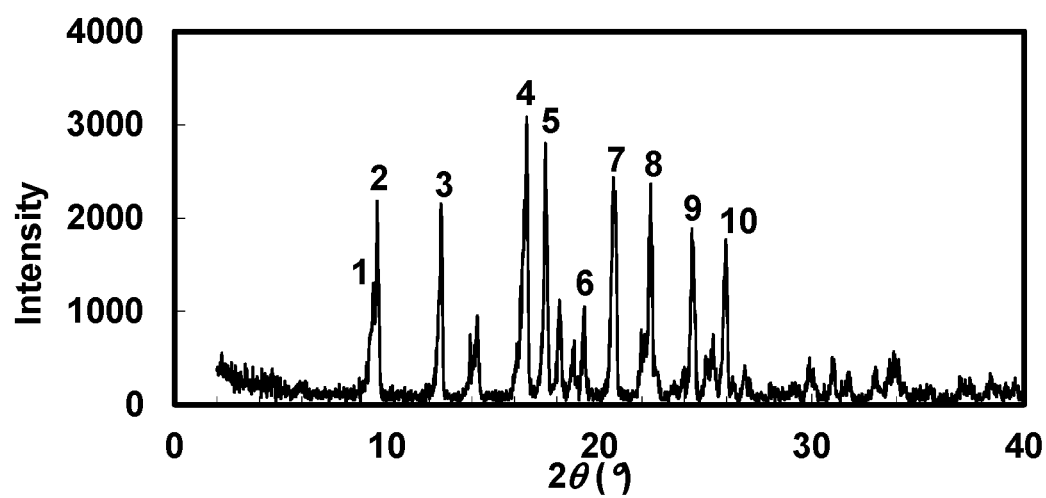
FIG. 8 is a powder X-ray diffraction diagram of a crystal obtained in Example 112. The ordinate indicates diffraction intensity (Intensity) in counts/sec (cps), and the abscissa indicates a value of the diffraction angle 2θ.

The powder X-ray diffraction of the solid obtained is shown in FIG. 8.

Table 17 shows peaks of relative intensity of 37 or more when the maximum peak intensity is set to 100 in the diffraction pattern of powder X-ray diffraction (CuKα, λ=1.54 angstroms, scanning speed=20°/min) in FIG. 8.

TABLE 17

| Peak number | 2θ | d value | Relative intensity |
| --- | --- | --- | --- |
| 1 | 9.36 | 9.44 | 45 |
| 2 | 9.54 | 9.26 | 70 |
| 3 | 12.56 | 7.04 | 76 |
| 4 | 16.58 | 5.34 | 100 |
| 5 | 17.48 | 5.07 | 92 |
| 6 | 19.28 | 4.60 | 37 |
| 7 | 20.74 | 4.28 | 79 |
| 8 | 22.42 | 3.96 | 74 |
| 9 | 24.40 | 3.65 | 60 |
| 10 | 25.96 | 3.43 | 58 |

Example 113

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide hydrobromide To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.66 mg) described in Example 60, 1-propanol (393 μL) 6.024 mol/L aqueous hydrobromic acid solution (7.18 μL) and water (13.48 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3$·HBr is
calculated value: C: 51.56%, H: 4.67%, N: 12.02%, F: 9.79%, Br: 13.72%.

found value: C: 51.01%, H: 4.54%, N: 11.77%, F: 10.79%, Br: 13.67%.

Figure 9:
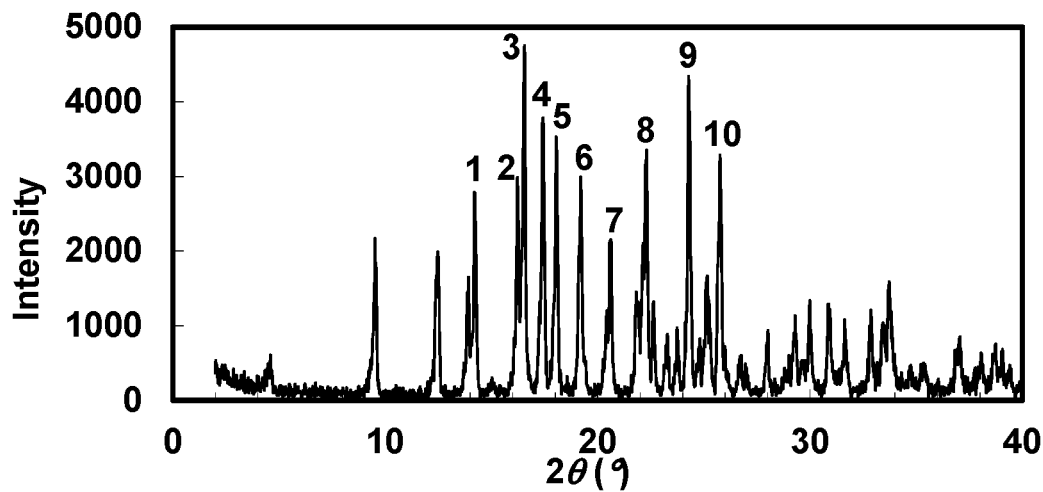
FIG. 9 is a powder X-ray diffraction diagram of a crystal obtained in Example 113. The ordinate indicates diffraction intensity (Intensity) in counts/sec (cps), and the abscissa indicates a value of the diffraction angle 2θ.

The powder X-ray diffraction of the solid obtained is shown in FIG. 9.

Table 18 shows peaks of relative intensity of 50 or more when the maximum peak intensity is set to 100 in the diffraction pattern of powder X-ray diffraction (CuKα, λ=1.54 angstroms, scanning speed=20°/min) in FIG. 9.

TABLE 18

| Peak number | 2θ | d value | Relative intensity |
|---|---|---|---|
| 1 | 14.22 | 6.22 | 59 |
| 2 | 16.22 | 5.46 | 59 |
| 3 | 16.54 | 5.36 | 100 |
| 4 | 17.42 | 5.09 | 82 |
| 5 | 18.06 | 4.91 | 73 |
| 6 | 19.20 | 4.62 | 60 |
| 7 | 20.60 | 4.31 | 50 |
| 8 | 22.28 | 3.99 | 73 |
| 9 | 24.30 | 3.66 | 92 |
| 10 | 25.78 | 3.45 | 66 |

Example 114

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide nitrate (Form 1)

To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.82 mg) described in Example 60, 1-propanol (396 μL), 6.001 mol/L aqueous nitric acid solution (7.26 μL) and water (13.56 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot HNO_3$ is
calculated value: C: 53.19%, H: 4.82%, N: 14.89%, F: 10.10%.
found value: C: 53.06%, H: 4.75%, N: 14.70%, F: 10.16%.

Figure 10:
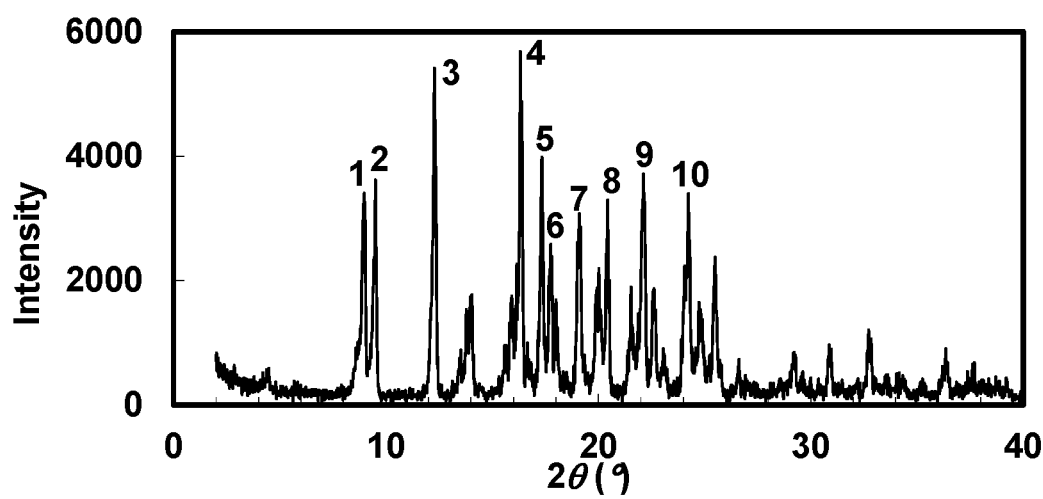
FIG. 10 is a powder X-ray diffraction diagram of a crystal obtained in Example 114. The ordinate indicates diffraction intensity (Intensity) in counts/sec (cps), and the abscissa indicates a value of the diffraction angle 2θ.

The powder X-ray diffraction of the solid obtained is shown in FIG. 10.

Table 19 shows peaks of relative intensity of 46 or more when the maximum peak intensity is set to 100 in the diffraction pattern of powder X-ray diffraction (CuKα, λ=1.54 angstroms, scanning speed=20°/min) in FIG. 10.

TABLE 19

| Peak number | 2θ | d value | Relative intensity |
|---|---|---|---|
| 1 | 8.96 | 9.86 | 67 |
| 2 | 9.50 | 9.30 | 59 |
| 3 | 12.30 | 7.19 | 97 |
| 4 | 16.36 | 5.41 | 100 |
| 5 | 17.34 | 5.11 | 73 |
| 6 | 17.76 | 4.99 | 46 |
| 7 | 19.12 | 4.64 | 58 |
| 8 | 20.42 | 4.35 | 55 |
| 9 | 22.14 | 4.01 | 69 |
| 10 | 24.24 | 3.67 | 58 |

Example 115

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide nitrate (Form 2)

To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.54 mg) described in Example 60, ethanol (390 μL), 6.001 mol/L aqueous nitric acid solution (7.17 μL) and water (13.37 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot HNO_3$ is
calculated value: C: 53.19%, H: 4.82%, N: 14.89%, F: 10.10%.
found value: C: 53.25%, H: 4.77%, N: 14.87%, F: 10.19%.

Figure 11:
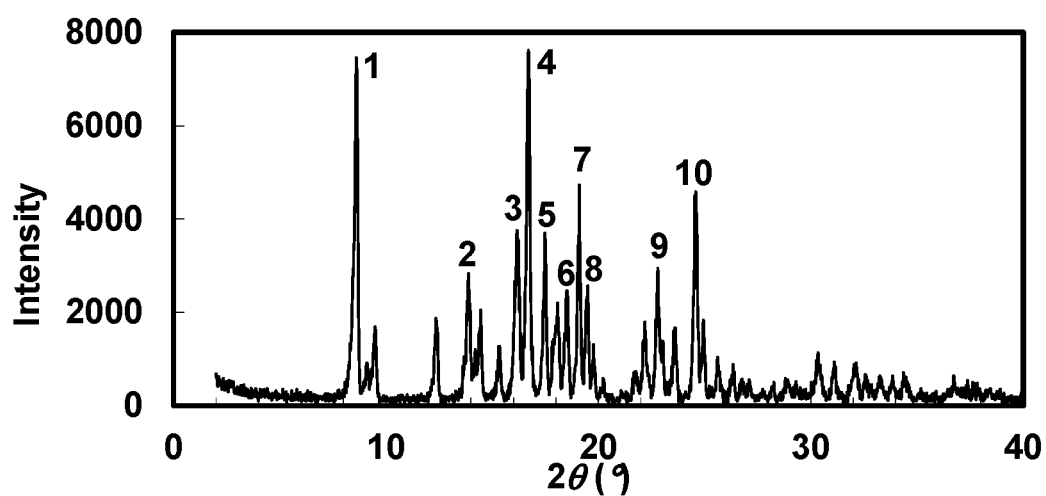
FIG. 11 is a powder X-ray diffraction diagram of a crystal obtained in Example 115. The ordinate indicates diffraction intensity (Intensity) in counts/sec (cps), and the abscissa indicates a value of the diffraction angle 2θ.

The powder X-ray diffraction of the solid obtained is shown in FIG. 11.

Table 20 shows peaks of relative intensity of 33 or more when the maximum peak intensity is set to 100 in the diffraction pattern of powder X-ray diffraction (CuKα, λ=1.54 angstroms, scanning speed=20°/min) in FIG. 11.

TABLE 20

| Peak number | 2θ | d value | Relative intensity |
|---|---|---|---|
| 1 | 8.62 | 10.25 | 98 |
| 2 | 13.88 | 6.37 | 35 |
| 3 | 16.20 | 5.47 | 51 |
| 4 | 16.70 | 5.30 | 100 |
| 5 | 17.50 | 5.06 | 46 |
| 6 | 18.52 | 4.79 | 34 |
| 7 | 19.08 | 4.65 | 53 |
| 8 | 19.48 | 4.55 | 33 |
| 9 | 22.78 | 3.90 | 34 |
| 10 | 24.58 | 3.62 | 61 |

Example 116

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide sulfate To (4R)-1-{[4,4-difluoro-1-(4-methoxyphenyl)cyclohexyl]carbonyl}-4-fluoro-N-1H-pyrazolo[4,3-b] pyridin-5-yl-D-prolinamide (20.74 mg) described in Example 60, 1-propanol (394 μL), 5.789 mol/L aqueous sulfuric acid solution (7.50 μL) and water (13.24 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot H_2SO_4 \cdot 0.8H_2O$ is
calculated value: C: 48.90%, H: 4.86%, N: 11.41%, F: 9.28%, δ: 5.22%.
found value: C, 48.29%, H: 4.59%, N: 11.12%: F, 10.40%, δ: 5.14%.

Figure 12:
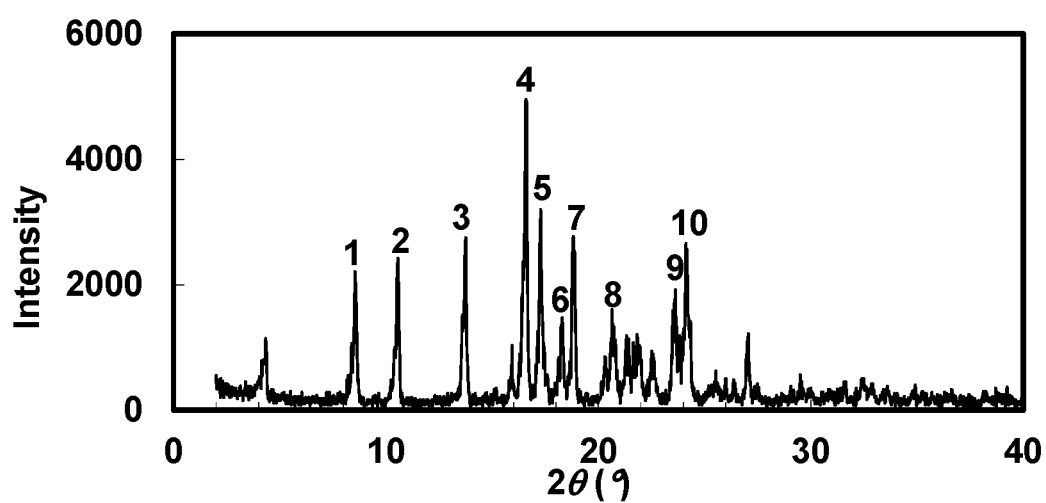
FIG. 12 is a powder X-ray diffraction diagram of a crystal obtained in Example 116. The ordinate indicates diffraction intensity (Intensity) in counts/sec (cps), and the abscissa indicates a value of the diffraction angle 2θ.

The powder X-ray diffraction of the solid obtained is shown in FIG. 12.

Table 21 shows peaks of relative intensity of 28 or more when the maximum peak intensity is set to 100 in the diffraction pattern of powder X-ray diffraction (CuKα, λ=1.54 angstroms, scanning speed=20°/min) in FIG. 12.

TABLE 21

| Peak number | 2θ | d value | Relative intensity |
|---|---|---|---|
| 1 | 8.56 | 10.32 | 44 |
| 2 | 10.56 | 8.37 | 50 |
| 3 | 13.74 | 6.44 | 53 |
| 4 | 16.60 | 5.34 | 100 |
| 5 | 17.28 | 5.13 | 59 |
| 6 | 18.28 | 4.85 | 31 |
| 7 | 18.82 | 4.71 | 58 |
| 8 | 20.66 | 4.30 | 28 |
| 9 | 23.60 | 3.77 | 37 |
| 10 | 24.14 | 3.68 | 55 |

Example 117

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide methanesulfonate To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.78 mg) described in Example 60, 1-propanol (395 μL), 5.932 mol/L aqueous methanesulfonic acid solution (7.33 μL) and water (13.45 μL) were added at room temperature. The mixture was stirred at 40° C. for about 24 hours, followed by at room temperature for about 30 minutes to obtain a precipitated solid. The solid was then dried at room temperature overnight to obtain the title compound.

The elemental analysis value as $C_{25}H_{26}N_5O_3F_3 \cdot CH_4O_3S \cdot H_2O$ is calculated value: C: 50.73%, H: 5.24%, N: 11.38%, F: 9.26%, δ: 5.21%.

found value: C: 50.45%, H: 5.09%, N: 11.23%, F: 9.48%, S: 5.18%.

Figure 13:
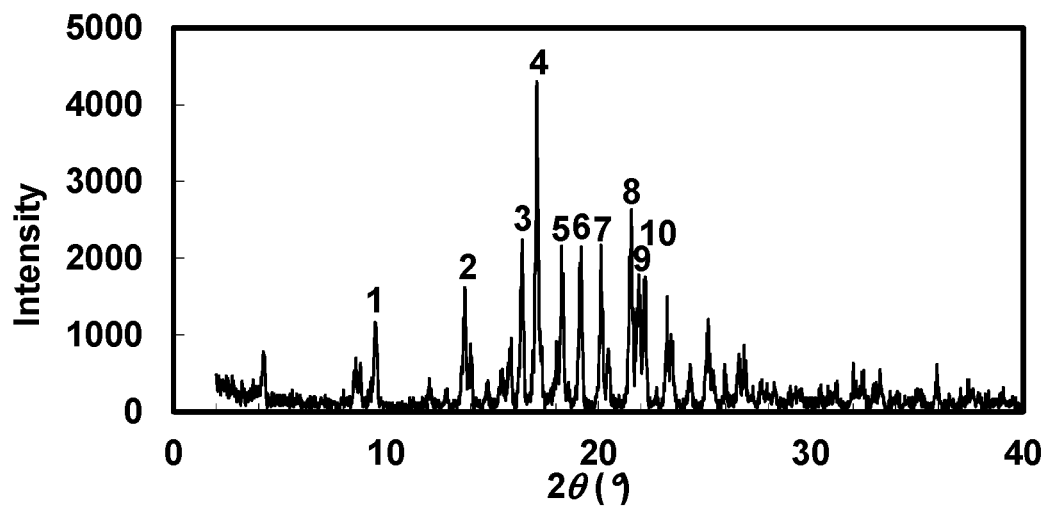
FIG. 13 is a powder X-ray diffraction diagram of a crystal obtained in Example 117. The ordinate indicates diffraction intensity (Intensity) in counts/sec (cps), and the abscissa indicates a value of the diffraction angle 2θ.

The powder X-ray diffraction of the solid obtained is shown in FIG. 13.

Table 22 shows peaks of relative intensity of 30 or more when the maximum peak intensity is set to 100 in the diffraction pattern of powder X-ray diffraction (CuKα, λ=1.54 angstroms, scanning speed=20°/min) in FIG. 13.

TABLE 22

| Peak number | 2θ | d value | Relative intensity |
|---|---|---|---|
| 1 | 9.52 | 9.28 | 30 |
| 2 | 13.70 | 6.46 | 40 |
| 3 | 16.42 | 5.39 | 50 |
| 4 | 17.10 | 5.18 | 100 |
| 5 | 18.30 | 4.84 | 49 |
| 6 | 19.16 | 4.63 | 52 |
| 7 | 20.14 | 4.41 | 45 |
| 8 | 21.54 | 4.12 | 57 |
| 9 | 21.92 | 4.05 | 41 |
| 10 | 22.20 | 4.00 | 46 |

Example 118

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide ethanesulfonate To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (19.94 mg) as described in Example 60, 1-propanol (379 μL), 6.013 mol/L aqueous ethanesulfonic acid solution (6.94 μL) and water (13.00 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot C_2H_6O_3S \cdot H_2O$ is calculated value: C: 51.50%, H: 5.44%, N: 11.12%, F: 9.05%, δ: 5.09%.

found value: C: 51.50%, H: 5.20%, N: 11.86%, F: 9.66%, S: 3.80%.

Figure 14:
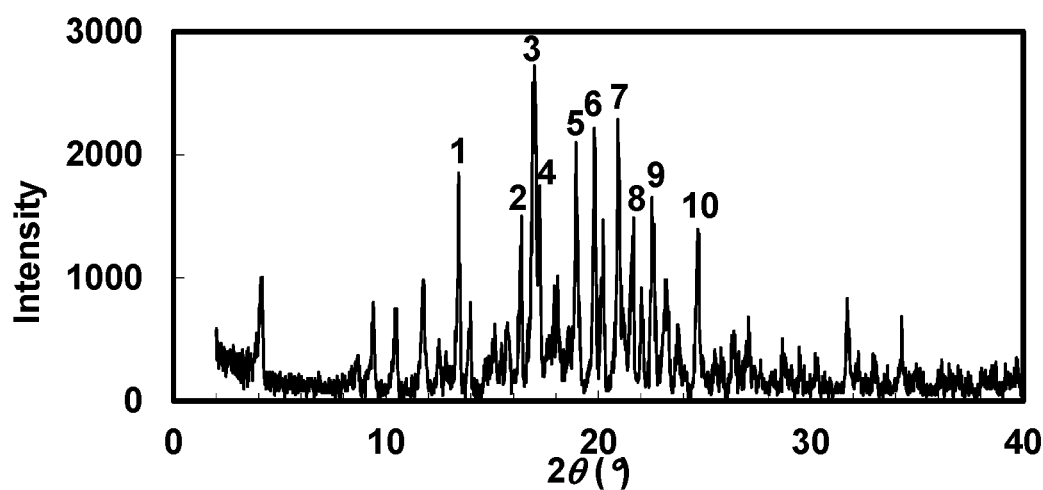
FIG. 14 is a powder X-ray diffraction diagram of a crystal obtained in Example 118. The ordinate indicates diffraction intensity (Intensity) in counts/sec (cps), and the abscissa indicates a value of the diffraction angle 2θ.

The powder X-ray diffraction of the solid obtained is shown in FIG. 14.

Table 23 shows peaks of relative intensity of 52 or more when the maximum peak intensity is set to 100 in the diffraction pattern of powder X-ray diffraction (CuKα, λ=1.54 angstroms, scanning speed=20°/min) in FIG. 14.

TABLE 23

| Peak number | 2θ | d value | Relative intensity |
|---|---|---|---|
| 1 | 13.42 | 6.59 | 60 |
| 2 | 16.36 | 5.41 | 52 |
| 3 | 16.98 | 5.22 | 100 |
| 4 | 17.22 | 5.15 | 62 |
| 5 | 18.96 | 4.68 | 74 |
| 6 | 19.82 | 4.48 | 81 |
| 7 | 20.94 | 4.24 | 85 |
| 8 | 21.62 | 4.11 | 56 |
| 9 | 22.56 | 3.94 | 52 |
| 10 | 24.68 | 3.60 | 53 |

Example 119

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide benzenesulfonate To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (19.98 mg) described in Example 60, 1-propanol (380 μL), 4.014 mol/L aqueous benzenesulfonic acid solution (10.42 μL) and water (9.56 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot C_6H_6O_3S$ is calculated value: C: 56.44%, H: 4.89%, N: 10.62%, F: 8.64%, δ: 4.86%.

found value: C: 55.58%, H: 4.68%, N: 10.55%, F: 9.49%, S: 4.78%.

Figure 15:
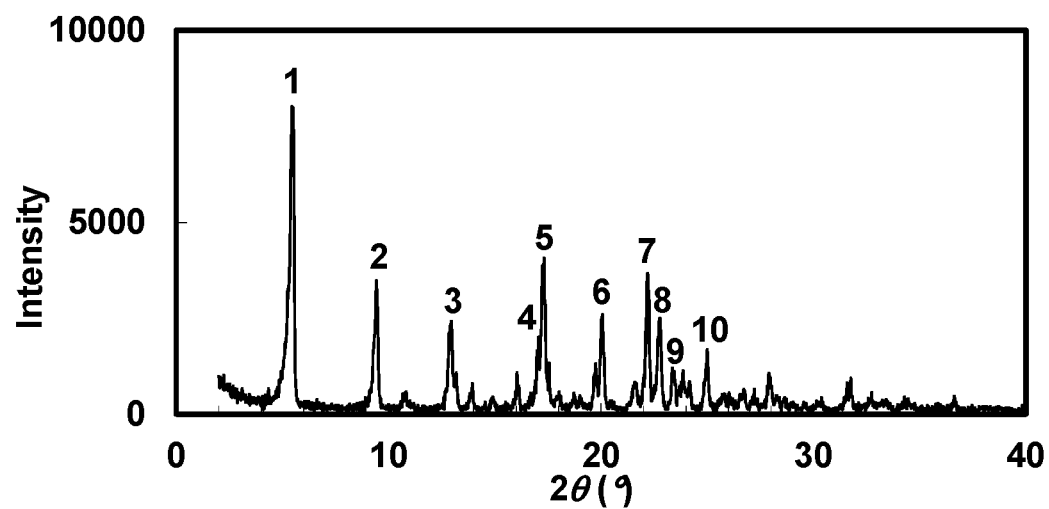
FIG. 15 is a powder X-ray diffraction diagram of a crystal obtained in Example 119. The ordinate indicates diffraction intensity (Intensity) in counts/sec (cps), and the abscissa indicates a value of the diffraction angle 2θ.

The powder X-ray diffraction of the solid obtained is shown in FIG. 15.

Table 24 shows peaks of relative intensity of 15 or more when the maximum peak intensity is set to 100 in the diffraction pattern of powder X-ray diffraction (CuKα, λ=1.54 angstroms, scanning speed=20°/min) in FIG. 15.

TABLE 24

| Peak number | 2θ | d value | Relative intensity |
|---|---|---|---|
| 1 | 5.48 | 16.11 | 100 |
| 2 | 9.44 | 9.36 | 42 |
| 3 | 12.92 | 6.85 | 30 |
| 4 | 17.02 | 5.21 | 22 |
| 5 | 17.30 | 5.12 | 46 |
| 6 | 20.04 | 4.43 | 32 |
| 7 | 22.20 | 4.00 | 47 |
| 8 | 22.76 | 3.90 | 32 |
| 9 | 23.38 | 3.80 | 15 |
| 10 | 25.00 | 3.56 | 19 |

Example 120

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide p-toluenesulfonate To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.30 mg) described in Example 60, 1-propanol (386 μL), 4.016 mol/L aqueous p-toluenesulfonic acid solution (10.58 μL) and water (9.72 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot C_7H_8O_3S$ is
calculated value: C: 57.05%, H: 5.09%, N: 10.40%, F: 8.46%, δ: 4.76%.
found value: C: 56.80%, H: 4.93%, N: 10.33%, F: 8.43%, S: 4.83%.

Figure 16:
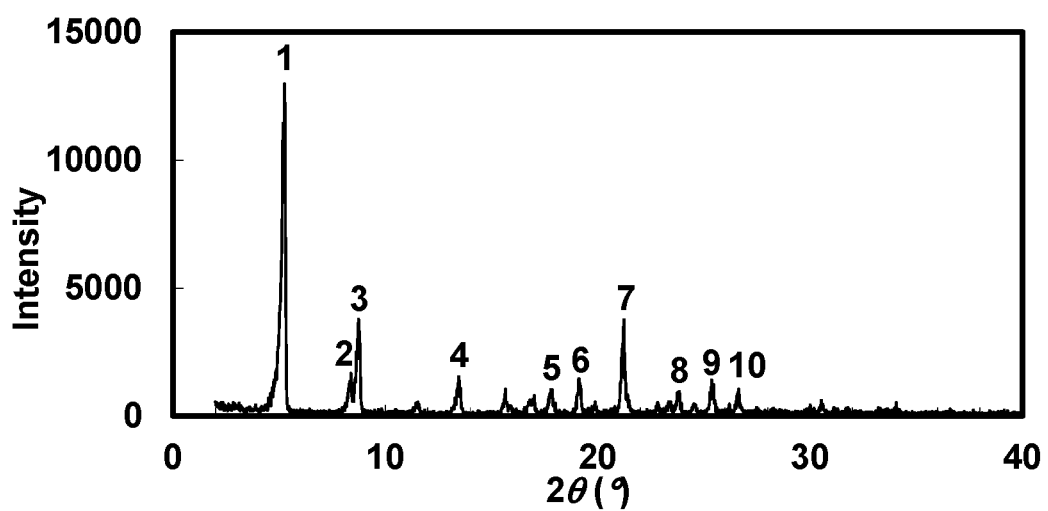
FIG. 16 is a powder X-ray diffraction diagram of a crystal obtained in Example 120. The ordinate indicates diffraction intensity (Intensity) in counts/sec (cps), and the abscissa indicates a value of the diffraction angle 2θ.

The powder X-ray diffraction of the solid obtained is shown in FIG. 16.

Table 25 shows peaks of relative intensity of 8 or more when the maximum peak intensity is set to 100 in the diffraction pattern of powder X-ray diffraction (CuKα, λ=1.54 angstroms, scanning speed=20°/min) in FIG. 16.

TABLE 25

| Peak number | 2θ | d value | Relative intensity |
|---|---|---|---|
| 1 | 5.24 | 16.85 | 100 |
| 2 | 8.34 | 10.59 | 12 |
| 3 | 8.76 | 10.09 | 30 |
| 4 | 13.46 | 6.57 | 11 |
| 5 | 17.82 | 4.97 | 8 |
| 6 | 19.14 | 4.63 | 11 |
| 7 | 21.22 | 4.18 | 26 |
| 8 | 23.80 | 3.74 | 8 |
| 9 | 25.38 | 3.51 | 9 |
| 10 | 26.62 | 3.35 | 8 |

Example 121

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide 1,2-ethanedisulfonate To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.65 mg) described in Example 60, 1-propanol (392 μL), 4.005 mol/L aqueous 1,2-ethanedisulfonic acid solution (5.40 μL) and water (15.25 μL) were added at room temperature. The mixture was stirred at 40° C. for about 24 hours, followed by at room temperature for about 30 minutes to obtain a precipitated solid. The solid was then dried at room temperature overnight to obtain the title compound.

The elemental analysis value as $C_{25}H_{26}N_5O_3F_3 \cdot 0.5C_2H_6O_6S_2 \cdot 1.2H_2O$ is
calculated value: C: 50.51%, H: 5.12%, N: 11.33%, F: 9.22%, δ: 5.19%.
found value: C: 50.34%, H: 4.90%, N: 11.32%, F: 10.09%, δ: 5.15%.

Figure 17:
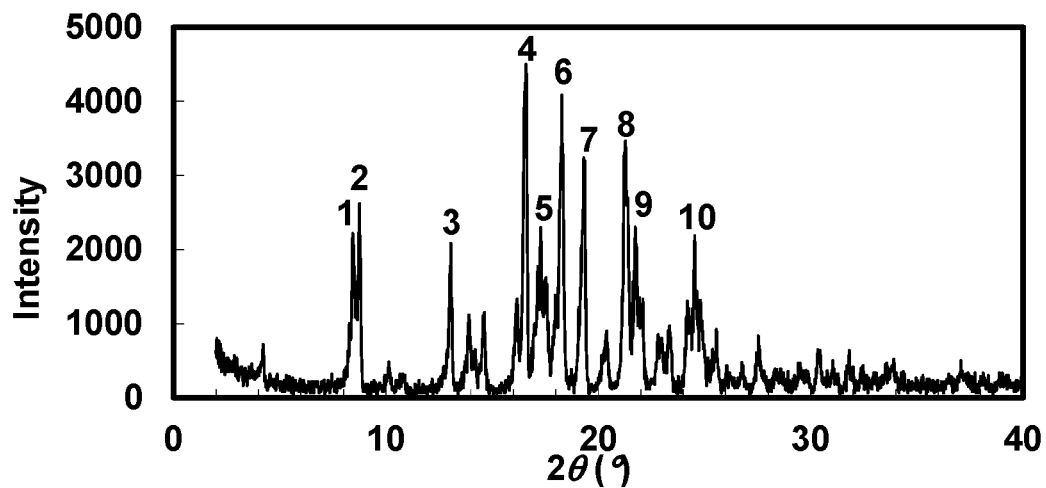
FIG. 17 is a powder X-ray diffraction diagram of a crystal obtained in Example 121. The ordinate indicates diffraction intensity (Intensity) in counts/sec (cps), and the abscissa indicates a value of the diffraction angle 2θ.

The powder X-ray diffraction of the solid obtained is shown in FIG. 17.

Table 26 shows peaks of relative intensity of 40 or more when the maximum peak intensity is set to 100 in the diffraction pattern of powder X-ray diffraction (CuKα, λ=1.54 angstroms, scanning speed=20°/min) in FIG. 17.

TABLE 26

| Peak number | 2θ | d value | Relative intensity |
|---|---|---|---|
| 1 | 8.46 | 10.44 | 46 |
| 2 | 8.76 | 10.09 | 52 |
| 3 | 13.06 | 6.77 | 40 |
| 4 | 16.58 | 5.34 | 100 |
| 5 | 17.30 | 5.12 | 47 |
| 6 | 18.28 | 4.85 | 82 |
| 7 | 19.34 | 4.59 | 68 |
| 8 | 21.26 | 4.18 | 76 |
| 9 | 21.76 | 4.08 | 48 |
| 10 | 24.54 | 3.62 | 40 |

Example 122

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide 1,5-naphthalenedisulfonate
(Form 1)

To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.28 mg) described in Example 60, 1-propanol (377 μL), 0.802 mol/L aqueous 1,5-naphthalenedisulfonic acid solution (26.47 μL) and water (1.92 μL) were added at room temperature. The mixture was stirred at 40° C. for about 24 hours, and then at room temperature for about 30 minutes to obtain a precipitated solid. The solid was then dried at room temperature overnight to obtain the title compound.

The elemental analysis value as $C_{25}H_{26}N_5O_3F_3 \cdot 0.5C_{10}H_8O_6S_2 \cdot 1.5H_2O$ is
calculated value: C: 53.57%, H: 4.94%, N: 10.41%, F: 8.47%, δ: 4.77%.
found value: C: 53.16%, H: 4.67%, N: 10.21%, F: 9.04%, δ: 4.74%.

Figure 18:
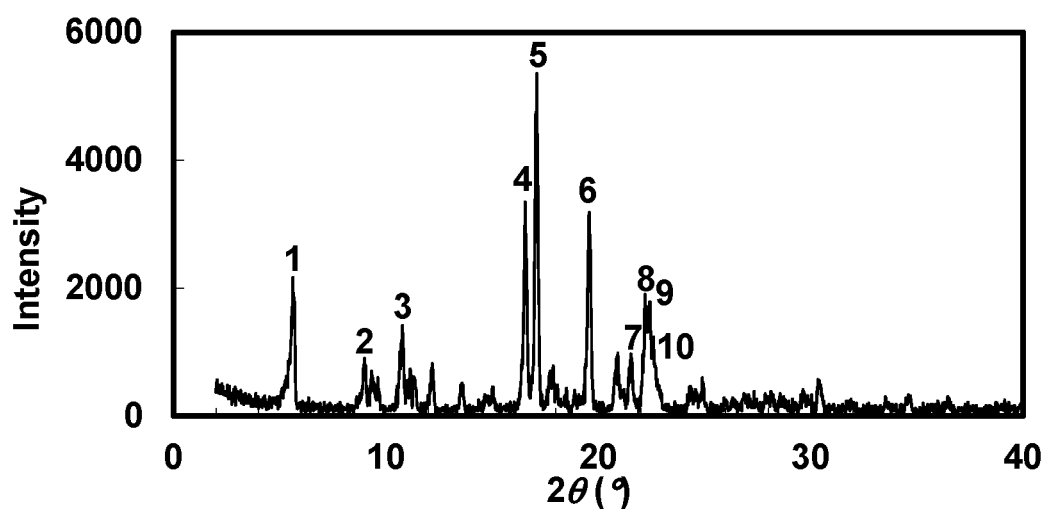
FIG. 18 is a powder X-ray diffraction diagram of a crystal obtained in Example 122. The ordinate indicates diffraction intensity (Intensity) in counts/sec (cps), and the abscissa indicates a value of the diffraction angle 2θ.

The powder X-ray diffraction of the solid obtained is shown in FIG. 18.

Table 27 shows peaks of relative intensity of 18 or more when the maximum peak intensity is set to 100 in the diffraction pattern of powder X-ray diffraction (CuKα, λ=1.54 angstroms, scanning speed=20°/min) in FIG. 18.

TABLE 27

| Peak number | 2θ | d value | Relative intensity |
|---|---|---|---|
| 1 | 5.64 | 15.66 | 42 |
| 2 | 9.00 | 9.82 | 18 |
| 3 | 10.78 | 8.20 | 28 |
| 4 | 16.56 | 5.35 | 61 |
| 5 | 17.10 | 5.18 | 100 |
| 6 | 19.58 | 4.53 | 65 |
| 7 | 21.59 | 4.12 | 19 |
| 8 | 22.22 | 4.00 | 37 |
| 9 | 22.42 | 3.96 | 34 |
| 10 | 22.60 | 3.93 | 22 |

Example 123

(4R)-1-{[4,4-Difluoro-1-(4-methoxyphenyl)cyclohexyl]carbonyl}-4-fluoro-N-1H-pyrazolo[4,3-b]pyridin-5-yl-D-prolinamide 1,5-naphthalenedisulfonate (Form 2)

To (4R)-1-{[4,4-difluoro-1-(4-methoxyphenyl)cyclohexyl]carbonyl}-4-fluoro-N-1H-pyrazolo[4,3-b]pyridin-5-yl-D-prolinamide (20.08 mg) described in Example 60, 1-propanol (321 μL), 0.802 mol/L aqueous 1,5-naphthalenedisulfonic acid solution (52.42 μL) and water (27.90 μL) were added at room temperature. The mixture was stirred at 40° C. for about 24 hours, followed by at room temperature for about 30 minutes to obtain a precipitated solid. The solid was then dried at room temperature overnight to obtain the title compound.

The elemental analysis value as $C_{25}H_{26}N_5O_3F_3 \cdot 0.5C_{10}H_8O_6S_2 \cdot 1.2H_2O$ is calculated value: C: 54.00%, H: 4.89%, N: 10.50%, F: 8.54%, δ: 4.81%.

found value: C: 53.74%, H: 4.66%, N: 10.21%, F: 9.59%, δ: 4.86%.

Figure 19:
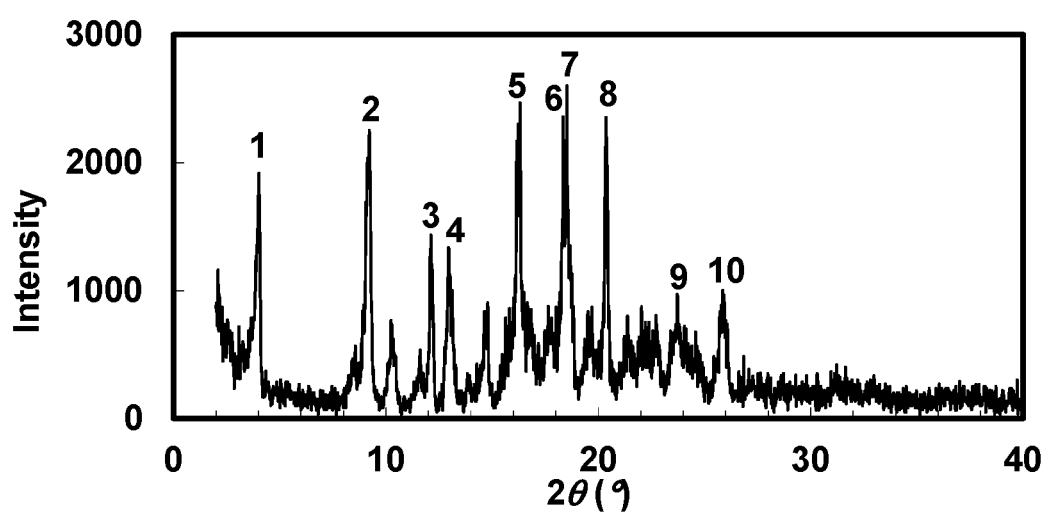
FIG. 19 is a powder X-ray diffraction diagram of a crystal obtained in Example 123. The ordinate indicates diffraction intensity (Intensity) in counts/sec (cps), and the abscissa indicates a value of the diffraction angle 2θ.

The powder X-ray diffraction of the solid obtained is shown in FIG. 19.

Table 28 shows peaks of relative intensity of 37 or more when the maximum peak intensity is set to 100 in the diffraction pattern of powder X-ray diffraction (CuKα, λ=1.54 angstroms, scanning speed=20°/min) in FIG. 19.

TABLE 28

| Peak number | 2θ | d value | Relative intensity |
|---|---|---|---|
| 1 | 4.02 | 21.96 | 80 |
| 2 | 9.20 | 9.60 | 91 |
| 3 | 12.14 | 7.28 | 58 |
| 4 | 12.96 | 6.83 | 56 |
| 5 | 16.28 | 5.44 | 95 |
| 6 | 18.34 | 4.83 | 79 |
| 7 | 18.52 | 4.79 | 93 |
| 8 | 20.38 | 4.35 | 100 |
| 9 | 23.74 | 3.74 | 37 |
| 10 | 25.88 | 3.44 | 40 |

Formulation Examples

Formulation Example 1 (Injection)

1.5% by weight of the compound of each example was stirred in 10% by volume of propylene glycol, water for injection was added to adjust the resultant to a prescribed volume, and the resultant was sterilized to obtain an injection.

Formulation Example 2 (Hard Capsule)

100 mg of the compound of each example in the form of a powder, 128.7 mg of lactose, 70 mg of cellulose and 1.3 mg of magnesium stearate were mixed, the mixture was sieved through a 60-mesh sieve, and the powder obtained was put in a 250 mg No. 3 gelatin capsule to obtain a capsule.

Formulation Example 3 (Tablet)

100 mg of the compound of each example in the form of a powder, 124 mg of lactose, 25 mg of cellulose and 1 mg of magnesium stearate were mixed, and the mixture was tableted into a 250 mg tablet. This tablet can be coated with a sugar coat if necessary.

Test Examples

The pharmacological activity of the compounds of the present invention was checked by the following tests.

[Test Example 1] Evaluation of Histone

Acetyltransferase Inhibitory Activity against EP300 and CREBBP

10 μL each of reaction solutions each containing a different concentration of the compound of each of Examples 1 to 108b (50 mM Tris-HCl (pH8.0), 0.1 mM EDTA, 1 mM dithiothreitol, 0.01% Tween-20, 0.01% Bovine serum albumin, 330 nM trichostatin A, 2 μM Acetyl-CoA (Sigma-Aldrich, #A2056), 100 nM Histone $H_4$(1-25)-GSGSK (Biotin) (Anaspec, #65242-1), 1% dimethyl sulfoxide, 10 to 0.0006 μM of each compound, 50 ng/mL EP300 or 125 ng/mL CREBBP) was added to respective wells of a 384-well plate, and cultured at 28° C. for 1 hour. Thereafter, 5 μL of 30 μM Lys-CoA (Daiichi Sankyo Co., Ltd.) dissolved in LANCE detection buffer (Perkin Elmer Co., Ltd., #CR97-100) was added to each well. Furthermore, 5 μL of LANCE detection buffer containing 2 nM Eu-anti pan-Ac (Perkin Elmer Co., Ltd., #TRF0412) and 50 nM Sta-Ulight (Perkin Elmer Co., Ltd., #TRF0102) was added to each well, and the resultant was cultured at room temperature overnight. EnVision (Perkin Elmer Co., Ltd., Model 2104-0020) was used to measure ULight signals. On the basis of the measured ULight signals, the enzyme inhibition rates at the respective concentrations of the compounds of Examples 1 to 108b were measured, and the data thus obtained were analyzed using medical statistical analysis software GraphPad Prism (GraphPad Software, Inc.) to calculate $IC_{50}$ values. EP300 and CREBBP were produced and purified by Daiichi Sankyo RD Novare Co., Ltd.

[Test Example 2] Evaluation of Intracellular H3K27Ac Inhibitory Activity

LK2 cells derived from human squamous cell lung cancer were seeded in a 96 well plate at 40000 cells/100 μL/well, and were cultured overnight at 37° C. in 5% $CO_2$. The LK2 cells were purchased from Human Science Research Resources Bank. Thereafter, 11 μL of a solution of the compound of each of Examples 1 to 108b (in which the final concentration of dimethyl sulfoxide was 0.1%) was added thereto, and the resultant was cultured at 37° C. in 5% $CO_2$ for 3 hours. The supernatant was discarded, 4% paraformaldehyde was added thereto at 100 μL/well, and the resultant was allowed to stand still at room temperature for 15 minutes. The 4% paraformaldehyde was discarded, and the resultant was washed with PBS-T. A quenching buffer (PBS-T containing 1% $H_2O_2$) was added thereto at of 100 μL/well, and the resultant was allowed to stand still at room temperature for 10 minutes. The resultant was washed with PBS-T, a blocking buffer (StartingBlocK T20 (TBS) Blocking Buffer (Thermo SCIENTIFIC, #37543)) was added thereto at 200 μL/well, and the resultant was allowed to stand still at room temperature for 1 hour. The supernatant was discarded, Acetyl-Histone H3 (Lys27) (D5E4) XP (registered trademark) Rabbit mAb (cell Signaling, #8173) diluted with a blocking buffer was added thereto at 50 μL/well, and the resultant was allowed to stand still at 4° C. overnight. The resultant was washed with PBS-T, Anti-Rabbit IgG-HRP (Cell Signaling, #7074S) diluted with a blocking buffer was added thereto at 50 μL/well, and the resultant was cultured at room temperature for 1 hour. The resultant was washed with PBS-T, SuperSignal (registered trademark) ELISA Pico Chemiluminescent Substrate (Thermo SCIENTIFIC, #37069) was added thereto at 50 μL/well, and a signal was measured using EnVision. Based on the measured signals, the enzyme inhibition rates at the respective concentrations of the compounds of Examples 1 to 108b were measured, and the data thus obtained were analyzed using medical statistical analysis software GraphPad Prism (GraphPad Software, Inc.) to calculate $IC_{50}$ values.

[Test Example 3] Evaluation of Cell Growth Inhibitory Activity

As a culture medium for each cell, a 10% FBS supplemented RPMI 1640 medium (for LK2 cells and TE-8 cells derived from human esophageal cancer) was used. LK2 cells were purchased from Human Science Research Resources Bank, and TE-8 cells were purchased from Riken Cell Bank. The compound of each of Examples 1 to 108b was prepared by dilution with Freedom EVO 150 (Tecan Trading AG) (4-fold diluted, 10 stages, 10 mM to 38 nM). The resultant was added to respective wells of a 384-well plate in an amount of 40 nL/well using Echo 555 (Labcyte Inc.). The LK2 or TE-8 cells were seeded in the plate at 400 cells/40 μL/well (day 0), and were cultured for 3 days. On the day of addition of the compound (day 0) and 3 days after the addition of the compound (day 3), an ATP measurement reagent of CellTiter-Glo (registered trademark) 2.0 Assay (Promega Corporation, #G9242) was added to each well in an amount of 10 μL/well, and the amount of luminescence of each well was measured using EnVision. Based on the amount of luminescence ($C_0$) on the day of the addition of the compound, and the amounts of luminescence of a compound non-addition group ($C_3$) and a compound addition group ($T_3$) obtained after the 3-day culture of the compound, a cell survival rate was calculated in accordance with the following expression:

Cell survival rate (%)=$(T_3-C_0)/(C_3-C_0) \times 100$

A concentration ($GI_{50}$ value) of each compound at which the growth of the TE-8 or LK-2 cells was inhibited by 50% was calculated by semilogarithmically plotting the cell survival rate at each concentration and the compound concentration.

The results of Test Examples 1 to 3 are shown in Table 29 below.

TABLE 29

| Example | Test Example 1 EP300 IC50 (μM) | Test Example 1 CREBBP IC50 (μM) | Test Example 2 H3K27Ac Inhibition (LK2) IC50 (μM) | Test Example 3 LK2 GI50 (nM) | Test Example 3 TE-8 GI50 (nM) |
|---|---|---|---|---|---|
| 1 | 0.176 | 0.218 | 0.693 | 2742.099 | 3406.506 |
| 2 | 0.193 | 0.128 | 1.014 | NT | NT |
| 3 | NT | NT | 10.56 | NT | NT |
| 4 | NT | NT | 11.729 | NT | NT |
| 5 | 0.259 | 0.334 | 1.031 | NT | NT |
| 6 | NT | NT | 9.644 | NT | NT |
| 7 | NT | NT | 8.753 | NT | NT |
| 8 | NT | NT | 6.532 | NT | NT |
| 9 | NT | NT | 8.447 | NT | NT |
| 10 | NT | NT | 6.106 | NT | NT |
| 11 | NT | NT | 8.064 | NT | NT |
| 12 | NT | NT | 2.583 | NT | NT |
| 13 | NT | NT | 3.993 | NT | NT |
| 14 | NT | NT | 6.667 | NT | NT |
| 15 | 0.218 | 0.353 | 0.908 | NT | NT |
| 16 | 0.061 | 0.095 | 0.304 | NT | NT |
| 17 | 0.213 | 0.237 | 0.709 | NT | NT |
| 18 | NT | NT | 3.340 | NT | NT |
| 19 | 0.171 | 0.169 | 1.054 | NT | NT |
| 20 | NT | NT | 7.721 | NT | NT |
| 21 | 0.130 | 0.036 | 0.458 | NT | NT |
| 22 | 0.962 | 0.676 | 2.247 | NT | NT |
| 23 | 0.101 | 0.171 | 0.121 | NT | NT |
| 24 | 0.254 | 0.128 | 0.916 | 1621.893 | 4064.001 |
| 25 | NT | NT | 5.321 | NT | NT |
| 27 | NT | NT | 2.534 | NT | NT |
| 28b | NT | NT | 6.884 | NT | NT |
| 29 | 0.020 | 0.125 | 0.474 | NT | NT |
| 30 | 0.182 | 0.233 | 0.577 | NT | NT |
| 31 | 0.364 | 0.652 | 1.550 | NT | NT |
| 32 | NT | NT | 1.647 | NT | NT |
| 34 | 0.040 | 0.039 | 0.307 | NT | NT |
| 35 | 0.024 | 0.010 | 0.021 | NT | NT |
| 36 | 0.017 | 0.023 | >10 | NT | NT |
| 37 | 0.014 | 0.018 | 0.016 | 85.917 | 112.922 |
| 38 | 0.057 | 0.109 | 0.038 | 116.852 | 175.928 |
| 40 | 0.022 | 0.029 | 0.027 | NT | NT |
| 42 | NT | NT | 4.010 | NT | NT |
| 43 | NT | NT | 6.453 | NT | NT |
| 44 | 0.048 | 0.048 | 0.246 | 589.405 | 1738.097 |
| 45 | 0.031 | 0.128 | 0.101 | 732.504 | 1352.373 |
| 46 | 0.024 | 0.045 | 0.014 | 147.223 | 144.862 |
| 47 | 0.013 | 0.059 | 0.077 | 584.601 | 1136.174 |
| 48 | 0.014 | 0.034 | 0.025 | 104.537 | 134.716 |
| 49 | 0.013 | 0.025 | 0.039 | 75.011 | 68.064 |
| 50 | 0.020 | 0.027 | 0.027 | 166.331 | 288.25 |
| 51 | 0.041 | 0.054 | 0.05 | 350.715 | 915.615 |
| 52 | 0.021 | 0.051 | 0.028 | 253.731 | 439.105 |
| 53 | NT | NT | 2.081 | 2641.288 | 6057.704 |
| 54 | 0.126 | 0.201 | 0.920 | 2970.041 | 4482.931 |
| 55 | NT | NT | 2.018 | NT | NT |
| 56 | 0.024 | 0.064 | 0.020 | 98.803 | 88.333 |
| 57 | 0.048 | 0.076 | 0.053 | 309.667 | 473.308 |
| 58 | 0.060 | 0.075 | 0.173 | 699.189 | 1280.061 |
| 59 | NT | NT | 2.502 | NT | NT |
| 60 | 0.028 | 0.067 | 0.054 | 211.045 | 310.523 |
| 61 | 0.056 | 0.095 | 0.021 | 148.858 | 215.717 |
| 62 | 0.076 | 0.087 | 0.142 | 488.943 | 880.114 |
| 63 | 0.034 | 0.043 | 0.015 | 86.013 | 117.029 |
| 64 | 0.056 | 0.121 | 0.188 | 643.443 | 1265.562 |
| 65 | 0.018 | 0.037 | 0.009 | 79.185 | 151.186 |
| 66 | 0.035 | 0.073 | 0.017 | 548.026 | 846.974 |
| 67 | 0.397 | 0.678 | 2.409 | NT | NT |
| 68 | 0.049 | 0.122 | 0.042 | 510.276 | 818.797 |
| 69 | 0.157 | 0.239 | 0.402 | 3123.397 | 4185.567 |
| 70 | 0.06 | 0.052 | 0.094 | 729.274 | 1067.009 |
| 71 | 0.099 | 0.094 | 0.139 | 797.01 | 1537.907 |
| 72 | 0.177 | 0.182 | 1.146 | >10000 | >10000 |
| 73 | 0.052 | 0.148 | 0.070 | 610.15 | 619.505 |

TABLE 29-continued

|  | Test Example 1 | | Test Example 2 H3K27Ac Inhibition | Test Example 3 | |
| --- | --- | --- | --- | --- | --- |
| Example | EP300 IC50 (µM) | CREBBP IC50 (µM) | (LK2) IC50 (µM) | LK2 GI50 (nM) | TE-8 GI50 (nM) |
| 74 | 0.058 | 0.086 | 0.086 | 271.378 | 598.886 |
| 75 | 0.043 | 0.077 | 0.067 | 397.776 | 612.981 |
| 76 | 0.043 | 0.092 | 0.012 | 68.857 | 127.162 |
| 77 | 0.041 | 0.053 | 0.015 | 102.326 | 198.737 |
| 78 | 0.259 | 0.323 | 0.769 | 2153.346 | 4627.538 |
| 79 | 0.181 | 0.193 | 0.268 | 1389.147 | 1674.672 |
| 80 | 0.078 | 0.091 | 0.017 | 141.123 | 277.467 |
| 81a | 0.052 | 0.083 | 0.023 | 166.898 | 175.745 |
| 81b | 0.041 | 0.064 | 0.016 | 230.522 | 258.29 |
| 82 | 0.012 | 0.021 | 0.013 | 75.106 | 89.338 |
| 83 | 0.033 | 0.061 | 0.019 | 203.077 | 150.781 |
| 84 | 0.026 | 0.039 | 0.022 | 97.163 | 152.484 |
| 85 | 0.031 | 0.053 | 0.029 | 205.711 | 411.6 |
| 86 | 0.023 | 0.04 | 0.014 | 86.795 | 101.474 |
| 87 | 0.038 | 0.082 | 0.073 | 237.036 | 300.186 |
| 88 | 0.037 | 0.08 | 0.053 | 201.338 | 351.393 |
| 89 | 0.038 | 0.061 | 0.062 | 279.332 | 491.26 |
| 90 | 0.004 | 0.007 | 0.009 | 73.425 | 106.169 |
| 91 | 0.031 | 0.075 | 0.089 | 216.557 | 364.429 |
| 92 | 0.022 | 0.053 | 0.051 | 194.638 | 308.155 |
| 93 | 0.056 | 0.076 | 0.311 | 746.402 | 1047.282 |
| 94 | 0.109 | 0.305 | 0.123 | 625.4 | 586.327 |
| 95 | 0.036 | 0.051 | 0.020 | 179.288 | 245.976 |
| 96 | 2.472 | 2.168 | >1 | >10000 | >10000 |
| 97 | 0.07 | 0.123 | 0.218 | 853.561 | 1182.275 |
| 98 | 0.076 | 0.202 | 0.062 | 266.961 | 330.607 |
| 99 | 0.076 | 0.205 | 0.062 | 299.935 | 399.163 |
| 100 | 0.067 | 0.095 | 0.243 | 659.544 | 1369.726 |
| 101 | 0.120 | 0.235 | 0.240 | 707.158 | 1054.383 |
| 102 | 0.040 | 0.084 | 0.126 | 323.095 | 438.808 |
| 103 | 0.041 | 0.077 | 0.034 | 183.812 | 303.878 |
| 104 | 0.026 | 0.058 | 0.138 | 512.083 | 656.352 |
| 105 | 0.050 | 0.078 | 0.192 | 752.796 | 988.65 |
| 106 | 0.024 | 0.043 | 0.039 | 249.509 | 336.706 |
| 107 | 0.049 | 0.155 | 0.014 | 99.874 | 194.755 |
| 108b | 0.050 | 0.083 | 0.125 | 1085.974 | 1164.696 |

NT: Not Tested.

[Test Example 4] Evaluation of Antitumor Activity in LK2 Cell Subcutaneous Transplant Model LK2 cells were transplanted at a rate of $2 \times 10^6$ cells/head subcutaneously into a right abdominal site of each of female BALB/c-nu/nu mice, and 7 days after, the mice were grouped into groups each consisting of 5 mice based on an estimated tumor volume (longer diameter×shorter diameter× shorter diameter/2) and the weight. The LK2 cells were purchased from Human Science Research Resources Bank. The female BALB/c-nu/nu mice were purchased from Charles River Laboratories Japan, Inc. From the day of grouping, the compound of Example 35 at a dose set to 12.5 mg/kg/day or the compound of Example 37 at a dose set to 6.25 mg/kg/day was orally administered in accordance with a schedule of twice a day continuously for 11 days (BID× 11). The estimated tumor volume of each individual was measured from the day of grouping until 18 days after the transplantation (test end day).

[Test Example 5] Evaluation of Antitumor Activity in TE-8 Cell Subcutaneous Transplant Model TE-8 cells were transplanted at a rate of $1 \times 10^7$ cells/head subcutaneously into a right abdominal site of each of female BALB/c-nu/nu mice, and 9 days after (Example 73) or 10 days after (Examples 35 and 84), the mice were grouped into groups each consisting of 5 mice based on an estimated tumor volume (longer diameter×shorter diameter×shorter diameter/2) and the weight. The TE-8 cells were purchased from Riken Cell Bank. The female BALB/c-nu/nu mice were purchased from Charles River Laboratories Japan, Inc.

From the day of grouping, the compound of Example 73 at a dose set to 2 mg/kg/day was orally administered in accordance with a schedule of twice a day continuously for 9 days (BID x 9). The estimated tumor volume of each individual was measured from the day of grouping until 18 days after the transplantation (test end day).

From the day of grouping, the compound of Example 35 at a dose set to 6 mg/kg/day was orally administered in accordance with a schedule of twice a day (BID) continuously for 5 days, drug withdrawal for 2 days, and then continuously for 4 days. Besides, from the day of grouping, the compound of Example 66 at a dose set to 2 mg/kg/day was orally administered in accordance with a schedule of twice a day continuously for 11 days (BID x 11). The estimated tumor volume of each individual was measured from the day of grouping until 21 days after the transplantation (test end day).

[Test Example 6] Evaluation of Antitumor Activity in KARPAS-422 Cell Subcutaneous Transplant Model KARPAS-422 cells of human diffuse large B-cell lymphoma were transplanted at a rate of $2 \times 10^7$ cells/head subcutaneously into a right abdominal site of each of female SCID mice, and 10 days after, the mice were grouped into groups each consisting of 5 mice based on an estimated tumor volume (longer diameter×shorter diameter×shorter diameter/2) and the weight. The KARPAS-422 cells were purchased from Deutsche Sammlung von Mikroorganismen und Zelkulturen GmbH. The female SCID mice were purchased from Charles River Laboratories Japan, Inc. From the day of grouping, the compound of Example 35 at a dose set to 6 mg/kg/day was orally administered in accordance with a schedule of twice a day continuously for 5 days, drug withdrawal for 2 days, continuously for 5 days, drug withdrawal for 2 days and continuously for 4 days. The estimated tumor volume of each individual was measured from the day of grouping until 28 days after the transplantation (test end day).

[Test Example 7] Evaluation of Antitumor Activity in NMC10-15 Cell Subcutaneous Transplant Model NMC10-15 cells derived from human nut midline carcinoma were transplanted at a rate of $5 \times 10^6$ cells/head subcutaneously into a right abdominal site of each of female BALB/c-nu/nu mice, and 6 days after, the mice were grouped into groups each consisting of 5 mice based on an estimated tumor volume (longer diameter×shorter diameter× shorter diameter/2) and the weight. The NMC10-15 cells were assigned from The Brigham and Women's Hospital, Inc. The female BALB/c-nu/nu mice were purchased from Charles River Laboratories Japan, Inc. From the day of grouping, the compound of Example 60 at a dose set to 3 mg/kg/day or the compound of Example 84 at a dose set to 0.3 mg/kg/day was orally administered in accordance with a schedule of once a day continuously for 9 days (QD×9). The estimated tumor volume of each individual was measured from the day of grouping until 15 days after the transplantation (test end day).

[Test Example 8] Evaluation of Antitumor Activity in VCaP Cell Subcutaneous Transplant Model VCaP cells derived from human prostate cancer were transplanted at a rate of 1×10⁷ cells/head subcutaneously into a right abdominal site of each of male NSG mice, and 8 days after, the mice were grouped into groups each consisting of 5 mice based on an estimated tumor volume (longer diameter×shorter diameter×shorter diameter/2) and the weight. The VCaP cells were purchased from American Type Culture Collection. The male NSG mice were purchased from Charles River Laboratories Japan, Inc. From the day of grouping, the compound of Example 60 at a dose set to 6 mg/kg/day was orally administered in accordance with a schedule of once a day for continuously 16 days (QD×16), or the compound of Example 84 at a dose set to 10 mg/kg/day was orally administered in accordance with a schedule of once every other day for eight doses (QOD×8). The estimated tumor volume of each individual was measured from the day of grouping until 24 days after the transplantation (test end day).

The antitumor activity in LK2 cell subcutaneous transplant model of Test Example 4, the antitumor activity in TE-8 cell subcutaneous transplant model of Test Example 5, the antitumor activity in KARPASS-422 cell subcutaneous transplant model of Test Example 6, the antitumor activity in NMC$_{10\text{-}15}$ cell subcutaneous transplant model of Test Example 7, and the antitumor activity in VCaP cell subcutaneous transplant model of Test Example 8 were respectively calculated on the end dates of the tests in accordance with the following equation:

Tumor Growth Inhibition Rate %=(1−*TVCt/TVCc*)× 100

*TVC*=(individual tumor volume on test end day)− (individual tumor volume on grouping day)

TVCt: average of TVC values of administration group
TVCc: average of TVC values of non-administration group The results of Test Example 4 to 8 are shown in Table 30.

ach cancer, blood cancer, pancreatic cancer, esophageal cancer, bladder cancer, gastrointestinal stromal tumor, NUT midline carcinoma and ovarian cancer, and more preferably for prostate cancer, lung cancer, blood cancer, esophageal cancer and NUT midline carcinoma.

The invention claimed is:
1. A compound represented by formula (1) or a pharmacologically acceptable salt thereof:

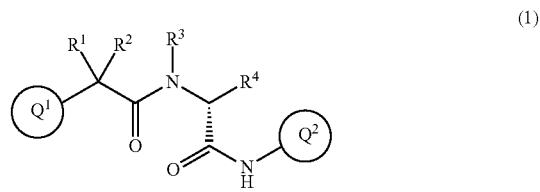

wherein ring $Q^1$ represents a phenyl group optionally having 1 to 3 substituents independently selected from group A;
ring $Q^2$ represents an 8-membered to 10-membered bicyclic aromatic heterocyclic group optionally having, in a ring, 1 to 4 hetero atoms independently selected from the group consisting of a nitrogen atom, an oxygen atom and a sulfur atom (wherein the 8-membered to 10-membered bicyclic aromatic heterocyclic group optionally has 1 to 3 substituents independently selected from group B);
$R^1$ and $R^2$ each independently represent a $C_{1-6}$ alkyl group or a $C_{1-6}$ alkoxy group, or
$R^1$ and $R^2$ form, together with a carbon atom to which $R^1$ and $R^2$ are bonded, a 3-membered to 7-membered cycloalkyl ring optionally having 1 to 3 substituents independently selected from group C, a tetrahydropyran ring optionally having 1 to 3 substituents independently selected from group C, or a dioxane ring optionally having 1 to 3 substituents independently selected from group C; and

TABLE 30

| | Test Example 4 LK2 | | Test Example 5 TE-8 | | Test Example 6 KARPAS422 | | Test Example 7 NMC10-15 | | Test Example 8 Vcap | |
|---|---|---|---|---|---|---|---|---|---|---|
| Example | Dose mg/kg/day | Tumor Growth Inhibition Rate | Dose mg/kg/day | Tumor Growth Inhibition Rate | Dose mg/kg/day | Tumor Growth Inhibition Rate | Dose mg/kg/day | Tumor Growth Inhibition Rate | Dose mg/kg/day | Tumor Growth Inhibition Rate |
| 35 | 12.5 | 44% | 6 | 51% | 6 | 66% | | NT | | NT |
| 37 | 6.25 | 42% | | NT | | NT | | NT | | NT |
| 60 | | NT | | NT | | NT | 3 | 99% | 6 | 89% |
| 66 | | NT | 2 | 54% | | NT | | NT | | NT |
| 73 | | NT | 2 | 65% | | NT | | NT | | NT |
| 84 | | NT | | NT | | NT | 0.3 | 66% | 10 | 77% |

INDUSTRIAL APPLICABILITY

A compound of the present invention represented by general formula (1) or a pharmacologically acceptable salt thereof has excellent histone acetyltransferase inhibitory activity against EP300/CREBBP, and hence is useful as a therapeutic agent for tumors. Specifically, a compound of the present invention represented by general formula (1) or a pharmacologically acceptable salt thereof is useful as a therapeutic agent for tumors, preferably for prostate cancer, liver cancer, lung cancer, breast cancer, colon cancer, stom- $R^3$ and $R^4$ form, together with a nitrogen atom to which $R^3$ is bonded and a carbon atom to which $R^4$ is bonded, an azetidine ring optionally having 1 to 3 substituents independently selected from group D, a pyrrolidine ring optionally having 1 to 3 substituents independently selected from group D, a hexamethyleneimine ring optionally having 1 to 3 substituents independently selected from group D, a thiazolidine ring optionally having 1 to 3 substituents independently selected from group D, a 1-oxothiazolidine ring optionally having 1 to 3 substituents independently selected from group D, a 1,1-dioxothiazolidine ring optionally having 1 to 3 substituents independently selected from group D, or a 4-oxopyrrolidine ring optionally having 1 to 3 substituents independently selected from group D:

Group A: a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group, a phenylsulfonylamino group, a carbamoyl group, a $C_{1-6}$ alkylcarbamoyl group, a di-$C_{1-6}$ alkylcarbamoyl group, a benzyloxycarbonyl group, a $C_{3-7}$ cycloalkylsulfonylcarbamoyl group, a halo $C_{1-6}$ alkylsulfonyloxy group and a phenyl sulfonyl group, Group B: a halogen atom, a cyano group, an amino group, a $C_{1-6}$ alkyl group, a $C_{1-6}$ alkoxy group, a hydroxy $C_{1-6}$ alkyl group, a $C_{1-6}$ alkylamino group, a $C_{1-6}$ alkylamino $C_{1-6}$ alkyl group, a morpholinyl $C_{1-6}$ alkyloxy group, a phenyl group, a benzyloxy group, a $C_{1-6}$ alkoxy $C_{1-6}$ alkyl group, a hydroxy group, a halo $C_{1-6}$ alkyl group, a $C_{1-6}$ alkoxycarbonyl group, a $C_{2-7}$ alkanoylamino group, a halo $C_{1-6}$ alkoxy group, a $C_{1-6}$ alkoxy $C_{1-6}$ alkoxy group, a $C_{1-6}$ alkylsulfonylamino group, a morpholinyl $C_{1-6}$ alkyl group and a $C_{1-6}$ alkylsulfonyl group, Group C: a halogen atom, a $C_{1-6}$ alkyl group and a $C_{1-6}$ alkoxy group, and Group D: a halogen atom, a hydroxy group, a $C_{1-6}$ alkyl group, a $C_{1-6}$ alkoxy group, a $C_{1-6}$ alkoxy $C_{1-6}$ alkoxy group, a $C_{2-6}$ alkynyl group, a $C_{2-7}$ alkanoylamino group, an amino group and a di-$C_{1-6}$ alkylamino group.

2. A compound according to claim 1, or a pharmacologically acceptable salt thereof, wherein the ring $Q^1$ represents formula (2A):

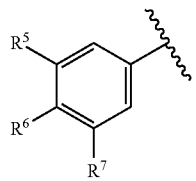

(2A)

wherein $R^5$, $R^6$ and $R^7$ each independently represent a hydrogen atom, a halogen atom, a hydroxy group, a carboxy group, a $C_{1-6}$ alkyl group, a hydroxy $C_{1-6}$ alkyl group, a $C_{1-6}$ alkoxy group, a halo $C_{1-6}$ alkoxy group, a $C_{1-6}$ alkoxycarbonyl group, a $C_{2-7}$ alkanoyl group, a halo $C_{2-7}$ alkanoyl group, a $C_{2-7}$ alkanoylamino group, a $C_{1-6}$ alkylsulfonyl group, a $C_{1-6}$ alkylsulfonylamino group, a $C_{3-7}$ cycloalkylsulfonylamino group, a phenyl group or a phenylsulfonylamino group.

3. A compound according to claim 1, or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group.

4. A compound according to claim 1, or a pharmacologically acceptable salt thereof, wherein the ring $Q^2$ represents any one of formulae (3A) to (3F):

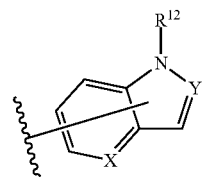

(3A)

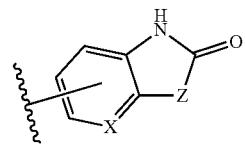

(3B)

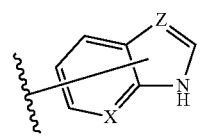

(3C)

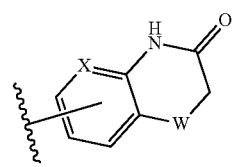

(3D)

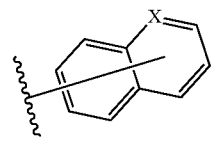

(3E)

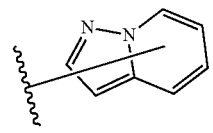

(3F)

wherein X represents a nitrogen atom or —$CR^{13}$;

Y represents a nitrogen atom or —$CR^{14}$;

Z represents —NH or —$CH_2$ in the formula (3B), and a nitrogen atom or —CH in the formula (3C);

W represents an oxygen atom or —$CH_2$;

$R^{12}$ represents a hydrogen atom or a $C_{1-6}$ alkyl group;

$R^{13}$ represents a hydrogen atom, a fluorine atom or a cyano group; and $R^{14}$ represents a hydrogen atom, a $C_{1-6}$ alkyl group, a hydroxy $C_{1-6}$ alkyl group, a $C_{1-6}$ alkylamino $C_{1-6}$ alkyl group or a phenyl group.

5. A compound according to claim 1, or a pharmacologically acceptable salt thereof, wherein the ring $Q^2$ represents any one of formulae (4A) to (4D):

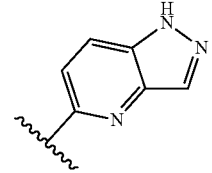

(4A)

-continued (4B)
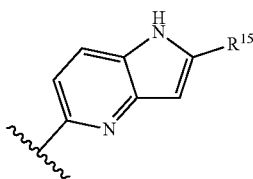

(4C)
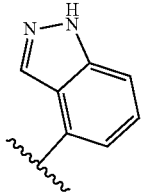

(4D)
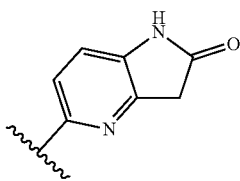

wherein $R^{15}$ represents a hydrogen atom, a methyl group, a hydroxymethyl group or a methylaminomethyl group.

6. A compound according to claim 1, or a pharmacologically acceptable salt thereof, wherein $R^1$ and $R^2$ each independently represent a methyl group.

7. A compound according to claim 1, or a pharmacologically acceptable salt thereof, wherein $R^1$ and $R^2$ form, together with a carbon atom to which to $R^1$ and $R^2$ are bonded, a cyclobutane ring, a 3,3-dihalocyclobutane ring, a 3,3-di-$C_{1-6}$ alkyl cyclobutane ring, a cyclopentane ring, a cyclohexane ring, a 4,4-dihalocyclohexane ring, a tetrahydropyran ring, a cycloheptane ring or a spiro[3.3]heptane ring.

8. A compound according to claim 1, or a pharmacologically acceptable salt thereof, wherein $R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring.

9. A compound according to claim 1, or a pharmacologically acceptable salt thereof, wherein $R^3$ and $R^4$ represent, together with a nitrogen atom to which $R^3$ is bonded and a carbon atom to which $R^4$ is bonded, any one of formulae (5A) to (5D):

(5A)
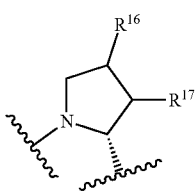

(5B)
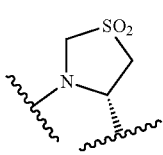

-continued (5C)
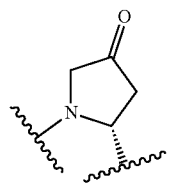

(5D)
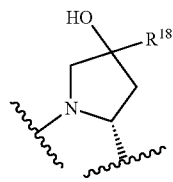

wherein $R^{16}$ represents a hydrogen atom, a halogen atom, a hydroxy group, a $C_{1-6}$ alkoxy group or a di-$C_{1-6}$ alkylamino group;

$R^{17}$ represents a hydrogen atom or a hydroxy group; and $R^{18}$ represents a $C_{1-6}$ alkyl group or a $C_{2-6}$ alkynyl group.

10. A compound according to claim 1, or a pharmacologically acceptable salt thereof, wherein $R^3$ and $R^4$ represent, together with a nitrogen atom to which $R^3$ is bonded and a carbon atom to which $R^4$ is bonded, any one of formulae (6A) to (6C):

(6A)
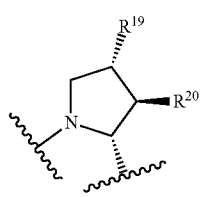

(6B)
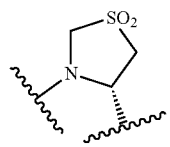

(6C)
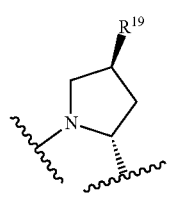

wherein $R^{19}$ represents a hydrogen atom, a fluorine atom or a hydroxy group; and $R^{20}$ represents a hydrogen atom or a hydroxy group.

11. A compound according to claim 1, or a pharmacologically acceptable salt thereof, wherein $R^3$ and $R^4$ represent, together with a nitrogen atom to which $R^3$ is bonded and a carbon atom to which $R^4$ is bonded, having formula (6A-2):

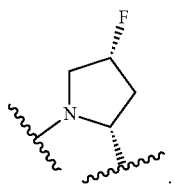

12. A compound according to claim 1, or a pharmacologically acceptable salt thereof, wherein the ring $Q^1$ is a p-hydroxyphenyl group, a p-methoxyphenyl group, a p-fluoromethoxyphenyl group, a p-difluoromethoxyphenyl group, a p-acetylphenyl group, a p-trifluoroacetylphenyl group, a p-(2-hydroxypropan-2-yl)phenyl group, a 6-methoxypyridin-3-yl group, a m-fluoro-p-methoxyphenyl group or a m-fluoro-p-difluoromethoxyphenyl group;

the ring $Q^2$ represents any one of formulae (4A) to (4D):

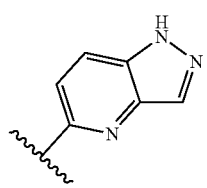

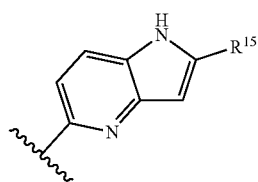

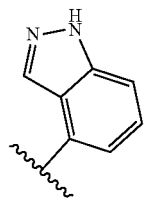

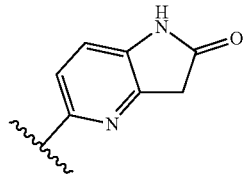

wherein $R^{15}$ represents a hydrogen atom, a methyl group, a hydroxymethyl group or a methylaminomethyl group;

$R^1$ and $R^2$ form, together with a carbon atom to which $R^1$ and $R^2$ are bonded, a 3,3-difluorocyclobutane ring, a 3,3-dimethylcyclobutane ring, a cyclopentane ring, a cyclohexane ring, a 4,4-difluorocyclohexane ring or a 4-tetrahydropyran ring; and $R^3$ and $R^4$ represent, together with a nitrogen atom to which $R^3$ is bonded and a carbon atom to which $R^4$ is bonded, any one of formulae (6A) to (6C):

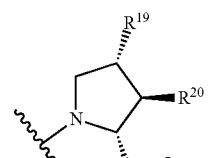

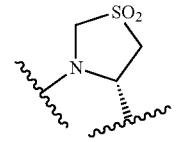

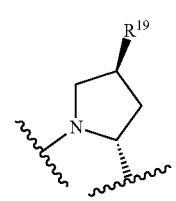

wherein $R^{19}$ represents a hydrogen atom, a fluorine atom or a hydroxy group; and $R^{20}$ represents a hydrogen atom or a hydroxy group.

13. A compound, or a pharmacologically acceptable salt thereof, selected from the group consisting of:

(4R)-4-fluoro-1-{[1-(4-methoxyphenyl)cyclohexyl]carbonyl}-N-1H-pyrazolo[4,3-b]pyridin-5-yl-D-prolineamide, (4R)-4-fluoro-1-{[1-(3-fluoro-4-methoxyphenyl)cyclohexyl]carbonyl}-N-1H-pyrazolo[4,3-b]pyridin-5-yl-D-prolineamide, (4R)-4-fluoro-1-{[4-(4-methoxyphenyl)tetrahydro-2H-pyran-4-yl]carbonyl}-N-1H-pyrazolo[4,3-b]pyridin-5-yl-D-prolineamide, (4R)-4-fluoro-1-[2-(4-methoxyphenyl)-2-methylpropanoyl]-N-1H-pyrazolo[4,3-b]pyridin-5-yl-D-prolineamide, (4R)-4-fluoro-1-({1-[4-(fluoromethoxy)phenyl]cyclopentyl}carbonyl)-N-1H-pyrazolo[4,3-b]pyridin-5-yl-D-prolineamide, (4R)-1-{[4,4-difluoro-1-(4-methoxyphenyl)cyclohexyl]carbonyl}-4-fluoro-N-1H-pyrazolo[4,3-b]pyridin-5-yl-D-prolineamide, (4R)-4-fluoro-N-1H-pyrazolo[4,3-b]pyridin-5-yl-1-({1-[4-(trifluoroacetyl)phenyl]cyclohexyl}carbonyl)-D-prolineamide, (4R)-4-fluoro-1-{[1-(4-methoxyphenyl)cyclohexyl]carbonyl}-N-1H-pyrrolo[3,2-b]pyridin-5-yl-D-prolineamide, (4R)-4-fluoro-1-{[1-(4-methoxyphenyl)cyclohexyl]carbonyl}-N-(2-oxo-2,3-dihydro-1H-pyrrolo[3,2-b]pyridin-5-yl)-D-prolineamide, (4R)-1-{[4,4-difluoro-1-(4-methoxyphenyl)cyclohexyl]carbonyl}-4-fluoro-N-(2-oxo-2,3-dihydro-1H-pyrrolo[3,2-b]pyridin-5-yl)-D-prolineamide, (4R)-4-fluoro-1-{2-methyl-2-[4-(trifluoromethoxy)phenyl]propanoyl}-N-1H-pyrazolo[4,3-b]pyridin-5-yl-D-prolineamide, (4R)-4-fluoro-1-({1-[4-(2-hydroxypropan-2-yl)phenyl]cyclohexyl}carbonyl)-N-1H-pyrazolo[4,3-b]pyridin-5-yl-D-prolineamide, (4R)-1-{[1-(4-acetylphenyl)cyclohexyl]carbonyl}-4-fluoro-N-1H-pyrazolo[4,3-b]pyridin-5-yl-D-prolineamide,
(4R)-1-({1-[4-(difluoromethoxy)phenyl]-4,4-difluorocyclohexyl}carbonyl)-4-fluoro-N-1H-pyrazolo[4,3-b]pyridin-5-yl-D-prolineamide,
(4R)-1-({4,4-difluoro-1-[3-fluoro-4-(fluoromethoxy)phenyl]cyclohexyl}carbonyl)-4-fluoro-N-1H-pyrazolo[4,3-b]pyridin-5-yl-D-prolineamide,
(4R)-1-({3,3-difluoro-1-[3-fluoro-4-(2,2,2-trifluoroethoxy)phenyl]cyclobutyl}carbonyl)-4-fluoro-N-1H-pyrazolo[4,3-b]pyridin-5-yl-D-prolineamide,
(4R)-1-[(4,4-difluoro-1-{3-fluoro-4-[($^2$H$_3$)methyloxy]phenyl}cyclohexyl)carbonyl]-4-fluoro-N-1H-pyrazolo[4,3-b]pyridin-5-yl-D-prolineamide,
(4R)-1-[(4,4-difluoro-1-{4-[($^2$H$_3$)methyloxy]phenyl}cyclohexyl)carbonyl]-4-fluoro-N-1H-pyrazolo[4,3-b]pyridin-5-yl-D-prolineamide,
(4R)-1-({4,4-difluoro-1-[4-(fluoromethoxy)phenyl]cyclohexyl}carbonyl)-4-fluoro-N-1H-pyrazolo[4,3-b]pyridin-5-yl-D-prolineamide,
(4R)-1-{[4,4-difluoro-1-(4-methoxyphenyl)cyclohexyl]carbonyl}-4-fluoro-N-(2-methyl-1H-pyrrolo[3,2-b]pyridin-5-yl)-D-prolineamide,
(4R)-1-({1-[4-(difluoromethoxy)phenyl]-3,3-difluorocyclobutyl}carbonyl)-4-fluoro-N-1H-pyrazolo[4,3-b]pyridin-5-yl-D-prolineamide,
(3S,4S)-1-({1-[4-(difluoromethoxy)phenyl]-4,4-difluorocyclohexyl}carbonyl)-4-fluoro-3-hydroxy-N-1H-pyrazolo[4,3-b]pyridin-5-yl-D-prolineamide,
(4R)-1-({1-[4-(difluoromethoxy)phenyl]-4,4-difluorocyclohexyl}carbonyl)-4-fluoro-N-[2-(hydroxymethyl)-1H-pyrrolo[3,2-b]pyridin-5-yl]-D-prolineamide,
(4R)-4-fluoro-1-{[1-(4-methoxyphenyl)cyclohexyl]carbonyl}-N-1H-pyrrolo[2,3-b]pyridin-6-yl-D-prolineamide, and
(4S)-3-{[4,4-difluoro-1-(4-methoxyphenyl)cyclohexyl]carbonyl}-N-(1H-pyrazolo[4,3-b]pyridin-5-yl)-1,3-thiazolidine-4-carboxamide 1,1-dioxide.

14. (4R)-4-Fluoro-1-{[1-(4-methoxyphenyl)cyclohexyl]carbonyl}-N-1H-pyrazolo[4,3-b]pyridin-5-yl-D-prolineamide, or a pharmacologically acceptable salt thereof.

15. (4R)-4-Fluoro-1-{[1-(3-fluoro-4-methoxyphenyl)cyclohexyl]carbonyl}-N-1H-pyrazolo[4,3-b]pyridin-5-yl-D-prolineamide, or a pharmacologically acceptable salt thereof.

16. (4R)-1-({1-[4-(Difluoromethoxy)phenyl]-4,4-difluorocyclohexyl}carbonyl)-4-fluoro-N-1H-pyrazolo[4,3-b]pyridin-5-yl-D-prolineamide, or a pharmacologically acceptable salt thereof.

17. A compound according to claim 14, wherein the pharmacologically acceptable salt is a hydrochloride salt.

18. (4R)-1-{[4,4-Difluoro-1-(4-methoxyphenyl)cyclohexyl]carbonyl}-4-fluoro-N-1H-pyrazolo[4,3-b]pyridin-5-yl-D-prolineamide, or a pharmacologically acceptable salt thereof.

19. The compound according to claim 18, wherein the pharmacologically acceptable salt is selected from the group consisting of a hydrochloride, a hydrobromide, a nitrate, a sulfate, a methanesulfonate, an ethanesulfonate, a benzenesulfonate, a p-toluenesulfonate, a 1,2-ethanedisulfonate, and a 1,5-naphthalenedisulfonate salt.

20. The compound according to claim 18, wherein the pharmacologically acceptable salt is a hydrochloride salt.

21. A pharmaceutical composition comprising, as an active ingredient, a compound according to claim 1 or a pharmacologically acceptable salt thereof.

22. A method for inhibiting EP300 and/or CREBBP in a subject comprising, administering to a subject an effective amount of a compound according to claim 1 or a pharmacologically acceptable salt thereof.

23. A pharmaceutical composition comprising, as an active ingredient, a compound according to claim 18 or a pharmacologically acceptable salt thereof.

24. The pharmaceutical composition according to claim 23, wherein the pharmacologically acceptable salt is selected from the group consisting of a hydrochloride, a hydrobromide, a nitrate, a sulfate, a methanesulfonate, an ethanesulfonate, a benzenesulfonate, a p-toluenesulfonate, a 1,2-ethanedisulfonate, and a 1,5-naphthalenedisulfonate salt.

25. The pharmaceutical composition according to claim 23, wherein the pharmacologically acceptable salt is a hydrochloride salt.

* * * * *